United States Patent
Matsunaga et al.

(10) Patent No.: US 11,197,858 B2
(45) Date of Patent: *Dec. 14, 2021

(54) SUBSTITUTED AMINES FOR TREATING CARDIAC DISEASES

(71) Applicant: Cardurion Pharmaceuticals, LLC, Boston, MA (US)

(72) Inventors: Nobuyuki Matsunaga, Kanagawa (JP); Takashi Nakahata, Kanagawa (JP); Yuta Tanaka, Kanagawa (JP); Hiroki Takahagi, Kanagawa (JP); Yasufumi Miyamoto, Kanagawa (JP); Rei Okamoto, Kanagawa (JP); Takeshi Yoshikawa, Kanagawa (JP); Yoshito Terao, Kanagawa (JP); Takafumi Yukawa, Kanagawa (JP); Keiko Kakegawa, Kanagawa (JP); Yoichi Nishikawa, Kanagawa (JP); Terufumi Takagi, Kanagawa (JP); Masashi Takahashi, Kanagawa (JP); Mallareddy Komandla, San Diego, CA (US); Lily Kwok, San Diego, CA (US); Joanne Miura, San Diego, CA (US); Mark Sabat, San Diego, CA (US); Nicholas Scorah, San Diego, CA (US); Paul Tanis, San Diego, CA (US); John Tyhonas, San Diego, CA (US); Phong H. Vu, San Diego, CA (US); Haixia Wang, San Diego, CA (US); Xiaolun Wang, San Diego, CA (US); Junya Shirai, Kanagawa (JP); Tomohiro Okawa, Kanagawa (JP); Zenyu Shiokawa, Kanagawa (JP); Akito Shibuya, Kanagawa (JP)

(73) Assignee: Cardurion Pharmaceuticals, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/773,730

(22) Filed: Jan. 27, 2020

(65) Prior Publication Data

US 2020/0230137 A1 Jul. 23, 2020

Related U.S. Application Data

(63) Continuation of application No. 15/933,889, filed on Mar. 23, 2018, now Pat. No. 10,543,212.

(60) Provisional application No. 62/476,970, filed on Mar. 27, 2017.

(51) Int. Cl.
*C07C 211/39* (2006.01)
*A61K 31/506* (2006.01)
*A61P 9/06* (2006.01)
*A61K 31/5377* (2006.01)

(52) U.S. Cl.
CPC ........ *A61K 31/506* (2013.01); *A61K 31/5377* (2013.01); *A61P 9/06* (2018.01)

(58) Field of Classification Search
CPC .................................................... C07C 211/39
USPC ............................................................ 564/1
See application file for complete search history.

(56) References Cited

U.S. PATENT DOCUMENTS

2007/0021419 A1   1/2007   Wang et al.

FOREIGN PATENT DOCUMENTS

| WO | 2002/011724 A2 | 2/2002 |
|----|----------------|--------|
| WO | 2002/024681 A2 | 3/2002 |
| WO | 2005/021529 A1 | 10/2005 |
| WO | 2009/032703 A1 | 3/2009 |
| WO | 2010/057833 A1 | 5/2010 |
| WO | 2012/062704 A1 | 5/2012 |
| WO | 2013/052394 A1 | 4/2013 |
| WO | 2013/157540 A1 | 10/2013 |
| WO | 2018/183112 A1 | 10/2018 |

OTHER PUBLICATIONS

Jul. 10, 2018 Written Opinion and International Search Report of the ISA issued in International Application No. PCT/US18/24043.
Degorce et al., Discovery of a Potent, Selective, Orally Bioavailable, and Efficacious Novel 2-(Pyrazol-4-ylamino)-pyrimidine Inhibitor of the Insulin-like Growth Factor-1 Receptor (IGF-1R), J. Med. Chem., 2016, vol. 59 (10), pp. 4859-4866.
Fischer, et al., "Ca2+/calmodulin-dependent protein kinase II equally induces sarcoplasmic reticulum Ca2+ leak in human ischaemic and dilated cardiomyopathy" European Journal of Herat Failure, 2014, vol. 16, 1292-1300.

(Continued)

*Primary Examiner* — Douglas M Willis
(74) *Attorney, Agent, or Firm* — Mintz Levin Cohn Ferris Glovsky and Popeo, P.C.

(57) ABSTRACT

The present invention provides a compound having a CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like.
The present invention relates to a compound represented by the formula (I):

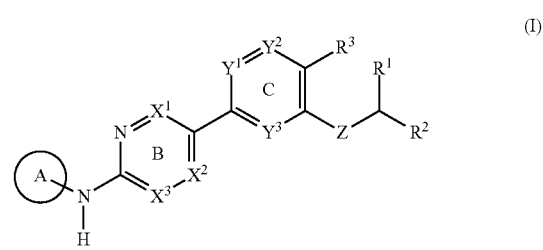

wherein each symbol is as defined in the specification, or a salt thereof.

8 Claims, No Drawings

(56) References Cited

OTHER PUBLICATIONS

Hoch, et al., "Identification and Expression of delta-Isoforms of the Multifunctional Ca (2+/Calmodulin-Dependent) Protein Kinase in Failing and Nonfailing Human Myocardium" Circulation Research, 1999, vol. 84, p. 713-721.

Colomer, et al., "Pressure Overload Selectively Up-Regulates Ca2+ / Calmodulin-Dependent Protein Kinase II in Vivo" Molecular Endocrinology, 2003, vol. 17 p. 183-192.

Zhang, et al., "The Isoform of CaMKII is Activated in Cardiac Hypertrophy and Induces Dilated Cardiomyopathy and Heart Failure" Circulation Research, 2002, vol. 92, p. 912-919.

Backs, et al., "The isoform of CaM kinase II is required for pathological cardiac hypertrophy and remodeling after pressure overload" Proceedings of the National Academy of Sciences, 2009, vol. 106, p. 2342-2347.

Ling, et al., "Ca2+/Calmodulin-Dependent Protein Kinase II δ Mediates Myocardial Ischemia/Reperfusion Injury Through Nuclear Factor-κB" Circulation Research, 2013, vol. 112, p. 935-944.

Erickson, et al., "Diabetic hyperglycaemia activates CaMKII and arrhythmias by O-linked glycosylation" Nature, 2013, vol. 502, p. 372-376.

Liu, et al., "Calmodulin kinase II inhibition prevents arrhythmias in RyR2R4496C+/-mice with catecholaminergic polymorphic ventricular tachycardia" Journal of Molecular and Cellular Cardiology, 2011, vol. 50, p. 214-222.

Yan-Yang, et al., "The emerging role of CaMKII in cancer" Oncotarget, 2015, vol. 20, p. 11725-11734.

House, et al., "CaMKII—Isoform Regulation of Neointima Formation After Vascular Injury" Arterioscler Thromb Vase Biol., 2008, vol. 28, p. 441-447.

Soliman, et al., "Intracellular calcium signals regulate growth of hepatic stellate cells via specific effects on cell cycle progression" Cell Calcium, 2009, vol. 45, pp. 284-292.

Timmins, et al., "Calcium/calmodulin-dependent protein kinase II links ER stress with Fas and mitochondrial apoptosis pathways" The Journal of Clinical Investigation, 2009, vol. 119, p. 2925-2941.

Vest, et al., "Effective Post-insult Neuroprotection by a Novel Ca2+/Calmodulin-dependent Protein Kinase II (CaMKII) Inhibitor" J. Biol Chem, 2010, vol. 285, p. 20675-20682.

Luo, et al., "Reversal of Chronic Inflammatory Pain by Acute Inhibition of Ca2+/Calmodulin-Dependent Protein Kinase II" J. Pharmacol Exp Ther, 2008, vol. 325, p. 267-275.

Westra, et al., "Expression and regulation of HIF-1alpha in macrophages under inflammatory conditions; significant reduction of VEGF by CaMKII inhibitor" BMC Musculoskeletal Disorders, 2010, vol. 30, 61 (11 pages).

Jordan, V.C., "Tamoxifen: A Most Unlikely Pioneering Medicine", Nature, 2003, vol. 2, p. 205-213.

Hackam, et al., "Translation of Research Evidence from Animals to Humans", JAMA, 2006, 296(14), p. 1731-1732.

Mavunkel et al. (Apr. 1, 2008, e-Pub (Mar. 4, 2008) "Pyrimidine-Based Inhibitors of CaMKIIdelta", Bioorganic & Medicinal Chemistry Letters, 18(7):2404-2408.

Pellicena et al. (Feb. 2014) "CaMKII Inhibitors: From Research Tools to Therapeutic Agents", Frontiers in Pharmacology, 5(21):1-10 pages.

SUBSTITUTED AMINES FOR TREATING CARDIAC DISEASES

CROSS-REFERENCE TO RELATED APPLICATIONS

This application is a continuation of U.S. application Ser. No. 15/933,889, filed on Mar. 23, 2018, which claims the benefit of Provisional Application No. 62/476,970, filed on Mar. 27, 2017, hereby incorporated herein by reference in their entirety.

TECHNICAL FIELD

The present invention relates to a heterocyclic compound having a calcium/calmodulin-dependent protein kinase II (sometimes to be abbreviated as "CaMKII" in the present specification) inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like.

BACKGROUND OF THE INVENTION

Cardiac diseases include heart failure, arrhythmia, myocardial infarction, angina, valvular heart disease and the like, and they are high-mortality diseases. In treatment of cardiac diseases with a drug, the symptoms are improved by control of each risk factor and symptomatic therapy. However, the satisfaction with treatment remains low level, and there is now no definitive therapy.

Calcium-calmodulin complex binds to $Ca^{2+}$/calmodulin-dependent protein kinase (CaMK) included in serine/threonine protein kinase, and activates the kinase. The CaMK family includes CaMKII, and four isoforms ($\alpha$, $\beta$, $\gamma$ and $\delta$) exist as CaMKII. CaMKII $\alpha$ and CaMKII $\beta$ are expressed mainly in cerebral tissue, and CaMKII $\gamma$ and CaMKII $\delta$ are expressed in many tissues including heart. CaMKII is activated by amino acid-modification due to oxidative stress or hyperglycemia, in addition to the binding of calcium-calmodulin complex. CaMKII regulates cell functions by phosphorylation of a transcription factor which is a substrate, a protein that plays a function in organelle uptake/excretion of $Ca^{2+}$, a protein that regulates contract and relax of muscles, a channel that regulates an intracellular ion concentration, and the like, due to its kinase activation.

Some documents suggest that CaMKII plays a harmful role in progress of cardiac disease conditions. Expression and activity of CaMKII are increased in heart of human patient or animal with heart failure (Non-Patent Documents 1-4). In transgenic mouse overexpressing CaMKII $\delta$ in heart, onsets of cardiac hypertrophy and heart failure are reported (Non-Patent Document 4). By studies using an inhibitor by a pharmacological method, and studies using a gene deletion by genetic method, protecting effects on heart failure, cardiac hypertrophy, myocardial infarction and arrhythmia by an inhibition of CaMKII and an overexpression of CaMKII inhibitory protein are reported in mouse (Non-Patent Documents 5-7). For catecholaminergic polymorphic ventricular tachycardia, improving effects on disease conditions by CaMKII inhibitor in mutant ryanodine knock-in mouse ($RyR2^{R4496C+/-}$ mouse) are reported (Non-Patent Document 8). These findings suggest availabilities of CaMKII inhibitors in the prophylaxis and/or treatment of cardiac diseases including heart failure, cardiac hypertrophy, myocardial infarction and cardiac arrhythmia.

Recently, CaMKII exacerbating action on growth or metastasis of a certain type of cancer is suggested (Non-Patent Document 9). In addition, therapeutic effect on acute renal failure, intimal hypertrophy, hepatic fibrosis, stroke, pain, rheumatoid arthritis and the like by CaMKII inhibition are also indicated (Non-Patent Documents 10-15).

However, genetic methods achieve only deficiency of protein or overexpression of inhibitory protein, and they are different from a mechanism which inhibits temporarily kinase activity, and therefore, effects by kinase inhibitor cannot be always expected. In addition, inhibitors which have been already reported are not suitable for application as a medicament for a CaMKII selective inhibitor, because they have a low kinase selectivity to CaMKII, or they are not suitable for oral administration or chronic administration.

As a heterocyclic compound, the following compounds are known. Patent Document 1 describes that a compound represented by the following formula (I):

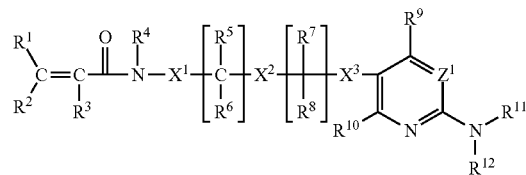

wherein each symbol is as defined in Patent Document 1, is a FLT3 inhibitor and useful for the treatment of acute myelogenous leukemia and the like.

Patent Document 2 describes that a compound represented by the following formula (I):

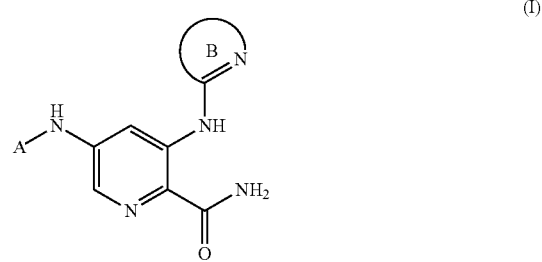

(I)

wherein each symbol is as defined in Patent Document 2, is a Syk (Spleen tyrosine kinase) inhibitor and useful for the treatment of diseases or conditions mediated by Syk (e.g., rheumatism).

Patent Document 3 describes that a compound represented by the following formula (I):

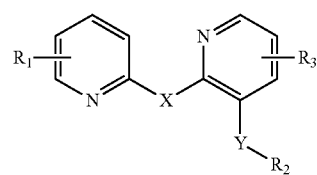

wherein each symbol is as defined in Patent Document 3, is a mGluR (metabotropic glutamate receptors) 5 modulator and useful for the treatment or prophylaxis of diseases or conditions in which mGluR5 is involved (e.g., pain disorder, anxiety, depression, Alzheimer's disease, Parkinson's disease, etc.).

Patent Document 4 describes that a compound represented by the following formula (I):

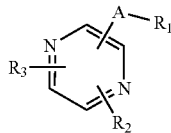

wherein each symbol is as defined in Patent Document 4, is a kinase inhibitor (particularly an inhibitor of kinase domain in VEGF receptor (VEGF receptor tyrosine kinase inhibitor)) and useful for the treatment of vascular abnormality, tumor, diabetic retinopathy, rheumatism, endometriosis, psoriasis and the like.

Patent Document 5 describes that a compound represented by the following formula (I):

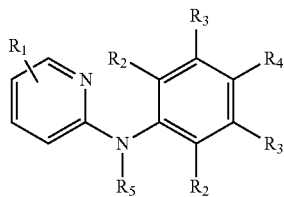

wherein each symbol is as defined in Patent Document 5, is a kinase (p38 kinase, etc.) inhibitor and useful for reduction of ischemic cell death (particularly reduction of traumatic neuronalcell death).

Patent Document 1: WO 2013/157540
Patent Document 2: WO 2013/052394
Patent Document 3: WO 2005/021529
Patent Document 4: WO 2002/024681
Patent Document 5: WO 2002/011724
Non-Patent Document 1: European Journal of Heart Failure, vol. 16, p. 1292-1300
Non-Patent Document 2: Circulation Research, vol. 84, p. 713-721
Non-Patent Document 3: Molecular Endocrinology, vol. 17, p. 183-192
Non-Patent Document 4: Circulation Research, vol. 92, p. 912-919
Non-Patent Document 5: Proceedings of the National Academy of Sciences, vol. 106, p. 2342-2347
Non-Patent Document 6: Circulation Research, vol. 112, p. 935-944
Non-Patent Document 7: Nature, vol. 502, p. 372-376
Non-Patent Document 8: Journal of Molecular and Cellular Cardiology, vol. 50, p. 214-222
Non-Patent Document 9: Oncotarget, vol. 20, p. 11725-11734
Non-Patent Document 10: Arterioscler Thromb Vasc Biol, vol. 28, p. 441-447
Non-Patent Document 11: Cell Calcium, vol. 45, p. 284-292
Non-Patent Document 12: J Clin Invest, vol. 119, p. 2925-2941
Non-Patent Document 13: J Biol Chem, vol. 285, p. 20675-20682
Non-Patent Document 14: J Pharmacol Exp Ther, vol. 325, p. 267-275
Non-Patent Document 15: BMC Musculoskelet Disord, vol. 30, p. 61

BRIEF SUMMARY OF THE INVENTION

An object of the present invention is to provide a compound having a CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like.

The present inventors have conducted intensive studies in an attempt to solve the above-mentioned problems and found that a compound represented by the following formula (I) has a CaMKII inhibitory action, and therefore, is expected to be useful as an agent for the prophylaxis or treatment of cardiac diseases (particularly catecholaminergic polymorphic ventricular tachycardia, postoperative atrial fibrillation, heart failure, fatal arrhythmia) and the like, which resulted in the completion of the present invention.

Accordingly, the present invention provides the following.

[1] A compound represented by the formula (I):

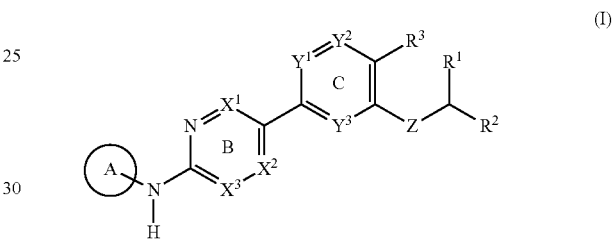

wherein
Ring A is an optionally further substituted 5- or 6-membered aromatic ring;
Ring B is an optionally further substituted nitrogen-containing 6-membered aromatic heterocycle ($X^1$, $X^2$ and $X^3$ are each independently a carbon atom or a nitrogen atom);
Ring C is an optionally further substituted 6-membered aromatic ring ($Y^1$, $Y^2$ and $Y^3$ are each independently a carbon atom or a nitrogen atom);
Z is an optionally substituted methylene group, —O—, —N($R^Z$)—, —S—, —S(O)— or —S(O$_2$)—;
$R^Z$ is a hydrogen atom or a substituent;
$R^1$ is a hydrogen atom or a substituent; and
$R^2$ and $R^3$ are each independently a substituent,
or a salt thereof (hereinafter sometimes to be referred to as compound (I)).

[2] The compound or salt of the above-mentioned [1], wherein Ring A is
(1) a benzene ring optionally further substituted by 1 to 3 substituents selected from
 (a) an optionally halogenated $C_{1-6}$ alkoxy group,
 (b) a $C_{1-6}$ alkyl group optionally substituted by 1 to 3 substituents selected from
  (i) a halogen atom,
  (ii) a hydroxy group,
  (iii) an amino group optionally mono- or di-substituted by substituent(s) selected from
   (I) a $C_{3-10}$ cycloalkyl group, and
   (II) a $C_{1-6}$ alkoxy-carbonyl group,
  (iv) a 5- to 14-membered aromatic heterocyclic group, and
  (v) a 3- to 14-membered non-aromatic heterocyclic group optionally substituted by 1 to 3 $C_{1-6}$ alkyl groups, (c) a $C_{3-10}$ cycloalkyl group optionally substituted by 1 to 3 substituents selected from
  (i) a 3- to 14-membered non-aromatic heterocyclic group,
(d) a halogen atom,
(e) a cyano group,
(f) a carboxy group,
(g) a $C_{1-6}$ alkoxy-carbonyl group,
(h) a $C_{1-6}$ alkylsulfanyl group,
(i) a $C_{1-6}$ alkylsulfonyl group,
(j) a carbamoyl group optionally mono- or di-substituted by substituent(s) selected from
  (i) a $C_{1-6}$ alkyl group optionally substituted by 1 to 3 substituents selected from
    (I) a hydroxy group,
    (II) a halogen atom,
    (III) an optionally halogenated $C_{1-6}$ alkoxy group,
    (IV) a mono- or di-$C_{1-6}$ alkylamino group,
    (V) a $C_{3-10}$ cycloalkyl group, and
    (VI) a 3- to 14-membered non-aromatic heterocyclic group optionally substituted by 1 to 3 substituents selected from a $C_{1-6}$ alkyl group and a $C_{1-6}$ alkyl-carbonyl group,
  (ii) a $C_{3-10}$ cycloalkyl group optionally substituted by 1 to 3 substituents selected from
    (I) a halogen atom,
    (II) an optionally halogenated $C_{1-6}$ alkyl group,
    (III) a carboxy group, and
    (IV) a $C_{1-6}$ alkoxy-carbonyl group, and
  (iii) a 3- to 14-membered non-aromatic heterocyclic group optionally substituted by 1 to 3 optionally halogenated $C_{1-6}$ alkyl groups,
(k) a sulfamoyl group optionally mono- or di-substituted by substituent(s) selected from
  (i) a 3- to 14-membered non-aromatic heterocyclic group optionally substituted by 1 to 3 $C_{1-6}$ alkyl groups,
(l) a 5- to 14-membered aromatic heterocyclic group optionally substituted by 1 to 3 $C_{1-6}$ alkyl groups,
(m) a 3- to 14-membered non-aromatic heterocyclic group optionally substituted by 1 to 3 substituents selected from
  (i) a $C_{1-6}$ alkyl group optionally substituted by 1 to 3 substituents selected from
    (I) a halogen atom,
    (II) a hydroxy group,
    (III) a cyano group,
    (IV) a carbamoyl group,
    (V) a $C_{1-6}$ alkoxy group,
    (VI) a $C_{1-6}$ alkylsulfonyl group,
    (VII) a mono- or di-$C_{1-6}$ alkylamino group, and
    (VIII) a 3- to 14-membered non-aromatic heterocyclic group,
  (ii) a $C_{1-6}$ alkyl-carbonyl group optionally substituted by 1 to 3 substituents selected from
    (I) a halogen atom,
    (II) a hydroxy group, and
    (III) a mono- or di-$C_{1-6}$ alkylamino group,
  (iii) a $C_{1-6}$ alkoxy-carbonyl group,
  (iv) a 3- to 14-membered non-aromatic heterocyclic group optionally substituted by 1 to 3 substituents selected from
    (I) a halogen atom,
    (II) a $C_{1-6}$ alkyl-carbonyl group, and
    (III) a $C_{1-6}$ alkoxy-carbonyl group,
  (v) an oxo group, and
  (vi) a mono- or di-$C_{1-6}$ alkyl-carbamoyl group,
(n) a 3- to 14-membered non-aromatic heterocyclylcarbonyl group optionally substituted by 1 to 3 substituents selected from
  (i) a halogen atom,
  (ii) a hydroxy group,
  (iii) a cyano group,
  (iv) a $C_{1-6}$ alkyl group optionally substituted by 1 to 3 substituents selected from
    (I) a hydroxy group,
    (II) a halogen atom,
    (III) a $C_{1-6}$ alkoxy group,
    (IV) a mono- or di-$C_{1-6}$ alkylamino group, and
    (V) a $C_{3-10}$ cycloalkyl group,
  (v) an optionally halogenated $C_{1-6}$ alkoxy group,
  (vi) a $C_{1-6}$ alkyl-carbonyl group optionally substituted by 1 to 3 substituents selected from
    (I) a hydroxy group, and
    (II) a $C_{1-6}$ alkoxy group,
  (vii) a $C_{1-6}$ alkoxy-carbonyl group,
  (viii) a $C_{3-10}$ cycloalkyl group,
  (ix) a $C_{3-10}$ cycloalkyl-carbonyl group,
  (x) a $C_{1-6}$ alkylsulfonyl group, and
  (xi) a 3- to 14-membered non-aromatic heterocyclic group optionally substituted by 1 to 3 $C_{1-6}$ alkyl groups, and
(o) a 3- to 14-membered non-aromatic heterocyclylsulfonyl group optionally substituted by 1 to 3 of 3- to 14-membered non-aromatic heterocyclic groups
(the two substituents on the benzene ring are optionally bonded to each other to form a 5- or 6-membered monocyclic aromatic heterocycle, a 3- to 8-membered monocyclic non-aromatic heterocycle or a $C_{5-6}$ cycloalkene ring, each of which is optionally substituted by 1 to 3 substituents selected from
  (a) an oxo group,
  (b) a $C_{1-6}$ alkyl group optionally substituted by 1 to 3 substituents selected from
    (i) a halogen atom,
    (ii) a hydroxy group,
    (iii) a carboxy group,
    (iv) a $C_{1-6}$ alkoxy group,
    (v) a $C_{1-6}$ alkyl-carbonyl group,
    (vi) a mono- or di-$C_{1-6}$ alkylamino group, and
    (vii) a 3- to 14-membered non-aromatic heterocyclic group optionally substituted by 1 to 3 $C_{1-6}$ alkyl groups,
  (c) a $C_{3-10}$ cycloalkyl group,
  (d) a formyl group,
  (e) a $C_{1-6}$ alkyl-carbonyl group optionally substituted by 1 to 3 substituents selected from
    (i) a halogen atom,
    (ii) a hydroxy group,
    (iii) a $C_{1-6}$ alkoxy group,
    (iv) a $C_{1-6}$ alkyl-carbonyloxy group,
    (v) a mono- or di-$C_{1-6}$ alkylamino group, and
    (vi) a 3- to 14-membered non-aromatic heterocyclic group,
  (f) a $C_{1-6}$ alkoxy-carbonyl group,
  (g) a 5- to 14-membered aromatic heterocyclic group optionally substituted by 1 to 3 $C_{1-6}$ alkyl groups,
  (h) a 3- to 14-membered non-aromatic heterocyclic group optionally substituted by 1 to 3 $C_{1-6}$ alkyl groups, and
  (i) a 3- to 14-membered non-aromatic heterocyclycarbonyl group optionally substituted by 1 to 3 $C_{1-6}$ alkyl groups), (2) a pyridine ring optionally further substituted by 1 to 3 substituents selected from
  (a) a $C_{1-6}$ alkyl group,
  (b) an optionally halogenated $C_{1-6}$ alkoxy group,
  (c) a $C_{3-10}$ cycloalkyl group optionally substituted by 1 to 3 halogen atoms,
  (d) an amino group, and
  (e) a 3- to 14-membered non-aromatic heterocyclic group optionally substituted by 1 to 3 substituents selected from
    (i) a hydroxy group,
    (ii) a $C_{1-6}$ alkyl group optionally substituted by 1 to 3 substituents selected from
      (I) a halogen atom, and
      (II) a 3- to 14-membered non-aromatic heterocyclic group,
    (iii) an optionally halogenated $C_{1-6}$ alkyl-carbonyl group,
    (iv) a $C_{1-6}$ alkoxy-carbonyl group,
    (v) a $C_{3-10}$ cycloalkyl group optionally substituted by 1 to 3 halogen atoms, and
    (vi) a 3- to 14-membered non-aromatic heterocyclic group,
(3) a pyrimidine ring optionally further substituted by 1 to 3 substituents selected from
  (a) a $C_{1-6}$ alkoxy group, and
  (b) a 3- to 14-membered non-aromatic heterocyclic group optionally substituted by 1 to 3 of 3- to 14-membered non-aromatic heterocyclic groups,
(4) a pyridazine ring,
(5) a pyrazine ring,
(6) a pyrazole ring optionally further substituted by 1 to 3 substituents selected from
  (a) a halogen atom,
  (b) a cyano group,
  (c) a carboxy group,
  (d) a $C_{1-6}$ alkyl group optionally substituted by 1 to 5 substituents selected from
    (i) a $C_{3-10}$ cycloalkyl group optionally substituted by 1 to 3 substituents selected from
      (I) an amino group,
      (II) a hydroxy group,
      (III) an oxo group,
      (IV) a $C_{1-6}$ alkyl group, and
      (V) a 3- to 14-membered non-aromatic heterocyclic group,
    (ii) a hydroxy group,
    (iii) a cyano group,
    (iv) a halogen atom,
    (v) a carboxy group,
    (vi) a $C_{1-6}$ alkoxy group optionally substituted by 1 to 3 substituents selected from
      (I) a halogen atom, and
      (II) a hydroxy group,
    (vii) a $C_{1-6}$ alkoxy-carbonyl group,
    (viii) a $C_{1-6}$ alkylsulfonyl group,
    (ix) an amino group optionally mono- or di-substituted by substituent(s) selected from
      (I) a $C_{1-6}$ alkyl-carbonyl group,
      (II) a $C_{1-6}$ alkoxy-carbonyl group,
      (III) a $C_{1-6}$ alkylsulfonyl group,
      (IV) a $C_{6-14}$ aryl-carbonyl group, and
      (V) a carbamoyl group,
    (x) a carbamoyl group optionally mono- or di-substituted by substituent(s) selected from
      (I) a $C_{1-6}$ alkyl group, and
      (II) a $C_{6-14}$ aryl group,
    (xi) a 5- to 14-membered aromatic heterocyclic group optionally substituted by 1 to 3 substituents selected from
      (I) a $C_{1-6}$ alkyl group, and
      (II) a $C_{1-6}$ alkoxy group,
    (xii) a 3- to 14-membered non-aromatic heterocyclic group optionally substituted by 1 to 3 substituents selected from
      (I) an oxo group,
      (II) a hydroxy group,
      (III) a carbamoyl group,
      (IV) a $C_{1-6}$ alkyl group optionally substituted by 1 to 3 hydroxy groups,
      (V) a $C_{1-6}$ alkoxy-carbonyl group,
      (VI) a $C_{3-10}$ cycloalkyl group,
      (VII) a $C_{7-16}$ aralkyl group, and
      (VIII) a 3- to 14-membered non-aromatic heterocyclic group, and
    (xiii) a 3- to 14-membered non-aromatic heterocyclyl-carbonyl group,
  (e) a $C_{2-6}$ alkynyl group,
  (f) a $C_{1-6}$ alkoxy group optionally substituted by 1 to 5 substituents selected from
    (i) a halogen atom, and
    (ii) a $C_{3-10}$ cycloalkyl group optionally substituted by 1 to 3 halogen atoms,
  (g) a $C_{3-10}$ cycloalkyl group (the $C_{3-10}$ cycloalkyl group is optionally fused with a benzene ring, or optionally bridged or may be a spiro group) optionally substituted by 1 to 3 substituents selected from
    (i) an oxo group,
    (ii) a hydroxy group,
    (iii) a carbamoyl group,
    (iv) a carboxy group,
    (v) a $C_{1-6}$ alkyl group optionally substituted by 1 to 3 substituents selected from
      (I) a hydroxy group,
      (II) a carboxy group,
      (III) a carbamoyl group, and
      (IV) a 3- to 14-membered non-aromatic heterocyclic group,
    (vi) a $C_{1-6}$ alkoxy-carbonyl group,
    (vii) a 3- to 14-membered non-aromatic heterocyclic group optionally substituted by 1 to 3 substituents selected from
      (I) a halogen atom,
      (II) a hydroxy group, and
      (III) a $C_{1-6}$ alkyl group optionally substituted by 1 to 3 substituents selected from a halogen atom and a hydroxy group, and
    (viii) an amino group optionally mono- or di-substituted by substituent(s) selected from
      (I) a $C_{1-6}$ alkoxy-carbonyl group, and
      (II) a 3- to 14-membered non-aromatic heterocyclic group,
  (h) an optionally halogenated $C_{1-6}$ alkyl-carbonyl group,
  (i) a $C_{1-6}$ alkoxy-carbonyl group,
  (j) a $C_{6-14}$ aryl group,
  (k) a $C_{7-16}$ aralkyl group,
  (l) a 5- to 14-membered aromatic heterocyclic group optionally substituted by 1 to 3 $C_{1-6}$ alkoxy groups,
  (m) a 3- to 14-membered non-aromatic heterocyclic group optionally substituted by 1 to 3 substituents selected from (i) an oxo group,
(ii) a hydroxy group,
(iii) a $C_{1-6}$ alkyl group optionally substituted by 1 to 3 substituents selected from
  (I) a halogen atom,
  (II) a hydroxy group,
  (III) a cyano group,
  (IV) a $C_{1-6}$ alkoxy group optionally substituted by 1 to 3 substituents selected from
    (A) a halogen atom,
    (B) a $C_{1-6}$ alkyl-carbonyloxy group, and
    (C) a $C_{1-6}$ alkoxy-carbonyloxy group,
  (V) a $C_{1-6}$ alkyl-carbonyloxy group,
  (VI) a $C_{3-10}$ cycloalkyl group,
  (VII) a 5- to 14-membered aromatic heterocyclic group optionally substituted by 1 to 3 $C_{1-6}$ alkyl groups, and
  (VIII) a 3- to 14-membered non-aromatic heterocyclic group,
(iv) a $C_{3-10}$ cycloalkyl group optionally substituted by 1 to 3 substituents selected from
  (I) a halogen atom,
  (II) a hydroxy group,
  (III) a $C_{1-6}$ alkyl group optionally substituted by 1 to 3 $C_{1-6}$ alkoxy groups, and
  (IV) a $C_{1-6}$ alkoxy group,
(v) a $C_{6-14}$ aryl group optionally substituted by 1 to 3 halogen atoms,
(vi) a $C_{7-16}$ aralkyl group,
(vii) a $C_{1-6}$ alkyl-carbonyl group,
(viii) a $C_{1-6}$ alkoxy-carbonyl group,
(ix) a 5- to 14-membered aromatic heterocyclic group optionally substituted by 1 to 3 $C_{1-6}$ alkyl groups, and
(x) a 3- to 14-membered non-aromatic heterocyclic group optionally substituted by 1 to 3 substituents selected from
  (I) a halogen atom,
  (II) a $C_{1-6}$ alkyl group optionally substituted by 1 to 3 substituents selected from a halogen atom and a $C_{1-6}$ alkoxy group,
  (III) a $C_{3-10}$ cycloalkyl group,
  (VI) a cyano group, and
  (V) a deuterium atom,
(n) a 3- to 14-membered non-aromatic heterocyclyloxy group, and
(o) a 3- to 14-membered non-aromatic heterocyclylcarbonyl group optionally substituted by 1 to 3 of 3- to 14-membered non-aromatic heterocyclic groups,
(7) a thiazole ring (the two substituents on the thiazole ring are optionally bonded to each other to form a benzene ring),
(8) an isothiazole ring optionally further substituted by 1 to 3 substituents selected from
  (a) a $C_{1-6}$ alkyl group optionally substituted by 1 to 3 hydroxy groups,
(9) an imidazole ring optionally further substituted by 1 to 3 substituents selected from
  (a) a $C_{1-6}$ alkyl group optionally substituted by 1 to 3 hydroxy groups
(the two substituents on the imidazole ring are optionally bonded to each other to form a benzene ring),
(10) an isoxazole ring optionally further substituted by 1 to 3 $C_{1-6}$ alkyl groups,
(11) a thiadiazole ring optionally further substituted by 1 to 3 substituents selected from
  (a) a $C_{6-14}$ aryl group optionally substituted by 1 to 3 halogen atoms, or
(12) a thiophene ring optionally further substituted by 1 to 3 cyano groups (the two substituents on the thiophene ring are optionally bonded to each other to form a $C_{5-6}$ cycloalkene ring);
Ring B is
(1) a pyrimidine ring ($X^1$ is a carbon atom, $X^2$ is a carbon atom and $X^3$ is a nitrogen atom),
(2) a pyrazine ring ($X^1$ is a carbon atom, $X^2$ is a nitrogen atom and $X^3$ is a carbon atom), or
(3) a pyridine ring ($X^1$ is a carbon atom, $X^2$ is a carbon atom and $X^3$ is a carbon atom);
Ring C is
(1) a benzene ring optionally further substituted by 1 to 3 halogen atoms, or
(2) a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom);
Z is
(1) —O—, or
(2) —NH—;
$R^1$ is
(1) a hydrogen atom,
(2) a $C_{1-6}$ alkyl group optionally substituted by 1 to 3 substituents selected from
  (a) a halogen atom, and
  (b) a hydroxy group, or
(3) a $C_{3-10}$ cycloalkyl group;
$R^2$ is
(1) a $C_{1-6}$ alkyl group optionally substituted by 1 to 3 substituents selected from
  (a) a 5- to 14-membered aromatic heterocyclic group optionally substituted by 1 to 3 substituents selected from
    (i) a cyano group,
    (ii) a halogen atom,
    (iii) a $C_{1-6}$ alkyl group, and
    (iv) a $C_{7-16}$ aralkyl group,
  (b) a 3- to 14-membered non-aromatic heterocyclic group optionally substituted by 1 to 3 substituents selected from
    (i) an oxo group, and
    (ii) a $C_{1-6}$ alkyl group,
  (c) a halogen atom,
  (d) a hydroxy group,
  (e) a cyano group,
  (f) an optionally halogenated $C_{1-6}$ alkoxy group,
  (g) a 5- to 14-membered aromatic heterocyclyloxy group,
  (h) a 3- to 14-membered non-aromatic heterocyclyloxy group,
  (i) an amino group optionally mono- or di-substituted by substituent(s) selected from
    (i) a $C_{1-6}$ alkyl group,
    (ii) a $C_{1-6}$ alkyl-carbonyl group optionally substituted by 1 to 3 $C_{1-6}$ alkoxy groups, and
    (iii) a $C_{1-6}$ alkylsulfonyl group, and
  (j) a mono- or di-$C_{1-6}$ alkyl-carbamoyl group,
(2) a 3- to 14-membered non-aromatic heterocyclic group optionally substituted by 1 to 3 substituents selected from
  (a) an oxo group, and
  (b) a $C_{1-6}$ alkyl group, or
(3) a mono- or di-$C_{1-6}$ alkyl-carbamoyl group optionally substituted by 1 to 3 halogen atoms; and
$R^3$ is
(1) a cyano group,
(2) a halogen atom,
(3) an optionally halogenated $C_{1-6}$ alkyl group,
(4) a carbamoyl group, (5) a mono- or di-$C_{1-6}$ alkyl-carbamoyl group, or
(6) a 3- to 14-membered non-aromatic heterocyclylcarbonyl group.

[3] The compound or salt of the above-mentioned [1], wherein Ring A is a pyrazole ring optionally further substituted by 1 to 3 substituents selected from
- (a) a halogen atom,
- (b) a cyano group,
- (c) a carboxy group,
- (d) a $C_{1-6}$ alkyl group optionally substituted by 1 to 5 substituents selected from
  - (i) a $C_{3-10}$ cycloalkyl group optionally substituted by 1 to 3 substituents selected from
    - (I) an amino group,
    - (II) a hydroxy group,
    - (III) an oxo group,
    - (IV) a $C_{1-6}$ alkyl group, and
    - (V) a 3- to 14-membered non-aromatic heterocyclic group,
  - (ii) a hydroxy group,
  - (iii) a cyano group,
  - (iv) a halogen atom,
  - (v) a carboxy group,
  - (vi) a $C_{1-6}$ alkoxy group optionally substituted by 1 to 3 substituents selected from
    - (I) a halogen atom, and
    - (II) a hydroxy group,
  - (vii) a $C_{1-6}$ alkoxy-carbonyl group,
  - (viii) a $C_{1-6}$ alkylsulfonyl group,
  - (ix) an amino group optionally mono- or di-substituted by substituent(s) selected from
    - (I) a $C_{1-6}$ alkyl-carbonyl group,
    - (II) a $C_{1-6}$ alkoxy-carbonyl group,
    - (III) a $C_{1-6}$ alkylsulfonyl group,
    - (IV) a $C_{6-14}$ aryl-carbonyl group, and
    - (V) a carbamoyl group,
  - (x) a carbamoyl group optionally mono- or di-substituted by substituent(s) selected from
    - (I) a $C_{1-6}$ alkyl group, and
    - (II) a $C_{6-14}$ aryl group,
  - (xi) a 5- to 14-membered aromatic heterocyclic group optionally substituted by 1 to 3 substituents selected from
    - (I) a $C_{1-6}$ alkyl group, and
    - (II) a $C_{1-6}$ alkoxy group,
  - (xii) a 3- to 14-membered non-aromatic heterocyclic group optionally substituted by 1 to 3 substituents selected from
    - (I) an oxo group,
    - (II) a hydroxy group,
    - (III) a carbamoyl group,
    - (IV) a $C_{1-6}$ alkyl group optionally substituted by 1 to 3 hydroxy groups,
    - (V) a $C_{1-6}$ alkoxy-carbonyl group,
    - (VI) a $C_{3-10}$ cycloalkyl group,
    - (VII) a $C_{7-16}$ aralkyl group, and
    - (VIII) a 3- to 14-membered non-aromatic heterocyclic group, and
  - (xiii) a 3- to 14-membered non-aromatic heterocyclylcarbonyl group,
- (e) a $C_{2-6}$ alkynyl group,
- (f) a $C_{1-6}$ alkoxy group optionally substituted by 1 to 5 substituents selected from
  - (i) a halogen atom, and
  - (ii) a $C_{3-10}$ cycloalkyl group optionally substituted by 1 to 3 halogen atoms,
- (g) a $C_{3-10}$ cycloalkyl group (the $C_{3-10}$ cycloalkyl group is optionally fused with a benzene ring, or optionally bridged or may be a spiro group) optionally substituted by 1 to 3 substituents selected from
  - (i) an oxo group,
  - (ii) a hydroxy group,
  - (iii) a carbamoyl group,
  - (iv) a carboxy group,
  - (v) a $C_{1-6}$ alkyl group optionally substituted by 1 to 3 substituents selected from
    - (I) a hydroxy group,
    - (II) a carboxy group,
    - (III) a carbamoyl group, and
    - (IV) a 3- to 14-membered non-aromatic heterocyclic group,
  - (vi) a $C_{1-6}$ alkoxy-carbonyl group,
  - (vii) a 3- to 14-membered non-aromatic heterocyclic group optionally substituted by 1 to 3 substituents selected from
    - (I) a halogen atom,
    - (II) a hydroxy group, and
    - (III) a $C_{1-6}$ alkyl group optionally substituted by 1 to 3 substituents selected from a halogen atom and a hydroxy group, and
  - (viii) an amino group optionally mono- or di-substituted by substituent(s) selected from
    - (I) a $C_{1-6}$ alkoxy-carbonyl group, and
    - (II) a 3- to 14-membered non-aromatic heterocyclic group,
- (h) an optionally halogenated $C_{1-6}$ alkyl-carbonyl group,
- (i) a $C_{1-6}$ alkoxy-carbonyl group,
- (j) a $C_{6-14}$ aryl group,
- (k) a $C_{7-16}$ aralkyl group,
- (l) a 5- to 14-membered aromatic heterocyclic group optionally substituted by 1 to 3 $C_{1-6}$ alkoxy groups,
- (m) a 3- to 14-membered non-aromatic heterocyclic group optionally substituted by 1 to 3 substituents selected from
  - (i) an oxo group,
  - (ii) a hydroxy group,
  - (iii) a $C_{1-6}$ alkyl group optionally substituted by 1 to 3 substituents selected from
    - (I) a halogen atom,
    - (II) a hydroxy group,
    - (III) a cyano group,
    - (IV) a $C_{1-6}$ alkoxy group optionally substituted by 1 to 3 substituents selected from
      - (A) a halogen atom,
      - (B) a $C_{1-6}$ alkyl-carbonyloxy group, and
      - (C) a $C_{1-6}$ alkoxy-carbonyloxy group,
    - (V) a $C_{1-6}$ alkyl-carbonyloxy group,
    - (VI) a $C_{3-10}$ cycloalkyl group,
    - (VII) a 5- to 14-membered aromatic heterocyclic group optionally substituted by 1 to 3 $C_{1-6}$ alkyl groups, and
    - (VIII) a 3- to 14-membered non-aromatic heterocyclic group,
  - (iv) a $C_{3-10}$ cycloalkyl group optionally substituted by 1 to 3 substituents selected from
    - (I) a halogen atom,
    - (II) a hydroxy group,
    - (III) a $C_{1-6}$ alkyl group optionally substituted by 1 to 3 $C_{1-6}$ alkoxy groups, and
    - (IV) a $C_{1-6}$ alkoxy group,
  - (v) a $C_{6-14}$ aryl group optionally substituted by 1 to 3 halogen atoms,
  - (vi) a $C_{7-16}$ aralkyl group, (vii) a $C_{1-6}$ alkyl-carbonyl group,
(viii) a $C_{1-6}$ alkoxy-carbonyl group,
(ix) a 5- to 14-membered aromatic heterocyclic group optionally substituted by 1 to 3 $C_{1-6}$ alkyl groups, and
(x) a 3- to 14-membered non-aromatic heterocyclic group optionally substituted by 1 to 3 substituents selected from
(I) a halogen atom,
(II) a $C_{1-6}$ alkyl group optionally substituted by 1 to 3 substituents selected from a halogen atom and a $C_{1-6}$ alkoxy group,
(III) a $C_{3-10}$ cycloalkyl group,
(VI) a cyano group, and
(V) a deuterium atom,
(n) a 3- to 14-membered non-aromatic heterocyclyloxy group, and
(o) a 3- to 14-membered non-aromatic heterocyclylcarbonyl group optionally substituted by 1 to 3 of 3- to 14-membered non-aromatic heterocyclic groups;
Ring B is
(1) a pyrimidine ring ($X^1$ is a carbon atom, $X^2$ is a carbon atom and $X^3$ is a nitrogen atom),
(2) a pyrazine ring ($X^1$ is a carbon atom, $X^2$ is a nitrogen atom and $X^3$ is a carbon atom), or
(3) a pyridine ring ($X^1$ is a carbon atom, $X^2$ is a carbon atom and $X^3$ is a carbon atom);
Ring C is
(1) a benzene ring optionally further substituted by 1 to 3 halogen atoms, or
(2) a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom);
Z is
(1) —O—, or
(2) —NH—;
$R^1$ is
(1) a hydrogen atom, or
(2) a $C_{1-6}$ alkyl group optionally substituted by 1 to 3 hydroxy groups;
$R^2$ is
(1) a $C_{1-6}$ alkyl group optionally substituted by 1 to 3 substituents selected from
(a) a 5- to 14-membered aromatic heterocyclic group optionally substituted by 1 to 3 substituents selected from
(i) a halogen atom, and
(ii) a $C_{1-6}$ alkyl group,
(b) a 3- to 14-membered non-aromatic heterocyclic group optionally substituted by 1 to 3 oxo groups,
(c) a halogen atom,
(d) a hydroxy group,
(e) a cyano group,
(f) an optionally halogenated $C_{1-6}$ alkoxy group,
(g) an amino group optionally mono- or di-substituted by substituent(s) selected from
(i) a $C_{1-6}$ alkyl-carbonyl group, and
(ii) a $C_{1-6}$ alkylsulfonyl group, and
(h) a mono- or di-$C_{1-6}$ alkyl-carbamoyl group,
(2) a 3- to 14-membered non-aromatic heterocyclic group optionally substituted by 1 to 3 substituents selected from
(a) an oxo group, and
(b) a $C_{1-6}$ alkyl group, or (3) a mono- or di-$C_{1-6}$ alkyl-carbamoyl group optionally substituted by 1 to 3 halogen atoms; and
$R^3$ is
(1) a cyano group,
(2) a halogen atom,
(3) a $C_{1-6}$ alkyl group, or
(4) a carbamoyl group.
[4] The compound or salt of the above-mentioned [1], wherein Ring A is a pyrazole ring
further substituted by one cyclohexyl group optionally substituted by 1 to 3 substituents selected from
(i) an oxo group,
(ii) a hydroxy group,
(iii) a carboxy group,
(iv) a $C_{1-6}$ alkyl group optionally substituted by 1 to 3 substituents selected from
(I) a carboxy group,
(II) a carbamoyl group, and
(III) a 3- to 8-membered monocyclic non-aromatic heterocyclic group,
(v) a $C_{1-6}$ alkoxy-carbonyl group, and
(vi) a 3- to 8-membered monocyclic non-aromatic heterocyclic group optionally substituted by 1 to 3 substituents selected from
(I) a halogen atom,
(II) a hydroxy group, and
(III) a $C_{1-6}$ alkyl group optionally substituted by 1 to 3 substituents selected from a halogen atom and a hydroxy group, and
further optionally substituted by one substituent selected from
(a) an optionally halogenated $C_{1-6}$ alkyl group,
(b) a $C_{1-6}$ alkoxy group optionally substituted by 1 to 5 substituents selected from
(i) a halogen atom, and
(ii) a $C_{3-10}$ cycloalkyl group optionally substituted by 1 to 3 halogen atoms,
(c) a 3- to 8-membered monocyclic non-aromatic heterocyclyloxy group,
(d) an optionally halogenated $C_{1-6}$ alkyl-carbonyl group,
(e) a $C_{3-10}$ cycloalkyl group, and
(f) a cyano group;
Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group;
$R^2$ is a $C_{1-6}$ alkyl group substituted by one substituents selected from
(a) a 5- or 6-membered monocyclic aromatic heterocyclic group optionally substituted by 1 to 3 halogen atoms, and
(b) a 3- to 8-membered monocyclic non-aromatic heterocyclic group optionally substituted by 1 to 3 oxo groups; and
$R^3$ is
(1) a cyano group,
(2) a halogen atom, or
(3) an optionally halogenated $C_{1-6}$ alkyl group.
[5] The compound or salt of the above-mentioned [1], wherein Ring A is a pyrazole ring
further substituted by one 2-azaspiro[3.3]heptyl group optionally substituted by 1 to 3 substituents selected from
(i) a $C_{1-6}$ alkyl group optionally substituted by 1 to 3 substituents selected from
(I) a halogen atom,
(II) a hydroxy group,
(III) a $C_{1-6}$ alkoxy group optionally substituted by 1 to 3 substituents selected from (A) a halogen atom,
(B) a $C_{1-6}$ alkyl-carbonyloxy group, and
(C) a $C_{1-6}$ alkoxy-carbonyloxy group,
(IV) a $C_{1-6}$ alkyl-carbonyloxy group, and
(V) a 5- to 6-membered monocyclic aromatic heterocyclic group,
(ii) a $C_{3-10}$ cycloalkyl group optionally substituted by 1 to 3 substituents selected from
  (I) a halogen atom,
  (II) a hydroxy group,
  (III) a $C_{1-6}$ alkyl group optionally substituted by 1 to 3 $C_{1-6}$ alkoxy groups, and
  (IV) a $C_{1-6}$ alkoxy group,
(iii) a $C_{1-6}$ alkoxy-carbonyl group,
(iv) a $C_{6-14}$ aryl group optionally substituted by 1 to 3 halogen atoms,
(v) a 5- to 6-membered monocyclic aromatic heterocyclic group optionally substituted by 1 to 3 $C_{1-6}$ alkyl groups, and
(vi) a 3- to 8-membered monocyclic non-aromatic heterocyclic group optionally substituted by 1 to 3 substituents selected from
  (I) a halogen atom,
  (II) a $C_{1-6}$ alkyl group optionally substituted by 1 to 3 substituents selected from a halogen atom and a $C_{1-6}$ alkoxy group,
  (III) a $C_{3-10}$ cycloalkyl group,
  (VI) a cyano group, and
  (V) a deuterium atom, and
further optionally substituted by one substituent selected from
  (a) an optionally halogenated $C_{1-6}$ alkyl group,
  (b) a $C_{1-6}$ alkoxy group optionally substituted by 1 to 5 substituents selected from
    (i) a halogen atom, and
    (ii) a $C_{3-10}$ cycloalkyl group optionally substituted by 1 to 3 halogen atoms,
  (c) a 3- to 8-membered monocyclic non-aromatic heterocyclyloxy group,
  (d) an optionally halogenated $C_{1-6}$ alkyl-carbonyl group,
  (e) a $C_{3-10}$ cycloalkyl group, and
  (f) a cyano group;
Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group;
$R^2$ is a $C_{1-6}$ alkyl group substituted by one substituents selected from
  (a) a 5- or 6-membered monocyclic aromatic heterocyclic group, and
  (b) an optionally halogenated $C_{1-6}$ alkoxy group; and
$R^3$ is
(1) a cyano group,
(2) a halogen atom, or
(3) an optionally halogenated $C_{1-6}$ alkyl group.
[6] The compound or salt of the above-mentioned [1], wherein Ring A is a pyrazole ring
further substituted by one piperidyl group optionally substituted by 1 to 3 substituents selected from
  (i) a hydroxy group,
  (ii) a $C_{1-6}$ alkyl group optionally substituted by 1 to 3 substituents selected from
    (I) a halogen atom,
    (II) a hydroxy group,
    (III) a cyano group,
    (IV) a $C_{1-6}$ alkoxy group,
    (V) a $C_{3-10}$ cycloalkyl group,
    (VI) a 5- to 6-membered monocyclic aromatic heterocyclic group optionally substituted by 1 to 3 $C_{1-6}$ alkyl groups, and
    (VII) a 3- to 8-membered monocyclic non-aromatic heterocyclic group,
  (iii) a $C_{3-10}$ cycloalkyl group optionally substituted by 1 to 3 substituents selected from
    (I) a halogen atom, and
    (II) a $C_{1-6}$ alkoxy group,
  (iv) a $C_{7-16}$ aralkyl group,
  (v) a $C_{1-6}$ alkyl-carbonyl group,
  (vi) a $C_{1-6}$ alkoxy-carbonyl group, and
  (vii) a 3- to 8-membered monocyclic non-aromatic heterocyclic group optionally substituted by 1 to 3 substituents selected from
    (I) a $C_{1-6}$ alkyl group, and
    (II) a $C_{3-10}$ cycloalkyl group, and
further optionally substituted by one substituent selected from
  (a) an optionally halogenated $C_{1-6}$ alkyl group,
  (b) a $C_{1-6}$ alkoxy group optionally substituted by 1 to 5 substituents selected from
    (i) a halogen atom, and
    (ii) a $C_{3-10}$ cycloalkyl group optionally substituted by 1 to 3 halogen atoms,
  (c) a 3- to 8-membered monocyclic non-aromatic heterocyclyloxy group,
  (d) an optionally halogenated $C_{1-6}$ alkyl-carbonyl group,
  (e) a $C_{3-10}$ cycloalkyl group, and
  (f) a cyano group;
Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group;
$R^2$ is a $C_{1-6}$ alkyl group substituted by one substituents selected from
  (a) a 5- or 6-membered monocyclic aromatic heterocyclic group optionally substituted by 1 to 3 halogen atoms; and
$R^3$ is
(1) a cyano group,
(2) a halogen atom, or
(3) an optionally halogenated $C_{1-6}$ alkyl group.
[7] A compound represented by the following formula (II-1A):

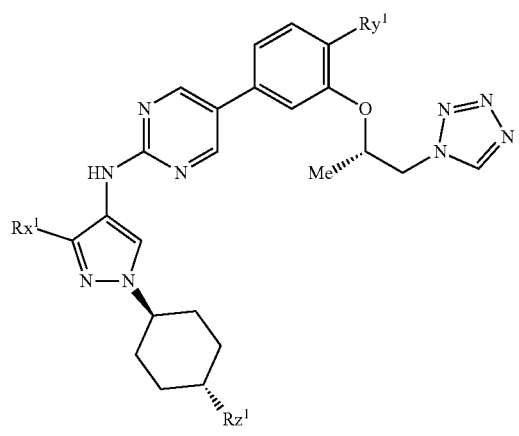

wherein
Rx$^1$ is
(1) an optionally halogenated C$_{1-6}$ alkyl group,
(2) a C$_{1-6}$ alkoxy group optionally substituted by 1 to 5 substituents selected from
    (a) a halogen atom, and
    (b) a C$_{3-10}$ cycloalkyl group optionally substituted by 1 to 3 halogen atoms,
(3) a 3- to 8-membered oxygen-containing monocyclic non-aromatic heterocyclyloxy group,
(4) an optionally halogenated C$_{1-6}$ alkyl-carbonyl group, or
(5) a C$_{3-10}$ cycloalkyl group;
Ry$^1$ is
(1) a cyano group,
(2) a halogen atom, or
(3) an optionally halogenated C$_{1-6}$ alkyl group; and
Rz$^1$ is
(1) a nitrogen-containing 3- to 8-membered monocyclic non-aromatic heterocyclic group optionally substituted by 1 or 2 substituents selected from
    (a) a hydroxy group, and
    (b) a C$_{1-6}$ alkyl group,
or a salt thereof.

[8] A compound represented by the following formula (II-2):

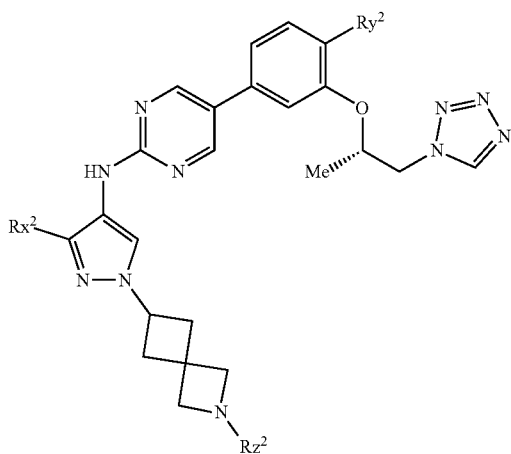

(II-2)

wherein
Rx$^2$ is
(1) an optionally halogenated C$_{1-6}$ alkyl group,
(2) a C$_{1-6}$ alkoxy group optionally substituted by 1 to 5 substituents selected from
    (a) a halogen atom, and
    (b) a C$_{3-10}$ cycloalkyl group optionally substituted by 1 to 3 halogen atoms,
(3) a 3- to 8-membered oxygen-containing monocyclic non-aromatic heterocyclyloxy group,
(4) an optionally halogenated C$_{1-6}$ alkyl-carbonyl group, or
(5) a C$_{3-10}$ cycloalkyl group;
Ry$^2$ is
(1) a cyano group,
(2) a halogen atom, or
(3) an optionally halogenated C$_{1-6}$ alkyl group; and Rz$^2$ is
(1) a C$_{1-6}$ alkyl group optionally substituted by 1 to 3 substituents selected from
    (a) a halogen atom,
    (b) a hydroxy group,
    (c) a C$_{1-6}$ alkoxy group optionally substituted by 1 to 3 substituents selected from
        (i) a halogen atom,
        (ii) a C$_{1-6}$ alkyl-carbonyloxy group, and
        (iii) a C$_{1-6}$ alkoxy-carbonyloxy group,
    (d) a C$_{1-6}$ alkyl-carbonyloxy group, and
    (e) a 5- to 6-membered nitrogen-containing monocyclic aromatic heterocyclic group,
(2) a C$_{3-10}$ cycloalkyl group optionally substituted by 1 to 3 substituents selected from
    (a) a halogen atom,
    (b) a hydroxy group,
    (c) a C$_{1-6}$ alkyl group optionally substituted by 1 to 3 C$_{1-6}$ alkoxy groups, and
    (d) a C$_{1-6}$ alkoxy group,
(3) a C$_{1-6}$ alkoxy-carbonyl group,
(4) a C$_{6-14}$ aryl group optionally substituted by 1 to 3 halogen atoms,
(5) a 5- to 6-membered nitrogen-containing monocyclic aromatic heterocyclic group optionally substituted by 1 to 3 C$_{1-6}$ alkyl groups, or
(6) a 3- to 8-membered oxygen-containing monocyclic non-aromatic heterocyclic group optionally substituted by 1 to 3 substituents selected from
    (a) a halogen atom,
    (b) a C$_{1-6}$ alkyl group optionally substituted by 1 to 3 substituents selected from a halogen atom and a C$_{1-6}$ alkoxy group,
    (c) a C$_{3-10}$ cycloalkyl group,
    (d) a cyano group, and
    (e) a deuterium atom,
or a salt thereof.

[9] A compound represented by the following formula (II-3):

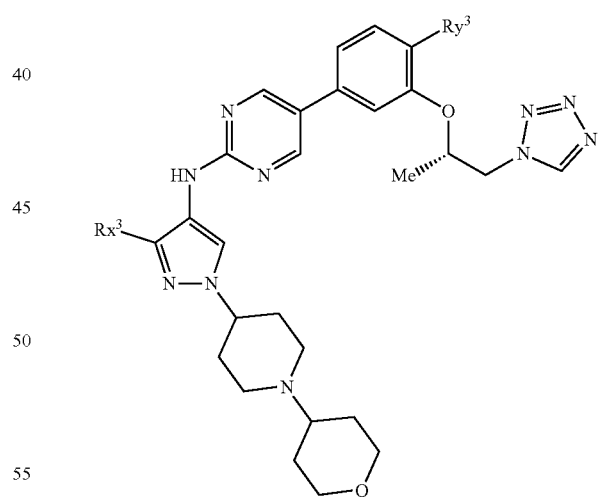

(II-3)

wherein
Rx$^3$ is
(1) an optionally halogenated C$_{1-6}$ alkyl group,
(2) a C$_{1-6}$ alkoxy group optionally substituted by 1 to 5 substituents selected from
    (a) a halogen atom, and
    (b) a C$_{3-10}$ cycloalkyl group optionally substituted by 1 to 3 halogen atoms,
(3) a 3- to 8-membered oxygen-containing monocyclic non-aromatic heterocyclyloxy group, (4) an optionally halogenated C$_{1-6}$ alkyl-carbonyl group, or
(5) a C$_{3-10}$ cycloalkyl group; and
Ry$^3$ is
(1) a cyano group,
(2) a halogen atom, or
(3) an optionally halogenated C$_{1-6}$ alkyl group,
or a salt thereof.

[10] A compound selected from the group consisting of 5-(3-(((S)-1-(1H-tetrazol-1-yl)propan-2-yl)oxy)-4-chlorophenyl)-N-(1-(trans-4-morpholinocyclohexyl)-3-(trifluoromethyl)-1H-pyrazol-4-yl)pyrimidin-2-amine, or a salt thereof;

5-(3-(((S)-1-(1H-tetrazol-1-yl)propan-2-yl)oxy)-4-chlorophenyl)-N-(1-(trans-4-morpholinocyclohexyl)-3-(2,2,2-trifluoroethoxy)-1H-pyrazol-4-yl)pyrimidin-2-amine, or a salt thereof;

5-(3-(((S)-1-(1H-tetrazol-1-yl)propan-2-yl)oxy)-4-chlorophenyl)-N-(3-(2,2-difluoroethoxy)-1-(trans-4-morpholinocyclohexyl)-1H-pyrazol-4-yl)pyrimidin-2-amine, or a salt thereof;

5-(3-(((S)-1-(1H-tetrazol-1-yl)propan-2-yl)oxy)-4-chlorophenyl)-N-(3-isopropyl-1-(trans-4-morpholinocyclohexyl)-1H-pyrazol-4-yl)pyrimidin-2-amine, or a salt thereof;

5-(3-(((S)-1-(1H-tetrazol-1-yl)propan-2-yl)oxy)-4-chlorophenyl)-N-(1-(trans-4-morpholinocyclohexyl)-3-(oxetan-3-yloxy)-1H-pyrazol-4-yl)pyrimidin-2-amine, or a salt thereof;

5-(3-(((S)-1-(1H-tetrazol-1-yl)propan-2-yl)oxy)-4-chlorophenyl)-N-(3-(((S)-2,2-difluorocyclopropyl)methoxy)-1-(trans-4-morpholinocyclohexyl)-1H-pyrazol-4-yl)pyrimidin-2-amine, or a salt thereof;

2-(((S)-1-(1H-tetrazol-1-yl)propan-2-yl)oxy)-4-(2-((1-(trans-4-morpholinocyclohexyl)-3-(2,2,2-trifluoroethoxy)-1H-pyrazol-4-yl)amino)pyrimidin-5-yl)benzonitrile, or a salt thereof;

5-(3-(((S)-1-(1H-tetrazol-1-yl)propan-2-yl)oxy)-4-chlorophenyl)-N-(1-(trans-4-((1R,5S)-3-oxa-8-azabicyclo[3.2.1]octan-8-yl)cyclohexyl)-3-(2,2-difluoroethoxy)-1H-pyrazol-4-yl)pyrimidin-2-amine, or a salt thereof;

1-(trans-4-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclohexyl)-3-methylazetidin-3-ol, or a salt thereof;

(S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(trifluoromethyl)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(2,2,2-trifluoroethoxy)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(1-(2-(oxetan-3-yl)-2-azaspiro[3.3]heptan-6-yl)-3-(2,2,2-trifluoroethoxy)-1H-pyrazol-4-yl)pyrimidin-2-amine, or a salt thereof;

(S)-1-(6-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-azaspiro[3.3]heptan-2-yl)-2-methylpropan-2-ol, or a salt thereof;

(S)-5-(3-((1-(1H-tetrazol-1-yl)propan-2-yl)oxy)-4-chlorophenyl)-N-(1-(2-(2,2-dimethyl-1,3-dioxan-5-yl)-2-azaspiro[3.3]heptan-6-yl)-3-(2,2,2-trifluoroethoxy)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(3-isopropyl-1-(2-(oxetan-3-yl)-2-azaspiro[3.3]heptan-6-yl)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(3-isopropyl-1-(2-(tetrahydro-2H-pyran-4-yl)-2-azaspiro[3.3]heptan-6-yl)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(1-(2-(4-methyltetrahydro-2H-pyran-4-yl)-2-azaspiro[3.3]heptan-6-yl)-3-(2,2,2-trifluoroethoxy)-1H-pyrazol-4-yl)pyrimidin-2-amine, or a salt thereof;

5-(4-chloro-3-{[(2S)-1-(1H-tetrazol-1-yl)propan-2-yl]oxy}phenyl)-N-(1-{2-[(4-$^2$H)tetrahydro-2H-pyran-4-yl]-2-azaspiro[3.3]heptan-6-yl}-3-(2,2,2-trifluoroethoxy)-1H-pyrazol-4-yl)pyrimidin-2-amine, or a salt thereof;

(S)-1-(6-4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-azaspiro[3.3]heptan-2-yl)-2-methylpropan-2-ol, or a salt thereof;

(S)-1-(6-(4-((5-(3-((1-(1H-tetrazol-1-yl)propan-2-yl)oxy)-4-chlorophenyl)pyrimidin-2-yl)amino)-3-isopropyl-1H-pyrazol-1-yl)-2-azaspiro[3.3]heptan-2-yl)-2-methylpropan-2-ol, or a salt thereof;

(S)-1-(4-((5-(3-((1-(1H-tetrazol-1-yl)propan-2-yl)oxy)-4-chlorophenyl)pyrimidin-2-yl)amino)-1-(2-(tetrahydro-2H-pyran-4-yl)-2-azaspiro[3.3]heptan-6-yl)-1H-pyrazol-3-yl)propan-1-one, or a salt thereof;

(S)-5-(3-((1-(1H-tetrazol-1-yl)propan-2-yl)oxy)-4-chlorophenyl)-N-(3-(perfluoroethyl)-1-(2-(tetrahydro-2H-pyran-4-yl)-2-azaspiro[3.3]heptan-6-yl)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(3-isopropyl-1-(2-(4-methyltetrahydro-2H-pyran-4-yl)-2-azaspiro[3.3]heptan-6-yl)-1H-pyrazol-4-yl)pyrimidin-2-amine, or a salt thereof;

(S)—N-(1-(2-(1,3-dioxan-5-yl)-2-azaspiro[3.3]heptan-6-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine, or a salt thereof;

(S)—N-(1-(2-(1,4-dioxepan-6-yl)-2-azaspiro[3.3]heptan-6-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine, or a salt thereof;

(S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(trifluoromethyl)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(2,2,2-trifluoroethoxy)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(3-(difluoromethoxy)-1-(1-(tetrahydro-2H-pyran-4-yl)piperidin-4-yl)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(3-isopropyl-1-(1-(tetrahydro-2H-pyran-4-yl)piperidin-4-yl)-1H-pyrazol-4-yl)pyrimidin-2-amine, or a salt thereof; and (S)-2-((1-(1H-tetrazol-1-yl)propan-2-yl)oxy)-4-(2-((1-(1-(tetrahydro-2H-pyran-4-yl)piperidin-4-yl)-3-(2,2,2-trifluoroethoxy)-1H-pyrazol-4-yl)amino)pyrimidin-5-yl)benzonitrile, or a salt thereof.

[11] A medicament comprising the compound or salt of the above-mentioned [1].

[12] The medicament of the above-mentioned [11], which is a calcium/calmodulin-dependent protein kinase II inhibitor.
[13] The medicament of the above-mentioned [11], which is an agent for the prophylaxis or treatment of cardiac diseases.
[14] The medicament of the above-mentioned [13], wherein the cardiac disease is selected from catecholaminergic polymorphic ventricular tachycardia, postoperative atrial fibrillation, heart failure and fatal arrhythmia.
[15] The compound or salt of the above-mentioned [1] for use in the prophylaxis or treatment of cardiac diseases.
[16] The compound or salt of the above-mentioned [15], wherein the cardiac disease is selected from catecholaminergic polymorphic ventricular tachycardia, postoperative atrial fibrillation, heart failure and fatal arrhythmia.
[17] A method of inhibiting calcium/calmodulin-dependent protein kinase II in a mammal, which comprises administering an effective amount of the compound or salt of the above-mentioned
[1] to the mammal.
[18] A method for the prophylaxis or treatment of cardiac diseases in a mammal, which comprises administering an effective amount of the compound or salt of the above-mentioned
[1] to the mammal.
[19] The method of the above-mentioned [18], wherein the cardiac disease is selected from catecholaminergic polymorphic ventricular tachycardia, postoperative atrial fibrillation, heart failure and fatal arrhythmia.
[20] Use of the compound or salt of the above-mentioned [1] for the production of an agent for the prophylaxis or treatment of cardiac diseases.
[21] The use of the above-mentioned [20], wherein the cardiac disease is selected from catecholaminergic polymorphic ventricular tachycardia, postoperative atrial fibrillation, heart failure and fatal arrhythmia.

According to the present invention, a compound having a superior CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like can be provided.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1] heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

Substituent group A.
[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,

(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbonsulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ arylcarbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_7$-16 aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_7$-16 aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., alkylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "$C_{6-14}$ aromatic hydrocarbon ring" include anthracene, phenanthrene, acenaphthylene, in addition to those exemplified as the above-mentioned "$C_{6-14}$ aromatic hydrocarbon ring".

The definition of each symbol in the formula (I) is explained in detail in the following.

Ring A is an optionally further substituted 5- or 6-membered aromatic ring.

Examples of the "5- or 6-membered aromatic ring" of the "optionally further substituted 5- or 6-membered aromatic ring" for Ring A include a benzene ring and a 5- or 6-membered aromatic heterocycle.

The "5- or 6-membered aromatic ring" of the "optionally further substituted 5- or 6-membered aromatic ring" for Ring A is preferably a benzene ring, a pyridine ring, a pyrimidine ring, a pyridazine ring, a pyrazine ring, a pyrazole ring, a thiazole ring, an isothiazole ring, an imidazole ring or an isoxazole ring, more preferably a benzene ring.

As another embodiment, the "5- or 6-membered aromatic ring" of the "optionally further substituted 5- or 6-membered aromatic ring" for Ring A is preferably a benzene ring, a pyridine ring, a pyrimidine ring, a pyridazine ring, a pyrazine ring, a pyrazole ring, a thiazole ring, an isothiazole ring, an imidazole ring, an isoxazole ring, a thiadiazole ring or a thiophene ring, more preferably a pyrazole ring.

The "5- or 6-membered aromatic ring" of the "optionally further substituted 5- or 6-membered aromatic ring" for Ring A optionally further has 1 to 5 (preferably 1 to 3) substituents at substitutable position(s), in addition to Ring B. Examples of the substituent include substituents selected from the above-mentioned Substituent group A. When the number of the substituents is plural, the respective substituents may be the same or different. In addition, the above-mentioned Substituent Group A is optionally substituted by substituent(s) selected from Substituent Group A. The number of the substituents is, for example, 1 to 3. When the number of the substituents is 2 or more, the respective substituents may be the same or different.

The two substituents on Ring A are optionally bonded to each other to form an optionally substituted ring (Ring A'), as shown below. That is, the two substituents are optionally bonded to each other to form a fused ring Ring A/Ring A' together with Ring A.

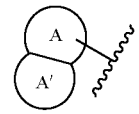

Examples of the ring of the optionally substituted ring for Ring A' include a $C_{6-14}$ aromatic hydrocarbon ring, a $C_{3-10}$ cycloalkane ring, a $C_{3-10}$ cycloalkene ring, a 5- to 14-membered (preferably 5- to 10-membered) aromatic heterocycle and a 3- to 14-membered (preferably 4- to 10-membered) non-aromatic heterocycle. Among them, a benzene ring, a $C_{5-6}$ cycloalkene ring (preferably cyclopentene) and a 3- to 8-membered monocyclic non-aromatic heterocycle (preferably pyrroline, dihydrofuran, tetrahydropyridine, dihydrooxazine, tetrahydroazepine) are preferable.

As another embodiment, a benzene ring, a $C_{5-6}$ cycloalkene ring (preferably cyclopentene, cyclohexene), a 3- to 8-membered monocyclic non-aromatic heterocycle (preferably pyrroline, dihydrofuran, tetrahydropyridine, dihydrooxazine, tetrahydroazepine, tetrahydrooxazepine) and a 5- or 6-membered monocyclic aromatic heterocycle (e.g., pyrrole) are preferable.

When the fused moiety of the fused ring Ring A/Ring A' is double bond, the ring of the optionally substituted ring for Ring A' is defined as a ring containing the double bond.

For example, when Ring A is a further substituted benzene ring, and the two substituents on the benzene ring are bonded to each other to form an optionally substituted isoindoline ring (Ring A/Ring A') together with the benzene ring, as shown below, then the ring of the optionally substituted ring for Ring A' is a pyrroline ring.

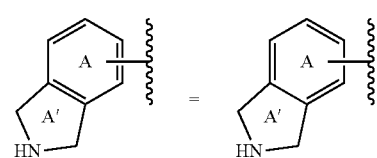

When Ring A is a further substituted thiazole ring, and the two substituents on the thiazole ring are bonded to each other to form an optionally substituted benzothiazole ring (Ring A/Ring A') together with the thiazole ring, as shown below, then the ring of the optionally substituted ring for Ring A' is a benzene ring.

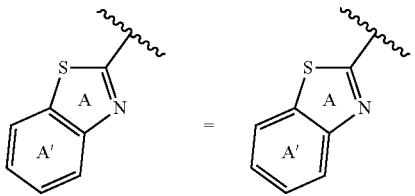

Ring A is preferably
(1) an optionally further substituted benzene ring (the two substituents on the benzene ring are optionally bonded to each other to form a 3- to 8-membered monocyclic non-aromatic heterocycle (preferably pyrroline, dihydrofuran, tetrahydropyridine, dihydrooxazine, tetrahydroazepine) or a $C_{5-6}$ cycloalkene ring (preferably cyclopentene), each of which is optionally substituted),
(2) an optionally further substituted pyridine ring,
(3) an optionally further substituted pyrimidine ring,
(4) an optionally further substituted pyridazine ring,
(5) an optionally further substituted pyrazine ring,
(6) an optionally further substituted pyrazole ring,
(7) an optionally further substituted thiazole ring (the two substituents on the thiazole ring are optionally bonded to each other to form an optionally substituted benzene ring),
(8) an optionally further substituted isothiazole ring,
(9) an optionally further substituted imidazole ring (the two substituents on the imidazole ring are optionally bonded to each other to form an optionally substituted benzene ring), or (10) an optionally further substituted isoxazole ring.

Ring A is more preferably an optionally further substituted benzene ring.

As another embodiment, Ring A is more preferably a 5- or 6-membered aromatic ring (e.g., benzene, pyridine, pyrimidine, pyridazine, pyrazine, pyrazole, thiazole, isothiazole, imidazole, isoxazole) optionally further substituted by 1 to 3 substituents selected from
(a) an optionally halogenated $C_{1-6}$ alkoxy group (e.g., methoxy, ethoxy, isopropyloxy, difluoromethoxy, trifluoromethoxy, trifluoroethoxy),
(b) a $C_{1-6}$ alkyl group (e.g., methyl, ethyl, propyl, isopropyl, isobutyl, tert-butyl, 2,2-dimethylpropyl) optionally substituted by 1 to 3 substituents selected from
 (i) a halogen atom (e.g., a fluorine atom),
 (ii) a hydroxy group,
 (iii) a cyano group,
 (iv) an amino group optionally mono- or di-substituted by substituent(s) selected from
  (I) a $C_{3-10}$ cycloalkyl group (e.g., cyclopropyl), and
  (II) a $C_{1-6}$ alkoxy-carbonyl group (e.g., tert-butoxycarbonyl),
 (v) a $C_{3-10}$ cycloalkyl group (e.g., cyclopropyl) optionally substituted by 1 to 3 substituents selected from
  (I) an amino group, and
  (II) a hydroxy group,
 (vi) a 5- to 14-membered (preferably 5- to 10-membered) aromatic heterocyclic group (preferably a 5- to 6-membered monocyclic aromatic heterocyclic group (e.g., pyrazolyl)), and
 (vii) a 3- to 14-membered (preferably 4- to 10-membered) non-aromatic heterocyclic group (preferably a 3- to 8-membered monocyclic non-aromatic heterocyclic group (e.g., morpholinyl, piperazinyl)) optionally substituted by 1 to 3 $C_{1-6}$ alkyl groups (e.g., methyl),
(c) a $C_{3-10}$ cycloalkyl group (e.g., cyclopropyl, cyclohexyl) optionally substituted by 1 to 3 substituents selected from
 (i) a 3- to 14-membered (preferably 4- to 10-membered) non-aromatic heterocyclic group (preferably a 3- to 8-membered monocyclic non-aromatic heterocyclic group (e.g., morpholinyl)),
(d) a halogen atom (e.g., a fluorine atom, a chlorine atom),
(e) a cyano group,
(f) a carboxy group,
(g) a $C_{1-6}$ alkoxy-carbonyl group (e.g., methoxycarbonyl, butoxycarbonyl),
(h) an amino group,
(i) a $C_{1-6}$ alkylsulfanyl group (e.g., methylsulfanyl),
(j) a $C_{1-6}$ alkylsulfonyl group (e.g., methylsulfonyl),
(k) a carbamoyl group optionally mono- or di-substituted by substituent(s) selected from
 (i) a $C_{1-6}$ alkyl group (e.g., methyl, ethyl, propyl, isopropyl) optionally substituted by 1 to 3 substituents selected from
  (I) a hydroxy group,
  (II) a halogen atom (e.g., a fluorine atom),
  (III) an optionally halogenated $C_{1-6}$ alkoxy group (e.g., methoxy, trifluoromethoxy),
  (IV) a mono- or di-$C_{1-6}$ alkylamino group (e.g., dimethylamino),
  (V) a $C_{3-10}$ cycloalkyl group (e.g., cyclopropyl, cyclohexyl), and
  (VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl),
 (ii) a $C_{3-10}$ cycloalkyl group (e.g., cyclopropyl, cyclobutyl, cyclohexyl) optionally substituted by 1 to 3 substituents selected from
  (I) a halogen atom (e.g., a fluorine atom),
  (II) an optionally halogenated $C_{1-6}$ alkyl group (e.g., trifluoromethyl),
  (III) a carboxy group, and
  (IV) a $C_{1-6}$ alkoxy-carbonyl group (e.g., methoxycarbonyl), and
 (iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl),
(l) a sulfamoyl group optionally mono- or di-substituted by substituent(s) selected from
 (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(m) a 5- to 14-membered (preferably 5- to 10-membered) aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl),
(n) a 3- to 14-membered (preferably 4- to 10-membered) non-aromatic heterocyclic group (preferably a 3- to 8-membered monocyclic non-aromatic heterocyclic group (e.g., azetidinyl, piperidyl, piperazinyl, pyrrolidinyl, diazepanyl, tetrahydropyridyl, oxetanyl)) optionally substituted by 1 to 3 substituents selected from
  (i) a $C_{1-6}$ alkyl group (e.g., methyl, ethyl, propyl, isobutyl) optionally substituted by 1 to 3 substituents selected from
    (I) a halogen atom (e.g., a fluorine atom),
    (II) a hydroxy group,
    (III) a cyano group,
    (IV) a $C_{1-6}$ alkoxy group (e.g., methoxy),
    (V) a $C_{1-6}$ alkylsulfonyl group (e.g., methylsulfonyl), and
    (VI) a 3- to 14-membered (preferably 4- to 10-membered) non-aromatic heterocyclic group (preferably a 3- to 8-membered monocyclic non-aromatic heterocyclic group (e.g., morpholinyl)),
  (ii) a $C_{1-6}$ alkyl-carbonyl group (e.g., acetyl) optionally substituted by 1 to 3 substituents selected from
    (I) a halogen atom (e.g., a fluorine atom), and
    (II) a hydroxy group,
  (iii) a $C_{1-6}$ alkoxy-carbonyl group (e.g., tert-butoxycarbonyl),
  (iv) a 3- to 14-membered (preferably 4- to 10-membered) non-aromatic heterocyclic group (e.g., morpholinyl, piperazinyl, piperidyl, oxetanyl, azetidinyl, tetrahydropyranyl, 3-oxa-8-azabicyclo[3.2.1]octyl, 8-oxa-3-azabicyclo[3.2.1]octyl) optionally substituted by 1 to 3 substituents selected from
    (I) a halogen atom (e.g., a fluorine atom),
    (II) a $C_{1-6}$ alkyl-carbonyl group (e.g., acetyl), and
    (III) a $C_{1-6}$ alkoxy-carbonyl group (e.g., tert-butoxycarbonyl), and
  (v) an oxo group,
(o) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from
  (i) a halogen atom (e.g., a fluorine atom),
  (ii) a hydroxy group,
  (iii) a cyano group,
  (iv) a $C_{1-6}$ alkyl group (e.g., methyl, ethyl) optionally substituted by 1 to 3 substituents selected from
    (I) a hydroxy group,
    (II) a halogen atom (e.g., a fluorine atom),
    (III) a $C_{1-6}$ alkoxy group (e.g., methoxy), and
    (IV) a mono- or di-$C_{1-6}$ alkylamino group (e.g., dimethylamino),
  (v) an optionally halogenated $C_{1-6}$ alkoxy group (e.g., methoxy, difluoromethoxy),
  (vi) a $C_{1-6}$ alkyl-carbonyl group (e.g., acetyl) optionally substituted by 1 to 3 substituents selected from
    (I) a hydroxy group, and
    (II) a $C_{1-6}$ alkoxy group (e.g., methoxy),
  (vii) a $C_{1-6}$ alkoxy-carbonyl group (e.g., tert-butoxycarbonyl),
  (viii) a $C_{3-10}$ cycloalkyl group (e.g., cyclopropyl),
  (ix) a $C_{3-10}$ cycloalkyl-carbonyl group (e.g., cyclopropylcarbonyl),
  (x) a $C_{1-6}$ alkylsulfonyl group (e.g., methylsulfonyl), and
  (xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), and
(p) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl))
(the two substituents on the 5- or 6-membered aromatic ring are optionally bonded to each other to form a 3- to 8-membered monocyclic non-aromatic heterocycle (e.g., pyrroline, dihydrofuran, tetrahydropyridine, dihydrooxazine, tetrahydroazepine), a $C_{3-6}$ cycloalkene ring (e.g., cyclopentene) or a benzene ring (e.g., indoline, isoindoline, dihydrobenzofuran, tetrahydroisoquinoline, dihydrobenzoxazine, tetrahydrobenzazepine, indane, benzothiazole, benzimidazole), each of which is optionally substituted by 1 to 3 substituents selected from
  (a) an oxo group,
  (b) a $C_{1-6}$ alkyl group (e.g., methyl) optionally substituted by 1 to 3 substituents selected from
    (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
  (c) a $C_{1-6}$ alkoxy-carbonyl group (e.g., tert-butoxycarbonyl), and
  (d) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl)) optionally substituted by 1 to 3 $C_{1-6}$ alkyl groups (e.g., methyl)).

In this embodiment, Ring A is further more preferably (1) a benzene ring optionally further substituted by 1 to 3 substituents selected from
  (a) an optionally halogenated $C_{1-6}$ alkoxy group (e.g., methoxy, ethoxy, isopropyloxy, difluoromethoxy, trifluoromethoxy, trifluoroethoxy),
  (b) a $C_{1-6}$ alkyl group (e.g., methyl, ethyl, propyl, isopropyl, tert-butyl) optionally substituted by 1 to 3 substituents selected from
    (i) a halogen atom (e.g., a fluorine atom),
    (ii) a hydroxy group,
    (iii) an amino group optionally mono- or di-substituted by substituent(s) selected from
      (I) a $C_{3-10}$ cycloalkyl group (e.g., cyclopropyl), and
      (II) a $C_{1-6}$ alkoxy-carbonyl group (e.g., tert-butoxycarbonyl), (iv) a 5- to 14-membered (preferably 5- to 10-membered) aromatic heterocyclic group (preferably a 5- to 6-membered monocyclic aromatic heterocyclic group (e.g., pyrazolyl)), and
(v) a 3- to 14-membered (preferably 4- to 10-membered) non-aromatic heterocyclic group (preferably a 3- to 8-membered monocyclic non-aromatic heterocyclic group (e.g., morpholinyl, piperazinyl)) optionally substituted by 1 to 3 $C_{1-6}$ alkyl groups (e.g., methyl),
(c) a $C_{3-10}$ cycloalkyl group (e.g., cyclopropyl, cyclohexyl) optionally substituted by 1 to 3 substituents selected from
(i) a 3- to 14-membered (preferably 4- to 10-membered) non-aromatic heterocyclic group (preferably a 3- to 8-membered monocyclic non-aromatic heterocyclic group (e.g., morpholinyl)),
(d) a halogen atom (e.g., a fluorine atom, a chlorine atom),
(e) a cyano group,
(f) a carboxy group,
(g) a $C_{1-6}$ alkoxy-carbonyl group (e.g., methoxycarbonyl, butoxycarbonyl),
(h) a $C_{1-6}$ alkylsulfanyl group (e.g., methylsulfanyl),
(i) a $C_{1-6}$ alkylsulfonyl group (e.g., methylsulfonyl),
(j) a carbamoyl group optionally mono- or di-substituted by substituent(s) selected from
(i) a $C_{1-6}$ alkyl group (e.g., methyl, ethyl, propyl, isopropyl) optionally substituted by 1 to 3 substituents selected from
(I) a hydroxy group,
(II) a halogen atom (e.g., a fluorine atom),
(III) an optionally halogenated $C_{1-6}$ alkoxy group (e.g., methoxy, trifluoromethoxy),
(IV) a mono- or di-$C_{1-6}$ alkylamino group (e.g., dimethylamino),
(V) a $C_{3-10}$ cycloalkyl group (e.g., cyclopropyl, cyclohexyl), and
(VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl),
(ii) a $C_{3-10}$ cycloalkyl group (e.g., cyclopropyl, cyclobutyl, cyclohexyl) optionally substituted by 1 to 3 substituents selected from
(I) a halogen atom (e.g., a fluorine atom),
(II) an optionally halogenated $C_{1-6}$ alkyl group (e.g., trifluoromethyl),
(III) a carboxy group, and
(IV) a $C_{1-6}$ alkoxy-carbonyl group (e.g., methoxycarbonyl), and
(iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl),
(k) a sulfamoyl group optionally mono- or di-substituted by substituent(s) selected from
(i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(l) a 5- to 14-membered (preferably 5- to 10-membered) aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl),
(m) a 3- to 14-membered (preferably 4- to 10-membered) non-aromatic heterocyclic group (preferably a 3- to 8-membered monocyclic non-aromatic heterocyclic group (e.g., azetidinyl, piperidyl, piperazinyl, pyrrolidinyl, diazepanyl, tetrahydropyridyl)) optionally substituted by 1 to 3 substituents selected from
(i) a $C_{1-6}$ alkyl group (e.g., methyl, ethyl, propyl, isobutyl) optionally substituted by 1 to 3 substituents selected from
(I) a halogen atom (e.g., a fluorine atom),
(II) a hydroxy group,
(III) a cyano group,
(IV) a $C_{1-6}$ alkoxy group (e.g., methoxy),
(V) a $C_{1-6}$ alkylsulfonyl group (e.g., methylsulfonyl), and
(VI) a 3- to 14-membered (preferably 4- to 10-membered) non-aromatic heterocyclic group (preferably a 3- to 8-membered monocyclic non-aromatic heterocyclic group (e.g., morpholinyl)),
(ii) a $C_{1-6}$ alkyl-carbonyl group (e.g., acetyl) optionally substituted by 1 to 3 substituents selected from
(I) a halogen atom (e.g., a fluorine atom), and
(II) a hydroxy group,
(iii) a $C_{1-6}$ alkoxy-carbonyl group (e.g., tert-butoxycarbonyl),
(iv) a 3- to 14-membered (preferably 4- to 10-membered) non-aromatic heterocyclic group (e.g., morpholinyl, piperazinyl, piperidyl, oxetanyl, azetidinyl, tetrahydropyranyl, 3-oxa-8-azabicyclo[3.2.1]octyl, 8-oxa-3-azabicyclo[3.2.1]octyl) optionally substituted by 1 to 3 substituents selected from
(I) a halogen atom (e.g., a fluorine atom),
(II) a $C_{1-6}$ alkyl-carbonyl group (e.g., acetyl), and
(III) a $C_{1-6}$ alkoxy-carbonyl group (e.g., tert-butoxycarbonyl), and
(v) an oxo group,
(n) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from
(i) a halogen atom (e.g., a fluorine atom),
(ii) a hydroxy group,
(iii) a cyano group,
(iv) a $C_{1-6}$ alkyl group (e.g., methyl, ethyl) optionally substituted by 1 to 3 substituents selected from
(I) a hydroxy group,
(II) a halogen atom (e.g., a fluorine atom),
(III) a $C_{1-6}$ alkoxy group (e.g., methoxy), and (IV) a mono- or di-$C_{1-6}$ alkylamino group (e.g., dimethylamino),
(v) an optionally halogenated $C_{1-6}$ alkoxy group (e.g., methoxy, difluoromethoxy),
(vi) a $C_{1-6}$ alkyl-carbonyl group (e.g., acetyl) optionally substituted by 1 to 3 substituents selected from
(I) a hydroxy group, and
(II) a $C_{1-6}$ alkoxy group (e.g., methoxy),
(vii) a $C_{1-6}$ alkoxy-carbonyl group (e.g., tert-butoxycarbonyl),
(viii) a $C_{3-10}$ cycloalkyl group (e.g., cyclopropyl),
(ix) a $C_{3-10}$ cycloalkyl-carbonyl group (e.g., cyclopropylcarbonyl),
(x) a $C_{1-6}$ alkylsulfonyl group (e.g., methylsulfonyl), and
(xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), and
(o) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl))
(the two substituents on the benzene ring are optionally bonded to each other to form a 3- to 8-membered monocyclic non-aromatic heterocycle (e.g., pyrroline, dihydrofuran, tetrahydropyridine, dihydrooxazine, tetrahydroazepine) or a $C_{5-6}$ cycloalkene ring (e.g., cyclopentene) (e.g., indoline, isoindoline, dihydrobenzofuran, tetrahydroisoquinoline, dihydrobenzoxazine, tetrahydrobenzazepine, indane), each of which is optionally substituted by 1 to 3 substituents selected from
(a) an oxo group,
(b) a $C_{1-6}$ alkyl group (e.g., methyl) optionally substituted by 1 to 3 substituents selected from
(i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(c) a $C_{1-6}$ alkoxy-carbonyl group (e.g., tert-butoxycarbonyl), and
(d) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl)) optionally substituted by 1 to 3 $C_{1-6}$ alkyl groups (e.g., methyl)), or
(2) a 5- or 6-membered aromatic heterocycle (e.g., pyridine, pyrimidine, pyridazine, pyrazine, pyrazole, thiazole, isothiazole, imidazole, isoxazole) optionally further substituted by 1 to 3 substituents selected from
(a) an amino group,
(b) a $C_{1-6}$ alkyl group (e.g., methyl, ethyl, propyl, isopropyl, isobutyl, tert-butyl, 2,2-dimethylpropyl) optionally substituted by 1 to 3 substituents selected from
(i) a $C_{3-10}$ cycloalkyl group (e.g., cyclopropyl) optionally substituted by 1 to 3 substituents selected from
(I) an amino group, and
(II) a hydroxy group,
(ii) a hydroxy group,
(iii) a cyano group, and
(iv) a halogen atom (e.g., a fluorine atom),
(c) a $C_{1-6}$ alkoxy group (e.g., methoxy),
(d) a $C_{3-10}$ cycloalkyl group (e.g., cyclopropyl), and
(e) a 3- to 14-membered (preferably 4- to 10-membered) non-aromatic heterocyclic group (preferably a 3- to 8-membered monocyclic non-aromatic heterocyclic group (e.g., piperidyl, oxetanyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl, oxetanyl))
(the two substituents on the 5- or 6-membered aromatic heterocycle are optionally bonded to each other to form a benzene ring (e.g., benzothiazole, benzimidazole)).

In this embodiment, Ring A is still more preferably (1) a benzene ring optionally further substituted by 1 to 3 substituents selected from
(a) an optionally halogenated $C_{1-6}$ alkoxy group (e.g., methoxy, ethoxy, isopropyloxy, difluoromethoxy, trifluoromethoxy, trifluoroethoxy),
(b) a $C_{1-6}$ alkyl group (e.g., methyl, ethyl, propyl, isopropyl, tert-butyl) optionally substituted by 1 to 3 substituents selected from
(i) a halogen atom (e.g., a fluorine atom),
(ii) a hydroxy group,
(iii) an amino group optionally mono- or di-substituted by substituent(s) selected from
(I) a $C_{3-10}$ cycloalkyl group (e.g., cyclopropyl), and
(II) a $C_{1-6}$ alkoxy-carbonyl group (e.g., tert-butoxycarbonyl),
(iv) a 5- to 14-membered (preferably 5- to 10-membered) aromatic heterocyclic group (preferably a 5- to 6-membered monocyclic aromatic heterocyclic group (e.g., pyrazolyl)), and
(v) a 3- to 14-membered (preferably 4- to 10-membered) non-aromatic heterocyclic group (preferably a 3- to 8-membered monocyclic non-aromatic heterocyclic group (e.g., morpholinyl, piperazinyl)) optionally substituted by 1 to 3 $C_{1-6}$ alkyl groups (e.g., methyl),
(c) a $C_{3-10}$ cycloalkyl group (e.g., cyclopropyl, cyclohexyl) optionally substituted by 1 to 3 substituents selected from
(i) a 3- to 14-membered (preferably 4- to 10-membered) non-aromatic heterocyclic group (preferably a 3- to 8-membered monocyclic non-aromatic heterocyclic group (e.g., morpholinyl)),
(d) a halogen atom (e.g., a fluorine atom, a chlorine atom),
(e) a cyano group,
(f) a carboxy group,
(g) a $C_{1-6}$ alkoxy-carbonyl group (e.g., methoxycarbonyl, butoxycarbonyl),
(h) a $C_{1-6}$ alkylsulfanyl group (e.g., methylsulfanyl),
(i) a $C_{1-6}$ alkylsulfonyl group (e.g., methylsulfonyl),
(j) a carbamoyl group optionally mono- or di-substituted by substituent(s) selected from
(i) a $C_{1-6}$ alkyl group (e.g., methyl, ethyl, propyl, isopropyl) optionally substituted by 1 to 3 substituents selected from
(I) a hydroxy group,
(II) a halogen atom (e.g., a fluorine atom),
(III) an optionally halogenated $C_{1-6}$ alkoxy group (e.g., methoxy, trifluoromethoxy),
(IV) a mono- or di-$C_{1-6}$ alkylamino group (e.g., dimethylamino), (V) a $C_{3-10}$ cycloalkyl group (e.g., cyclopropyl, cyclohexyl), and (VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl), (ii) a $C_{3-10}$ cycloalkyl group (e.g., cyclopropyl, cyclobutyl, cyclohexyl) optionally substituted by 1 to 3 substituents selected from (I) a halogen atom (e.g., a fluorine atom), (II) an optionally halogenated $C_{1-6}$ alkyl group (e.g., trifluoromethyl), (III) a carboxy group, and (IV) a $C_{1-6}$ alkoxy-carbonyl group (e.g., methoxycarbonyl), and (iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl), (k) a sulfamoyl group optionally mono- or di-substituted by substituent(s) selected from (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl), (l) a 5- to 14-membered (preferably 5- to 10-membered) aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl), (m) a 3- to 14-membered (preferably 4- to 10-membered) non-aromatic heterocyclic group (preferably a 3- to 8-membered monocyclic non-aromatic heterocyclic group (e.g., azetidinyl, piperidyl, piperazinyl, pyrrolidinyl, diazepanyl, tetrahydropyridyl)) optionally substituted by 1 to 3 substituents selected from (i) a $C_{1-6}$ alkyl group (e.g., methyl, ethyl, propyl, isobutyl) optionally substituted by 1 to 3 substituents selected from (I) a halogen atom (e.g., a fluorine atom), (II) a hydroxy group, (III) a cyano group, (IV) a $C_{1-6}$ alkoxy group (e.g., methoxy), (V) a $C_{1-6}$ alkylsulfonyl group (e.g., methylsulfonyl), and (VI) a 3- to 14-membered (preferably 4- to 10-membered) non-aromatic heterocyclic group (preferably a 3- to 8-membered monocyclic non-aromatic heterocyclic group (e.g., morpholinyl)), (ii) a $C_{1-6}$ alkyl-carbonyl group (e.g., acetyl) optionally substituted by 1 to 3 substituents selected from (I) a halogen atom (e.g., a fluorine atom), and (II) a hydroxy group, (iii) a $C_{1-6}$ alkoxy-carbonyl group (e.g., tert-butoxycarbonyl), (iv) a 3- to 14-membered (preferably 4- to 10-membered) non-aromatic heterocyclic group (e.g., morpholinyl, piperazinyl, piperidyl, oxetanyl, azetidinyl, tetrahydropyranyl, 3-oxa-8-azabicyclo[3.2.1]octyl, 8-oxa-3-azabicyclo[3.2.1]octyl) optionally substituted by 1 to 3 substituents selected from (I) a halogen atom (e.g., a fluorine atom), (II) a $C_{1-6}$ alkyl-carbonyl group (e.g., acetyl), and (III) a $C_{1-6}$ alkoxy-carbonyl group (e.g., tert-butoxycarbonyl), and (v) an oxo group, (n) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from (i) a halogen atom (e.g., a fluorine atom), (ii) a hydroxy group, (iii) a cyano group, (iv) a $C_{1-6}$ alkyl group (e.g., methyl, ethyl) optionally substituted by 1 to 3 substituents selected from (I) a hydroxy group, (II) a halogen atom (e.g., a fluorine atom), (III) a $C_{1-6}$ alkoxy group (e.g., methoxy), and (IV) a mono- or di-$C_{1-6}$ alkylamino group (e.g., dimethylamino), (v) an optionally halogenated $C_{1-6}$ alkoxy group (e.g., methoxy, difluoromethoxy), (vi) a $C_{1-6}$ alkyl-carbonyl group (e.g., acetyl) optionally substituted by 1 to 3 substituents selected from (I) a hydroxy group, and (II) a $C_{1-6}$ alkoxy group (e.g., methoxy), (vii) a $C_{1-6}$ alkoxy-carbonyl group (e.g., tert-butoxycarbonyl), (viii) a $C_{3-10}$ cycloalkyl group (e.g., cyclopropyl), (ix) a $C_{3-10}$ cycloalkyl-carbonyl group (e.g., cyclopropylcarbonyl), (x) a $C_{1-6}$ alkylsulfonyl group (e.g., methylsulfonyl), and (xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), and (o) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl))

(the two substituents on the benzene ring are optionally bonded to each other to form a 3- to 8-membered monocyclic non-aromatic heterocycle (e.g., pyrroline, dihydrofuran, tetrahydropyridine, dihydrooxazine, tetrahydroazepine) or a $C_{5-6}$ cycloalkene ring (e.g., cyclopentene) (e.g., indoline, isoindoline, dihydrobenzofuran, tetrahydroisoquinoline, dihydrobenzoxazine, tetrahydrobenzazepine, indane), each of which is optionally substituted by 1 to 3 substituents selected from
- (a) an oxo group,
- (b) a $C_{1-6}$ alkyl group (e.g., methyl) optionally substituted by 1 to 3 substituents selected from
  - (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
- (c) a $C_{1-6}$ alkoxy-carbonyl group (e.g., tert-butoxycarbonyl), and
- (d) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl)) optionally substituted by 1 to 3 $C_{1-6}$ alkyl groups (e.g., methyl)), (2) a pyridine ring optionally further substituted by 1 to 3 substituents selected from
- (a) a $C_{1-6}$ alkoxy group (e.g., methoxy),
- (b) an amino group, and
- (c) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)), (3) a pyrimidine ring optionally further substituted by 1 to 3 substituents selected from
- (a) a $C_{1-6}$ alkoxy group (e.g., methoxy), and
- (b) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)), (4) a pyridazine ring,
(5) a pyrazine ring,
(6) a pyrazole ring optionally further substituted by 1 to 3 substituents selected from
- (a) a $C_{1-6}$ alkyl group (e.g., methyl, ethyl, propyl, isopropyl, isobutyl, tert-butyl, 2,2-dimethylpropyl) optionally substituted by 1 to 3 substituents selected from
  - (i) a $C_{3-10}$ cycloalkyl group (e.g., cyclopropyl) optionally substituted by 1 to 3 substituents selected from
    - (I) an amino group, and
    - (II) a hydroxy group,
  - (ii) a hydroxy group,
  - (iii) a cyano group, and
  - (iv) a halogen atom (e.g., a fluorine atom),
- (b) a $C_{1-6}$ alkoxy group (e.g., methoxy),
- (c) a $C_{3-10}$ cycloalkyl group (e.g., cyclopropyl), and
- (d) a 3- to 14-membered (preferably 4- to 10-membered) non-aromatic heterocyclic group (preferably a 3- to 8-membered monocyclic non-aromatic heterocyclic group (e.g., oxetanyl, piperidyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., oxetanyl)), (7) a thiazole ring (the two substituents on the thiazole ring are optionally bonded to each other to form a benzene ring (e.g., benzothiazole ring)),
(8) an isothiazole ring optionally further substituted by 1 to 3 substituents selected from
- (a) a $C_{1-6}$ alkyl group (e.g., methyl) optionally substituted by 1 to 3 hydroxy groups, (9) an imidazole ring optionally further substituted by 1 to 3 $C_{1-6}$ alkyl groups (e.g., methyl) (the two substituents on the imidazole ring are optionally bonded to each other to form a benzene ring (e.g., benzimidazole ring)), or
(10) an isoxazole ring.

Ring A is particularly preferably a benzene ring optionally further substituted by 1 to 3 substituents selected from
- (a) a $C_{1-6}$ alkoxy group (e.g., methoxy), and
- (b) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl, oxetanyl)).

As another embodiment, Ring A is preferably
(1) an optionally further substituted benzene ring (the two substituents on the benzene ring are optionally bonded to each other to form a 5- or 6-membered monocyclic aromatic heterocycle (preferably pyrrole), a 3- to 8-membered monocyclic non-aromatic heterocycle (preferably pyrroline, dihydrofuran, tetrahydropyridine, dihydrooxazine, tetrahydroazepine, tetrahydrooxazepine) or a $C_{5-6}$ cycloalkene ring (preferably cyclopentene), each of which is optionally substituted),
(2) an optionally further substituted pyridine ring,
(3) an optionally further substituted pyrimidine ring,
(4) an optionally further substituted pyridazine ring,
(5) an optionally further substituted pyrazine ring,
(6) an optionally further substituted pyrazole ring,
(7) an optionally further substituted thiazole ring (the two substituents on the thiazole ring are optionally bonded to each other to form an optionally substituted benzene ring),
(8) an optionally further substituted isothiazole ring,
(9) an optionally further substituted imidazole ring (the two substituents on the imidazole ring are optionally bonded to each other to form an optionally substituted benzene ring),
(10) an optionally further substituted isoxazole ring,
(11) an optionally further substituted thiadiazole ring, or
(12) an optionally further substituted thiophene ring (the two substituents on the thiophene ring are optionally bonded to each other to form an optionally substituted $C_{5-6}$ cycloalkene ring (preferably cyclopentene, cyclohexene)).

In this embodiment, Ring A is more preferably a 5- or 6-membered aromatic ring (e.g., benzene, pyridine, pyrimidine, pyridazine, pyrazine, pyrazole, thiazole, isothiazole, imidazole, isoxazole, thiadiazole, thiophene) optionally further substituted by 1 to 3 substituents selected from
- (a) a $C_{1-6}$ alkoxy group (e.g., methoxy, ethoxy, propyloxy, isopropyloxy) optionally substituted by 1 to 5 substituents selected from
  - (i) a halogen atom (e.g., a fluorine atom), and
  - (ii) a $C_{3-10}$ cycloalkyl group (e.g., cyclopropyl) optionally substituted by 1 to 3 halogen atoms (e.g., a fluorine atom),
- (b) a $C_{1-6}$ alkyl group (e.g., methyl, ethyl, propyl, isopropyl, butyl, isobutyl, sec-butyl, tert-butyl, 2,2-dimethylpropyl) optionally substituted by 1 to 5 substituents selected from (i) a halogen atom (e.g., a fluorine atom),
(ii) a hydroxy group,
(iii) a cyano group,
(iv) a carboxy group,
(v) a $C_{1-6}$ alkoxy group (e.g., methoxy, ethoxy) optionally substituted by 1 to 3 substituents selected from
  (I) a halogen atom (e.g., a fluorine atom), and
  (II) a hydroxy group,
(vi) a $C_{1-6}$ alkoxy-carbonyl group (e.g., ethoxycarbonyl),
(vii) a $C_{1-6}$ alkylsulfonyl group (e.g., methylsulfonyl),
(viii) an amino group optionally mono- or di-substituted by substituent(s) selected from
  (I) a $C_{3-10}$ cycloalkyl group (e.g., cyclopropyl),
  (II) a $C_{1-6}$ alkyl-carbonyl group (e.g., acetyl),
  (III) a $C_{1-6}$ alkoxy-carbonyl group (e.g., tert-butoxycarbonyl),
  (IV) a $C_{1-6}$ alkylsulfonyl group (e.g., methylsulfonyl),
  (V) a $C_{6-14}$ aryl-carbonyl group (e.g., benzoyl), and
  (VI) a carbamoyl group,
(ix) a $C_{3-10}$ cycloalkyl group (e.g., cyclopropyl, cyclobutyl, cyclohexyl) optionally substituted by 1 to 3 substituents selected from
  (I) an amino group,
  (II) a hydroxy group,
  (III) an oxo group,
  (IV) a $C_{1-6}$ alkyl group (e.g., methyl), and
  (V) a 3- to 14-membered (preferably 4- to 10-membered) non-aromatic heterocyclic group (preferably a 3- to 8-membered monocyclic non-aromatic heterocyclic group (e.g., morpholinyl)),
(x) a carbamoyl group optionally mono- or di-substituted by substituent(s) selected from
  (I) a $C_{1-6}$ alkyl group (e.g., ethyl), and
  (II) a $C_{6-14}$ aryl group (e.g., phenyl),
(xi) a 5- to 14-membered (preferably 5- to 10-membered) aromatic heterocyclic group (e.g., pyrazolyl, pyridyl, isoxazolyl, benzimidazolyl) optionally substituted by 1 to 3 substituents selected from
  (I) a $C_{1-6}$ alkyl group (e.g., methyl), and
  (II) a $C_{1-6}$ alkoxy group (e.g., methoxy),
(xii) a 3- to 14-membered (preferably 4- to 10-membered) non-aromatic heterocyclic group (e.g., morpholinyl, piperazinyl, 1,1-dioxidothiomorpholinyl, azetidinyl, pyrrolidinyl, piperidyl, oxetanyl, tetrahydrofuryl, tetrahydropyranyl, dihydropyridyl, dihydrotriazolyl, tetrahydrooxazolyl, dihydroquinazolinyl, 1,4-dioxaspiro[4.5]decyl) optionally substituted by 1 to 3 by 1 to 3 substituents selected from
  (I) an oxo group,
  (II) a hydroxy group,
  (III) a carbamoyl group,
  (IV) a $C_{1-6}$ alkyl groups (e.g., methyl) optionally substituted by 1 to 3 hydroxy groups,
  (V) a $C_{1-6}$ alkoxy-carbonyl group (e.g., tert-butoxycarbonyl),
  (VI) a $C_{3-10}$ cycloalkyl group (e.g., cyclobutyl),
  (VII) a $C_{7-16}$ aralkyl group (e.g., benzyl), and
  (VIII) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl)), and
(xiii) a 3- to 14-membered (preferably 4- to 10-membered) non-aromatic heterocyclylcarbonyl group (preferably a 3- to 8-membered monocyclic non-aromatic heterocyclylcarbonyl group (e.g., morpholinylcarbonyl)),
(c) a $C_{3-10}$ cycloalkyl group (the $C_{3-10}$ cycloalkyl group is optionally fused with a benzene ring, or optionally bridged or may be a spiro group; e.g., cyclopropyl, cyclobutyl, cyclopentyl, cyclohexyl, indanyl, bicyclo[2.2.1]heptyl, spiro[3.3]hexyl) optionally substituted by 1 to 3 substituents selected from
  (i) a halogen atom (e.g., a fluorine atom),
  (ii) an oxo group,
  (iii) a hydroxy group,
  (iv) a carbamoyl group,
  (v) a carboxy group,
  (vi) a $C_{1-6}$ alkyl group (e.g., methyl) optionally substituted by 1 to 3 substituents selected from
    (I) a hydroxy group,
    (II) a carboxy group,
    (III) a carbamoyl group, and
    (IV) a 3- to 14-membered (preferably 4- to 10-membered) non-aromatic heterocyclic group (preferably a 3- to 8-membered monocyclic non-aromatic heterocyclic group (e.g., morpholinyl)),
  (vii) a $C_{1-6}$ alkoxy-carbonyl group (e.g., ethoxycarbonyl),
  (viii) a 3- to 14-membered (preferably 4- to 10-membered) non-aromatic heterocyclic group (e.g., azetidinyl, pyrrolidinyl, morpholinyl, 2-oxa-6-azaspiro[3.3]heptyl, 3-oxa-8-azabicyclo[3.2.1]octyl) optionally substituted by 1 to 3 substituents selected from
    (I) a halogen atom (e.g., a fluorine atom),
    (II) a hydroxy group, and
    (III) a $C_{1-6}$ alkyl group (e.g., methyl) optionally substituted by 1 to 3 substituents selected from a halogen atom (e.g., a fluorine atom) and a hydroxy group, and
  (ix) an amino group optionally mono- or di-substituted by substituent(s) selected from
    (I) a $C_{1-6}$ alkoxy-carbonyl group (e.g., tert-butoxycarbonyl), and
    (II) a 3- to 14-membered (preferably 4- to 10-membered) non-aromatic heterocyclic group (preferably a 3- to 8-membered monocyclic non-aromatic heterocyclic group (e.g., tetrahydropyranyl)),
(d) a halogen atom (e.g., a fluorine atom, a chlorine atom),
(e) a cyano group,
(f) a carboxy group,
(g) an optionally halogenated $C_{1-6}$ alkyl-carbonyl group (e.g., acetyl, propionyl),
(h) a $C_{1-6}$ alkoxy-carbonyl group (e.g., methoxycarbonyl, ethoxycarbonyl, butoxycarbonyl),
(i) an amino group,
(j) a $C_{1-6}$ alkylsulfanyl group (e.g., methylsulfanyl),
(k) a $C_{1-6}$ alkylsulfonyl group (e.g., methylsulfonyl),
(l) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 substituents selected from
    (I) a hydroxy group,
    (II) a halogen atom (e.g., a fluorine atom),
    (III) an optionally halogenated $C_{1-6}$ alkoxy group (e.g., methoxy, trifluoromethoxy),
    (IV) a mono- or di-$C_{1-6}$ alkylamino group (e.g., dimethylamino), (V) a $C_{3-10}$ cycloalkyl group (e.g., cyclopropyl, cyclohexyl), and
(VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl),
(ii) a $C_{3-10}$ cycloalkyl group (e.g., cyclopropyl, cyclobutyl, cyclohexyl) optionally substituted by 1 to 3 substituents selected from
  (I) a halogen atom (e.g., a fluorine atom),
  (II) an optionally halogenated $C_{1-6}$ alkyl group (e.g., trifluoromethyl),
  (III) a carboxy group, and
  (IV) a $C_{1-6}$ alkoxy-carbonyl group (e.g., methoxycarbonyl), and
(iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl),
(m) a sulfamoyl group optionally mono- or di-substituted by substituent(s) selected from
  (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(n) a $C_{2-6}$ alkynyl group (e.g., (prop-2-ynyl)),
(o) a $C_{6-14}$ aryl group (e.g., phenyl) optionally substituted by 1 to 3 halogen atoms (e.g., a chlorine atom),
(p) a $C_{7-16}$ aralkyl group (e.g., benzyl),
(q) a 5- to 14-membered (preferably 5- to 10-membered) aromatic heterocyclic group (preferably a 5- to 6-membered monocyclic aromatic heterocyclic group (e.g., pyrazolyl, pyridyl, pyrazolyl, thienyl)) optionally substituted by 1 to 3 substituents selected from
  (i) a $C_{1-6}$ alkyl group (e.g., methyl), and
  (ii) a $C_{1-6}$ alkoxy group (e.g., methoxy),
(r) a 3- to 14-membered (preferably 4- to 10-membered) non-aromatic heterocyclic group (e.g., azetidinyl, piperidyl, piperazinyl, pyrrolidinyl, diazepanyl, tetrahydropyridyl, oxetanyl, morpholinyl, 2,5-diazabicyclo[2.2.1]heptyl, hexahydropyrrolo[1,2-a]pyrazinyl, hexahydropyrazino[2,1-c][1,4]oxazinyl, azepanyl, tetrahydrofuryl, tetrahydropyranyl, tetrahydrothiopyranyl, dihydropyridyl, 8-azabicyclo[3.2.1]octyl, 2-azaspiro[3.3]heptyl) optionally substituted by 1 to 3 substituents selected from
  (i) a $C_{1-6}$ alkyl group (e.g., methyl, ethyl, propyl, isopropyl, isobutyl, sec-butyl, 3,3-dimethylbutyl) optionally substituted by 1 to 3 substituents selected from
    (I) a halogen atom (e.g., a fluorine atom),
    (II) a hydroxy group,
    (III) a cyano group,
    (IV) a carbamoyl group,
    (V) a $C_{1-6}$ alkoxy group (e.g., methoxy, ethoxy) optionally substituted by 1 to 3 substituents selected from
      (A) a halogen atom (e.g., a fluorine atom),
      (B) a $C_{1-6}$ alkyl-carbonyloxy group (e.g., acetyloxy, 2-methylpropanoyloxy, 2,2-dimethylpropanoyloxy, 3-methylbutanoyloxy), and
      (C) a $C_{1-6}$ alkoxy-carbonyloxy group (e.g., ethoxycarbonyloxy, isopropoxycarbonyloxy),
    (VI) a $C_{1-6}$ alkyl-carbonyloxy group (e.g., acetyloxy),
    (VII) a $C_{1-6}$ alkylsulfonyl group (e.g., methylsulfonyl),
    (VIII) a $C_{3-10}$ cycloalkyl group (e.g., cyclopropyl),
    (IV) a mono- or di-$C_{1-6}$ alkylamino group (e.g., dimethylamino),
    (X) a 5- to 14-membered (preferably 5- to 10-membered) aromatic heterocyclic group (preferably a 5- to 6-membered monocyclic aromatic heterocyclic group (e.g., pyridyl, pyrazolyl, pyrrolyl, thiazolyl, thienyl, pyrimidinyl)) optionally substituted by 1 to 3 $C_{1-6}$ alkyl groups (e.g., methyl), and
    (XI) a 3- to 14-membered (preferably 4- to 10-membered) non-aromatic heterocyclic group (preferably a 3- to 8-membered monocyclic non-aromatic heterocyclic group (e.g., morpholinyl, oxetanyl)),
  (ii) a $C_{1-6}$ alkyl-carbonyl group (e.g., acetyl) optionally substituted by 1 to 3 substituents selected from
    (I) a halogen atom (e.g., a fluorine atom),
    (II) a hydroxy group, and
    (III) a mono- or di-$C_{1-6}$ alkylamino group (e.g., dimethylamino),
  (iii) a $C_{1-6}$ alkoxy-carbonyl group (e.g., tert-butoxycarbonyl),
  (iv) a $C_{3-10}$ cycloalkyl group (e.g., cyclopropyl, cyclobutyl, cyclopentyl, cyclohexyl) optionally substituted by 1 to 3 substituents selected from
    (I) a halogen atom (e.g., a fluorine atom),
    (II) a hydroxy group,
    (III) a $C_{1-6}$ alkyl group (e.g., methyl) optionally substituted by 1 to 3 $C_{1-6}$ alkoxy groups (e.g., methoxy), and
    (IV) a $C_{1-6}$ alkoxy group (e.g., methoxy),
  (v) a $C_{6-14}$ aryl group (e.g., phenyl) optionally substituted by 1 to 3 halogen atoms (e.g., a fluorine atom),
  (vi) a $C_{7-16}$ aralkyl group (e.g., benzyl),
  (vii) a 5- to 14-membered (preferably 5- to 10-membered) aromatic heterocyclic group (preferably a 5- to 6-membered monocyclic aromatic heterocyclic group (e.g., pyrimidinyl, pyridyl)) optionally substituted by 1 to 3 $C_{1-6}$ alkyl groups (e.g., methyl),
  (viii) a 3- to 14-membered (preferably 4- to 10-membered) non-aromatic heterocyclic group (e.g., morpholinyl, piperazinyl, piperidyl, oxetanyl, azetidinyl, tetrahydropyranyl, oxepanyl, dioxepanyl, 3-oxa-8-azabicyclo[3.2.1]octyl, 8-oxa-3-azabicyclo[3.2.1]octyl, tetrahydrofuryl, 1,1-dioxidotetrahydrothiopyranyl, dioxanyl, 2-oxabicyclo[2.2.2]octyl) optionally substituted by 1 to 3 substituents selected from
    (I) a halogen atom (e.g., a fluorine atom),
    (II) a $C_{1-6}$ alkyl-carbonyl group (e.g., acetyl),
    (III) a $C_{1-6}$ alkoxy-carbonyl group (e.g., tert-butoxycarbonyl),
    (IV) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
    (V) a $C_{3-10}$ cycloalkyl group (e.g., cyclopropyl),
    (VI) a cyano group, and
    (VII) a deuterium atom, (ix) an oxo group,
(x) a hydroxy group, and
(xi) a mono- or di-$C_{1-6}$ alkyl-carbamoyl group (e.g., methylcarbamoyl), (s) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from
  (i) a halogen atom (e.g., a fluorine atom),
  (ii) a hydroxy group,
  (iii) a cyano group,
  (iv) a $C_{1-6}$ alkyl group (e.g., methyl, ethyl) optionally substituted by 1 to 3 substituents selected from
    (I) a hydroxy group,
    (II) a halogen atom (e.g., a fluorine atom),
    (III) a $C_{1-6}$ alkoxy group (e.g., methoxy),
    (IV) a mono- or di-$C_{1-6}$ alkylamino group (e.g., dimethylamino), and
    (V) a $C_{3-10}$ cycloalkyl group (e.g., cyclopropyl),
  (v) an optionally halogenated $C_{1-6}$ alkoxy group (e.g., methoxy, difluoromethoxy),
  (vi) a $C_{1-6}$ alkyl-carbonyl group (e.g., acetyl) optionally substituted by 1 to 3 substituents selected from
    (I) a hydroxy group, and
    (II) a $C_{1-6}$ alkoxy group (e.g., methoxy),
  (vii) a $C_{1-6}$ alkoxy-carbonyl group (e.g., tert-butoxycarbonyl),
  (viii) a $C_{3-10}$ cycloalkyl group (e.g., cyclopropyl),
  (ix) a $C_{3-10}$ cycloalkyl-carbonyl group (e.g., cyclopropylcarbonyl),
  (x) a $C_{1-6}$ alkylsulfonyl group (e.g., methylsulfonyl), and
  (xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), (t) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl)), and (u) a 3- to 14-membered (preferably 4- to 10-membered) non-aromatic heterocyclyloxy group (preferably a 3- to 8-membered monocyclic non-aromatic heterocyclyloxy group (e.g., oxetanyloxy))
(the two substituents on the 5- or 6-membered aromatic ring are optionally bonded to each other to form a 5- or 6-membered monocyclic aromatic heterocycle (e.g., pyrrole), a 3- to 8-membered monocyclic non-aromatic heterocycle (e.g., pyrroline, dihydrofuran, tetrahydropyridine, dihydrooxazine, tetrahydroazepine, tetrahydrooxazepine), a $C_{5-6}$ cycloalkene ring (e.g., cyclopentene, cyclohexene) or a benzene ring (e.g., indole, indoline, isoindoline, dihydrobenzofuran, tetrahydroquinoline, tetrahydroisoquinoline, dihydrobenzoxazine, tetrahydrobenzazepine, tetrahydrobenzoxazepine, indane, benzothiazole, benzimidazole, tetrahydrobenzothiophene, cyclopentathiophene), each of which is optionally substituted by 1 to 3 substituents selected from
  (a) an oxo group,
  (b) a $C_{1-6}$ alkyl group (e.g., methyl, ethyl) optionally substituted by 1 to 3 substituents selected from
    (i) a halogen atom (e.g., a fluorine atom),
    (ii) a hydroxy group,
    (iii) a carboxy group,
    (iv) a $C_{1-6}$ alkoxy group (e.g., methoxy),
    (v) a $C_{1-6}$ alkyl-carbonyl group (e.g., acetyl),
    (vi) a mono- or di-$C_{1-6}$ alkylamino group (e.g., dimethylamino), and
    (vii) a 3- to 14-membered (preferably 4- to 10-membered) non-aromatic heterocyclic group (preferably a 3- to 8-membered monocyclic non-aromatic heterocyclic group (e.g., piperidyl, oxetanyl)) optionally substituted by 1 to 3 $C_{1-6}$ alkyl groups (e.g., methyl),
  (c) a $C_{3-10}$ cycloalkyl group (e.g., cyclobutyl),
  (d) a formyl group,
  (e) a $C_{1-6}$ alkyl-carbonyl group (e.g., acetyl, propanoyl, butanoyl, 2-methylpropanoyl) optionally substituted by 1 to 3 substituents selected from
    (i) a halogen atom (e.g., a fluorine atom),
    (ii) a hydroxy group,
    (iii) a $C_{1-6}$ alkoxy group (e.g., methoxy),
    (iv) a $C_{1-6}$ alkyl-carbonyloxy group (e.g., acetyloxy),
    (v) a mono- or di-$C_{1-6}$ alkylamino group (e.g., dimethylamino, N-ethyl-N-methylamino), and
    (vi) a 3- to 14-membered (preferably 4- to 10-membered) non-aromatic heterocyclic group (preferably a 3- to 8-membered monocyclic non-aromatic heterocyclic group (e.g., morpholinyl)),
  (f) a $C_{1-6}$ alkoxy-carbonyl group (e.g., tert-butoxycarbonyl),
  (g) a 5- to 14-membered (preferably 5- to 10-membered) aromatic heterocyclic group (preferably a 5- to 6-membered monocyclic aromatic heterocyclic group (e.g., pyrimidinyl)) optionally substituted by 1 to 3 $C_{1-6}$ alkyl groups (e.g., methyl),
  (h) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl, oxetanyl)) optionally substituted by 1 to 3 $C_{1-6}$ alkyl groups (e.g., methyl), and
  (i) a 3- to 14-membered (preferably 4- to 10-membered) non-aromatic heterocyclycarbonyl group (preferably a 3- to 8-membered monocyclic non-aromatic heterocyclycarbonyl group (e.g., piperidylcarbonyl)) optionally substituted by 1 to 3 $C_{1-6}$ alkyl groups (e.g., methyl)).

In this embodiment, Ring A is further more preferably (1) a benzene ring optionally further substituted by 1 to 3 substituents selected from
  (a) an optionally halogenated $C_{1-6}$ alkoxy group (e.g., methoxy, ethoxy, isopropyloxy, difluoromethoxy, trifluoromethoxy, trifluoroethoxy),
  (b) a $C_{1-6}$ alkyl group (e.g., methyl, ethyl, propyl, isopropyl, tert-butyl) optionally substituted by 1 to 3 substituents selected from
    (i) a halogen atom (e.g., a fluorine atom),
    (ii) a hydroxy group, (iii) an amino group optionally mono- or di-substituted by substituent(s) selected from
(I) a $C_{3-10}$ cycloalkyl group (e.g., cyclopropyl), and
(II) a $C_{1-6}$ alkoxy-carbonyl group (e.g., tert-butoxycarbonyl),
(iv) a 5- to 14-membered (preferably 5- to 10-membered) aromatic heterocyclic group (preferably a 5- to 6-membered monocyclic aromatic heterocyclic group (e.g., pyrazolyl)), and
(v) a 3- to 14-membered (preferably 4- to 10-membered) non-aromatic heterocyclic group (preferably a 3- to 8-membered monocyclic non-aromatic heterocyclic group (e.g., morpholinyl, piperazinyl, 1,1-dioxidothiomorpholinyl)) optionally substituted by 1 to 3 $C_{1-6}$ alkyl groups (e.g., methyl),
(c) a $C_{3-10}$ cycloalkyl group (e.g., cyclopropyl, cyclohexyl) optionally substituted by 1 to 3 substituents selected from
(i) a 3- to 14-membered (preferably 4- to 10-membered) non-aromatic heterocyclic group (preferably a 3- to 8-membered monocyclic non-aromatic heterocyclic group (e.g., morpholinyl)),
(d) a halogen atom (e.g., a fluorine atom, a chlorine atom),
(e) a cyano group,
(f) a carboxy group,
(g) a $C_{1-6}$ alkoxy-carbonyl group (e.g., methoxycarbonyl, butoxycarbonyl),
(h) a $C_{1-6}$ alkylsulfanyl group (e.g., methylsulfanyl),
(i) a $C_{1-6}$ alkylsulfonyl group (e.g., methylsulfonyl),
(j) a carbamoyl group optionally mono- or di-substituted by substituent(s) selected from
(i) a $C_{1-6}$ alkyl group (e.g., methyl, ethyl, propyl, isopropyl) optionally substituted by 1 to 3 substituents selected from
(I) a hydroxy group,
(II) a halogen atom (e.g., a fluorine atom),
(III) an optionally halogenated $C_{1-6}$ alkoxy group (e.g., methoxy, trifluoromethoxy),
(IV) a mono- or di-$C_{1-6}$ alkylamino group (e.g., dimethylamino),
(V) a $C_{3-10}$ cycloalkyl group (e.g., cyclopropyl, cyclohexyl), and
(VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl),
(ii) a $C_{3-10}$ cycloalkyl group (e.g., cyclopropyl, cyclobutyl, cyclohexyl) optionally substituted by 1 to 3 substituents selected from
(I) a halogen atom (e.g., a fluorine atom),
(II) an optionally halogenated $C_{1-6}$ alkyl group (e.g., trifluoromethyl),
(III) a carboxy group, and
(IV) a $C_{1-6}$ alkoxy-carbonyl group (e.g., methoxycarbonyl), and
(iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl), (k) a sulfamoyl group optionally mono- or di-substituted by substituent(s) selected from
(i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(l) a 5- to 14-membered (preferably 5- to 10-membered) aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl),
(m) a 3- to 14-membered (preferably 4- to 10-membered) non-aromatic heterocyclic group (e.g., azetidinyl, piperidyl, piperazinyl, pyrrolidinyl, diazepanyl, tetrahydropyridyl, morpholinyl, 2,5-diazabicyclo[2.2.1]heptyl, hexahydropyrrolo[1,2-a]pyrazinyl, hexahydropyrazino[2,1-c][1,4]oxazinyl) optionally substituted by 1 to 3 substituents selected from
(i) a $C_{1-6}$ alkyl group (e.g., methyl, ethyl, propyl, isobutyl) optionally substituted by 1 to 3 substituents selected from
(I) a halogen atom (e.g., a fluorine atom),
(II) a hydroxy group,
(III) a cyano group,
(IV) a carbamoyl group,
(V) a $C_{1-6}$ alkoxy group (e.g., methoxy),
(VI) a $C_{1-6}$ alkylsulfonyl group (e.g., methylsulfonyl),
(VII) a mono- or di-$C_{1-6}$ alkylamino group (e.g., dimethylamino), and
(VIII) a 3- to 14-membered (preferably 4- to 10-membered) non-aromatic heterocyclic group (preferably a 3- to 8-membered monocyclic non-aromatic heterocyclic group (e.g., morpholinyl)),
(ii) a $C_{1-6}$ alkyl-carbonyl group (e.g., acetyl) optionally substituted by 1 to 3 substituents selected from
(I) a halogen atom (e.g., a fluorine atom),
(II) a hydroxy group, and
(III) a mono- or di-$C_{1-6}$ alkylamino group (e.g., dimethylamino),
(iii) a $C_{1-6}$ alkoxy-carbonyl group (e.g., tert-butoxycarbonyl),
(iv) a 3- to 14-membered (preferably 4- to 10-membered) non-aromatic heterocyclic group (e.g., morpholinyl, piperazinyl, piperidyl, oxetanyl, azetidinyl, tetrahydropyranyl, 3-oxa-8-azabicyclo[3.2.1]octyl, 8-oxa-3-azabicyclo[3.2.1]octyl) optionally substituted by 1 to 3 substituents selected from
(I) a halogen atom (e.g., a fluorine atom),
(II) a $C_{1-6}$ alkyl-carbonyl group (e.g., acetyl), and
(III) a $C_{1-6}$ alkoxy-carbonyl group (e.g., tert-butoxycarbonyl),
(v) an oxo group, and
(vi) a mono- or di-$C_{1-6}$ alkyl-carbamoyl group (e.g., methylcarbamoyl),
(n) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7- azaspiro[2.5]octylcarbonyl, 2,6-diazaspiro[3.3] heptylcarbonyl, 2-oxa-6-azaspiro[3.3]heptylcarbonyl, 2,7-diazaspiro[3.5]nonylcarbonyl) optionally substituted by 1 to 3 substituents selected from
  (i) a halogen atom (e.g., a fluorine atom),
  (ii) a hydroxy group,
  (iii) a cyano group,
  (iv) a $C_{1-6}$ alkyl group (e.g., methyl, ethyl) optionally substituted by 1 to 3 substituents selected from
    (I) a hydroxy group,
    (II) a halogen atom (e.g., a fluorine atom),
    (III) a $C_{1-6}$ alkoxy group (e.g., methoxy),
    (IV) a mono- or di-$C_{1-6}$ alkylamino group (e.g., dimethylamino), and
    (V) a $C_{3-10}$ cycloalkyl group (e.g., cyclopropyl),
  (v) an optionally halogenated $C_{1-6}$ alkoxy group (e.g., methoxy, difluoromethoxy),
  (vi) a $C_{1-6}$ alkyl-carbonyl group (e.g., acetyl) optionally substituted by 1 to 3 substituents selected from
    (I) a hydroxy group, and
    (II) a $C_{1-6}$ alkoxy group (e.g., methoxy),
  (vii) a $C_{1-6}$ alkoxy-carbonyl group (e.g., tert-butoxycarbonyl),
  (viii) a $C_{3-10}$ cycloalkyl group (e.g., cyclopropyl),
  (ix) a $C_{3-10}$ cycloalkyl-carbonyl group (e.g., cyclopropylcarbonyl),
  (x) a $C_{1-6}$ alkylsulfonyl group (e.g., methylsulfonyl), and
  (xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), and
(o) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl))
(the two substituents on the benzene ring are optionally bonded to each other to form a 5- or 6-membered monocyclic aromatic heterocycle (e.g., pyrrole), a 3- to 8-membered monocyclic non-aromatic heterocycle (e.g., pyrroline, dihydrofuran, tetrahydropyridine, dihydrooxazine, tetrahydroazepine, tetrahydrooxazepine) or a $C_{5-6}$ cycloalkene ring (e.g., cyclopentene) (e.g., indole, indoline, isoindoline, dihydrobenzofuran, tetrahydroquinoline, tetrahydroisoquinoline, dihydrobenzoxazine, tetrahydrobenzazepine, tetrahydrobenzoxazepine, indane), each of which is optionally substituted by 1 to 3 substituents selected from
  (a) an oxo group,
  (b) a $C_{1-6}$ alkyl group (e.g., methyl, ethyl) optionally substituted by 1 to 3 substituents selected from
    (i) a halogen atom (e.g., a fluorine atom),
    (ii) a hydroxy group,
    (iii) a carboxy group,
    (iv) a $C_{1-6}$ alkoxy group (e.g., methoxy),
    (v) a $C_{1-6}$ alkyl-carbonyl group (e.g., acetyl),
    (vi) a mono- or di-$C_{1-6}$ alkylamino group (e.g., dimethylamino), and
    (vii) a 3- to 14-membered (preferably 4- to 10-membered) non-aromatic heterocyclic group (preferably a 3- to 8-membered monocyclic non-aromatic heterocyclic group (e.g., piperidyl, oxetanyl)) optionally substituted by 1 to 3 $C_{1-6}$ alkyl groups (e.g., methyl),
  (c) a $C_{3-10}$ cycloalkyl group (e.g., cyclobutyl),
  (d) a formyl group,
  (e) a $C_{1-6}$ alkyl-carbonyl group (e.g., acetyl, propanoyl, butanoyl, 2-methylpropanoyl) optionally substituted by 1 to 3 substituents selected from
    (i) a halogen atom (e.g., a fluorine atom),
    (ii) a hydroxy group,
    (iii) a $C_{1-6}$ alkoxy group (e.g., methoxy),
    (iv) a $C_{1-6}$ alkyl-carbonyloxy group (e.g., acetyloxy),
    (v) a mono- or di-$C_{1-6}$ alkylamino group (e.g., dimethylamino, N-ethyl-N-methylamino), and
    (vi) a 3- to 14-membered (preferably 4- to 10-membered) non-aromatic heterocyclic group (preferably a 3- to 8-membered monocyclic non-aromatic heterocyclic group (e.g., morpholinyl)),
  (f) a $C_{1-6}$ alkoxy-carbonyl group (e.g., tert-butoxycarbonyl),
  (g) a 5- to 14-membered (preferably 5- to 10-membered) aromatic heterocyclic group (preferably a 5- to 6-membered monocyclic aromatic heterocyclic group (e.g., pyrimidinyl)) optionally substituted by 1 to 3 $C_{1-6}$ alkyl groups (e.g., methyl),
  (h) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl, oxetanyl)) optionally substituted by 1 to 3 $C_{1-6}$ alkyl groups (e.g., methyl), and
  (i) a 3- to 14-membered (preferably 4- to 10-membered) non-aromatic heterocyclycarbonyl group (preferably a 3- to 8-membered monocyclic non-aromatic heterocyclycarbonyl group (e.g., piperidylcarbonyl)) optionally substituted by 1 to 3 $C_{1-6}$ alkyl groups (e.g., methyl)), or
(2) a 5- or 6-membered aromatic heterocycle (e.g., pyridine, pyrimidine, pyridazine, pyrazine, pyrazole, thiazole, isothiazole, imidazole, isoxazole, thiadiazole, thiophene) optionally further substituted by 1 to 3 substituents selected from
  (a) an amino group,
  (b) a halogen atom (e.g., a chlorine atom),
  (c) a cyano group,
  (d) a carboxy group,
  (e) a $C_{1-6}$ alkyl group (e.g., methyl, ethyl, propyl, isopropyl, butyl, isobutyl, sec-butyl, tert-butyl, 2,2-dimethylpropyl) optionally substituted by 1 to 5 substituents selected from
    (i) a $C_{3-10}$ cycloalkyl group (e.g., cyclopropyl, cyclobutyl, cyclohexyl) optionally substituted by 1 to 3 substituents selected from
      (I) an amino group,
      (II) a hydroxy group,
      (III) an oxo group,
      (IV) a $C_{1-6}$ alkyl group (e.g., methyl), and
      (V) a 3- to 14-membered (preferably 4- to 10-membered) non-aromatic heterocyclic group (preferably a 3- to 8-membered monocyclic non-aromatic heterocyclic group (e.g., morpholinyl)),
    (ii) a hydroxy group,
    (iii) a cyano group,
    (iv) a halogen atom (e.g., a fluorine atom),
    (v) a carboxy group,
    (vi) a $C_{1-6}$ alkoxy group (e.g., methoxy, ethoxy) optionally substituted by 1 to 3 substituents selected from
      (I) a halogen atom (e.g., a fluorine atom), and
      (II) a hydroxy group, (vii) a $C_{1-6}$ alkoxy-carbonyl group (e.g., ethoxycarbonyl),
(viii) a $C_{1-6}$ alkylsulfonyl group (e.g., methylsulfonyl),
(ix) an amino group optionally mono- or di-substituted by substituent(s) selected from
  (I) a $C_{1-6}$ alkyl-carbonyl group (e.g., acetyl),
  (II) a $C_{1-6}$ alkoxy-carbonyl group (e.g., tert-butoxycarbonyl),
  (III) a $C_{1-6}$ alkylsulfonyl group (e.g., methylsulfonyl),
  (IV) a $C_{6-14}$ aryl-carbonyl group (e.g., benzoyl), and
  (V) a carbamoyl group,
(x) a carbamoyl group optionally mono- or di-substituted by substituent(s) selected from
  (I) a $C_{1-6}$ alkyl group (e.g., ethyl), and
  (II) a $C_{6-14}$ aryl group (e.g., phenyl),
(xi) a 5- to 14-membered (preferably 5- to 10-membered) aromatic heterocyclic group (e.g., pyridyl, isoxazolyl, benzimidazolyl) optionally substituted by 1 to 3 substituents selected from
  (I) a $C_{1-6}$ alkyl group (e.g., methyl), and
  (II) a $C_{1-6}$ alkoxy group (e.g., methoxy),
(xii) a 3- to 14-membered (preferably 4- to 10-membered) non-aromatic heterocyclic group (e.g., azetidinyl, pyrrolidinyl, piperidyl, morpholinyl, oxetanyl, tetrahydrofuryl, tetrahydropyranyl, dihydropyridyl, dihydrotriazolyl, tetrahydrooxazolyl, dihydroquinazolinyl, 1,4-dioxaspiro[4.5]decyl) optionally substituted by 1 to 3 substituents selected from
  (I) an oxo group,
  (II) a hydroxy group,
  (III) a carbamoyl group,
  (IV) a $C_{1-6}$ alkyl group (e.g., methyl) optionally substituted by 1 to 3 hydroxy groups,
  (V) a $C_{1-6}$ alkoxy-carbonyl group (e.g., tert-butoxycarbonyl),
  (VI) a $C_{3-10}$ cycloalkyl group (e.g., cyclobutyl),
  (VII) a $C_{7-16}$ aralkyl group (e.g., benzyl), and
  (VIII) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl)), and
(xiii) a 3- to 14-membered (preferably 4- to 10-membered) non-aromatic heterocyclylcarbonyl group (preferably a 3- to 8-membered monocyclic non-aromatic heterocyclylcarbonyl group (e.g., morpholinylcarbonyl)),
(f) a $C_{2-6}$ alkynyl group (e.g., (prop-2-ynyl)),
(g) a $C_{1-6}$ alkoxy group (e.g., methoxy, ethoxy, propyloxy) optionally substituted by 1 to 5 substituents selected from
  (i) a halogen atom (e.g., a fluorine atom), and
  (ii) a $C_{3-10}$ cycloalkyl group (e.g., cyclopropyl) optionally substituted by 1 to 3 halogen atoms (e.g., a fluorine atom),
(h) a $C_{3-10}$ cycloalkyl group (the $C_{3-10}$ cycloalkyl group is optionally fused with a benzene ring, or optionally bridged or may be a spiro group; e.g., cyclopropyl, cyclobutyl, cyclopentyl, cyclohexyl, indanyl, bicyclo[2.2.1]heptyl, spiro[3.3]hexyl) optionally substituted by 1 to 3 substituents selected from
  (i) a halogen atom (e.g., a fluorine atom),
  (ii) an oxo group,
  (iii) a hydroxy group,
  (iv) a carbamoyl group,
  (v) a carboxy group,
  (vi) a $C_{1-6}$ alkyl group (e.g., methyl) optionally substituted by 1 to 3 substituents selected from
    (I) a hydroxy group,
    (II) a carboxy group,
    (III) a carbamoyl group, and
    (IV) a 3- to 14-membered (preferably 4- to 10-membered) non-aromatic heterocyclic group (preferably a 3- to 8-membered monocyclic non-aromatic heterocyclic group (e.g., morpholinyl)),
  (vii) a $C_{1-6}$ alkoxy-carbonyl group (e.g., ethoxycarbonyl),
  (viii) a 3- to 14-membered (preferably 4- to 10-membered) non-aromatic heterocyclic group (preferably a 3- to 8-membered monocyclic non-aromatic heterocyclic group (e.g., azetidinyl, pyrrolidinyl, morpholinyl, 2-oxa-6-azaspiro[3.3]heptyl, 3-oxa-8-azabicyclo[3.2.1]octyl)) optionally substituted by 1 to 3 substituents selected from
    (I) a halogen atom (e.g., a fluorine atom),
    (II) a hydroxy group, and
    (III) a $C_{1-6}$ alkyl group (e.g., methyl) optionally substituted by 1 to 3 substituents selected from a halogen atom (e.g., a fluorine atom) and a hydroxy group, and
  (ix) an amino group optionally mono- or di-substituted by substituent(s) selected from
    (I) a $C_{1-6}$ alkoxy-carbonyl group (e.g., tert-butoxycarbonyl), and
    (II) a 3- to 14-membered (preferably 4- to 10-membered) non-aromatic heterocyclic group (preferably a 3- to 8-membered monocyclic non-aromatic heterocyclic group (e.g., tetrahydropyranyl)),
(i) an optionally halogenated $C_{1-6}$ alkyl-carbonyl group (e.g., acetyl, propionyl),
(j) a $C_{1-6}$ alkoxy-carbonyl group (e.g., ethoxycarbonyl),
(k) a $C_{6-14}$ aryl group (e.g., phenyl) optionally substituted by 1 to 3 halogen atoms (e.g., a chlorine atom),
(l) a $C_{7-16}$ aralkyl group (e.g., benzyl),
(m) a 5- to 14-membered (preferably 5- to 10-membered) aromatic heterocyclic group (preferably a 5- to 6-membered monocyclic aromatic heterocyclic group (e.g., pyridyl, pyrazolyl, thienyl)) optionally substituted by 1 to 3 $C_{1-6}$ alkoxy groups (e.g., methoxy),
(n) a 3- to 14-membered (preferably 4- to 10-membered) non-aromatic heterocyclic group (preferably a 3- to 8-membered monocyclic non-aromatic heterocyclic group (e.g., oxetanyl, piperidyl, azetidinyl, piperazinyl, pyrrolidinyl, morpholinyl, azepanyl, diazepanyl, tetrahydrofuryl, tetrahydropyranyl, tetrahydrothiopyranyl, dihydropyridyl, 8-azabicyclo[3.2.1]octyl, 2-azaspiro[3.3]heptyl)) optionally substituted by 1 to 3 substituents selected from
  (i) an oxo group,
  (ii) a hydroxy group,
  (iii) a $C_{1-6}$ alkyl group (e.g., methyl, ethyl, propyl, isopropyl, isobutyl, 3,3-dimethylbutyl) optionally substituted by 1 to 3 substituents selected from
    (I) a halogen atom (e.g., a fluorine atom),
    (II) a hydroxy group,
    (III) a cyano group,
    (IV) a $C_{1-6}$ alkoxy group (e.g., methoxy, ethoxy) optionally substituted by 1 to 3 substituents selected from (A) a halogen atom (e.g., a fluorine atom),
(B) a $C_{1-6}$ alkyl-carbonyloxy group (e.g., acetyloxy, 2-methylpropanoyloxy, 2,2-dimethylpropanoyloxy, 3-methylbutanoyloxy), and
(C) a $C_{1-6}$ alkoxy-carbonyloxy group (e.g., ethoxycarbonyloxy, isopropoxycarbonyloxy),
(V) a $C_{1-6}$ alkyl-carbonyloxy group (e.g., acetyloxy),
(VI) a $C_{3-10}$ cycloalkyl group (e.g., cyclopropyl),
(VII) a 5- to 14-membered (preferably 5- to 10-membered) aromatic heterocyclic group (preferably a 5- to 6-membered monocyclic aromatic heterocyclic group (e.g., pyridyl, pyrazolyl, pyrrolyl, thiazolyl, thienyl, pyrimidinyl)) optionally substituted by 1 to 3 $C_{1-6}$ alkyl groups (e.g., methyl), and
(VIII) a 3- to 14-membered (preferably 4- to 10-membered) non-aromatic heterocyclic group (preferably a 3- to 8-membered monocyclic non-aromatic heterocyclic group (e.g., oxetanyl, morpholinyl)),
(iv) a $C_{3-10}$ cycloalkyl group (e.g., cyclopropyl, cyclobutyl, cyclopentyl, cyclohexyl) optionally substituted by 1 to 3 substituents selected from
(I) a halogen atom (e.g., a fluorine atom),
(II) a hydroxy group,
(III) a $C_{1-6}$ alkyl group (e.g., methyl) optionally substituted by 1 to 3 $C_{1-6}$ alkoxy groups (e.g., methoxy), and
(IV) a $C_{1-6}$ alkoxy group (e.g., methoxy),
(v) a $C_{6-14}$ aryl group (e.g., phenyl) optionally substituted by 1 to 3 halogen atoms (e.g., a fluorine atom),
(vi) a $C_{7-16}$ aralkyl group (e.g., benzyl),
(vii) an optionally halogenated $C_{1-6}$ alkyl-carbonyl group (e.g., acetyl, trifluoroacetyl),
(viii) a $C_{1-6}$ alkoxy-carbonyl group (e.g., tert-butoxycarbonyl),
(ix) a 5- to 14-membered (preferably 5- to 10-membered) aromatic heterocyclic group (preferably a 5- to 6-membered monocyclic aromatic heterocyclic group (e.g., pyrimidinyl, pyridyl)) optionally substituted by 1 to 3 $C_{1-6}$ alkyl groups (e.g., methyl), and
(x) a 3- to 14-membered (preferably 4- to 10-membered) non-aromatic heterocyclic group (preferably a 3- to 8-membered monocyclic non-aromatic heterocyclic group (e.g., morpholinyl, oxetanyl, piperidyl, tetrahydrofuryl, tetrahydropyranyl, oxepanyl, dioxepanyl, 1,1-dioxidotetrahydrothiopyranyl, dioxanyl, 2-oxabicyclo[2.2.2]octyl)) optionally substituted by 1 to 3 substituents selected from
(I) a halogen atom (e.g., a fluorine atom),
(II) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
(III) a $C_{3-10}$ cycloalkyl group (e.g., cyclopropyl),
(VI) a cyano group, and
(V) a deuterium atom,
(o) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)), and
(p) a 3- to 14-membered (preferably 4- to 10-membered) non-aromatic heterocyclylcarbonyl group (preferably a 3- to 8-membered monocyclic non-aromatic heterocyclylcarbonyl group (e.g., piperidylcarbonyl, morpholinylcarbonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)),
(the two substituents on the 5- or 6-membered aromatic heterocycle are optionally bonded to each other to form a benzene ring (e.g., benzothiazole, benzimidazole), or a $C_{5-6}$ cycloalkene ring (e.g., cyclopentene, cyclohexene) (e.g., tetrahydrobenzothiophene ring, cyclopentathiophene ring)).

In this embodiment, Ring A is still more preferably
(1) a benzene ring optionally further substituted by 1 to 3 substituents selected from
(a) an optionally halogenated $C_{1-6}$ alkoxy group (e.g., methoxy, ethoxy, isopropyloxy, difluoromethoxy, trifluoromethoxy, trifluoroethoxy),
(b) a $C_{1-6}$ alkyl group (e.g., methyl, ethyl, propyl, isopropyl, tert-butyl) optionally substituted by 1 to 3 substituents selected from
(i) a halogen atom (e.g., a fluorine atom),
(ii) a hydroxy group,
(iii) an amino group optionally mono- or di-substituted by substituent(s) selected from
(I) a $C_{3-10}$ cycloalkyl group (e.g., cyclopropyl), and
(II) a $C_{1-6}$ alkoxy-carbonyl group (e.g., tert-butoxycarbonyl),
(iv) a 5- to 14-membered (preferably 5- to 10-membered) aromatic heterocyclic group (preferably a 5- to 6-membered monocyclic aromatic heterocyclic group (e.g., pyrazolyl)), and
(v) a 3- to 14-membered (preferably 4- to 10-membered) non-aromatic heterocyclic group (preferably a 3- to 8-membered monocyclic non-aromatic heterocyclic group (e.g., morpholinyl, piperazinyl, 1,1-dioxidothiomorpholinyl)) optionally substituted by 1 to 3 $C_{1-6}$ alkyl groups (e.g., methyl),
(c) a $C_{3-10}$ cycloalkyl group (e.g., cyclopropyl, cyclohexyl) optionally substituted by 1 to 3 substituents selected from
(i) a 3- to 14-membered (preferably 4- to 10-membered) non-aromatic heterocyclic group (preferably a 3- to 8-membered monocyclic non-aromatic heterocyclic group (e.g., morpholinyl)),
(d) a halogen atom (e.g., a fluorine atom, a chlorine atom),
(e) a cyano group,
(f) a carboxy group,
(g) a $C_{1-6}$ alkoxy-carbonyl group (e.g., methoxycarbonyl, butoxycarbonyl),
(h) a $C_{1-6}$ alkylsulfanyl group (e.g., methylsulfanyl),
(i) a $C_{1-6}$ alkylsulfonyl group (e.g., methylsulfonyl),
(j) a carbamoyl group optionally mono- or di-substituted by substituent(s) selected from
(i) a $C_{1-6}$ alkyl group (e.g., methyl, ethyl, propyl, isopropyl) optionally substituted by 1 to 3 substituents selected from
(I) a hydroxy group,
(II) a halogen atom (e.g., a fluorine atom),
(III) an optionally halogenated $C_{1-6}$ alkoxy group (e.g., methoxy, trifluoromethoxy),
(IV) a mono- or di-$C_{1-6}$ alkylamino group (e.g., dimethylamino),
(V) a $C_{3-10}$ cycloalkyl group (e.g., cyclopropyl, cyclohexyl), and
(VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl),
(ii) a $C_{3-10}$ cycloalkyl group (e.g., cyclopropyl, cyclobutyl, cyclohexyl) optionally substituted by 1 to 3 substituents selected from
(I) a halogen atom (e.g., a fluorine atom),
(II) an optionally halogenated $C_{1-6}$ alkyl group (e.g., trifluoromethyl),
(III) a carboxy group, and
(IV) a $C_{1-6}$ alkoxy-carbonyl group (e.g., methoxycarbonyl), and
(iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl),
(k) a sulfamoyl group optionally mono- or di-substituted by substituent(s) selected from
(i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(l) a 5- to 14-membered (preferably 5- to 10-membered) aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl),
(m) a 3- to 14-membered (preferably 4- to 10-membered) non-aromatic heterocyclic group (e.g., azetidinyl, piperidyl, piperazinyl, pyrrolidinyl, diazepanyl, tetrahydropyridyl, morpholinyl, 2,5-diazabicyclo[2.2.1]heptyl, hexahydropyrrolo[1,2-a]pyrazinyl, hexahydropyrazino[2,1-c][1,4]oxazinyl) optionally substituted by 1 to 3 substituents selected from
(i) a $C_{1-6}$ alkyl group (e.g., methyl, ethyl, propyl, isobutyl) optionally substituted by 1 to 3 substituents selected from
(I) a halogen atom (e.g., a fluorine atom),
(II) a hydroxy group,
(III) a cyano group,
(IV) a carbamoyl group,
(V) a $C_{1-6}$ alkoxy group (e.g., methoxy),
(VI) a $C_{1-6}$ alkylsulfonyl group (e.g., methylsulfonyl),
(VII) a mono- or di-$C_{1-6}$ alkylamino group (e.g., dimethylamino), and
(VIII) a 3- to 14-membered (preferably 4- to 10-membered) non-aromatic heterocyclic group (preferably a 3- to 8-membered monocyclic non-aromatic heterocyclic group (e.g., morpholinyl)),
(ii) a $C_{1-6}$ alkyl-carbonyl group (e.g., acetyl) optionally substituted by 1 to 3 substituents selected from
(I) a halogen atom (e.g., a fluorine atom),
(II) a hydroxy group, and
(III) a mono- or di-$C_{1-6}$ alkylamino group (e.g., dimethylamino),
(iii) a $C_{1-6}$ alkoxy-carbonyl group (e.g., tert-butoxycarbonyl),
(iv) a 3- to 14-membered (preferably 4- to 10-membered) non-aromatic heterocyclic group (e.g., morpholinyl, piperazinyl, piperidyl, oxetanyl, azetidinyl, tetrahydropyranyl, 3-oxa-8-azabicyclo[3.2.1]octyl, 8-oxa-3-azabicyclo[3.2.1]octyl) optionally substituted by 1 to 3 substituents selected from
(I) a halogen atom (e.g., a fluorine atom),
(II) a $C_{1-6}$ alkyl-carbonyl group (e.g., acetyl), and
(III) a $C_{1-6}$ alkoxy-carbonyl group (e.g., tert-butoxycarbonyl),
(v) an oxo group, and
(vi) a mono- or di-$C_{1-6}$ alkyl-carbamoyl group (e.g., methylcarbamoyl),
(n) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from
(i) a halogen atom (e.g., a fluorine atom),
(ii) a hydroxy group,
(iii) a cyano group,
(iv) a $C_{1-6}$ alkyl group (e.g., methyl, ethyl) optionally substituted by 1 to 3 substituents selected from
(I) a hydroxy group,
(II) a halogen atom (e.g., a fluorine atom),
(III) a $C_{1-6}$ alkoxy group (e.g., methoxy),
(IV) a mono- or di-$C_{1-6}$ alkylamino group (e.g., dimethylamino), and
(V) a $C_{3-10}$ cycloalkyl group (e.g., cyclopropyl),
(v) an optionally halogenated $C_{1-6}$ alkoxy group (e.g., methoxy, difluoromethoxy),
(vi) a $C_{1-6}$ alkyl-carbonyl group (e.g., acetyl) optionally substituted by 1 to 3 substituents selected from
(I) a hydroxy group, and
(II) a $C_{1-6}$ alkoxy group (e.g., methoxy),
(vii) a $C_{1-6}$ alkoxy-carbonyl group (e.g., tert-butoxycarbonyl),
(viii) a $C_{3-10}$ cycloalkyl group (e.g., cyclopropyl),
(ix) a $C_{3-10}$ cycloalkyl-carbonyl group (e.g., cyclopropylcarbonyl),
(x) a $C_{1-6}$ alkylsulfonyl group (e.g., methylsulfonyl), and
(xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), and
(o) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl))
(the two substituents on the benzene ring are optionally bonded to each other to form a 5- or 6-membered monocyclic aromatic heterocycle (e.g., pyrrole), a 3- to 8-membered monocyclic non-aromatic heterocycle (e.g., pyrroline, dihydrofuran, tetrahydropyridine, dihydrooxazine, tetrahydroazepine, tetrahydrooxazepine) or a $C_{5-6}$ cycloalkene ring (e.g., cyclopentene) (e.g., indole, indoline, isoindoline, dihydrobenzofuran, tetrahydroquinoline, tetrahydroisoquinoline, dihydrobenzoxazine, tetrahydrobenzazepine, tetrahydrobenzoxazepine, indane), each of which is optionally substituted by 1 to 3 substituents selected from
  (a) an oxo group,
  (b) a $C_{1-6}$ alkyl group (e.g., methyl, ethyl) optionally substituted by 1 to 3 substituents selected from
    (i) a halogen atom (e.g., a fluorine atom),
    (ii) a hydroxy group,
    (iii) a carboxy group,
    (iv) a $C_{1-6}$ alkoxy group (e.g., methoxy),
    (v) a $C_{1-6}$ alkyl-carbonyl group (e.g., acetyl),
    (vi) a mono- or di-$C_{1-6}$ alkylamino group (e.g., dimethylamino), and
    (vii) a 3- to 14-membered (preferably 4- to 10-membered) non-aromatic heterocyclic group (preferably a 3- to 8-membered monocyclic non-aromatic heterocyclic group (e.g., piperidyl, oxetanyl)) optionally substituted by 1 to 3 $C_{1-6}$ alkyl groups (e.g., methyl),
  (c) a $C_{3-10}$ cycloalkyl group (e.g., cyclobutyl),
  (d) a formyl group,
  (e) a $C_{1-6}$ alkyl-carbonyl group (e.g., acetyl, propanoyl, butanoyl, 2-methylpropanoyl) optionally substituted by 1 to 3 substituents selected from
    (i) a halogen atom (e.g., a fluorine atom),
    (ii) a hydroxy group,
    (iii) a $C_{1-6}$ alkoxy group (e.g., methoxy),
    (iv) a $C_{1-6}$ alkyl-carbonyloxy group (e.g., acetyloxy),
    (v) a mono- or di-$C_{1-6}$ alkylamino group (e.g., dimethylamino, N-ethyl-N-methylamino), and
    (vi) a 3- to 14-membered (preferably 4- to 10-membered) non-aromatic heterocyclic group (preferably a 3- to 8-membered monocyclic non-aromatic heterocyclic group (e.g., morpholinyl)),
  (f) a $C_{1-6}$ alkoxy-carbonyl group (e.g., tert-butoxycarbonyl),
  (g) a 5- to 14-membered (preferably 5- to 10-membered) aromatic heterocyclic group (preferably a 5- to 6-membered monocyclic aromatic heterocyclic group (e.g., pyrimidinyl)) optionally substituted by 1 to 3 $C_{1-6}$ alkyl groups (e.g., methyl),
  (h) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl, oxetanyl)) optionally substituted by 1 to 3 $C_{1-6}$ alkyl groups (e.g., methyl), and
  (i) a 3- to 14-membered (preferably 4- to 10-membered) non-aromatic heterocyclylcarbonyl group (preferably a 3- to 8-membered monocyclic non-aromatic heterocyclycarbonyl group (e.g., piperidylcarbonyl)) optionally substituted by 1 to 3 $C_{1-6}$ alkyl groups (e.g., methyl)),
(2) a pyridine ring optionally further substituted by 1 to 3 substituents selected from
  (a) a $C_{1-6}$ alkyl group (e.g., methyl),
  (b) an optionally halogenated $C_{1-6}$ alkoxy group (e.g., methoxy, trifluoromethoxy, 2,2,2-trifluoroethoxy),
  (c) a $C_{3-10}$ cycloalkyl group (e.g., cyclohexyl) optionally substituted by 1 to 3 halogen atoms (e.g., a fluorine atom),
  (d) an amino group, and
  (e) a 3- to 14-membered (preferably 4- to 10-membered) non-aromatic heterocyclic group (preferably a 3- to 8-membered monocyclic non-aromatic heterocyclic group (e.g., piperidyl, azetidinyl, piperazinyl, diazepanyl, tetrahydropyranyl)) optionally substituted by 1 to 3 substituents selected from
    (i) a hydroxy group,
    (ii) a $C_{1-6}$ alkyl group (e.g., methyl, ethyl) optionally substituted by 1 to 3 substituents selected from
      (I) a halogen atom (e.g., a fluorine atom), and
      (II) a 3- to 14-membered (preferably 4- to 10-membered) non-aromatic heterocyclic group (preferably 3- to 8-membered monocyclic non-aromatic heterocyclic group (e.g., morpholinyl, oxetanyl)),
    (iii) an optionally halogenated $C_{1-6}$ alkyl-carbonyl group (e.g., trifluoroacetyl),
    (iv) a $C_{1-6}$ alkoxy-carbonyl group (e.g., tert-butoxycarbonyl),
    (v) a $C_{3-10}$ cycloalkyl group (e.g., cyclopropyl, cyclohexyl) optionally substituted by 1 to 3 halogen atoms (e.g., a fluorine atom), and
    (vi) a 3- to 14-membered (preferably 4- to 10-membered) non-aromatic heterocyclic group (preferably a 3- to 8-membered monocyclic non-aromatic heterocyclic group (e.g., morpholinyl, tetrahydrofuryl, tetrahydropyranyl)),
(3) a pyrimidine ring optionally further substituted by 1 to 3 substituents selected from
  (a) a $C_{1-6}$ alkoxy group (e.g., methoxy), and
  (b) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)),
(4) a pyridazine ring,
(5) a pyrazine ring,
(6) a pyrazole ring optionally further substituted by 1 to 3 substituents selected from
  (a) a halogen atom (e.g., a chlorine atom),
  (b) a cyano group,
  (c) a carboxy group,
  (d) a $C_{1-6}$ alkyl group (e.g., methyl, ethyl, propyl, isopropyl, butyl, isobutyl, sec-butyl, tert-butyl, 2,2-dimethylpropyl) optionally substituted by 1 to 5 substituents selected from
    (i) a $C_{3-10}$ cycloalkyl group (e.g., cyclopropyl, cyclobutyl, cyclohexyl) optionally substituted by 1 to 3 substituents selected from
      (I) an amino group,
      (II) a hydroxy group,
      (III) an oxo group,
      (IV) a $C_{1-6}$ alkyl group (e.g., methyl), and
      (V) a 3- to 14-membered (preferably 4- to 10-membered) non-aromatic heterocyclic group (preferably a 3- to 8-membered monocyclic non-aromatic heterocyclic group (e.g., morpholinyl)),
    (ii) a hydroxy group,
    (iii) a cyano group,
    (iv) a halogen atom (e.g., a fluorine atom),
    (v) a carboxy group,
    (vi) a $C_{1-6}$ alkoxy group (e.g., methoxy, ethoxy) optionally substituted by 1 to 3 substituents selected from
      (I) a halogen atom (e.g., a fluorine atom), and
      (II) a hydroxy group,
    (vii) a $C_{1-6}$ alkoxy-carbonyl group (e.g., ethoxycarbonyl),
    (viii) a $C_{1-6}$ alkylsulfonyl group (e.g., methylsulfonyl),
    (ix) an amino group optionally mono- or di-substituted by substituent(s) selected from (I) a $C_{1-6}$ alkyl-carbonyl group (e.g., acetyl),
(II) a $C_{1-6}$ alkoxy-carbonyl group (e.g., tert-butoxycarbonyl),
(III) a $C_{1-6}$ alkylsulfonyl group (e.g., methylsulfonyl),
(IV) a $C_{6-14}$ aryl-carbonyl group (e.g., benzoyl), and
(V) a carbamoyl group,
(x) a carbamoyl group optionally mono- or di-substituted by substituent(s) selected from
(I) a $C_{1-6}$ alkyl group (e.g., ethyl), and
(II) a $C_{6-14}$ aryl group (e.g., phenyl),
(xi) a 5- to 14-membered (preferably 5- to 10-membered) aromatic heterocyclic group (e.g., pyridyl, isoxazolyl, benzimidazolyl) optionally substituted by 1 to 3 substituents selected from
(I) a $C_{1-6}$ alkyl group (e.g., methyl), and
(II) a $C_{1-6}$ alkoxy group (e.g., methoxy),
(xii) a 3- to 14-membered (preferably 4- to 10-membered) non-aromatic heterocyclic group (e.g., azetidinyl, pyrrolidinyl, piperidyl, morpholinyl, oxetanyl, tetrahydrofuryl, tetrahydropyranyl, dihydropyridyl, dihydrotriazolyl, tetrahydrooxazolyl, dihydroquinazolinyl, 1,4-dioxaspiro[4.5]decyl) optionally substituted by 1 to 3 substituents selected from
(I) an oxo group,
(II) a hydroxy group,
(III) a carbamoyl group,
(IV) a $C_{1-6}$ alkyl group (e.g., methyl) optionally substituted by 1 to 3 hydroxy groups,
(V) a $C_{1-6}$ alkoxy-carbonyl group (e.g., tert-butoxycarbonyl),
(VI) a $C_{3-10}$ cycloalkyl group (e.g., cyclobutyl),
(VII) a $C_{7-16}$ aralkyl group (e.g., benzyl), and
(VIII) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl)), and
(xiii) a 3- to 14-membered (preferably 4- to 10-membered) non-aromatic heterocyclylcarbonyl group (preferably a 3- to 8-membered monocyclic non-aromatic heterocyclylcarbonyl group (e.g., morpholinylcarbonyl)),
(e) a $C_{2-6}$ alkynyl group (e.g., (prop-2-ynyl)),
(f) a $C_{1-6}$ alkoxy group (e.g., methoxy, ethoxy, propyloxy) optionally substituted by 1 to 5 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom),
(g) a $C_{3-10}$ cycloalkyl group (the $C_{3-10}$ cycloalkyl group is optionally fused with a benzene ring, or optionally bridged or may be a spiro group; e.g., cyclopropyl, cyclobutyl, cyclopentyl, cyclohexyl, indanyl, bicyclo[2.2.1]heptyl, spiro[3.3]hexyl) optionally substituted by 1 to 3 substituents selected from
(i) an oxo group,
(ii) a hydroxy group,
(iii) a carbamoyl group,
(iv) a carboxy group,
(v) a $C_{1-6}$ alkyl group (e.g., methyl) optionally substituted by 1 to 3 substituents selected from
(I) a hydroxy group,
(II) a carboxy group,
(III) a carbamoyl group, and
(IV) a 3- to 14-membered (preferably 4- to 10-membered) non-aromatic heterocyclic group (preferably a 3- to 8-membered monocyclic non-aromatic heterocyclic group (e.g., morpholinyl)),
(vi) a $C_{1-6}$ alkoxy-carbonyl group (e.g., ethoxycarbonyl),
(vii) a 3- to 14-membered (preferably 4- to 10-membered) non-aromatic heterocyclic group (preferably a 3- to 8-membered monocyclic non-aromatic heterocyclic group (e.g., azetidinyl, pyrrolidinyl, morpholinyl, 2-oxa-6-azaspiro[3.3]heptyl, 3-oxa-8-azabicyclo[3.2.1]octyl)) optionally substituted by 1 to 3 substituents selected from
(I) a halogen atom (e.g., a fluorine atom),
(II) a hydroxy group, and
(III) a $C_{1-6}$ alkyl group (e.g., methyl) optionally substituted by 1 to 3 substituents selected from a halogen atom (e.g., a fluorine atom) and a hydroxy group, and
(viii) an amino group optionally mono- or di-substituted by substituent(s) selected from
(I) a $C_{1-6}$ alkoxy-carbonyl group (e.g., tert-butoxycarbonyl), and
(II) a 3- to 14-membered (preferably 4- to 10-membered) non-aromatic heterocyclic group (preferably a 3- to 8-membered monocyclic non-aromatic heterocyclic group (e.g., tetrahydropyranyl)),
(h) an optionally halogenated $C_{1-6}$ alkyl-carbonyl group (e.g., acetyl, propionyl),
(i) a $C_{1-6}$ alkoxy-carbonyl group (e.g., ethoxycarbonyl),
(j) a $C_{6-14}$ aryl group (e.g., phenyl),
(k) a $C_{7-16}$ aralkyl group (e.g., benzyl),
(l) a 5- to 14-membered (preferably 5- to 10-membered) aromatic heterocyclic group (preferably a 5- to 6-membered monocyclic aromatic heterocyclic group (e.g., pyridyl, pyrazolyl, thienyl)) optionally substituted by 1 to 3 $C_{1-6}$ alkoxy groups (e.g., methoxy),
(m) a 3- to 14-membered (preferably 4- to 10-membered) non-aromatic heterocyclic group (preferably a 3- to 8-membered monocyclic non-aromatic heterocyclic group (e.g., oxetanyl, piperidyl, azetidinyl, pyrrolidinyl, morpholinyl, azepanyl, tetrahydrofuryl, tetrahydropyranyl, tetrahydrothiopyranyl, dihydropyridyl, 8-azabicyclo[3.2.1]octyl, 2-azaspiro[3.3]heptyl)) optionally substituted by 1 to 3 substituents selected from
(i) an oxo group,
(ii) a hydroxy group,
(iii) a $C_{1-6}$ alkyl group (e.g., methyl, ethyl, propyl, isopropyl, isobutyl, 3,3-dimethylbutyl) optionally substituted by 1 to 3 substituents selected from
(I) a halogen atom (e.g., a fluorine atom),
(II) a hydroxy group,
(III) a cyano group,
(IV) a $C_{1-6}$ alkoxy group (e.g., methoxy, ethoxy) optionally substituted by 1 to 3 substituents selected from
(A) a halogen atom (e.g., a fluorine atom),
(B) a $C_{1-6}$ alkyl-carbonyloxy group (e.g., acetyloxy, 2-methylpropanoyloxy, 2,2-dimethylpropanoyloxy, 3-methylbutanoyloxy), and
(C) a $C_{1-6}$ alkoxy-carbonyloxy group (e.g., ethoxycarbonyloxy, isopropoxycarbonyloxy),
(V) a $C_{1-6}$ alkyl-carbonyloxy group (e.g., acetyloxy),
(VI) a $C_{3-10}$ cycloalkyl group (e.g., cyclopropyl), (VII) a 5- to 14-membered (preferably 5- to 10-membered) aromatic heterocyclic group (preferably a 5- to 6-membered monocyclic aromatic heterocyclic group (e.g., pyridyl, pyrazolyl, pyrrolyl, thiazolyl, thienyl, pyrimidinyl)) optionally substituted by 1 to 3 $C_{1-6}$ alkyl groups (e.g., methyl), and (VIII) a 3- to 14-membered (preferably 4- to 10-membered) non-aromatic heterocyclic group (preferably a 3- to 8-membered monocyclic non-aromatic heterocyclic group (e.g., oxetanyl)), (iv) a $C_{3-10}$ cycloalkyl group (e.g., cyclopropyl, cyclobutyl, cyclopentyl, cyclohexyl) optionally substituted by 1 to 3 substituents selected from (I) a halogen atom (e.g., a fluorine atom), (II) a hydroxy group, (III) a $C_{1-6}$ alkyl group (e.g., methyl) optionally substituted by 1 to 3 $C_{1-6}$ alkoxy groups (e.g., methoxy), and (IV) a $C_{1-6}$ alkoxy group (e.g., methoxy), (v) a $C_{6-14}$ aryl group (e.g., phenyl) optionally substituted by 1 to 3 halogen atoms (e.g., a fluorine atom), (vi) a $C_{7-16}$ aralkyl group (e.g., benzyl), (vii) a $C_{1-6}$ alkyl-carbonyl group (e.g., acetyl), (viii) a $C_{1-6}$ alkoxy-carbonyl group (e.g., tert-butoxycarbonyl), (ix) a 5- to 14-membered (preferably 5- to 10-membered) aromatic heterocyclic group (preferably a 5- to 6-membered monocyclic aromatic heterocyclic group (e.g., pyrimidinyl, pyridyl)) optionally substituted by 1 to 3 $C_{1-6}$ alkyl groups (e.g., methyl), and (x) a 3- to 14-membered (preferably 4- to 10-membered) non-aromatic heterocyclic group (preferably a 3- to 8-membered monocyclic non-aromatic heterocyclic group (e.g., oxetanyl, piperidyl, tetrahydrofuryl, tetrahydropyranyl, oxepanyl, dioxepanyl, 1,1-dioxidotetrahydrothiopyranyl, dioxanyl, 2-oxabicyclo[2.2.2]octyl)) optionally substituted by 1 to 3 substituents selected from (I) a halogen atom (e.g., a fluorine atom), (II) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy), (III) a $C_{3-10}$ cycloalkyl group (e.g., cyclopropyl), (VI) a cyano group, and (V) a deuterium atom, (n) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)), and (o) a 3- to 14-membered (preferably 4- to 10-membered) non-aromatic heterocyclylcarbonyl group (preferably a 3- to 8-membered monocyclic non-aromatic heterocyclylcarbonyl group (e.g., piperidylcarbonyl, morpholinylcarbonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)), (7) a thiazole ring (the two substituents on the thiazole ring are optionally bonded to each other to form a benzene ring (e.g., benzothiazole ring)), (8) an isothiazole ring optionally further substituted by 1 to 3 substituents selected from (a) a $C_{1-6}$ alkyl group (e.g., methyl) optionally substituted by 1 to 3 hydroxy groups, (9) an imidazole ring optionally further substituted by 1 to 3 substituents selected from (a) a $C_{1-6}$ alkyl group (e.g., methyl) optionally substituted by 1 to 3 hydroxy groups (the two substituents on the imidazole ring are optionally bonded to each other to form a benzene ring (e.g., benzimidazole ring)),

(10) an isoxazole ring optionally further substituted by 1 to 3 $C_{1-6}$ alkyl groups (e.g., methyl),

(11) a thiadiazole ring optionally further substituted by 1 to 3 substituents selected from (a) a $C_{6-14}$ aryl group (e.g., phenyl) optionally substituted by 1 to 3 halogen atoms (e.g., a chlorine atom), or

(12) a thiophene ring optionally further substituted by 1 to 3 cyano groups (the two substituents on the thiophene ring are optionally bonded to each other to form a $C_{5-6}$ cycloalkene ring (e.g., cyclopentene, cyclohexene) (e.g., tetrahydrobenzothiophene ring, cyclopentathiophene ring)).

As another embodiment, Ring A is more preferably an optionally further substituted pyrazine ring.

In this embodiment, Ring A is further more preferably a pyrazole ring optionally further substituted by 1 to 3 substituents selected from (a) a halogen atom (e.g., a chlorine atom), (b) a cyano group, (c) a carboxy group, (d) a $C_{1-6}$ alkyl group (e.g., methyl, ethyl, propyl, isopropyl, butyl, isobutyl, sec-butyl, tert-butyl, 2,2-dimethylpropyl) optionally substituted by 1 to 5 substituents selected from (i) a $C_{3-10}$ cycloalkyl group (e.g., cyclopropyl, cyclobutyl, cyclohexyl) optionally substituted by 1 to 3 substituents selected from (I) an amino group, (II) a hydroxy group, (III) an oxo group, (IV) a $C_{1-6}$ alkyl group (e.g., methyl), and (V) a 3- to 14-membered (preferably 4- to 10-membered) non-aromatic heterocyclic group (preferably a 3- to 8-membered monocyclic non-aromatic heterocyclic group (e.g., morpholinyl)), (ii) a hydroxy group, (iii) a cyano group, (iv) a halogen atom (e.g., a fluorine atom), (v) a carboxy group, (vi) a $C_{1-6}$ alkoxy group (e.g., methoxy, ethoxy) optionally substituted by 1 to 3 substituents selected from (I) a halogen atom (e.g., a fluorine atom), and (II) a hydroxy group, (vii) a $C_{1-6}$ alkoxy-carbonyl group (e.g., ethoxycarbonyl), (viii) a $C_{1-6}$ alkylsulfonyl group (e.g., methylsulfonyl), (ix) an amino group optionally mono- or di-substituted by substituent(s) selected from (I) a $C_{1-6}$ alkyl-carbonyl group (e.g., acetyl), (II) a $C_{1-6}$ alkoxy-carbonyl group (e.g., tert-butoxycarbonyl), (III) a $C_{1-6}$ alkylsulfonyl group (e.g., methylsulfonyl), (IV) a $C_{6-14}$ aryl-carbonyl group (e.g., benzoyl), and (V) a carbamoyl group, (x) a carbamoyl group optionally mono- or di-substituted by substituent(s) selected from (I) a $C_{1-6}$ alkyl group (e.g., ethyl), and (II) a $C_{6-14}$ aryl group (e.g., phenyl), (xi) a 5- to 14-membered (preferably 5- to 10-membered) aromatic heterocyclic group (e.g., pyridyl, isoxazolyl, benzimidazolyl) optionally substituted by 1 to 3 substituents selected from
(I) a $C_{1-6}$ alkyl group (e.g., methyl), and
(II) a $C_{1-6}$ alkoxy group (e.g., methoxy),
(xii) a 3- to 14-membered (preferably 4- to 10-membered) non-aromatic heterocyclic group (e.g., azetidinyl, pyrrolidinyl, piperidyl, morpholinyl, oxetanyl, tetrahydrofuryl, tetrahydropyranyl, dihydropyridyl, dihydrotriazolyl, tetrahydrooxazolyl, dihydroquinazolinyl, 1,4-dioxaspiro[4.5]decyl) optionally substituted by 1 to 3 substituents selected from
(I) an oxo group,
(II) a hydroxy group,
(III) a carbamoyl group,
(IV) a $C_{1-6}$ alkyl group (e.g., methyl) optionally substituted by 1 to 3 hydroxy groups,
(V) a $C_{1-6}$ alkoxy-carbonyl group (e.g., tert-butoxycarbonyl),
(VI) a $C_{3-10}$ cycloalkyl group (e.g., cyclobutyl),
(VII) a $C_{7-16}$ aralkyl group (e.g., benzyl), and
(VIII) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl)), and
(xiii) a 3- to 14-membered (preferably 4- to 10-membered) non-aromatic heterocyclylcarbonyl group (preferably a 3- to 8-membered monocyclic non-aromatic heterocyclylcarbonyl group (e.g., morpholinylcarbonyl)),
(e) a $C_{2-6}$ alkynyl group (e.g., (prop-2-ynyl)),
(f) a $C_{1-6}$ alkoxy group (e.g., methoxy, ethoxy, propyloxy) optionally substituted by 1 to 5 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom),
(g) a $C_{3-10}$ cycloalkyl group (the $C_{3-10}$ cycloalkyl group is optionally fused with a benzene ring, or optionally bridged or may be a spiro group; e.g., cyclopropyl, cyclobutyl, cyclopentyl, cyclohexyl, indanyl, bicyclo[2.2.1]heptyl, spiro[3.3]hexyl) optionally substituted by 1 to 3 substituents selected from
(i) an oxo group,
(ii) a hydroxy group,
(iii) a carbamoyl group,
(iv) a carboxy group,
(v) a $C_{1-6}$ alkyl group (e.g., methyl) optionally substituted by 1 to 3 substituents selected from
(I) a hydroxy group,
(II) a carboxy group,
(III) a carbamoyl group, and
(IV) a 3- to 14-membered (preferably 4- to 10-membered) non-aromatic heterocyclic group (preferably a 3- to 8-membered monocyclic non-aromatic heterocyclic group (e.g., morpholinyl)),
(vi) a $C_{1-6}$ alkoxy-carbonyl group (e.g., ethoxycarbonyl),
(vii) a 3- to 14-membered (preferably 4- to 10-membered) non-aromatic heterocyclic group (preferably a 3- to 8-membered monocyclic non-aromatic heterocyclic group (e.g., azetidinyl, pyrrolidinyl, morpholinyl, 2-oxa-6-azaspiro[3.3]heptyl, 3-oxa-8-azabicyclo[3.2.1]octyl)) optionally substituted by 1 to 3 substituents selected from
(I) a halogen atom (e.g., a fluorine atom),
(II) a hydroxy group, and
(III) a $C_{1-6}$ alkyl group (e.g., methyl) optionally substituted by 1 to 3 substituents selected from a halogen atom (e.g., a fluorine atom) and a hydroxy group, and
(viii) an amino group optionally mono- or di-substituted by substituent(s) selected from
(I) a $C_{1-6}$ alkoxy-carbonyl group (e.g., tert-butoxycarbonyl), and
(II) a 3- to 14-membered (preferably 4- to 10-membered) non-aromatic heterocyclic group (preferably a 3- to 8-membered monocyclic non-aromatic heterocyclic group (e.g., tetrahydropyranyl)),
(h) an optionally halogenated $C_{1-6}$ alkyl-carbonyl group (e.g., acetyl, propionyl),
(i) a $C_{1-6}$ alkoxy-carbonyl group (e.g., ethoxycarbonyl),
(j) a $C_{6-14}$ aryl group (e.g., phenyl),
(k) a $C_{7-16}$ aralkyl group (e.g., benzyl),
(l) a 5- to 14-membered (preferably 5- to 10-membered) aromatic heterocyclic group (preferably a 5- to 6-membered monocyclic aromatic heterocyclic group (e.g., pyridyl, pyrazolyl, thienyl)) optionally substituted by 1 to 3 $C_{1-6}$ alkoxy groups (e.g., methoxy),
(m) a 3- to 14-membered (preferably 4- to 10-membered) non-aromatic heterocyclic group (preferably a 3- to 8-membered monocyclic non-aromatic heterocyclic group (e.g., oxetanyl, piperidyl, azetidinyl, pyrrolidinyl, morpholinyl, azepanyl, tetrahydrofuryl, tetrahydropyranyl, tetrahydrothiopyranyl, dihydropyridyl, 8-azabicyclo[3.2.1]octyl, 2-azaspiro[3.3]heptyl)) optionally substituted by 1 to 3 substituents selected from
(i) an oxo group,
(ii) a hydroxy group,
(iii) a $C_{1-6}$ alkyl group (e.g., methyl, ethyl, propyl, isopropyl, isobutyl, 3,3-dimethylbutyl) optionally substituted by 1 to 3 substituents selected from
(I) a halogen atom (e.g., a fluorine atom),
(II) a hydroxy group,
(III) a cyano group,
(IV) a $C_{1-6}$ alkoxy group (e.g., methoxy, ethoxy) optionally substituted by 1 to 3 substituents selected from
(A) a halogen atom (e.g., a fluorine atom),
(B) a $C_{1-6}$ alkyl-carbonyloxy group (e.g., acetyloxy, 2-methylpropanoyloxy, 2,2-dimethylpropanoyloxy, 3-methylbutanoyloxy), and
(C) a $C_{1-6}$ alkoxy-carbonyloxy group (e.g., ethoxycarbonyloxy, isopropoxycarbonyloxy),
(V) a $C_{1-6}$ alkyl-carbonyloxy group (e.g., acetyloxy),
(VI) a $C_{3-10}$ cycloalkyl group (e.g., cyclopropyl),
(VII) a 5- to 14-membered (preferably 5- to 10-membered) aromatic heterocyclic group (preferably a 5- to 6-membered monocyclic aromatic heterocyclic group (e.g., pyridyl, pyrazolyl, pyrrolyl, thiazolyl, thienyl, pyrimidinyl)) optionally substituted by 1 to 3 $C_{1-6}$ alkyl groups (e.g., methyl), and
(VIII) a 3- to 14-membered (preferably 4- to 10-membered) non-aromatic heterocyclic group (preferably a 3- to 8-membered monocyclic non-aromatic heterocyclic group (e.g., oxetanyl)),
(iv) a $C_{3-10}$ cycloalkyl group (e.g., cyclopropyl, cyclobutyl, cyclopentyl, cyclohexyl) optionally substituted by 1 to 3 substituents selected from (I) a halogen atom (e.g., a fluorine atom),
(II) a hydroxy group,
(III) a $C_{1-6}$ alkyl group (e.g., methyl) optionally substituted by 1 to 3 $C_{1-6}$ alkoxy groups (e.g., methoxy), and
(IV) a $C_{1-6}$ alkoxy group (e.g., methoxy),
(v) a $C_{6-14}$ aryl group (e.g., phenyl) optionally substituted by 1 to 3 halogen atoms (e.g., a fluorine atom),
(vi) a $C_{7-16}$ aralkyl group (e.g., benzyl),
(vii) a $C_{1-6}$ alkyl-carbonyl group (e.g., acetyl),
(viii) a $C_{1-6}$ alkoxy-carbonyl group (e.g., tert-butoxycarbonyl),
(ix) a 5- to 14-membered (preferably 5- to 10-membered) aromatic heterocyclic group (preferably a 5- to 6-membered monocyclic aromatic heterocyclic group (e.g., pyrimidinyl, pyridyl)) optionally substituted by 1 to 3 $C_{1-6}$ alkyl groups (e.g., methyl), and
(x) a 3- to 14-membered (preferably 4- to 10-membered) non-aromatic heterocyclic group (preferably a 3- to 8-membered monocyclic non-aromatic heterocyclic group (e.g., oxetanyl, piperidyl, tetrahydrofuryl, tetrahydropyranyl, oxepanyl, dioxepanyl, 1,1-dioxidotetrahydrothiopyranyl, dioxanyl, 2-oxabicyclo[2.2.2]octyl)) optionally substituted by 1 to 3 substituents selected from
(I) a halogen atom (e.g., a fluorine atom),
(II) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
(III) a $C_{3-10}$ cycloalkyl group (e.g., cyclopropyl),
(VI) a cyano group, and
(V) a deuterium atom,
(n) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)), and
(o) a 3- to 14-membered (preferably 4- to 10-membered) non-aromatic heterocyclylcarbonyl group (preferably a 3- to 8-membered monocyclic non-aromatic heterocyclylcarbonyl group (e.g., piperidylcarbonyl, morpholinylcarbonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)).

In this embodiment, Ring A is still more preferably a pyrazole ring
further substituted (preferably at the 1-position) by one cyclohexyl group optionally substituted by 1 to 3 substituents selected from
(i) an oxo group,
(ii) a hydroxy group,
(iii) a carboxy group,
(iv) a $C_{1-6}$ alkyl group (e.g., methyl) optionally substituted by 1 to 3 substituents selected from
(I) a carboxy group,
(II) a carbamoyl group, and
(III) a 3- to 8-membered monocyclic non-aromatic heterocyclic group (e.g., morpholinyl),
(v) a $C_{1-6}$ alkoxy-carbonyl group (e.g., ethoxycarbonyl), and
(vi) a 3- to 8-membered monocyclic non-aromatic heterocyclic group (e.g., azetidinyl, pyrrolidinyl, morpholinyl, 2-oxa-6-azaspiro[3.3]heptyl, 3-oxa-8-azabicyclo[3.2.1]octyl) optionally substituted by 1 to 3 substituents selected from
(I) a halogen atom (e.g., a fluorine atom),
(II) a hydroxy group, and
(III) a $C_{1-6}$ alkyl group (e.g., methyl) optionally substituted by 1 to 3 substituents selected from a halogen atom (e.g., a fluorine atom) and a hydroxy group, and
further optionally substituted (preferably at the 3-position) by one substituent selected from
(a) an optionally halogenated $C_{1-6}$ alkyl group (e.g., ethyl, isopropyl, tert-butyl, difluoromethyl, trifluoromethyl, 3,3,3-trifluoropropyl, 1,1,2,2,2-pentafluoroethyl),
(b) a $C_{1-6}$ alkoxy group (e.g., methoxy, ethoxy, propoxy) optionally substituted by 1 to 5 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom),
(c) a 3- to 8-membered monocyclic non-aromatic heterocyclyloxy group (e.g., oxetanyloxy),
(d) an optionally halogenated $C_{1-6}$ alkyl-carbonyl group (e.g., acetyl, propionyl),
(e) a $C_{3-10}$ cycloalkyl group (e.g., cyclopropyl, cyclobutyl), and
(f) a cyano group
(preferably further optionally substituted (preferably at the 3-position) by one substituent selected from
(a) an optionally halogenated $C_{1-6}$ alkyl group (e.g., trifluoromethyl, isopropyl),
(b) a $C_{1-6}$ alkoxy group (e.g., methoxy, ethoxy) optionally substituted by 1 to 3 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom), and
(c) a 3- to 8-membered monocyclic non-aromatic heterocyclyloxy group (e.g., oxetanyloxy)).

In this embodiment, Ring A is even more preferably a pyrazole ring
further substituted (preferably at the 1-position) by one cyclohexyl group substituted by one substituent selected from
(i) a nitrogen-containing 3- to 8-membered (preferably 4- to 6-membered) monocyclic non-aromatic heterocyclic group (e.g., azetidinyl, morpholinyl, 3-oxa-8-azabicyclo[3.2.1]octyl) optionally substituted by 1 or 2 substituents selected from
(I) a hydroxy group, and
(II) a $C_{1-6}$ alkyl group (e.g., methyl), and
further substituted (preferably at the 3-position) by one substituent selected from
(a) an optionally halogenated $C_{1-6}$ alkyl group (e.g., isopropyl, tert-butyl, difluoromethyl, trifluoromethyl, 3,3,3-trifluoropropyl, 1,1,2,2,2-pentafluoroethyl),
(b) a $C_{1-6}$ alkoxy group (e.g., methoxy, ethoxy, propoxy) optionally substituted by 1 to 5 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom),
(c) a 3- to 8-membered oxygen-containing monocyclic non-aromatic heterocyclyloxy group (e.g., oxetanyloxy),
(d) an optionally halogenated $C_{1-6}$ alkyl-carbonyl group (e.g., acetyl, propionyl), and (e) a $C_{3-10}$ cycloalkyl group (e.g., cyclopropyl, cyclobutyl) (preferably further substituted (preferably at the 3-position) by one substituent selected from
  (a) an optionally halogenated $C_{1-6}$ alkyl group (e.g., trifluoromethyl, isopropyl),
  (b) a $C_{1-6}$ alkoxy group (e.g., methoxy, ethoxy) optionally substituted by 1 to 3 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom), and
  (c) a 3- to 8-membered oxygen-containing monocyclic non-aromatic heterocyclyloxy group (e.g., oxetanyloxy)).

In this embodiment, Ring A is particularly preferably a pyrazole ring
further substituted (preferably at the 1-position) by one cyclohexyl group substituted by one morpholinyl group, and
further substituted (preferably at the 3-position) by one substituent selected from
  (a) an optionally halogenated $C_{1-6}$ alkyl group (e.g., trifluoromethyl, isopropyl),
  (b) a $C_{1-6}$ alkoxy group (e.g., methoxy, ethoxy) optionally substituted by 1 to 3 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom), and
  (c) a 3- to 8-membered oxygen-containing monocyclic non-aromatic heterocyclyloxy group (e.g., oxetanyloxy).

As another embodiment, Ring A is particularly preferably a pyrazole ring
further substituted (preferably at the 1-position) by one cyclohexyl group substituted by one substituent selected from
  (i) a 3-oxa-8-azabicyclo[3.2.1]octyl group, and
  (ii) an azetidinyl group optionally substituted by 1 or 2 substituents selected from
    (I) a hydroxy group, and
    (II) a $C_{1-6}$ alkyl group (e.g., methyl), and
further substituted (preferably at the 3-position) by one substituent selected from
  (a) an optionally halogenated $C_{1-6}$ alkoxy group (e.g., 2,2-difluoroethoxy, 2,2,2-trifluoroethoxy).

As another embodiment, Ring A is still more preferably a pyrazole ring
further substituted (preferably at the 1-position) by one 2-azaspiro[3.3]heptyl group optionally substituted by 1 to 3 substituents selected from
  (i) a $C_{1-6}$ alkyl group (e.g., methyl, ethyl, propyl, isopropyl, isobutyl) optionally substituted by 1 to 3 substituents selected from
    (I) a halogen atom (e.g., a fluorine atom),
    (II) a hydroxy group,
    (III) a $C_{1-6}$ alkoxy group (e.g., methoxy, ethoxy) optionally substituted by 1 to 3 substituents selected from
      (A) a halogen atom (e.g., a fluorine atom),
      (B) a $C_{1-6}$ alkyl-carbonyloxy group (e.g., acetyloxy, 2-methylpropanoyloxy, 2,2-dimethylpropanoyloxy, 3-methylbutanoyloxy), and
      (C) a $C_{1-6}$ alkoxy-carbonyloxy group (e.g., ethoxycarbonyloxy, isopropoxycarbonyloxy),
    (IV) a $C_{1-6}$ alkyl-carbonyloxy group (e.g., acetyloxy), and
    (V) a 5- to 6-membered monocyclic aromatic heterocyclic group (e.g., pyrimidinyl),
  (ii) a $C_{3-10}$ cycloalkyl group (e.g., cyclobutyl, cyclopentyl, cyclohexyl) optionally substituted by 1 to 3 substituents selected from
    (I) a halogen atom (e.g., a fluorine atom),
    (II) a hydroxy group,
    (III) a $C_{1-6}$ alkyl group (e.g., methyl) optionally substituted by 1 to 3 $C_{1-6}$ alkoxy groups (e.g., methoxy), and
    (IV) a $C_{1-6}$ alkoxy group (e.g., methoxy),
  (iii) a $C_{1-6}$ alkoxy-carbonyl group (e.g., tert-butoxycarbonyl),
  (iv) a $C_{6-14}$ aryl group (e.g., phenyl) optionally substituted by 1 to 3 halogen atoms (e.g., a fluorine atom),
  (v) a 5- to 6-membered monocyclic aromatic heterocyclic group (e.g., pyrimidinyl, pyridyl) optionally substituted by 1 to 3 $C_{1-6}$ alkyl groups (e.g., methyl), and
  (vi) a 3- to 8-membered monocyclic non-aromatic heterocyclic group (e.g., oxetanyl, tetrahydrofuryl, tetrahydropyranyl, oxepanyl, dioxepanyl, dioxanyl, 2-oxabicyclo[2.2.2]octyl) optionally substituted by 1 to 3 substituents selected from
    (I) a halogen atom (e.g., a fluorine atom),
    (II) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
    (III) a $C_{3-10}$ cycloalkyl group (e.g., cyclopropyl),
    (VI) a cyano group, and
    (V) a deuterium atom, and
further optionally substituted (preferably at the 3-position) by one substituent selected from
  (a) an optionally halogenated $C_{1-6}$ alkyl group (e.g., ethyl, isopropyl, tert-butyl, difluoromethyl, trifluoromethyl, 3,3,3-trifluoropropyl, 1,1,2,2,2-pentafluoroethyl),
  (b) a $C_{1-6}$ alkoxy group (e.g., methoxy, ethoxy, propoxy) optionally substituted by 1 to 5 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom),
  (c) a 3- to 8-membered monocyclic non-aromatic heterocyclyloxy group (e.g., oxetanyloxy),
  (d) an optionally halogenated $C_{1-6}$ alkyl-carbonyl group (e.g., acetyl, propionyl),
  (e) a $C_{3-10}$ cycloalkyl group (e.g., cyclopropyl, cyclobutyl), and
  (f) a cyano group
(preferably further substituted (preferably at the 3-position) by one substituent selected from
  (a) an optionally halogenated $C_{1-6}$ alkyl group (e.g., isopropyl, tert-butyl, difluoromethyl, trifluoromethyl, 3,3,3-trifluoropropyl, 1,1,2,2,2-pentafluoroethyl),
  (b) an optionally halogenated $C_{1-6}$ alkoxy group (e.g., trifluoromethoxy, 2,2,2-trifluoroethoxy, 2,2,3,3,3-pentafluoropropoxy),
  (c) a $C_{1-6}$ alkyl-carbonyl group (e.g., acetyl, propionyl),
  (d) a 3- to 8-membered monocyclic non-aromatic heterocyclyloxy group (e.g., oxetanyloxy), and
  (e) a $C_{3-10}$ cycloalkyl group (e.g., cyclobutyl)).

In this embodiment, Ring A is even more preferably a pyrazole ring
further substituted (preferably at the 1-position) by one 2-azaspiro[3.3]heptyl group substituted by one substituent selected from (i) a $C_{1-6}$ alkyl group (e.g., methyl, ethyl, propyl, isobutyl) optionally substituted by 1 to 3 substituents selected from
  (I) a halogen atom (e.g., a fluorine atom),
  (II) a hydroxy group,
  (III) a $C_{1-6}$ alkoxy group (e.g., methoxy, ethoxy) optionally substituted by 1 to 3 substituents selected from
    (A) a halogen atom (e.g., a fluorine atom),
    (B) a $C_{1-6}$ alkyl-carbonyloxy group (e.g., acetyloxy, 2-methylpropanoyloxy, 2,2-dimethylpropanoyloxy, 3-methylbutanoyloxy), and
    (C) a $C_{1-6}$ alkoxy-carbonyloxy group (e.g., ethoxycarbonyloxy, isopropoxycarbonyloxy),
  (IV) a $C_{1-6}$ alkyl-carbonyloxy group (e.g., acetyloxy), and
  (V) a 5- to 6-membered nitrogen-containing monocyclic aromatic heterocyclic group (e.g., pyrimidinyl),
(ii) a $C_{3-10}$ cycloalkyl group (e.g., cyclobutyl, cyclopentyl, cyclohexyl) optionally substituted by 1 to 3 substituents selected from
  (I) a halogen atom (e.g., a fluorine atom),
  (II) a hydroxy group,
  (III) a $C_{1-6}$ alkyl group (e.g., methyl) optionally substituted by 1 to 3 $C_{1-6}$ alkoxy groups (e.g., methoxy), and
  (IV) a $C_{1-6}$ alkoxy group (e.g., methoxy),
(iii) a $C_{1-6}$ alkoxy-carbonyl group (e.g., tert-butoxycarbonyl),
(iv) a $C_{6-14}$ aryl group (e.g., phenyl) optionally substituted by 1 to 3 halogen atoms (e.g., a fluorine atom),
(v) a 5- to 6-membered nirtogen-containing monocyclic aromatic heterocyclic group (e.g., pyrimidinyl, pyridyl) optionally substituted by 1 to 3 $C_{1-6}$ alkyl groups (e.g., methyl), and
(vi) a 3- to 8-membered oxygen-containing monocyclic non-aromatic heterocyclic group (e.g., oxetanyl, tetrahydrofuryl, tetrahydropyranyl, oxepanyl, dioxepanyl, dioxanyl, 2-oxabicyclo[2.2.2]octyl) optionally substituted by 1 to 3 substituents selected from
  (I) a halogen atom (e.g., a fluorine atom),
  (II) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
  (III) a $C_{3-10}$ cycloalkyl group (e.g., cyclopropyl),
  (VI) a cyano group, and
  (V) a deuterium atom, and
further substituted (preferably at the 3-position) by one substituent selected from
  (a) an optionally halogenated $C_{1-6}$ alkyl group (e.g., isopropyl, tert-butyl, difluoromethyl, trifluoromethyl, 3,3,3-trifluoropropyl, 1,1,2,2,2-pentafluoroethyl),
  (b) a $C_{1-6}$ alkoxy group (e.g., methoxy, ethoxy, propoxy) optionally substituted by 1 to 5 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom),
  (c) a 3- to 8-membered oxygen-containing monocyclic non-aromatic heterocyclyloxy group (e.g., oxetanyloxy),
  (d) an optionally halogenated $C_{1-6}$ alkyl-carbonyl group (e.g., acetyl, propionyl), and
  (e) a $C_{3-10}$ cycloalkyl group (e.g., cyclopropyl, cyclobutyl)

(preferably further substituted (preferably at the 3-position) by one substituent selected from
  (a) an optionally halogenated $C_{1-6}$ alkyl group (e.g., isopropyl, tert-butyl, difluoromethyl, trifluoromethyl, 3,3,3-trifluoropropyl, 1,1,2,2,2-pentafluoroethyl),
  (b) an optionally halogenated $C_{1-6}$ alkoxy group (e.g., trifluoromethoxy, 2,2,2-trifluoroethoxy, 2,2,3,3,3-pentafluoropropoxy),
  (c) a 3- to 8-membered oxygen-containing monocyclic non-aromatic heterocyclyloxy group (e.g., oxetanyloxy),
  (d) a $C_{1-6}$ alkyl-carbonyl group (e.g., acetyl, propionyl), and
  (e) a $C_{3-10}$ cycloalkyl group (e.g., cyclobutyl)).

As another embodiment, Ring A is still more preferably a pyrazole ring
further substituted (preferably at the 1-position) by one piperidyl group optionally substituted by 1 to 3 substituents selected from
  (i) a hydroxy group,
  (ii) a $C_{1-6}$ alkyl group (e.g., methyl, ethyl, isopropyl, 3,3-dimethylbutyl) optionally substituted by 1 to 3 substituents selected from
    (I) a halogen atom (e.g., a fluorine atom),
    (II) a hydroxy group,
    (III) a cyano group,
    (IV) a $C_{1-6}$ alkoxy group (e.g., methoxy),
    (V) a $C_{3-10}$ cycloalkyl group (e.g., cyclopropyl),
    (VI) a 5- to 6-membered monocyclic aromatic heterocyclic group (e.g., pyridyl, pyrazolyl, pyrrolyl, thiazolyl, thienyl) optionally substituted by 1 to 3 $C_{1-6}$ alkyl groups (e.g., methyl), and
    (VII) a 3- to 8-membered monocyclic non-aromatic heterocyclic group (e.g., oxetanyl),
  (iii) a $C_{3-10}$ cycloalkyl group (e.g., cyclopropyl, cyclobutyl, cyclohexyl) optionally substituted by 1 to 3 substituents selected from
    (I) a halogen atom (e.g., a fluorine atom), and
    (II) a $C_{1-6}$ alkoxy group (e.g., methoxy),
  (iv) a $C_{7-16}$ aralkyl group (e.g., benzyl),
  (v) a $C_{1-6}$ alkyl-carbonyl group (e.g., acetyl),
  (vi) a $C_{1-6}$ alkoxy-carbonyl group (e.g., tert-butoxycarbonyl), and
  (vii) a 3- to 8-membered monocyclic non-aromatic heterocyclic group (e.g., oxetanyl, piperidyl, tetrahydrofuryl, tetrahydropyranyl, 1,1-dioxidotetrahydrothiopyranyl) optionally substituted by 1 to 3 substituents selected from
    (I) a $C_{1-6}$ alkyl group (e.g., methyl), and
    (II) a $C_{3-10}$ cycloalkyl group (e.g., cyclopropyl), and
    further optionally substituted (preferably at the 3-position) by one substituent selected from
  (a) an optionally halogenated $C_{1-6}$ alkyl group (e.g., ethyl, isopropyl, tert-butyl, difluoromethyl, trifluoromethyl, 3,3,3-trifluoropropyl, 1,1,2,2,2-pentafluoroethyl),
  (b) a $C_{1-6}$ alkoxy group (e.g., methoxy, ethoxy, propoxy) optionally substituted by 1 to 5 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom),
  (c) a 3- to 8-membered monocyclic non-aromatic heterocyclyloxy group (e.g., oxetanyloxy),
  (d) an optionally halogenated $C_{1-6}$ alkyl-carbonyl group (e.g., acetyl, propionyl), (e) a $C_{3-10}$ cycloalkyl group (e.g., cyclopropyl, cyclobutyl), and
(f) a cyano group
(preferably further substituted (preferably at the 3-position) by one substituent selected from
  (a) an optionally halogenated $C_{1-6}$ alkyl group (e.g., ethyl, isopropyl, difluoromethyl, trifluoromethyl),
  (b) an optionally halogenated $C_{1-6}$ alkoxy group (e.g., methoxy, ethoxy, difluoromethoxy, 2-fluoroethoxy, 2,2-difluoroethoxy, 2,2,2-trifluoroethoxy),
  (c) a $C_{3-10}$ cycloalkyl group (e.g., cyclopropyl), and
  (d) a cyano group).

In this embodiment, Ring A is even more preferably a pyrazole ring
further substituted (preferably at the 1-position) by one piperidyl group substituted by one tetrahydropyranyl group, and
further substituted (preferably at the 3-position) by one substituent selected from
  (a) an optionally halogenated $C_{1-6}$ alkyl group (e.g., isopropyl, tert-butyl, difluoromethyl, trifluoromethyl, 3,3,3-trifluoropropyl, 1,1,2,2,2-pentafluoroethyl),
  (b) a $C_{1-6}$ alkoxy group (e.g., methoxy, ethoxy, propoxy) optionally substituted by 1 to 5 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom),
  (c) a 3- to 8-membered oxygen-containing monocyclic non-aromatic heterocyclyloxy group (e.g., oxetanyloxy),
  (d) an optionally halogenated $C_{1-6}$ alkyl-carbonyl group (e.g., acetyl, propionyl), and
  (e) a $C_{3-10}$ cycloalkyl group (e.g., cyclopropyl, cyclobutyl)
(preferably further substituted (preferably at the 3-position) by one substituent selected from
  (a) an optionally halogenated $C_{1-6}$ alkyl group (e.g., isopropyl, trifluoromethyl), and
  (b) an optionally halogenated $C_{1-6}$ alkoxy group (e.g., difluoromethoxy, 2,2,2-trifluoroethoxy)).

Ring B is an optionally further substituted nitrogen-containing 6-membered aromatic heterocycle, and $X^1$, $X^2$ and $X^3$ are each independently a carbon atom or a nitrogen atom.

Examples of the "nitrogen-containing 6-membered aromatic heterocycle" of the "optionally further substituted nitrogen-containing 6-membered aromatic heterocycle" for Ring B include a pyridine ring, a pyrimidine ring, a pyridazine ring and a pyrazine ring.

The "nitrogen-containing 6-membered aromatic heterocycle" of the "optionally further substituted nitrogen-containing 6-membered aromatic heterocycle" for Ring B is preferably a pyrimidine ring, a pyrazine ring or a pyridine ring, more preferably a pyrimidine ring.

The "nitrogen-containing 6-membered aromatic heterocycle" of the "optionally further substituted nitrogen-containing 6-membered aromatic heterocycle" for Ring B optionally further has 1 to 5 (preferably 1 to 3) substituents at substitutable position(s), in addition to —NH-Ring A and Ring C. Examples of the substituent include substituents selected from the above-mentioned Substituent group A. When the number of the substituents is plural, the respective substituents may be the same or different.

Ring B is preferably an optionally further substituted pyrimidine ring ($X^1$ is a carbon atom, $X^2$ is a carbon atom and $X^3$ is a nitrogen atom), an optionally further substituted pyrazine ring ($X^1$ is a carbon atom, $X^2$ is a nitrogen atom and $X^3$ is a carbon atom), or an optionally further substituted pyridine ring ($X^1$ is a carbon atom, $X^2$ is a carbon atom and $X^3$ is a carbon atom).

Ring B is more preferably
(1) a pyrimidine ring ($X^1$ is a carbon atom, $X^2$ is a carbon atom and $X^3$ is a nitrogen atom),
(2) a pyrazine ring ($X^1$ is a carbon atom, $X^2$ is a nitrogen atom and $X^3$ is a carbon atom), or
(3) a pyridine ring ($X^1$ is a carbon atom, $X^2$ is a carbon atom and $X^3$ is a carbon atom).

Ring B is further more preferably a pyrimidine ring ($X^1$ is a carbon atom, $X^2$ is a carbon atom and $X^3$ is a nitrogen atom).

Ring C is an optionally further substituted 6-membered aromatic ring, and $Y^1$, $Y^2$ and $Y^3$ are each independently a carbon atom or a nitrogen atom.

Examples of the "6-membered aromatic ring" of the "optionally further substituted 6-membered aromatic ring" for Ring C include a benzene ring, a pyridine ring, a pyrimidine ring, a pyridazine ring and a pyrazine ring.

The "6-membered aromatic ring" of the "optionally further substituted 6-membered aromatic ring" for Ring C is preferably a benzene ring or a pyridine ring, more preferably a benzene ring.

The "6-membered aromatic ring" of the "optionally further substituted 6-membered aromatic ring" for Ring C optionally further has 1 to 5 (preferably 1 to 3) substituents at substitutable position(s), in addition to Ring B, $R^3$ and —Z—CH($R^1$)($R^2$). Examples of the substituent include substituents selected from the above-mentioned Substituent group A. When the number of the substituents is plural, the respective substituents may be the same or different.

Ring C is preferably an optionally further substituted benzene ring, or an optionally further substituted pyridine ring ($Y^2$ is a carbon atom, $Y^2$ is a carbon atom and $Y^3$ is a nitrogen atom, or $Y^1$ is a nitrogen atom, $Y^2$ is a carbon atom and $Y^3$ is a carbon atom).

Ring C is more preferably an optionally further substituted benzene ring.

As another embodiment, Ring C is more preferably a benzene ring or a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom), each of which is optionally further substituted by 1 to 3 halogen atoms (e.g., a fluorine atom, a chlorine atom).

In this embodiment, Ring C is further more preferably
(1) a benzene ring optionally further substituted by 1 to 3 halogen atoms (e.g., a fluorine atom, a chlorine atom), or
(2) a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom).

Ring C is particularly preferably a benzene ring.

$R^3$ is a substituent.
$R^3$ is preferably
(1) a cyano group,
(2) a halogen atom,
(3) an optionally substituted $C_{1-6}$ alkyl group,
(4) an optionally substituted carbamoyl group, or
(5) an optionally substituted 3- to 14-membered (preferably 4- to 10-membered) non-aromatic heterocyclylcarbonyl group (preferably a 3- to 8-membered monocyclic non-aromatic heterocyclylcarbonyl group).

$R^3$ is more preferably
(1) a cyano group,
(2) a halogen atom (e.g., a fluorine atom, a chlorine atom), (3) an optionally halogenated $C_{1-6}$ alkyl group (e.g., methyl, difluoromethyl, trifluoromethyl),
(4) a carbamoyl group,
(5) a mono- or di-$C_{1-6}$ alkyl-carbamoyl group (e.g., dimethylcarbamoyl), or
(6) a 3- to 14-membered (preferably 4- to 10-membered) non-aromatic heterocyclylcarbonyl group (preferably a 3- to 8-membered monocyclic non-aromatic heterocyclylcarbonyl group (e.g., pyrrolidinylcarbonyl)).

$R^3$ is further more preferably
(1) a cyano group,
(2) a halogen atom (e.g., a fluorine atom, a chlorine atom),
(3) an optionally halogenated $C_{1-6}$ alkyl group (e.g., methyl, difluoromethyl), or
(4) a carbamoyl group.

$R^3$ is still more preferably
(1) a cyano group,
(2) a halogen atom (e.g., a fluorine atom, a chlorine atom, preferably a chlorine atom), or
(3) an optionally halogenated $C_{1-6}$ alkyl group (e.g., methyl, difluoromethyl).

$R^3$ is still further more preferably
(1) a cyano group,
(2) a halogen atom (e.g., a fluorine atom, a chlorine atom, preferably a chlorine atom), or
(3) a $C_{1-6}$ alkyl group (e.g., methyl).

$R^3$ is even more preferably
(1) a cyano group, or
(2) a halogen atom (preferably a chlorine atom).

$R^3$ is particularly preferably a halogen atom (preferably a chlorine atom).

$R^3$ is most preferably a chlorine atom.

Z is an optionally substituted methylene group, —O—, —N($R^Z$)—, —S—, —S(O)— or —S($O_2$)—, and $R^Z$ is a hydrogen atom or a substituent.

Z is preferably
(1) —O—, or
(2) —N($R^Z$)— ($R^Z$ is as defined above).

Z is more preferably
(1) —O—, or
(2) —NH—.

Z is further more preferably —O—.

$R^1$ is a hydrogen atom or a substituent.

$R^1$ is preferably
(1) a hydrogen atom,
(2) an optionally substituted $C_{1-6}$ alkyl group, or
(3) an optionally substituted $C_{3-10}$ cycloalkyl group (e.g., cyclopropyl).

$R^1$ is more preferably
(1) a hydrogen atom,
(2) a $C_{1-6}$ alkyl group (e.g., methyl, ethyl) optionally substituted by 1 to 3 substituents selected from
 (a) a halogen atom (e.g., a fluorine atom), and
 (b) a hydroxy group, or
(3) a $C_{3-10}$ cycloalkyl group (e.g., cyclopropyl).

$R^1$ is further more preferably
(1) a hydrogen atom, or
(2) a $C_{1-6}$ alkyl group (e.g., methyl, ethyl) optionally substituted by 1 to 3 hydroxy groups.

$R^1$ is still more preferably a $C_{1-6}$ alkyl group (e.g., methyl).

$R^2$ is a substituent.
$R^2$ is preferably
(1) an optionally substituted $C_{1-6}$ alkyl group,
(2) an optionally substituted 3- to 14-membered (preferably 4- to 10-membered) non-aromatic heterocyclic group (preferably a 3- to 8-membered monocyclic non-aromatic heterocyclic group), or
(3) an optionally substituted mono- or di-$C_{1-6}$ alkyl-carbamoyl group.

$R^2$ is more preferably
(1) a $C_{1-6}$ alkyl group (e.g., methyl, ethyl, isobutyl) optionally substituted by 1 to 3 substituents selected from
 (a) a 5- to 14-membered (preferably 5- to 10-membered) aromatic heterocyclic group (e.g., triazolyl (e.g., 1,2,4-triazolyl, 1,2,3-triazolyl), tetrazolyl, pyrazolyl, imidazolyl, oxadiazolyl (e.g., 1,2,4-oxadiazolyl, 1,3,4-oxadiazolyl), pyridyl, benzimidazolyl) optionally substituted by 1 to 3 substituents selected from
  (i) a cyano group,
  (ii) a halogen atom (e.g., a fluorine atom),
  (iii) a $C_{1-6}$ alkyl group (e.g., methyl), and
  (iv) a $C_{7-16}$ aralkyl group (e.g., trityl),
 (b) a 3- to 14-membered (preferably 4- to 10-membered) non-aromatic heterocyclic group (preferably a 3- to 8-membered monocyclic non-aromatic heterocyclic group (e.g., imidazolidinyl, morpholinyl, triazolinyl, pyrrolidinyl)) optionally substituted by 1 to 3 substituents selected from
  (i) an oxo group, and
  (ii) a $C_{1-6}$ alkyl group (e.g., methyl),
 (c) a halogen atom (e.g., a fluorine atom),
 (d) a hydroxy group,
 (e) a cyano group,
 (f) an optionally halogenated $C_{1-6}$ alkoxy group (e.g., methoxy, difluoromethoxy),
 (g) a 5- to 14-membered (preferably 5- to 10-membered) aromatic heterocyclyloxy group (preferably a 5- or 6-membered monocyclic aromatic heterocyclyloxy group (e.g., triazolyloxy (e.g., 1,2,4-triazolyloxy))),
 (h) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)),
 (i) an amino group optionally mono- or di-substituted by substituent(s) selected from
  (i) a $C_{1-6}$ alkyl group (e.g., methyl),
  (ii) a $C_{1-6}$ alkyl-carbonyl group (e.g., acetyl) optionally substituted by 1 to 3 $C_{1-6}$ alkoxy groups (e.g., methoxy), and
  (iii) a $C_{1-6}$ alkylsulfonyl group (e.g., methylsulfonyl), and
 (j) a mono- or di-$C_{1-6}$ alkyl-carbamoyl group (e.g., methylcarbamoyl),
(2) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 substituents selected from
 (a) an oxo group, and
 (b) a $C_{1-6}$ alkyl group (e.g., methyl), or
(3) a mono- or di-$C_{1-6}$ alkyl-carbamoyl group (e.g., ethylcarbamoyl) optionally substituted by 1 to 3 halogen atoms (e.g., a fluorine atom).

$R^2$ is further more preferably
(1) a $C_{1-6}$ alkyl group (e.g., methyl, ethyl, isobutyl) optionally substituted by 1 to 3 substituents selected from
 (a) a 5- to 14-membered (preferably 5- to 10-membered) aromatic heterocyclic group (preferably a 5- or 6-membered monocyclic aromatic heterocyclic group (e.g., triazolyl (e.g., 1,2,4-triazolyl, 1,2,3-triazolyl), tetrazolyl, pyrazolyl, imidazolyl, oxadiazolyl (e.g., 1,2,4-oxadiazolyl, 1,3,4-oxadiazolyl), pyridyl)) optionally substituted by 1 to 3 substituents selected from
  (i) a halogen atom (e.g., a fluorine atom), and
  (ii) a $C_{1-6}$ alkyl group (e.g., methyl),
(b) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
(c) a halogen atom (e.g., a fluorine atom),
(d) a hydroxy group,
(e) a cyano group,
(f) an optionally halogenated $C_{1-6}$ alkoxy group (e.g., methoxy, difluoromethoxy),
(g) an amino group optionally mono- or di-substituted by substituent(s) selected from
  (i) a $C_{1-6}$ alkyl-carbonyl group (e.g., acetyl), and
  (ii) a $C_{1-6}$ alkylsulfonyl group (e.g., methylsulfonyl), and
(h) a mono- or di-$C_{1-6}$ alkyl-carbamoyl group (e.g., methylcarbamoyl),
(2) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 substituents selected from
  (a) an oxo group, and
  (b) a $C_{1-6}$ alkyl group (e.g., methyl), or
(3) a mono- or di-$C_{1-6}$ alkyl-carbamoyl group (e.g., ethylcarbamoyl) optionally substituted by 1 to 3 halogen atoms (e.g., a fluorine atom).

$R^2$ is still more preferably a $C_{1-6}$ alkyl group (e.g., methyl) substituted by one substituents selected from
  (a) a 5- or 6-membered monocyclic aromatic heterocyclic group (e.g., tetrazolyl, pyrazolyl) optionally substituted by 1 to 3 halogen atoms (e.g., a fluorine atom), and
  (b) a 3- to 8-membered monocyclic non-aromatic heterocyclic group (e.g., pyrrolidinyl) optionally substituted by 1 to 3 oxo groups.

As another embodiment, $R^2$ is still more preferably a $C_{1-6}$ alkyl group (e.g., methyl) substituted by one substituents selected from
  (a) a 5- or 6-membered monocyclic aromatic heterocyclic group (e.g., tetrazolyl), and
  (b) an optionally halogenated $C_{1-6}$ alkoxy group (e.g., difluoromethoxy).

As another embodiment, $R^2$ is still more preferably a $C_{1-6}$ alkyl group (e.g., methyl) substituted by one substituents selected from
  (a) a 5- or 6-membered monocyclic aromatic heterocyclic group (e.g., triazolyl (e.g., 1,2,4-triazolyl), tetrazolyl, pyrazolyl) optionally substituted by 1 to 3 halogen atoms (e.g., a fluorine atom).

As another embodiment, $R^2$ is still more preferably a $C_{1-6}$ alkyl group (e.g., methyl) optionally substituted by 1 to 3 of 5- or 6-membered monocyclic aromatic heterocyclic groups (e.g., triazolyl (e.g., 1,2,4-triazolyl), tetrazolyl).

$R^2$ is particularly more preferably a $C_{1-6}$ alkyl group (e.g., methyl) substituted by one tetrazolyl group.

$R^2$ is most preferably a tetrazolylmethyl group (e.g., tetrazolyl-1-ylmethyl).

Preferable examples of compound (I) include the following compounds.

[Compound A-1]
Compound (I) wherein
Ring A is
(1) an optionally further substituted benzene ring (the two substituents on the benzene ring are optionally bonded to each other to form a 3- to 8-membered monocyclic non-aromatic heterocycle (preferably pyrroline, dihydrofuran, tetrahydropyridine, dihydrooxazine, tetrahydroazepine) or a $C_{5-6}$ cycloalkene ring (preferably cyclopentene), each of which is optionally substituted),
(2) an optionally further substituted pyridine ring,
(3) an optionally further substituted pyrimidine ring,
(4) an optionally further substituted pyridazine ring,
(5) an optionally further substituted pyrazine ring,
(6) an optionally further substituted pyrazole ring,
(7) an optionally further substituted thiazole ring (the two substituents on the thiazole ring are optionally bonded to each other to form an optionally substituted benzene ring),
(8) an optionally further substituted isothiazole ring,
(9) an optionally further substituted imidazole ring (the two substituents on the imidazole ring are optionally bonded to each other to form an optionally substituted benzene ring), or
(10) an optionally further substituted isoxazole ring;

Ring B is an optionally further substituted pyrimidine ring ($X^1$ is a carbon atom, $X^2$ is a carbon atom and $X^3$ is a nitrogen atom), an optionally further substituted pyrazine ring ($X^1$ is a carbon atom, $X^2$ is a nitrogen atom and $X^3$ is a carbon atom), or an optionally further substituted pyridine ring ($X^1$ is a carbon atom, $X^2$ is a carbon atom and $X^3$ is a carbon atom);

Ring C is an optionally further substituted benzene ring, or an optionally further substituted pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom);

Z is
(1) —O—, or
(2) —N($R^Z$)— ($R^Z$ is as defined above);

$R^1$— is
(1) a hydrogen atom,
(2) an optionally substituted $C_{1-6}$ alkyl group, or
(3) an optionally substituted $C_{3-10}$ cycloalkyl group (e.g., cyclopropyl);

$R^2$ is
(1) an optionally substituted $C_{1-6}$ alkyl group,
(2) an optionally substituted 3- to 14-membered (preferably 4- to 10-membered) non-aromatic heterocyclic group (preferably a 3- to 8-membered monocyclic non-aromatic heterocyclic group), or
(3) an optionally substituted mono- or di-$C_{1-6}$ alkyl-carbamoyl group; and $R^3$ is
(1) a cyano group,
(2) a halogen atom,
(3) an optionally substituted $C_{1-6}$ alkyl group,
(4) an optionally substituted carbamoyl group, or
(5) an optionally substituted 3- to 14-membered (preferably 4- to 10-membered) non-aromatic heterocyclylcarbonyl group (preferably a 3- to 8-membered monocyclic non-aromatic heterocyclylcarbonyl group).

[Compound Ba-1]
Compound (I) wherein
Ring A is a 5- or 6-membered aromatic ring (e.g., benzene, pyridine, pyrimidine, pyridazine, pyrazine, pyrazole, thiazole, isothiazole, imidazole, isoxazole) optionally further substituted by 1 to 3 substituents selected from
  (a) an optionally halogenated $C_{1-6}$ alkoxy group (e.g., methoxy, ethoxy, isopropyloxy, difluoromethoxy, trifluoromethoxy, trifluoroethoxy), (b) a $C_{1-6}$ alkyl group (e.g., methyl, ethyl, propyl, isopropyl, isobutyl, tert-butyl, 2,2-dimethylpropyl) optionally substituted by 1 to 3 substituents selected from
  (i) a halogen atom (e.g., a fluorine atom),
  (ii) a hydroxy group,
  (iii) a cyano group,
  (iv) an amino group optionally mono- or di-substituted by substituent(s) selected from
    (I) a $C_{3-10}$ cycloalkyl group (e.g., cyclopropyl), and
    (II) a $C_{1-6}$ alkoxy-carbonyl group (e.g., tert-butoxycarbonyl),
  (v) a $C_{3-10}$ cycloalkyl group (e.g., cyclopropyl) optionally substituted by 1 to 3 substituents selected from
    (I) an amino group, and
    (II) a hydroxy group,
  (vi) a 5- to 14-membered (preferably 5- to 10-membered) aromatic heterocyclic group (preferably a 5- to 6-membered monocyclic aromatic heterocyclic group (e.g., pyrazolyl)), and
  (vii) a 3- to 14-membered (preferably 4- to 10-membered) non-aromatic heterocyclic group (preferably a 3- to 8-membered monocyclic non-aromatic heterocyclic group (e.g., morpholinyl, piperazinyl)) optionally substituted by 1 to 3 $C_{1-6}$ alkyl groups (e.g., methyl),
(c) a $C_{3-10}$ cycloalkyl group (e.g., cyclopropyl, cyclohexyl) optionally substituted by 1 to 3 substituents selected from
  (i) a 3- to 14-membered (preferably 4- to 10-membered) non-aromatic heterocyclic group (preferably a 3- to 8-membered monocyclic non-aromatic heterocyclic group (e.g., morpholinyl)),
(d) a halogen atom (e.g., a fluorine atom, a chlorine atom),
(e) a cyano group,
(f) a carboxy group,
(g) a $C_{1-6}$ alkoxy-carbonyl group (e.g., methoxycarbonyl, butoxycarbonyl),
(h) an amino group,
(i) a $C_{1-6}$ alkylsulfanyl group (e.g., methylsulfanyl),
(j) a $C_{1-6}$ alkylsulfonyl group (e.g., methylsulfonyl),
(k) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 substituents selected from
    (I) a hydroxy group,
    (II) a halogen atom (e.g., a fluorine atom),
    (III) an optionally halogenated $C_{1-6}$ alkoxy group (e.g., methoxy, trifluoromethoxy),
    (IV) a mono- or di-$C_{1-6}$ alkylamino group (e.g., dimethylamino),
    (V) a $C_{3-10}$ cycloalkyl group (e.g., cyclopropyl, cyclohexyl), and
    (VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl),
  (ii) a $C_{3-10}$ cycloalkyl group (e.g., cyclopropyl, cyclobutyl, cyclohexyl) optionally substituted by 1 to 3 substituents selected from
    (I) a halogen atom (e.g., a fluorine atom), and
    (II) an optionally halogenated $C_{1-6}$ alkyl group (e.g., trifluoromethyl),
    (III) a carboxy group, and
    (IV) a $C_{1-6}$ alkoxy-carbonyl group (e.g., methoxycarbonyl), and
  (iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl),
(l) a sulfamoyl group optionally mono- or di-substituted by substituent(s) selected from
  (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(m) a 5- to 14-membered (preferably 5- to 10-membered) aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl),
(n) a 3- to 14-membered (preferably 4- to 10-membered) non-aromatic heterocyclic group (preferably a 3- to 8-membered monocyclic non-aromatic heterocyclic group (e.g., azetidinyl, piperidyl, piperazinyl, pyrrolidinyl, diazepanyl, tetrahydropyridyl, oxetanyl)) optionally substituted by 1 to 3 substituents selected from
  (i) a $C_{1-6}$ alkyl group (e.g., methyl, ethyl, propyl, isobutyl) optionally substituted by 1 to 3 substituents selected from
    (I) a halogen atom (e.g., a fluorine atom),
    (II) a hydroxy group,
    (III) a cyano group,
    (IV) a $C_{1-6}$ alkoxy group (e.g., methoxy),
    (V) a $C_{1-6}$ alkylsulfonyl group (e.g., methylsulfonyl), and
    (VI) a 3- to 14-membered (preferably 4- to 10-membered) non-aromatic heterocyclic group (preferably a 3- to 8-membered monocyclic non-aromatic heterocyclic group (e.g., morpholinyl)),
  (ii) a $C_{1-6}$ alkyl-carbonyl group (e.g., acetyl) optionally substituted by 1 to 3 substituents selected from
    (I) a halogen atom (e.g., a fluorine atom), and
    (II) a hydroxy group,
  (iii) a $C_{1-6}$ alkoxy-carbonyl group (e.g., tert-butoxycarbonyl),
  (iv) a 3- to 14-membered (preferably 4- to 10-membered) non-aromatic heterocyclic group (e.g., morpholinyl, piperazinyl, piperidyl, oxetanyl, azetidinyl, tetrahydropyranyl, 3-oxa-8-azabicyclo[3.2.1]octyl, 8-oxa-3-azabicyclo[3.2.1]octyl) optionally substituted by 1 to 3 substituents selected from
    (I) a halogen atom (e.g., a fluorine atom),
    (II) a $C_{1-6}$ alkyl-carbonyl group (e.g., acetyl), and
    (III) a $C_{1-6}$ alkoxy-carbonyl group (e.g., tert-butoxycarbonyl), and
  (v) an oxo group,
(o) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from
(i) a halogen atom (e.g., a fluorine atom),
(ii) a hydroxy group,
(iii) a cyano group,
(iv) a $C_{1-6}$ alkyl group (e.g., methyl, ethyl) optionally substituted by 1 to 3 substituents selected from
　(I) a hydroxy group,
　(II) a halogen atom (e.g., a fluorine atom),
　(III) a $C_{1-6}$ alkoxy group (e.g., methoxy), and
　(IV) a mono- or di-$C_{1-6}$ alkylamino group (e.g., dimethylamino),
(v) an optionally halogenated $C_{1-6}$ alkoxy group (e.g., methoxy, difluoromethoxy),
(vi) a $C_{1-6}$ alkyl-carbonyl group (e.g., acetyl) optionally substituted by 1 to 3 substituents selected from
　(I) a hydroxy group, and
　(II) a $C_{1-6}$ alkoxy group (e.g., methoxy),
(vii) a $C_{1-6}$ alkoxy-carbonyl group (e.g., tert-butoxycarbonyl),
(viii) a $C_{3-10}$ cycloalkyl group (e.g., cyclopropyl),
(ix) a $C_{3-10}$ cycloalkyl-carbonyl group (e.g., cyclopropylcarbonyl),
(x) a $C_{1-6}$ alkylsulfonyl group (e.g., methylsulfonyl), and
(xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), and
(p) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl))
(the two substituents on the 5- or 6-membered aromatic ring are optionally bonded to each other to form a 3- to 8-membered monocyclic non-aromatic heterocycle (e.g., pyrroline, dihydrofuran, tetrahydropyridine, dihydrooxazine, tetrahydroazepine), a $C_{3-6}$ cycloalkene ring (e.g., cyclopentene) or a benzene ring (e.g., indoline, isoindoline, dihydrobenzofuran, tetrahydroisoquinoline, dihydrobenzoxazine, tetrahydrobenzazepine, indane, benzothiazole, benzimidazole), each of which is optionally substituted by 1 to 3 substituents selected from
(a) an oxo group,
(b) a $C_{1-6}$ alkyl group (e.g., methyl) optionally substituted by 1 to 3 substituents selected from
　(i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(c) a $C_{1-6}$ alkoxy-carbonyl group (e.g., tert-butoxycarbonyl), and
(d) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl)) optionally substituted by 1 to 3 $C_{1-6}$ alkyl groups (e.g., methyl));

Ring B is
(1) a pyrimidine ring ($X^1$ is a carbon atom, $X^2$ is a carbon atom and $X^3$ is a nitrogen atom),
(2) a pyrazine ring ($X^1$ is a carbon atom, $X^2$ is a nitrogen atom and $X^3$ is a carbon atom), or
(3) a pyridine ring ($X^1$ is a carbon atom, $X^2$ is a carbon atom and $X^3$ is a carbon atom);

Ring C is a benzene ring or a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom), each of which is optionally further substituted by 1 to 3 halogen atoms (e.g., a fluorine atom, a chlorine atom);

Z is
(1) —O—, or
(2) —NH—;

$R^1$ is
(1) a hydrogen atom,
(2) a $C_{1-6}$ alkyl group (e.g., methyl, ethyl) optionally substituted by 1 to 3 substituents selected from
　(a) a halogen atom (e.g., a fluorine atom), and
　(b) a hydroxy group, or
(3) a $C_{3-10}$ cycloalkyl group (e.g., cyclopropyl);

$R^2$ is
(1) a $C_{1-6}$ alkyl group (e.g., methyl, ethyl, isobutyl) optionally substituted by 1 to 3 substituents selected from
　(a) a 5- to 14-membered (preferably 5- to 10-membered) aromatic heterocyclic group (e.g., triazolyl (e.g., 1,2,4-triazolyl, 1,2,3-triazolyl), tetrazolyl, pyrazolyl, imidazolyl, oxadiazolyl (e.g., 1,2,4-oxadiazolyl, 1,3,4-oxadiazolyl), pyridyl, benzimidazolyl) optionally substituted by 1 to 3 substituents selected from
　　(i) a cyano group,
　　(ii) a halogen atom (e.g., a fluorine atom),
　　(iii) a $C_{1-6}$ alkyl group (e.g., methyl), and
　　(iv) a $C_{7-16}$ aralkyl group (e.g., trityl),
　(b) a 3- to 14-membered (preferably 4- to 10-membered) non-aromatic heterocyclic group (preferably a 3- to 8-membered monocyclic non-aromatic heterocyclic group (e.g., imidazolidinyl, morpholinyl, triazolinyl)) optionally substituted by 1 to 3 substituents selected from
　　(i) an oxo group, and
　　(ii) a $C_{1-6}$ alkyl group (e.g., methyl),
　(c) a halogen atom (e.g., a fluorine atom),
　(d) a hydroxy group,
　(e) a cyano group,
　(f) an optionally halogenated $C_{1-6}$ alkoxy group (e.g., methoxy, difluoromethoxy),
　(g) a 5- to 14-membered (preferably 5- to 10-membered) aromatic heterocyclyloxy group (preferably a 5- or 6-membered monocyclic aromatic heterocyclyloxy group (e.g., triazolyloxy (e.g., 1,2,4-triazolyloxy))),
　(h) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)),
　(i) an amino group optionally mono- or di-substituted by substituent(s) selected from
　　(i) a $C_{1-6}$ alkyl group (e.g., methyl),
　　(ii) a $C_{1-6}$ alkyl-carbonyl group (e.g., acetyl) optionally substituted by 1 to 3 $C_{1-6}$ alkoxy groups (e.g., methoxy), and
　　(iii) a $C_{1-6}$ alkylsulfonyl group (e.g., methylsulfonyl), and (j) a mono- or di-$C_{1-6}$ alkyl-carbamoyl group (e.g., methylcarbamoyl), (2) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 substituents selected from
    (a) an oxo group, and
    (b) a $C_{1-6}$ alkyl group (e.g., methyl), or (3) a mono- or di-$C_{1-6}$ alkyl-carbamoyl group (e.g., ethylcarbamoyl) optionally substituted by 1 to 3 halogen atoms (e.g., a fluorine atom); and $R^3$ is (1) a cyano group, (2) a halogen atom (e.g., a fluorine atom, a chlorine atom), (3) an optionally halogenated $C_{1-6}$ alkyl group (e.g., methyl, trifluoromethyl), (4) a carbamoyl group, (5) a mono- or di-$C_{1-6}$ alkyl-carbamoyl group (e.g., dimethylcarbamoyl), or (6) a 3- to 14-membered (preferably 4- to 10-membered) non-aromatic heterocyclylcarbonyl group (preferably a 3- to 8-membered monocyclic non-aromatic heterocyclylcarbonyl group (e.g., pyrrolidinylcarbonyl)).

[Compound Bb-1]

Compound (I) wherein

Ring A is (1) a benzene ring optionally further substituted by 1 to 3 substituents selected from
    (a) an optionally halogenated $C_{1-6}$ alkoxy group (e.g., methoxy, ethoxy, isopropyloxy, difluoromethoxy, trifluoromethoxy, trifluoroethoxy),
    (b) a $C_{1-6}$ alkyl group (e.g., methyl, ethyl, propyl, isopropyl, tert-butyl) optionally substituted by 1 to 3 substituents selected from
        (i) a halogen atom (e.g., a fluorine atom),
        (ii) a hydroxy group,
        (iii) an amino group optionally mono- or di-substituted by substituent(s) selected from
            (I) a $C_{3-10}$ cycloalkyl group (e.g., cyclopropyl), and
            (II) a $C_{1-6}$ alkoxy-carbonyl group (e.g., tert-butoxycarbonyl),
        (iv) a 5- to 14-membered (preferably 5- to 10-membered) aromatic heterocyclic group (preferably a 5- to 6-membered monocyclic aromatic heterocyclic group (e.g., pyrazolyl)), and
        (v) a 3- to 14-membered (preferably 4- to 10-membered) non-aromatic heterocyclic group (preferably a 3- to 8-membered monocyclic non-aromatic heterocyclic group (e.g., morpholinyl, piperazinyl)) optionally substituted by 1 to 3 $C_{1-6}$ alkyl groups (e.g., methyl),
    (c) a $C_{3-10}$ cycloalkyl group (e.g., cyclopropyl, cyclohexyl) optionally substituted by 1 to 3 substituents selected from
        (i) a 3- to 14-membered (preferably 4- to 10-membered) non-aromatic heterocyclic group (preferably a 3- to 8-membered monocyclic non-aromatic heterocyclic group (e.g., morpholinyl)),
    (d) a halogen atom (e.g., a fluorine atom, a chlorine atom),
    (e) a cyano group,
    (f) a carboxy group,
    (g) a $C_{1-6}$ alkoxy-carbonyl group (e.g., methoxycarbonyl, butoxycarbonyl),
    (h) a $C_{1-6}$ alkylsulfanyl group (e.g., methylsulfanyl),
    (i) a $C_{1-6}$ alkylsulfonyl group (e.g., methylsulfonyl),
    (j) a carbamoyl group optionally mono- or di-substituted by substituent(s) selected from
        (i) a $C_{1-6}$ alkyl group (e.g., methyl, ethyl, propyl, isopropyl) optionally substituted by 1 to 3 substituents selected from
            (I) a hydroxy group,
            (II) a halogen atom (e.g., a fluorine atom),
            (III) an optionally halogenated $C_{1-6}$ alkoxy group (e.g., methoxy, trifluoromethoxy),
            (IV) a mono- or di-$C_{1-6}$ alkylamino group (e.g., dimethylamino),
            (V) a $C_{3-10}$ cycloalkyl group (e.g., cyclopropyl, cyclohexyl), and
            (VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl),
        (ii) a $C_{3-10}$ cycloalkyl group (e.g., cyclopropyl, cyclobutyl, cyclohexyl) optionally substituted by 1 to 3 substituents selected from
            (I) a halogen atom (e.g., a fluorine atom),
            (II) an optionally halogenated $C_{1-6}$ alkyl group (e.g., trifluoromethyl),
            (III) a carboxy group, and
            (IV) a $C_{1-6}$ alkoxy-carbonyl group (e.g., methoxycarbonyl), and
        (iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl),
    (k) a sulfamoyl group optionally mono- or di-substituted by substituent(s) selected from
        (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
    (l) a 5- to 14-membered (preferably 5- to 10-membered) aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl),
    (m) a 3- to 14-membered (preferably 4- to 10-membered) non-aromatic heterocyclic group (preferably a 3- to 8-membered monocyclic non-aromatic heterocyclic group (e.g., azetidinyl, piperidyl, piperazinyl, pyrrolidinyl, diazepanyl, tetrahydropyridyl)) optionally substituted by 1 to 3 substituents selected from
        (i) a $C_{1-6}$ alkyl group (e.g., methyl, ethyl, propyl, isobutyl) optionally substituted by 1 to 3 substituents selected from
            (I) a halogen atom (e.g., a fluorine atom),
            (II) a hydroxy group,
            (III) a cyano group,
            (IV) a $C_{1-6}$ alkoxy group (e.g., methoxy),
            (V) a $C_{1-6}$ alkylsulfonyl group (e.g., methylsulfonyl), and
            (VI) a 3- to 14-membered (preferably 4- to 10-membered) non-aromatic heterocyclic group (preferably a 3- to 8-membered monocyclic non-aromatic heterocyclic group (e.g., morpholinyl)),
(ii) a $C_{1-6}$ alkyl-carbonyl group (e.g., acetyl) optionally substituted by 1 to 3 substituents selected from
 (I) a halogen atom (e.g., a fluorine atom), and
 (II) a hydroxy group,
(iii) a $C_{1-6}$ alkoxy-carbonyl group (e.g., tert-butoxycarbonyl),
(iv) a 3- to 14-membered (preferably 4- to 10-membered) non-aromatic heterocyclic group (e.g., morpholinyl, piperazinyl, piperidyl, oxetanyl, azetidinyl, tetrahydropyranyl, 3-oxa-8-azabicyclo[3.2.1]octyl, 8-oxa-3-azabicyclo[3.2.1]octyl) optionally substituted by 1 to 3 substituents selected from
 (I) a halogen atom (e.g., a fluorine atom),
 (II) a $C_{1-6}$ alkyl-carbonyl group (e.g., acetyl), and
 (III) a $C_{1-6}$ alkoxy-carbonyl group (e.g., tert-butoxycarbonyl), and
(v) an oxo group,
(n) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from
(i) a halogen atom (e.g., a fluorine atom),
(ii) a hydroxy group,
(iii) a cyano group,
(iv) a $C_{1-6}$ alkyl group (e.g., methyl, ethyl) optionally substituted by 1 to 3 substituents selected from
 (I) a hydroxy group,
 (II) a halogen atom (e.g., a fluorine atom),
 (III) a $C_{1-6}$ alkoxy group (e.g., methoxy), and
 (IV) a mono- or di-$C_{1-6}$ alkylamino group (e.g., dimethylamino),
(v) an optionally halogenated $C_{1-6}$ alkoxy group (e.g., methoxy, difluoromethoxy),
(vi) a $C_{1-6}$ alkyl-carbonyl group (e.g., acetyl) optionally substituted by 1 to 3 substituents selected from
 (I) a hydroxy group, and
 (II) a $C_{1-6}$ alkoxy group (e.g., methoxy),
(vii) a $C_{1-6}$ alkoxy-carbonyl group (e.g., tert-butoxycarbonyl),
(viii) a $C_{3-10}$ cycloalkyl group (e.g., cyclopropyl),
(ix) a $C_{3-10}$ cycloalkyl-carbonyl group (e.g., cyclopropylcarbonyl),
(x) a $C_{1-6}$ alkylsulfonyl group (e.g., methylsulfonyl), and
(xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), and
(o) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl))
(the two substituents on the benzene ring are optionally bonded to each other to form a 3- to 8-membered monocyclic non-aromatic heterocycle (e.g., pyrroline, dihydrofuran, tetrahydropyridine, dihydrooxazine, tetrahydroazepine) or a $C_{5-6}$ cycloalkene ring (e.g., cyclopentene) (e.g., indoline, isoindoline, dihydrobenzofuran, tetrahydroisoquinoline, dihydrobenzoxazine, tetrahydrobenzazepine, indane), each of which is optionally substituted by 1 to 3 substituents selected from
 (a) an oxo group,
 (b) a $C_{1-6}$ alkyl group (e.g., methyl) optionally substituted by 1 to 3 substituents selected from
  (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
 (c) a $C_{1-6}$ alkoxy-carbonyl group (e.g., tert-butoxycarbonyl), and
 (d) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl)) optionally substituted by 1 to 3 $C_{1-6}$ alkyl groups (e.g., methyl)),
or
(2) a 5- or 6-membered aromatic heterocycle (e.g., pyridine, pyrimidine, pyridazine, pyrazine, pyrazole, thiazole, isothiazole, imidazole, isoxazole) optionally further substituted by 1 to 3 substituents selected from
 (a) an amino group,
 (b) a $C_{1-6}$ alkyl group (e.g., methyl, ethyl, propyl, isopropyl, isobutyl, tert-butyl, 2,2-dimethylpropyl) optionally substituted by 1 to 3 substituents selected from
  (i) a $C_{3-10}$ cycloalkyl group (e.g., cyclopropyl) optionally substituted by 1 to 3 substituents selected from
   (I) an amino group, and
   (II) a hydroxy group,
  (ii) a hydroxy group,
  (iii) a cyano group, and
  (iv) a halogen atom (e.g., a fluorine atom),
 (c) a $C_{1-6}$ alkoxy group (e.g., methoxy),
 (d) a $C_{3-10}$ cycloalkyl group (e.g., cyclopropyl), and
 (e) a 3- to 14-membered (preferably 4- to 10-membered) non-aromatic heterocyclic group (preferably a 3- to 8-membered monocyclic non-aromatic heterocyclic group (e.g., piperidyl, oxetanyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl, oxetanyl))
(the two substituents on the 5- or 6-membered aromatic heterocycle are optionally bonded to each other to form a benzene ring (e.g., benzothiazole, benzimidazole));
Ring B is
(1) a pyrimidine ring ($X^1$ is a carbon atom, $X^2$ is a carbon atom and $X^3$ is a nitrogen atom),
(2) a pyrazine ring ($X^1$ is a carbon atom, $X^2$ is a nitrogen atom and $X^3$ is a carbon atom), or
(3) a pyridine ring ($X^1$ is a carbon atom, $X^2$ is a carbon atom and $X^3$ is a carbon atom);
Ring C is
(1) a benzene ring optionally further substituted by 1 to 3 halogen atoms (e.g., a fluorine atom, a chlorine atom), or (2) a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom);

Z is
(1) —O—, or
(2) —NH—;

$R^1$ is
(1) a hydrogen atom,
(2) a $C_{1-6}$ alkyl group (e.g., methyl, ethyl) optionally substituted by 1 to 3 substituents selected from
 (a) a halogen atom (e.g., a fluorine atom), and
 (b) a hydroxy group, or
(3) a $C_{3-10}$ cycloalkyl group (e.g., cyclopropyl);

$R^2$ is
(1) a $C_{1-6}$ alkyl group (e.g., methyl, ethyl, isobutyl) optionally substituted by 1 to 3 substituents selected from
 (a) a 5- to 14-membered (preferably 5- to 10-membered) aromatic heterocyclic group (e.g., triazolyl (e.g., 1,2,4-triazolyl, 1,2,3-triazolyl), tetrazolyl, pyrazolyl, imidazolyl, oxadiazolyl (e.g., 1,2,4-oxadiazolyl, 1,3,4-oxadiazolyl), pyridyl, benzimidazolyl) optionally substituted by 1 to 3 substituents selected from
  (i) a cyano group,
  (ii) a halogen atom (e.g., a fluorine atom),
  (iii) a $C_{1-6}$ alkyl group (e.g., methyl), and
  (iv) a $C_{7-16}$ aralkyl group (e.g., trityl),
 (b) a 3- to 14-membered (preferably 4- to 10-membered) non-aromatic heterocyclic group (preferably a 3- to 8-membered monocyclic non-aromatic heterocyclic group (e.g., imidazolidinyl, morpholinyl, triazolinyl)) optionally substituted by 1 to 3 substituents selected from
  (i) an oxo group, and
  (ii) a $C_{1-6}$ alkyl group (e.g., methyl),
 (c) a halogen atom (e.g., a fluorine atom),
 (d) a hydroxy group,
 (e) a cyano group,
 (f) an optionally halogenated $C_{1-6}$ alkoxy group (e.g., methoxy, difluoromethoxy),
 (g) a 5- to 14-membered (preferably 5- to 10-membered) aromatic heterocyclyloxy group (preferably a 5- or 6-membered monocyclic aromatic heterocyclyloxy group (e.g., triazolyloxy (e.g., 1,2,4-triazolyloxy))),
 (h) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)),
 (i) an amino group optionally mono- or di-substituted by substituent(s) selected from
  (i) a $C_{1-6}$ alkyl group (e.g., methyl),
  (ii) a $C_{1-6}$ alkyl-carbonyl group (e.g., acetyl) optionally substituted by 1 to 3 $C_{1-6}$ alkoxy groups (e.g., methoxy), and
  (iii) a $C_{1-6}$ alkylsulfonyl group (e.g., methylsulfonyl), and
 (j) a mono- or di-$C_{1-6}$ alkyl-carbamoyl group (e.g., methylcarbamoyl),
(2) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 substituents selected from
 (a) an oxo group, and
 (b) a $C_{1-6}$ alkyl group (e.g., methyl), or
(3) a mono- or di-$C_{1-6}$ alkyl-carbamoyl group (e.g., ethylcarbamoyl) optionally substituted by 1 to 3 halogen atoms (e.g., a fluorine atom); and $R^3$ is
(1) a cyano group,
(2) a halogen atom (e.g., a fluorine atom, a chlorine atom),
(3) an optionally halogenated $C_{1-6}$ alkyl group (e.g., methyl, trifluoromethyl),
(4) a carbamoyl group,
(5) a mono- or di-$C_{1-6}$ alkyl-carbamoyl group (e.g., dimethylcarbamoyl), or
(6) a 3- to 14-membered (preferably 4- to 10-membered) non-aromatic heterocyclylcarbonyl group (preferably a 3- to 8-membered monocyclic non-aromatic heterocyclylcarbonyl group (e.g., pyrrolidinylcarbonyl)).

[Compound Bc-1]
Compound (I) wherein

Ring A is
(1) a benzene ring optionally further substituted by 1 to 3 substituents selected from
 (a) an optionally halogenated $C_{1-6}$ alkoxy group (e.g., methoxy, ethoxy, isopropyloxy, difluoromethoxy, trifluoromethoxy, trifluoroethoxy),
 (b) a $C_{1-6}$ alkyl group (e.g., methyl, ethyl, propyl, isopropyl, tert-butyl) optionally substituted by 1 to 3 substituents selected from
  (i) a halogen atom (e.g., a fluorine atom),
  (ii) a hydroxy group,
  (iii) an amino group optionally mono- or di-substituted by substituent(s) selected from
   (I) a $C_{3-10}$ cycloalkyl group (e.g., cyclopropyl), and
   (II) a $C_{1-6}$ alkoxy-carbonyl group (e.g., tert-butoxycarbonyl),
  (iv) a 5- to 14-membered (preferably 5- to 10-membered) aromatic heterocyclic group (preferably a 5- to 6-membered monocyclic aromatic heterocyclic group (e.g., pyrazolyl)), and
  (v) a 3- to 14-membered (preferably 4- to 10-membered) non-aromatic heterocyclic group (preferably a 3- to 8-membered monocyclic non-aromatic heterocyclic group (e.g., morpholinyl, piperazinyl)) optionally substituted by 1 to 3 $C_{1-6}$ alkyl groups (e.g., methyl),
 (c) a $C_{3-10}$ cycloalkyl group (e.g., cyclopropyl, cyclohexyl) optionally substituted by 1 to 3 substituents selected from
  (i) a 3- to 14-membered (preferably 4- to 10-membered) non-aromatic heterocyclic group (preferably a 3- to 8-membered monocyclic non-aromatic heterocyclic group (e.g., morpholinyl)),
 (d) a halogen atom (e.g., a fluorine atom, a chlorine atom),
 (e) a cyano group,
 (f) a carboxy group,
 (g) a $C_{1-6}$ alkoxy-carbonyl group (e.g., methoxycarbonyl, butoxycarbonyl),
 (h) a $C_{1-6}$ alkylsulfanyl group (e.g., methylsulfanyl),
 (i) a $C_{1-6}$ alkylsulfonyl group (e.g., methylsulfonyl),
 (j) a carbamoyl group optionally mono- or di-substituted by substituent(s) selected from
  (i) a $C_{1-6}$ alkyl group (e.g., methyl, ethyl, propyl, isopropyl) optionally substituted by 1 to 3 substituents selected from
   (I) a hydroxy group,
   (II) a halogen atom (e.g., a fluorine atom),
   (III) an optionally halogenated $C_{1-6}$ alkoxy group (e.g., methoxy, trifluoromethoxy),
   (IV) a mono- or di-$C_{1-6}$ alkylamino group (e.g., dimethylamino),
   (V) a $C_{3-10}$ cycloalkyl group (e.g., cyclopropyl, cyclohexyl), and (VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl), (ii) a $C_{3-10}$ cycloalkyl group (e.g., cyclopropyl, cyclobutyl, cyclohexyl) optionally substituted by 1 to 3 substituents selected from
  (I) a halogen atom (e.g., a fluorine atom),
  (II) an optionally halogenated $C_{1-6}$ alkyl group (e.g., trifluoromethyl),
  (III) a carboxy group, and
  (IV) a $C_{1-6}$ alkoxy-carbonyl group (e.g., methoxycarbonyl), and (iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl), (k) a sulfamoyl group optionally mono- or di-substituted by substituent(s) selected from
  (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl), (l) a 5- to 14-membered (preferably 5- to 10-membered) aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl), (m) a 3- to 14-membered (preferably 4- to 10-membered) non-aromatic heterocyclic group (preferably a 3- to 8-membered monocyclic non-aromatic heterocyclic group (e.g., azetidinyl, piperidyl, piperazinyl, pyrrolidinyl, diazepanyl, tetrahydropyridyl)) optionally substituted by 1 to 3 substituents selected from
  (i) a $C_{1-6}$ alkyl group (e.g., methyl, ethyl, propyl, isobutyl) optionally substituted by 1 to 3 substituents selected from
    (I) a halogen atom (e.g., a fluorine atom),
    (II) a hydroxy group,
    (III) a cyano group,
    (IV) a $C_{1-6}$ alkoxy group (e.g., methoxy),
    (V) a $C_{1-6}$ alkylsulfonyl group (e.g., methylsulfonyl), and
    (VI) a 3- to 14-membered (preferably 4- to 10-membered) non-aromatic heterocyclic group (preferably a 3- to 8-membered monocyclic non-aromatic heterocyclic group (e.g., morpholinyl)),
  (ii) a $C_{1-6}$ alkyl-carbonyl group (e.g., acetyl) optionally substituted by 1 to 3 substituents selected from
    (I) a halogen atom (e.g., a fluorine atom), and
    (II) a hydroxy group,
  (iii) a $C_{1-6}$ alkoxy-carbonyl group (e.g., tert-butoxycarbonyl),
  (iv) a 3- to 14-membered (preferably 4- to 10-membered) non-aromatic heterocyclic group (e.g., morpholinyl, piperazinyl, piperidyl, oxetanyl, azetidinyl, tetrahydropyranyl, 3-oxa-8-azabicyclo[3.2.1]octyl, 8-oxa-3-azabicyclo[3.2.1]octyl) optionally substituted by 1 to 3 substituents selected from
    (I) a halogen atom (e.g., a fluorine atom),
    (II) a $C_{1-6}$ alkyl-carbonyl group (e.g., acetyl), and
    (III) a $C_{1-6}$ alkoxy-carbonyl group (e.g., tert-butoxycarbonyl), and
  (v) an oxo group, (n) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from
  (i) a halogen atom (e.g., a fluorine atom),
  (ii) a hydroxy group,
  (iii) a cyano group,
  (iv) a $C_{1-6}$ alkyl group (e.g., methyl, ethyl) optionally substituted by 1 to 3 substituents selected from
    (I) a hydroxy group,
    (II) a halogen atom (e.g., a fluorine atom),
    (III) a $C_{1-6}$ alkoxy group (e.g., methoxy), and
    (IV) a mono- or di-$C_{1-6}$ alkylamino group (e.g., dimethylamino),
  (v) an optionally halogenated $C_{1-6}$ alkoxy group (e.g., methoxy, difluoromethoxy),
  (vi) a $C_{1-6}$ alkyl-carbonyl group (e.g., acetyl) optionally substituted by 1 to 3 substituents selected from
    (I) a hydroxy group, and
    (II) a $C_{1-6}$ alkoxy group (e.g., methoxy),
  (vii) a $C_{1-6}$ alkoxy-carbonyl group (e.g., tert-butoxycarbonyl),
  (viii) a $C_{3-10}$ cycloalkyl group (e.g., cyclopropyl),
  (ix) a $C_{3-10}$ cycloalkyl-carbonyl group (e.g., cyclopropylcarbonyl),
  (x) a $C_{1-6}$ alkylsulfonyl group (e.g., methylsulfonyl), and
  (xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), and (o) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl))

(the two substituents on the benzene ring are optionally bonded to each other to form a 3- to 8-membered monocyclic non-aromatic heterocycle (e.g., pyrroline, dihydrofuran, tetrahydropyridine, dihydrooxazine, tetrahydroazepine) or a $C_{5-6}$ cycloalkene ring (e.g., cyclopentene) (e.g., indoline, isoindoline, dihydrobenzofuran, tetrahydroisoquinoline, dihydrobenzoxazine, tetrahydrobenzazepine, indane), each of which is optionally substituted by 1 to 3 substituents selected from (a) an oxo group,
(b) a $C_{1-6}$ alkyl group (e.g., methyl) optionally substituted by 1 to 3 substituents selected from
  (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(c) a $C_{1-6}$ alkoxy-carbonyl group (e.g., tert-butoxycarbonyl), and
(d) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl)) optionally substituted by 1 to 3 $C_{1-6}$ alkyl groups (e.g., methyl)),
(2) a pyridine ring optionally further substituted by 1 to 3 substituents selected from
  (a) a $C_{1-6}$ alkoxy group (e.g., methoxy),
  (b) an amino group, and
  (c) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)),
(3) a pyrimidine ring optionally further substituted by 1 to 3 substituents selected from
  (a) a $C_{1-6}$ alkoxy group (e.g., methoxy), and
  (b) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)),
(4) a pyridazine ring,
(5) a pyrazine ring,
(6) a pyrazole ring optionally further substituted by 1 to 3 substituents selected from
  (a) a $C_{1-6}$ alkyl group (e.g., methyl, ethyl, propyl, isopropyl, isobutyl, tert-butyl, 2,2-dimethylpropyl) optionally substituted by 1 to 3 substituents selected from
    (i) a $C_{3-10}$ cycloalkyl group (e.g., cyclopropyl) optionally substituted by 1 to 3 substituents selected from
      (I) an amino group, and
      (II) a hydroxy group,
    (ii) a hydroxy group,
    (iii) a cyano group, and
    (iv) a halogen atom (e.g., a fluorine atom),
  (b) a $C_{1-6}$ alkoxy group (e.g., methoxy),
  (c) a $C_{3-10}$ cycloalkyl group (e.g., cyclopropyl), and
  (d) a 3- to 14-membered (preferably 4- to 10-membered) non-aromatic heterocyclic group (preferably a 3- to 8-membered monocyclic non-aromatic heterocyclic group (e.g., oxetanyl, piperidyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., oxetanyl)),
(7) a thiazole ring (the two substituents on the thiazole ring are optionally bonded to each other to form a benzene ring (e.g., benzothiazole ring)),
(8) an isothiazole ring optionally further substituted by 1 to 3 substituents selected from
  (a) a $C_{1-6}$ alkyl group (e.g., methyl) optionally substituted by 1 to 3 hydroxy groups,
(9) an imidazole ring optionally further substituted by 1 to 3 $C_{1-6}$ alkyl groups (e.g., methyl) (the two substituents on the imidazole ring are optionally bonded to each other to form a benzene ring (e.g., benzimidazole ring)), or
(10) an isoxazole ring;
Ring B is
(1) a pyrimidine ring ($X^1$ is a carbon atom, $X^2$ is a carbon atom and $X^3$ is a nitrogen atom),
(2) a pyrazine ring ($X^1$ is a carbon atom, $X^2$ is a nitrogen atom and $X^3$ is a carbon atom), or
(3) a pyridine ring ($X^1$ is a carbon atom, $X^2$ is a carbon atom and $X^3$ is a carbon atom);
Ring C is
(1) a benzene ring optionally further substituted by 1 to 3 halogen atoms (e.g., a fluorine atom, a chlorine atom), or
(2) a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom);
Z is
(1) —O—, or
(2) —NH—;
$R^1$ is
(1) a hydrogen atom,
(2) a $C_{1-6}$ alkyl group (e.g., methyl, ethyl) optionally substituted by 1 to 3 substituents selected from
  (a) a halogen atom (e.g., a fluorine atom), and
  (b) a hydroxy group, or
(3) a $C_{3-10}$ cycloalkyl group (e.g., cyclopropyl);
$R^2$ is
(1) a $C_{1-6}$ alkyl group (e.g., methyl, ethyl, isobutyl) optionally substituted by 1 to 3 substituents selected from
  (a) a 5- to 14-membered (preferably 5- to 10-membered) aromatic heterocyclic group (e.g., triazolyl (e.g., 1,2,4-triazolyl, 1,2,3-triazolyl), tetrazolyl, pyrazolyl, imidazolyl, oxadiazolyl (e.g., 1,2,4-oxadiazolyl, 1,3,4-oxadiazolyl), pyridyl, benzimidazolyl) optionally substituted by 1 to 3 substituents selected from
    (i) a cyano group,
    (ii) a halogen atom (e.g., a fluorine atom),
    (iii) a $C_{1-6}$ alkyl group (e.g., methyl), and
    (iv) a $C_{7-16}$ aralkyl group (e.g., trityl),
  (b) a 3- to 14-membered (preferably 4- to 10-membered) non-aromatic heterocyclic group (preferably a 3- to 8-membered monocyclic non-aromatic heterocyclic group (e.g., imidazolidinyl, morpholinyl, triazolinyl)) optionally substituted by 1 to 3 substituents selected from
    (i) an oxo group, and
    (ii) a $C_{1-6}$ alkyl group (e.g., methyl),
  (c) a halogen atom (e.g., a fluorine atom),
  (d) a hydroxy group,
  (e) a cyano group,
  (f) an optionally halogenated $C_{1-6}$ alkoxy group (e.g., methoxy, difluoromethoxy),
  (g) a 5- to 14-membered (preferably 5- to 10-membered) aromatic heterocyclyloxy group (preferably a 5- or 6-membered monocyclic aromatic heterocyclyloxy group (e.g., triazolyloxy (e.g., 1,2,4-triazolyloxy))),
  (h) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)),
  (i) an amino group optionally mono- or di-substituted by substituent(s) selected from (i) a $C_{1-6}$ alkyl group (e.g., methyl),
(ii) a $C_{1-6}$ alkyl-carbonyl group (e.g., acetyl) optionally substituted by 1 to 3 $C_{1-6}$ alkoxy groups (e.g., methoxy), and
(iii) a $C_{1-6}$ alkylsulfonyl group (e.g., methylsulfonyl), and
(j) a mono- or di-$C_{1-6}$ alkyl-carbamoyl group (e.g., methylcarbamoyl),
(2) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 substituents selected from
  (a) an oxo group, and
  (b) a $C_{1-6}$ alkyl group (e.g., methyl), or
(3) a mono- or di-$C_{1-6}$ alkyl-carbamoyl group (e.g., ethylcarbamoyl) optionally substituted by 1 to 3 halogen atoms (e.g., a fluorine atom); and
$R^3$ is
(1) a cyano group,
(2) a halogen atom (e.g., a fluorine atom, a chlorine atom),
(3) an optionally halogenated $C_{1-6}$ alkyl group (e.g., methyl, trifluoromethyl),
(4) a carbamoyl group,
(5) a mono- or di-$C_{1-6}$ alkyl-carbamoyl group (e.g., dimethylcarbamoyl), or
(6) a 3- to 14-membered (preferably 4- to 10-membered) non-aromatic heterocyclylcarbonyl group (preferably a 3- to 8-membered monocyclic non-aromatic heterocyclylcarbonyl group (e.g., pyrrolidinylcarbonyl)).
[Compound C-1]
  Compound (I) wherein
Ring A is a benzene ring optionally further substituted by 1 to 3 substituents selected from
  (a) a $C_{1-6}$ alkoxy group (e.g., methoxy), and
  (b) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl, oxetanyl));
Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group (e.g., methyl);
$R^2$ is a $C_{1-6}$ alkyl group (e.g., methyl) optionally substituted by 1 to 3 of 5- or 6-membered monocyclic aromatic heterocyclic groups (e.g., triazolyl (e.g., 1,2,4-triazolyl), tetrazolyl); and
$R^3$ is
(1) a cyano group, or
(2) a halogen atom (e.g., a chlorine atom).
[Compound A-2]
  Compound (I) wherein
Ring A is
(1) an optionally further substituted benzene ring (the two substituents on the benzene ring are optionally bonded to each other to form a 5- or 6-membered monocyclic aromatic heterocycle (preferably pyrrole), a 3- to 8-membered monocyclic non-aromatic heterocycle (preferably pyrroline, dihydrofuran, tetrahydropyridine, dihydrooxazine, tetrahydroazepine, tetrahydrooxazepine) or a $C_{5-6}$ cycloalkene ring (preferably cyclopentene), each of which is optionally substituted),
(2) an optionally further substituted pyridine ring,
(3) an optionally further substituted pyrimidine ring,
(4) an optionally further substituted pyridazine ring,
(5) an optionally further substituted pyrazine ring,
(6) an optionally further substituted pyrazole ring,
(7) an optionally further substituted thiazole ring (the two substituents on the thiazole ring are optionally bonded to each other to form an optionally substituted benzene ring),
(8) an optionally further substituted isothiazole ring,
(9) an optionally further substituted imidazole ring (the two substituents on the imidazole ring are optionally bonded to each other to form an optionally substituted benzene ring),
(10) an optionally further substituted isoxazole ring,
(11) an optionally further substituted thiadiazole ring, or
(12) an optionally further substituted thiophene ring (the two substituents on the thiophene ring are optionally bonded to each other to form an optionally substituted $C_{5-6}$ cycloalkene ring (preferably cyclopentene, cyclohexene));
Ring B is an optionally further substituted pyrimidine ring ($X^1$ is a carbon atom, $X^2$ is a carbon atom and $X^3$ is a nitrogen atom), an optionally further substituted pyrazine ring ($X^1$ is a carbon atom, $X^2$ is a nitrogen atom and $X^3$ is a carbon atom), or an optionally further substituted pyridine ring ($X^1$ is a carbon atom, $X^2$ is a carbon atom and $X^3$ is a carbon atom);
Ring C is an optionally further substituted benzene ring, or an optionally further substituted pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom);
Z is
(1) —O—, or
(2) —N($R^Z$)— ($R^Z$ is as defined above);
$R^1$ is
(1) a hydrogen atom,
(2) an optionally substituted $C_{1-6}$ alkyl group, or
(3) an optionally substituted $C_{3-10}$ cycloalkyl group (e.g., cyclopropyl);
$R^2$ is
(1) an optionally substituted $C_{1-6}$ alkyl group,
(2) an optionally substituted 3- to 14-membered (preferably 4- to 10-membered) non-aromatic heterocyclic group (preferably a 3- to 8-membered monocyclic non-aromatic heterocyclic group), or
(3) an optionally substituted mono- or di-$C_{1-6}$ alkyl-carbamoyl group; and
$R^3$ is
(1) a cyano group,
(2) a halogen atom,
(3) an optionally substituted $C_{1-6}$ alkyl group,
(4) an optionally substituted carbamoyl group, or
(5) an optionally substituted 3- to 14-membered (preferably 4- to 10-membered) non-aromatic heterocyclylcarbonyl group (preferably a 3- to 8-membered monocyclic non-aromatic heterocyclylcarbonyl group).
[Compound Ba-2]
  Compound (I) wherein
Ring A is a 5- or 6-membered aromatic ring (e.g., benzene, pyridine, pyrimidine, pyridazine, pyrazine, pyrazole, thiazole, isothiazole, imidazole, isoxazole, thiadiazole, thiophene) optionally further substituted by 1 to 3 substituents selected from
  (a) a $C_{1-6}$ alkoxy group (e.g., methoxy, ethoxy, propyloxy, isopropyloxy) optionally substituted by 1 to 5 substituents selected from (i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom),
(b) a $C_{1-6}$ alkyl group (e.g., methyl, ethyl, propyl, isopropyl, butyl, isobutyl, sec-butyl, tert-butyl, 2,2-dimethylpropyl) optionally substituted by 1 to 5 substituents selected from
(i) a halogen atom (e.g., a fluorine atom),
(ii) a hydroxy group,
(iii) a cyano group,
(iv) a carboxy group,
(v) a $C_{1-6}$ alkoxy group (e.g., methoxy, ethoxy) optionally substituted by 1 to 3 substituents selected from
(I) a halogen atom (e.g., a fluorine atom), and
(II) a hydroxy group,
(vi) a $C_{1-6}$ alkoxy-carbonyl group (e.g., ethoxycarbonyl),
(vii) a $C_{1-6}$ alkylsulfonyl group (e.g., methylsulfonyl),
(viii) an amino group optionally mono- or di-substituted by substituent(s) selected from
(I) a $C_{3-10}$ cycloalkyl group (e.g., cyclopropyl),
(II) a $C_{1-6}$ alkyl-carbonyl group (e.g., acetyl),
(III) a $C_{1-6}$ alkoxy-carbonyl group (e.g., tert-butoxycarbonyl),
(IV) a $C_{1-6}$ alkylsulfonyl group (e.g., methylsulfonyl),
(V) a $C_{6-14}$ aryl-carbonyl group (e.g., benzoyl), and
(VI) a carbamoyl group,
(ix) a $C_{3-10}$ cycloalkyl group (e.g., cyclopropyl, cyclobutyl, cyclohexyl) optionally substituted by 1 to 3 substituents selected from
(I) an amino group,
(II) a hydroxy group,
(III) an oxo group,
(IV) a $C_{1-6}$ alkyl group (e.g., methyl), and
(V) a 3- to 14-membered (preferably 4- to 10-membered) non-aromatic heterocyclic group (preferably a 3- to 8-membered monocyclic non-aromatic heterocyclic group (e.g., morpholinyl)),
(x) a carbamoyl group optionally mono- or di-substituted by substituent(s) selected from
(I) a $C_{1-6}$ alkyl group (e.g., ethyl), and
(II) a $C_{6-14}$ aryl group (e.g., phenyl),
(xi) a 5- to 14-membered (preferably 5- to 10-membered) aromatic heterocyclic group (e.g., pyrazolyl, pyridyl, isoxazolyl, benzimidazolyl) optionally substituted by 1 to 3 substituents selected from
(I) a $C_{1-6}$ alkyl group (e.g., methyl), and
(II) a $C_{1-6}$ alkoxy group (e.g., methoxy),
(xii) a 3- to 14-membered (preferably 4- to 10-membered) non-aromatic heterocyclic group (e.g., morpholinyl, piperazinyl, 1,1-dioxidothiomorpholinyl, azetidinyl, pyrrolidinyl, piperidyl, oxetanyl, tetrahydrofuryl, tetrahydropyranyl, dihydropyridyl, dihydrotriazolyl, tetrahydrooxazolyl, dihydroquinazolinyl, 1,4-dioxaspiro[4.5]decyl) optionally substituted by 1 to 3 by 1 to 3 substituents selected from
(I) an oxo group,
(II) a hydroxy group,
(III) a carbamoyl group,
(IV) a $C_{1-6}$ alkyl groups (e.g., methyl) optionally substituted by 1 to 3 hydroxy groups,
(V) a $C_{1-6}$ alkoxy-carbonyl group (e.g., tert-butoxycarbonyl),
(VI) a $C_{3-10}$ cycloalkyl group (e.g., cyclobutyl),
(VII) a $C_{7-16}$ aralkyl group (e.g., benzyl), and
(VIII) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl)), and
(xiii) a 3- to 14-membered (preferably 4- to 10-membered) non-aromatic heterocyclylcarbonyl group (preferably a 3- to 8-membered monocyclic non-aromatic heterocyclylcarbonyl group (e.g., morpholinylcarbonyl)),
(c) a $C_{3-10}$ cycloalkyl group (the $C_{3-10}$ cycloalkyl group is optionally fused with a benzene ring, or optionally bridged or may be a spiro group; e.g., cyclopropyl, cyclobutyl, cyclopentyl, cyclohexyl, indanyl, bicyclo[2.2.1]heptyl, spiro[3.3]hexyl) optionally substituted by 1 to 3 substituents selected from
(i) a halogen atom (e.g., a fluorine atom),
(ii) an oxo group,
(iii) a hydroxy group,
(iv) a carbamoyl group,
(v) a carboxy group,
(vi) a $C_{1-6}$ alkyl group (e.g., methyl) optionally substituted by 1 to 3 substituents selected from
(I) a hydroxy group,
(II) a carboxy group,
(III) a carbamoyl group, and
(IV) a 3- to 14-membered (preferably 4- to 10-membered) non-aromatic heterocyclic group (preferably a 3- to 8-membered monocyclic non-aromatic heterocyclic group (e.g., morpholinyl)),
(vii) a $C_{1-6}$ alkoxy-carbonyl group (e.g., ethoxycarbonyl),
(viii) a 3- to 14-membered (preferably 4- to 10-membered) non-aromatic heterocyclic group (e.g., azetidinyl, pyrrolidinyl, morpholinyl, 2-oxa-6-azaspiro[3.3]heptyl, 3-oxa-8-azabicyclo[3.2.1]octyl) optionally substituted by 1 to 3 substituents selected from
(I) a halogen atom (e.g., a fluorine atom),
(II) a hydroxy group, and
(III) a $C_{1-6}$ alkyl group (e.g., methyl) optionally substituted by 1 to 3 substituents selected from a halogen atom (e.g., a fluorine atom) and a hydroxy group, and
(ix) an amino group optionally mono- or di-substituted by substituent(s) selected from
(I) a $C_{1-6}$ alkoxy-carbonyl group (e.g., tert-butoxycarbonyl), and
(II) a 3- to 14-membered (preferably 4- to 10-membered) non-aromatic heterocyclic group (preferably a 3- to 8-membered monocyclic non-aromatic heterocyclic group (e.g., tetrahydropyranyl)),
(d) a halogen atom (e.g., a fluorine atom, a chlorine atom),
(e) a cyano group,
(f) a carboxy group,
(g) an optionally halogenated $C_{1-6}$ alkyl-carbonyl group (e.g., acetyl, propionyl),
(h) a $C_{1-6}$ alkoxy-carbonyl group (e.g., methoxycarbonyl, ethoxycarbonyl, butoxycarbonyl),
(i) an amino group,
(j) a $C_{1-6}$ alkylsulfanyl group (e.g., methylsulfanyl),
(k) a $C_{1-6}$ alkylsulfonyl group (e.g., methylsulfonyl),
(l) a carbamoyl group optionally mono- or di-substituted by substituent(s) selected from (i) a $C_{1-6}$ alkyl group (e.g., methyl, ethyl, propyl, isopropyl) optionally substituted by 1 to 3 substituents selected from
  (I) a hydroxy group,
  (II) a halogen atom (e.g., a fluorine atom),
  (III) an optionally halogenated $C_{1-6}$ alkoxy group (e.g., methoxy, trifluoromethoxy),
  (IV) a mono- or di-$C_{1-6}$ alkylamino group (e.g., dimethylamino),
  (V) a $C_{3-10}$ cycloalkyl group (e.g., cyclopropyl, cyclohexyl), and
  (VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl),
(ii) a $C_{3-10}$ cycloalkyl group (e.g., cyclopropyl, cyclobutyl, cyclohexyl) optionally substituted by 1 to 3 substituents selected from
  (I) a halogen atom (e.g., a fluorine atom),
  (II) an optionally halogenated $C_{1-6}$ alkyl group (e.g., trifluoromethyl),
  (III) a carboxy group, and
  (IV) a $C_{1-6}$ alkoxy-carbonyl group (e.g., methoxycarbonyl), and
(iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl),
(m) a sulfamoyl group optionally mono- or di-substituted by substituent(s) selected from
  (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(n) a $C_{2-6}$ alkynyl group (e.g., (prop-2-ynyl)),
(o) a $C_{6-14}$ aryl group (e.g., phenyl) optionally substituted by 1 to 3 halogen atoms (e.g., a chlorine atom),
(p) a $C_{7-16}$ aralkyl group (e.g., benzyl),
(q) a 5- to 14-membered (preferably 5- to 10-membered) aromatic heterocyclic group (preferably a 5- to 6-membered monocyclic aromatic heterocyclic group (e.g., pyrazolyl, pyridyl, pyrazolyl, thienyl)) optionally substituted by 1 to 3 substituents selected from
  (i) a $C_{1-6}$ alkyl group (e.g., methyl), and
  (ii) a $C_{1-6}$ alkoxy group (e.g., methoxy),
(r) a 3- to 14-membered (preferably 4- to 10-membered) non-aromatic heterocyclic group (e.g., azetidinyl, piperidyl, piperazinyl, pyrrolidinyl, diazepanyl, tetrahydropyridyl, oxetanyl, morpholinyl, 2,5-diazabicyclo[2.2.1]heptyl, hexahydropyrrolo[1,2-a]pyrazinyl, hexahydropyrazino[2,1-c][1,4]oxazinyl, azepanyl, tetrahydrofuryl, tetrahydropyranyl, tetrahydrothiopyranyl, dihydropyridyl, 8-azabicyclo[3.2.1]octyl, 2-azaspiro[3.3]heptyl) optionally substituted by 1 to 3 substituents selected from
  (i) a $C_{1-6}$ alkyl group (e.g., methyl, ethyl, propyl, isopropyl, isobutyl, sec-butyl, 3,3-dimethylbutyl) optionally substituted by 1 to 3 substituents selected from
    (I) a halogen atom (e.g., a fluorine atom),
    (II) a hydroxy group,
    (III) a cyano group,
    (IV) a carbamoyl group,
    (V) a $C_{1-6}$ alkoxy group (e.g., methoxy, ethoxy) optionally substituted by 1 to 3 substituents selected from
      (A) a halogen atom (e.g., a fluorine atom),
      (B) a $C_{1-6}$ alkyl-carbonyloxy group (e.g., acetyloxy, 2-methylpropanoyloxy, 2,2-dimethylpropanoyloxy, 3-methylbutanoyloxy), and
      (C) a $C_{1-6}$ alkoxy-carbonyloxy group (e.g., ethoxycarbonyloxy, isopropoxycarbonyloxy),
    (VI) a $C_{1-6}$ alkyl-carbonyloxy group (e.g., acetyloxy),
    (VII) a $C_{1-6}$ alkylsulfonyl group (e.g., methylsulfonyl),
    (VIII) a $C_{3-10}$ cycloalkyl group (e.g., cyclopropyl),
    (IV) a mono- or di-$C_{1-6}$ alkylamino group (e.g., dimethylamino),
    (X) a 5- to 14-membered (preferably 5- to 10-membered) aromatic heterocyclic group (preferably a 5- to 6-membered monocyclic aromatic heterocyclic group (e.g., pyridyl, pyrazolyl, pyrrolyl, thiazolyl, thienyl, pyrimidinyl)) optionally substituted by 1 to 3 $C_{1-6}$ alkyl groups (e.g., methyl), and
    (XI) a 3- to 14-membered (preferably 4- to 10-membered) non-aromatic heterocyclic group (preferably a 3- to 8-membered monocyclic non-aromatic heterocyclic group (e.g., morpholinyl, oxetanyl)),
  (ii) a $C_{1-6}$ alkyl-carbonyl group (e.g., acetyl) optionally substituted by 1 to 3 substituents selected from
    (I) a halogen atom (e.g., a fluorine atom),
    (II) a hydroxy group, and
    (III) a mono- or di-$C_{1-6}$ alkylamino group (e.g., dimethylamino),
  (iii) a $C_{1-6}$ alkoxy-carbonyl group (e.g., tert-butoxycarbonyl),
  (iv) a $C_{3-10}$ cycloalkyl group (e.g., cyclopropyl, cyclobutyl, cyclopentyl, cyclohexyl) optionally substituted by 1 to 3 substituents selected from
    (I) a halogen atom (e.g., a fluorine atom),
    (II) a hydroxy group,
    (III) a $C_{1-6}$ alkyl group (e.g., methyl) optionally substituted by 1 to 3 $C_{1-6}$ alkoxy groups (e.g., methoxy), and
    (IV) a $C_{1-6}$ alkoxy group (e.g., methoxy),
  (v) a $C_{6-14}$ aryl group (e.g., phenyl) optionally substituted by 1 to 3 halogen atoms (e.g., a fluorine atom),
  (vi) a $C_{7-16}$ aralkyl group (e.g., benzyl),
  (vii) a 5- to 14-membered (preferably 5- to 10-membered) aromatic heterocyclic group (preferably a 5- to 6-membered monocyclic aromatic heterocyclic group (e.g., pyrimidinyl, pyridyl)) optionally substituted by 1 to 3 $C_{1-6}$ alkyl groups (e.g., methyl),
  (viii) a 3- to 14-membered (preferably 4- to 10-membered) non-aromatic heterocyclic group (e.g., morpholinyl, piperazinyl, piperidyl, oxetanyl, azetidinyl, tetrahydropyranyl, oxepanyl, dioxepanyl, 3-oxa-8-azabicyclo[3.2.1]octyl, 8-oxa-3-azabicyclo[3.2.1]octyl, tetrahydrofuryl, 1,1-dioxidotetrahydrothiopyranyl, dioxanyl, 2-oxabicyclo[2.2.2]octyl) optionally substituted by 1 to 3 substituents selected from
    (I) a halogen atom (e.g., a fluorine atom),
    (II) a $C_{1-6}$ alkyl-carbonyl group (e.g., acetyl), (III) a $C_{1-6}$ alkoxy-carbonyl group (e.g., tert-butoxycarbonyl),
(IV) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
(V) a $C_{3-10}$ cycloalkyl group (e.g., cyclopropyl),
(VI) a cyano group, and
(VII) a deuterium atom,
(ix) an oxo group,
(x) a hydroxy group, and
(xi) a mono- or di-$C_{1-6}$ alkyl-carbamoyl group (e.g., methylcarbamoyl),
(s) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from
(i) a halogen atom (e.g., a fluorine atom),
(ii) a hydroxy group,
(iii) a cyano group,
(iv) a $C_{1-6}$ alkyl group (e.g., methyl, ethyl) optionally substituted by 1 to 3 substituents selected from
(I) a hydroxy group,
(II) a halogen atom (e.g., a fluorine atom),
(III) a $C_{1-6}$ alkoxy group (e.g., methoxy),
(IV) a mono- or di-$C_{1-6}$ alkylamino group (e.g., dimethylamino), and
(V) a $C_{3-10}$ cycloalkyl group (e.g., cyclopropyl),
(v) an optionally halogenated $C_{1-6}$ alkoxy group (e.g., methoxy, difluoromethoxy),
(vi) a $C_{1-6}$ alkyl-carbonyl group (e.g., acetyl) optionally substituted by 1 to 3 substituents selected from
(I) a hydroxy group, and
(II) a $C_{1-6}$ alkoxy group (e.g., methoxy),
(vii) a $C_{1-6}$ alkoxy-carbonyl group (e.g., tert-butoxycarbonyl),
(viii) a $C_{3-10}$ cycloalkyl group (e.g., cyclopropyl),
(ix) a $C_{3-10}$ cycloalkyl-carbonyl group (e.g., cyclopropylcarbonyl),
(x) a $C_{1-6}$ alkylsulfonyl group (e.g., methylsulfonyl), and
(xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl),
(t) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl)), and
(u) a 3- to 14-membered (preferably 4- to 10-membered) non-aromatic heterocyclyloxy group (preferably a 3- to 8-membered monocyclic non-aromatic heterocyclyloxy group (e.g., oxetanyloxy))
(the two substituents on the 5- or 6-membered aromatic ring are optionally bonded to each other to form a 5- or 6-membered monocyclic aromatic heterocycle (e.g., pyrrole), a 3- to 8-membered monocyclic non-aromatic heterocycle (e.g., pyrroline, dihydrofuran, tetrahydropyridine, dihydrooxazine, tetrahydroazepine, tetrahydrooxazepine), a $C_{5-6}$ cycloalkene ring (e.g., cyclopentene, cyclohexene) or a benzene ring (e.g., indole, indoline, isoindoline, dihydrobenzofuran, tetrahydroquinoline, tetrahydroisoquinoline, dihydrobenzoxazine, tetrahydrobenzazepine, tetrahydrobenzoxazepine, indane, benzothiazole, benzimidazole, tetrahydrobenzothiophene, cyclopentathiophene), each of which is optionally substituted by 1 to 3 substituents selected from
(a) an oxo group,
(b) a $C_{1-6}$ alkyl group (e.g., methyl, ethyl) optionally substituted by 1 to 3 substituents selected from
(i) a halogen atom (e.g., a fluorine atom),
(ii) a hydroxy group,
(iii) a carboxy group,
(iv) a $C_{1-6}$ alkoxy group (e.g., methoxy),
(v) a $C_{1-6}$ alkyl-carbonyl group (e.g., acetyl),
(vi) a mono- or di-$C_{1-6}$ alkylamino group (e.g., dimethylamino), and
(vii) a 3- to 14-membered (preferably 4- to 10-membered) non-aromatic heterocyclic group (preferably a 3- to 8-membered monocyclic non-aromatic heterocyclic group (e.g., piperidyl, oxetanyl)) optionally substituted by 1 to 3 $C_{1-6}$ alkyl groups (e.g., methyl),
(c) a $C_{3-10}$ cycloalkyl group (e.g., cyclobutyl),
(d) a formyl group,
(e) a $C_{1-6}$ alkyl-carbonyl group (e.g., acetyl, propanoyl, butanoyl, 2-methylpropanoyl) optionally substituted by 1 to 3 substituents selected from
(i) a halogen atom (e.g., a fluorine atom),
(ii) a hydroxy group,
(iii) a $C_{1-6}$ alkoxy group (e.g., methoxy),
(iv) a $C_{1-6}$ alkyl-carbonyloxy group (e.g., acetyloxy),
(v) a mono- or di-$C_{1-6}$ alkylamino group (e.g., dimethylamino, N-ethyl-N-methylamino), and
(vi) a 3- to 14-membered (preferably 4- to 10-membered) non-aromatic heterocyclic group (preferably a 3- to 8-membered monocyclic non-aromatic heterocyclic group (e.g., morpholinyl)),
(f) a $C_{1-6}$ alkoxy-carbonyl group (e.g., tert-butoxycarbonyl),
(g) a 5- to 14-membered (preferably 5- to 10-membered) aromatic heterocyclic group (preferably a 5- to 6-membered monocyclic aromatic heterocyclic group (e.g., pyrimidinyl)) optionally substituted by 1 to 3 $C_{1-6}$ alkyl groups (e.g., methyl),
(h) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl, oxetanyl)) optionally substituted by 1 to 3 $C_{1-6}$ alkyl groups (e.g., methyl), and
(i) a 3- to 14-membered (preferably 4- to 10-membered) non-aromatic heterocyclycarbonyl group (preferably a 3- to 8-membered monocyclic non-aromatic heterocyclycarbonyl group (e.g., piperidylcarbonyl)) optionally substituted by 1 to 3 $C_{1-6}$ alkyl groups (e.g., methyl));

Ring B is
(1) a pyrimidine ring ($X^1$ is a carbon atom, $X^2$ is a carbon atom and $X^3$ is a nitrogen atom),
(2) a pyrazine ring ($X^1$ is a carbon atom, $X^2$ is a nitrogen atom and $X^3$ is a carbon atom), or
(3) a pyridine ring ($X^1$ is a carbon atom, $X^2$ is a carbon atom and $X^3$ is a carbon atom);
Ring C is a benzene ring or a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom), each of which is optionally further substituted by 1 to 3 halogen atoms (e.g., a fluorine atom, a chlorine atom);
Z is
(1) —O—, or
(2) —NH—;
$R^1$ is
(1) a hydrogen atom,
(2) a $C_{1-6}$ alkyl group (e.g., methyl, ethyl) optionally substituted by 1 to 3 substituents selected from
  (a) a halogen atom (e.g., a fluorine atom), and
  (b) a hydroxy group, or
(3) a $C_{3-10}$ cycloalkyl group (e.g., cyclopropyl);
$R^2$ is
(1) a $C_{1-6}$ alkyl group (e.g., methyl, ethyl, isobutyl) optionally substituted by 1 to 3 substituents selected from
  (a) a 5- to 14-membered (preferably 5- to 10-membered) aromatic heterocyclic group (e.g., triazolyl (e.g., 1,2,4-triazolyl, 1,2,3-triazolyl), tetrazolyl, pyrazolyl, imidazolyl, oxadiazolyl (e.g., 1,2,4-oxadiazolyl, 1,3,4-oxadiazolyl), pyridyl, benzimidazolyl) optionally substituted by 1 to 3 substituents selected from
    (i) a cyano group,
    (ii) a halogen atom (e.g., a fluorine atom),
    (iii) a $C_{1-6}$ alkyl group (e.g., methyl), and
    (iv) a $C_{7-16}$ aralkyl group (e.g., trityl),
  (b) a 3- to 14-membered (preferably 4- to 10-membered) non-aromatic heterocyclic group (preferably a 3- to 8-membered monocyclic non-aromatic heterocyclic group (e.g., imidazolidinyl, morpholinyl, triazolinyl, pyrrolidinyl)) optionally substituted by 1 to 3 substituents selected from
    (i) an oxo group, and
    (ii) a $C_{1-6}$ alkyl group (e.g., methyl),
  (c) a halogen atom (e.g., a fluorine atom),
  (d) a hydroxy group,
  (e) a cyano group,
  (f) an optionally halogenated $C_{1-6}$ alkoxy group (e.g., methoxy, difluoromethoxy),
  (g) a 5- to 14-membered (preferably 5- to 10-membered) aromatic heterocyclyloxy group (preferably a 5- or 6-membered monocyclic aromatic heterocyclyloxy group (e.g., triazolyloxy (e.g., 1,2,4-triazolyloxy))),
  (h) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)),
  (i) an amino group optionally mono- or di-substituted by substituent(s) selected from
    (i) a $C_{1-6}$ alkyl group (e.g., methyl),
    (ii) a $C_{1-6}$ alkyl-carbonyl group (e.g., acetyl) optionally substituted by 1 to 3 $C_{1-6}$ alkoxy groups (e.g., methoxy), and
    (iii) a $C_{1-6}$ alkylsulfonyl group (e.g., methylsulfonyl), and
  (j) a mono- or di-$C_{1-6}$ alkyl-carbamoyl group (e.g., methylcarbamoyl),
  (2) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 substituents selected from
    (a) an oxo group, and
    (b) a $C_{1-6}$ alkyl group (e.g., methyl), or
  (3) a mono- or di-$C_{1-6}$ alkyl-carbamoyl group (e.g., ethylcarbamoyl) optionally substituted by 1 to 3 halogen atoms (e.g., a fluorine atom); and
$R^3$ is
(1) a cyano group,
(2) a halogen atom (e.g., a fluorine atom, a chlorine atom),
(3) an optionally halogenated $C_{1-6}$ alkyl group (e.g., methyl, difluoromethyl, trifluoromethyl),
(4) a carbamoyl group,
(5) a mono- or di-$C_{1-6}$ alkyl-carbamoyl group (e.g., dimethylcarbamoyl), or
(6) a 3- to 14-membered (preferably 4- to 10-membered) non-aromatic heterocyclylcarbonyl group (preferably a 3- to 8-membered monocyclic non-aromatic heterocyclylcarbonyl group (e.g., pyrrolidinylcarbonyl)).
[Compound Bb-2]
Compound (I) wherein
Ring A is
(1) a benzene ring optionally further substituted by 1 to 3 substituents selected from
  (a) an optionally halogenated $C_{1-6}$ alkoxy group (e.g., methoxy, ethoxy, isopropyloxy, difluoromethoxy, trifluoromethoxy, trifluoroethoxy),
  (b) a $C_{1-6}$ alkyl group (e.g., methyl, ethyl, propyl, isopropyl, tert-butyl) optionally substituted by 1 to 3 substituents selected from
    (i) a halogen atom (e.g., a fluorine atom),
    (ii) a hydroxy group,
    (iii) an amino group optionally mono- or di-substituted by substituent(s) selected from
      (I) a $C_{3-10}$ cycloalkyl group (e.g., cyclopropyl), and
      (II) a $C_{1-6}$ alkoxy-carbonyl group (e.g., tert-butoxycarbonyl),
    (iv) a 5- to 14-membered (preferably 5- to 10-membered) aromatic heterocyclic group (preferably a 5- to 6-membered monocyclic aromatic heterocyclic group (e.g., pyrazolyl)), and
    (v) a 3- to 14-membered (preferably 4- to 10-membered) non-aromatic heterocyclic group (preferably a 3- to 8-membered monocyclic non-aromatic heterocyclic group (e.g., morpholinyl, piperazinyl, 1,1-dioxidothiomorpholinyl)) optionally substituted by 1 to 3 $C_{1-6}$ alkyl groups (e.g., methyl),
  (c) a $C_{3-10}$ cycloalkyl group (e.g., cyclopropyl, cyclohexyl) optionally substituted by 1 to 3 substituents selected from
    (i) a 3- to 14-membered (preferably 4- to 10-membered) non-aromatic heterocyclic group (preferably a 3- to 8-membered monocyclic non-aromatic heterocyclic group (e.g., morpholinyl)),
  (d) a halogen atom (e.g., a fluorine atom, a chlorine atom),
  (e) a cyano group,
  (f) a carboxy group,
  (g) a $C_{1-6}$ alkoxy-carbonyl group (e.g., methoxycarbonyl, butoxycarbonyl),
  (h) a $C_{1-6}$ alkylsulfanyl group (e.g., methylsulfanyl),
  (i) a $C_{1-6}$ alkylsulfonyl group (e.g., methylsulfonyl),
  (j) a carbamoyl group optionally mono- or di-substituted by substituent(s) selected from
    (i) a $C_{1-6}$ alkyl group (e.g., methyl, ethyl, propyl, isopropyl) optionally substituted by 1 to 3 substituents selected from (I) a hydroxy group,
(II) a halogen atom (e.g., a fluorine atom),
(III) an optionally halogenated $C_{1-6}$ alkoxy group (e.g., methoxy, trifluoromethoxy),
(IV) a mono- or di-$C_{1-6}$ alkylamino group (e.g., dimethylamino),
(V) a $C_{3-10}$ cycloalkyl group (e.g., cyclopropyl, cyclohexyl), and
(VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl),
(ii) a $C_{3-10}$ cycloalkyl group (e.g., cyclopropyl, cyclobutyl, cyclohexyl) optionally substituted by 1 to 3 substituents selected from
(I) a halogen atom (e.g., a fluorine atom),
(II) an optionally halogenated $C_{1-6}$ alkyl group (e.g., trifluoromethyl),
(III) a carboxy group, and
(IV) a $C_{1-6}$ alkoxy-carbonyl group (e.g., methoxycarbonyl), and
(iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl),
(k) a sulfamoyl group optionally mono- or di-substituted by substituent(s) selected from
(i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
(l) a 5- to 14-membered (preferably 5- to 10-membered) aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl),
(m) a 3- to 14-membered (preferably 4- to 10-membered) non-aromatic heterocyclic group (e.g., azetidinyl, piperidyl, piperazinyl, pyrrolidinyl, diazepanyl, tetrahydropyridyl, morpholinyl, 2,5-diazabicyclo[2.2.1]heptyl, hexahydropyrrolo[1,2-a]pyrazinyl, hexahydropyrazino[2,1-c][1,4]oxazinyl) optionally substituted by 1 to 3 substituents selected from
(i) a $C_{1-6}$ alkyl group (e.g., methyl, ethyl, propyl, isobutyl) optionally substituted by 1 to 3 substituents selected from
(I) a halogen atom (e.g., a fluorine atom),
(II) a hydroxy group,
(III) a cyano group,
(IV) a carbamoyl group,
(V) a $C_{1-6}$ alkoxy group (e.g., methoxy),
(VI) a $C_{1-6}$ alkylsulfonyl group (e.g., methylsulfonyl),
(VII) a mono- or di-$C_{1-6}$ alkylamino group (e.g., dimethylamino), and
(VIII) a 3- to 14-membered (preferably 4- to 10-membered) non-aromatic heterocyclic group (preferably a 3- to 8-membered monocyclic non-aromatic heterocyclic group (e.g., morpholinyl)),
(ii) a $C_{1-6}$ alkyl-carbonyl group (e.g., acetyl) optionally substituted by 1 to 3 substituents selected from
(I) a halogen atom (e.g., a fluorine atom),
(II) a hydroxy group, and
(III) a mono- or di-$C_{1-6}$ alkylamino group (e.g., dimethylamino),
(iii) a $C_{1-6}$ alkoxy-carbonyl group (e.g., tert-butoxycarbonyl),
(iv) a 3- to 14-membered (preferably 4- to 10-membered) non-aromatic heterocyclic group (e.g., morpholinyl, piperazinyl, piperidyl, oxetanyl, azetidinyl, tetrahydropyranyl, 3-oxa-8-azabicyclo[3.2.1]octyl, 8-oxa-3-azabicyclo[3.2.1]octyl) optionally substituted by 1 to 3 substituents selected from
(I) a halogen atom (e.g., a fluorine atom),
(II) a $C_{1-6}$ alkyl-carbonyl group (e.g., acetyl), and
(III) a $C_{1-6}$ alkoxy-carbonyl group (e.g., tert-butoxycarbonyl),
(v) an oxo group, and
(vi) a mono- or di-$C_{1-6}$ alkyl-carbamoyl group (e.g., methylcarbamoyl),
(n) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from
(i) a halogen atom (e.g., a fluorine atom),
(ii) a hydroxy group,
(iii) a cyano group,
(iv) a $C_{1-6}$ alkyl group (e.g., methyl, ethyl) optionally substituted by 1 to 3 substituents selected from
(I) a hydroxy group,
(II) a halogen atom (e.g., a fluorine atom),
(III) a $C_{1-6}$ alkoxy group (e.g., methoxy),
(IV) a mono- or di-$C_{1-6}$ alkylamino group (e.g., dimethylamino), and
(V) a $C_{3-10}$ cycloalkyl group (e.g., cyclopropyl),
(v) an optionally halogenated $C_{1-6}$ alkoxy group (e.g., methoxy, difluoromethoxy),
(vi) a $C_{1-6}$ alkyl-carbonyl group (e.g., acetyl) optionally substituted by 1 to 3 substituents selected from
(I) a hydroxy group, and
(II) a $C_{1-6}$ alkoxy group (e.g., methoxy),
(vii) a $C_{1-6}$ alkoxy-carbonyl group (e.g., tert-butoxycarbonyl),
(viii) a $C_{3-10}$ cycloalkyl group (e.g., cyclopropyl),
(ix) a $C_{3-10}$ cycloalkyl-carbonyl group (e.g., cyclopropylcarbonyl),
(x) a $C_{1-6}$ alkylsulfonyl group (e.g., methylsulfonyl), and
(xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), and (o) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl))

(the two substituents on the benzene ring are optionally bonded to each other to form a 5- or 6-membered monocyclic aromatic heterocycle (e.g., pyrrole), a 3- to 8-membered monocyclic non-aromatic heterocycle (e.g., pyrroline, dihydrofuran, tetrahydropyridine, dihydrooxazine, tetrahydroazepine, tetrahydrooxazepine) or a $C_{5-6}$ cycloalkene ring (e.g., cyclopentene) (e.g., indole, indoline, isoindoline, dihydrobenzofuran, tetrahydroquinoline, tetrahydroisoquinoline, dihydrobenzoxazine, tetrahydrobenzazepine, tetrahydrobenzoxazepine, indane), each of which is optionally substituted by 1 to 3 substituents selected from (a) an oxo group,
(b) a $C_{1-6}$ alkyl group (e.g., methyl, ethyl) optionally substituted by 1 to 3 substituents selected from
  (i) a halogen atom (e.g., a fluorine atom),
  (ii) a hydroxy group,
  (iii) a carboxy group,
  (iv) a $C_{1-6}$ alkoxy group (e.g., methoxy),
  (v) a $C_{1-6}$ alkyl-carbonyl group (e.g., acetyl),
  (vi) a mono- or di-$C_{1-6}$ alkylamino group (e.g., dimethylamino), and
  (vii) a 3- to 14-membered (preferably 4- to 10-membered) non-aromatic heterocyclic group (preferably a 3- to 8-membered monocyclic non-aromatic heterocyclic group (e.g., piperidyl, oxetanyl)) optionally substituted by 1 to 3 $C_{1-6}$ alkyl groups (e.g., methyl),
(c) a $C_{3-10}$ cycloalkyl group (e.g., cyclobutyl),
(d) a formyl group,
(e) a $C_{1-6}$ alkyl-carbonyl group (e.g., acetyl, propanoyl, butanoyl, 2-methylpropanoyl) optionally substituted by 1 to 3 substituents selected from
  (i) a halogen atom (e.g., a fluorine atom),
  (ii) a hydroxy group,
  (iii) a $C_{1-6}$ alkoxy group (e.g., methoxy),
  (iv) a $C_{1-6}$ alkyl-carbonyloxy group (e.g., acetyloxy),
  (v) a mono- or di-$C_{1-6}$ alkylamino group (e.g., dimethylamino, N-ethyl-N-methylamino), and
  (vi) a 3- to 14-membered (preferably 4- to 10-membered) non-aromatic heterocyclic group (preferably a 3- to 8-membered monocyclic non-aromatic heterocyclic group (e.g., morpholinyl)),
(f) a $C_{1-6}$ alkoxy-carbonyl group (e.g., tert-butoxycarbonyl),
(g) a 5- to 14-membered (preferably 5- to 10-membered) aromatic heterocyclic group (preferably a 5- to 6-membered monocyclic aromatic heterocyclic group (e.g., pyrimidinyl)) optionally substituted by 1 to 3 $C_{1-6}$ alkyl groups (e.g., methyl),
(h) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl, oxetanyl)) optionally substituted by 1 to 3 $C_{1-6}$ alkyl groups (e.g., methyl), and
(i) a 3- to 14-membered (preferably 4- to 10-membered) non-aromatic heterocyclycarbonyl group (preferably a 3- to 8-membered monocyclic non-aromatic heterocyclycarbonyl group (e.g., piperidylcarbonyl)) optionally substituted by 1 to 3 $C_{1-6}$ alkyl groups (e.g., methyl)), or (2) a 5- or 6-membered aromatic heterocycle (e.g., pyridine, pyrimidine, pyridazine, pyrazine, pyrazole, thiazole, isothiazole, imidazole, isoxazole, thiadiazole, thiophene) optionally further substituted by 1 to 3 substituents selected from
(a) an amino group,
(b) a halogen atom (e.g., a chlorine atom),
(c) a cyano group,
(d) a carboxy group,
(e) a $C_{1-6}$ alkyl group (e.g., methyl, ethyl, propyl, isopropyl, butyl, isobutyl, sec-butyl, tert-butyl, 2,2-dimethylpropyl) optionally substituted by 1 to 5 substituents selected from
  (i) a $C_{3-10}$ cycloalkyl group (e.g., cyclopropyl, cyclobutyl, cyclohexyl) optionally substituted by 1 to 3 substituents selected from
    (I) an amino group,
    (II) a hydroxy group,
    (III) an oxo group,
    (IV) a $C_{1-6}$ alkyl group (e.g., methyl), and
    (V) a 3- to 14-membered (preferably 4- to 10-membered) non-aromatic heterocyclic group (preferably a 3- to 8-membered monocyclic non-aromatic heterocyclic group (e.g., morpholinyl)),
  (ii) a hydroxy group,
  (iii) a cyano group,
  (iv) a halogen atom (e.g., a fluorine atom),
  (v) a carboxy group,
  (vi) a $C_{1-6}$ alkoxy group (e.g., methoxy, ethoxy) optionally substituted by 1 to 3 substituents selected from
    (I) a halogen atom (e.g., a fluorine atom), and
    (II) a hydroxy group,
  (vii) a $C_{1-6}$ alkoxy-carbonyl group (e.g., ethoxycarbonyl),
  (viii) a $C_{1-6}$ alkylsulfonyl group (e.g., methylsulfonyl),
  (ix) an amino group optionally mono- or di-substituted by substituent(s) selected from
    (I) a $C_{1-6}$ alkyl-carbonyl group (e.g., acetyl),
    (II) a $C_{1-6}$ alkoxy-carbonyl group (e.g., tert-butoxycarbonyl),
    (III) a $C_{1-6}$ alkylsulfonyl group (e.g., methylsulfonyl),
    (IV) a $C_{6-14}$ aryl-carbonyl group (e.g., benzoyl), and
    (V) a carbamoyl group,
  (x) a carbamoyl group optionally mono- or di-substituted by substituent(s) selected from
    (I) a $C_{1-6}$ alkyl group (e.g., ethyl), and
    (II) a $C_{6-14}$ aryl group (e.g., phenyl),
  (xi) a 5- to 14-membered (preferably 5- to 10-membered) aromatic heterocyclic group (e.g., pyridyl, isoxazolyl, benzimidazolyl) optionally substituted by 1 to 3 substituents selected from
    (I) a $C_{1-6}$ alkyl group (e.g., methyl), and
    (II) a $C_{1-6}$ alkoxy group (e.g., methoxy),
  (xii) a 3- to 14-membered (preferably 4- to 10-membered) non-aromatic heterocyclic group (e.g., azetidinyl, pyrrolidinyl, piperidyl, morpholinyl, oxetanyl, tetrahydrofuryl, tetrahydropyranyl, dihydropyridyl, dihydrotriazolyl, tetrahydrooxazolyl, dihydroquinazolinyl, 1,4-dioxaspiro[4.5]decyl) optionally substituted by 1 to 3 substituents selected from
    (I) an oxo group,
    (II) a hydroxy group,
    (III) a carbamoyl group, (IV) a $C_{1-6}$ alkyl group (e.g., methyl) optionally substituted by 1 to 3 hydroxy groups,
(V) a $C_{1-6}$ alkoxy-carbonyl group (e.g., tert-butoxycarbonyl),
(VI) a $C_{3-10}$ cycloalkyl group (e.g., cyclobutyl),
(VII) a $C_{7-16}$ aralkyl group (e.g., benzyl), and
(VIII) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl)), and
(xiii) a 3- to 14-membered (preferably 4- to 10-membered) non-aromatic heterocyclylcarbonyl group (preferably a 3- to 8-membered monocyclic non-aromatic heterocyclylcarbonyl group (e.g., morpholinylcarbonyl)),
(f) a $C_{2-6}$ alkynyl group (e.g., (prop-2-ynyl)),
(g) a $C_{1-6}$ alkoxy group (e.g., methoxy, ethoxy, propyloxy) optionally substituted by 1 to 5 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom),
(h) a $C_{3-10}$ cycloalkyl group (the $C_{3-10}$ cycloalkyl group is optionally fused with a benzene ring, or optionally bridged or may be a spiro group; e.g., cyclopropyl, cyclobutyl, cyclopentyl, cyclohexyl, indanyl, bicyclo[2.2.1]heptyl, spiro[3.3]hexyl) optionally substituted by 1 to 3 substituents selected from
(i) a halogen atom (e.g., a fluorine atom),
(ii) an oxo group,
(iii) a hydroxy group,
(iv) a carbamoyl group,
(v) a carboxy group,
(vi) a $C_{1-6}$ alkyl group (e.g., methyl) optionally substituted by 1 to 3 substituents selected from
(I) a hydroxy group,
(II) a carboxy group,
(III) a carbamoyl group, and
(IV) a 3- to 14-membered (preferably 4- to 10-membered) non-aromatic heterocyclic group (preferably a 3- to 8-membered monocyclic non-aromatic heterocyclic group (e.g., morpholinyl)),
(vii) a $C_{1-6}$ alkoxy-carbonyl group (e.g., ethoxycarbonyl),
(viii) a 3- to 14-membered (preferably 4- to 10-membered) non-aromatic heterocyclic group (preferably a 3- to 8-membered monocyclic non-aromatic heterocyclic group (e.g., azetidinyl, pyrrolidinyl, morpholinyl, 2-oxa-6-azaspiro[3.3]heptyl, 3-oxa-8-azabicyclo[3.2.1]octyl)) optionally substituted by 1 to 3 substituents selected from
(I) a halogen atom (e.g., a fluorine atom),
(II) a hydroxy group, and
(III) a $C_{1-6}$ alkyl group (e.g., methyl) optionally substituted by 1 to 3 substituents selected from a halogen atom (e.g., a fluorine atom) and a hydroxy group, and
(ix) an amino group optionally mono- or di-substituted by substituent(s) selected from
(I) a $C_{1-6}$ alkoxy-carbonyl group (e.g., tert-butoxycarbonyl), and
(II) a 3- to 14-membered (preferably 4- to 10-membered) non-aromatic heterocyclic group (preferably a 3- to 8-membered monocyclic non-aromatic heterocyclic group (e.g., tetrahydropyranyl)),
(i) an optionally halogenated $C_{1-6}$ alkyl-carbonyl group (e.g., acetyl, propionyl),
(j) a $C_{1-6}$ alkoxy-carbonyl group (e.g., ethoxycarbonyl),
(k) a $C_{6-14}$ aryl group (e.g., phenyl) optionally substituted by 1 to 3 halogen atoms (e.g., a chlorine atom),
(l) a $C_{7-16}$ aralkyl group (e.g., benzyl),
(m) a 5- to 14-membered (preferably 5- to 10-membered) aromatic heterocyclic group (preferably a 5- to 6-membered monocyclic aromatic heterocyclic group (e.g., pyridyl, pyrazolyl, thienyl)) optionally substituted by 1 to 3 $C_{1-6}$ alkoxy groups (e.g., methoxy),
(n) a 3- to 14-membered (preferably 4- to 10-membered) non-aromatic heterocyclic group (preferably a 3- to 8-membered monocyclic non-aromatic heterocyclic group (e.g., oxetanyl, piperidyl, azetidinyl, piperazinyl, pyrrolidinyl, morpholinyl, azepanyl, diazepanyl, tetrahydrofuryl, tetrahydropyranyl, tetrahydrothiopyranyl, dihydropyridyl, 8-azabicyclo[3.2.1]octyl, 2-azaspiro[3.3]heptyl)) optionally substituted by 1 to 3 substituents selected from
(i) an oxo group,
(ii) a hydroxy group,
(iii) a $C_{1-6}$ alkyl group (e.g., methyl, ethyl, propyl, isopropyl, isobutyl, 3,3-dimethylbutyl) optionally substituted by 1 to 3 substituents selected from
(I) a halogen atom (e.g., a fluorine atom),
(II) a hydroxy group,
(III) a cyano group,
(IV) a $C_{1-6}$ alkoxy group (e.g., methoxy, ethoxy) optionally substituted by 1 to 3 substituents selected from
(A) a halogen atom (e.g., a fluorine atom),
(B) a $C_{1-6}$ alkyl-carbonyloxy group (e.g., acetyloxy, 2-methylpropanoyloxy, 2,2-dimethylpropanoyloxy, 3-methylbutanoyloxy), and
(C) a $C_{1-6}$ alkoxy-carbonyloxy group (e.g., ethoxycarbonyloxy, isopropoxycarbonyloxy),
(V) a $C_{1-6}$ alkyl-carbonyloxy group (e.g., acetyloxy),
(VI) a $C_{3-10}$ cycloalkyl group (e.g., cyclopropyl),
(VII) a 5- to 14-membered (preferably 5- to 10-membered) aromatic heterocyclic group (preferably a 5- to 6-membered monocyclic aromatic heterocyclic group (e.g., pyridyl, pyrazolyl, pyrrolyl, thiazolyl, thienyl, pyrimidinyl)) optionally substituted by 1 to 3 $C_{1-6}$ alkyl groups (e.g., methyl), and
(VIII) a 3- to 14-membered (preferably 4- to 10-membered) non-aromatic heterocyclic group (preferably a 3- to 8-membered monocyclic non-aromatic heterocyclic group (e.g., oxetanyl, morpholinyl)),
(iv) a $C_{3-10}$ cycloalkyl group (e.g., cyclopropyl, cyclobutyl, cyclopentyl, cyclohexyl) optionally substituted by 1 to 3 substituents selected from
(I) a halogen atom (e.g., a fluorine atom),
(II) a hydroxy group,
(III) a $C_{1-6}$ alkyl group (e.g., methyl) optionally substituted by 1 to 3 $C_{1-6}$ alkoxy groups (e.g., methoxy), and
(IV) a $C_{1-6}$ alkoxy group (e.g., methoxy),
(v) a $C_{6-14}$ aryl group (e.g., phenyl) optionally substituted by 1 to 3 halogen atoms (e.g., a fluorine atom),
(vi) a $C_{7-16}$ aralkyl group (e.g., benzyl),
(vii) an optionally halogenated $C_{1-6}$ alkyl-carbonyl group (e.g., acetyl, trifluoroacetyl), (viii) a $C_{1-6}$ alkoxy-carbonyl group (e.g., tert-butoxy-carbonyl), (ix) a 5- to 14-membered (preferably 5- to 10-membered) aromatic heterocyclic group (preferably a 5- to 6-membered monocyclic aromatic heterocyclic group (e.g., pyrimidinyl, pyridyl)) optionally substituted by 1 to 3 $C_{1-6}$ alkyl groups (e.g., methyl), and (x) a 3- to 14-membered (preferably 4- to 10-membered) non-aromatic heterocyclic group (preferably a 3- to 8-membered monocyclic non-aromatic heterocyclic group (e.g., morpholinyl, oxetanyl, piperidyl, tetrahydrofuryl, tetrahydropyranyl, oxepanyl, dioxepanyl, 1,1-dioxidotetrahydrothiopyranyl, dioxanyl, 2-oxabicyclo[2.2.2]octyl)) optionally substituted by 1 to 3 substituents selected from
  (I) a halogen atom (e.g., a fluorine atom),
  (II) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
  (III) a $C_{3-10}$ cycloalkyl group (e.g., cyclopropyl),
  (VI) a cyano group, and
  (V) a deuterium atom, (o) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)), and (p) a 3- to 14-membered (preferably 4- to 10-membered) non-aromatic heterocyclylcarbonyl group (preferably a 3- to 8-membered monocyclic non-aromatic heterocyclylcarbonyl group (e.g., piperidylcarbonyl, morpholinylcarbonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)), (the two substituents on the 5- or 6-membered aromatic heterocycle are optionally bonded to each other to form a benzene ring (e.g., benzothiazole, benzimidazole), or a $C_{5-6}$ cycloalkene ring (e.g., cyclopentene, cyclohexene) (e.g., tetrahydrobenzothiophene ring, cyclopentathiophene ring));

Ring B is
(1) a pyrimidine ring ($X^1$ is a carbon atom, $X^2$ is a carbon atom and $X^3$ is a nitrogen atom),
(2) a pyrazine ring ($X^1$ is a carbon atom, $X^2$ is a nitrogen atom and $X^3$ is a carbon atom), or
(3) a pyridine ring ($X^1$ is a carbon atom, $X^2$ is a carbon atom and $X^3$ is a carbon atom);

Ring C is
(1) a benzene ring optionally further substituted by 1 to 3 halogen atoms (e.g., a fluorine atom, a chlorine atom), or
(2) a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom);

Z is
(1) —O—, or
(2) —NH—;

$R^1$ is
(1) a hydrogen atom,
(2) a $C_{1-6}$ alkyl group (e.g., methyl, ethyl) optionally substituted by 1 to 3 substituents selected from
  (a) a halogen atom (e.g., a fluorine atom), and
  (b) a hydroxy group, or
(3) a $C_{3-10}$ cycloalkyl group (e.g., cyclopropyl);

$R^2$ is
(1) a $C_{1-6}$ alkyl group (e.g., methyl, ethyl, isobutyl) optionally substituted by 1 to 3 substituents selected from
  (a) a 5- to 14-membered (preferably 5- to 10-membered) aromatic heterocyclic group (e.g., triazolyl (e.g., 1,2,4-triazolyl, 1,2,3-triazolyl), tetrazolyl, pyrazolyl, imidazolyl, oxadiazolyl (e.g., 1,2,4-oxadiazolyl, 1,3,4-oxadiazolyl), pyridyl, benzimidazolyl) optionally substituted by 1 to 3 substituents selected from
    (i) a cyano group,
    (ii) a halogen atom (e.g., a fluorine atom),
    (iii) a $C_{1-6}$ alkyl group (e.g., methyl), and
    (iv) a $C_{7-16}$ aralkyl group (e.g., trityl),
  (b) a 3- to 14-membered (preferably 4- to 10-membered) non-aromatic heterocyclic group (preferably a 3- to 8-membered monocyclic non-aromatic heterocyclic group (e.g., imidazolidinyl, morpholinyl, triazolinyl, pyrrolidinyl)) optionally substituted by 1 to 3 substituents selected from
    (i) an oxo group, and
    (ii) a $C_{1-6}$ alkyl group (e.g., methyl),
  (c) a halogen atom (e.g., a fluorine atom),
  (d) a hydroxy group,
  (e) a cyano group,
  (f) an optionally halogenated $C_{1-6}$ alkoxy group (e.g., methoxy, difluoromethoxy),
  (g) a 5- to 14-membered (preferably 5- to 10-membered) aromatic heterocyclyloxy group (preferably a 5- or 6-membered monocyclic aromatic heterocyclyloxy group (e.g., triazolyloxy (e.g., 1,2,4-triazolyloxy))),
  (h) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)),
  (i) an amino group optionally mono- or di-substituted by substituent(s) selected from
    (i) a $C_{1-6}$ alkyl group (e.g., methyl),
    (ii) a $C_{1-6}$ alkyl-carbonyl group (e.g., acetyl) optionally substituted by 1 to 3 $C_{1-6}$ alkoxy groups (e.g., methoxy), and
    (iii) a $C_{1-6}$ alkylsulfonyl group (e.g., methylsulfonyl), and
  (j) a mono- or di-$C_{1-6}$ alkyl-carbamoyl group (e.g., methylcarbamoyl),
(2) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 substituents selected from
  (a) an oxo group, and
  (b) a $C_{1-6}$ alkyl group (e.g., methyl), or
(3) a mono- or di-$C_{1-6}$ alkyl-carbamoyl group (e.g., ethylcarbamoyl) optionally substituted by 1 to 3 halogen atoms (e.g., a fluorine atom); and $R^3$ is
(1) a cyano group,
(2) a halogen atom (e.g., a fluorine atom, a chlorine atom),
(3) an optionally halogenated $C_{1-6}$ alkyl group (e.g., methyl, difluoromethyl, trifluoromethyl),
(4) a carbamoyl group,
(5) a mono- or di-$C_{1-6}$ alkyl-carbamoyl group (e.g., dimethylcarbamoyl), or
(6) a 3- to 14-membered (preferably 4- to 10-membered) non-aromatic heterocyclylcarbonyl group (preferably a 3- to 8-membered monocyclic non-aromatic heterocyclylcarbonyl group (e.g., pyrrolidinylcarbonyl)).

[Compound Bc-2]
Compound (I) wherein
Ring A is
(1) a benzene ring optionally further substituted by 1 to 3 substituents selected from
   (a) an optionally halogenated $C_{1-6}$ alkoxy group (e.g., methoxy, ethoxy, isopropyloxy, difluoromethoxy, trifluoromethoxy, trifluoroethoxy),
   (b) a $C_{1-6}$ alkyl group (e.g., methyl, ethyl, propyl, isopropyl, tert-butyl) optionally substituted by 1 to 3 substituents selected from
      (i) a halogen atom (e.g., a fluorine atom),
      (ii) a hydroxy group,
      (iii) an amino group optionally mono- or di-substituted by substituent(s) selected from
         (I) a $C_{3-10}$ cycloalkyl group (e.g., cyclopropyl), and
         (II) a $C_{1-6}$ alkoxy-carbonyl group (e.g., tert-butoxycarbonyl),
      (iv) a 5- to 14-membered (preferably 5- to 10-membered) aromatic heterocyclic group (preferably a 5- to 6-membered monocyclic aromatic heterocyclic group (e.g., pyrazolyl)), and
      (v) a 3- to 14-membered (preferably 4- to 10-membered) non-aromatic heterocyclic group (preferably a 3- to 8-membered monocyclic non-aromatic heterocyclic group (e.g., morpholinyl, piperazinyl, 1,1-dioxidothiomorpholinyl)) optionally substituted by 1 to 3 $C_{1-6}$ alkyl groups (e.g., methyl),
   (c) a $C_{3-10}$ cycloalkyl group (e.g., cyclopropyl, cyclohexyl) optionally substituted by 1 to 3 substituents selected from
      (i) a 3- to 14-membered (preferably 4- to 10-membered) non-aromatic heterocyclic group (preferably a 3- to 8-membered monocyclic non-aromatic heterocyclic group (e.g., morpholinyl)),
   (d) a halogen atom (e.g., a fluorine atom, a chlorine atom),
   (e) a cyano group,
   (f) a carboxy group,
   (g) a $C_{1-6}$ alkoxy-carbonyl group (e.g., methoxycarbonyl, butoxycarbonyl),
   (h) a $C_{1-6}$ alkylsulfanyl group (e.g., methylsulfanyl),
   (i) a $C_{1-6}$ alkylsulfonyl group (e.g., methylsulfonyl),
   (j) a carbamoyl group optionally mono- or di-substituted by substituent(s) selected from
      (i) a $C_{1-6}$ alkyl group (e.g., methyl, ethyl, propyl, isopropyl) optionally substituted by 1 to 3 substituents selected from
         (I) a hydroxy group,
         (II) a halogen atom (e.g., a fluorine atom),
         (III) an optionally halogenated $C_{1-6}$ alkoxy group (e.g., methoxy, trifluoromethoxy),
         (IV) a mono- or di-$C_{1-6}$ alkylamino group (e.g., dimethylamino),
         (V) a $C_{3-10}$ cycloalkyl group (e.g., cyclopropyl, cyclohexyl), and
         (VI) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl, piperidyl, morpholinyl)) optionally substituted by 1 to 3 substituents selected from a $C_{1-6}$ alkyl group (e.g., methyl) and a $C_{1-6}$ alkyl-carbonyl group (e.g., acetyl),
      (ii) a $C_{3-10}$ cycloalkyl group (e.g., cyclopropyl, cyclobutyl, cyclohexyl) optionally substituted by 1 to 3 substituents selected from
         (I) a halogen atom (e.g., a fluorine atom),
         (II) an optionally halogenated $C_{1-6}$ alkyl group (e.g., trifluoromethyl),
         (III) a carboxy group, and
         (IV) a $C_{1-6}$ alkoxy-carbonyl group (e.g., methoxycarbonyl), and
      (iii) a 3- to 14-membered (preferably 4- to 10-membered) non-aromatic heterocyclic group (preferably a 3- to 8-membered monocyclic non-aromatic heterocyclic group (e.g., tetrahydropyranyl, oxetanyl, piperidyl)) optionally substituted by 1 to 3 optionally halogenated $C_{1-6}$ alkyl groups (e.g., methyl, trifluoroethyl),
   (k) a sulfamoyl group optionally mono- or di-substituted by substituent(s) selected from
      (i) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 $C_{1-6}$ alkyl groups (e.g., methyl),
   (l) a 5- to 14-membered (preferably 5- to 10-membered) aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl),
   (m) a 3- to 14-membered (preferably 4- to 10-membered) non-aromatic heterocyclic group (e.g., azetidinyl, piperidyl, piperazinyl, pyrrolidinyl, diazepanyl, tetrahydropyridyl, morpholinyl, 2,5-diazabicyclo[2.2.1]heptyl, hexahydropyrrolo[1,2-a]pyrazinyl, hexahydropyrazino[2,1-c][1,4]oxazinyl) optionally substituted by 1 to 3 substituents selected from
      (i) a $C_{1-6}$ alkyl group (e.g., methyl, ethyl, propyl, isobutyl) optionally substituted by 1 to 3 substituents selected from
         (I) a halogen atom (e.g., a fluorine atom),
         (II) a hydroxy group,
         (III) a cyano group,
         (IV) a carbamoyl group,
         (V) a $C_{1-6}$ alkoxy group (e.g., methoxy),
         (VI) a $C_{1-6}$ alkylsulfonyl group (e.g., methylsulfonyl),
         (VII) a mono- or di-$C_{1-6}$ alkylamino group (e.g., dimethylamino), and
         (VIII) a 3- to 14-membered (preferably 4- to 10-membered) non-aromatic heterocyclic group (preferably a 3- to 8-membered monocyclic non-aromatic heterocyclic group (e.g., morpholinyl)),
      (ii) a $C_{1-6}$ alkyl-carbonyl group (e.g., acetyl) optionally substituted by 1 to 3 substituents selected from
         (I) a halogen atom (e.g., a fluorine atom),
         (II) a hydroxy group, and
         (III) a mono- or di-$C_{1-6}$ alkylamino group (e.g., dimethylamino),
      (iii) a $C_{1-6}$ alkoxy-carbonyl group (e.g., tert-butoxycarbonyl),
      (iv) a 3- to 14-membered (preferably 4- to 10-membered) non-aromatic heterocyclic group (e.g., morpholinyl, piperazinyl, piperidyl, oxetanyl, azetidinyl, tetrahydropyranyl, 3-oxa-8-azabicyclo[3.2.1]octyl, 8-oxa-3-azabicyclo[3.2.1]octyl) optionally substituted by 1 to 3 substituents selected from
         (I) a halogen atom (e.g., a fluorine atom),
         (II) a $C_{1-6}$ alkyl-carbonyl group (e.g., acetyl), and
         (III) a $C_{1-6}$ alkoxy-carbonyl group (e.g., tert-butoxycarbonyl), (v) an oxo group, and
(vi) a mono- or di-$C_{1-6}$ alkyl-carbamoyl group (e.g., methylcarbamoyl),
(n) a 3- to 14-membered (preferably 4- to 10-membered) non-aromatic heterocyclylcarbonyl group (e.g., morpholinylcarbonyl, piperazinylcarbonyl, piperidylcarbonyl, pyrrolidinylcarbonyl, azetidinylcarbonyl, azepanylcarbonyl, diazepanylcarbonyl, oxazepanylcarbonyl, 1,1-dioxidothiomorpholinylcarbonyl, 2-oxa-5-azabicyclo[2.2.1]heptylcarbonyl, 8-oxa-3-azabicyclo[3.2.1]octylcarbonyl, 2,5-diazabicyclo[2.2.1]heptylcarbonyl, 3,8-diazabicyclo[3.2.1]octylcarbonyl, 1,4-diazabicyclo[3.2.1]octylcarbonyl, 7-oxa-4-azaspiro[2.5]octylcarbonyl, 2-oxa-7-azaspiro[3.5]nonylcarbonyl, 4-oxa-7-azaspiro[2.5]octylcarbonyl, 2,6-diazaspiro[3.3]heptylcarbonyl, 2-oxa-6-azaspiro[3.3]heptylcarbonyl, 2,7-diazaspiro[3.5]nonylcarbonyl) optionally substituted by 1 to 3 substituents selected from
(i) a halogen atom (e.g., a fluorine atom),
(ii) a hydroxy group,
(iii) a cyano group,
(iv) a $C_{1-6}$ alkyl group (e.g., methyl, ethyl) optionally substituted by 1 to 3 substituents selected from
(I) a hydroxy group,
(II) a halogen atom (e.g., a fluorine atom),
(III) a $C_{1-6}$ alkoxy group (e.g., methoxy),
(IV) a mono- or di-$C_{1-6}$ alkylamino group (e.g., dimethylamino), and
(V) a $C_{3-10}$ cycloalkyl group (e.g., cyclopropyl),
(v) an optionally halogenated $C_{1-6}$ alkoxy group (e.g., methoxy, difluoromethoxy),
(vi) a $C_{1-6}$ alkyl-carbonyl group (e.g., acetyl) optionally substituted by 1 to 3 substituents selected from
(I) a hydroxy group, and
(II) a $C_{1-6}$ alkoxy group (e.g., methoxy),
(vii) a $C_{1-6}$ alkoxy-carbonyl group (e.g., tert-butoxycarbonyl),
(viii) a $C_{3-10}$ cycloalkyl group (e.g., cyclopropyl),
(ix) a $C_{3-10}$ cycloalkyl-carbonyl group (e.g., cyclopropylcarbonyl),
(x) a $C_{1-6}$ alkylsulfonyl group (e.g., methylsulfonyl), and
(xi) a 3- to 14-membered (preferably 4- to 10-membered) non-aromatic heterocyclic group (preferably a 3- to 8-membered monocyclic non-aromatic heterocyclic group (e.g., piperidyl, piperazinyl, morpholinyl, oxetanyl)) optionally substituted by 1 to 3 $C_{1-6}$ alkyl groups (e.g., methyl), and
(o) a 3- to 14-membered (preferably 4- to 10-membered) non-aromatic heterocyclylsulfonyl group (preferably a 3- to 8-membered monocyclic non-aromatic heterocyclylsulfonyl group (e.g., piperidylsulfonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., piperidyl))
(the two substituents on the benzene ring are optionally bonded to each other to form a 5- or 6-membered monocyclic aromatic heterocycle (e.g., pyrrole), a 3- to 8-membered monocyclic non-aromatic heterocycle (e.g., pyrroline, dihydrofuran, tetrahydropyridine, dihydrooxazine, tetrahydroazepine, tetrahydrooxazepine) or a $C_{5-6}$ cycloalkene ring (e.g., cyclopentene) (e.g., indole, indoline, isoindoline, dihydrobenzofuran, tetrahydroquinoline, tetrahydroisoquinoline, dihydrobenzoxazine, tetrahydrobenzazepine, tetrahydrobenzoxazepine, indane), each of which is optionally substituted by 1 to 3 substituents selected from (a) an oxo group,
(b) a $C_{1-6}$ alkyl group (e.g., methyl, ethyl) optionally substituted by 1 to 3 substituents selected from
(i) a halogen atom (e.g., a fluorine atom),
(ii) a hydroxy group,
(iii) a carboxy group,
(iv) a $C_{1-6}$ alkoxy group (e.g., methoxy),
(v) a $C_{1-6}$ alkyl-carbonyl group (e.g., acetyl),
(vi) a mono- or di-$C_{1-6}$ alkylamino group (e.g., dimethylamino), and
(vii) a 3- to 14-membered (preferably 4- to 10-membered) non-aromatic heterocyclic group (preferably a 3- to 8-membered monocyclic non-aromatic heterocyclic group (e.g., piperidyl, oxetanyl)) optionally substituted by 1 to 3 $C_{1-6}$ alkyl groups (e.g., methyl),
(c) a $C_{3-10}$ cycloalkyl group (e.g., cyclobutyl),
(d) a formyl group,
(e) a $C_{1-6}$ alkyl-carbonyl group (e.g., acetyl, propanoyl, butanoyl, 2-methylpropanoyl) optionally substituted by 1 to 3 substituents selected from
(i) a halogen atom (e.g., a fluorine atom),
(ii) a hydroxy group,
(iii) a $C_{1-6}$ alkoxy group (e.g., methoxy),
(iv) a $C_{1-6}$ alkyl-carbonyloxy group (e.g., acetyloxy),
(v) a mono- or di-$C_{1-6}$ alkylamino group (e.g., dimethylamino, N-ethyl-N-methylamino), and
(vi) a 3- to 14-membered (preferably 4- to 10-membered) non-aromatic heterocyclic group (preferably a 3- to 8-membered monocyclic non-aromatic heterocyclic group (e.g., morpholinyl)),
(f) a $C_{1-6}$ alkoxy-carbonyl group (e.g., tert-butoxycarbonyl),
(g) a 5- to 14-membered (preferably 5- to 10-membered) aromatic heterocyclic group (preferably a 5- to 6-membered monocyclic aromatic heterocyclic group (e.g., pyrimidinyl)) optionally substituted by 1 to 3 $C_{1-6}$ alkyl groups (e.g., methyl),
(h) a 3- to 14-membered (preferably 4- to 10-membered) non-aromatic heterocyclic group (preferably a 3- to 8-membered monocyclic non-aromatic heterocyclic group (e.g., tetrahydropyranyl, piperidyl, oxetanyl)) optionally substituted by 1 to 3 $C_{1-6}$ alkyl groups (e.g., methyl), and (i) a 3- to 14-membered (preferably 4- to 10-membered) non-aromatic heterocyclycarbonyl group (preferably a 3- to 8-membered monocyclic non-aromatic heterocyclycarbonyl group (e.g., piperidylcarbonyl)) optionally substituted by 1 to 3 $C_{1-6}$ alkyl groups (e.g., methyl)),
(2) a pyridine ring optionally further substituted by 1 to 3 substituents selected from
(a) a $C_{1-6}$ alkyl group (e.g., methyl),
(b) an optionally halogenated $C_{1-6}$ alkoxy group (e.g., methoxy, trifluoromethoxy, 2,2,2-trifluoroethoxy),
(c) a $C_{3-10}$ cycloalkyl group (e.g., cyclohexyl) optionally substituted by 1 to 3 halogen atoms (e.g., a fluorine atom),
(d) an amino group, and
(e) a 3- to 14-membered (preferably 4- to 10-membered) non-aromatic heterocyclic group (preferably a 3- to 8-membered monocyclic non-aromatic heterocyclic group (e.g., piperidyl, azetidinyl, piperazinyl, diazepanyl, tetrahydropyranyl)) optionally substituted by 1 to 3 substituents selected from
(i) a hydroxy group,
(ii) a $C_{1-6}$ alkyl group (e.g., methyl, ethyl) optionally substituted by 1 to 3 substituents selected from (I) a halogen atom (e.g., a fluorine atom), and
(II) a 3- to 14-membered (preferably 4- to 10-membered) non-aromatic heterocyclic group (preferably 3- to 8-membered monocyclic non-aromatic heterocyclic group (e.g., morpholinyl, oxetanyl)),
(iii) an optionally halogenated $C_{1-6}$ alkyl-carbonyl group (e.g., trifluoroacetyl),
(iv) a $C_{1-6}$ alkoxy-carbonyl group (e.g., tert-butoxycarbonyl),
(v) a $C_{3-10}$ cycloalkyl group (e.g., cyclopropyl, cyclohexyl) optionally substituted by 1 to 3 halogen atoms (e.g., a fluorine atom), and
(vi) a 3- to 14-membered (preferably 4- to 10-membered) non-aromatic heterocyclic group (preferably a 3- to 8-membered monocyclic non-aromatic heterocyclic group (e.g., morpholinyl, tetrahydrofuryl, tetrahydropyranyl)),
(3) a pyrimidine ring optionally further substituted by 1 to 3 substituents selected from
  (a) a $C_{1-6}$ alkoxy group (e.g., methoxy), and
  (b) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)),
(4) a pyridazine ring,
(5) a pyrazine ring,
(6) a pyrazole ring optionally further substituted by 1 to 3 substituents selected from
  (a) a halogen atom (e.g., a chlorine atom),
  (b) a cyano group,
  (c) a carboxy group,
  (d) a $C_{1-6}$ alkyl group (e.g., methyl, ethyl, propyl, isopropyl, butyl, isobutyl, sec-butyl, tert-butyl, 2,2-dimethylpropyl) optionally substituted by 1 to 5 substituents selected from
    (i) a $C_{3-10}$ cycloalkyl group (e.g., cyclopropyl, cyclobutyl, cyclohexyl) optionally substituted by 1 to 3 substituents selected from
      (I) an amino group,
      (II) a hydroxy group,
      (III) an oxo group,
      (IV) a $C_{1-6}$ alkyl group (e.g., methyl), and
      (V) a 3- to 14-membered (preferably 4- to 10-membered) non-aromatic heterocyclic group (preferably a 3- to 8-membered monocyclic non-aromatic heterocyclic group (e.g., morpholinyl)),
    (ii) a hydroxy group,
    (iii) a cyano group,
    (iv) a halogen atom (e.g., a fluorine atom),
    (v) a carboxy group,
    (vi) a $C_{1-6}$ alkoxy group (e.g., methoxy, ethoxy) optionally substituted by 1 to 3 substituents selected from
      (I) a halogen atom (e.g., a fluorine atom), and
      (II) a hydroxy group,
    (vii) a $C_{1-6}$ alkoxy-carbonyl group (e.g., ethoxycarbonyl),
    (viii) a $C_{1-6}$ alkylsulfonyl group (e.g., methylsulfonyl),
    (ix) an amino group optionally mono- or di-substituted by substituent(s) selected from
      (I) a $C_{1-6}$ alkyl-carbonyl group (e.g., acetyl),
      (II) a $C_{1-6}$ alkoxy-carbonyl group (e.g., tert-butoxycarbonyl),
      (III) a $C_{1-6}$ alkylsulfonyl group (e.g., methylsulfonyl),
      (IV) a $C_{6-14}$ aryl-carbonyl group (e.g., benzoyl), and
      (V) a carbamoyl group,
    (x) a carbamoyl group optionally mono- or di-substituted by substituent(s) selected from
      (I) a $C_{1-6}$ alkyl group (e.g., ethyl), and
      (II) a $C_{6-14}$ aryl group (e.g., phenyl),
    (xi) a 5- to 14-membered (preferably 5- to 10-membered) aromatic heterocyclic group (e.g., pyridyl, isoxazolyl, benzimidazolyl) optionally substituted by 1 to 3 substituents selected from
      (I) a $C_{1-6}$ alkyl group (e.g., methyl), and
      (II) a $C_{1-6}$ alkoxy group (e.g., methoxy),
    (xii) a 3- to 14-membered (preferably 4- to 10-membered) non-aromatic heterocyclic group (e.g., azetidinyl, pyrrolidinyl, piperidyl, morpholinyl, oxetanyl, tetrahydrofuryl, tetrahydropyranyl, dihydropyridyl, dihydrotriazolyl, tetrahydrooxazolyl, dihydroquinazolinyl, 1,4-dioxaspiro[4.5]decyl) optionally substituted by 1 to 3 substituents selected from
      (I) an oxo group,
      (II) a hydroxy group,
      (III) a carbamoyl group,
      (IV) a $C_{1-6}$ alkyl group (e.g., methyl) optionally substituted by 1 to 3 hydroxy groups,
      (V) a $C_{1-6}$ alkoxy-carbonyl group (e.g., tert-butoxycarbonyl),
      (VI) a $C_{3-10}$ cycloalkyl group (e.g., cyclobutyl),
      (VII) a $C_{7-16}$ aralkyl group (e.g., benzyl), and
      (VIII) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl)), and
    (xiii) a 3- to 14-membered (preferably 4- to 10-membered) non-aromatic heterocyclylcarbonyl group (preferably a 3- to 8-membered monocyclic non-aromatic heterocyclylcarbonyl group (e.g., morpholinylcarbonyl)),
  (e) a $C_{2-6}$ alkynyl group (e.g., (prop-2-ynyl)),
  (f) a $C_{1-6}$ alkoxy group (e.g., methoxy, ethoxy, propyloxy) optionally substituted by 1 to 5 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom),
  (g) a $C_{3-10}$ cycloalkyl group (the $C_{3-10}$ cycloalkyl group is optionally fused with a benzene ring, or optionally bridged or may be a spiro group; e.g., cyclopropyl, cyclobutyl, cyclopentyl, cyclohexyl, indanyl, bicyclo[2.2.1]heptyl, spiro[3.3]hexyl) optionally substituted by 1 to 3 substituents selected from
    (i) an oxo group,
    (ii) a hydroxy group,
    (iii) a carbamoyl group,
    (iv) a carboxy group,
    (v) a $C_{1-6}$ alkyl group (e.g., methyl) optionally substituted by 1 to 3 substituents selected from
      (I) a hydroxy group,
      (II) a carboxy group,
      (III) a carbamoyl group, and
      (IV) a 3- to 14-membered (preferably 4- to 10-membered) non-aromatic heterocyclic group (preferably a 3- to 8-membered monocyclic non-aromatic heterocyclic group (e.g., morpholinyl)), (vi) a $C_{1-6}$ alkoxy-carbonyl group (e.g., ethoxycarbonyl),
(vii) a 3- to 14-membered (preferably 4- to 10-membered) non-aromatic heterocyclic group (preferably a 3- to 8-membered monocyclic non-aromatic heterocyclic group (e.g., azetidinyl, pyrrolidinyl, morpholinyl, 2-oxa-6-azaspiro[3.3]heptyl, 3-oxa-8-azabicyclo[3.2.1]octyl)) optionally substituted by 1 to 3 substituents selected from
(I) a halogen atom (e.g., a fluorine atom),
(II) a hydroxy group, and
(III) a $C_{1-6}$ alkyl group (e.g., methyl) optionally substituted by 1 to 3 substituents selected from a halogen atom (e.g., a fluorine atom) and a hydroxy group, and
(viii) an amino group optionally mono- or di-substituted by substituent(s) selected from
(I) a $C_{1-6}$ alkoxy-carbonyl group (e.g., tert-butoxycarbonyl), and
(II) a 3- to 14-membered (preferably 4- to 10-membered) non-aromatic heterocyclic group (preferably a 3- to 8-membered monocyclic non-aromatic heterocyclic group (e.g., tetrahydropyranyl)),
(h) an optionally halogenated $C_{1-6}$ alkyl-carbonyl group (e.g., acetyl, propionyl),
(i) a $C_{1-6}$ alkoxy-carbonyl group (e.g., ethoxycarbonyl),
(j) a $C_{6-14}$ aryl group (e.g., phenyl),
(k) a $C_{7-16}$ aralkyl group (e.g., benzyl),
(l) a 5- to 14-membered (preferably 5- to 10-membered) aromatic heterocyclic group (preferably a 5- to 6-membered monocyclic aromatic heterocyclic group (e.g., pyridyl, pyrazolyl, thienyl)) optionally substituted by 1 to 3 $C_{1-6}$ alkoxy groups (e.g., methoxy),
(m) a 3- to 14-membered (preferably 4- to 10-membered) non-aromatic heterocyclic group (preferably a 3- to 8-membered monocyclic non-aromatic heterocyclic group (e.g., oxetanyl, piperidyl, azetidinyl, pyrrolidinyl, morpholinyl, azepanyl, tetrahydrofuryl, tetrahydropyranyl, tetrahydrothiopyranyl, dihydropyridyl, 8-azabicyclo[3.2.1]octyl, 2-azaspiro[3.3]heptyl)) optionally substituted by 1 to 3 substituents selected from
(i) an oxo group,
(ii) a hydroxy group,
(iii) a $C_{1-6}$ alkyl group (e.g., methyl, ethyl, propyl, isopropyl, isobutyl, 3,3-dimethylbutyl) optionally substituted by 1 to 3 substituents selected from
(I) a halogen atom (e.g., a fluorine atom),
(II) a hydroxy group,
(III) a cyano group,
(IV) a $C_{1-6}$ alkoxy group (e.g., methoxy, ethoxy) optionally substituted by 1 to 3 substituents selected from
(A) a halogen atom (e.g., a fluorine atom),
(B) a $C_{1-6}$ alkyl-carbonyloxy group (e.g., acetyloxy, 2-methylpropanoyloxy, 2,2-dimethylpropanoyloxy, 3-methylbutanoyloxy), and
(C) a $C_{1-6}$ alkoxy-carbonyloxy group (e.g., ethoxycarbonyloxy, isopropoxycarbonyloxy),
(V) a $C_{1-6}$ alkyl-carbonyloxy group (e.g., acetyloxy),
(VI) a $C_{3-10}$ cycloalkyl group (e.g., cyclopropyl),
(VII) a 5- to 14-membered (preferably 5- to 10-membered) aromatic heterocyclic group (preferably a 5- to 6-membered monocyclic aromatic heterocyclic group (e.g., pyridyl, pyrazolyl, pyrrolyl, thiazolyl, thienyl, pyrimidinyl)) optionally substituted by 1 to 3 $C_{1-6}$ alkyl groups (e.g., methyl), and
(VIII) a 3- to 14-membered (preferably 4- to 10-membered) non-aromatic heterocyclic group (preferably a 3- to 8-membered monocyclic non-aromatic heterocyclic group (e.g., oxetanyl)),
(iv) a $C_{3-10}$ cycloalkyl group (e.g., cyclopropyl, cyclobutyl, cyclopentyl, cyclohexyl) optionally substituted by 1 to 3 substituents selected from
(I) a halogen atom (e.g., a fluorine atom),
(II) a hydroxy group,
(III) a $C_{1-6}$ alkyl group (e.g., methyl) optionally substituted by 1 to 3 $C_{1-6}$ alkoxy groups (e.g., methoxy), and
(IV) a $C_{1-6}$ alkoxy group (e.g., methoxy),
(v) a $C_{6-14}$ aryl group (e.g., phenyl) optionally substituted by 1 to 3 halogen atoms (e.g., a fluorine atom),
(vi) a $C_{7-16}$ aralkyl group (e.g., benzyl),
(vii) a $C_{1-6}$ alkyl-carbonyl group (e.g., acetyl),
(viii) a $C_{1-6}$ alkoxy-carbonyl group (e.g., tert-butoxycarbonyl),
(ix) a 5- to 14-membered (preferably 5- to 10-membered) aromatic heterocyclic group (preferably a 5- to 6-membered monocyclic aromatic heterocyclic group (e.g., pyrimidinyl, pyridyl)) optionally substituted by 1 to 3 $C_{1-6}$ alkyl groups (e.g., methyl), and
(x) a 3- to 14-membered (preferably 4- to 10-membered) non-aromatic heterocyclic group (preferably a 3- to 8-membered monocyclic non-aromatic heterocyclic group (e.g., oxetanyl, piperidyl, tetrahydrofuryl, tetrahydropyranyl, oxepanyl, dioxepanyl, 1,1-dioxidotetrahydrothiopyranyl, dioxanyl, 2-oxabicyclo[2.2.2]octyl)) optionally substituted by 1 to 3 substituents selected from
(I) a halogen atom (e.g., a fluorine atom),
(II) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
(III) a $C_{3-10}$ cycloalkyl group (e.g., cyclopropyl),
(VI) a cyano group, and
(V) a deuterium atom,
(n) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)), and
(o) a 3- to 14-membered (preferably 4- to 10-membered) non-aromatic heterocyclylcarbonyl group (preferably a 3- to 8-membered monocyclic non-aromatic heterocyclylcarbonyl group (e.g., piperidylcarbonyl, morpholinylcarbonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl)),
(7) a thiazole ring (the two substituents on the thiazole ring are optionally bonded to each other to form a benzene ring (e.g., benzothiazole ring)),
(8) an isothiazole ring optionally further substituted by 1 to 3 substituents selected from
(a) a $C_{1-6}$ alkyl group (e.g., methyl) optionally substituted by 1 to 3 hydroxy groups,
(9) an imidazole ring optionally further substituted by 1 to 3 substituents selected from
(a) a $C_{1-6}$ alkyl group (e.g., methyl) optionally substituted by 1 to 3 hydroxy groups (the two substituents on the imidazole ring are optionally bonded to each other to form a benzene ring (e.g., benzimidazole ring)),
(10) an isoxazole ring optionally further substituted by 1 to 3 $C_{1-6}$ alkyl groups (e.g., methyl),
(11) a thiadiazole ring optionally further substituted by 1 to 3 substituents selected from
   (a) a $C_{6-14}$ aryl group (e.g., phenyl) optionally substituted by 1 to 3 halogen atoms (e.g., a chlorine atom), or
(12) a thiophene ring optionally further substituted by 1 to 3 cyano groups (the two substituents on the thiophene ring are optionally bonded to each other to form a $C_{5-6}$ cycloalkene ring (e.g., cyclopentene, cyclohexene) (e.g., tetrahydrobenzothiophene ring, cyclopentathiophene ring));
Ring B is
(1) a pyrimidine ring ($X^1$ is a carbon atom, $X^2$ is a carbon atom and $X^3$ is a nitrogen atom),
(2) a pyrazine ring ($X^1$ is a carbon atom, $X^2$ is a nitrogen atom and $X^3$ is a carbon atom), or
(3) a pyridine ring ($X^1$ is a carbon atom, $X^2$ is a carbon atom and $X^3$ is a carbon atom);
Ring C is
(1) a benzene ring optionally further substituted by 1 to 3 halogen atoms (e.g., a fluorine atom, a chlorine atom), or
(2) a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom);
Z is
(1) —O—, or
(2) —NH—;
$R^1$ is
(1) a hydrogen atom,
(2) a $C_{1-6}$ alkyl group (e.g., methyl, ethyl) optionally substituted by 1 to 3 substituents selected from
   (a) a halogen atom (e.g., a fluorine atom), and
   (b) a hydroxy group, or
(3) a $C_{3-10}$ cycloalkyl group (e.g., cyclopropyl);
$R^2$ is
(1) a $C_{1-6}$ alkyl group (e.g., methyl, ethyl, isobutyl) optionally substituted by 1 to 3 substituents selected from
   (a) a 5- to 14-membered (preferably 5- to 10-membered) aromatic heterocyclic group (e.g., triazolyl (e.g., 1,2,4-triazolyl, 1,2,3-triazolyl), tetrazolyl, pyrazolyl, imidazolyl, oxadiazolyl (e.g., 1,2,4-oxadiazolyl, 1,3,4-oxadiazolyl), pyridyl, benzimidazolyl) optionally substituted by 1 to 3 substituents selected from
      (i) a cyano group,
      (ii) a halogen atom (e.g., a fluorine atom),
      (iii) a $C_{1-6}$ alkyl group (e.g., methyl), and
      (iv) a $C_{7-16}$ aralkyl group (e.g., trityl),
   (b) a 3- to 14-membered (preferably 4- to 10-membered) non-aromatic heterocyclic group (preferably a 3- to 8-membered monocyclic non-aromatic heterocyclic group (e.g., imidazolidinyl, morpholinyl, triazolinyl, pyrrolidinyl)) optionally substituted by 1 to 3 substituents selected from
      (i) an oxo group, and
      (ii) a $C_{1-6}$ alkyl group (e.g., methyl),
   (c) a halogen atom (e.g., a fluorine atom),
   (d) a hydroxy group,
   (e) a cyano group,
   (f) an optionally halogenated $C_{1-6}$ alkoxy group (e.g., methoxy, difluoromethoxy),
   (g) a 5- to 14-membered (preferably 5- to 10-membered) aromatic heterocyclyloxy group (preferably a 5- or 6-membered monocyclic aromatic heterocyclyloxy group (e.g., triazolyloxy (e.g., 1,2,4-triazolyloxy))),
   (h) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)),
   (i) an amino group optionally mono- or di-substituted by substituent(s) selected from
      (i) a $C_{1-6}$ alkyl group (e.g., methyl),
      (ii) a $C_{1-6}$ alkyl-carbonyl group (e.g., acetyl) optionally substituted by 1 to 3 $C_{1-6}$ alkoxy groups (e.g., methoxy), and
      (iii) a $C_{1-6}$ alkylsulfonyl group (e.g., methylsulfonyl), and
   (j) a mono- or di-$C_{1-6}$ alkyl-carbamoyl group (e.g., methylcarbamoyl),
(2) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 substituents selected from
   (a) an oxo group, and
   (b) a $C_{1-6}$ alkyl group (e.g., methyl), or
(3) a mono- or di-$C_{1-6}$ alkyl-carbamoyl group (e.g., ethylcarbamoyl) optionally substituted by 1 to 3 halogen atoms (e.g., a fluorine atom); and $R^3$ is
(1) a cyano group,
(2) a halogen atom (e.g., a fluorine atom, a chlorine atom),
(3) an optionally halogenated $C_{1-6}$ alkyl group (e.g., methyl, difluoromethyl, trifluoromethyl),
(4) a carbamoyl group,
(5) a mono- or di-$C_{1-6}$ alkyl-carbamoyl group (e.g., dimethylcarbamoyl), or
(6) a 3- to 14-membered (preferably 4- to 10-membered) non-aromatic heterocyclylcarbonyl group (preferably a 3- to 8-membered monocyclic non-aromatic heterocyclylcarbonyl group (e.g., pyrrolidinylcarbonyl)).
[Compound C-2]
Compound (I) wherein
Ring A is a pyrazole ring optionally further substituted by 1 to 3 substituents selected from
   (a) a halogen atom (e.g., a chlorine atom),
   (b) a cyano group,
   (c) a carboxy group,
   (d) a $C_{1-6}$ alkyl group (e.g., methyl, ethyl, propyl, isopropyl, butyl, isobutyl, sec-butyl, tert-butyl, 2,2-dimethylpropyl) optionally substituted by 1 to 5 substituents selected from
      (i) a $C_{3-10}$ cycloalkyl group (e.g., cyclopropyl, cyclobutyl, cyclohexyl) optionally substituted by 1 to 3 substituents selected from
         (I) an amino group,
         (II) a hydroxy group,
         (III) an oxo group,
         (IV) a $C_{1-6}$ alkyl group (e.g., methyl), and
         (V) a 3- to 14-membered (preferably 4- to 10-membered) non-aromatic heterocyclic group (preferably a 3- to 8-membered monocyclic non-aromatic heterocyclic group (e.g., morpholinyl)),
      (ii) a hydroxy group,
      (iii) a cyano group,
      (iv) a halogen atom (e.g., a fluorine atom),
      (v) a carboxy group,
      (vi) a $C_{1-6}$ alkoxy group (e.g., methoxy, ethoxy) optionally substituted by 1 to 3 substituents selected from
         (I) a halogen atom (e.g., a fluorine atom), and
         (II) a hydroxy group,
      (vii) a $C_{1-6}$ alkoxy-carbonyl group (e.g., ethoxycarbonyl), (viii) a $C_{1-6}$ alkylsulfonyl group (e.g., methylsulfonyl),
(ix) an amino group optionally mono- or di-substituted by substituent(s) selected from
  (I) a $C_{1-6}$ alkyl-carbonyl group (e.g., acetyl),
  (II) a $C_{1-6}$ alkoxy-carbonyl group (e.g., tert-butoxycarbonyl),
  (III) a $C_{1-6}$ alkylsulfonyl group (e.g., methylsulfonyl),
  (IV) a $C_{6-14}$ aryl-carbonyl group (e.g., benzoyl), and
  (V) a carbamoyl group,
(x) a carbamoyl group optionally mono- or di-substituted by substituent(s) selected from
  (I) a $C_{1-6}$ alkyl group (e.g., ethyl), and
  (II) a $C_{6-14}$ aryl group (e.g., phenyl),
(xi) a 5- to 14-membered (preferably 5- to 10-membered) aromatic heterocyclic group (e.g., pyridyl, isoxazolyl, benzimidazolyl) optionally substituted by 1 to 3 substituents selected from
  (I) a $C_{1-6}$ alkyl group (e.g., methyl), and
  (II) a $C_{1-6}$ alkoxy group (e.g., methoxy),
(xii) a 3- to 14-membered (preferably 4- to 10-membered) non-aromatic heterocyclic group (e.g., azetidinyl, pyrrolidinyl, piperidyl, morpholinyl, oxetanyl, tetrahydrofuryl, tetrahydropyranyl, dihydropyridyl, dihydrotriazolyl, tetrahydrooxazolyl, dihydroquinazolinyl, 1,4-dioxaspiro[4.5]decyl) optionally substituted by 1 to 3 substituents selected from
  (I) an oxo group,
  (II) a hydroxy group,
  (III) a carbamoyl group,
  (IV) a $C_{1-6}$ alkyl group (e.g., methyl) optionally substituted by 1 to 3 hydroxy groups,
  (V) a $C_{1-6}$ alkoxy-carbonyl group (e.g., tert-butoxycarbonyl),
  (VI) a $C_{3-10}$ cycloalkyl group (e.g., cyclobutyl),
  (VII) a $C_{7-16}$ aralkyl group (e.g., benzyl), and
  (VIII) a 3- to 14-membered (preferably 4- to 10-membered) non-aromatic heterocyclic group (preferably a 3- to 8-membered monocyclic non-aromatic heterocyclic group (e.g., oxetanyl, tetrahydropyranyl)), and
(xiii) a 3- to 14-membered (preferably 4- to 10-membered) non-aromatic heterocyclylcarbonyl group (preferably a 3- to 8-membered monocyclic non-aromatic heterocyclylcarbonyl group (e.g., morpholinylcarbonyl)),
(e) a $C_{2-6}$ alkynyl group (e.g., (prop-2-ynyl)),
(f) a $C_{1-6}$ alkoxy group (e.g., methoxy, ethoxy, propyloxy) optionally substituted by 1 to 5 substituents selected from
  (i) a halogen atom (e.g., a fluorine atom), and
  (ii) a $C_{3-10}$ cycloalkyl group (e.g., cyclopropyl) optionally substituted by 1 to 3 halogen atoms (e.g., a fluorine atom),
(g) a $C_{3-10}$ cycloalkyl group (the $C_{3-10}$ cycloalkyl group is optionally fused with a benzene ring, or optionally bridged or may be a spiro group; e.g., cyclopropyl, cyclobutyl, cyclopentyl, cyclohexyl, indanyl, bicyclo[2.2.1]heptyl, spiro[3.3]hexyl) optionally substituted by 1 to 3 substituents selected from
  (i) an oxo group,
  (ii) a hydroxy group,
  (iii) a carbamoyl group,
  (iv) a carboxy group,
  (v) a $C_{1-6}$ alkyl group (e.g., methyl) optionally substituted by 1 to 3 substituents selected from
    (I) a hydroxy group,
    (II) a carboxy group,
    (III) a carbamoyl group, and
    (IV) a 3- to 14-membered (preferably 4- to 10-membered) non-aromatic heterocyclic group (preferably a 3- to 8-membered monocyclic non-aromatic heterocyclic group (e.g., morpholinyl)),
  (vi) a $C_{1-6}$ alkoxy-carbonyl group (e.g., ethoxycarbonyl),
  (vii) a 3- to 14-membered (preferably 4- to 10-membered) non-aromatic heterocyclic group (preferably a 3- to 8-membered monocyclic non-aromatic heterocyclic group (e.g., azetidinyl, pyrrolidinyl, morpholinyl, 2-oxa-6-azaspiro[3.3]heptyl, 3-oxa-8-azabicyclo[3.2.1]octyl)) optionally substituted by 1 to 3 substituents selected from
    (I) a halogen atom (e.g., a fluorine atom),
    (II) a hydroxy group, and
    (III) a $C_{1-6}$ alkyl group (e.g., methyl) optionally substituted by 1 to 3 substituents selected from a halogen atom (e.g., a fluorine atom) and a hydroxy group, and
  (viii) an amino group optionally mono- or di-substituted by substituent(s) selected from
    (I) a $C_{1-6}$ alkoxy-carbonyl group (e.g., tert-butoxycarbonyl), and
    (II) a 3- to 14-membered (preferably 4- to 10-membered) non-aromatic heterocyclic group (preferably a 3- to 8-membered monocyclic non-aromatic heterocyclic group (e.g., tetrahydropyranyl)),
(h) an optionally halogenated $C_{1-6}$ alkyl-carbonyl group (e.g., acetyl, propionyl),
(i) a $C_{1-6}$ alkoxy-carbonyl group (e.g., ethoxycarbonyl),
(j) a $C_{6-14}$ aryl group (e.g., phenyl),
(k) a $C_{7-16}$ aralkyl group (e.g., benzyl),
(l) a 5- to 14-membered (preferably 5- to 10-membered) aromatic heterocyclic group (preferably a 5- to 6-membered monocyclic aromatic heterocyclic group (e.g., pyridyl, pyrazolyl, thienyl)) optionally substituted by 1 to 3 $C_{1-6}$ alkoxy groups (e.g., methoxy),
(m) a 3- to 14-membered (preferably 4- to 10-membered) non-aromatic heterocyclic group (preferably a 3- to 8-membered monocyclic non-aromatic heterocyclic group (e.g., oxetanyl, piperidyl, azetidinyl, pyrrolidinyl, morpholinyl, azepanyl, tetrahydrofuryl, tetrahydropyranyl, tetrahydrothiopyranyl, dihydropyridyl, 8-azabicyclo[3.2.1]octyl, 2-azaspiro[3.3]heptyl)) optionally substituted by 1 to 3 substituents selected from
  (i) an oxo group,
  (ii) a hydroxy group,
  (iii) a $C_{1-6}$ alkyl group (e.g., methyl, ethyl, propyl, isopropyl, isobutyl, 3,3-dimethylbutyl) optionally substituted by 1 to 3 substituents selected from
    (I) a halogen atom (e.g., a fluorine atom),
    (II) a hydroxy group,
    (III) a cyano group,
    (IV) a $C_{1-6}$ alkoxy group (e.g., methoxy, ethoxy) optionally substituted by 1 to 3 substituents selected from
      (A) a halogen atom (e.g., a fluorine atom),
      (B) a $C_{1-6}$ alkyl-carbonyloxy group (e.g., acetyloxy, 2-methylpropanoyloxy, 2,2-dimethylpropanoyloxy, 3-methylbutanoyloxy), and
      (C) a $C_{1-6}$ alkoxy-carbonyloxy group (e.g., ethoxycarbonyloxy, isopropoxycarbonyloxy), (V) a $C_{1-6}$ alkyl-carbonyloxy group (e.g., acetyloxy),
(VI) a $C_{3-10}$ cycloalkyl group (e.g., cyclopropyl),
(VII) a 5- to 14-membered (preferably 5- to 10-membered) aromatic heterocyclic group (preferably a 5- to 6-membered monocyclic aromatic heterocyclic group (e.g., pyridyl, pyrazolyl, pyrrolyl, thiazolyl, thienyl, pyrimidinyl)) optionally substituted by 1 to 3 $C_{1-6}$ alkyl groups (e.g., methyl), and
(VIII) a 3- to 14-membered (preferably 4- to 10-membered) non-aromatic heterocyclic group (preferably a 3- to 8-membered monocyclic non-aromatic heterocyclic group (e.g., oxetanyl)), (iv) a $C_{3-10}$ cycloalkyl group (e.g., cyclopropyl, cyclobutyl, cyclopentyl, cyclohexyl) optionally substituted by 1 to 3 substituents selected from
(I) a halogen atom (e.g., a fluorine atom),
(II) a hydroxy group,
(III) a $C_{1-6}$ alkyl group (e.g., methyl) optionally substituted by 1 to 3 $C_{1-6}$ alkoxy groups (e.g., methoxy), and
(IV) a $C_{1-6}$ alkoxy group (e.g., methoxy),
(v) a $C_{6-14}$ aryl group (e.g., phenyl) optionally substituted by 1 to 3 halogen atoms (e.g., a fluorine atom),
(vi) a $C_{7-16}$ aralkyl group (e.g., benzyl),
(vii) a $C_{1-6}$ alkyl-carbonyl group (e.g., acetyl),
(viii) a $C_{1-6}$ alkoxy-carbonyl group (e.g., tert-butoxycarbonyl),
(ix) a 5- to 14-membered (preferably 5- to 10-membered) aromatic heterocyclic group (preferably a 5- to 6-membered monocyclic aromatic heterocyclic group (e.g., pyrimidinyl, pyridyl)) optionally substituted by 1 to 3 $C_{1-6}$ alkyl groups (e.g., methyl), and
(x) a 3- to 14-membered (preferably 4- to 10-membered) non-aromatic heterocyclic group (preferably a 3- to 8-membered monocyclic non-aromatic heterocyclic group (e.g., oxetanyl, piperidyl, tetrahydrofuryl, tetrahydropyranyl, oxepanyl, dioxepanyl, 1,1-dioxidotetrahydrothiopyranyl, dioxanyl, 2-oxabicyclo[2.2.2]octyl)) optionally substituted by 1 to 3 substituents selected from
(I) a halogen atom (e.g., a fluorine atom),
(II) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
(III) a $C_{3-10}$ cycloalkyl group (e.g., cyclopropyl),
(VI) a cyano group, and
(V) a deuterium atom,
(n) a 3- to 14-membered (preferably 4- to 10-membered) non-aromatic heterocyclyloxy group (preferably a 3- to 8-membered monocyclic non-aromatic heterocyclyloxy group (e.g., oxetanyloxy)), and
(o) a 3- to 14-membered (preferably 4- to 10-membered) non-aromatic heterocyclylcarbonyl group (preferably a 3- to 8-membered monocyclic non-aromatic heterocyclylcarbonyl group (e.g., piperidylcarbonyl, morpholinylcarbonyl)) optionally substituted by 1 to 3 of 3- to 14-membered (preferably 4- to 10-membered) non-aromatic heterocyclic groups (preferably 3- to 8-membered monocyclic non-aromatic heterocyclic groups (e.g., morpholinyl));

Ring B is
(1) a pyrimidine ring ($X^1$ is a carbon atom, $X^2$ is a carbon atom and $X^3$ is a nitrogen atom),
(2) a pyrazine ring ($X^1$ is a carbon atom, $X^2$ is a nitrogen atom and $X^3$ is a carbon atom), or
(3) a pyridine ring ($X^1$ is a carbon atom, $X^2$ is a carbon atom and $X^3$ is a carbon atom);

Ring C is
(1) a benzene ring optionally further substituted by 1 to 3 halogen atoms (e.g., a fluorine atom, a chlorine atom), or
(2) a pyridine ring ($Y^1$ is a carbon atom, $Y^2$ is a carbon atom and $Y^3$ is a nitrogen atom, or $Y^1$ is a nitrogen atom, $Y^2$ is a carbon atom and $Y^3$ is a carbon atom);

Z is
(1) —O—, or
(2) —NH—;

$R^1$ is
(1) a hydrogen atom, or
(2) a $C_{1-6}$ alkyl group (e.g., methyl, ethyl) optionally substituted by 1 to 3 hydroxy groups;

$R^2$ is
(1) a $C_{1-6}$ alkyl group (e.g., methyl, ethyl, isobutyl) optionally substituted by 1 to 3 substituents selected from
 (a) a 5- to 14-membered (preferably 5- to 10-membered) aromatic heterocyclic group (preferably a 5- or 6-membered monocyclic aromatic heterocyclic group (e.g., triazolyl (e.g., 1,2,4-triazolyl, 1,2,3-triazolyl), tetrazolyl, pyrazolyl, imidazolyl, oxadiazolyl (e.g., 1,2,4-oxadiazolyl, 1,3,4-oxadiazolyl), pyridyl)) optionally substituted by 1 to 3 substituents selected from
  (i) a halogen atom (e.g., a fluorine atom), and
  (ii) a $C_{1-6}$ alkyl group (e.g., methyl),
 (b) a 3- to 14-membered (preferably 4- to 10-membered) non-aromatic heterocyclic group (preferably a 3- to 8-membered monocyclic non-aromatic heterocyclic group (e.g., pyrrolidinyl)) optionally substituted by 1 to 3 oxo groups,
 (c) a halogen atom (e.g., a fluorine atom),
 (d) a hydroxy group,
 (e) a cyano group,
 (f) an optionally halogenated $C_{1-6}$ alkoxy group (e.g., methoxy, difluoromethoxy),
 (g) an amino group optionally mono- or di-substituted by substituent(s) selected from
  (i) a $C_{1-6}$ alkyl-carbonyl group (e.g., acetyl), and
  (ii) a $C_{1-6}$ alkylsulfonyl group (e.g., methylsulfonyl), and
 (h) a mono- or di-$C_{1-6}$ alkyl-carbamoyl group (e.g., methylcarbamoyl),
(2) a 3- to 14-membered (preferably 4- to 10-membered) non-aromatic heterocyclic group (preferably a 3- to 8-membered monocyclic non-aromatic heterocyclic group (e.g., piperidyl)) optionally substituted by 1 to 3 substituents selected from
 (a) an oxo group, and
 (b) a $C_{1-6}$ alkyl group (e.g., methyl), or
(3) a mono- or di-$C_{1-6}$ alkyl-carbamoyl group (e.g., ethylcarbamoyl) optionally substituted by 1 to 3 halogen atoms (e.g., a fluorine atom); and $R^3$ is
(1) a cyano group,
(2) a halogen atom (e.g., a fluorine atom, a chlorine atom),
(3) an optionally halogenated $C_{1-6}$ alkyl group (e.g., methyl, difluoromethyl), or
(4) a carbamoyl group.

[Compound D-1]
Compound (I) wherein
Ring A is a pyrazole ring
further substituted (preferably at the 1-position) by one cyclohexyl group optionally substituted by 1 to 3 substituents selected from
 (i) an oxo group,
 (ii) a hydroxy group,
 (iii) a carboxy group, (iv) a $C_{1-6}$ alkyl group (e.g., methyl) optionally substituted by 1 to 3 substituents selected from
(I) a carboxy group,
(II) a carbamoyl group, and
(III) a 3- to 8-membered monocyclic non-aromatic heterocyclic group (e.g., morpholinyl),
(v) a $C_{1-6}$ alkoxy-carbonyl group (e.g., ethoxycarbonyl), and
(vi) a 3- to 8-membered monocyclic non-aromatic heterocyclic group (e.g., azetidinyl, pyrrolidinyl, morpholinyl, 2-oxa-6-azaspiro[3.3]heptyl, 3-oxa-8-azabicyclo[3.2.1]octyl) optionally substituted by 1 to 3 substituents selected from
(I) a halogen atom (e.g., a fluorine atom),
(II) a hydroxy group, and
(III) a $C_{1-6}$ alkyl group (e.g., methyl) optionally substituted by 1 to 3 substituents selected from a halogen atom (e.g., a fluorine atom) and a hydroxy group, and further optionally substituted (preferably at the 3-position) by one substituent selected from
(a) an optionally halogenated $C_{1-6}$ alkyl group (e.g., ethyl, isopropyl, tert-butyl, difluoromethyl, trifluoromethyl, 3,3,3-trifluoropropyl, 1,1,2,2,2-pentafluoroethyl),
(b) a $C_{1-6}$ alkoxy group (e.g., methoxy, ethoxy, propoxy) optionally substituted by 1 to 5 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom),
(c) a 3- to 8-membered monocyclic non-aromatic heterocyclyloxy group (e.g., oxetanyloxy),
(d) an optionally halogenated $C_{1-6}$ alkyl-carbonyl group (e.g., acetyl, propionyl),
(e) a $C_{3-10}$ cycloalkyl group (e.g., cyclopropyl, cyclobutyl), and
(f) a cyano group
(preferably further optionally substituted (preferably at the 3-position) by one substituent selected from
(a) an optionally halogenated $C_{1-6}$ alkyl group (e.g., trifluoromethyl, isopropyl),
(b) a $C_{1-6}$ alkoxy group (e.g., methoxy, ethoxy) optionally substituted by 1 to 3 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom), and
(c) a 3- to 8-membered monocyclic non-aromatic heterocyclyloxy group (e.g., oxetanyloxy));
Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group (e.g., methyl);
$R^2$ is a $C_{1-6}$ alkyl group (e.g., methyl) substituted by one substituents selected from
(a) a 5- or 6-membered monocyclic aromatic heterocyclic group (e.g., tetrazolyl, pyrazolyl) optionally substituted by 1 to 3 halogen atoms (e.g., a fluorine atom), and
(b) a 3- to 8-membered monocyclic non-aromatic heterocyclic group (e.g., pyrrolidinyl) optionally substituted by 1 to 2 oxo groups; and $R^3$ is
(1) a cyano group,
(2) a halogen atom (e.g., a fluorine atom, a chlorine atom, preferably a chlorine atom), or
(3) an optionally halogenated $C_{1-6}$ alkyl group (e.g., methyl, difluoromethyl).
[Compound E-1A]
Compound (I) wherein
Ring A is a pyrazole ring
further substituted (preferably at the 1-position) by one cyclohexyl group substituted by one substituent selected from
(i) a nitrogen-containing 3- to 8-membered (preferably 4- to 6-membered) monocyclic non-aromatic heterocyclic group (e.g., azetidinyl, morpholinyl, 3-oxa-8-azabicyclo[3.2.1]octyl) optionally substituted by 1 or 2 substituents selected from
(I) a hydroxy group, and
(II) a $C_{1-6}$ alkyl group (e.g., methyl), and
further substituted (preferably at the 3-position) by one substituent selected from
(a) an optionally halogenated $C_{1-6}$ alkyl group (e.g., isopropyl, tert-butyl, difluoromethyl, trifluoromethyl, 3,3,3-trifluoropropyl, 1,1,2,2,2-pentafluoroethyl),
(b) a $C_{1-6}$ alkoxy group (e.g., methoxy, ethoxy, propoxy) optionally substituted by 1 to 5 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom),
(c) a 3- to 8-membered oxygen-containing monocyclic non-aromatic heterocyclyloxy group (e.g., oxetanyloxy), (d) an optionally halogenated $C_{1-6}$ alkyl-carbonyl group (e.g., acetyl, propionyl), and
(e) a $C_{3-10}$ cycloalkyl group (e.g., cyclopropyl, cyclobutyl) (preferably further substituted (preferably at the 3-position) by one substituent selected from
(a) an optionally halogenated $C_{1-6}$ alkyl group (e.g., trifluoromethyl, isopropyl),
(b) a $C_{1-6}$ alkoxy group (e.g., methoxy, ethoxy) optionally substituted by 1 to 3 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom), and
(c) a 3- to 8-membered oxygen-containing monocyclic non-aromatic heterocyclyloxy group (e.g., oxetanyloxy));
Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group (e.g., methyl);
$R^2$ is a $C_{1-6}$ alkyl group (e.g., methyl) substituted by one tetrazolyl group (preferably a tetrazolylmethyl group (e.g., tetrazolyl-1-ylmethyl)); and
$R^3$ is
(1) a cyano group,
(2) a halogen atom (preferably a chlorine atom), or
(3) an optionally halogenated $C_{1-6}$ alkyl group (e.g., methyl, difluoromethyl).
[Compound E-1Aa]
Compound (I) wherein
Ring A is a pyrazole ring
further substituted (preferably at the 1-position) by one cyclohexyl group substituted by one morpholinyl group, and further substituted (preferably at the 3-position) by one substituent selected from (a) an optionally halogenated $C_{1-6}$ alkyl group (e.g., trifluoromethyl, isopropyl),
(b) a $C_{1-6}$ alkoxy group (e.g., methoxy, ethoxy) optionally substituted by 1 to 3 substituents selected from
  (i) a halogen atom (e.g., a fluorine atom), and
  (ii) a $C_{3-10}$ cycloalkyl group (e.g., cyclopropyl) optionally substituted by 1 to 3 halogen atoms (e.g., a fluorine atom), and
(c) a 3- to 8-membered oxygen-containing monocyclic non-aromatic heterocyclyloxy group (e.g., oxetanyloxy);

Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group (e.g., methyl);
$R^2$ is a $C_{1-6}$ alkyl group (e.g., methyl) substituted by one tetrazolyl group (preferably a tetrazolylmethyl group (e.g., tetrazolyl-1-ylmethyl)); and
$R^3$ is
(1) a cyano group, or
(2) a halogen atom (preferably a chlorine atom).

[Compound E-1Ab]
Compound (I) wherein
Ring A is a pyrazole ring
further substituted (preferably at the 1-position) by one cyclohexyl group substituted by one substituent selected from
  (i) a 3-oxa-8-azabicyclo[3.2.1]octyl group, and
  (ii) an azetidinyl group optionally substituted by 1 or 2 substituents selected from
    (I) a hydroxy group, and
    (II) a $C_{1-6}$ alkyl group (e.g., methyl), and
further substituted (preferably at the 3-position) by one substituent selected from
  (a) an optionally halogenated $C_{1-6}$ alkoxy group (e.g., 2,2-difluoroethoxy, 2,2,2-trifluoroethoxy);

Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group (e.g., methyl);
$R^2$ is a $C_{1-6}$ alkyl group (e.g., methyl) substituted by one tetrazolyl group (preferably a tetrazolylmethyl group (e.g., tetrazolyl-1-ylmethyl)); and
$R^3$ is
(1) a cyano group, or
(2) a halogen atom (preferably a chlorine atom).

[Compound D-2]
Compound (I) wherein
Ring A is a pyrazole ring
further substituted (preferably at the 1-position) by one 2-azaspiro[3.3]heptyl group optionally substituted by 1 to 3 substituents selected from
  (i) a $C_{1-6}$ alkyl group (e.g., methyl, ethyl, propyl, isopropyl, isobutyl) optionally substituted by 1 to 3 substituents selected from
    (I) a halogen atom (e.g., a fluorine atom),
    (II) a hydroxy group,
    (III) a $C_{1-6}$ alkoxy group (e.g., methoxy, ethoxy) optionally substituted by 1 to 3 substituents selected from
      (A) a halogen atom (e.g., a fluorine atom),
      (B) a $C_{1-6}$ alkyl-carbonyloxy group (e.g., acetyloxy, 2-methylpropanoyloxy, 2,2-dimethylpropanoyloxy, 3-methylbutanoyloxy), and
      (C) a $C_{1-6}$ alkoxy-carbonyloxy group (e.g., ethoxycarbonyloxy, isopropoxycarbonyloxy),
    (IV) a $C_{1-6}$ alkyl-carbonyloxy group (e.g., acetyloxy), and
    (V) a 5- to 6-membered monocyclic aromatic heterocyclic group (e.g., pyrimidinyl),
  (ii) a $C_{3-10}$ cycloalkyl group (e.g., cyclobutyl, cyclopentyl, cyclohexyl) optionally substituted by 1 to 3 substituents selected from
    (I) a halogen atom (e.g., a fluorine atom),
    (II) a hydroxy group,
    (III) a $C_{1-6}$ alkyl group (e.g., methyl) optionally substituted by 1 to 3 $C_{1-6}$ alkoxy groups (e.g., methoxy), and
    (IV) a $C_{1-6}$ alkoxy group (e.g., methoxy),
  (iii) a $C_{1-6}$ alkoxy-carbonyl group (e.g., tert-butoxycarbonyl),
  (iv) a $C_{6-14}$ aryl group (e.g., phenyl) optionally substituted by 1 to 3 halogen atoms (e.g., a fluorine atom),
  (v) a 5- to 6-membered monocyclic aromatic heterocyclic group (e.g., pyrimidinyl, pyridyl) optionally substituted by 1 to 3 $C_{1-6}$ alkyl groups (e.g., methyl), and
  (vi) a 3- to 8-membered monocyclic non-aromatic heterocyclic group (e.g., oxetanyl, tetrahydrofuryl, tetrahydropyranyl, oxepanyl, dioxepanyl, dioxanyl, 2-oxabicyclo[2.2.2]octyl) optionally substituted by 1 to 3 substituents selected from
    (I) a halogen atom (e.g., a fluorine atom),
    (II) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
    (III) a $C_{3-10}$ cycloalkyl group (e.g., cyclopropyl),
    (VI) a cyano group, and
    (V) a deuterium atom, and
further optionally substituted (preferably at the 3-position) by one substituent selected from
  (a) an optionally halogenated $C_{1-6}$ alkyl group (e.g., ethyl, isopropyl, tert-butyl, difluoromethyl, trifluoromethyl, 3,3,3-trifluoropropyl, 1,1,2,2,2-pentafluoroethyl),
  (b) a $C_{1-6}$ alkoxy group (e.g., methoxy, ethoxy, propoxy) optionally substituted by 1 to 5 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom),
  (c) a 3- to 8-membered monocyclic non-aromatic heterocyclyloxy group (e.g., oxetanyloxy),
  (d) an optionally halogenated $C_{1-6}$ alkyl-carbonyl group (e.g., acetyl, propionyl),
  (e) a $C_{3-10}$ cycloalkyl group (e.g., cyclopropyl, cyclobutyl), and
  (f) a cyano group
(preferably further substituted (preferably at the 3-position) by one substituent selected from
  (a) an optionally halogenated $C_{1-6}$ alkyl group (e.g., isopropyl, tert-butyl, difluoromethyl, trifluoromethyl, 3,3,3-trifluoropropyl, 1,1,2,2,2-pentafluoroethyl),
  (b) an optionally halogenated $C_{1-6}$ alkoxy group (e.g., trifluoromethoxy, 2,2,2-trifluoroethoxy, 2,2,3,3,3-pentafluoropropoxy),
  (c) a $C_{1-6}$ alkyl-carbonyl group (e.g., acetyl, propionyl),
  (d) a 3- to 8-membered monocyclic non-aromatic heterocyclyloxy group (e.g., oxetanyloxy), and
  (e) a $C_{3-10}$ cycloalkyl group (e.g., cyclobutyl));

Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group (e.g., methyl);
$R^2$ is a $C_{1-6}$ alkyl group (e.g., methyl) substituted by one substituents selected from
  (a) a 5- or 6-membered monocyclic aromatic heterocyclic group (e.g., tetrazolyl), and
  (b) an optionally halogenated $C_{1-6}$ alkoxy group (e.g., difluoromethoxy); and
$R^3$ is
(1) a cyano group,
(2) a halogen atom (e.g., a fluorine atom, a chlorine atom, preferably a chlorine atom), or
(3) an optionally halogenated $C_{1-6}$ alkyl group (e.g., methyl, difluoromethyl).

[Compound E-2]
  Compound (I) wherein
Ring A is a pyrazole ring
further substituted (preferably at the 1-position) by one 2-azaspiro[3.3]heptyl group substituted by one substituent selected from
  (i) a $C_{1-6}$ alkyl group (e.g., methyl, ethyl, propyl, isobutyl) optionally substituted by 1 to 3 substituents selected from
    (I) a halogen atom (e.g., a fluorine atom),
    (II) a hydroxy group,
    (III) a $C_{1-6}$ alkoxy group (e.g., methoxy, ethoxy) optionally substituted by 1 to 3 substituents selected from
      (A) a halogen atom (e.g., a fluorine atom),
      (B) a $C_{1-6}$ alkyl-carbonyloxy group (e.g., acetyloxy, 2-methylpropanoyloxy, 2,2-dimethylpropanoyloxy, 3-methylbutanoyloxy), and
      (C) a $C_{1-6}$ alkoxy-carbonyloxy group (e.g., ethoxycarbonyloxy, isopropoxycarbonyloxy),
    (IV) a $C_{1-6}$ alkyl-carbonyloxy group (e.g., acetyloxy), and
    (V) a 5- to 6-membered nirtogen-containing monocyclic aromatic heterocyclic group (e.g., pyrimidinyl),
  (ii) a $C_{3-10}$ cycloalkyl group (e.g., cyclobutyl, cyclopentyl, cyclohexyl) optionally substituted by 1 to 3 substituents selected from
    (I) a halogen atom (e.g., a fluorine atom),
    (II) a hydroxy group,
    (III) a $C_{1-6}$ alkyl group (e.g., methyl) optionally substituted by 1 to 3 $C_{1-6}$ alkoxy groups (e.g., methoxy), and
    (IV) a $C_{1-6}$ alkoxy group (e.g., methoxy),
  (iii) a $C_{1-6}$ alkoxy-carbonyl group (e.g., tert-butoxycarbonyl),
  (iv) a $C_{6-14}$ aryl group (e.g., phenyl) optionally substituted by 1 to 3 halogen atoms (e.g., a fluorine atom),
  (v) a 5- to 6-membered nitrogen-containing monocyclic aromatic heterocyclic group (e.g., pyrimidinyl, pyridyl) optionally substituted by 1 to 3 $C_{1-6}$ alkyl groups (e.g., methyl), and
  (vi) a 3- to 8-membered oxygen-containing monocyclic non-aromatic heterocyclic group (e.g., oxetanyl, tetrahydrofuryl, tetrahydropyranyl, oxepanyl, dioxepanyl, dioxanyl, 2-oxabicyclo[2.2.2]octyl) optionally substituted by 1 to 3 substituents selected from
    (I) a halogen atom (e.g., a fluorine atom),
    (II) a $C_{1-6}$ alkyl group (e.g., methyl, ethyl) optionally substituted by 1 to 3 substituents selected from a halogen atom (e.g., a fluorine atom) and a $C_{1-6}$ alkoxy group (e.g., methoxy),
    (III) a $C_{3-10}$ cycloalkyl group (e.g., cyclopropyl),
    (VI) a cyano group, and
    (V) a deuterium atom, and
further substituted (preferably at the 3-position) by one substituent selected from
  (a) an optionally halogenated $C_{1-6}$ alkyl group (e.g., isopropyl, tert-butyl, difluoromethyl, trifluoromethyl, 3,3,3-trifluoropropyl, 1,1,2,2,2-pentafluoroethyl),
  (b) a $C_{1-6}$ alkoxy group (e.g., methoxy, ethoxy, propoxy) optionally substituted by 1 to 5 substituents selected from
    (i) a halogen atom (e.g., a fluorine atom), and
    (ii) a $C_{3-10}$ cycloalkyl group (e.g., cyclopropyl) optionally substituted by 1 to 3 halogen atoms (e.g., a fluorine atom),
  (c) a 3- to 8-membered oxygen-containing monocyclic non-aromatic heterocyclyloxy group (e.g., oxetanyloxy),
  (d) an optionally halogenated $C_{1-6}$ alkyl-carbonyl group (e.g., acetyl, propionyl), and
  (e) a $C_{3-10}$ cycloalkyl group (e.g., cyclopropyl, cyclobutyl) (preferably further substituted (preferably at the 3-position) by one substituent selected from
    (a) an optionally halogenated $C_{1-6}$ alkyl group (e.g., isopropyl, tert-butyl, difluoromethyl, trifluoromethyl, 3,3,3-trifluoropropyl, 1,1,2,2,2-pentafluoroethyl),
    (b) an optionally halogenated $C_{1-6}$ alkoxy group (e.g., trifluoromethoxy, 2,2,2-trifluoroethoxy, 2,2,3,3,3-pentafluoropropoxy),
    (c) a 3- to 8-membered oxygen-containing monocyclic non-aromatic heterocyclyloxy group (e.g., oxetanyloxy),
    (d) a $C_{1-6}$ alkyl-carbonyl group (e.g., acetyl, propionyl), and
    (e) a $C_{3-10}$ cycloalkyl group (e.g., cyclobutyl));
Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group (e.g., methyl);
$R^2$ is a $C_{1-6}$ alkyl group (e.g., methyl) substituted by one tetrazolyl group (preferably a tetrazolylmethyl group (e.g., tetrazolyl-1-ylmethyl)); and
$R^3$ is
(1) a cyano group,
(2) a halogen atom (preferably a chlorine atom), or
(3) an optionally halogenated $C_{1-6}$ alkyl group (e.g., methyl, difluoromethyl).

[Compound D-3]
  Compound (I) wherein
Ring A is a pyrazole ring
further substituted (preferably at the 1-position) by one piperidyl group optionally substituted by 1 to 3 substituents selected from
  (i) a hydroxy group,
  (ii) a $C_{1-6}$ alkyl group (e.g., methyl, ethyl, isopropyl, 3,3-dimethylbutyl) optionally substituted by 1 to 3 substituents selected from
    (I) a halogen atom (e.g., a fluorine atom),
    (II) a hydroxy group,
    (III) a cyano group,
    (IV) a $C_{1-6}$ alkoxy group (e.g., methoxy),
    (V) a $C_{3-10}$ cycloalkyl group (e.g., cyclopropyl),
    (VI) a 5- to 6-membered monocyclic aromatic heterocyclic group (e.g., pyridyl, pyrazolyl, pyrrolyl, thiazolyl, thienyl) optionally substituted by 1 to 3 $C_{1-6}$ alkyl groups (e.g., methyl), and
(VII) a 3- to 8-membered monocyclic non-aromatic heterocyclic group (e.g., oxetanyl),
(iii) a $C_{3-10}$ cycloalkyl group (e.g., cyclopropyl, cyclobutyl, cyclohexyl) optionally substituted by 1 to 3 substituents selected from
(I) a halogen atom (e.g., a fluorine atom), and
(II) a $C_{1-6}$ alkoxy group (e.g., methoxy),
(iv) a $C_{7-16}$ aralkyl group (e.g., benzyl),
(v) a $C_{1-6}$ alkyl-carbonyl group (e.g., acetyl),
(vi) a $C_{1-6}$ alkoxy-carbonyl group (e.g., tert-butoxycarbonyl), and
(vii) a 3- to 8-membered monocyclic non-aromatic heterocyclic group (e.g., oxetanyl, piperidyl, tetrahydrofuryl, tetrahydropyranyl, 1,1-dioxidotetrahydrothiopyranyl) optionally substituted by 1 to 3 substituents selected from
(I) a $C_{1-6}$ alkyl group (e.g., methyl), and
(II) a $C_{3-10}$ cycloalkyl group (e.g., cyclopropyl), and
further optionally substituted (preferably at the 3-position) by one substituent selected from
(a) an optionally halogenated $C_{1-6}$ alkyl group (e.g., ethyl, isopropyl, tert-butyl, difluoromethyl, trifluoromethyl, 3,3,3-trifluoropropyl, 1,1,2,2,2-pentafluoroethyl),
(b) a $C_{1-6}$ alkoxy group (e.g., methoxy, ethoxy, propoxy) optionally substituted by 1 to 5 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom),
(c) a 3- to 8-membered monocyclic non-aromatic heterocyclyloxy group (e.g., oxetanyloxy),
(d) an optionally halogenated $C_{1-6}$ alkyl-carbonyl group (e.g., acetyl, propionyl),
(e) a $C_{3-10}$ cycloalkyl group (e.g., cyclopropyl, cyclobutyl), and
(f) a cyano group
(preferably further substituted (preferably at the 3-position) by one substituent selected from
(a) an optionally halogenated $C_{1-6}$ alkyl group (e.g., ethyl, isopropyl, difluoromethyl, trifluoromethyl),
(b) an optionally halogenated $C_{1-6}$ alkoxy group (e.g., methoxy, ethoxy, difluoromethoxy, 2-fluoroethoxy, 2,2-difluoroethoxy, 2,2,2-trifluoroethoxy),
(c) a $C_{3-10}$ cycloalkyl group (e.g., cyclopropyl), and
(d) a cyano group);
Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group (e.g., methyl);
$R^2$ is a $C_{1-6}$ alkyl group (e.g., methyl) substituted by one substituents selected from
(a) a 5- or 6-membered monocyclic aromatic heterocyclic group (e.g., triazolyl (e.g., 1,2,4-triazolyl), tetrazolyl, pyrazolyl) optionally substituted by 1 to 3 halogen atoms (e.g., a fluorine atom); and
$R^3$ is
(1) a cyano group,
(2) a halogen atom (e.g., a fluorine atom, a chlorine atom, preferably a chlorine atom), or
(3) an optionally halogenated $C_{1-6}$ alkyl group (e.g., methyl, difluoromethyl).

[Compound E-3]
Compound (I) wherein
Ring A is a pyrazole ring
further substituted (preferably at the 1-position) by one piperidyl group substituted by one tetrahydropyranyl group, and
further substituted (preferably at the 3-position) by one substituent selected from
(a) an optionally halogenated $C_{1-6}$ alkyl group (e.g., isopropyl, tert-butyl, difluoromethyl, trifluoromethyl, 3,3,3-trifluoropropyl, 1,1,2,2,2-pentafluoroethyl),
(b) a $C_{1-6}$ alkoxy group (e.g., methoxy, ethoxy, propoxy) optionally substituted by 1 to 5 substituents selected from
(i) a halogen atom (e.g., a fluorine atom), and
(ii) a $C_{3-10}$ cycloalkyl group (e.g., cyclopropyl) optionally substituted by 1 to 3 halogen atoms (e.g., a fluorine atom),
(c) a 3- to 8-membered oxygen-containing monocyclic non-aromatic heterocyclyloxy group (e.g., oxetanyloxy),
(d) an optionally halogenated $C_{1-6}$ alkyl-carbonyl group (e.g., acetyl, propionyl), and
(e) a $C_{3-10}$ cycloalkyl group (e.g., cyclopropyl, cyclobutyl) (preferably further substituted (preferably at the 3-position) by one substituent selected from
(a) an optionally halogenated $C_{1-6}$ alkyl group (e.g., isopropyl, trifluoromethyl), and
(b) an optionally halogenated $C_{1-6}$ alkoxy group (e.g., difluoromethoxy, 2,2,2-trifluoroethoxy));
Ring B is a pyrimidine ring ($X^1$ is a carbon atom, $X^2$ is a carbon atom and $X^3$ is a nitrogen atom);
Ring C is a benzene ring;
Z is —O—;
$R^1$ is a $C_{1-6}$ alkyl group (e.g., methyl);
$R^2$ is a $C_{1-6}$ alkyl group (e.g., methyl) substituted by one tetrazolyl group (preferably a tetrazolylmethyl group (e.g., tetrazolyl-1-ylmethyl)); and
$R^3$ is
(1) a cyano group,
(2) a halogen atom (preferably a chlorine atom), or
(3) an optionally halogenated $C_{1-6}$ alkyl group (e.g., methyl, difluoromethyl).

Compound (I) is preferably a compound represented by the following formula (II-1A), (II-2) or (II-3) (hereinafter sometimes to be referred to as compound (II-1A), compound (II-2) and compound (II-3), respectively).

(1) A compound represented by the following formula (II-1A):

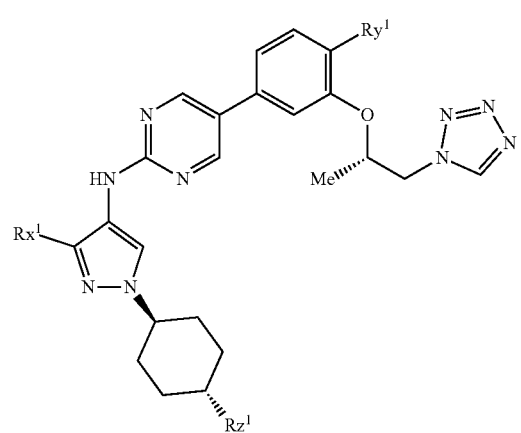

(II-1A)

wherein
Rx$^1$ is
(1) an optionally halogenated C$_{1-6}$ alkyl group (e.g., isopropyl, tert-butyl, difluoromethyl, trifluoromethyl, 3,3,3-trifluoropropyl, 1,1,2,2,2-pentafluoroethyl),
(2) a C$_{1-6}$ alkoxy group (e.g., methoxy, ethoxy, propoxy) optionally substituted by 1 to 5 substituents selected from
  (a) a halogen atom (e.g., a fluorine atom), and
  (b) a C$_{3-10}$ cycloalkyl group (e.g., cyclopropyl) optionally substituted by 1 to 3 halogen atoms (e.g., a fluorine atom),
(3) a 3- to 8-membered oxygen-containing monocyclic non-aromatic heterocyclyloxy group (e.g., oxetanyloxy),
(4) an optionally halogenated C$_{1-6}$ alkyl-carbonyl group (e.g., acetyl, propionyl), or
(5) a C$_{3-10}$ cycloalkyl group (e.g., cyclopropyl, cyclobutyl);
Ry$^1$ is
(1) a cyano group,
(2) a halogen atom (preferably a chlorine atom), or
(3) an optionally halogenated C$_{1-6}$ alkyl group (e.g., methyl, difluoromethyl); and
Rz$^1$ is
(1) a nitrogen-containing 3- to 8-membered (preferably 4- to 6-membered) monocyclic non-aromatic heterocyclic group (e.g., azetidinyl, morpholinyl, 3-oxa-8-azabicyclo[3.2.1]octyl) optionally substituted by 1 or 2 substituents selected from
  (a) a hydroxy group, and
  (b) a C$_{1-6}$ alkyl group (e.g., methyl), or a salt thereof.

Compound (II-1A) is preferably a compound represented by the following formula (II-1Aa) or (II-1Ab) (hereinafter sometimes to be referred to as compound (II-1Aa) and compound (II-1Ab), respectively).

(1a) A compound represented by the following formula (II-1Aa):

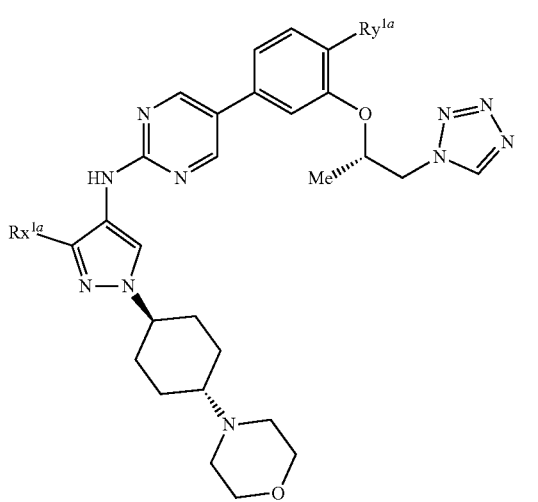

(II-1Aa)

wherein
Rx$^{1a}$ is
(1) an optionally halogenated C$_{1-6}$ alkyl group (e.g., trifluoromethyl, isopropyl),
(2) a C$_{1-6}$ alkoxy group (e.g., methoxy, ethoxy) optionally substituted by 1 to 3 substituents selected from
  (a) a halogen atom (e.g., a fluorine atom), and
  (b) a C$_{3-10}$ cycloalkyl group (e.g., cyclopropyl) optionally substituted by 1 to 3 halogen atoms (e.g., a fluorine atom), or
(3) a 3- to 8-membered oxygen-containing monocyclic non-aromatic heterocyclyloxy group (e.g., oxetanyloxy); and
Ry$^{1a}$ is
(1) a cyano group, or
(2) a halogen atom (preferably a chlorine atom), or a salt thereof.

Compound (II-1Aa) is preferably a compound wherein
Rx$^{1a}$ is
(1) an optionally halogenated C$_{1-6}$ alkyl group (e.g., trifluoromethyl, isopropyl), or
(2) an optionally halogenated C$_{1-6}$ alkoxy group (e.g., 2,2,2-trifluoroethoxy); and
Ry$^{1a}$ is a halogen atom (preferably a chlorine atom), particularly preferably a compound wherein
Rx$^{1a}$ is a trifluoromethyl group, an isopropyl group or a 2,2,2-trifluoroethoxy group; and
Ry$^{1a}$ is a chlorine atom.

(1b) A compound represented by the following formula (II-1Ab):

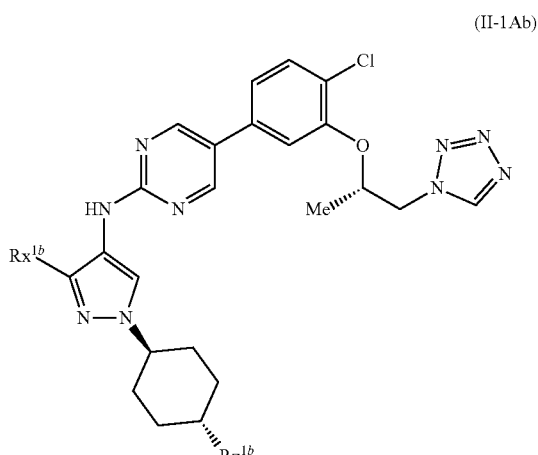

(II-1Ab)

wherein
Rx$^{1b}$ is an optionally halogenated C$_{1-6}$ alkoxy group (e.g., 2,2-difluoroethoxy, 2,2,2-trifluoroethoxy); and
Rz$^{1b}$ is
(1) a 3-oxa-8-azabicyclo[3.2.1]octyl group, or
(2) an azetidinyl group optionally substituted by 1 or 2 substituents selected from
  (a) a hydroxy group, and
  (b) a C$_{1-6}$ alkyl group (e.g., methyl), or a salt thereof.

Compound (II-1Ab) is preferably a compound wherein
Rx$^{1b}$ is a 2,2-difluoroethoxy group or a 2,2,2-trifluoroethoxy group; and
Rz$^{1b}$ is
(1) a 3-oxa-8-azabicyclo[3.2.1]octyl group, or
(2) an azetidinyl group substituted by a hydroxy group and a methyl group.

(2) A compound represented by the following formula (II-2):

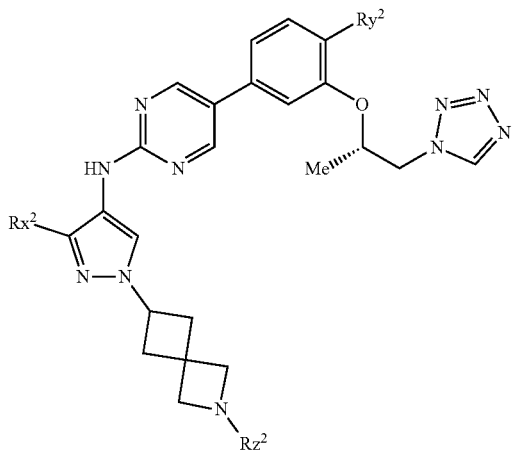

wherein
Rx² is
(1) an optionally halogenated C₁₋₆ alkyl group (e.g., isopropyl, tert-butyl, difluoromethyl, trifluoromethyl, 3,3,3-trifluoropropyl, 1,1,2,2,2-pentafluoroethyl),
(2) a C₁₋₆ alkoxy group (e.g., methoxy, ethoxy, propoxy) optionally substituted by 1 to 5 substituents selected from
    (a) a halogen atom (e.g., a fluorine atom), and
    (b) a C₃₋₁₀ cycloalkyl group (e.g., cyclopropyl) optionally substituted by 1 to 3 halogen atoms (e.g., a fluorine atom),
(3) a 3- to 8-membered oxygen-containing monocyclic non-aromatic heterocyclyloxy group (e.g., oxetanyloxy),
(4) an optionally halogenated C₁₋₆ alkyl-carbonyl group (e.g., acetyl, propionyl), or
(5) a C₃₋₁₀ cycloalkyl group (e.g., cyclopropyl, cyclobutyl);
Ry² is
(1) a cyano group,
(2) a halogen atom (preferably a chlorine atom), or
(3) an optionally halogenated C₁₋₆ alkyl group (e.g., methyl, difluoromethyl); and
Rz² is
(1) a C₁₋₆ alkyl group (e.g., methyl, ethyl, propyl, isobutyl) optionally substituted by 1 to 3 substituents selected from
    (a) a halogen atom (e.g., a fluorine atom),
    (b) a hydroxy group,
    (c) a C₁₋₆ alkoxy group (e.g., methoxy, ethoxy) optionally substituted by 1 to 3 substituents selected from
        (i) a halogen atom (e.g., a fluorine atom),
        (ii) a C₁₋₆ alkyl-carbonyloxy group (e.g., acetyloxy, 2-methylpropanoyloxy, 2,2-dimethylpropanoyloxy, 3-methylbutanoyloxy), and
        (iii) a C₁₋₆ alkoxy-carbonyloxy group (e.g., ethoxycarbonyloxy, isopropoxycarbonyloxy),
    (d) a C₁₋₆ alkyl-carbonyloxy group (e.g., acetyloxy), and
    (e) a 5- to 6-membered nitrogen-containing monocyclic aromatic heterocyclic group (e.g., pyrimidinyl),
(2) a C₃₋₁₀ cycloalkyl group (e.g., cyclobutyl, cyclopentyl, cyclohexyl) optionally substituted by 1 to 3 substituents selected from
    (a) a halogen atom (e.g., a fluorine atom),
    (b) a hydroxy group,
    (c) a C₁₋₆ alkyl group (e.g., methyl) optionally substituted by 1 to 3 C₁₋₆ alkoxy groups (e.g., methoxy), and
    (d) a C₁₋₆ alkoxy group (e.g., methoxy),
(3) a C₁₋₆ alkoxy-carbonyl group (e.g., tert-butoxycarbonyl),
(4) a C₆₋₁₄ aryl group (e.g., phenyl) optionally substituted by 1 to 3 halogen atoms (e.g., a fluorine atom),
(5) a 5- to 6-membered nitrogen-containing monocyclic aromatic heterocyclic group (e.g., pyrimidinyl, pyridyl) optionally substituted by 1 to 3 C₁₋₆ alkyl groups (e.g., methyl), or
(6) a 3- to 8-membered oxygen-containing monocyclic non-aromatic heterocyclic group (e.g., oxetanyl, tetrahydrofuryl, tetrahydropyranyl, oxepanyl, dioxepanyl, dioxanyl, 2-oxabicyclo[2.2.2]octyl) optionally substituted by 1 to 3 substituents selected from
    (a) a halogen atom (e.g., a fluorine atom),
    (b) a C₁₋₆ alkyl group (e.g., methyl, ethyl) optionally substituted by 1 to 3 substituents selected from a halogen atom (e.g., a fluorine atom) and a C₁₋₆ alkoxy group (e.g., methoxy),
    (c) a C₃₋₁₀ cycloalkyl group (e.g., cyclopropyl),
    (d) a cyano group, and
    (e) a deuterium atom,
or a salt thereof.

Compound (II-2) is preferably a compound wherein
Rx² is
(1) an optionally halogenated C₁₋₆ alkyl group (e.g., trifluoromethyl), or
(2) an optionally halogenated C₁₋₆ alkoxy group (e.g., 2,2,2-trifluoroethoxy),
Ry² is a halogen atom (preferably a chlorine atom); and
Rz² is an oxygen-containing 4- to 6-membered monocyclic non-aromatic heterocyclic group (e.g., tetrahydropyranyl), particularly preferably a compound wherein
Rx² is a trifluoromethyl group or a 2,2,2-trifluoroethoxy group,
Ry² is a chlorine atom; and
Rz² is a tetrahydropyranyl group.

(3) A compound represented by the following formula (II-3):

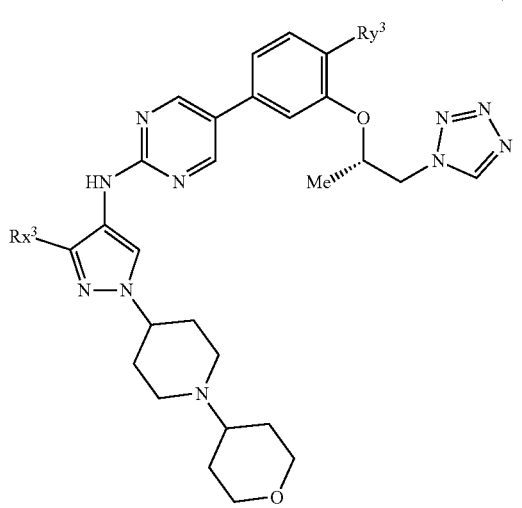

wherein
Rx³ is
(1) an optionally halogenated C₁₋₆ alkyl group (e.g., isopropyl, tert-butyl, difluoromethyl, trifluoromethyl, 3,3,3-trifluoropropyl, 1,1,2,2,2-pentafluoroethyl),
(2) a $C_{1-6}$ alkoxy group (e.g., methoxy, ethoxy, propoxy) optionally substituted by 1 to 5 substituents selected from
(a) a halogen atom (e.g., a fluorine atom), and
(b) a $C_{3-10}$ cycloalkyl group (e.g., cyclopropyl) optionally substituted by 1 to 3 halogen atoms (e.g., a fluorine atom),
(3) a 3- to 8-membered oxygen-containing monocyclic non-aromatic heterocyclyloxy group (e.g., oxetanyloxy),
(4) an optionally halogenated $C_{1-6}$ alkyl-carbonyl group (e.g., acetyl, propionyl), or
(5) a $C_{3-10}$ cycloalkyl group (e.g., cyclopropyl, cyclobutyl); and
$Ry^3$ is
(1) a cyano group,
(2) a halogen atom (preferably a chlorine atom), or
(3) an optionally halogenated $C_{1-6}$ alkyl group (e.g., methyl, difluoromethyl),
or a salt thereof.

Compound (II-3) is preferably a compound wherein $Rx^3$ is
(1) an optionally halogenated $C_{1-6}$ alkyl group (e.g., isopropyl, trifluoromethyl), or
(2) an optionally halogenated $C_{1-6}$ alkoxy group (e.g., difluoromethoxy, 2,2,2-trifluoroethoxy); and
$Ry^3$ is
(1) a cyano group, or
(2) a halogen atom (preferably a chlorine atom), particularly preferably a compound wherein
$Rx^3$ is an isopropyl group, a trifluoromethyl group, a difluoromethoxy group or a 2,2,2-trifluoroethoxy group; and
$Ry^3$ is a cyano group or a chlorine atom.

Specific preferable examples of compound (II-1Aa) are
5-(3-(((S)-1-(1H-tetrazol-1-yl)propan-2-yl)oxy)-4-chlorophenyl)-N-(1-(trans-4-morpholinocyclohexyl)-3-(trifluoromethyl)-1H-pyrazol-4-yl)pyrimidin-2-amine, or a salt thereof;
5-(3-(((S)-1-(1H-tetrazol-1-yl)propan-2-yl)oxy)-4-chlorophenyl)-N-(1-(trans-4-morpholinocyclohexyl)-3-(2,2,2-trifluoroethoxy)-1H-pyrazol-4-yl)pyrimidin-2-amine, or a salt thereof;
5-(3-(((S)-1-(1H-tetrazol-1-yl)propan-2-yl)oxy)-4-chlorophenyl)-N-(3-(2,2-difluoroethoxy)-1-(trans-4-morpholinocyclohexyl)-1H-pyrazol-4-yl)pyrimidin-2-amine, or a salt thereof;
5-(3-(((S)-1-(1H-tetrazol-1-yl)propan-2-yl)oxy)-4-chlorophenyl)-N-(3-isopropyl-1-(trans-4-morpholinocyclohexyl)-1H-pyrazol-4-yl)pyrimidin-2-amine, or a salt thereof;
5-(3-(((S)-1-(1H-tetrazol-1-yl)propan-2-yl)oxy)-4-chlorophenyl)-N-(1-(trans-4-morpholinocyclohexyl)-3-(oxetan-3-yloxy)-1H-pyrazol-4-yl)pyrimidin-2-amine, or a salt thereof;
5-(3-(((S)-1-(1H-tetrazol-1-yl)propan-2-yl)oxy)-4-chlorophenyl)-N-(3-(((S)-2,2-difluorocyclopropyl)methoxy)-1-(trans-4-morpholinocyclohexyl)-1H-pyrazol-4-yl)pyrimidin-2-amine, or a salt thereof; and
2-(((S)-1-(1H-tetrazol-1-yl)propan-2-yl)oxy)-4-(2-((1-(trans-4-morpholinocyclohexyl)-3-(2,2,2-trifluoroethoxy)-1H-pyrazol-4-yl)amino)pyrimidin-5-yl)benzonitrile, or a salt thereof.

Among them, particularly preferable examples are
5-(3-(((S)-1-(1H-tetrazol-1-yl)propan-2-yl)oxy)-4-chlorophenyl)-N-(1-(trans-4-morpholinocyclohexyl)-3-(trifluoromethyl)-1H-pyrazol-4-yl)pyrimidin-2-amine, or a salt thereof;

5-(3-(((S)-1-(1H-tetrazol-1-yl)propan-2-yl)oxy)-4-chlorophenyl)-N-(1-(trans-4-morpholinocyclohexyl)-3-(2,2,2-trifluoroethoxy)-1H-pyrazol-4-yl)pyrimidin-2-amine, or a salt thereof; and
5-(3-(((S)-1-(1H-tetrazol-1-yl)propan-2-yl)oxy)-4-chlorophenyl)-N-(3-isopropyl-1-(trans-4-morpholinocyclohexyl)-1H-pyrazol-4-yl)pyrimidin-2-amine, or a salt thereof.

Specific preferable examples of compound (II-1Ab) are
5-(3-(((S)-1-(1H-tetrazol-1-yl)propan-2-yl)oxy)-4-chlorophenyl)-N-(1-(trans-4-((1R,5S)-3-oxa-8-azabicyclo[3.2.1]octan-8-yl)cyclohexyl)-3-(2,2-difluoroethoxy)-1H-pyrazol-4-yl)pyrimidin-2-amine, or a salt thereof; and
1-(trans-4-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclohexyl)-3-methylazetidin-3-ol, or a salt thereof.

Specific preferable examples of compound (II-2) are
(S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(trifluoromethyl)-1H-pyrazol-4-yl)pyrimidin-2-amine, or a salt thereof;
(S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(2,2,2-trifluoroethoxy)-1H-pyrazol-4-yl)pyrimidin-2-amine, or a salt thereof;
(S)-5-(3-((1-(1H-tetrazol-1-yl)propan-2-yl)oxy)-4-chlorophenyl)-N-(1-(2-(oxetan-3-yl)-2-azaspiro[3.3]heptan-6-yl)-3-(2,2,2-trifluoroethoxy)-1H-pyrazol-4-yl)pyrimidin-2-amine, or a salt thereof;
(S)-1-(6-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-azaspiro[3.3]heptan-2-yl)-2-methylpropan-2-ol, or a salt thereof;
(S)-5-(3-((1-(1H-tetrazol-1-yl)propan-2-yl)oxy)-4-chlorophenyl)-N-(1-(2-(2,2-dimethyl-1,3-dioxan-5-yl)-2-azaspiro[3.3]heptan-6-yl)-3-(2,2,2-trifluoroethoxy)-1H-pyrazol-4-yl)pyrimidin-2-amine, or a salt thereof;
(S)-5-(3-((1-(1H-tetrazol-1-yl)propan-2-yl)oxy)-4-chlorophenyl)-N-(3-isopropyl-1-(2-(oxetan-3-yl)-2-azaspiro[3.3]heptan-6-yl)-1H-pyrazol-4-yl)pyrimidin-2-amine, or a salt thereof;
(S)-5-(3-((1-(1H-tetrazol-1-yl)propan-2-yl)oxy)-4-chlorophenyl)-N-(3-isopropyl-1-(2-(tetrahydro-2H-pyran-4-yl)-2-azaspiro[3.3]heptan-6-yl)-1H-pyrazol-4-yl)pyrimidin-2-amine, or a salt thereof;
(S)-5-(3-((1-(1H-tetrazol-1-yl)propan-2-yl)oxy)-4-chlorophenyl)-N-(1-(2-(4-methyltetrahydro-2H-pyran-4-yl)-2-azaspiro[3.3]heptan-6-yl)-3-(2,2,2-trifluoroethoxy)-1H-pyrazol-4-yl)pyrimidin-2-amine, or a salt thereof;
5-(4-chloro-3-{[(2S)-1-(1H-tetrazol-1-yl)propan-2-yl]oxy}phenyl)-N-(1-{2-[(4-$^2$H)tetrahydro-2H-pyran-4-yl]-2-azaspiro[3.3]heptan-6-yl}-3-(2,2,2-trifluoroethoxy)-1H-pyrazol-4-yl)pyrimidin-2-amine, or a salt thereof;
(S)-1-(6-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-azaspiro[3.3]heptan-2-yl)-2-methylpropan-2-ol, or a salt thereof;
(S)-1-(6-(4-((5-(3-((1-(1H-tetrazol-1-yl)propan-2-yl)oxy)-4-chlorophenyl)pyrimidin-2-yl)amino)-3-isopropyl-1H-pyrazol-1-yl)-2-azaspiro[3.3]heptan-2-yl)-2-methylpropan-2-ol, or a salt thereof;
(S)-1-(4-((5-(3-((1-(1H-tetrazol-1-yl)propan-2-yl)oxy)-4-chlorophenyl)pyrimidin-2-yl)amino)-1-(2-(tetrahydro-2H-pyran-4-yl)-2-azaspiro[3.3]heptan-6-yl)-1H-pyrazol-3-yl)propan-1-one, or a salt thereof;

(S)-5-(3-((1-(1H-tetrazol-1-yl)propan-2-yl)oxy)-4-chlorophenyl)-N-(3-(perfluoroethyl)-1-(2-(tetrahydro-2H-pyran-4-yl)-2-azaspiro[3.3]heptan-6-yl)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(3-isopropyl-1-(2-(4-methyltetrahydro-2H-pyran-4-yl)-2-azaspiro[3.3]heptan-6-yl)-1H-pyrazol-4-yl)pyrimidin-2-amine, or a salt thereof;

(S)—N-(1-(2-(1,3-dioxan-5-yl)-2-azaspiro[3.3]heptan-6-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine, or a salt thereof; and (S)—N-(1-(2-(1,4-dioxepan-6-yl)-2-azaspiro[3.3]heptan-6-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine, or a salt thereof.

Among them, particularly preferable examples are (S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(trifluoromethyl)-1H-pyrazol-4-yl)pyrimidin-2-amine, or a salt thereof; and (S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(2,2,2-trifluoroethoxy)-1H-pyrazol-4-yl)pyrimidin-2-amine, or a salt thereof.

Specific preferable examples of compound (II-3) are (S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(trifluoromethyl)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(2,2,2-trifluoroethoxy)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(3-(difluoromethoxy)-1-(1-(tetrahydro-2H-pyran-4-yl)piperidin-4-yl)-1H-pyrazol-4-yl)pyrimidin-2-amine, or a salt thereof;

(S)-5-(3-((1-(1H-tetrazol-1-yl)propan-2-yl)oxy)-4-chlorophenyl)-N-(3-isopropyl-1-(1-(tetrahydro-2H-pyran-4-yl)piperidin-4-yl)-1H-pyrazol-4-yl)pyrimidin-2-amine, or a salt thereof; and (S)-2-((1-(1H-tetrazol-1-yl)propan-2-yl)oxy)-4-(2-((1-(1-(tetrahydro-2H-pyran-4-yl)piperidin-4-yl)-3-(2,2,2-trifluoroethoxy)-1H-pyrazol-4-yl)amino)pyrimidin-5-yl)benzonitrile, or a salt thereof.

Specific examples of compound (I) include the compounds of Examples 1 to 5, 7 to 69, 71 to 150, 152 to 160, 162 to 167, 169 to 318, 320 to 380, 382 to 385 and 387 to 956, 958 to 960, 965, 974, 975, 979 to 984, 998, 1000, 1001 and 1010 to 1014.

When compound (I) is a salt, examples of the salt include metal salts, ammonium salts, salts with organic base, salts with inorganic acid, salts with organic acid, and salts with basic or acidic amino acid. Preferable examples of the metal salt include alkali metal salts such as sodium salts, potassium salts and the like; alkali earth metal salts such as calcium salts, magnesium salts, barium salts and the like; and aluminum salts. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acid include salts with arginine, lysine, ornithine and the like. Preferable examples of the salt with acidic amino acid include salts with aspartic acid, glutamic acid and the like. Among them, a pharmaceutically acceptable salt is preferable. For example, when a compound has an acidic functional group, examples of the salt include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples of the salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

When compound (I) contains isomers such as tautomers, optical isomers, stereoisomers, position isomers and rotational isomers, any of isomers or mixture are also encompassed in the compound of the present invention. Further, when compound (I) contains an optical isomer, the optical isomer separated from the racemate is encompassed in compound (I).

Compound (I) can be obtained in the crystal form. Either single crystalline form or crystalline mixture can be encompassed in compound (I).

Compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to co-crystallization method known per se.

Compound (I) may be a solvate (e.g., a hydrate) or a non-solvate and both are encompassed in compound (I).

Compounds labeled with or substituted by isotopes (e.g., $^{2}H$, $^{3}H$, $^{11}C$, $^{14}C$, $^{18}F$, $^{35}S$, $^{125}I$, etc.) are also encompassed in compound (I). The compound labeled with or substituted by isotopes can be used as, for example, a tracer used for Positron Emission Tomography (PET) (PET tracer), and are expected to be useful in the field of medical diagnosis and the like.

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a ligand, the reagent is used in an amount of 0.001 equivalent-equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.
alcohols: methanol, ethanol, tert-butyl alcohol, 2-methoxyethanol, benzyl alcohol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like;
water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts. inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of a functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond or a nitro group or a benzyloxycarbonyl group is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a combination of a nucleophile (e.g., an amine, imidazole etc.) and a base (e.g., an organic base etc.), or a combination of a nucleophile and an acid (e.g., an organic acid etc.) is used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, borane-2-methylpyridine complex, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, a combination of an azodicarboxylate (e.g., diethyl azodicarboxylate (DEAD), diisopropyl azodicarboxylate (DIAD) etc.) and triphenylphosphine, or a phosphorane reagent (e.g., cyanomethylenetributylphosphorane (Tsunoda reagent) is used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, (tri-tert-butylphosphine)palladium(0) and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide, copper(II) diacetate and the like; platinum compounds and the like. In addition, a base can be added to the reaction system, and examples thereof include organic bases (e.g., 1,8-diazabicyclo[5.4.0]undec-7-ene, N,N-diisopropylethylamine), inorganic bases and the like. Moreover, a ligand can be added to the reaction system, and examples thereof include organic amines such as N,N'-dimethylethylenediamine, N,N'-dimethyl-cyclohexane-1,2-diamine, 2,2-bipyridyl and the like; organophosphorus compounds such as triphenylphosphine, tri-tert-butylphosphine, tricyclohexylphosphine, BINAP (2,2'-bis(diphenylphosphino)-1,1-binaphthyl) and the like, and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When Curtius reaction is carried out in each step, a combination of an azidating agent (e.g., diphenylphosphorylazide (DPPA) and sodium azide etc.) and water or alcohols and base (e.g., triethylamine) is used as a reagent.

When Strecker reaction is carried out in each step, examples of the cyanation agent to be used include sodium cyanide, cyanotrimethylsilane and the like.

When Bruylants reaction is carried out in each step, examples of the alkylation agent to be used include arylmagnesium halides such as phenylmagnesium bromide and the like; and alkylmagnesium halides such as methylmagnesium bromide and the like.

When Corey-Chaykovsky reaction is carried out in each step, examples of the epoxydation agent to be used include trialkylsulfonium salt, trialkylsulfoxonium salt and the like. In addition, a base can be added to the reaction system, and examples thereof include metal alkoxides (e.g., potassium tert-butoxide) or alkali metal hydrides (e.g., sodium hydride) and the like.

Compound (I) of the present invention can be produced according the methods explained below.

Ring A, Ring B, Ring C, $R^1$, $R^2$, $R^3$, xl, $X^2$, $X^3$, $Y^1$, $Y^2$, $Y^3$, Z and $R^Z$ in the following schemes are as defined above.

In any step of the following schemes, the substituent on Ring A, Ring B or Ring C can be converted to the objective functional group by chemical reactions per se singly or two or more thereof in combination. The substituent on Ring A, Ring B or Ring C is not limited as long as it is a substituent that does not adversely influence the reaction.

Compound (I) can be produced from compound (2) according to the method shown in Scheme 1-1.

[Scheme 1-1]

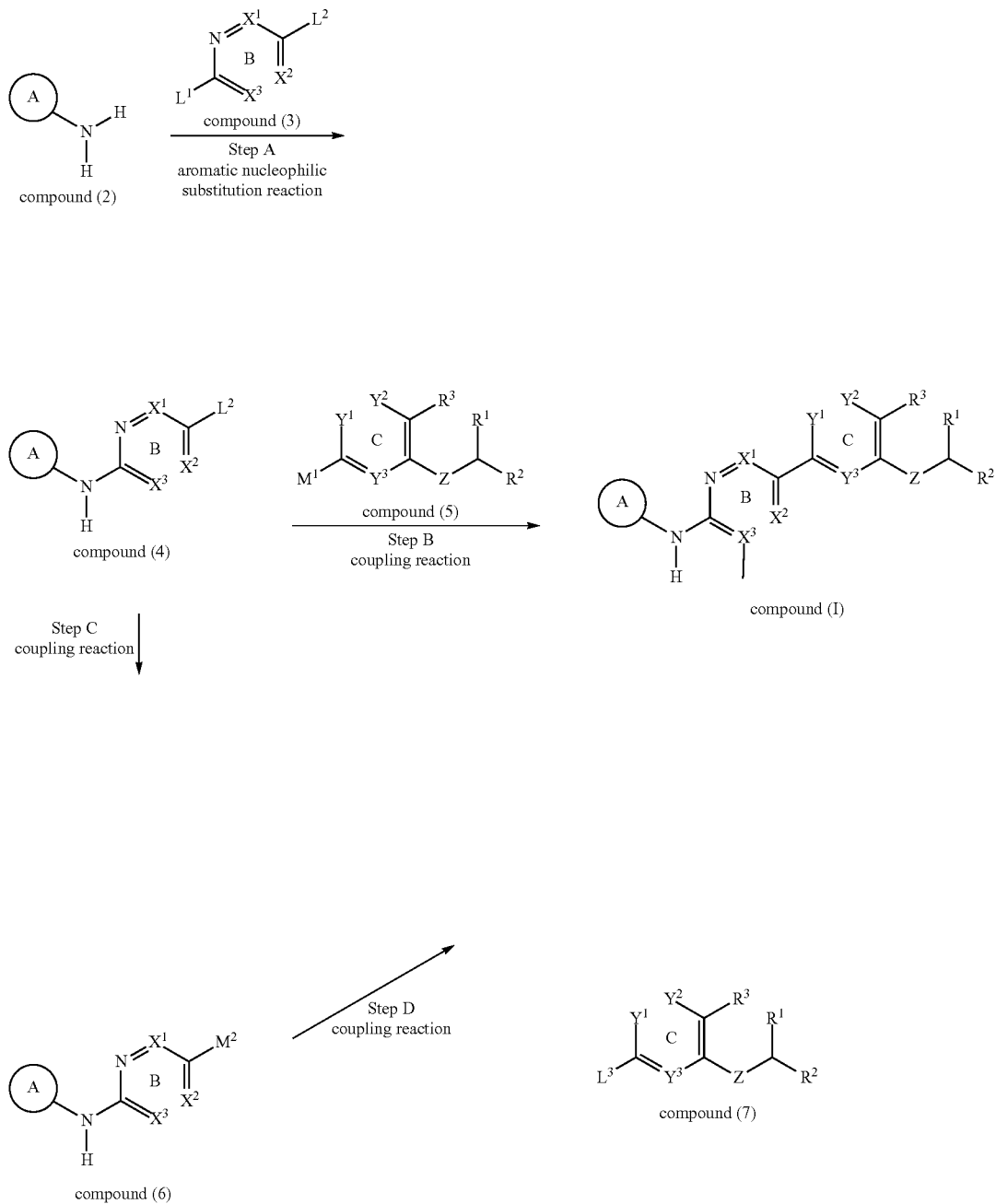

wherein $L^1$, $L^2$ and $L^3$ are each independently a leaving group, $M^1$ and $M^2$ are each independently a boronic acid group (—$B(OH)_2$), or a boronate ester group (—$B(OR)_2$; R is a $C_{1-6}$ alkyl group) or a cyclic group thereof (e.g., a 4,4,5,5-tetramethyl-1,3,2-dioxaborolan-2-yl, etc.), and the other symbols are as defined above.

Examples of the "leaving group" for $L^1$, $L^2$ or $L^3$ include a halogen atom (e.g., a fluorine atom, a chlorine atom, a bromine atom, an iodine atom etc.), an optionally halogenated $C_{1-6}$ alkylsulfonyloxy group (e.g., methanesulfonyloxy, ethanesulfonyloxy, trifluoromethanesulfonyloxy etc.), an optionally substituted $C_{6-14}$ arylsulfonyloxy group [e.g., a $C_{6-14}$ arylsulfonyloxy group optionally having 1 to 3 substituents selected from a $C_{1-6}$ alkyl group (e.g., methyl, etc.), a $C_{1-6}$ alkoxy group (e.g., methoxy, etc.) and a nitro group, and the like, and the examples thereof include benzenesulfonyloxy, m-nitrobenzenesulfonyloxy, p-toluenesulfonyloxy, naphthylsulfonyloxy and the like], a boronic acid group (—$B(OH)_2$) and the like.

Compounds (3), (5) and (7) may be a commercially available product, or can be produced according to a method known per se.

Compound (Ia), which is compound (I) wherein Z is —O—, —N($R^Z$)—, —S—, —S(O)— or —$S(O_2)$—, can be produced from compound (4) according to the method shown in Scheme 1-2.

[Scheme 1-2]

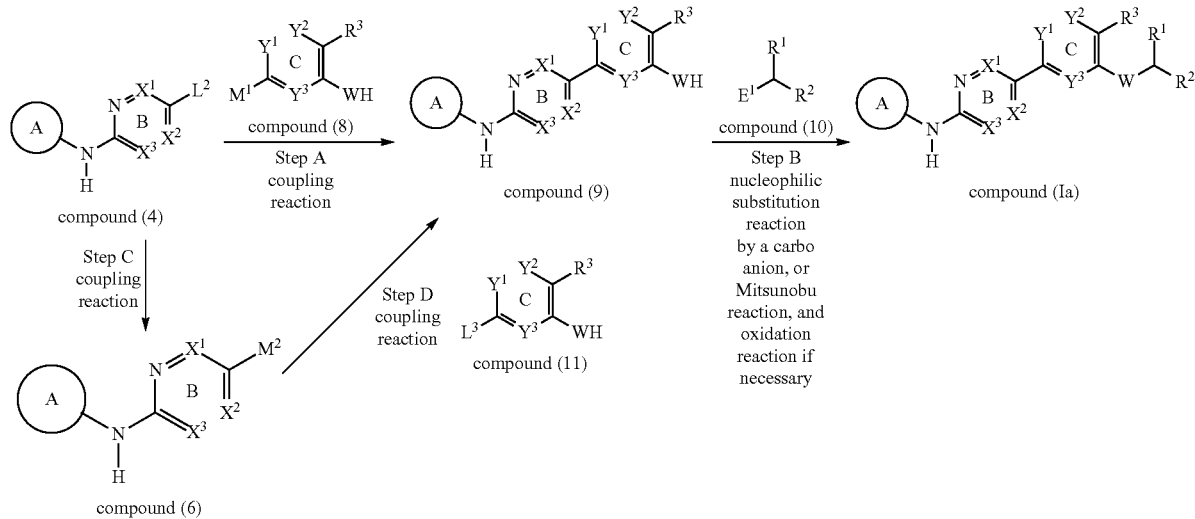

wherein $E^1$ is a hydroxyl group or a leaving group, W is —O—, —N($R^Z$)— or —S—, and the other symbols are as defined above.

Examples of the "leaving group" for $E^1$ include those exemplified as the "leaving group" for $L^1$, $L^2$ or $L^3$.

Compounds (8), (10) and (11) may be a commercially available product, or can be produced according to a method known per se.

Compound (Ia) can also be produced from compound (12) according to the method shown in Scheme 1-3 ($R^2$ is optionally substituted methyl, and examples of the substituent include an aromatic heterocyclic group (e.g., tetrazolyl-1-yl, 1,2,3-triazolyl-1-yl, 1,2,4-triazolyl-1-yl, 1H-pyrazol-1-yl, 1H-imidazol-1-yl, etc.), an alkoxy group, an amino group, an amido group etc.).

[Scheme 1-3]

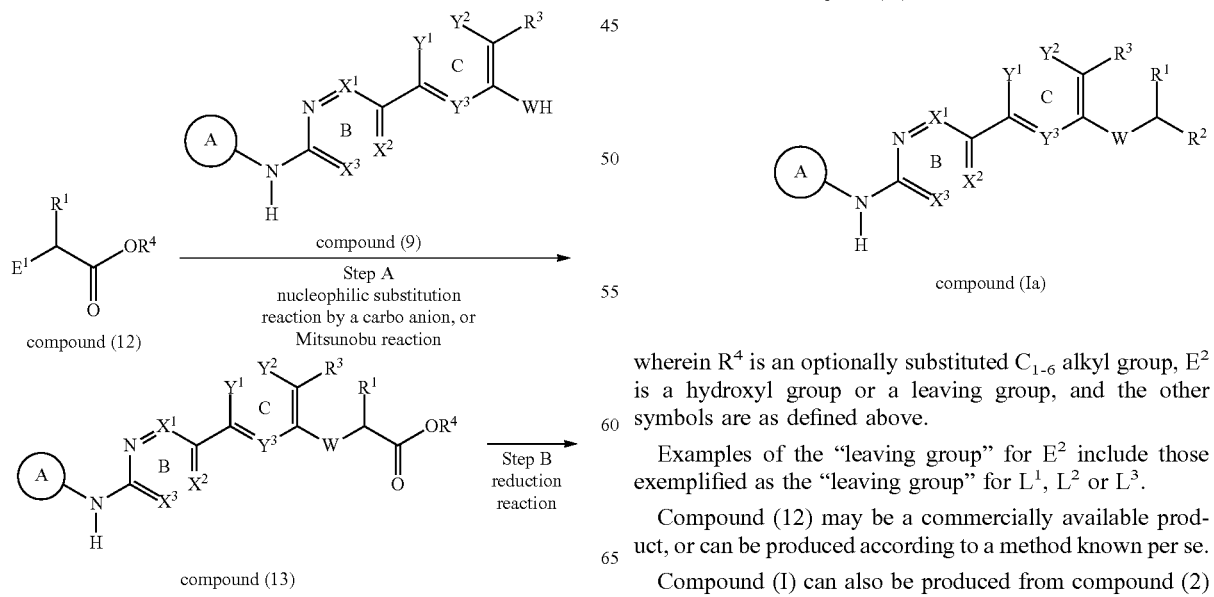

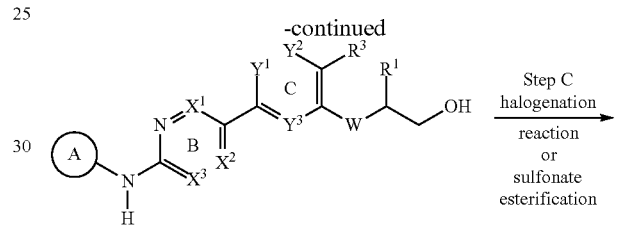

wherein $R^4$ is an optionally substituted $C_{1-6}$ alkyl group, $E^2$ is a hydroxyl group or a leaving group, and the other symbols are as defined above.

Examples of the "leaving group" for $E^2$ include those exemplified as the "leaving group" for $L^1$, $L^2$ or $L^3$.

Compound (12) may be a commercially available product, or can be produced according to a method known per se.

Compound (I) can also be produced from compound (2) according to the method shown in Scheme 1-4.

[Scheme 1-4]

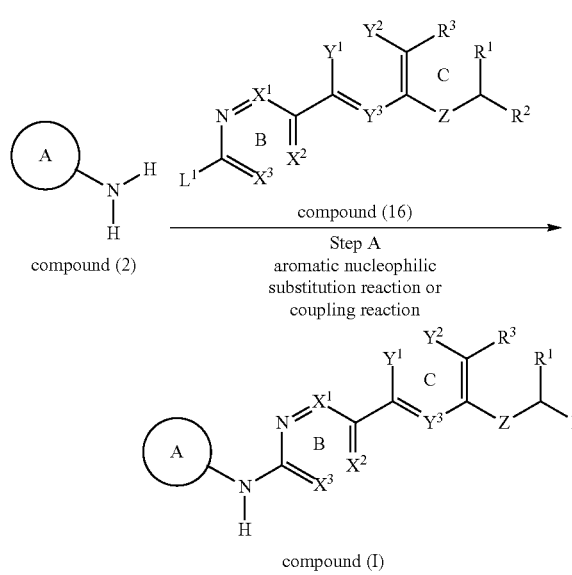

wherein each symbol is as defined above.

Compound (16) may be a commercially available product, or can be produced according to a method known per se.

Compound (5a) and compound (7a), which are compound (5) and compound (7) wherein Z is —O—, —N($R^Z$)—, —S—, —S(O)— or —S($O_2$)—, can be produced from compound (11) according to the method shown in Scheme 2-1, respectively.

Examples of the "leaving group" for $E^3$ include those exemplified as the "leaving group" for $L^1$, $L^2$ or $L^3$.

Compounds (17) and (18) may be a commercially available product, or can be produced according to a method known per se.

Compound (7a) can also be produced from compound (12) according to the method shown in Scheme 2-2 ($R^2$ is optionally substituted methyl, and examples of the substituent include an aromatic heterocyclic group (e.g., tetrazolyl-1-yl, 1,2,3-triazolyl-1-yl, 1,2,4-triazolyl-1-yl, 1H-pyrazol-1-yl, 1H-imidazol-1-yl, etc.), an alkoxy group, an amino group, an amido group etc.).

[Scheme 2-2]

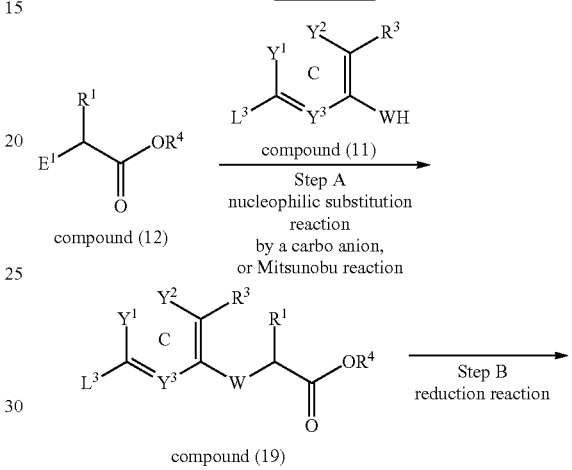

[Scheme 2-1]

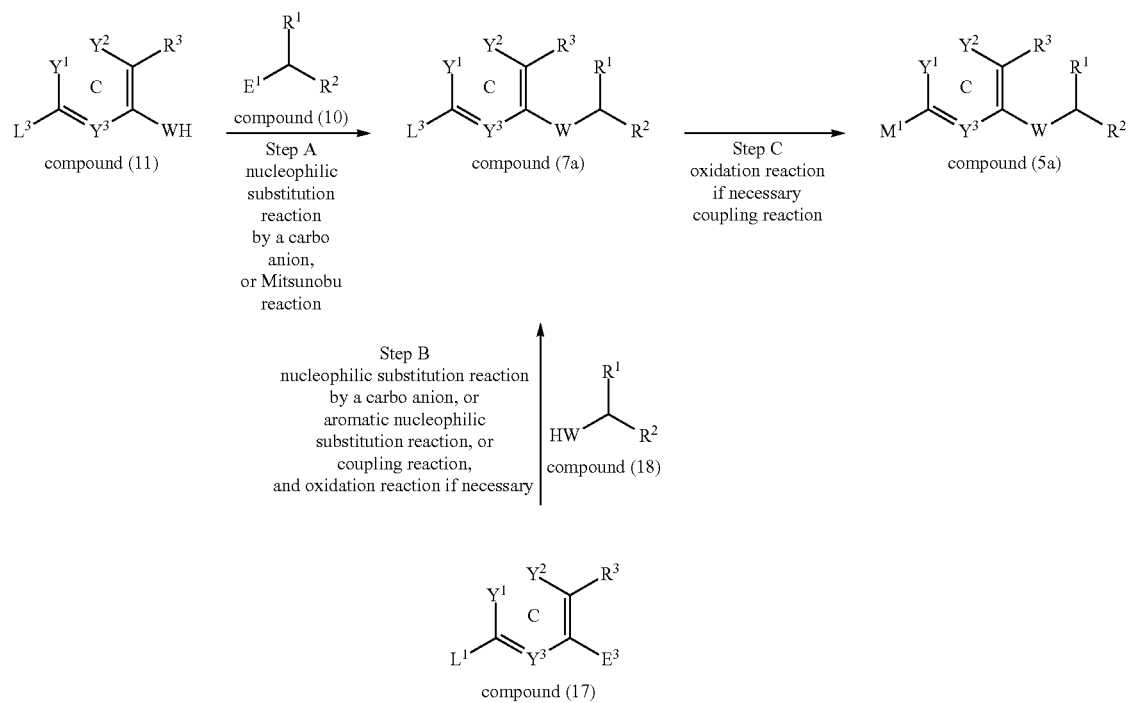

wherein $E^3$ is a hydroxyl group or a leaving group, and the other symbols are as defined above.

-continued

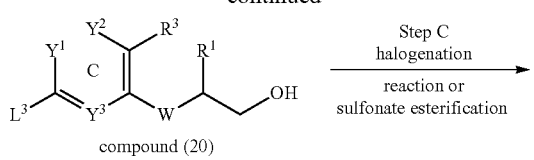
compound (20)

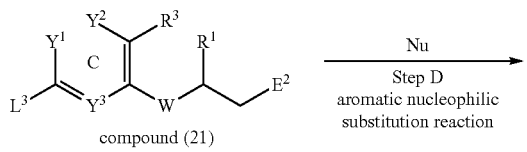
compound (21)

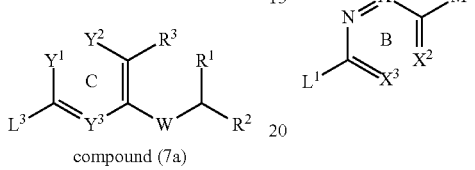
compound (7a)

wherein each symbol is as defined above.

Compound (10) can be produced from compound (22) according to the method shown in Scheme 3.

[Scheme 3]

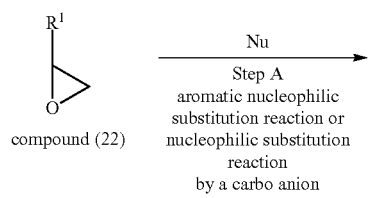

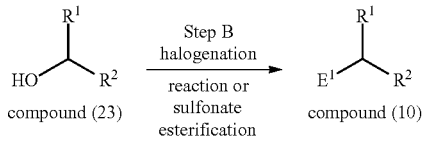

wherein each symbol is as defined above.

Compound (22) may be a commercially available product, or can be produced according to a method known per se.

Compound (16) can be produced from compound (24) or compound (3) according to the method shown in Scheme 4.

[Scheme 4]

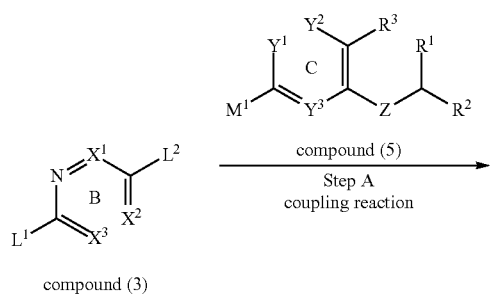
compound (3)

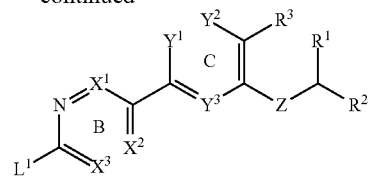
compound (16)

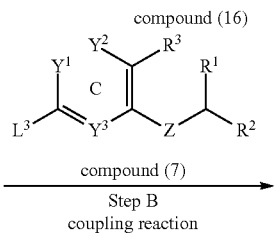

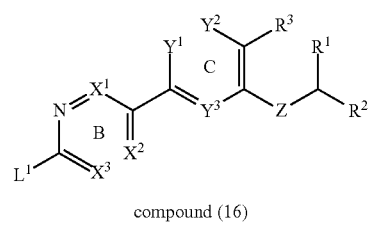
compound (16)

wherein each symbol is as defined above.

Compound (24) may be a commercially available product, or can be produced according to a method known per se.

Compound (2) can be produced from compound (25) according to the method shown in Scheme 5.

[Scheme 5]

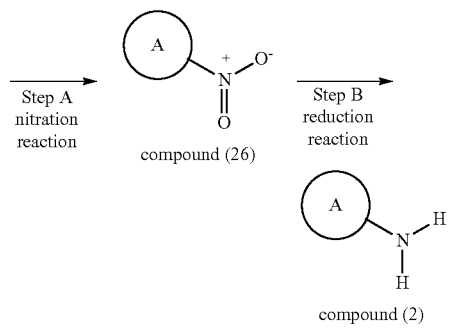

wherein each symbol is as defined above.

In Step A, compound (26) can be produced by subjecting compound (25) to nitration with a nitrating agent.

Examples of the nitrating agent include mineral acids such as mixed acid, nitric acid and the like; nitrates such as potassium nitrate, sodium nitrate, tetramethylammonium nitrate, silver nitrate and the like, and the like.

The amount of the nitrating agent to be used is about 1.0 to 10.0 mol, preferably about 1.0 to 5.0 mol, per 1 mol of compound (25).

This reaction is preferably carried out in a solvent inert to the reaction. While the solvent is not particularly limited as long as the reaction proceeds, examples thereof include aromatic hydrocarbons, ethers, alcohols, halogenated hydrocarbons, nitriles, amides, organic acids, inorganic acids, water and the like. These solvents may be used in a mixture of two or more kinds thereof in an appropriate ratio.

The reaction time is generally 15 min to 60 hr, preferably 30 min to 24 hr. The reaction temperature is generally −78° C. to 150° C., preferably −20° C. to 100° C.

The obtained compound (26) can be used directly as a reaction solution or as a crude product in the next reaction, or isolated from the reaction mixture by a conventional method, and can be easily purified by a separation means such as washing, recrystallization, distillation, chromatography and the like.

Compound (25) may be a commercially available product, or can be produced according to a method known per se.

Compound (2) can also be produced from compound (27) according to the method shown in Scheme 6.

[Scheme 6]

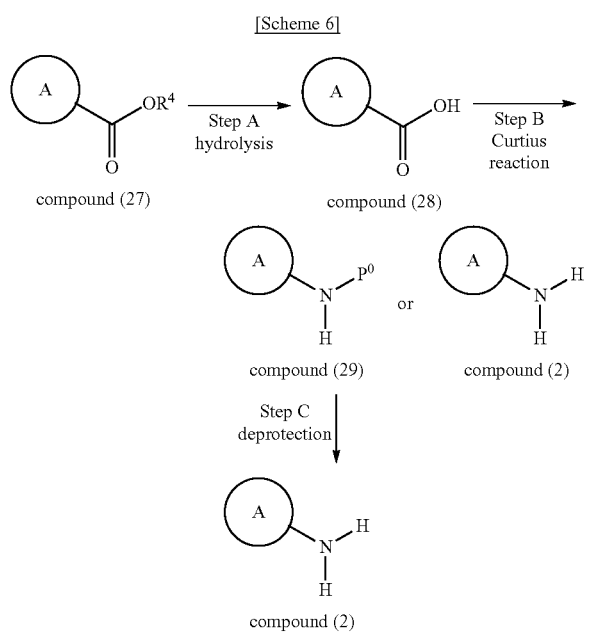

wherein $P^0$ is a protecting group for an amino group and the like, and the other symbols are as defined above.

Compound (27) may be a commercially available product, or can be produced according to a method known per se.

Compound (Ib), which is compound (I) wherein ring A is a pyrazole ring, can be produced from compound (2a) according to the method shown in Scheme 7-1.

[Scheme 7-1]

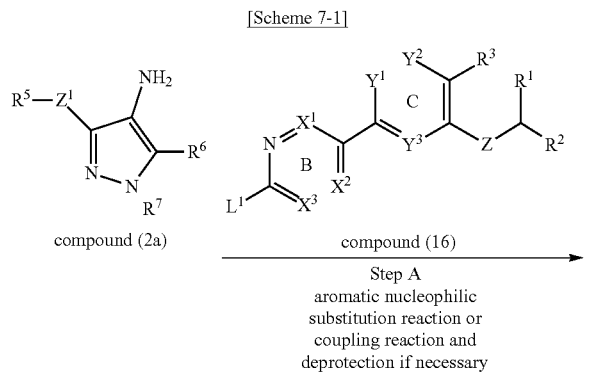

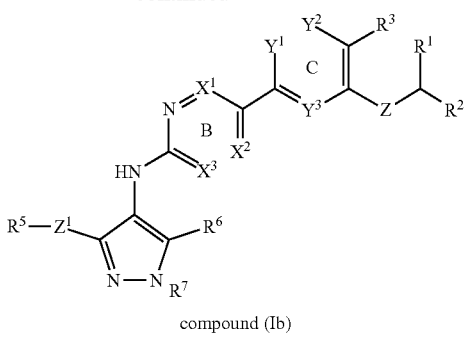

compound (Ib)

wherein $R^5$ and $R^7$ are each independently a substituent, $R^6$ is a hydrogen atom, or a substituent, $Z^1$ is —O— or bond, and the other symbols are as defined above.

Compound (2a) may be a commercially available product, or can be produced according to a method known per se.

Compound (Ic), which is compound (I) wherein ring A is a pyrazole ring, can be produced from compound (2b) or compound (2b') according to the method shown in Scheme 7-2, respectively.

[Scheme 7-2]

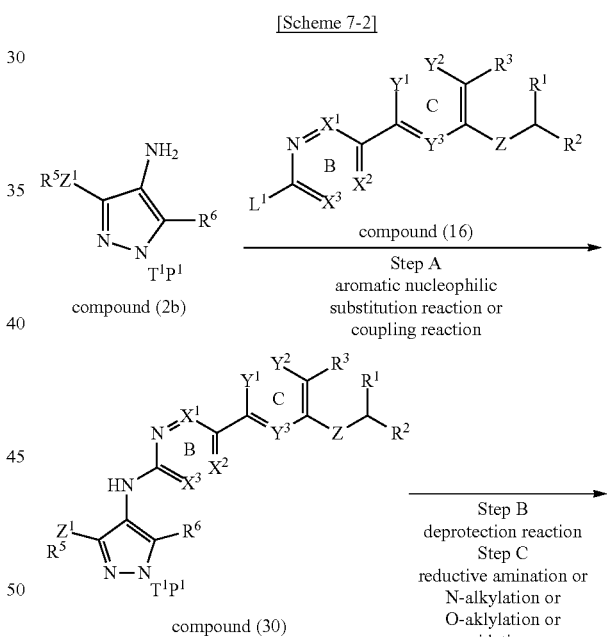

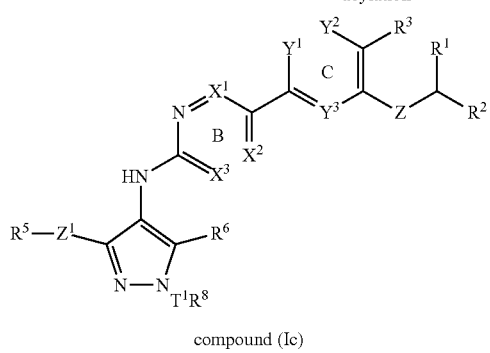

compound (Ic)

-continued

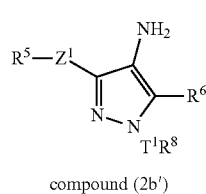 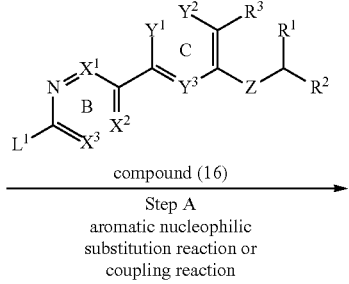

compound (2b')   compound (16)
→ Step A
aromatic nucleophilic substitution reaction or coupling reaction -continued compound (31)
→ Step B deprotection reaction
Step C reductive amination or N-alkylation compound (Id)

compound (Ic)

wherein $T^1$ is an amino group-containing $C_{1-6}$ alkyl group optionally substituted by 1 to 3 substituents or an oxo group-containing $C_{1-6}$ alkyl group optionally substituted by 1 to 3 substituents or a carboxyl group-containing $C_{1-6}$ alkyl group optionally substituted by 1 to 3 substituents or an optionally further substituted 5- or 6-membered aromatic ring, $P^1$ is a protecting group for an amino group, or carbonyl group, or a carboxyl group and the like, $R^8$ is a hydrogen atom or a substituent, and the other symbols are as defined above.

Compound (2b) and compound (2b') may be a commercially available product, or can be produced according to a method known per se.

Compound (Id), which is compound (I) wherein ring A is a pyrazole ring, can be produced from compound (2c) or compound (2c') according to the method shown in Scheme 7-3, respectively.

[Scheme 7-3]

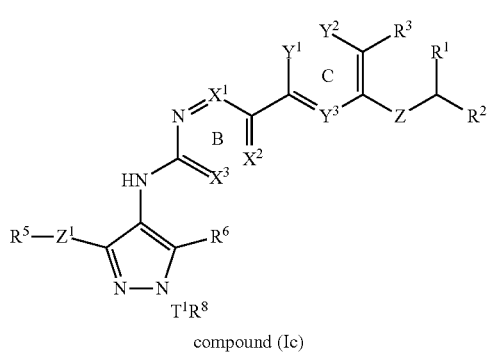

compound (2c)   compound (16)
→ Step A aromatic nucleophilic substitution reaction or coupling reaction compound (2c')   compound (16)
→ Step A aromatic nucleophilic substitution reaction or coupling reaction compound (Id)

wherein $Z^2$ is a $C_{1-6}$ alkyl group optionally substituted by 1 to 3 substituents or bond, $Cy^N$ is a nitrogen-containing 3- to 14-membered non-aromatic heterocyclic group optionally substituted by 1 to 3 substituents, $P^2$ is a protecting group for an amino group and the like, and the other symbols are as defined above.

Compound (2c) and compound (2c') may be a commercially available product, or can be produced according to a method known per se.

Compound (Ie), which is compound (I) wherein ring A is a pyrazole ring, can be produced from compound (2d) or compound (2d') according to the method shown in Scheme 7-4, respectively.

[Scheme 7-4]

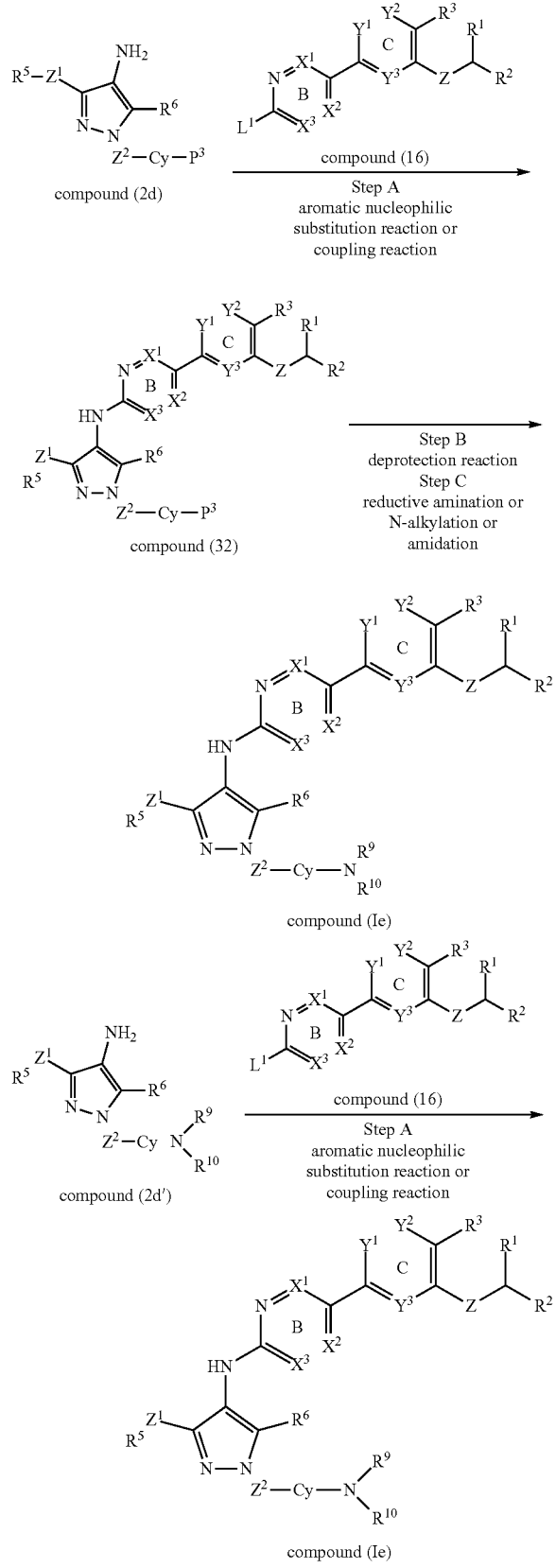

[Scheme 7-5]

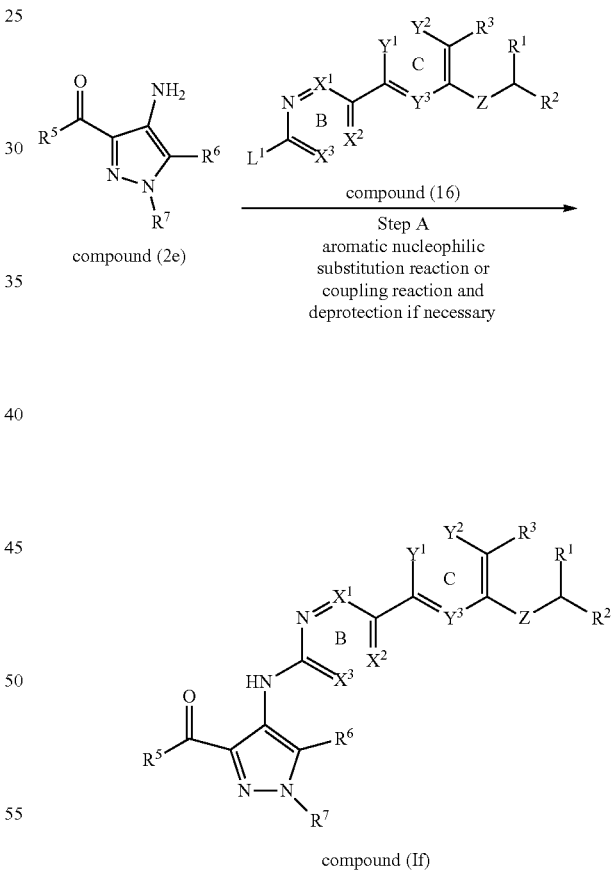

wherein Cy is a $C_{3-10}$ cycloalkyl group optionally substituted by 1 to 3 substituents such as an amino group, or a carboxyl group, or hydroxyl group and the like, or an oxo group-containing $C_{3-10}$ cycloalkyl group optionally substituted by 1 to 3 substituents, $P^3$ is a protecting group for an amino group, or a carbonyl group, or a carboxyl group, or a hydroxyl group and the like, $R^9$ and $R^{10}$ are each independently a hydrogen atom or a substituent, and the other symbols are as defined above.

Compound (2d) and compound (2d') may be a commercially available product, or can be produced according to a method known per se.

Compound (If), which is compound (I) wherein ring A is a pyrazole ring, can be produced from compound (2e) according to the method shown in Scheme 7-5.

wherein each symbol is as defined above.

Compound (2e) may be a commercially available product, or can be produced according to a method known per se.

Compound (2a) can be produced from compound (33), or compound (37) according to the method shown in Scheme 8-1, respectively.

[Scheme 8-1]

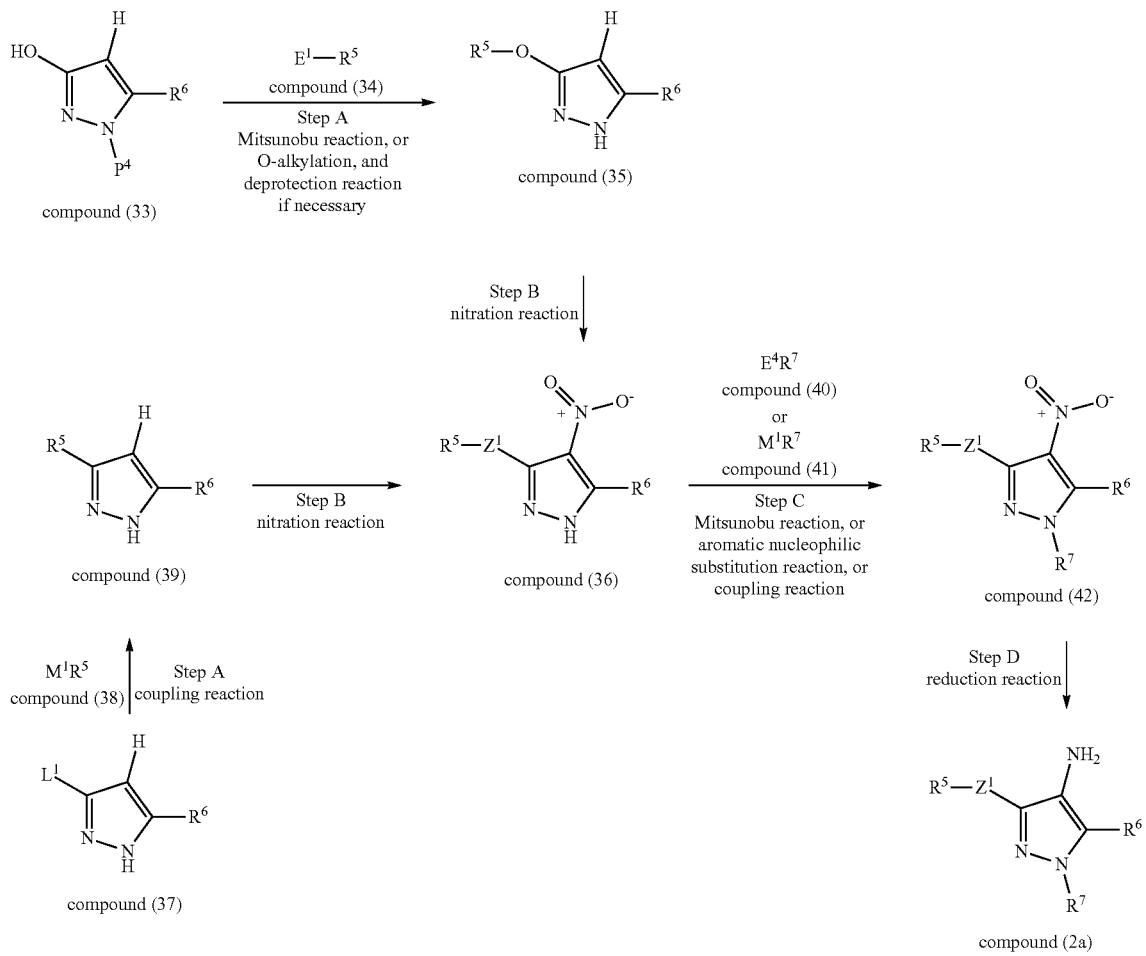

wherein $P^4$ is a protecting group for 5-membered monocyclic aromatic heterocycle group and the like, $E^4$ is a hydroxyl group or an epoxide-containing group or a leaving group, and the other symbols are as defined above.

Examples of the "leaving group" for $E^4$ include those exemplified as the "leaving group" for $L^1$, $L^2$ or $L^3$.

Compound (33), compound (34), compound (37), compound (38), compound (40) and compound (41) may be a commercially available product, or can be produced according to a method known per se.

Compound (2a) can also be produced from compound (43), or compound (46) according to the method shown in Scheme 8-2, respectively.

[Scheme 8-2]

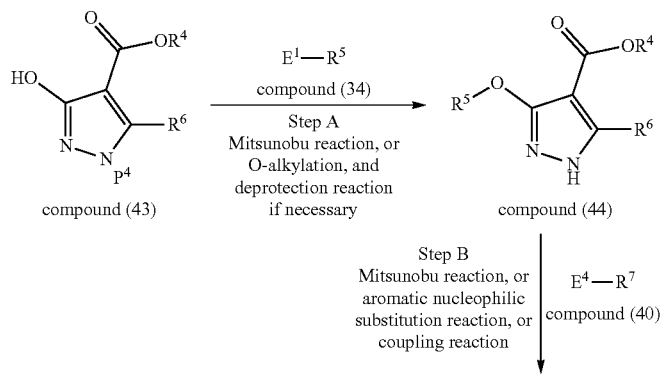

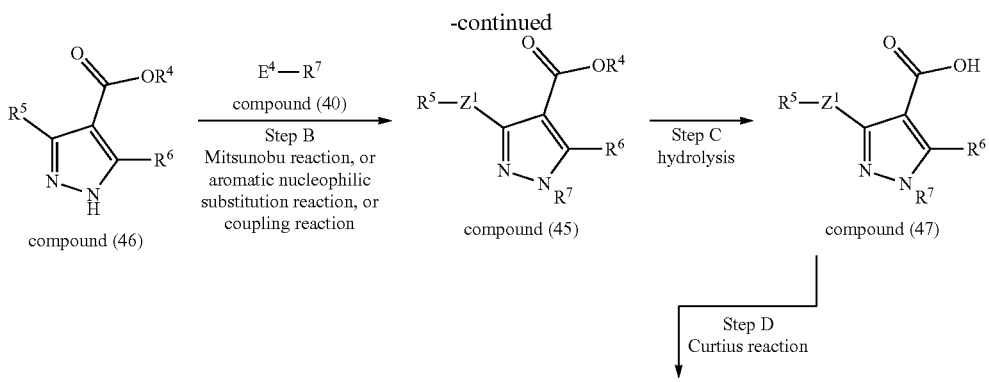
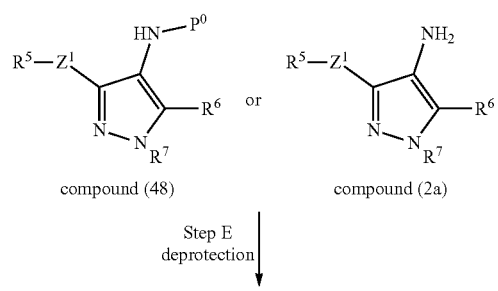
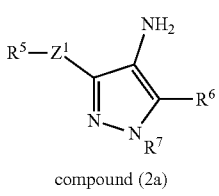
wherein each symbol is as defined above.

Compound (43), and compound (46) may be a commercially available product, or can be produced according to a method known per se.

Compound (2b) and compound (2b') can be produced from compound (36), or compound (46) according to the method shown in Scheme 8-3, respectively.

[Scheme 8-3]

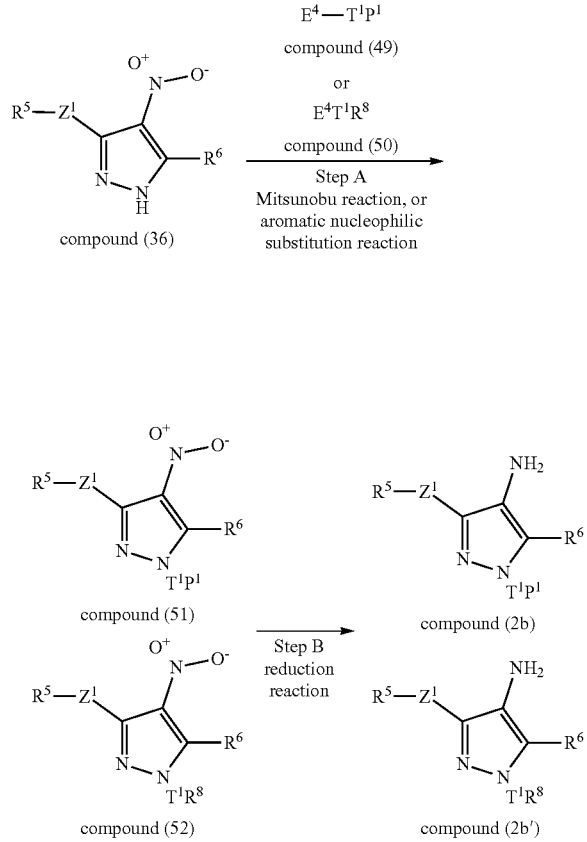

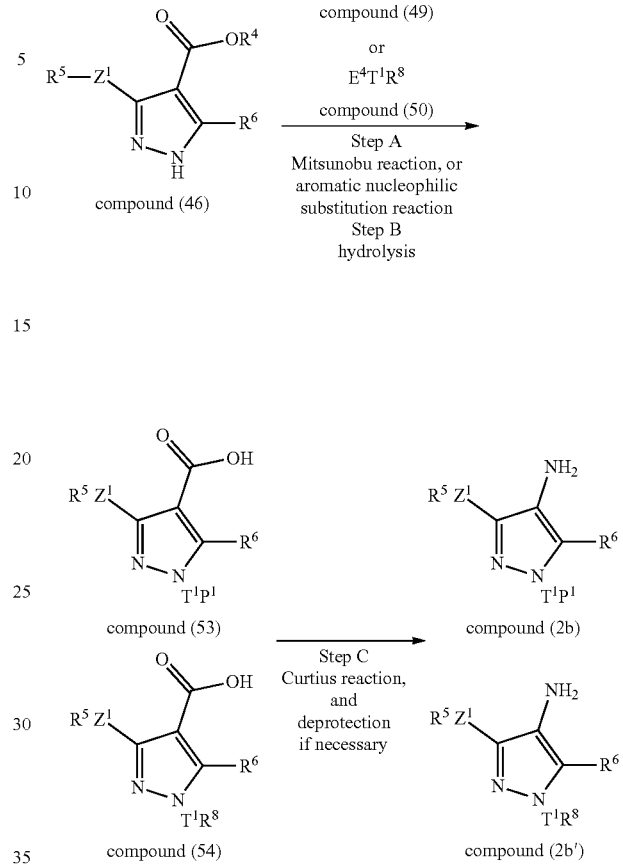

wherein each symbol is as defined above.

Compound (49), and compound (50) may be a commercially available product, or can be produced according to a method known per se.

Compound (2c) and compound (2c') can be produced from compound (36), or compound (46) according to the method shown in Scheme 8-4, respectively.

[Scheme 8-4]

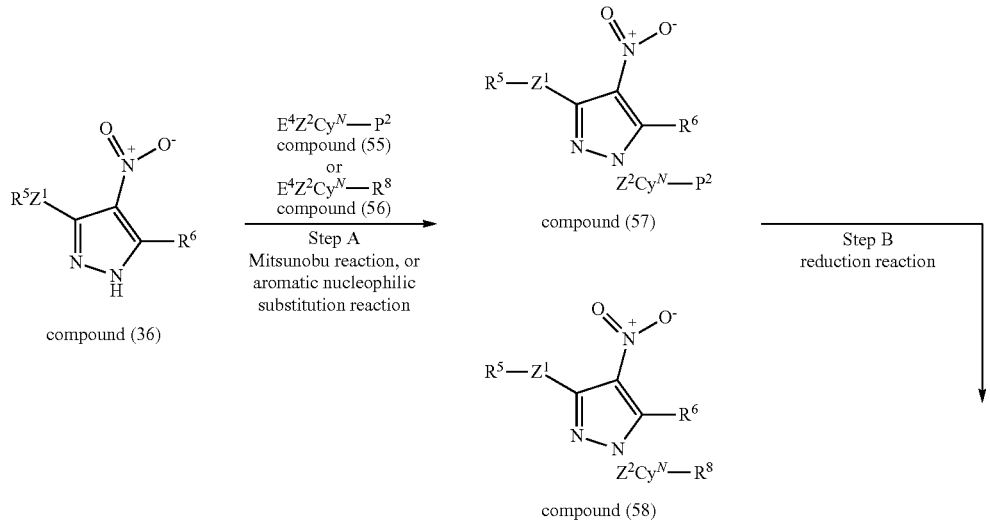

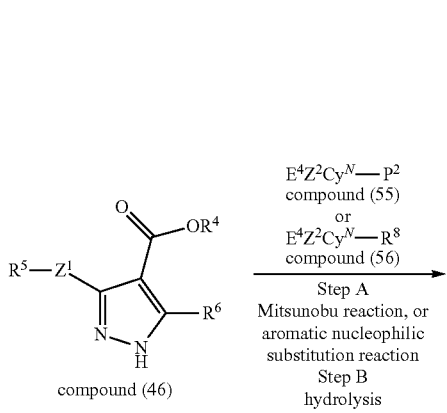
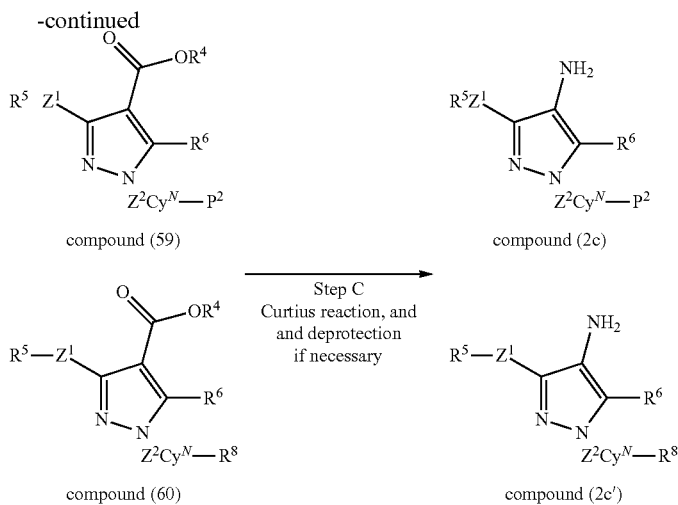
wherein each symbol is as defined above.
Compound (55), and compound (56) may be a commercially available product, or can be produced according to a method known per se.
Compound (2d) and compound (2d') can be produced from compound (36), or compound (46) according to the method shown in Scheme 8-5, respectively.
[Scheme 8-5]
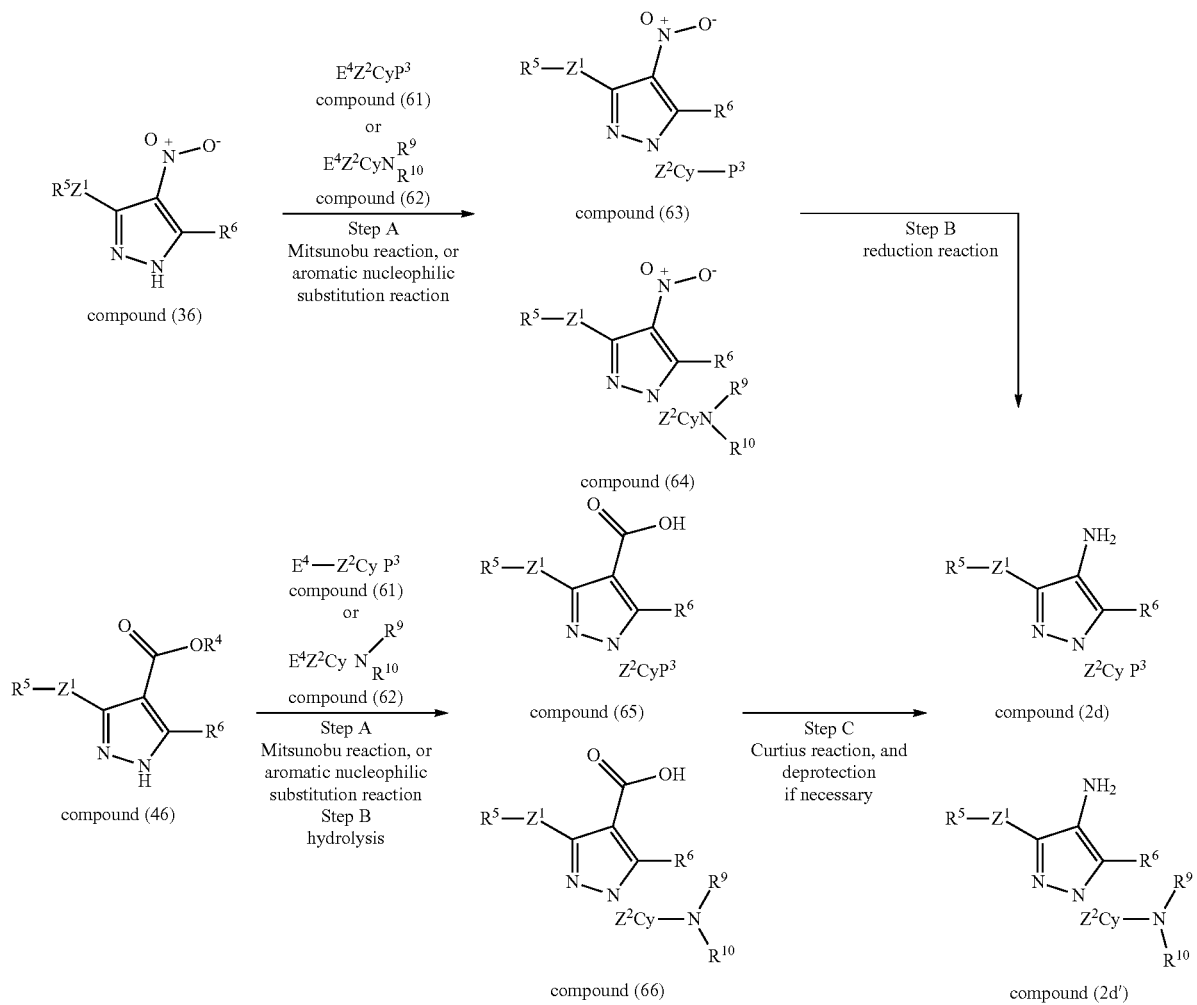
wherein each symbol is as defined above.

Compound (61), and compound (62) may be a commercially available product, or can be produced according to a method known per se.

Compound (2e) can be produced from compound (67) according to the method shown in Scheme 8-6.

[Scheme 8-6]

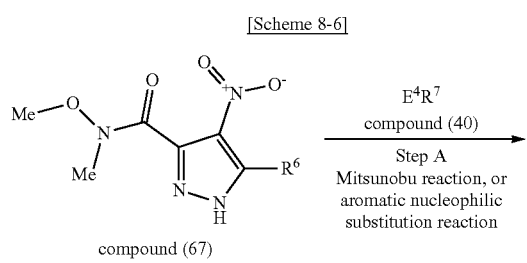

compound (67)

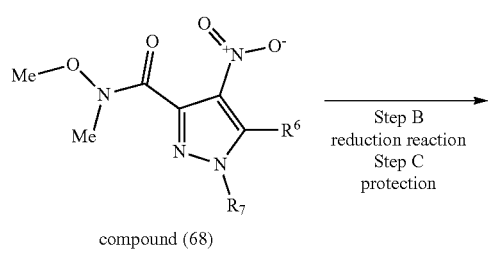

compound (68)

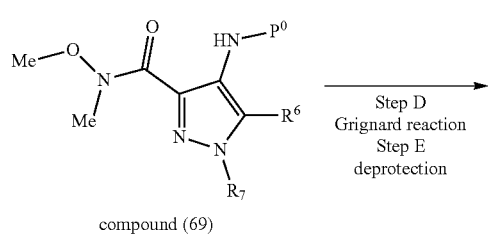

compound (69)

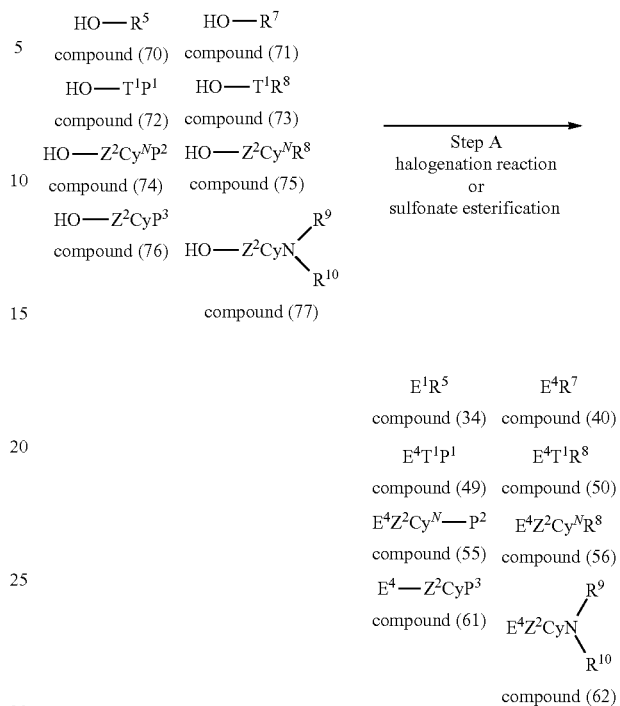

compound (2e)

wherein each symbol is as defined above.

Compound (67) may be a commercially available product, or can be produced according to a method known per se.

Compound (34), compound (40), compound (49), compound (50), compound (55), compound (56), compound (61), and compound (62) can be produced from compound (70), compound (71), compound (72), compound (73), compound (74), compound (75), compound (76), and compound (77) according to the method shown in Scheme 9-1, respectively.

[Scheme 9-1]

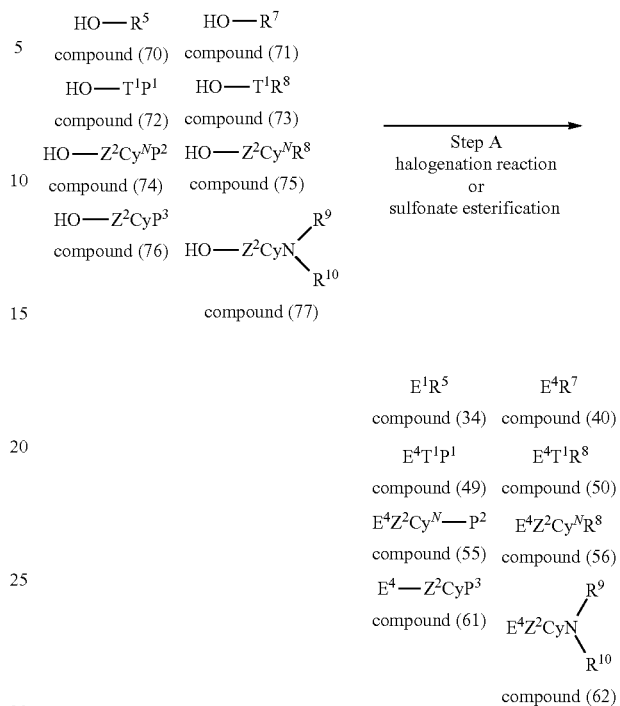

wherein each symbol is as defined above.

Compound (70), compound (71), compound (72), compound (73), compound (74), compound (75), compound (76), and compound (77) may be a commercially available product, or can be produced according to a method known per se.

Compound (73) can be produced from compound (72) according to the method shown in Scheme 9-2.

[Scheme 9-2]

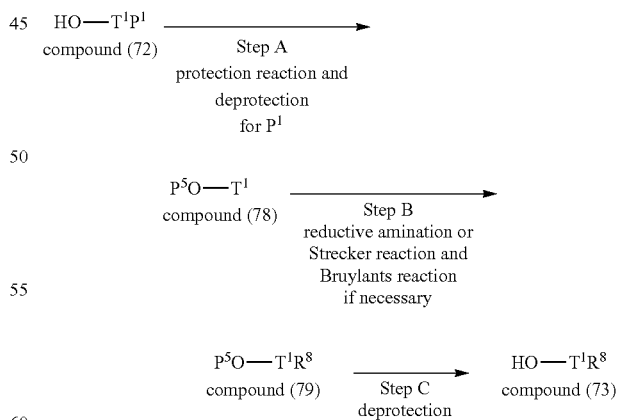

wherein $P^5$ is a protecting group for a hydroxyl group and the like, and the other symbols are as defined above.

Compound (75) and compound (77) can be produced from compound (74) and compound (76) according to the method shown in Scheme 9-3, respectively.

[Scheme 9-3]

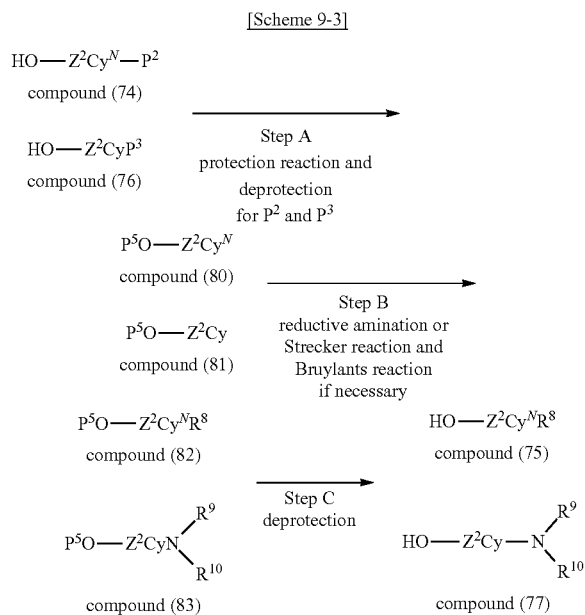

wherein each symbol is as defined above.

Compound (85), which is compound (40) wherein $E^4$ is an epoxide group, can be produced from compound (84) according to the method shown in Scheme 9-4.

[Scheme 9-4]

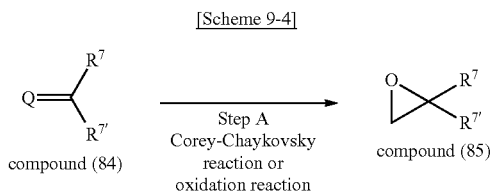

wherein $R^{7'}$ is a hydrogen atom, or a substituent, Q is a oxygen atom, or a methylene group, and the other symbols are as defined above.

Compound (84) may be a commercially available product, or can be produced according to a method known per se.

The starting compound and/or production intermediate for compound (I) may form a salt. While the salt is not particularly limited as long as the reaction can be performed, examples thereof include those similar to the salts optionally formed by compound (I) and the like, and the like.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending on the kind of a substituent, and each stereoisomer and a mixture thereof are encompassed in the present invention.

Compound (I) may be a hydrate or a non-hydrate.

When desired, compound (I) can be synthesized by performing deprotection reaction, acylation reaction, alkylation reaction, hydrogenation reaction, oxidation reaction, reduction reaction, reaction of carbon chain extension, halogenation reaction, substituent exchange reaction, coupling reaction, reductive amination, nucleophilic addition reaction by a carbo anion, Grignard reagent and deoxofluorination reaction singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form can be isolated according to a conventional optical resolution.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

When compound (I) contains a configurational isomer, a diastereomer, a conformer and the like, each can be isolated according to the above-mentioned separation and purification methods, if desired. In addition, when compound (I) is racemic, S-form and R-form can be isolated according to a conventional optical resolution.

When compound (I) contains a stereoisomer, each isomer and a mixture thereof are encompassed in the present invention.

Compound (I) may be a prodrug. A prodrug of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

Compound (I) or a prodrug thereof (to be abbreviated as the compound of the present invention) is superior in vivo kinetics (e.g., plasma drug half-life, intracerebral transferability, metabolic stability), shows low toxicity (e.g., more superior as a medicament in terms of acute toxicity, chronic toxicity, genetic toxicity, reproductive toxicity, cardiotoxicity, drug interaction, carcinogenicity etc.). The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

Since the compound of the present invention has a superior CaMKII inhibitory action, it is expected to be useful for the prophylaxis or treatment of, for example, cardiac diseases (cardiac hypertrophy, acute heart failure and chronic heart failure including congestive heart failure, cardiomyopathy, angina, myocarditis, atrial/ventricular arrhythmia, tachycardia, myocardial infarction, etc.), myocardial ischemia, venous insufficiency, post-myocardial infarction transition to heart failure, hypertension, cor pulmonale, arteriosclerosis including atherosclerosis (aneurysm, coronary arterial sclerosis, cerebral arterial sclerosis, peripheral arterial sclerosis, etc.), vascular thickening, vascular thickening/occlusion and organ damages after intervention (percutaneous coronary angioplasty, stent placement, coronary angioscopy, intravascular ultrasound, coronary thrombolytic therapy, etc.), vascular reocclusion/restenosis after bypass surgery, cardiac hypofunction after artificial heart lung surgery, respiratory diseases (cold syndrome, pneumonia, asthma, pulmonary hypertension, pulmonary thrombus/pulmonary embolism, etc.), bone disorders (nonmetabolic bone disorders such as bone fracture, refracture, bone malformation/spondylosis deformans, osteosarcoma, myeloma, dysostosis and scoliosis, bone defect, osteoporosis, osteomalacia, rickets, osteitis fibrosis, renal osteodystrophy, Paget's disease of bone, myelitis with rigidity, chronic rheumatoid arthritis, gonarthrosis and articular tissue destruction in similar disorders thereof, etc.), inflammatory diseases (diabetic complication such as retinopathy, nephropathy, nerve damage, macroangiopathy etc.; arthritis such as chronic rheumatoid arthritis, osteoarthritis, rheumatoid myelitis, periostitis etc.; inflammation after surgery/trauma; reduction of swelling; pharyngitis; cystitis; pneumonia; atopic dermatitis; inflammatory enteric diseases such as Crohn's disease, ulcerative colitis etc.; meningitis; inflammatory eye diseases; inflammatory pulmonary diseases such as pneumonia, silicosis, pulmonary sarcoidosis, pulmonary tuberculosis etc, and the like), allergic diseases (allergic rhinitis, conjunctivitis, gastrointestinal allergy, pollen allergy, anaphylaxis, etc.), drug dependence, neurodegenerative diseases (Alzheimer's disease, Parkinson's disease, amyotrophic lateral sclerosis, AIDS encephalopathy, etc.), central nervous system damage (disorders such as cerebral hemorrhage and cerebral infarction and aftereffects and complications thereof, head injury, spinal damage, cerebral edema, sensory dysfunction, sensory abnormality, autonomic dysfunction, abnormal autonomic function, multiple sclerosis etc.), dementia, disturbed memory, disturbed consciousness, amnesia, anxiety symptoms, nervous symptoms, unpleasant condition, mental disorders (depression, epilepsy, alcohol dependency, etc.), ischemic peripheral circulatory disorder, deep-vein thrombosis, occlusive peripheral circulatory disorder, arteriosclerosis obliterans (ASO), occlusive thromboangiitis, diabetes (type 1 diabetes, type 2 diabetes, pregnancy diabetes etc.), diabetic complications (nerve damage, nephropathy, retinopathy, cataract, macroangiopathy, osteopenia, diabetic hyperosmolar diabetic coma, infectious diseases, diabetic gangrene, xerostomia, deterioration in hearing, cerebrovascular damage, peripheral circulatory disorder, etc.), urinary incontinence, metabolic/nutritional disorders (obesity, hyperlipidemia, hypercholesterolemia, diabetes, impaired glucose tolerance, hyperuricemia, hyperkalemia, hypernatremia etc.), metabolic syndrome, vesceral obesity syndrome, male or female sexual dysfunction and the like, and for the prophylaxis or treatment of dysgeusia, smell disturbance, abnormal circadian rhythm of blood pressure, cerebrovascular damage (asymptomatic cerebrovascular damage, transient cerebral ischemia attack, stroke, cerebrovascular dementia, hypertensive encephalopathy, cerebral infarction, etc.), cerebral edema, cerebral circulatory disturbance, recurrence and aftereffects of cerebrovascular damages (neurological symptoms, mental symptoms, subjective symptoms, impairment of activities of daily living, etc.), kidney diseases (nephritis, glomerulonephritis, glomerulosclerosis, renal failure, thrombotic microangiopathy, diabetic nephropathy, nephrotic syndrome, hypertensive nephrosclerosis, complications of dialysis, organ damage including nephropathy by irradiation, etc.), erythrocytosis/hypertension/organ damage/vascular thickening after transplantation, rejection after transplantation, ocular disorders (glaucoma, ocular hypertension, etc.), thrombosis, multiple organ failure, endothelial dysfunction, hypertensive tinnitus, other circulatory diseases (ischemic cerebral circulatory disturbance, Raynaud's disease, Buerger's disease, etc.), chronic occlusive pulmonary diseases, interstitial pneumonia, carinii pneumonia, connective tissue disorders (e.g., systemic erythematosus, scleroderma, polyarteritis, etc.), liver disorders (hepatitis and cirrhosis including chronic types, etc.), portal hypertension, digestive disorders (gastritis, gastric ulcer, gastric cancer, disorder after gastric surgery, poor digestion, esophageal ulcer, pancreatitis, colon polyp, cholelithiasis, hemorrhoidal problem, esophageal and gastric variceal rupture, etc.), hematological/hematopoietic disorders (erythrocytosis, vascular purpura, autoimmune hemolytic anemia, disseminated intravascular coagulation syndrome, multiple myelosis, etc.), solid tumor, tumors (malignant melanoma, malignant lymphoma, digestive organs (e.g., stomach, intestine, etc.) cancers, etc.), cancers and cachexia associated therewith, cancer metastases, endocrine disorders (Addison's disease, Cushing's syndrome, pheochromocytoma, primary aldosteronism, etc.), Creutzfeldt-Jakob disease, urological/male genital diseases (cystitis, prostatic enlargement, prostate cancer, sexually transmitted diseases, etc.), gynecological disorders (menopausal disorders, pregnancy toxemia, endometriosis, uterine fibroid, ovarian diseases, mammary gland diseases, sexually transmitted diseases, etc.), diseases caused by environmental/occupational factor (e.g., radiation damage, damage from ultraviolet/infrared/laser beam, altitude sickness etc.), infectious diseases (viral infectious diseases of, for example, cytomegalovirus, influenza virus and herpesvirus, rickettsial infectious diseases, bacterial infectious diseases, etc.), toxemia (septicemia, septic shock, endotoxic shock, gram-negative septicemia, toxin shock syndrome, etc.), ear nose throat diseases (Meniere's disease, tinnitus, dysgeusia, vertigo, balance disorder, deglutition disorder etc.), cutaneous diseases (keloid, hemangioma, psoriasis, etc.), dialysis hypotension, myasthenia gravis, systemic diseases such as chronic fatigue syndrome, and the like, particularly cardiac diseases (particularly catecholaminergic polymorphic ventricular tachycardia, postoperative atrial fibrillation, heart failure, fatal arrhythmia) and the like, in animals, particularly mammals (e.g., humans, monkeys, cats, pigs, horses, bovines, mice, rats, guinea pigs, dogs, rabbits etc.).

Herein, the concept of prophylaxis of cardiac diseases include treatment of prognosis of myocardial infarction, angina attack, cardiac bypass surgery, thrombolytic therapy, coronary revascularization and the like, and the concept of treatment of cardiac diseases include suppress of progress or severity of heart failure (including both contractile failure HFrEF, and heart failure HFpEF with maintained ejection fraction), and maintenance of cardiac function when performing non-drug therapies (e.g., an implantable defibrillator, resection of cardiac sympathetic nerve, catheter ablation, cardiac pacemaker, intra aortic balloon pumping, auxiliary artificial heart, Batista operation, cell transplantation, gene therapy, heart transplantation and the like) for severe heart failure/arrhythmia, and the like. When the compound of the present invention is applied to prophylaxis or treatment of heart failure, improvement of heart contractility or atonicity is expected to be achieved by short-time administration, without side effects such as pressure decrease, tachycardia, reduced renal blood flow and the like, regardless of differences in causative diseases such as ischemic cardiac disease, cardiomyopathy, hypertension and the like and symptoms such as contractile failure, diastolic failure and the like. Moreover, long-term improvement of prognosis (survival rate, readmission rate, cardiac event rate etc.) is expected to be achieved, in addition to short-term improvement of cardiac function. When the compound of the present invention is applied to prophylaxis or treatment of arrhythmia, improvement or remission of the symptom is expected to be achieved, regardless of differences in etiology and atrial/ventricular. In addition, long-term improvement of prognosis (survival rate, readmission rate, cardiac event rate etc.) is expected to be achieved.

While the dose of the compound of the present invention varies depending on the administration route, symptom and the like, when, for example, the compound is orally administered to a patient with cardiac disease (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like. Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

When the compound of the present invention is applied to each of the above-mentioned diseases, it can be used in appropriate combination with a pharmaceutical agent (hereinafter to be abbreviated as a concomitant drug) or a treatment method generally employed for such diseases. For heart failure, for example, it can be used concurrently with angiotensin converting enzyme (ACE) inhibitors (e.g., alacepril, captopril, cilazapril, delapril, enalapril, lisinopril, temocapril, trandolapril, quinapril, imidapril, benazepril, perendopril and the like), angiotensin II receptor antagonists (e.g., losartan, candesartan cillexetil, valsartan, termisartan, irbesartan, forasartan and the like), angiotensin II receptor antagonist/NEP inhibitor combination agent (entresto), β receptor antagonists (e.g., propranolol, nadolol, timolol, nipradilol, bunitorolol, indenolol, penbutolol, carteolol, carvedilol, pindolol, acebutolol, atenolol, bisoprolol, metoprolol, labetalol, amosulalol, arotinolol and the like), Ca antagonists (e.g., manidipine, nicardipine, nilvadipine, nisoldipine, nitrendipine, benidipine, amlodipine, aranidipine and the like), diuretics (e.g., thiazide diuretics such as benzylhydrochlorothiazide, cyclopentiazide, ethiazide, hydrochlorothiazide, hydroflumethiazide, methyclothiazide, penfluthiazide, polythiazide, trichlormethiazide and the like; loop diuretics such as chlorthalidone, clofenamide, indapamide, mefruside, meticrane, sotolazone, tribamide, quinetazone, metolazone, furosemide, mefruside and the like; potassium retention diuretics such as spironolactone, triamterene and the like; and the like), *digitalis* preparations (e.g., digitoxin, digoxin, methyldigoxin, lanatoside C, proscillaridin and the like), ANP or BNP preparations, Ca sensitizers (e.g., pimobendan and the like), anticoagulants (e.g., warfarin, sodium citrate, activated protein C, tissue factor pathway inhibitor, antithrombin III, dalteparin sodium, aragatroban, gabexate, sodium ozagrel, ethyl icosapentate, beraprost sodium, alprostadil, pentoxifyline, tisokinase, streptokinase and the like), antiarrhythmic drugs (e.g., sodium channel blockers such as quinidine, procainamide, disopyramide, ajmaline, cibenzoline, lidocain, diphenylhydantoin, mexiletine, propafenone, flecainide, pilsicainide, phenytoin and the like; potassium channel blockers such as amiodarone and the like; calcium channel blockers such as verapamil, diltiazem and the like; and the like), PDE inhibitors (e.g., amrinone, milrinone, olprinone hydrochloride and the like), therapeutic drugs for diabetes (e.g., sulfonylureas such as tolbutamide, chlorpropamide, glyclopyramide, acetohexamide, tolazamide, glibenclamide, glybuzole and the like; biguanides such as metformin hydrochloride, buformin hydrochloride and the like; a-glucosidase inhibitors such as voglibose, acarbose and the like, insulin sensitizers such as pioglitazone, troglitazone and the like; SGLT2 inhibitors such as ipragliflozin, dapagliflozin, ruseogurifurojin, tofogliflozin, canagliflozin, empagliflozin and the like; insulin, glucagon; therapeutic drugs for diabetic complications such as epalrestat and the like; and the like), anti-obesity drugs and the like, and is also applicable when an implantable artificial heart, an implantable defibrillator, a ventricular pacing, Batista operation, heart transplantation or cell transplantation is performed. In addition, for arrhythmia, for example, it can be used concurrently with other antiarrhythmic drugs (e.g., sodium channel blockers such as flecainide, quinidine, procainamide, disopyramide, ajmaline, cibenzoline, lidocain, diphenylhydantoin, mexiletine, propafenone, pilsicainide, phenytoin and the like; potassium channel blockers such as amiodarone and the like; calcium channel blockers such as verapamil, diltiazem and the like, and the like) and β receptor antagonists, non-drug therapies (e.g., an implantable defibrillator, resection of cardiac sympathetic nerve, catheter ablation, cardiac pacemaker and the like). In addition, after acute myocardial infarction or during myocardial infarction prognosis, for example, the compound can be used in combination with antithrombotics (e.g., anticoagulants such as heparin sodium, heparin calcium, warfarin and the like; thrombolytic agents such as urokinase and the like; anti-platelet drugs such as aspirin, sulfinpyrazone (anturan), dipyridamole (persantin), ticropidine (panaldine), cilostazol (pletal), clopidogrel and the like; and the like), angiotensin converting enzyme inhibitors, angiotensin II receptor antagonists, β receptor antagonists, therapeutic drugs for diabetes, therapeutic drugs for hyperlipidemia (e.g., HMG-CoA reductase inhibitors such as pravastatine, fluvastatine, cerivastatine, atorvastatine and the like; fibrate drugs such as sinfibrate, clofibrate aluminum, clinofibrate, fenofibrate and the like; and the like), coronary vessel reconstructive surgery such as PTCA, CABG and the like; and the like. Furthermore, in chronic rheumatoid arthritis, for example, the compound can be used in combination with non-steroidal antiinflammatory agents (e.g., acetaminophen, phenacetin, ethenzamide, sulpyrine, antipyrine, migrenine, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesilate, ulinastatine, colchicine, probenecid, sulfinpyrazone, benzbromarone, allopurinol, sodium aurothiomalate, sodium hyaluronate, sodium salicylate, morphine hydrochloride, salicylic acid, atropine, scopolamine, morphine, pethidine, levorphanol, ketoprofen, naproxen, oxymorphone or a salt thereof and the like), immunomodulators or immunosuppressants (e.g., methotrexate, cyclosporine, tacrolimus, gusperimus, azathioprine, antilymphocyte serum, dried sulfonated immunoglobulin, erythropoietin, colony stimulating factor, interleukin, interferon and the like), steroids (e.g., dexamethasone, hexestrol, methimazole, betamethasone, triamcinolone, triamcinoloneacetonide, fluocinonide, fluocinoloneacetonide, prednisolone, methylprednisolone, cortisone acetate, hydrocortisone, fluorometholone, beclometasone dipropionate, estriol and the like), p38 MAP kinase inhibitors, anti-TNF-α drugs (e.g., etanercept, infliximab, D2E7, CDP-571, PASS TNF-α, soluble TNF-α receptor, TNF-α binding protein, anti-TNF-α antibody and the like), cyclooxygenase inhibitors (e.g., salicylic acid derivatives such as celecoxib, rofecoxib, aspirin and the like, MK-663, valdecoxib, SC-57666, tiracoxib, S—2474, diclofenac, indomethacin, loxoprofen and the like) and the like.

Moreover, it is possible to use the compound of the present invention in combination with biological products (e.g.: antibody, vaccine preparation and the like) when applying to the above-mentioned respective diseases, and it is also possible to apply the compound in combination with a gene therapy and the like as a combination therapy. As antibody and vaccine preparation, for example, vaccine preparation to angiotensin II, vaccine preparation to CETP, CETP antibody, TNF α antibody, antibody to other cytokine, amiloid β vaccine preparation, type 1 diabetes vaccine (DIAPEP-277 of Peptor Ltd. and the like), anti-HIV antibody, HIV vaccine preparation and the like, antibody and vaccine preparation to cytokine, renin-angiotensin enzyme and products thereof, antibody and vaccine preparation to enzyme and protein involved in blood lipid metabolism, antibody and vaccine preparation to enzyme and protein involved in blood coagulation-fibrinolytic system, antibody and vaccine preparation to protein involved in glucose metabolism and insulin resistance and the like can be mentioned. In addition, a combined use with biological products involved in growth factors such as GH, IGF and the like is possible. As a gene therapy, for example, a treatment method using a gene relating to cytokine, renin-angiotensin enzyme and products thereof, G protein, G protein-coupled receptor and phosphorylation enzyme thereof, a therapeutic method using a DNA decoy such as NFκB decoy and the like, a therapeutic method using antisense, a therapeutic method using a gene relating to enzyme and protein involved in blood lipid metabolism (e.g., gene relating to metabolism, excretion and absorption of cholesterol or triglyceride or HDL-cholesterol or blood phospholipid, and the like), a therapeutic method using a gene relating to enzyme and protein (e.g., growth factors such as HGF, VEGF and the like, and the like) involved in angiogenetic therapy aiming at obstruction of peripheral vessel and the like, a therapeutic method using a gene relating protein involved in glucose metabolism and insulin resistance, antisense to cytokine such as TNF-α and the like, and the like can be mentioned. In addition, it is possible to use the compound in combination with various organ regeneration methods such as heart regeneration, kidney regeneration, pancreas regeneration, blood vessel regeneration and the like, cell transplantation therapy using bone marrow cells (bone marrow mononuclear cell, bone marrow mesenchymal stem cell and the like), and artificial organs (artificial blood vessels and cardiac muscle cell sheet) using tissue engineering.

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like. The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination agent of the present invention exhibits low toxicity. For example, the compound of the present invention or (and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent of the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, an appropriate amount of conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

Unless particularly specified, the elution in column chromatography in Example was performed under observation by TLC (Thin Layer Chromatography). For TLC observation, 60F254 manufactured by Merck was used as a TLC plate, and the solvent used as an elution solvent for column chromatography was used as a developing solvent. For detection, a UV detector was adopted. In silica gel column chromatography, NH means use of aminopropylsilane-bonded silica gel, and Diol means use of 3-(2,3-dihydroxypropoxy)propylsilane-bonded silica gel. In preparative HPLC (high performance liquid chromatography), C18 means use of octadecyl-bonded silica gel. The ratios indicated for elution solvents are volume mixing ratios, unless otherwise specified.

For $^1$H NMR analysis, ACD/SpecManager (trade name) software and the like were used. Peaks with very mild protons such as a hydroxy group, an amino group and the like may not be described.

MS was measured by LC/MS. As ionization method, ESI method or APCI method was used. The data indicates actual measured value (found). Generally, molecular ion peaks are observed, and may be observed as a fragment ion. In the case of a salt, a molecular ion peak or fragment ion peak of free form is generally observed.

The unit of sample concentration (c) for optical rotation ($[\alpha]_D$) is g/100 mL.

Elemental analysis value (Anal.) was described as calculated value (Calcd) and actual measured value (Found).

The peak by powder X-RAY diffraction in Example means the peak measured using Cu Kα-ray as a source by Ultima IV (Rigaku Corporation, Japan) at room temperature. The measurement conditions are as follows.

Electric pressure/Electric current: 40 kV/50 mA Scan speed: 6 degree/min

Scan range of 2 Theta: 2-35 degree

The crystallinity by powder X-RAY diffraction in Example was calculated by Hermans method.

In Examples, the following abbreviations are used.

mp: melting point
MS: mass spectrum
M: mol concentration
N: normality
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: electrospray ionization, Electron Spray Ionization
APCI: atmospheric pressure chemical ionization, atmospheric pressure chemical ionization
Boc: tert-butoxycarbonyl
AcOH: acetic acid
DME: 1,2-dimethoxyethane
TFA: trifluoroacetic acid
DMSO: dimethyl sulfoxide
Pd(PPh$_3$)$_4$: tetrakis(triphenylphosphine)palladium(0)
MeOH: methanol
EtOH: ethanol
n-BuOH: normal butanol
THF: tetrahydrofuran DMF: N,N-dimethylformamide
CH₃CN: acetonitrile Example 1

4-(2-((2-methoxy-4-(4-(morpholin-4-yl)piperidin-1-yl)phenyl)amino)pyrimidin-5-yl)-2-(((2S)-1-(1H-1,2,4-triazol-1-yl)propan-2-yl)oxy)benzonitrile A) 4-bromo-2-(((2S)-1-(1H-1,2,4-triazol-1-yl)propan-2-yl)oxy)benzonitrile To a mixture of (2S)-1-(1H-1,2,4-triazol-1-yl)propan-2-ol (6.79 g) and DMF (120 ml) was added 60% sodium hydride (2.56 g) at 0° C. The mixture was stirred at 0° C. for 15 min, 4-bromo-2-fluorobenzonitrile (11.75 g) was added to the mixture, and the mixture was stirred at room temperature for 2 days. To the mixture was added water at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane). After a mixture of the solid and diisopropyl ether was stirred at room temperature for 1 hr, the precipitated solid was collected by filtration to give the title compound (9.60 g).
$^1$H NMR (300 MHz, DMSO-$d_6$) δ1.32 (3H, d, J=6.1 Hz), 4.52 (2H, d, J=5.6 Hz), 5.05-5.19 (1H, m), 7.28 (1H, dd, J=8.3, 1.7 Hz), 7.45 (1H, d, J=1.5 Hz), 7.64 (1H, d, J=8.2 Hz), 7.95 (1H, s), 8.46 (1H, s); MS m/z 306.9 [M+H]⁺.

B) 4-(4,4,5,5-tetramethyl-1,3,2-dioxaborolan-2-yl)-2-(((2S)-1-(1H-1,2,4-triazol-1-yl)propan-2-yl)oxy)benzonitrile To a mixture of 4-bromo-2-(((2S)-1-(1H-1,2,4-triazol-1-yl)propan-2-yl)oxy)benzonitrile (5.69 g) and DMSO (60 mL) were added 4,4,4',4',5,5,5',5'-octamethyl-2,2'-bi-1,3,2-dioxaborolane (7.06 g), potassium acetate (4.55 g) and dichloro[1,1'-bis(diphenylphosphino)ferrocene]palladium (II) dichloromethane adduct (0.756 g) at room temperature. The mixture was stirred at 100° C. overnight under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure to give the title compound. The obtained title compound was directly used in the next reaction.
MS m/z 355.4 [M+H]⁺.

C) 4-(1-(3-methoxy-4-nitrophenyl)piperidin-4-yl)morpholine

To a mixture of 4-fluoro-2-methoxy-1-nitrobenzene (21.22 g) and DMF (250 mL) were added 4-(piperidin-4-yl)morpholine (21.11 g) and potassium carbonate (42.8 g) at room temperature. The mixture was stirred at 60° C. overnight, and then water (750 mL) was added dropwise to the mixture at 0° C. The resulting precipitate was collected by filtration, and washed with water to give the title compound (34.38 g).
$^1$H NMR (300 MHz, DMSO-$d_6$) δ1.32-1.52 (2H, m), 1.86 (2H, d, J=10.7 Hz), 2.34-2.58 (5H, m), 2.87-3.05 (2H, m), 3.47-3.65 (4H, m), 3.90 (3H, s), 4.04 (2H, d, J=13.2 Hz), 6.50 (1H, d, J=2.5 Hz), 6.59 (1H, dd, J=9.4, 2.6 Hz), 7.87 (1H, d, J=9.4 Hz); MS m/z 322.3 [M+H]⁺.

D) 2-methoxy-4-(4-(morpholin-4-yl)piperidin-1-yl)aniline

A mixture of 4-(1-(3-methoxy-4-nitrophenyl)piperidin-4-yl)morpholine (27.75 g), 10% palladium-carbon (3.10 g) and MeOH (200 mL)/THF (200 mL) was stirred at room temperature overnight under normal pressure of hydrogen atmosphere. The catalyst was removed by filtration, and the filtrate was concentrated under reduced pressure. The obtained solid was washed with ethanol/hexane to give the title compound (21.01 g).
$^1$H NMR (300 MHz, DMSO-$d_6$) δ1.49 (2H, qd, J=11.8, 3.6 Hz), 1.83 (2H, d, J=12.1 Hz), 2.09-2.26 (1H, m), 2.41-2.56 (6H, m), 3.42 (2H, d, J=12.2 Hz), 3.52-3.62 (4H, m), 3.73 (3H, s), 4.19 (2H, s), 6.29 (1H, dd, J=8.3, 2.4 Hz), 6.44-6.54 (2H, m).

E) 5-bromo-N-(2-methoxy-4-(4-(morpholin-4-yl)piperidin-1-yl)phenyl)pyrimidin-2-amine To a mixture of 2-methoxy-4-(4-(morpholin-4-yl)piperidin-1-yl)aniline (30.98 g) and n-BuOH (350 mL) were added 5-bromo-2-chloropyrimidine (22.62 g) and trifluoroacetic acid (36.4 g) at room temperature. The mixture was stirred at 120° C. overnight under nitrogen atmosphere, and concentrated under reduced pressure. To the obtained residue were added water (280 mL) and ethyl acetate (700 mL), and the mixture was neutralized with 2N aqueous sodium hydroxide solution. The obtained precipitate was collected by filtration, and washed with water and ethyl acetate to give the title compound (32.94 g).
$^1$H NMR (300 MHz, DMSO-$d_6$) δ1.39-1.59 (2H, m), 1.86 (2H, d, J=11.9 Hz), 2.16-2.34 (1H, m), 2.50 (4H, brs), 2.65 (2H, t, J=11.7 Hz), 3.58 (4H, brs), 3.64-3.83 (5H, m), 6.47 (1H, d, J=8.5 Hz), 6.60 (1H, s), 7.39 (1H, d, J=8.6 Hz), 8.36 (1H, s), 8.42 (2H, s).

F) 4-(2-((2-methoxy-4-(4-(morpholin-4-yl)piperidin-1-yl)phenyl)amino)pyrimidin-5-yl)-2-(((2S)-1-(1H-1,2,4-triazol-1-yl)propan-2-yl)oxy)benzonitrile To a mixture of 4-(4,4,5,5-tetramethyl-1,3,2-dioxaborolan-2-yl)-2-(((2S)-1-(1H-1,2,4-triazol-1-yl)propan-2-yl)oxy)benzonitrile (6.56 g) and THF (80 mL)/water (16.00 mL) were added 5-bromo-N-(2-methoxy-4-(4-(morpholin-4-yl)piperidin-1-yl)phenyl)pyrimidin-2-amine (6.92 g), bis(tri-tert-butylphosphine)palladium (0) (0.789 g) and cesium carbonate (15.09 g) at room temperature, and the mixture was stirred at 70° C. for 3 hr under nitrogen atmosphere. To the mixture were added water and ethyl acetate at room temperature, the impurity was removed by filtration, and the filtrate was extracted with ethyl acetate. The organic layer was separated, and dried over anhydrous magnesium sulfate. The mixture was purified by silica gel column chromatography (NH, ethyl acetate). A mixture of the obtained solid and 4M hydrogen chloride-ethyl acetate solution (20 mL) was stirred at room temperature and then concentrated under reduced pressure. 2N Aqueous sodium hydroxide solution (25 mL) was added to a mixture of the obtained residue (7.78 g) and water (100 mL) at room temperature. The mixture was stirred at room temperature for 30 min. Then, the obtained solid was collected by filtration, washed with water, ethanol/water (1:1) and diisopropyl ether to give the title compound (6.13 g).

¹H NMR (300 MHz, DMSO-d₆) δ1.35 (3H, d, J=6.1 Hz), 1.50 (2H, qd, J=11.9, 3.7 Hz), 1.87 (2H, d, J=11.3 Hz), 2.20-2.33 (1H, m), 2.41-2.55 (4H, m), 2.66 (2H, t, J=11.2 Hz), 3.51-3.62 (4H, m), 3.71 (2H, d, J=12.5 Hz), 3.79 (3H, s), 4.55 (2H, d, J=5.4 Hz), 5.24 (1H, sxt, J=5.8 Hz), 6.50 (1H, dd, J=8.8, 2.4 Hz), 6.63 (1H, d, J=2.3 Hz), 7.32-7.47 (2H, m), 7.59 (1H, d, J=8.7 Hz), 7.73 (1H, d, J=8.1 Hz), 7.94 (1H, s), 8.40 (1H, s), 8.49 (1H, s), 8.78 (2H, s).

Example 8

4-(2-((2-methoxy-4-(4-(morpholin-4-yl)piperidin-1-yl)phenyl)amino)pyrimidin-5-yl)-2-(((2S)-1-(1H-1,2,4-triazol-1-yl)propan-2-yl)oxy)benzonitrile hydrochloride To a mixture of 4-(2-((2-methoxy-4-(4-(morpholin-4-yl)piperidin-1-yl)phenyl)amino)pyrimidin-5-yl)-2-(((2S)-1-(1H-1,2,4-triazol-1-yl)propan-2-yl)oxy)benzonitrile (5.91 g) and MeOH (100 mL) was added 4M hydrogen chloride-ethyl acetate solution (2.73 mL) at room temperature. The mixture was stirred at room temperature for 1 hr, and concentrated under reduced pressure. The obtained solid was crystallized from ethanol/water to give the title compound (4.74 g).
¹H NMR (300 MHz, DMSO-d₆) δ1.35 (3H, d, J=6.1 Hz), 1.76 (2H, d, J=8.7 Hz), 2.16 (2H, d, J=10.2 Hz), 2.70 (2H, t, J=11.8 Hz), 2.99-3.20 (2H, m), 3.32 (1H, s), 3.48 (2H, d, J=11.6 Hz), 3.68-3.93 (7H, m), 4.01 (2H, d, J=11.2 Hz), 4.56 (2H, d, J=5.6 Hz), 5.15-5.34 (1H, m), 6.50-6.59 (1H, m), 6.68 (1H, s), 7.34-7.46 (2H, m), 7.61 (1H, d, J=8.7 Hz), 7.74 (1H, d, J=8.1 Hz), 7.94 (1H, s), 8.44 (1H, s), 8.50 (1H, s), 8.78 (2H, s), 10.31 (1H, brs).

Example 9

4-(2-((2-methoxy-4-(4-(morpholin-4-yl)piperidin-1-yl)phenyl)amino)pyrimidin-5-yl)-2-(((2S)-1-(1H-tetrazol-1-yl)propan-2-yl)oxy)benzonitrile A) methyl (2S)-2-(5-bromo-2-cyanophenoxy)propanoate To a mixture of 4-bromo-2-hydroxybenzonitrile (14.5 g), methyl (2R)-2-hydroxypropanoate (15.25 g), triphenylphosphine (57.6 g) and THF (dry) (150 mL) was added 2.2M diethyl (E)-diazene-1,2-dicarboxylate-toluene (116 mL) at 0° C. The mixture was stirred at room temperature overnight under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (20 g).
¹H NMR (300 MHz, DMSO-d₆) δ1.57 (3H, d, J=6.8 Hz), 3.71 (3H, s), 5.40 (1H, q, J=6.8 Hz), 7.35 (1H, dd, J=8.3, 1.7 Hz), 7.47 (1H, d, J=1.6 Hz), 7.72 (1H, d, J=8.3 Hz).

B) 4-bromo-2-(((2S)-1-hydroxypropan-2-yl)oxy)benzonitrile

To a mixture of methyl (2S)-2-(5-bromo-2-cyanophenoxy)propanoate (20 g) and THF (dry) (100 mL)/MeOH (170 mL) was added sodium tetrahydroborate (2.66 g) at 0° C., and the mixture was stirred at room temperature under nitrogen atmosphere. After have been stirred for 3 hr, additional sodium tetrahydroborate (2.13 g) was added to the mixture at 0° C. and the mixture was stirred at room temperature overnight. To the mixture was added saturated aqueous ammonium chloride solution at 0° C., and the mixture was concentrated under reduced pressure, and extracted with ethyl acetate. The organic layer was separated, washed with water and saturated brine, dried over anhydrous magnesium sulfate, and concentrated under reduced pressure to give the title compound (18 g). This product was subjected to the next reaction without further purification.
¹H NMR (300 MHz, DMSO-d₆) δ1.23 (3H, d, J=6.1 Hz), 3.50-3.57 (2H, m), 4.71 (1H, sxt, J=5.7 Hz), 4.97 (1H, t, J=5.5 Hz), 7.28 (1H, dd, J=8.3, 1.7 Hz), 7.60 (1H, d, J=1.7 Hz), 7.66 (1H, d, J=8.3 Hz).

C) (2S)-2-(5-bromo-2-cyanophenoxy)propyl methanesulfonate

To a mixture of 4-bromo-2-(((2S)-1-hydroxypropan-2-yl)oxy)benzonitrile (32.6 g), triethylamine (25.8 g) and THF (dry) (300 mL) was added methanesulfonyl chloride (20.41 g) at 0° C. The mixture was stirred at room temperature for 2 hr under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate) to give the title compound (42.5 g).
¹H NMR (300 MHz, DMSO-d₆) δ1.33 (3H, d, J=6.2 Hz), 3.21-3.25 (3H, m), 4.31-4.40 (1H, m), 4.42-4.49 (1H, m), 5.07 (1H, quind, J=6.2, 3.0 Hz), 7.34 (1H, dd, J=8.3, 1.7 Hz), 7.66 (1H, d, J=1.6 Hz), 7.71 (1H, d, J=8.3 Hz); MS m/z 334.1 [M+H]⁺.

D) 4-bromo-2-(((2S)-1-(1H-tetrazol-1-yl)propan-2-yl)oxy)benzonitrile

To a mixture of (2S)-2-(5-bromo-2-cyanophenoxy)propyl methanesulfonate (25 g), 1H-tetrazole (10.48 g) and DMF (dry) (100 mL) was added potassium carbonate (20.68 g) at room temperature, and the mixture was stirred at 80° C. overnight. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (10.25 g).
¹H NMR (300 MHz, CDCl₃) δ1.44-1.51 (3H, m), 4.64-4.77 (1H, m), 4.79-4.89 (2H, m), 7.01 (1H, d, J=1.6 Hz), 7.21 (1H, dd, J=8.3, 1.7 Hz), 7.42 (1H, d, J=8.2 Hz), 8.88-9.02 (1H, m); MS m/z 308.2 [M+H]⁺.

E) 4-(4,4,5,5-tetramethyl-1,3,2-dioxaborolan-2-yl)-2-(((2S)-1-(1H-tetrazol-1-yl)propan-2-yl)oxy)benzonitrile To a mixture of 4-bromo-2-(((2S)-1-(1H-tetrazol-1-yl)propan-2-yl)oxy)benzonitrile (6.3 g) and DMSO (120 mL) were added 4,4,4',4',5,5,5',5'-octamethyl-2,2'-bi-1,3,2-dioxaborolane (7.79 g) and dichloro[1,1'-bis(diphenylphosphino)ferrocene]palladium(II) dichloromethane adduct (1.670 g) at room temperature, and the mixture was stirred at 100° C. for 3 hr under nitrogen atmosphere. To the reaction solution was added water at room temperature, and the insoluble substance was removed by filtration. The filtrate was partitioned with ethyl acetate-water, and the organic layer was washed with water and saturated brine, dried over anhydrous magnesium sulfate, and concentrated under reduced pressure to give the title compound. The obtained title compound was used in the next reaction without purification.

MS m/z 356.3 [M+H]$^+$.

F) 4-(2-((2-methoxy-4-(4-(morpholin-4-yl)piperidin-1-yl)phenyl)amino)pyrimidin-5-yl)-2-(((2S)-1-(1H-tetrazol-1-yl)propan-2-yl)oxy)benzonitrile To a mixture of 4-(4,4,5,5-tetramethyl-1,3,2-dioxaborolan-2-yl)-2-(((2S)-1-(1H-tetrazol-1-yl)propan-2-yl)oxy)benzonitrile (4.66 g) and THF (40 mL)-water (4 mL) were added 5-bromo-N-(2-methoxy-4-(4-(morpholin-4-yl)piperidin-1-yl)phenyl)pyrimidin-2-amine (3.92 g), bis(tri-tert-butylphosphine)palladium (0) (0.447 g) and cesium carbonate (8.55 g) at room temperature, and the mixture was stirred at 70° C. for 2 hr under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (NH, MeOH/ethyl acetate) to give the title compound (2 g).

$^1$H NMR (300 MHz, DMSO-d$_6$) δ1.35 (3H, d, J=6.2 Hz), 1.51 (2H, d, J=9.4 Hz), 1.87 (2H, d, J=9.9 Hz), 2.62-2.76 (2H, m), 3.25-3.33 (5H, m), 3.54-3.61 (4H, m), 3.71 (2H, d, J=13.3 Hz), 3.79 (3H, s), 4.79-4.99 (2H, m), 5.30-5.40 (1H, m), 6.47-6.55 (1H, m), 6.63 (1H, s), 7.41 (1H, d, J=7.0 Hz), 7.47 (1H, s), 7.58 (1H, d, J=8.8 Hz), 7.75 (1H, d, J=8.1 Hz), 8.42 (1H, s), 8.80 (2H, s), 9.35 (1H, s).

Example 10

4-(2-((2-methoxy-4-(4-(morpholin-4-yl)piperidin-1-yl)phenyl)amino)pyrimidin-5-yl)-2-(((2S)-1-(1H-tetrazol-1-yl)propan-2-yl)oxy)benzonitrile hydrochloride To a mixture of 4-(2-((2-methoxy-4-(4-(morpholin-4-yl)piperidin-1-yl)phenyl)amino)pyrimidin-5-yl)-2-(((2S)-1-(1H-tetrazol-1-yl)propan-2-yl)oxy)benzonitrile (5 g) and MeOH (50 mL) was added 4M hydrogen chloride-ethyl acetate solution (2.1 mL) at room temperature. The mixture was stirred at room temperature for 20 min, and the reaction solution was concentrated. The obtained solid was recrystallized from ethanol (50 mL)/water (12 mL) to give the title compound (3.8 g).

$^1$H NMR (300 MHz, DMSO-d$_6$) δ1.36 (3H, d, J=6.2 Hz), 1.90-2.16 (2H, m), 2.27 (2H, brs), 2.89-3.21 (4H, m), 3.47 (3H, d, J=11.5 Hz), 3.81-4.06 (9H, m), 4.74-4.98 (2H, m), 5.36 (1H, td, J=6.5, 3.5 Hz), 6.73-6.92 (1H, m), 6.93-7.09 (1H, m), 7.35-7.45 (1H, m), 7.49 (1H, s), 7.76 (2H, d, J=8.1 Hz), 8.57 (1H, s), 8.85 (2H, s), 9.37 (1H, s), 11.32-11.57 (1H, m).

Example 60

5-(4-chloro-3-(((2S)-1-(1H-tetrazol-1-yl)propan-2-yl)oxy)phenyl)-N-(2-methoxy-4-(4-(morpholin-4-yl)piperidin-1-yl)phenyl)pyrimidin-2-amine A) methyl (2S)-2-(5-bromo-2-chlorophenoxy)propanoate To a mixture of 5-bromo-2-chlorophenol (31 g), methyl (2R)-2-hydroxypropanoate (31.1 g), triphenylphosphine (118 g) and THF (dry) (250 mL) was added 2.2M diethyl (E)-diazene-1,2-dicarboxylate-toluene (238 mL) at 0° C., and the mixture was stirred at room temperature overnight under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure. To the obtained residue were added hexane and diisopropyl ether (1:1, 200 mL), the mixture was stirred at 0° C. for 20 min, and the reaction solution was concentrated. To the obtained solid were added diisopropyl ether and ethyl acetate (2:1, 400 mL) and the mixture was stirred at 0° C. for 30 min. The insoluble material was removed by filtration, and the filtrate was concentrated under reduced pressure. The residue was purified by silica gel column chromatography (ethyl acetate/hexane) to give the title compound (43.9 g).

$^1$H NMR (300 MHz, DMSO-d$_6$) δ1.54 (3H, d, J=6.7 Hz), 3.70 (3H, s), 5.24 (1H, q, J=6.8 Hz), 7.18 (1H, dd, J=8.4, 2.1 Hz), 7.26 (1H, d, J=2.1 Hz), 7.41 (1H, d, J=8.4 Hz).

B) (2S)-2-(5-bromo-2-chlorophenoxy)propan-1-ol

To a mixture of methyl (2S)-2-(5-bromo-2-chlorophenoxy)propanoate (43.9 g) and MeOH (204 mL)/THF (dry) (120 mL) was added sodium tetrahydroborate (5.66 g) at 0° C. The mixture was stirred at room temperature overnight. To the mixture was added saturated aqueous ammonium chloride solution at 0° C., and the mixture was concentrated under reduced pressure. The obtained residue was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (40.4 g).

$^1$H NMR (300 MHz, DMSO-d$_6$) δ1.22 (3H, d, J=6.2 Hz), 3.44-3.62 (2H, m), 4.47-4.62 (1H, m), 4.91 (1H, t, J=5.6 Hz), 7.12 (1H, dd, J=8.4, 2.2 Hz), 7.37 (1H, d, J=8.4 Hz), 7.43 (1H, d, J=2.2 Hz).

C) (2S)-2-(5-bromo-2-chlorophenoxy)propyl methanesulfonate

To a mixture of (2S)-2-(5-bromo-2-chlorophenoxy)propan-1-ol (40.4 g), triethylamine (30.8 g) and THF (dry) (200 mL) was added methanesulfonyl chloride (24.40 g) at 0° C. The mixture was stirred at room temperature for 1 hr under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate) to give the title compound (52 g).

$^1$H NMR (300 MHz, DMSO-d$_6$) δ1.30 (3H, d, J=6.2 Hz), 3.21 (3H, s), 4.27-4.37 (1H, m), 4.37-4.46 (1H, m), 4.85-5.02 (1H, m), 7.18 (1H, d, J=8.4 Hz), 7.40 (1H, d, J=8.4 Hz), 7.49 (1H, s).

D) 1-((2S)-2-(5-bromo-2-chlorophenoxy)propyl)-1H-tetrazole

To a mixture of (2S)-2-(5-bromo-2-chlorophenoxy)propyl methanesulfonate (52 g), potassium carbonate (41.8 g) and DMF (dry) (100 mL) was added 1H-tetrazole (21.20 g) at room temperature. The mixture was stirred at 80° C. overnight. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (26 g).
$^1$H NMR (300 MHz, CDCl$_3$) δ1.40 (3H, d, J=5.9 Hz), 4.64-4.87 (3H, m), 6.97 (1H, s), 7.09 (1H, d, J=8.5 Hz), 7.21-7.26 (1H, m), 8.92 (1H, s); MS m/z 317.0 [M+H]$^+$.

E) 1-((2S)-2-(2-chloro-5-(4,4,5,5-tetramethyl-1,3,2-dioxaborolan-2-yl)phenoxy)propyl)-1H-tetrazole To a mixture of 4,4,4',4',5,5,5',5'-octamethyl-2,2'-bi-1,3,2-dioxaborolane (11.99 g), 1-((2S)-2-(5-bromo-2-chlorophenoxy)propyl)-1H-tetrazole (10 g), potassium acetate (9.27 g) and DMSO (100 mL) was added [1,1'-bis(diphenylphosphino)ferrocene]palladium(II) dichloride dichloromethane adduct (2.57 g) at room temperature. The mixture was stirred at 100° C. for 2 hr under nitrogen atmosphere. To the mixture were added water and ethyl acetate at room temperature, the insoluble material was removed by filtration through Celite, and the filtrate was extracted with ethyl acetate. The organic layer was separated, washed with water and saturated brine, dried over anhydrous magnesium sulfate, and concentrated under reduced pressure to give the title compound (16.88 g). This product was subjected to the next reaction without further purification.
MS m/z 365.2 [M+H]$^+$.

F) 5-(4-chloro-3-(((2S)-1-(1H-tetrazol-1-yl)propan-2-yl)oxy)phenyl)-N-(2-methoxy-4-(4-(morpholin-4-yl)piperidin-1-yl)phenyl)pyrimidin-2-amine To a mixture of 5-bromo-N-(2-methoxy-4-(4-(morpholin-4-yl)piperidin-1-yl)phenyl)pyrimidin-2-amine (11.76 g), 1-((2S)-2-(2-chloro-5-(4,4,5,5-tetramethyl-1,3,2-dioxaborolan-2-yl)phenoxy)propyl)-1H-tetrazole (11.48 g), cesium carbonate (17.10 g) and THF (100 mL)/water (20.00 mL) was added bis(tri-tert-butylphosphine)palladium (0) (1.341 g) at room temperature. The mixture was stirred at 70° C. for 3 hr under nitrogen atmosphere. To the mixture was added water at room temperature, and the mixture was extracted with ethyl acetate. The organic layer was separated, washed with water and saturated brine, dried over anhydrous magnesium sulfate, and concentrated under reduced pressure. The residue was purified by both silica gel column chromatography (MeOH/ethyl acetate) and silica gel column chromatography (NH, ethyl acetate/hexane). The obtained solid was recrystallized from ethanol/ethyl acetate to give the title compound (9.92 g).
$^1$H NMR (300 MHz, DMSO-d$_6$) δ1.33 (3H, d, J=6.1 Hz), 1.51 (2H, d, J=11.5 Hz), 1.85 (2H, brs), 2.27 (1H, brs), 2.47-2.48 (2H, m), 2.54 (2H, brs), 2.66 (2H, t, J=11.4 Hz), 3.58 (4H, brs), 3.71 (2H, d, J=12.0 Hz), 3.80 (3H, s), 4.74-4.85 (1H, m), 4.86-4.96 (1H, m), 5.17 (1H, brs), 6.49-6.54 (1H, m), 6.64 (1H, s), 7.25 (1H, d, J=8.8 Hz), 7.37 (1H, s), 7.45 (1H, d, J=8.6 Hz), 7.65 (1H, d, J=8.6 Hz), 8.22 (1H, s), 8.71 (2H, s), 9.37 (1H, s).

Example 75

4-(2-((2-methoxy-4-(1-(oxetan-3-yl)piperidin-4-yl)phenyl)amino)pyrimidin-5-yl)-2-(((2S)-1-(1H-tetrazol-1-yl)propan-2-yl)oxy)benzonitrile A) tert-butyl 4-(3-methoxy-4-nitrophenyl)-3,6-dihydropyridine-1(2H)-carboxylate To a mixture of 4-bromo-2-methoxy-1-nitrobenzene (15 g), tert-butyl 4-(4,4,5,5-tetramethyl-1,3,2-dioxaborolan-2-yl)-3,6-dihydropyridine-1(2H)-carboxylate (19.99 g), potassium carbonate (9.83 g) and EtOH (150 mL)/toluene (150 mL) was added Pd(PPh$_3$)$_4$ (3.74 g) at room temperature, and the mixture was stirred at 100° C. for 5 hr under argon atmosphere. The impurity was removed by filtration, and the filtrate was concentrated under reduced pressure. The obtained solid was collected by filtration, washed with diisopropyl ether, and dried under reduced pressure to give the title compound (20.6 g).
$^1$H NMR (300 MHz, DMSO-d$_6$) δ1.43 (9H, s), 2.51-2.56 (2H, m), 3.49-3.63 (2H, m), 3.96 (3H, s), 4.00-4.11 (2H, m), 6.33-6.49 (1H, m), 7.16 (1H, dd, J=8.5, 1.7 Hz), 7.30 (1H, d, J=1.6 Hz), 7.87 (1H, d, J=8.5 Hz); MS m/z 235.3 [M+H-Boc]$^+$.

B) 4-(3-methoxy-4-nitrophenyl)-1,2,3,6-tetrahydropyridine

To a mixture of tert-butyl 4-(3-methoxy-4-nitrophenyl)-3,6-dihydropyridine-1(2H)-carboxylate (20.6 g) and CH3CN (200 mL) was added TFA (35.1 g) at room temperature. The mixture was stirred at the same temperature overnight, and the reaction solution was concentrated. The obtained residue was partitioned with ethyl acetate-6 M hydrochloric acid, and the aqueous layer was basified with 8 M aqueous sodium hydroxide solution, and extracted with ethyl acetate. The organic layer was separated, washed with saturated brine, dried over anhydrous sodium sulfate, and concentrated under reduced pressure. The obtained solid was collected by filtration to give the title compound (10.6 g).
$^1$H NMR (300 MHz, DMSO-d$_6$) δ2.30-2.43 (2H, m), 2.92 (2H, t, J=5.6 Hz), 3.37-3.46 (2H, m), 3.96 (3H, s), 6.44-6.53 (1H, m), 7.14 (1H, dd, J=8.6, 1.7 Hz), 7.27 (1H, d, J=1.6 Hz), 7.86 (1H, d, J=8.5 Hz); MS m/z 235.3 [M+H]$^+$.

C) 2,2,2-trifluoro-1-(4-(3-methoxy-4-nitrophenyl)-3,6-dihydropyridin-1(2H)-yl)ethanone To a mixture of 4-(3-methoxy-4-nitrophenyl)-1,2,3,6-tetrahydropyridine (10.6 g) and THF (dry) (200 mL) was added trifluoroacetic acid anhydride (10.45 g) at room temperature. The mixture was stirred at the same temperature for 1 hr. To the mixture was added saturated aqueous sodium hydrogencarbonate solution, and the mixture was extracted with ethyl acetate. The organic layer was separated, washed with saturated brine, dried over anhydrous sodium sulfate, and concentrated under reduced pressure. The resulting solid was collected by filtration to give the title compound (14.1 g).
$^1$H NMR (300 MHz, DMSO-d$_6$) δ2.60-2.76 (2H, m), 3.75-3.88 (2H, m), 3.97 (3H, s), 4.25-4.37 (2H, m), 6.39-6.50 (1H, m), 7.19 (1H, dd, J=8.5, 1.7 Hz), 7.33 (1H, s), 7.89 (1H, d, J=8.5 Hz); MS m/z 331.3 [M+H]$^+$.

D) 1-(4-(4-amino-3-methoxyphenyl)piperidin-1-yl)-2,2,2-trifluoroethanone

A mixture of 2,2,2-trifluoro-1-(4-(3-methoxy-4-nitrophenyl)-3,6-dihydropyridin-1(2H)-yl)ethanone (14.1 g), 10% palladium-carbon (2.272 g), MeOH (100 mL) and THF (200 mL) was stirred at room temperature overnight under normal pressure of hydrogen atmosphere. The catalyst was removed by filtration, and the filtrate was concentrated under reduced pressure. The residue was purified by silica gel column chromatography (ethyl acetate/hexane) to give the title compound (12.7 g).

¹H NMR (300 MHz, DMSO-d₆) δ1.47-1.66 (2H, m), 1.77-1.91 (2H, m), 2.63-2.78 (1H, m), 2.86-2.99 (1H, m), 3.32-3.39 (1H, m), 3.75 (3H, s), 3.87-3.99 (1H, m), 4.36-4.47 (1H, m), 4.51 (2H, s), 6.54 (2H, d, J=0.8 Hz), 6.69 (1H, s); MS m/z 303.3 [M+H]⁺.

E) 1-(4-(4-((5-bromopyrimidin-2-yl)amino)-3-methoxyphenyl)piperidin-1-yl)-2,2,2-trifluoroethanone To a mixture of 1-(4-(4-amino-3-methoxyphenyl)piperidin-1-yl)-2,2,2-trifluoroethanone (12.7 g) and n-BuOH (300 mL) were added 5-bromo-2-chloropyrimidine (8.13 g) and TFA (47.9 g) at room temperature. The mixture was stirred at 100° C. overnight, and the reaction solution was concentrated. The obtained residue was partitioned with ethyl acetate-saturated aqueous sodium hydrogencarbonate solution, and the organic layer was washed with saturated brine, dried over anhydrous sodium sulfate, and concentrated under reduced pressure. The residue was purified by silica gel column chromatography (ethyl acetate/hexane) to give the title compound (4.45 g).

¹H NMR (300 MHz, DMSO-d₆) δ1.56-1.77 (2H, m), 1.83-1.98 (2H, m), 2.79-3.05 (2H, m), 3.33-3.43 (1H, m), 3.81 (3H, s), 3.91-4.03 (1H, m), 4.38-4.51 (1H, m), 6.82 (1H, dd, J=8.2, 1.6 Hz), 6.96 (1H, d, J=1.7 Hz), 7.69 (1H, d, J=8.2 Hz), 8.43 (1H, s), 8.50 (2H, s); MS m/z 459.2 [M+H]⁺.

F) 4-(2-((2-methoxy-4-(1-(trifluoroacetyl)piperidin-4-yl)phenyl)amino)pyrimidin-5-yl)-2-(((2S)-1-(1H-tetrazol-1-yl)propan-2-yl)oxy)benzonitrile To a mixture of 4-(4,4,5,5-tetramethyl-1,3,2-dioxaborolan-2-yl)-2-(((2S)-1-(1H-tetrazol-1-yl)propan-2-yl)oxy)benzonitrile (232 mg), 1-(4-(4-((5-bromopyrimidin-2-yl)amino)-3-methoxyphenyl)piperidin-1-yl)-2,2,2-trifluoroethanone (200 mg), cesium carbonate (284 mg) and THF (5.00 mL)/water (0.5 mL) was added bis(tri-tert-butylphosphine)palladium (0) (22.26 mg) at room temperature, the mixture was stirred at 70° C. for 2 hr, and the reaction solution was concentrated. The residue was purified by silica gel column chromatography (NH, ethyl acetate/hexane) to give the title compound (120 mg).

¹H NMR (300 MHz, DMSO-d₆) δ1.36 (3H, d, J=6.2 Hz), 1.60-1.79 (2H, m), 1.84-1.97 (2H, m), 2.79-3.06 (2H, m), 3.35-3.43 (1H, m), 3.85 (3H, s), 3.93-4.03 (1H, m), 4.37-4.57 (1H, m), 4.77-5.02 (2H, m), 5.27-5.45 (1H, m), 6.86 (1H, dd, J=8.2, 1.6 Hz), 6.99 (1H, d, J=1.7 Hz), 7.39-7.46 (1H, m), 7.50 (1H, s), 7.77 (1H, d, J=8.1 Hz), 7.90 (1H, d, J=8.1 Hz), 8.47 (1H, s), 8.87 (2H, s), 9.35 (1H, s); MS m/z 606.2 [M+H]⁺.

G) 4-(2-((2-methoxy-4-(piperidin-4-yl)phenyl)amino)pyrimidin-5-yl)-2-(((2S)-1-(1H-tetrazol-1-yl)propan-2-yl)oxy)benzonitrile To a mixture of 4-(2-((2-methoxy-4-(1-(trifluoroacetyl)piperidin-4-yl)phenyl)amino)pyrimidin-5-yl)-2-(((2S)-1-(1H-tetrazol-1-yl)propan-2-yl)oxy)benzonitrile (120 mg) and MeOH (5.0 mL) was added 2M aqueous sodium hydroxide solution (0.296 mL) at room temperature. The mixture was stirred at the same temperature for 1 hr. To the mixture was added saturated aqueous ammonium chloride solution, and the mixture was extracted with ethyl acetate. The organic layer was separated, washed with saturated brine, dried over anhydrous sodium sulfate, and concentrated under reduced pressure. The resulting solid was collected by filtration to give the title compound (87.5 mg).

¹H NMR (300 MHz, DMSO-d₆) δ1.36 (3H, d, J=6.1 Hz), 1.47-1.64 (2H, m), 1.66-1.78 (2H, m), 2.34-2.48 (2H, m), 2.54-2.67 (2H, m), 2.99-3.11 (2H, m), 3.84 (3H, s), 4.77-5.02 (2H, m), 5.29-5.45 (1H, m), 6.77-6.85 (1H, m), 6.91 (1H, s), 7.43 (1H, d, J=8.1 Hz), 7.50 (1H, s), 7.77 (1H, d, J=8.2 Hz), 7.86 (1H, d, J=8.1 Hz), 8.46 (1H, s), 8.86 (2H, s), 9.35 (1H, s); MS m/z 512.4 [M+H]⁺.

H) 4-(2-((2-methoxy-4-(1-(oxetan-3-yl)piperidin-4-yl)phenyl)amino)pyrimidin-5-yl)-2-(((2S)-1-(1H-tetrazol-1-yl)propan-2-yl)oxy)benzonitrile To a mixture of 4-(2-((2-methoxy-4-(piperidin-4-yl)phenyl)amino)pyrimidin-5-yl)-2-(((2S)-1-(1H-tetrazol-1-yl)propan-2-yl)oxy)benzonitrile (85.0 mg), MeOH (5.0 mL) and AcOH (0.5 mL) were added oxetan-3-one (59.9 mg) and 2-methylpyridine-borane (21.33 mg) at room temperature. The mixture was stirred at 60° C. overnight, and the reaction solution was concentrated. The residue was purified by silica gel column chromatography (NH, ethyl acetate/hexane) to give the title compound (73.2 mg).

¹H NMR (300 MHz, DMSO-d₆) δ1.36 (3H, d, J=6.1 Hz), 1.60-1.92 (6H, m), 2.43-2.47 (1H, m), 2.76-2.87 (2H, m), 3.36-3.46 (1H, m), 3.84 (3H, s), 4.41-4.49 (2H, m), 4.51-4.60 (2H, m), 4.78-4.99 (2H, m), 5.27-5.44 (1H, m), 6.85 (1H, d, J=8.3 Hz), 6.95 (1H, s), 7.43 (1H, d, J=8.2 Hz), 7.50 (1H, s), 7.77 (1H, d, J=8.1 Hz), 7.87 (1H, d, J=8.2 Hz), 8.46 (1H, s), 8.86 (2H, s), 9.35 (1H, s).

Example 206

5-(4-chloro-3-(((2S)-1-(1H-tetrazol-1-yl)propan-2-yl)oxy)phenyl)-N-(2-methoxy-4-(1-(oxetan-3-yl)piperidin-4-yl)phenyl)pyrimidin-2-amine A) tert-butyl 4-(4-amino-3-methoxyphenyl)piperidine-1-carboxylate A mixture of tert-butyl 4-(3-methoxy-4-nitrophenyl)-3,6-dihydropyridine-1(2H)-carboxylate (10.37 g), 10% palladium-carbon (3.30 g) and MeOH (250 mL) was stirred at room temperature overnight under normal pressure of hydrogen atmosphere. The catalyst was removed by filtration, and the filtrate was concentrated under reduced pressure. The obtained solid was collected by filtration, washed with ethanol-diisopropyl ether, and dried under reduced pressure to give the title compound (7.00 g).

¹H NMR (300 MHz, DMSO-d₆) δ1.34-1.53 (12H, m), 1.69 (2H, d, J=12.8 Hz), 2.65-2.86 (2H, m), 3.74 (3H, d, J=1.3 Hz), 3.96-4.10 (2H, m), 4.48 (2H, s), 6.48-6.57 (2H, m), 6.65 (1H, s); MS m/z 251.2 [M+1-t-Bu]⁺;

B) 2-chloro-5-(4-chloro-3-(((2S)-1-(1H-tetrazol-1-yl)propan-2-yl)oxy)phenyl)pyrimidine To a mixture of 1-((2S)-2-(2-chloro-5-(4,4,5,5-tetramethyl-1,3,2-dioxaborolan-2-yl)phenoxy)propyl)-1H-tetrazole (12.34 g), 5-bromo-2-chloropyrimidine (9.82 g), cesium carbonate (33.1 g), DME (100 mL) and water (25 mL) was added [1,1'-bis(diphenylphosphino)ferrocene]dichloropalladium(II) (2.76 g) at room temperature. The mixture was stirred at 100° C. for 5 hr under nitrogen atmosphere. To the reaction solution was added water at room temperature, and the insoluble substance was removed by filtration. The filtrate was partitioned with ethyl acetate-water, and the organic layer was washed with saturated brine, dried over anhydrous magnesium sulfate, and concentrated under reduced pressure. The residue was purified by silica gel column chromatography (ethyl acetate/hexane) to give the title compound (3.18 g).

$^1$H NMR (300 MHz, DMSO-$d_6$) δ1.34 (3H, d, J=6.3 Hz), 4.76-5.00 (2H, m), 5.21 (1H, td, J=6.6, 3.6 Hz), 7.37-7.44 (1H, m), 7.51-7.61 (2H, m), 9.08-9.16 (2H, m), 9.33-9.40 (1H, m); MS m/z 351.1 [M+H]$^+$.

C) tert-butyl 4-(4-((5-(4-chloro-3-(((2S)-1-(1H-tetrazol-1-yl)propan-2-yl)oxy)phenyl)pyrimidin-2-yl)amino)-3-methoxyphenyl)piperidine-1-carboxylate To a mixture of 2-chloro-5-(4-chloro-3-(((2S)-1-(1H-tetrazol-1-yl)propan-2-yl)oxy)phenyl)pyrimidine (3 g), tert-butyl 4-(4-amino-3-methoxyphenyl)piperidine-1-carboxylate (3.14 g), cesium carbonate (5.57 g) and toluene (100 mL) were added palladium acetate (0.288 g) and 2,2'-bis(diphenylphosphino)-1,1'-binaphthyl (1.596 g) at room temperature. The mixture was stirred at 100° C. for 2 hr under nitrogen atmosphere. To the reaction solution was added water at room temperature, the insoluble substance was removed by filtration, and the filtrate was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (3.15 g).

$^1$H NMR (300 MHz, DMSO-$d_6$) δ1.33 (3H, d, J=6.1 Hz), 1.42 (9H, d, J=1.6 Hz), 1.49-1.63 (2H, m), 1.70-1.83 (2H, m), 2.66 (1H, t, J=12.0 Hz), 2.80 (2H, brs), 3.85 (3H, s), 4.06-4.16 (2H, m), 4.74-4.96 (2H, m), 5.13-5.25 (1H, m), 6.82 (1H, d, J=8.4 Hz), 6.94 (1H, s), 7.28 (1H, d, J=8.3 Hz), 7.40-7.50 (2H, m), 7.97 (1H, d, J=8.1 Hz), 8.27 (1H, s), 8.79 (2H, s), 9.35-9.41 (1H, m); MS m/z 621.3 [M+H]$^+$.

D) 5-(4-chloro-3-(((2S)-1-(1H-tetrazol-1-yl)propan-2-yl)oxy)phenyl)-N-(2-methoxy-4-(piperidin-4-yl)phenyl)pyrimidin-2-amine To a mixture of tert-butyl 4-(4-((5-(4-chloro-3-(((2S)-1-(1H-tetrazol-1-yl)propan-2-yl)oxy)phenyl)pyrimidin-2-yl)amino)-3-methoxyphenyl)piperidine-1-carboxylate (3.15 g) and ethyl acetate (10 mL) was added 4M hydrogen chloride-ethyl acetate solution at room temperature. The mixture was stirred at room temperature for 2 hr, and the reaction solution was concentrated under reduced pressure. The obtained residue was partitioned with ethyl acetate-saturated aqueous sodium hydrogencarbonate solution, and the organic layer was washed with saturated brine, dried over anhydrous magnesium sulfate, and concentrated under reduced pressure to give the title compound (2.12 g). This product was subjected to the next reaction without further purification.

$^1$H NMR (300 MHz, DMSO-$d_6$) δ1.30-1.36 (4H, m), 1.61-1.86 (4H, m), 2.58-2.80 (3H, m), 3.82-3.86 (3H, m), 4.75-4.96 (2H, m), 5.11-5.25 (1H, m), 6.81 (1H, d, J=8.3 Hz), 6.91 (1H, d, J=0.6 Hz), 7.28 (1H, d, J=8.3 Hz), 7.37-7.48 (2H, m), 7.94 (1H, d, J=8.1 Hz), 8.29 (1H, s), 8.78 (2H, s), 9.39 (1H, s), 2H were not assigned; MS m/z 521.3 [M+H]$^+$.

E) 5-(4-chloro-3-(((2S)-1-(1H-tetrazol-1-yl)propan-2-yl)oxy)phenyl)-N-(2-methoxy-4-(1-(oxetan-3-yl)piperidin-4-yl)phenyl)pyrimidin-2-amine To a mixture of 5-(4-chloro-3-(((2S)-1-(1H-tetrazol-1-yl)propan-2-yl)oxy)phenyl)-N-(2-methoxy-4-(piperidin-4-yl)phenyl)pyrimidin-2-amine (2.12 g), oxetan-3-one (1.466 g), MeOH (40 mL) and AcOH (4 mL) was added 2-methylpyridine-borane complex (1:1) (0.522 g) at room temperature. The mixture was stirred at 60° C. overnight under nitrogen atmosphere. The mixture was concentrated under reduced pressure. To the residue was added saturated aqueous sodium hydrogencarbonate solution at room temperature, and the mixture was extracted with ethyl acetate-THF. The organic layer was separated, washed with water and saturated brine, dried over anhydrous magnesium sulfate, and concentrated under reduced pressure. The residue was purified by silica gel column chromatography (NH, ethyl acetate/hexane). A suspension of the obtained solid and ethyl acetate was added to diisopropyl ether at 60° C. After been stirred for 30 min, an insoluble solid was collected by filtration to give the title compound (1.04 g).

$^1$H NMR (300 MHz, DMSO-$d_6$) δ1.33 (3H, d, J=6.1 Hz), 1.67-1.91 (6H, m), 2.45-2.56 (1H, m), 2.81 (2H, d, J=11.4 Hz), 3.40 (1H, t, J=6.4 Hz), 3.85 (3H, s), 4.40-4.50 (2H, m), 4.52-4.61 (2H, m), 4.76-4.98 (2H, m), 5.11-5.25 (1H, m), 6.84 (1H, d, J=8.2 Hz), 6.95 (1H, s), 7.28 (1H, d, J=8.3 Hz), 7.41 (1H, s), 7.47 (1H, d, J=8.4 Hz), 7.94 (1H, d, J=8.3 Hz), 8.28 (1H, s), 8.79 (2H, d, J=1.1 Hz), 9.37 (1H, s).

Example 484

(S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(trifluoromethyl)-1H-pyrazol-4-yl)pyrimidin-2-amine

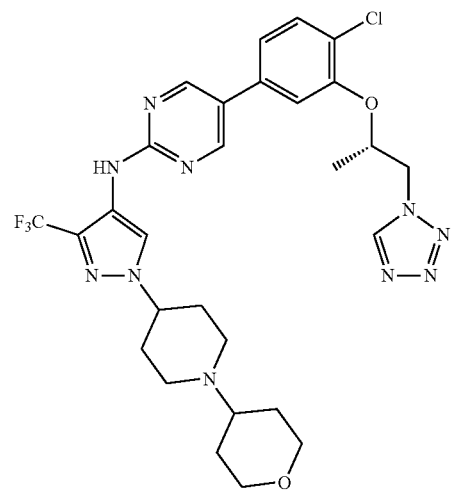 [SMILES: C[C@@H](Cn1cnnn1)Oc1cc(-c2cnc(Nc3cn(C4CCN(C5CCOCC5)CC4)nc3C(F)(F)F)nc2)ccc1Cl]

A) tert-butyl 4-(4-nitro-3-(trifluoromethyl)-1H-pyrazol-1-yl) piperidine-1-carboxylate To a solution of 4-nitro-3-(trifluoromethyl)-1H-pyrazole (1.94 g) in DMF (40 mL) was added 60% sodium hydride (505 mg) at 0° C. After being stirred at 0° C. for 10 min, tert-butyl 4-iodopiperidine-1-carboxylate (4.32 g) was added to the mixture. After being stirred at 70° C. overnight, the mixture was quenched with water and extracted with ethyl acetate. The organic layer was separated, washed with saturated brine, dried over anhydrous sodium sulfate and concentrated in vacuo. The residue was purified by silica gel column chromatography (NH, ethyl acetate/hexane) to give the title compound (956 mg). MS m/z 265.2 [M+1-(Boc)]+.

B) tert-butyl 4-(4-amino-3-(trifluoromethyl)-1H-pyrazol-1-yl)piperidine-1-carboxylate A mixture of tert-butyl 4-(4-nitro-3-(trifluoromethyl)-1H-pyrazol-1-yl)piperidine-1-carboxylate (1.58 g) and 10% palladium-carbon (462 mg) in MeOH (30 mL) and THF (30 mL) was stirred under normal pressure of hydrogen atmosphere at room temperature for 2 hr. The catalyst was removed by filtration and the filtrate was concentrated in vacuo to give the title compound (1.45 g). The obtained compound was used in the next reaction without purification.
MS m/z 279.2 [M+1-(tBu)]+.

C) (S)-tert-butyl 4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)piperidine-1-carboxylate To a solution of 2-chloro-5-(4-chloro-3-(((2S)-1-(1H-tetrazol-1-yl)propan-2-yl)oxy)phenyl)pyrimidine (378 mg), tert-butyl 4-(4-amino-3-(trifluoromethyl)-1H-pyrazol-1-yl) piperidine-1-carboxylate (300 mg), BINAP (112 mg) and DBU (0.203 mL) in DMA (4.00 mL) was added Pd2(dba)3 (82 mg) at room temperature. The mixture was stirred at 100° C. under nitrogen atmosphere for 2 hr. The mixture was diluted with ethyl acetate, and filtered through celite and the filtrate was evaporated in vacuo. The residue was purified by silica gel column chromatography (MeOH/ethyl acetate) and silica gel column chromatography (NH, ethyl acetate/hexane) to give the title compound (270 mg).
MS m/z 649.3 [M+1]+.

D) (S)-5-(3-((1-(1H-tetrazol-1-yl)propan-2-yl)oxy)-4-chlorophenyl)-N-(1-(piperidin-4-yl)-3-(trifluoromethyl)-1H-pyrazol-4-yl)pyrimidin-2-amine hydrochloride To a solution of (S)-tert-butyl 4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)piperidine-1-carboxylate (170 mg) in MeOH (2.00 mL) was added 4 M hydrogen chloride-ethyl acetate (2.00 mL) at room temperature. The mixture was stirred at room temperature for 30 min. The mixture was concentrated in vacuo and the residue was washed with ethyl acetate to give the title compound (150 mg).
MS m/z 549.3 [M+1]+.

E) (S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(trifluoromethyl)-1H-pyrazol-4-yl)pyrimidin-2-amine To a solution of (S)-5-(3-((1-(1H-tetrazol-1-yl)propan-2-yl)oxy)-4-chlorophenyl)-N-(1-(piperidin-4-yl)-3-(trifluoromethyl)-1H-pyrazol-4-yl)pyrimidin-2-amine hydrochloride (100 mg) in MeOH (4.0 mL) was added triethylamine (0.024 mL) at room temperature. The mixture was stirred at room temperature for 10 min. Dihydro-2H-pyran-4(3H)-one (0.047 mL), AcOH (0.102 mL) and 2-methylpyridine-borane (36.5 mg) were added to the mixture, and the mixture was stirred at room temperature overnight. The mixture was neutralized with saturated aqueous sodium hydrogencarbonate solution at 0° C. and extracted with ethyl acetate. The organic layer was separated, washed with water and saturated brine, dried over anhydrous magnesium sulfate and concentrated in vacuo. The residue was purified by silica gel column chromatography (NH, ethyl acetate/hexane) and silica gel column chromatography (MeOH/ethyl acetate) to give the title compound (58.0 mg). 1H NMR (300 MHz, CDCl3) δ1.45 (3H, d, J=6.0 Hz), 1.61-1.71 (2H, m), 1.72-1.84 (2H, m), 2.00-2.16 (2H, m), 2.18-2.41 (4H, m), 2.47-2.63 (1H, m), 3.05-3.19 (2H, m), 3.40 (2H, t, J=11.4 Hz), 3.98-4.27 (3H, m), 4.66-4.77 (1H, m), 4.80-4.93 (2H, m), 6.87 (1H, s), 7.09 (1H, d, J=8.2 Hz), 7.15 (1H, s), 7.47 (1H, d, J=8.1 Hz), 8.39 (1H, s), 8.55 (2H, s), 8.95 (1H, s).

Example 664

(S)-5-(3-((1-(1H-tetrazol-1-yl)propan-2-yl)oxy)-4-chlorophenyl)-N-(3-(difluoromethoxy)-1-(1-(tetrahydro-2H-pyran-4-yl)piperidin-4-yl)-1H-pyrazol-4-yl)pyrimidin-2-amine

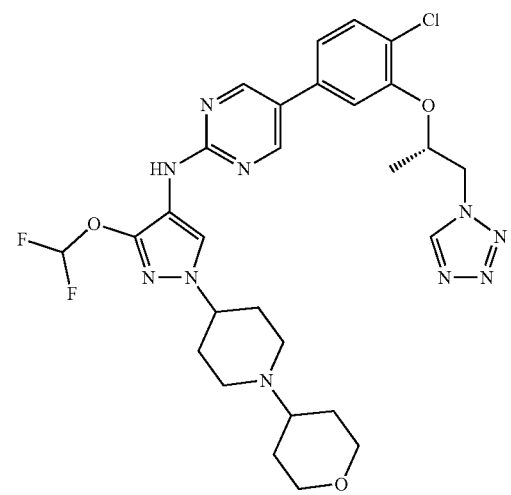 [SMILES: C[C@@H](Cn1cnnn1)Oc1cc(-c2cnc(Nc3cn(C4CCN(C5CCOCC5)CC4)nc3OC(F)F)nc2)ccc1Cl]

A) 3-(difluoromethoxy)-1H-pyrazole

A mixture of 1-(3-hydroxy-1H-pyrazol-1-yl)ethanone (20.0 g), methyl 2-chloro-2,2-difluoroacetate (23.6 g), ethyl 2-chloro-2,2-difluoroacetate (3.99 g) and potassium carbonate (32.6 g) in DMF (160 mL) was stirred at 50° C. for 19.5 hr. The reaction mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane) to give the title compound (623 mg). 1H NMR (300 MHz, CDCl3) δ5.98 (1H, d, J=2.7 Hz), 6.83 (1H, t, J=73.0 Hz), 7.45 (1H, d, J=2.7 Hz), 8.06 (1H, brs); MS m/z 135.1 [M+1]+.

B) 3-(difluoromethoxy)-4-nitro-1H-pyrazole

Sulfuric acid (2.85 g) was added to 3-(difluoromethoxy)-1H-pyrazole (620 mg) at 0° C. Nitric acid (1.47 g) was added to the mixture at 0° C. The mixture was stirred at 60° C. for 2 hr. The reaction mixture was quenched at 0° C. The resulting mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane) to give the title compound (146 mg).

¹H NMR (300 MHz, CDCl₃) δ7.06 (1H, t, J=72.0 Hz), 8.27 (1H, s), NH was not assigned.

C) tert-butyl 4-(3-(difluoromethoxy)-4-nitro-1H-pyrazol-1-yl) piperidine-1-carboxylate 60% Sodium hydride (38.1 mg) was added to a solution of 3-(difluoromethoxy)-4-nitro-1H-pyrazole (143 mg) in DMF (5.00 mL) at 0° C. tert-Butyl 4-((methylsulfonyl)oxy)piperidine-1-carboxylate (267 mg) was added to the mixture at 0° C. The mixture was stirred at 70° C. for 14 hr. The reaction mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane) to give the title compound (195 mg).

¹H NMR (300 MHz, CDCl₃) δ1.48 (9H, s), 1.86 (2H, qd, J=12.2, 4.4 Hz), 2.09-2.17 (2H, m), 2.87 (2H, t, J=12.9 Hz), 4.09-4.20 (1H, m), 4.22-4.37 (2H, m), 7.05 (1H, t, J=71.4 Hz), 8.09 (1H, s); MS m/z 307.1 [M+1-t-Bu]⁺.

D) tert-butyl 4-(4-amino-3-(difluoromethoxy)-1H-pyrazol-1-yl)piperidine-1-carboxylate A mixture of tert-butyl 4-(3-(difluoromethoxy)-4-nitro-1H-pyrazol-1-yl)piperidine-1-carboxylate (192 mg) and 10% palladium-carbon (57.9 mg) in MeOH (5.00 mL) and THF (5.00 mL) was stirred under normal pressure of hydrogen atmosphere at room temperature for 2.5 hr. The catalyst was removed by filtration, and then the filtrate was concentrated under reduced pressure. The residue was purified by silica gel column chromatography (ethyl acetate/hexane) to give the title compound (158 mg).

¹H NMR (300 MHz, CDCl₃) δ1.47 (9H, s), 1.79 (2H, qd, J=12.2, 4.5 Hz), 1.99-2.06 (2H, m), 2.65-2.91 (4H, m), 3.99 (1H, tt, J=11.4, 4.0 Hz), 4.14-4.28 (2H, m), 6.78 (1H, t, J=74.0 Hz), 6.97 (1H, s); MS m/z 277.1 [M+1-t-Bu]⁺.

E) (S)-tert-butyl 4-(4-((5-(3-((1-(1H-tetrazol-1-yl)propan-2-yl)oxy)-4-chlorophenyl)pyrimidin-2-yl)amino)-3-(difluoromethoxy)-1H-pyrazol-1-yl)piperidine-1-carboxylate A mixture of 2-chloro-5-(4-chloro-3-(((2S)-1-(1H-tetrazol-1-yl)propan-2-yl)oxy)phenyl)pyrimidine (181 mg), tert-butyl 4-(4-amino-3-(difluoromethoxy)-1H-pyrazol-1-yl)piperidine-1-carboxylate (156 mg), Pd₂(dba)₃ (26.7 mg), BINAP (29.2 mg) and DBU (107 mg) in DMA (4.70 mL) was stirred at 100° C. for 2 hr under argon atmosphere. The reaction mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane) to give the title compound (145 mg) including tert-butyl 4-(4-amino-3-(difluoromethoxy)-1H-pyrazol-1-yl)piperidine-1-carboxylate. This product was used in the next step without further purification.

2,2,2-Trifluoroacetic anhydride (70.5 mg) was added to a solution of a mixture (145 mg) of (S)-tert-butyl 4-(4-((5-(3-((1-(1H-tetrazol-1-yl)propan-2-yl)oxy)-4-chlorophenyl)pyrimidin-2-yl)amino)-3-(difluoromethoxy)-1H-pyrazol-1-yl)piperidine-1-carboxylate and tert-butyl 4-(4-amino-3-(difluoromethoxy)-1H-pyrazol-1-yl)piperidine-1-carboxylate and triethylamine (67.9 mg) in THF (5.00 mL) at 0° C. The mixture was stirred at room temperature for 30 min. The reaction mixture was partitioned between ethyl acetate and saturated aqueous sodium hydrogencarbonate solution. The organic layer was separated, washed with saturated brine, dried over anhydrous sodium sulfate and concentrated under reduced pressure. The residue was purified by silica gel column chromatography (ethyl acetate/hexane) to give the title compound (55.0 mg).

MS m/z 647.3 [M+1]⁺.

F) (S)-5-(3-((1-(1H-tetrazol-1-yl)propan-2-yl)oxy)-4-chlorophenyl)-N-(3-(difluoromethoxy)-1-(piperidin-4-yl)-1H-pyrazol-4-yl)pyrimidin-2-amine A solution of 4 M hydrogen chloride-ethyl acetate (1.04 mL) was added to a solution of (S)-tert-butyl 4-(4-((5-(3-((1-(1H-tetrazol-1-yl)propan-2-yl)oxy)-4-chlorophenyl)pyrimidin-2-yl)amino)-3-(difluoromethoxy)-1H-pyrazol-1-yl)piperidine-1-carboxylate (54.0 mg) in ethyl acetate (1.00 mL) at room temperature. The mixture was stirred at room temperature for 3.5 hr. The reaction mixture was partitioned between ethyl acetate and saturated aqueous sodium hydrogencarbonate solution. The organic layer was separated, washed with saturated brine, dried over anhydrous sodium sulfate and concentrated under reduced pressure to give the title compound (45.5 mg).

MS m/z 547.2 [M+1]⁺.

G) (S)-5-(3-((1-(1H-tetrazol-1-yl)propan-2-yl)oxy)-4-chlorophenyl)-N-(3-(difluoromethoxy)-1-(1-(tetrahydro-2H-pyran-4-yl)piperidin-4-yl)-1H-pyrazol-4-yl)pyrimidin-2-amine A mixture of (S)-5-(3-((1-(1H-tetrazol-1-yl)propan-2-yl)oxy)-4-chlorophenyl)-N-(3-(difluoromethoxy)-1-(piperidin-4-yl)-1H-pyrazol-4-yl)pyrimidin-2-amine (45.3 mg), dihydro-2H-pyran-4(3H)-one (41.5 mg) and 2-methylpyridine-borane (26.0 mg) in MeOH (2.00 mL) and AcOH (0.20 mL) was stirred at 60° C. for 1 hr. The reaction mixture was concentrated under reduced pressure. The reaction mixture was partitioned between ethyl acetate and saturated aqueous sodium hydrogencarbonate solution. The organic layer was separated, washed with saturated brine, dried over anhydrous sodium sulfate and concentrated under reduced pressure. The residue was purified by silica gel column chromatography (NH, ethyl acetate/hexane and MeOH/ethyl acetate) and by preparative HPLC (water/CH₃CN containing 0.1% TFA). The desired fractions were concentrated under reduced pressure. The residue was partitioned between ethyl acetate and saturated aqueous sodium hydrogencarbonate solution. The organic layer was separated, washed with saturated brine, dried over anhydrous sodium sulfate and concentrated under reduced pressure. The residue was purified by recrystallization from ethyl acetate and hexane to give the title compound (15.1 mg).

¹H NMR (300 MHz, CDCl₃) δ1.45 (3H, d, J=6.1 Hz), 1.86 (2H, brs), 2.08 (2H, brs), 2.37 (3H, brs), 2.75 (4H, brs), 3.36-3.56 (4H, m), 4.11 (2H, dd, J=11.3, 2.4 Hz), 4.16-4.57 (1H, m), 4.67-4.76 (1H, m), 4.86 (2H, d, J=11.8 Hz), 6.59 (1H, s), 6.82-6.90 (1H, m), 6.97 (1H, s), 7.08 (1H, d, J=7.2 Hz), 7.45 (1H, d, J=8.3 Hz), 8.10 (1H, s), 8.55 (2H, s), 8.96 (1H, s).

Example 677

(S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(2,2,2-trifluoroethoxy)-1H-pyrazol-4-yl)pyrimidin-2-amine

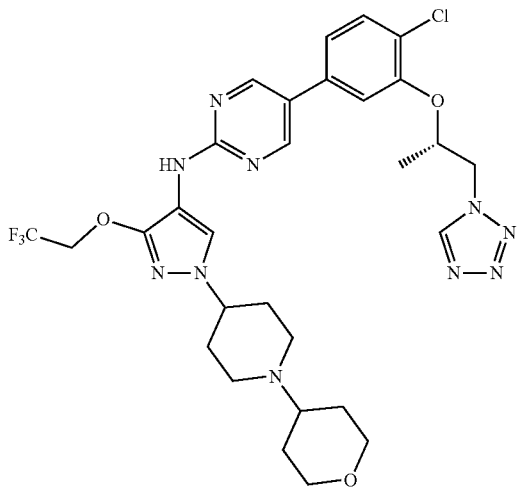 [SMILES: C[C@@H](Cn1cnnn1)Oc1cc(-c2cnc(Nc3cn(C4CCN(C5CCOCC5)CC4)nc3OCC(F)(F)F)nc2)ccc1Cl]

A) tert-butyl 4-(4-nitro-3-(2,2,2-trifluoroethoxy)-1H-pyrazol-1-yl) piperidine-1-carboxylate To a solution of 4-nitro-3-(2,2,2-trifluoroethoxy)-1H-pyrazole (520 mg) in DMF (10 mL) was added 60% sodium hydride (118 mg) at 0° C. tert-Butyl 4-((methylsulfonyl)oxy)piperidine-1-carboxylate (895 mg) was added to the mixture at 0° C. The mixture was stirred at 70° C. overnight. The mixture was quenched with water at room temperature and extracted with ethyl acetate. The organic layer was separated, washed with saturated brine, dried over anhydrous magnesium sulfate and concentrated in vacuo. The residue was purified by silica gel column chromatography (ethyl acetate/hexane) to give the title compound (471 mg).

MS m/z 295.1 [M+1-(Boc)]$^+$.

B) tert-butyl 4-(4-amino-3-(2,2,2-trifluoroethoxy)-1H-pyrazol-1-yl)piperidine-1-carboxylate A mixture of tert-butyl 4-(4-nitro-3-(2,2,2-trifluoroethoxy)-1H-pyrazol-1-yl)piperidine-1-carboxylate (471 mg) and 10% palladium-carbon (63.6 mg) in THF (5.00 mL) and MeOH (5.00 mL) was stirred under normal pressure of hydrogen atmosphere at room temperature for 3 hr. The catalyst was removed by filtration and the filtrate was concentrated in vacuo to give the title compound (425 mg).

MS m/z 266.1 [M+1-(Boc)]$^+$.

C) (S)-tert-butyl 4-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)piperidine-1-carboxylate To a solution of 2-chloro-5-(4-chloro-3-(((2S)-1-(1H-tetrazol-1-yl)propan-2-yl)oxy)phenyl)pyrimidine (451 mg), tert-butyl 4-(4-amino-3-(2,2,2-trifluoroethoxy)-1H-pyrazol-1-yl)piperidine-1-carboxylate (425 mg), BINAP (145 mg) and DBU (0.264 mL) in DMA (5.0 mL) was added Pd$_2$(dba)$_3$ (107 mg) at room temperature. The mixture was stirred at 100° C. under nitrogen atmosphere for 2 hr. Additional Pd$_2$(dba)$_3$ (107 mg) and DMA (5.00 mL) were added to the mixture at 90° C. The mixture was stirred at 100° C. under N$_2$ for 2 hr. The residue was purified by silica gel column chromatography (NH, ethyl acetate/hexane) and silica gel column chromatography (ethyl acetate/hexane) to give the title compound (303 mg).

MS m/z 679.1 [M+1]$^+$.

D) (S)-5-(3-((1-(1H-tetrazol-1-yl)propan-2-yl)oxy)-4-chlorophenyl)-N-(1-(piperidin-4-yl)-3-(2,2,2-trifluoroethoxy)-1H-pyrazol-4-yl)pyrimidin-2-amine hydrochloride To a solution of (S)-tert-butyl 4-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)piperidine-1-carboxylate (300 mg) in MeOH (3.00 mL) was added 4 M hydrogen chloride-ethyl acetate (3.00 mL) at room temperature. The mixture was stirred at room temperature for 2 hr. The mixture was diluted with ethyl acetate and the precipitating solid was collected by filtration. The solid was washed with IPE and dried in in vacuo to give the title compound (233 mg).

MS m/z 579.1 [M+1]$^+$.

E) (S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(2,2,2-trifluoroethoxy)-1H-pyrazol-4-yl)pyrimidin-2-amine To a solution of (S)-5-(3-((1-(1H-tetrazol-1-yl)propan-2-yl)oxy)-4-chlorophenyl)-N-(1-(piperidin-4-yl)-3-(2,2,2-trifluoroethoxy)-1H-pyrazol-4-yl)pyrimidin-2-amine hydrochloride (100 mg) in MeOH (4.00 mL) was added triethylamine (0.023 mL) at room temperature. The mixture was stirred at room temperature for 10 min. Dihydro-2H-pyran-4(3H)-one (0.045 mL), AcOH (0.097 mL) and 2-methylpyridine-borane (34.8 mg) were added to the mixture, and the mixture was stirred at room temperature overnight. The mixture was neutralized with saturated aqueous sodium hydrogencarbonate solution at 0° C. and extracted with ethyl acetate. The organic layer was separated, washed with water and saturated brine, dried over anhydrous magnesium sulfate and concentrated in vacuo. The residue was purified by silica gel column chromatography (NH, ethyl acetate/hexane) to give the title compound (37.0 mg).

$^1$H NMR (300 MHz, DMSO-d$_6$) δ1.26-1.53 (6H, m), 1.68 (2H, d, J=12.7 Hz), 1.80-2.06 (4H, m), 2.15-2.33 (2H, m), 2.89-3.06 (2H, m), 3.19-3.36 (2H, m), 3.81-3.99 (3H, m), 4.69-4.97 (4H, m), 5.09-5.25 (1H, m), 7.23 (1H, d, J=8.3 Hz), 7.36 (1H, s), 7.45 (1H, d, J=8.2 Hz), 7.81 (1H, s), 8.67-8.75 (3H, m), 9.37 (1H, s).

Example 682

(S)-5-(3-((1-(1H-tetrazol-1-yl)propan-2-yl)oxy)-4-chlorophenyl)-N-(3-isopropyl-1-(1-(tetrahydro-2H-pyran-4-yl)piperidin-4-yl)-1H-pyrazol-4-yl)pyrimidin-2-amine

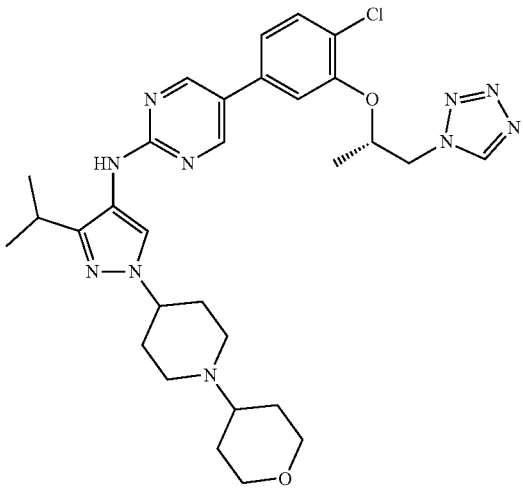 [SMILES: CC(C)c1nn(C2CCN(C3CCOCC3)CC2)cc1Nc1ncc(-c2ccc(Cl)c(O[C@@H](C)Cn3cnnn3)c2)cn1]

A) tert-butyl 4-(3-bromo-1H-pyrazol-1-yl)piperidine-1-carboxylate

A mixture of 3-bromo-1H-pyrazole (2.76 g), tert-butyl 4-((methylsulfonyl)oxy)piperidine-1-carboxylate (5.25 g) and cesium carbonate (12.25 g) in DMF (50 mL) was stirred at 100° C. for 15 hr. The mixture was poured into water and extracted with ethyl acetate. The organic layer was separated, washed with saturated brine, dried over anhydrous magnesium sulfate and concentrated in vacuo. The residue was purified by silica gel column chromatography (NH, ethyl acetate/hexane) to give the title compound (3.43 g).
$^1$H NMR (300 MHz, DMSO-d$_6$) δ1.41 (9H, s), 1.62-1.81 (2H, m), 1.88-2.04 (2H, m), 2.76-2.97 (2H, m), 3.92-4.10 (2H, m), 4.25-4.43 (1H, m), 6.35-6.40 (1H, m), 7.80-7.85 (1H, m).

B) 4-(3-bromo-1H-pyrazol-1-yl)-1-(tetrahydro-2H-pyran-4-yl)piperidine

A mixture of tert-butyl 4-(3-bromo-1H-pyrazol-1-yl)piperidine-1-carboxylate (1.1 g) and 4 M hydrogen chloride-cyclopentyl methyl ether (2.50 mL) in MeOH (10 mL) was stirred at room temperature for 3 days. The mixture was neutralized with 8 M aqueous sodium hydroxide solution and extracted with ethyl acetate. The organic layer was separated, washed with water and saturated brine, dried over anhydrous magnesium sulfate and concentrated in vacuo to give 4-(3-bromo-1H-pyrazol-1-yl)piperidine as colorless oil. A mixture of 4-(3-bromo-1H-pyrazol-1-yl)piperidine, dihydro-2H-pyran-4(3H)-one (1.00 g) and 2-methylpyridine-borane (0.71 g) in MeOH (10 mL) and AcOH (1.00 mL) was stirred at 60° C. for 1 hr. The mixture was neutralized with saturated aqueous sodium hydrogencarbonate solution at 0° C. and extracted with ethyl acetate. The organic layer was washed with water and saturated brine, dried over anhydrous magnesium sulfate and concentrated in vacuo. The residue was purified by silica gel column chromatography (MeOH/ethyl acetate) to give the title compound (0.92 g).
$^1$H NMR (300 MHz, DMSO-d$_6$) δ1.29-1.51 (2H, m), 1.60-1.74 (2H, m), 1.74-1.92 (2H, m), 1.92-2.05 (2H, m), 2.15-2.31 (2H, m), 2.85-3.03 (2H, m), 3.20-3.34 (6H, m), 3.78-3.93 (2H, m), 3.97-4.25 (1H, m), 6.23-6.28 (1H, m), 7.55-7.61 (1H, m).

C) 4-(3-bromo-4-nitro-1H-pyrazol-1-yl)-1-(tetrahydro-2H-pyran-4-yl)piperidine

To a solution of 4-(3-bromo-1H-pyrazol-1-yl)-1-(tetrahydro-2H-pyran-4-yl)piperidine (920 mg) in sulfuric acid (5.00 mL) was added fuming nitric acid (473 mg) dropwise at room temperature and the mixture was stirred at 50° C. for 1 hr. The mixture was poured into iced water and neutralized with saturated aqueous sodium hydrogencarbonate solution. The mixture was extracted with ethyl acetate. The organic layer was separated, washed with saturated brine, dried over anhydrous magnesium sulfate and concentrated in vacuo to give the title compound (915 mg).
$^1$H NMR (300 MHz, DMSO-d$_6$) δ1.29-1.51 (2H, m), 1.60-1.74 (2H, m), 1.74-1.92 (2H, m), 1.92-2.05 (2H, m), 2.15-2.31 (2H, m), 2.85-3.03 (2H, m), 3.20-3.34 (6H, m), 3.78-3.93 (2H, m), 3.97-4.25 (1H, m), 6.23-6.28 (1H, m), 7.55-7.61 (1H, m); MS m/z 359.1 [M+1]$^+$.

D) 4-(4-nitro-3-(prop-1-en-2-yl)-1H-pyrazol-1-yl)-1-(tetrahydro-2H-pyran-4-yl)piperidine A mixture of 4-(3-bromo-4-nitro-1H-pyrazol-1-yl)-1-(tetrahydro-2H-pyran-4-yl)piperidine (200 mg), 4,4,5,5-tetramethyl-2-(prop-1-en-2-yl)-1,3,2-dioxaborolane (187 mg), cesium carbonate (363 mg) and Pd(dppf)C$_{12}$ (20.4 mg) in DME (10 mL) and water (5.00 mL) was stirred at 80° C. under nitrogen atmosphere for 15 hr. The mixture was poured into water and extracted with ethyl acetate. The organic layer was separated, washed with saturated brine, dried over anhydrous magnesium sulfate and concentrated in vacuo. The residue was purified by silica gel column chromatography (NH, ethyl acetate/hexane) to give the title compound (167 mg).
$^1$H NMR (300 MHz, DMSO-d$_6$) δ1.34-1.48 (2H, m), 1.60-1.75 (2H, m), 1.77-2.07 (8H, m), 2.14-2.32 (2H, m), 2.85-3.07 (2H, m), 3.15-3.31 (2H, m), 3.79-3.94 (2H, m), 4.10-4.29 (1H, m), 5.24-5.52 (2H, m), 8.56-8.62 (1H, m); MS m/z 321.2 [M+1]$^+$.

E) 3-isopropyl-1-(1-(tetrahydro-2H-pyran-4-yl)piperidin-4-yl)-1H-pyrazol-4-amine A mixture of 4-(4-nitro-3-(prop-1-en-2-yl)-1H-pyrazol-1-yl)-1-(tetrahydro-2H-pyran-4-yl)piperidine (167 mg) and 10% palladium-carbon (40 mg) in MeOH (10 mL) was stirred under normal pressure of hydrogen atmosphere at room temperature for 3 days. The catalyst was removed by filtration, and the filtrate was concentrated in vacuo to give the title compound (112 mg). $^1$H NMR (300 MHz, DMSO-d$_6$) δ1.09-1.17 (6H, m), 1.33-1.50 (2H, m), 1.61-1.81 (4H, m), 1.84-1.96 (2H, m), 2.13-2.27 (2H, m), 2.34-2.47 (1H, m), 2.76-2.99 (3H, m), 3.20-3.30 (2H, m), 3.36-3.54 (2H, m), 3.69-3.97 (4H, m), 6.87-6.91 (1H, m); MS m/z 293.3 [M+1]$^+$.

F) (S)-5-(3-((1-(1H-tetrazol-1-yl)propan-2-yl)oxy)-4-chlorophenyl)-N-(3-isopropyl-1-(1-(tetrahydro-2H-pyran-4-yl)piperidin-4-yl)-1H-pyrazol-4-yl)pyrimidin-2-amine A mixture of 2-chloro-5-(4-chloro-3-(((2S)-1-(1H-tetrazol-1-yl)propan-2-yl)oxy)phenyl)pyrimidine (148 mg), 3-isopropyl-1-(1-(tetrahydro-2H-pyran-4-yl)piperidin-4-yl)-1H-pyrazol-4-amine (112 mg), BINAP (23.9 mg), DBU (87 mg) and Pd$_2$(dba)$_3$ (17.5 mg) in DMA (5.00 mL) was stirred at 100° C. for 3 hr. The mixture was poured into water and extracted with ethyl acetate. The organic layer was separated, washed with saturated brine, dried over anhydrous magnesium sulfate and concentrated in vacuo. The residue was purified by silica gel column chromatography (NH, ethyl acetate/hexane) to give the title compound (92.0 mg).
$^1$H NMR (300 MHz, DMSO-d$_6$) δ1.11-1.20 (7H, m), 1.29-1.35 (3H, m), 1.35-1.55 (2H, m), 1.57-1.74 (2H, m), 1.74-1.93 (2H, m), 1.93-2.09 (3H, m), 2.16-2.33 (2H, m), 2.39-2.48 (1H, m), 2.90-3.11 (3H, m), 3.20-3.31 (2H, m), 3.81-4.10 (3H, m), 4.66-4.97 (2H, m), 5.05-5.25 (1H, m), 7.14-7.18 (1H, m), 7.32-7.36 (1H, m), 7.40-7.45 (1H, m), 7.79-7.84 (1H, m), 8.55-8.60 (2H, m), 8.75-8.80 (1H, m), 9.21-9.26 (1H, m).

Example 695

5-(3-(((S)-1-(1H-tetrazol-1-yl)propan-2-yl)oxy)-4-chlorophenyl)-N-(1-(trans-4-morpholinocyclohexyl)-3-(trifluoromethyl)-1H-pyrazol-4-yl)pyrimidin-2-amine

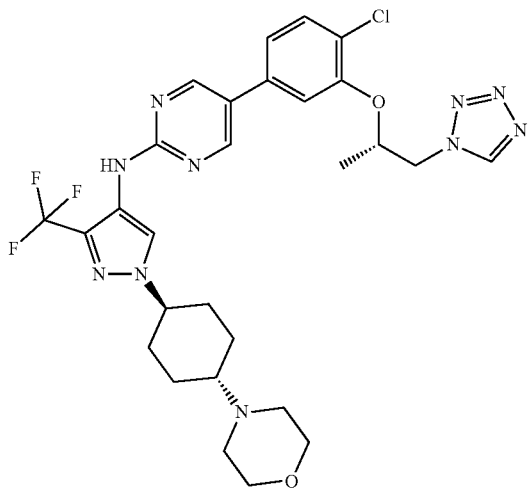 [SMILES: C[C@@H](Cn1cnnn1)Oc1cc(-c2cnc(Nc3cn([C@H]4CC[C@H](N5CCOCC5)CC4)nc3C(F)(F)F)nc2)ccc1Cl]

A) 4-nitro-1-(1,4-dioxaspiro[4.5]decan-8-yl)-3-(trifluoromethyl)-1H-pyrazole

The mixture of 4-nitro-3-(trifluoromethyl)-1H-pyrazole (3.55 g), 1,4-dioxaspiro[4.5]decan-8-yl methanesulfonate (4.63 g) and cesium carbonate (12.77 g) in DMF (50 mL) was stirred at 100° C. for 15 hr. The mixture was poured into water and extracted with ethyl acetate. The organic layer was separated, washed with saturated brine, dried over anhydrous magnesium sulfate and concentrated in vacuo. The residue was purified by silica gel column chromatography (ethyl acetate/hexane) to give the title compound (2.85 g).
$^1$H NMR (300 MHz, DMSO-d$_6$) δ1.57-1.86 (4H, m), 2.00-2.13 (4H, m), 3.84-3.93 (4H, m), 4.39-4.58 (1H, m), 9.21 (1H, s); MS m/z 322.2 [M+1]$^+$.

B) 1-(1,4-dioxaspiro[4.5]decan-8-yl)-3-(trifluoromethyl)-1H-pyrazol-4-amine

A mixture of 4-nitro-1-(1,4-dioxaspiro[4.5]decan-8-yl)-3-(trifluoromethyl)-1H-pyrazole (2.85 g) and 10% palladium-carbon (300 mg) in MeOH (50 mL) was stirred under normal pressure of hydrogen atmosphere at 50° C. for 1 hr. The catalyst was removed by filtration, and the filtrate was concentrated in vacuo. The residue was crystallized from IPE to give the title compound (2.50 g).
$^1$H NMR (300 MHz, DMSO-d$_6$) δ1.54-1.81 (4H, m), 1.81-2.04 (4H, m), 3.84-3.90 (4H, m), 4.09-4.28 (3H, m), 6.99 (1H, s); MS m/z 292.1 [M+1]$^+$.

C) (S)—N-(1-(1,4-dioxaspiro[4.5]decan-8-yl)-3-(trifluoromethyl)-1H-pyrazol-4-yl)-5-(3-((1-(1H-tetrazol-1-yl)propan-2-yl)oxy)-4-chlorophenyl)pyrimidin-2-amine A mixture of 2-chloro-5-(4-chloro-3-(((2S)-1-(1H-tetrazol-1-yl)propan-2-yl)oxy)phenyl)pyrimidine (3.01 g), 1-(1,4-dioxaspiro[4.5]decan-8-yl)-3-(trifluoromethyl)-1H-pyrazol-4-amine (2.5 g), BINAP (534 mg), DBU (1.96 g) and Pd$_2$(dba)$_3$ (393 mg) in DMA (30 mL) was stirred at 120° C. for 1 hr. The mixture was poured into water and extracted with ethyl acetate. The organic layer was separated, washed with saturated brine, dried over anhydrous magnesium sulfate and concentrated in vacuo to give the title compound (2.64 g). This product was subjected to the next reaction without further purification.
MS m/z 606.2 [M+1]$^+$.

D) (S)-4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)cyclohexanone A mixture of (S)—N-(1-(1,4-dioxaspiro[4.5]decan-8-yl)-3-(trifluoromethyl)-1H-pyrazol-4-yl)-5-(3-((1-(1H-tetrazol-1-yl)propan-2-yl)oxy)-4-chlorophenyl)pyrimidin-2-amine (2.64 g) and 1 M aqueous hydrogen chloride solution (5.00 mL) in THF (10 mL) was stirred at 50° C. for 15 hr. The mixture was neutralized with saturated aqueous sodium hydrogencarbonate solution and extracted with ethyl acetate. The organic layer was separated, washed with water and saturated brine, dried over anhydrous magnesium sulfate and concentrated in vacuo. The residue was crystallized from ethyl acetate to give the title compound (1.50 g).
$^1$H NMR (300 MHz, DMSO-d$_6$) δ1.33 (3H, d, J=6.1 Hz), 2.17-2.39 (7H, m), 2.56-2.76 (2H, m), 4.71-4.97 (2H, m), 5.06-5.27 (1H, m), 7.23-7.28 (1H, m), 7.39 (1H, s), 7.44-7.48 (1H, m), 8.23 (1H, s), 8.75 (2H, s), 9.01 (1H, s), 9.37 (1H, s); MS m/z 562.2 [M+1]$^+$.

E) 5-(3-(((S)-1-(1H-tetrazol-1-yl)propan-2-yl)oxy)-4-chlorophenyl)-N-(1-(trans-4-morpholinocyclohexyl)-3-(trifluoromethyl)-1H-pyrazol-4-yl)pyrimidin-2-amine 2-Methylpyridine-borane (114 mg) was added to a solution of (S)-4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)cyclohexanone (200 mg) and morpholine (154 mg) in MeOH (5.00 mL) and AcOH (0.50 mL) at room temperature and the mixture was stirred at 70° C. for 1 hr. The mixture was neutralized with saturated aqueous sodium hydrogencarbonate solution and extracted with ethyl acetate. The organic layer was separated, washed with water and saturated brine, dried over anhydrous magnesium sulfate and concentrated in vacuo. The residue was purified by silica gel column chromatography (NH, ethyl acetate/hexane) to give the more polar compound, the title compound (85.0 mg).

$^1$H NMR (300 MHz, DMSO-$d_6$) δ1.33 (3H, d, J=6.0 Hz), 1.68-1.88 (2H, m), 1.69-1.70 (1H, m), 1.87-2.03 (1H, m), 2.05-2.17 (2H, m), 2.22-2.41 (m, 1H), 2.45-2.50 (4H, m), 3.54-3.60 (4H, m), 4.15-4.29 (1H, m), 4.75-4.94 (2H, m), 5.13-5.22 (1H, m), 7.23-7.28 (1H, m), 7.39 (1H, s), 7.41-7.52 (1H, m), 8.14 (s, 1H), 8.74 (s, 2H), 8.96 (s, 1H), 9.37 (s, 1H).

Example 772

5-(3-(((S)-1-(1H-tetrazol-1-yl)propan-2-yl)oxy)-4-chlorophenyl)-N-(1-(trans-4-morpholinocyclohexyl)-3-(2,2,2-trifluoroethoxy)-1H-pyrazol-4-yl)pyrimidin-2-amine

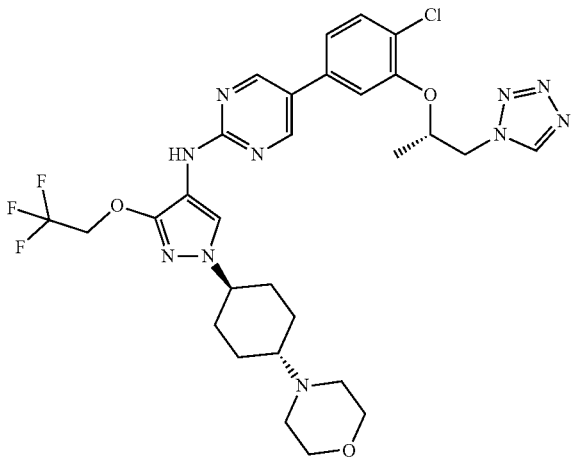 [SMILES: C[C@@H](Cn1cnnn1)Oc1cc(-c2cnc(Nc3cn([C@H]4CC[C@H](N5CCOCC5)CC4)nc3OCC(F)(F)F)nc2)ccc1Cl]

A) 1-{1,4-dioxaspiro[4.5]decan-8-yl}-4-nitro-3-(2,2,2-trifluoroethoxy)-1H-pyrazole To a solution of 1,4-dioxaspiro[4.5]decan-8-yl methanesulfonate (1.50 g) and 4-nitro-5-(2,2,2-trifluoroethoxy)-1H-pyrazole (1.35 g) in DMF (29 mL) was added cesium carbonate (4.13 g) at room temperature and the mixture was stirred at 100° C. for 15 hr. The mixture was poured into water and extracted with ethyl acetate. The organic layer was separated, washed with saturated brine, dried over anhydrous magnesium sulfate and concentrated in vacuo. The residue was purified by silica gel column chromatography (NH, ethyl acetate/hexane) to give the title compound (961 mg).

$^1$H NMR (300 MHz, DMSO-$d_6$) δ1.58-1.88 (4H, m), 1.93-2.05 (4H, m), 3.85-3.93 (4H, m), 4.18-4.28 (1H, m), 4.98 (2H, q, J=9.0 Hz), 8.80 (1H, s); MS m/z 352.1 [M+1]$^+$.

B) 1-{1,4-dioxaspiro[4.5]decan-8-yl}-3-(2,2,2-trifluoroethoxy)-1H-pyrazol-4-amine A mixture of 1-{1,4-dioxaspiro[4.5]decan-8-yl}-4-nitro-3-(2,2,2-trifluoroethoxy)-1H-pyrazole (4.7 g) and 10% palladium-carbon (430 mg) in EtOH (40 mL) and ethyl acetate (40 mL) was stirred under normal pressure of hydrogen atmosphere at room temperature for 15 hr. The catalyst was removed by filtration, and then the filtrate was concentrated in vacuo to give the title compound (4.00 g). This product was subjected to the next reaction without further purification.

$^1$H NMR (300 MHz, DMSO-$d_6$) δ1.56-1.89 (8H, m), 3.41 (2H, brs), 3.82-3.94 (5H, m), 4.69 (2H, q, J=9.1 Hz), 7.02 (1H, s); MS m/z 322.1 [M+1]$^+$.

[0401]

C) (S)—N-(1-(1,4-dioxaspiro[4.5]decan-8-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine To a solution of 1-{1,4-dioxaspiro[4.5]decan-8-yl}-3-(2,2,2-trifluoroethoxy)-1H-pyrazol-4-amine (865 mg), 2-chloro-5-(4-chloro-3-(((2S)-1-(1H-tetrazol-1-yl)propan-2-yl)oxy)phenyl)pyrimidine (944 mg), BINAP (167 mg) and DBU (819 mg) in DMA (20 mL) was added Pd$_2$(dba)$_3$ (123 mg) at room temperature and the mixture was stirred at 120° C. under nitrogen atmosphere for 2 hr. The mixture was poured into water and extracted with ethyl acetate. The organic layer was separated, washed with saturated brine, dried over anhydrous magnesium sulfate and concentrated in vacuo. The residue was purified by silica gel column chromatography (ethyl acetate/hexane) to give the title compound (501 mg).

$^1$H NMR (300 MHz, DMSO-$d_6$) δ1.33 (3H, d, J=6.3 Hz), 1.67-1.88 (4H, m), 1.88-1.98 (4H, m), 3.86-3.92 (4H, m), 4.40-4.13 (1H, m), 4.73-4.94 (2H, m), 5.12-5.22 (1H, m), 7.21-7.26 (1H, m), 7.37 (1H, s), 7.44-7.47 (1H, m), 7.80 (1H, s), 8.71 (2H, s), 8.75 (1H, s), 9.37 (s, 1H).

MS m/z 636.2 [M+1]$^+$.

D) (S)-4-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclohexanone 1 M Aqueous hydrogen chloride solution (3.00 mL) was added to a solution of (S)—N-(1-(1,4-dioxaspiro[4.5]decan-8-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine (501 mg) in MeOH (10 mL) at room temperature and the mixture was stirred for 2 days. The mixture was poured into water and extracted with ethyl acetate. The organic layer was separated, washed with saturated brine, dried over anhydrous magnesium sulfate and concentrated in vacuo. The residue was purified by silica gel column chromatography (ethyl acetate/hexane) to give the title compound (300 mg).

$^1$H NMR (300 MHz, DMSO-$d_6$) δ1.32 (3H, d, J=6.3 Hz), 2.08-2.40 (6H, m), 2.52-2.65 (2H, m), 4.48-4.58 (1H, m), 4.77-4.94 (2H, m), 5.14-5.22 (1H, m), 7.21-7.27 (1H, m), 7.37 (1H, s), 7.42-7.47 (1H, m), 7.88 (1H, s), 8.71 (2H, s), 8.77 (1H, s), 9.37 (1H, s); MS m/z 592.2 [M+1]⁺.

E) 5-(3-(((S)-1-(1H-tetrazol-1-yl)propan-2-yl)oxy)-4-chlorophenyl)-N-(1-(trans-4-morpholinocyclohexyl)-3-(2,2,2-trifluoroethoxy)-1H-pyrazol-4-yl)pyrimidin-2-amine 2-Methylpyridine-borane (81.2 mg) was added to a solution of (S)-4-(4-((5-(3-(((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclohexanone (150 mg) and morpholine (109 mg) in MeOH (5.00 mL) and AcOH (0.5 mL) at room temperature. The mixture was stirred at 60° C. for 1 hr. The mixture was neutralized with saturated aqueous sodium hydrogencarbonate solution and extracted with ethyl acetate. The organic layer was separated, washed with water and saturated brine, dried over anhydrous magnesium sulfate and concentrated in vacuo. The residue was purified by silica gel column chromatography (NH, ethyl acetate/hexane) to give the more polar compound, the title compound (48.0 mg).
¹H NMR (300 MHz, DMSO-d₆) δ1.26-1.46 (5H, m), 1.60-1.80 (2H, m), 1.84-1.97 (2H, m), 2.00-2.13 (2H, m), 2.20-2.25 (1H, m), 2.45-2.50 (4H, m), 3.49-3.68 (4H, m), 3.91-4.09 (1H, m), 4.75-4.96 (2H, m), 5.07-5.24 (1H, m), 7.13-7.30 (1H, m), 7.30-7.40 (1H, m), 7.39-7.51 (1H, m), 7.74-7.84 (1H, m), 8.58-8.80 (3H, m), 9.29-9.45 (1H, m).

Example 790

(S)-2-((1-(1H-tetrazol-1-yl)propan-2-yl)oxy)-4-(2-((1-(1-(tetrahydro-2H-pyran-4-yl)piperidin-4-yl)-3-(2,2,2-trifluoroethoxy)-1H-pyrazol-4-yl)amino)pyrimidin-5-yl)benzonitrile

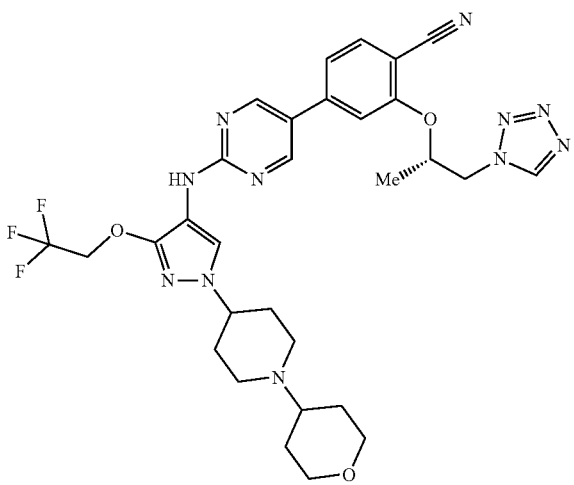 [SMILES: C[C@@H](Cn1cnnn1)Oc1cc(-c2cnc(Nc3cn(C4CCN(C5CCOCC5)CC4)nc3OCC(F)(F)F)nc2)ccc1C#N]

A) 4-(4-nitro-3-(2,2,2-trifluoroethoxy)-1H-pyrazol-1-yl)piperidine hydrochloride To a solution of tert-butyl 4-(4-nitro-3-(2,2,2-trifluoroethoxy)-1H-pyrazol-1-yl)piperidine-1-carboxylate (4.31 g) in MeOH (20 mL) was added 4 M hydrogen chloride-ethyl acetate (40 mL) at room temperature. The mixture was stirred at room temperature for 4 hr. The mixture was concentrated in vacuo to give the title compound (3.60 g). The obtained solid was used in the next reaction without purification.
MS m/z 295.1 [M+1]⁺.

B) 4-(4-nitro-3-(2,2,2-trifluoroethoxy)-1H-pyrazol-1-yl)-1-(tetrahydro-2H-pyran-4-yl)piperidine To a solution of 4-(4-nitro-3-(2,2,2-trifluoroethoxy)-1H-pyrazol-1-yl)piperidine hydrochloride (3.82 g) in MeOH (40 mL) was added triethylamine (1.59 mL) at 0° C. The mixture was stirred at room temperature for 10 min. Dihydro-2H-pyran-4(3H)-one (3.45 g), AcOH (6.77 mL) and 2-methylpyridine-borane (2.46 g) were added to the mixture at room temperature. The mixture was stirred at room temperature for 14 hr. The mixture was neutralized with saturated aqueous sodium hydrogencarbonate solution at 0° C. and extracted with ethyl acetate. The organic layer was separated, washed with water and saturated brine, dried over anhydrous magnesuim sulfate and concentrated in vacuo. The residue was purified by silica gel column chromatography (ethyl acetate/hexane) to give the title compound (2.98 g).
MS m/z 379.1 [M+1]⁺.

C) 1-(1-(tetrahydro-2H-pyran-4-yl)piperidin-4-yl)-3-(2,2,2-trifluoroethoxy)-1H-pyrazol-4-amine A mixture of 4-(4-nitro-3-(2,2,2-trifluoroethoxy)-1H-pyrazol-1-yl)-1-(tetrahydro-2H-pyran-4-yl)piperidine (570 mg) and 10% palladium-carbon (32.4 mg) in EtOH (20 mL)/ethyl acetate (20 mL) was stirred under normal pressure of hydrogen atmosphere for 14 hr. The catalyst was removed by filtration, and then the filtrate was concentrated in vacuo to give the title compound (500 mg). This product was subjected to the next reaction without further purification.
MS m/z 349.2 [M+1]⁺.

D) (S)-2-((1-(1H-tetrazol-1-yl)propan-2-yl)oxy)-4-(2-((1-(1-(tetrahydro-2H-pyran-4-yl)piperidin-4-yl)-3-(2,2,2-trifluoroethoxy)-1H-pyrazol-4-yl)amino)pyrimidin-5-yl)benzonitrile A mixture of 1-(1-(tetrahydro-2H-pyran-4-yl)piperidin-4-yl)-3-(2,2,2-trifluoroethoxy)-1H-pyrazol-4-amine (100 mg), (S)-2-((1-(1H-tetrazol-1-yl)propan-2-yl)oxy)-4-(2-chloropyrimidin-5-yl)benzonitrile (98.0 mg), DBU (65.5 mg), BINAP (35.7 mg) and Pd₂(dba)₃ (26.2 mg) in DMA (4.00 mL) was heated at 100° C. for 2 hr under microwave irradiation. The mixture was poured into water at room temperature and extracted with ethyl acetate. The organic layer was separated, washed with water and saturated brine, dried over anhydrous magnesium sulfate and concentrated in vacuo. The residue was purified by silica gel column chromatography (MeOH/ethyl acetate) and column chromatography (NH, ethyl acetate/hexane) and the desired fractions were concentrated in vacuo. The residue was crystallized from ethyl acetate/hexane to give the title compound (26.0 mg).
¹H NMR (300 MHz, DMSO-d₆) δ1.35 (3H, d, J=6.1 Hz), 1.38-1.51 (2H, m), 1.68 (2H, d, J=13.4 Hz), 1.81-1.91 (2H, m), 1.93-2.02 (2H, m), 2.21-2.30 (2H, m), 2.40-2.47 (1H, m), 2.92-3.02 (2H, m), 3.22-3.30 (2H, m), 3.85-3.99 (3H, m), 4.72-4.99 (4H, m), 5.29-5.39 (1H, m), 7.39 (1H, d, J=8.3 Hz), 7.47 (1H, s), 7.75 (1H, d, J=8.1 Hz), 7.82 (1H, s), 8.80 (2H, s), 8.89 (1H, s), 9.35 (1H, s).

Example 795

(S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(2,2,2-trifluoroethoxy)-1H-pyrazol-4-yl)pyrimidin-2-amine

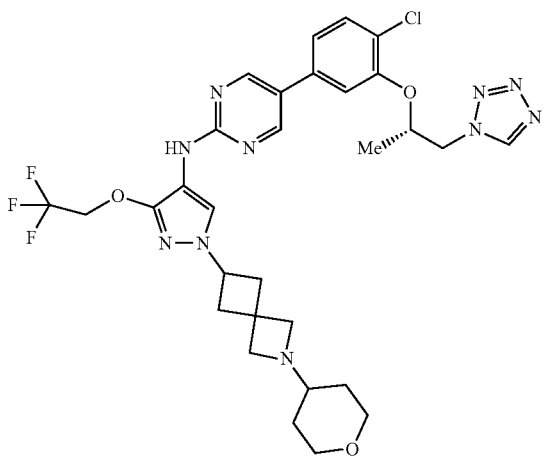 [SMILES: C[C@@H](Cn1cnnn1)Oc1cc(-c2cnc(Nc3cn(C4CC5(C4)CN(C4CCOCC4)C5)nc3OCC(F)(F)F)nc2)ccc1Cl]

A) tert-butyl 6-(methanesulfonyloxy)-2-azaspiro[3.3]heptane-2-carboxylate

To a solution of tert-butyl 6-hydroxy-2-azaspiro[3.3]heptane-2-carboxylate (30.0 g) and triethylamine (29.2 mL) in THF (600 mL) was added methanesulfonyl chloride (13.0 mL) at 0° C. The mixture was stirred at room temperature under nitrogen atmosphere for 2 hr. The mixture was quenched with water at 0° C. and extracted with ethyl acetate. The organic layer was separated, washed with saturated brine, dried over anhydrous magnesium sulfate and concentrated in vacuo to give the title compound (40.7 g).

$^1$H NMR (300 MHz, CDCl$_3$) δ1.43 (9H, s), 2.39-2.55 (2H, m), 2.61-2.76 (2H, m), 2.98 (3H, s), 3.93 (4H, s) 4.89 (1H, quin, J=7.18 Hz).

B) tert-butyl 6-[4-nitro-3-(2,2,2-trifluoroethoxy)-1H-pyrazol-1-yl]-2-azaspiro[3.3]heptane-2-carboxylate To a solution of 4-nitro-3-(2,2,2-trifluoroethoxy)-1H-pyrazole (28.9 g) and tert-butyl 6-(methanesulfonyloxy)-2-azaspiro[3.3]heptane-2-carboxylate (32.9 g) in DMF (500 mL) was added cesium carbonate (92.2 g) at room temperature. The mixture was stirred at 100° C. for 14 hr. The mixture was quenched with water at 0° C. and extracted with ethyl acetate. The organic layer was separated, washed with water and saturated brine, dried over anhydrous magnesuim sulfate and concentrated in vacuo. The residue was purified by silica gel column chromatography (NH, ethyl acetate/hexane) and silica gel column chromatography (ethyl acetate/hexane) to give the title compound (36.0 g).

MS m/z 407.2 [M+1]$^+$.

C) 6-[4-nitro-3-(2,2,2-trifluoroethoxy)-1H-pyrazol-1-yl]-2-azaspiro[3.3]heptane To a solution of tert-butyl 6-[4-nitro-3-(2,2,2-trifluoroethoxy)-1H-pyrazol-1-yl]-2-azaspiro[3.3]heptane-2-carboxylate (20.0 g) in toluene (200 mL) was added TFA (32.3 mL) at 0° C. The mixture was stirred at room temperature for 1 hr. After concentration to remove TFA, the mixture was neutralized with saturated aqueous sodium hydrogencarbonate solution at 0° C. and extracted with ethyl acetate. The organic layer was separated, washed with water and saturated brine, dried over anhydrous magnesium sulfate and concentrated in vacuo to give the title compound (15.0 g). The obtained compound was used in the next reaction without purification.

MS m/z 307.1 [M+1]$^+$.

D) 6-[4-nitro-3-(2,2,2-trifluoroethoxy)-1H-pyrazol-1-yl]-2-(tetrahydro-2H-pyran-4-yl)-2-azaspiro[3.3]heptane To a solution of 6-[4-nitro-3-(2,2,2-trifluoroethoxy)-1H-pyrazol-1-yl]-2-azaspiro[3.3]heptane (15.0 g) and dihydro-2H-pyran-4(3H)-one (14.6 g) in THF (150 mL) and MeOH (150 mL) was added AcOH (13.9 mL) at room temperature. The mixture was stirred at room temperature for 10 min. Sodium triacetoxyborohydride (12.4 g) was added to the mixture portionwise at 0° C. The mixture was stirred at room temperature for 1 hr. After concentration to reduce the solvent volume, the mixture was neutralized with saturated aqueous sodium hydrogencarbonate solution at 0° C. and extracted with ethyl acetate. The organic layer was separated, washed with water and saturated brine, dried over anhydrous magnesuim sulfate and concentrated in vacuo. The residue was purified by silica gel column chromatography (NH, ethyl acetate/hexane) to give the title compound (17.7 g).

MS m/z 391.1 [M+1]$^+$.

E) 1-[2-(tetrahydro-2H-pyran-4-yl)-2-azaspiro[3.3]heptan-6-yl]-3-(2,2,2-trifluoroethoxy)-1H-pyrazol-4-amine A mixture of 6-[4-nitro-3-(2,2,2-trifluoroethoxy)-1H-pyrazol-1-yl]-2-(tetrahydro-2H-pyran-4-yl)-2-azaspiro[3.3]heptane (10.0 g) and 10% palladium-carbon (1.36 g) in MeOH (100 mL) and THF (100 mL) was stirred under normal pressure of hydrogen atmosphere at room temperature for 2 hr. The catalyst was removed by filtration, and then the filtrate was concentrated in vacuo to give the title compound (9.22 g). The obtained compound was used in the next reaction without purification.

MS m/z 361.3 [M+1]$^+$.

F) (S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(2,2,2-trifluoroethoxy)-1H-pyrazol-4-yl)pyrimidin-2-amine To a solution of 2-chloro-5-(4-chloro-3-(((2S)-1-(1H-tetrazol-1-yl)propan-2-yl)oxy)phenyl)pyrimidine (8.95 g), 1-[2-(tetrahydro-2H-pyran-4-yl)-2-azaspiro[3.3]heptan-6-yl]-3-(2,2,2-trifluoroethoxy)-1H-pyrazol-4-amine (9.22 g), BINAP (1.58 g) and Pd$_2$(dba)$_3$ (1.16 g) in DMA (100 mL) was added DBU (7.60 mL) at room temperature. The mixture was stirred at 100° C. under nitrogen atmosphere for 1 hr. The mixture was quenched with water at 0° C. and extracted with ethyl acetate. The organic layer was separated, washed with water and saturated brine, dried over anhydrous magnesium sulfate and concentrated in vacuo. After azeotropy with toluene, the residue was purified by silica gel column chromatography (NH, ethyl acetate/

213 hexane) to give the title compound (6.00 g). The obtained compound (3.05 g) was recrystallized from ethyl acetate-hexane to give the title compound (2.67 g).

$^1$H NMR (300 MHz, CDCl$_3$) δ1.24-1.47 (5H, m), 1.60-1.68 (2H, m), 2.09-2.23 (1H, m), 2.63 (4H, d, J=8.1 Hz), 3.20-3.43 (6H, m), 3.91-4.02 (2H, m), 4.46 (1H, quin, J=7.9 Hz), 4.58-4.77 (3H, m), 4.78-4.90 (2H, m), 6.84 (2H, d, J=14.8 Hz), 7.04-7.11 (1H, m), 7.44 (1H, d, J=8.3 Hz), 7.89 (1H, s), 8.52 (2H, s), 8.95 (1H, s).

Example 802

1-(trans-4-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclohexyl)-3-methylazetidin-3-ol

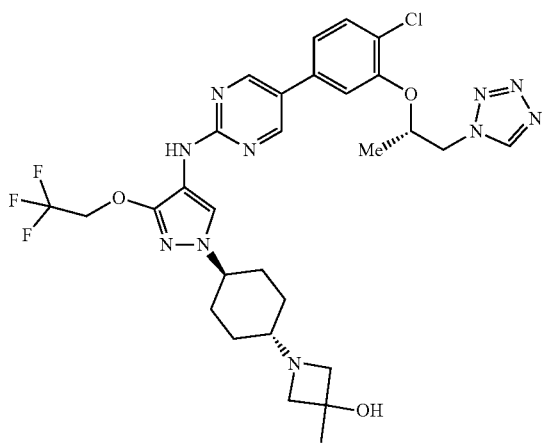 [SMILES: C[C@@H](Cn1cnnn1)Oc1cc(-c2cnc(Nc3cn([C@H]4CC[C@H](N5CC(C)(O)C5)CC4)nc3OCC(F)(F)F)nc2)ccc1Cl]

A mixture of (S)-4-(4-((5-(3-(((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclohexanone (200 mg), 2-methylpyridine-borane (90.3 mg), triethylamine (119 mg) and 3-methylazetidin-3-ol hydrochloride (124 mg) in MeOH (10 mL) and AcOH (1.0 mL) was stirred at 60° C. for 2 hr. The reaction mixture was concentrated under reduced pressure. The residue was partitioned between ethyl acetate and saturated aqueous sodium hydrogencarbonate solution. The organic layer was separated, washed with saturated brine, dried over anhydrous sodium sulfate and concentrated under reduced pressure. The residue was purified by silica gel column chromatography (ethyl acetate/hexane and MeOH/ethyl acetate) to give the title compound (123 mg) and the compound of Example 801 (98.1 mg, cis form), respectively.

$^1$H NMR (300 MHz, DMSO-d$_6$) δ0.99-1.14 (2H, m), 1.32 (3H, d, J=5.3 Hz), 1.33 (3H, s), 1.59-1.73 (2H, m), 1.80 (2H, d, J=12.0 Hz), 1.92-1.99 (3H, m), 2.81 (2H, d, J=6.5 Hz), 3.14 (2H, d, J=6.3 Hz), 3.85-3.98 (1H, m), 4.70-4.94 (4H, m), 5.07 (1H, s), 5.12-5.22 (1H, m), 7.24 (1H, d, J=8.2 Hz), 7.36 (1H, s), 7.45 (1H, d, J=8.3 Hz), 7.78 (1H, s), 8.70 (2H, s), 8.72 (1H, brs), 9.37 (1H, s).

214

Example 806

5-(3-(((S)-1-(1H-tetrazol-1-yl)propan-2-yl)oxy)-4-chlorophenyl)-N-(3-(2,2-difluoroethoxy)-1-(trans-4-morpholinocyclohexyl)-1H-pyrazol-4-yl)pyrimidin-2-amine

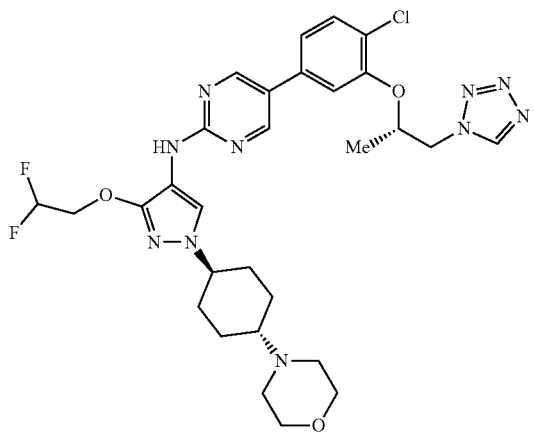 [SMILES: C[C@@H](Cn1cnnn1)Oc1cc(-c2cnc(Nc3cn([C@H]4CC[C@H](N5CCOCC5)CC4)nc3OCC(F)F)nc2)ccc1Cl]

A) 1-(3-(2,2-difluoroethoxy)-1H-pyrazol-1-yl)ethanone

A mixture of 1-(3-hydroxy-1H-pyrazol-1-yl)ethanone (5.00 g), 2,2-difluoroethyl trifluoromethanesulfonate (12.7 g) and potassium carbonate (8.20 g) in DMF (80 mL) was stirred at room temperature for 42 hr. The reaction mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane) to give the title compound (2.85 g).

$^1$H NMR (300 MHz, CDCl$_3$) δ2.59 (3H, s), 4.47 (2H, td, J=13.3, 4.2 Hz), 6.13 (1H, tt, J=55.1, 4.0 Hz), 6.01 (1H, d, J=2.9 Hz), 8.08 (1H, d, J=2.9 Hz); MS m/z 191.0 [M+1]$^+$.

B) 3-(2,2-difluoroethoxy)-1H-pyrazole

A mixture of 1-(3-(2,2-difluoroethoxy)-1H-pyrazol-1-yl)ethanone (2.84 g) and potassium carbonate (4.11 g) in MeOH (45 mL) was stirred at room temperature for 2.5 hr. The reaction mixture was concentrated under reduced pressure. The residue was diluted with ethyl acetate (100 mL). The resulting mixture was stirred at room temperature for 3 hr and then filtered. The filtrate was concentrated under reduced pressure to give the title compound (2.22 g).

$^1$H NMR (300 MHz, CDCl$_3$) δ4.39 (2H, td, J=13.4, 4.1 Hz), 5.80 (1H, s), 6.12 (1H, tt, J=55.8, 4.3 Hz), 7.38 (1H, s), 9.18 (1H, brs); MS m/z 149.1 [M+1]$^+$.

C) 3-(2,2-difluoroethoxy)-4-nitro-1H-pyrazole

Sulfuric acid (9.22 g) was added to 3-(2,2-difluoroethoxy)-1H-pyrazole (2.21 g) at 0° C. Nitric acid (4.80 g) was added to the mixture at 0° C. The mixture was stirred at 60° C. for 75 min. The reaction mixture was poured into ice water (ca. 150 mL). The resulting mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane) to give the title compound (2.29 g).

$^1$H NMR (300 MHz, CDCl$_3$) δ4.55 (2H, td, J=12.9, 4.2 Hz), 6.19 (1H, tt, J=54.9, 3.9 Hz), 8.21 (1H, s), NH was not assigned;
MS m/z 194.1 [M+1]$^+$.

D) 3-(2,2-difluoroethoxy)-1-{1,4-dioxaspiro[4.5]
decan-8-yl}-4-nitro-1H-pyrazole A mixture of 3-(2,2-difluoroethoxy)-4-nitro-1H-pyrazole (1.45 g), 1,4-dioxaspiro[4.5]decan-8-yl methanesulfonate (3.54 g) and cesium carbonate (4.88 g) in DMF (30 mL) was stirred at 120° C. for 3 hr. The reaction mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane) to give the title compound (2.32 g). $^1$H NMR (300 MHz, CDCl$_3$) δ1.67-1.79 (2H, m), 1.86-1.94 (2H, m), 1.96-2.05 (2H, m), 2.08-2.17 (2H, m), 3.98 (5H, s), 4.51 (2H, td, J=12.9, 4.3 Hz), 6.18 (1H, tt, J=56.0, 5.4 Hz), 8.05 (1H, s); MS m/z 334.1 [M+1]$^+$.

E) 3-(2,2-difluoroethoxy)-1-{1,4-dioxaspiro[4.5]
decan-8-yl}-1H-pyrazol-4-amine

A mixture of 3-(2,2-difluoroethoxy)-1-{1,4-dioxaspiro[4.5]decan-8-yl}-4-nitro-1H-pyrazole (2.14 g) and 10% palladium-carbon (620 mg) in MeOH (40 mL) and THF (40 mL) was stirred at room temperature under normal pressure of hydrogen atmosphere for 4 hr. The reaction mixture was filtered through Celite. The filtrate was concentrated under reduced pressure to give the title compound (2.30 g). This product was used in the next step without further purification.

$^1$H NMR (300 MHz, CDCl$_3$) δ 1.70 (2H, dd, J=12.9, 4.4 Hz), 1.81-2.03 (6H, m), 2.63 (2H, brs), 3.83-3.92 (1H, m), 3.97 (4H, s), 4.37 (2H, td, J=13.4, 4.3 Hz), 5.92-6.35 (1H, m), 6.94 (1H, s); MS m/z 304.1 [M+1]$^+$.

F) 5-(4-chloro-3-{[(2S)-1-(1H-tetrazol-1-yl)propan-
2-yl]oxy}phenyl)-N-[3-(2,2-difluoroethoxy)-1-{1,4-
dioxaspiro[4.5]decan-8-yl}-1H-pyrazol-4-yl]pyrimi-
din-2-amine A mixture of 2-chloro-5-(4-chloro-3-(((2S)-1-(1H-tetrazol-1-yl)propan-2-yl)oxy)phenyl)pyrimidine (1.74 g), 3-(2,2-difluoroethoxy)-1-{1,4-dioxaspiro[4.5]decan-8-yl}-1H-pyrazol-4-amine (1.37 g), Pd$_2$(dba)$_3$ (257 mg), BINAP (281 mg) and DBU (1.03 g) in DMA (30 mL) was stirred at 100° C. for 1.5 hr under argon atmosphere. The reaction mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane) and silica gel column chromatography (NH, ethyl acetate/hexane) to give the title compound (2.12 g). $^1$H NMR (300 MHz, CDCl$_3$) δ1.44 (3H, d, J=6.1 Hz), 1.67-1.78 (2H, m), 1.86-1.95 (2H, m), 2.05-2.22 (4H, m), 3.97-4.04 (5H, m), 4.44 (2H, td, J=13.3, 4.3 Hz), 4.67-4.77 (1H, m), 4.82-4.91 (2H, m), 6.14 (1H, tt, J=55.7, 4.3 Hz), 6.80 (1H, s), 6.89 (1H, s), 7.08 (1H, dd, J=8.3, 1.6 Hz), 7.45 (1H, d, J=8.2 Hz), 7.93 (1H, s), 8.52 (2H, s), 8.97 (1H, s); MS m/z 618.2 [M+1]$^+$.

G) 4-(4-{[5-(4-chloro-3-{[(2S)-1-(1H-tetrazol-1-yl)
propan-2-yl]oxy}phenyl)pyrimidin-2-yl]amino}-3-
(2,2-difluoroethoxy)-1H-pyrazol-1-yl)cyclohexan-1-
one 2 M aqueous hydrogen chloride solution (19 mL) was added to a solution of 5-(4-chloro-3-{[(2S)-1-(1H-tetrazol-1-yl)propan-2-yl]oxy}phenyl)-N-[3-(2,2-difluoroethoxy)-1-{1,4-dioxaspiro[4.5]decan-8-yl}-1H-pyrazol-4-yl]pyrimidin-2-amine (2.11 g) in MeOH (40 mL) at room temperature. The mixture was stirred at room temperature for 15 hr. The reaction mixture was concentrated under reduced pressure. The residue was partitioned between ethyl acetate and saturated aqueous sodium hydrogencarbonate solution. The organic layer was separated, washed with saturated brine, dried over anhydrous sodium sulfate and concentrated under reduced pressure. The residue was purified by silica gel column chromatography (ethyl acetate/hexane and MeOH/ethyl acetate) and by recrystallization from ethyl acetate/hexane to give the title compound (1.10 g).

$^1$H NMR (300 MHz, DMSO-d$_6$) δ1.33 (3H, d, J=6.1 Hz), 2.11-2.38 (6H, m), 2.53-2.66 (2H, m), 4.39 (2H, td, J=14.6, 3.5 Hz), 4.48-4.58 (1H, m), 4.75-4.85 (1H, m), 4.86-4.96 (1H, m), 5.13-5.22 (1H, m), 6.34 (1H, tt, J=55.2, 4.0 Hz), 7.24 (1H, d, J=8.3 Hz), 7.37 (1H, s), 7.45 (1H, d, J=8.3 Hz), 7.86 (1H, s), 8.71 (3H, s), 9.37 (1H, s); MS m/z 574.2 [M+1]$^+$.

H) 5-(3-(((S)-1-(1H-tetrazol-1-yl)propan-2-yl)oxy)-
4-chlorophenyl)-N-(3-(2,2-difluoroethoxy)-1-(trans-
4-morpholinocyclohexyl)-1H-pyrazol-4-yl)pyrimi-
din-2-amine A mixture of 4-(4-{[5-(4-chloro-3-{[(2S)-1-(1H-tetrazol-1-yl)propan-2-yl]oxy}phenyl)pyrimidin-2-yl]amino}-3-(2, 2-difluoroethoxy)-1H-pyrazol-1-yl)cyclohexan-1-one (200 mg), morpholine (90.6 mg) and 2-methylpyridine-borane (109 mg, 85%) in MeOH (10 mL) and AcOH (1.00 mL) was stirred at 60° C. for 40 min. The reaction mixture was partitioned between ethyl acetate and saturated aqueous sodium hydrogencarbonate solution. The organic layer was separated, washed with saturated brine, dried over anhydrous sodium sulfate and concentrated under reduced pressure. The residue was purified by silica gel column chromatography (NH, ethyl acetate/hexane and MeOH/ethyl acetate) to give the title compound (86.3 mg) and the compound of Example 805 (120 mg, cis form), respectively.

$^1$H NMR (300 MHz, DMSO-d$_6$) δ1.33 (3H, d, J=6.1 Hz), 1.34-1.46 (2H, m), 1.63-1.77 (2H, m), 1.93 (2H, d, J=12.1 Hz), 2.06 (2H, d, J=11.0 Hz), 2.21-2.32 (1H, m), 3.57 (4H, d, J=3.7 Hz), 3.85-3.97 (1H, m), 4.36 (2H, td, J=14.6, 4.1 Hz), 4.74-4.85 (1H, m), 4.86-4.96 (1H, m), 5.11-5.23 (1H, m), 6.33 (1H, tt, J=55.3, 3.9 Hz), 7.24 (1H, d, J=9.2 Hz), 7.36 (1H, s), 7.45 (1H, d, J=8.3 Hz), 7.77 (1H, s), 8.66 (1H, s), 8.70 (2H, s), 9.37 (1H, s), 4H were hidden by the residue of DMSO.

Example 817

2-(((S)-1-(1H-tetrazol-1-yl)propan-2-yl)oxy)-4-(2-((1-(trans-4-morpholinocyclohexyl)-3-(2,2,2-trifluoroethoxy)-1H-pyrazol-4-yl)amino)pyrimidin-5-yl)benzonitrile hydrochloride

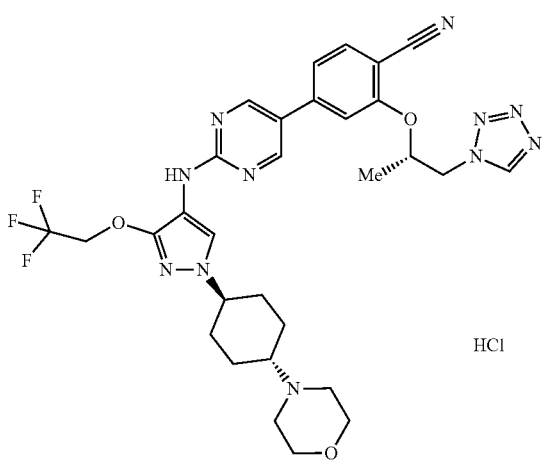 [SMILES: C[C@@H](Cn1cnnn1)Oc1cc(-c2cnc(Nc3cn([C@H]4CC[C@H](N5CCOCC5)CC4)nc3OCC(F)(F)F)nc2)ccc1C#N ; Cl]

A) (S)-2-((1-(1H-tetrazol-1-yl)propan-2-yl)oxy)-4-(2-chloropyrimidin-5-yl)benzonitrile A mixture of 4-(4,4,5,5-tetramethyl-1,3,2-dioxaborolan-2-yl)-2-(((2S)-1-(1H-tetrazol-1-yl)propan-2-yl)oxy)benzonitrile (7.26 g), 5-bromo-2-chloropyrimidine (5.93 g), Pd(dppf)Cl$_2$—CH$_2$C$_{12}$ (1.67 g), cesium carbonate (19.99 g) and DME (80 mL)/water (20 mL) was stirred at 100° C. under normal pressure of nitrogen atmosphere for 5 hr. The mixture was quenched with water. The insoluble material was removed by filtration, and the filtrate was extracted with ethyl acetate. The organic layer was separated, dried over anhydrous magnesium sulfate and concentrated in vacuo. The residue was purified by silica gel column chromatography (ethyl acetate/hexane) and crystallized from ethyl acetate/diisopropyl ether to give the title compound (2.00 g).
$^1$H NMR (300 MHz, DMSO-d$_6$) δ1.37 (3H, d, J=6.0 Hz), 4.79-5.03 (2H, m), 5.28-5.45 (1H, m), 7.55 (1H, d, J=8.3 Hz), 7.66 (1H, s), 7.89 (1H, d, J=8.0 Hz), 9.14-9.24 (2H, m), 9.35 (1H, s); MS m/z 342.1[M+1]$^+$.

B) 4-{2-[(1-{1,4-dioxaspiro[4.5]decan-8-yl}-3-(2,2,2-trifluoroethoxy)-1H-pyrazol-4-yl)amino]pyrimidin-5-yl}-2-{[(2S)-1-(1H-tetrazol-1-yl)propan-2-yl]oxy}benzonitrile A mixture of 1-(1,4-dioxaspiro[4.5]decan-8-yl)-3-(2,2,2-trifluoroethoxy)-1H-pyrazol-4-amine (500 mg), (S)-2-((1-(1H-tetrazol-1-yl)propan-2-yl)oxy)-4-(2-chloropyrimidin-5-yl)benzonitrile (529 mg), BINAP (193 mg), DBU (353 mg) and Pd$_2$(dba)$_3$ (141 mg) in DMA (10 mL) was heated at 100° C. for 2 hr under microwave irradiation. The mixture was neutralized with water at room temperature and extracted with ethyl acetate. The organic layer was separated, washed with water and saturated brine, dried over anhydrous magnesium sulfate and concentrated in vacuo. The residue was purified by silica gel column chromatography (ethyl acetate/hexane) to give the title compound (311 mg).
$^1$H NMR (300 MHz, DMSO-d$_6$) δ1.35 (3H, d, J=6.0 Hz), 1.59-1.80 (4H, m), 1.88-1.98 (4H, m), 3.89 (4H, s), 4.06-4.15 (1H, m), 4.72-4.99 (4H, m), 5.29-5.39 (1H, m), 7.40 (1H, d, J=8.0 Hz), 7.47 (1H, s), 7.75 (1H, d, J=8.0 Hz), 7.81 (1H, s), 8.81 (2H, s), 8.92 (1H, s), 9.35 (1H, s); MS m/z 627.4 [M+1]$^+$.

C) 4-(2-{[1-(4-oxocyclohexyl)-3-(2,2,2-trifluoroethoxy)-1H-pyrazol-4-yl]amino}pyrimidin-5-yl)-2-{[(2S)-1-(1H-tetrazol-1-yl)propan-2-yl]oxy}benzonitrile To a solution of 4-{2-[(1-{1,4-dioxaspiro[4.5]decan-8-yl}-3-(2,2,2-trifluoroethoxy)-1H-pyrazol-4-yl)amino]pyrimidin-5-yl}-2-{[(2S)-1-(1H-tetrazol-1-yl)propan-2-yl]oxy}benzonitrile (311 mg) in MeOH (10 mL) was added 2 M aqueous hydrogen chloride solution (2.00 mL) at room temperature. The mixture was stirred at room temperature under normal pressure of nitrogen atmosphere overnight. The mixture was concentrated in vacuo. Saturated aqueous sodium hydrogencarbonate solution was added to the solution to adjust the pH of the solution to 7-8 and then the mixture was extracted with ethyl acetate. The organic layer was separated, washed with water and saturated brine, dried over anhydrous magnesium sulfate and concentrated in vacuo. The residue was purified by silica gel column chromatography (ethyl acetate/hexane) to give the title compound (255 mg).
$^1$H NMR (300 MHz, DMSO-d$_6$) δ1.35 (3H, d, J=6.1 Hz), 2.11-2.41 (6H, m), 2.54-2.66 (2H, m), 4.47-4.60 (1H, m), 4.73-4.89 (3H, m), 4.91-4.99 (1H, m), 5.29-5.40 (1H, m), 7.40 (1H, d, J=7.9 Hz), 7.47 (1H, s), 7.75 (1H, d, J=8.1 Hz), 7.89 (1H, s), 8.80 (2H, s), 8.94 (1H, s), 9.35 (1H, s); MS m/z 583.4 [M+1]$^+$.

D) 2-(((S)-1-(1H-tetrazol-1-yl)propan-2-yl)oxy)-4-(2-((1-(trans-4-morpholinocyclohexyl)-3-(2,2,2-trifluoroethoxy)-1H-pyrazol-4-yl)amino)pyrimidin-5-yl)benzonitrile hydrochloride To a solution of 4-(2-{[1-(4-oxocyclohexyl)-3-(2,2,2-trifluoroethoxy)-1H-pyrazol-4-yl]amino}pyrimidin-5-yl)-2-{[(2S)-1-(1H-tetrazol-1-yl)propan-2-yl]oxy}benzonitrile (255 mg) and morpholine (114 mg) in MeOH (10 mL)/AcOH (1.00 mL) was added 2-methylpyridine-borane (140 mg) at room temperature. The mixture was stirred at 60° C. under normal pressure of nitrogen atmosphere for 4 hr. 2 M Aqueous sodium hydroxide solution was added to the solution to adjust the pH of the solution to 8-9 and the mixture was concentrated in vacuo. The residue was diluted with ethyl acetate/water and the mixture was extracted with ethyl acetate. The organic layer was separated, washed with water and saturated brine, dried over anhydrous magnesium sulfate and concentrated in vacuo. The residue was purified by silica gel column chromatography (NH, ethyl acetate/hexane) to give the more polar compound, 2-(((S)-1-(1H-tetrazol-1-yl)propan-2-yl)oxy)-4-(2-((1-(trans-4-morpholinocyclohexyl)-3-(2,2,2-trifluoroethoxy)-1H-pyrazol-4-yl)amino)pyrimidin-5-yl)benzonitrile and the less polar compound, 2-(((S)-1-(1H-tetrazol-1-yl)propan-2-yl)oxy)-4-(2-((1-(cis-4-morpholinocyclohexyl)-3-(2,2,2-trifluoroethoxy)-1H-pyrazol-4-yl)amino)pyrimidin-5-yl)benzonitrile, respectively. Each compound was stirred in 4 M hydrogen chloride-ethyl acetate solution (3.00 mL) at room temperature under nitrogen atmosphere for 10 min. Each mixture was concentrated in vacuo. Each compound was crystallized from EtOH/ethyl acetate to give the title compound (70.0 mg) and the compound of Example 818 (86.0 mg, cis form), respectively.

$^1$H NMR (300 MHz, DMSO-$d_6$) δ1.36 (3H, d, J=5.8 Hz), 1.57 (4H, s), 2.10-2.26 (3H, m), 3.05-3.19 (2H, m), 3.37-3.45 (2H, m), 3.79-3.86 (3H, m), 3.94-4.10 (4H, m), 4.72-4.99 (4H, m), 5.28-5.38 (1H, m), 7.32-7.41 (1H, m), 7.46 (1H, s), 7.76 (1H, d, J=8.1 Hz), 7.83 (1H, s), 8.79 (2H, s), 8.95 (1H, s), 9.35 (1H, s), 10.31 (1H, brs).

Example 821

5-(3-(((S)-1-(1H-tetrazol-1-yl)propan-2-yl)oxy)-4-chlorophenyl)-N-(1-(trans-4-morpholinocyclohexyl)-3-(oxetan-3-yloxy)-1H-pyrazol-4-yl)pyrimidin-2-amine

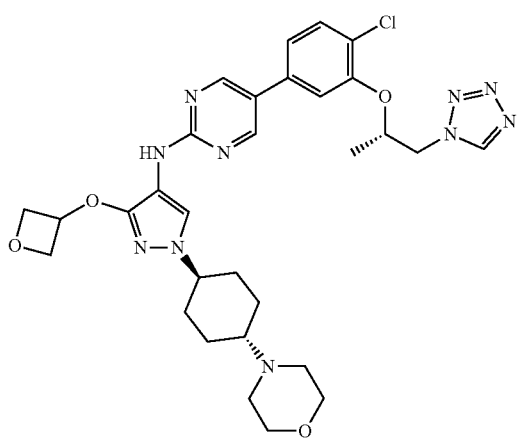 [SMILES: C[C@@H](Cn1cnnn1)Oc1cc(-c2cnc(Nc3cn([C@H]4CC[C@H](N5CCOCC5)CC4)nc3OC3COC3)nc2)ccc1Cl]

A) ethyl 1-acetyl-3-(oxetan-3-yloxy)-1H-pyrazole-4-carboxylate

To a mixture of ethyl 1-acetyl-3-hydroxy-1H-pyrazole-4-carboxylate (3.32 g), oxetan-3-ol (1.31 g), triphenylphosphine (5.26 g) and toluene (50 mL) was added diisopropyl azodicarboxylate (3.9 mL). After being stirred at 60° C. for 1 hr, the mixture was concentrated in vacuo. The residue was purified by silica gel column chromatography (ethyl acetate/hexane) to give the title compound (4.24 g).

MS m/z 255.1 [M+1]$^+$.

B) ethyl 3-(oxetan-3-yloxy)-1H-pyrazole-4-carboxylate

To a mixture of ethyl 1-acetyl-3-(oxetan-3-yloxy)-1H-pyrazole-4-carboxylate (4.24 g) and MeOH (50 mL) was added potassium carbonate (4.56 g). After being stirred at room temperature for 30 min, the mixture was poured into water and extracted with ethyl acetate. The organic layer was washed with saturated brine, dried over anhydrous sodium sulfate and concentrated in vacuo. The residue was purified by silica gel column chromatography (ethyl acetate/hexane) to give the title compound (1.35 g).

$^1$H NMR (300 MHz, DMSO-$d_6$) δ1.25 (3H, t, J=7.1 Hz), 4.17 (2H, q, J=7.1 Hz), 4.50-4.60 (2H, m), 4.77-4.92 (2H, m), 5.37 (1H, quin, J=5.5 Hz), 8.12 (1H, s), 12.62 (1H, d, J=1.3 Hz); MS m/z 213.1 [M+1]$^+$.

C) ethyl 1-{1,4-dioxaspiro[4.5]decan-8-yl}-3-(oxetan-3-yloxy)-1H-pyrazole-4-carboxylate To a mixture of ethyl 3-(oxetan-3-yloxy)-1H-pyrazole-4-carboxylate (1.35 g) and DMF (20 mL) was added 60% sodium hydride (272 mg) at 0° C. After being stirred at 0° C. for 10 min, 1,4-dioxaspiro[4.5]decan-8-yl methanesulfonate (1.81 g) was added to the mixture. After being stirred at 50° C. for 14 hr, the mixture was poured into saturated aqueous ammonium chloride solution and extracted with ethyl acetate. The organic layer was washed with saturated brine, dried over anhydrous sodium sulfate and concentrated in vacuo. The residue was purified by silica gel column chromatography (ethyl acetate/hexane) to give the title compound (720 mg).

$^1$H NMR (300 MHz, CDCl$_3$) δ1.33 (3H, t, J=7.2 Hz), 1.63-1.77 (2H, m), 1.80-2.01 (4H, m), 2.02-2.15 (2H, m), 3.89-4.02 (5H, m), 4.27 (2H, q, J=7.2 Hz), 4.77-4.85 (2H, m), 4.88-4.97 (2H, m), 5.45 (1H, quin, J=5.9 Hz), 7.74 (1H, s); MS m/z 353.2 [M+1]$^+$.

D) 1-{1,4-dioxaspiro[4.5]decan-8-yl}-3-(oxetan-3-yloxy)-1H-pyrazole-4-carboxylic acid To a of ethyl 1-{1,4-dioxaspiro[4.5]decan-8-yl}-3-(oxetan-3-yloxy)-1H-pyrazole-4-carboxylate (719 mg) and EtOH (10 mL) was added 8 M aqueous sodium hydroxide solution (0.50 mL). After being stirred at 80° C. for 2 hr, the mixture was neutralized with 1 M aqueous hydrogen chloride solution and extracted with ethyl acetate. The organic layer was washed with saturated brine, dried over anhydrous sodium sulfate and concentrated in vacuo. The product was subjected to the next step without further purification.

E) benzyl N-(1-{1,4-dioxaspiro[4.5]decan-8-yl}-3-(oxetan-3-yloxy)-1H-pyrazol-4-yl) carbamate To a mixture of 1-{1,4-dioxaspiro[4.5]decan-8-yl}-3-(oxetan-3-yloxy)-1H-pyrazole-4-carboxylic acid (661 mg), triethylamine (0.45 mL), benzyl alcohol (0.32 mL) and toluene (10 mL) was added diphenylphosphoryl azide (0.65 mL). After being stirred at room temperature for 1 hr and then at 100° C. for 2 hr, the mixture was concentrated in vacuo. The residue was purified by silica gel column chromatography (ethyl acetate/hexane) to give the title compound (741 mg).

$^1$H NMR (300 MHz, DMSO-$d_6$) δ1.59-1.76 (4H, m), 1.78-1.95 (4H, m), 3.87 (4H, s), 3.92-4.07 (1H, m), 4.48-4.58 (2H, m), 4.74-4.84 (2H, m), 5.08 (2H, s), 5.22-5.34 (1H, m), 7.27-7.45 (5H, m), 7.61 (1H, s), 8.75 (1H, brs); MS m/z 430.2 [M+1]$^+$.

F) 5-(4-chloro-3-{[(2S)-1-(1H-tetrazol-1-yl)propan-2-yl]oxy}phenyl)-N-(1-{1,4-dioxaspiro[4.5]decan-8-yl}-3-(oxetan-3-yloxy)-1H-pyrazol-4-yl)pyrimidin-2-amine To a mixture of benzyl N-(1-{1,4-dioxaspiro[4.5]decan-8-yl}-3-(oxetan-3-yloxy)-1H-pyrazol-4-yl)carbamate (523 mg) and MeOH (10 mL) was added 10% palladium-carbon (141 mg). After being stirred under normal pressure of hydrogen atmosphere at room temperature for 1 hr, the insoluble material was removed by filtration, and the filtrate was concentrated in vacuo. To a mixture of the residue and DMA (10 mL) were added 2-chloro-5-(4-chloro-3-(((2S)-1-(1H-tetrazol-1-yl)propan-2-yl)oxy)phenyl)pyrimidine (501 mg), BINAP (74 mg), Pd$_2$(dba)$_3$ (109 mg) and DBU (0.27 mL). After being stirred under nitrogen atmosphere at 100° C. for 20 hr, the mixture was poured into water and extracted with ethyl acetate. The organic layer was washed with brine, dried over anhydrous sodium sulfate and concentrated in vacuo. The residue was purified by silica gel column chromatography (ethyl acetate/hexane) to give the title compound (267 mg).

$^1$H NMR (300 MHz, DMSO-d$_6$) δ1.33 (3H, d, J=6.24 Hz), 1.57-1.82 (4H, m), 1.83-1.96 (4H, m), 3.84-3.93 (4H, m), 3.98-4.08 (1H, m), 4.51-4.59 (2H, m), 4.75-4.85 (3H, m), 4.86-4.96 (1H, m), 5.12-5.24 (1H, m), 5.28-5.39 (1H, m), 7.25 (1H, d, J=8.25 Hz), 7.38 (s, 1H), 7.45 (1H, d, J=8.34 Hz), 7.79 (1H, s), 8.68-8.77 (3H, m), 9.37 (1H, s); MS m/z 610.4 [M+1]$^+$.

G) 4-(4-{[5-(4-chloro-3-{[(2S)-1-(1H-tetrazol-1-yl)propan-2-yl]oxy}phenyl)pyrimidin-2-yl]amino}-3-(oxetan-3-yloxy)-1H-pyrazol-1-yl)cyclohexan-1-one A mixture of 5-(4-chloro-3-{[(2S)-1-(1H-tetrazol-1-yl)propan-2-yl]oxy}phenyl)-N-(1-{1,4-dioxaspiro[4.5]decan-8-yl}-3-(oxetan-3-yloxy)-1H-pyrazol-4-yl)pyrimidin-2-amine (249 mg), AcOH (2.0 mL) and water (0.50 mL) was stirred at 80° C. for 3 hr. Then the mixture was concentrated in vacuo. The residue was subjected to the next step without further purification.

MS m/z 566.4 [M+1]$^+$.

H) 5-(3-(((S)-1-(1H-tetrazol-1-yl)propan-2-yl)oxy)-4-chlorophenyl)-N-(1-(trans-4-morpholinocyclohexyl)-3-(oxetan-3-yloxy)-1H-pyrazol-4-yl)pyrimidin-2-amine To a mixture of 4-(4-{[5-(4-chloro-3-{[(2S)-1-(1H-tetrazol-1-yl)propan-2-yl]oxy}phenyl)pyrimidin-2-yl]amino}-3-(oxetan-3-yloxy)-1H-pyrazol-1-yl)cyclohexan-1-one (230 mg), MeOH (5 mL) and AcOH (0.5 mL) was added morpholine (0.11 mL). After being stirred at room temperature for 5 min, 2-methylpyridine-borane (129 mg) was added to the mixture. After being stirred at room temperature for 3 hr, the mixture was poured into water and extracted with ethyl acetate. The organic layer was washed with saturated brine, dried over anhydrous sodium sulfate and concentrated in vacuo. The residue was purified by silica gel column chromatography (ethyl acetate/hexane) to give the more polar compound, the title compound (43.0 mg) and the less polar compound, the compound of Example 820 (61.0 mg, cis form), respectively.

$^1$H NMR (300 MHz, DMSO-d$_6$) δ1.27-1.44 (5H, m), 1.55-1.74 (2H, m), 1.86-1.96 (2H, m), 1.97-2.10 (2H, m), 2.24-2.33 (1H, m), 2.35-2.48 (4H, m), 3.51-3.62 (4H, m), 3.79-3.94 (1H, m), 4.50-4.60 (2H, m), 4.74-4.85 (3H, m), 4.86-4.97 (1H, m), 5.13-5.23 (1H, m), 5.27-5.38 (1H, m), 7.25 (1H, d, J=8.3 Hz), 7.37 (1H, s), 7.45 (1H, d, J=8.3 Hz), 7.76 (1H, s), 8.67-8.76 (3H, m), 9.37 (1H, s).

Example 831

(S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(trifluoromethyl)-1H-pyrazol-4-yl)pyrimidin-2-amine

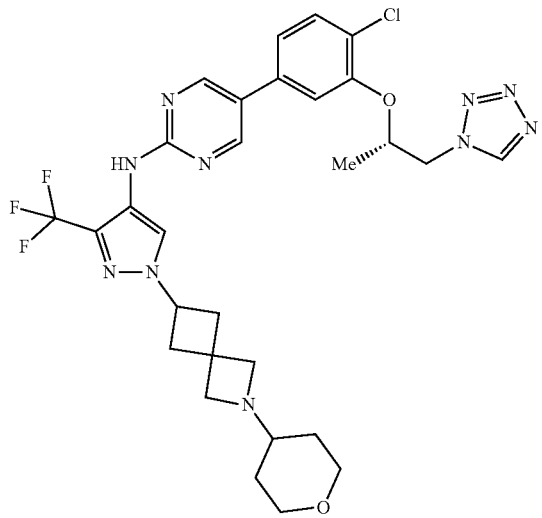 [SMILES: C[C@@H](Cn1cnnn1)Oc1cc(-c2cnc(Nc3cn(C4CC5(C4)CN(C4CCOCC4)C5)nc3C(F)(F)F)nc2)ccc1Cl]

A) tert-butyl 6-[4-nitro-3-(trifluoromethyl)-1H-pyrazol-1-yl]-2-azaspiro[3.3]heptane-2-carboxylate To a mixture of 4-nitro-3-(trifluoromethyl)-1H-pyrazole (20.7 g), tert-butyl 6-(methanesulfonyloxy)-2-azaspiro[3.3]heptane-2-carboxylate (27.1 g) and DMF (300 mL) was added cesium carbonate (46.1 g). After being stirred at 100° C. for 24 hr, the mixture was poured into water and extracted with ethyl acetate. The organic layer was washed with saturated brine, dried over anhydrous sodium sulfate and concentrated in vacuo. The residue was purified by silica gel column chromatography (ethyl acetate/hexane) to give the title compound (26.0 g).

$^1$H NMR (300 MHz, DMSO-d$_6$) δ1.37 (9H, s), 2.62-2.79 (4H, m), 3.86 (2H, s), 3.95 (2H, s), 4.93 (1H, quin, J=8.0 Hz), 9.26 (1H, s).

B) 6-[4-nitro-3-(trifluoromethyl)-1H-pyrazol-1-yl]-2-azaspiro[3.3]heptane

To a mixture of tert-butyl 6-[4-nitro-3-(trifluoromethyl)-1H-pyrazol-1-yl]-2-azaspiro[3.3]heptane-2-carboxylate (16.0 g) and toluene (160 mL) was added TFA (33 mL) at 0° C. After being stirred at room temperature for 2 hr, the mixture was concentrated in vacuo. The residue was dissolved in MeOH (100 mL) and Amberlyst® A21 (18 g) was added to the solution. After being stirred at room temperature for 1 hr, the insoluble material was removed by filtration and the filtrate was concentrated in vacuo. The residue was subjected to the next step without further purification.

MS m/z 277.1 [M+1]$^+$.

C) 6-[4-nitro-3-(trifluoromethyl)-1H-pyrazol-1-yl]-2-(tetrahydro-2H-pyran-4-yl)-2-azaspiro[3.3]heptane To a mixture of 6-[4-nitro-3-(trifluoromethyl)-1H-pyrazol-1-yl]-2-azaspiro[3.3]heptane (11.7 g), MeOH (250 mL)

and AcOH (25 mL) was added dihydro-2H-pyran-4(3H)-one (7.8 mL) at 0° C. After being stirred at room temperature for 10 min, 2-methylpyridine-borane (9.07 g) was added to the mixture at 0° C. After being stirred at room temperature for 2 hr, the mixture was neutralized with saturated aqueous sodium hydrogencarbonate solution and extracted with ethyl acetate. The organic layer was washed with saturated brine, dried over anhydrous sodium sulfate and concentrated in vacuo. The residue was purified by silica gel column chromatography (MeOH/ethyl acetate) to give the title compound (9.05 g).

MS m/z 361.2 [M+1]+.

D) 1-[2-(tetrahydro-2H-pyran-4-yl)-2-azaspiro[3.3]heptan-6-yl]-3-(trifluoromethyl)-1H-pyrazol-4-amine To a mixture of 6-[4-nitro-3-(trifluoromethyl)-1H-pyrazol-1-yl]-2-(tetrahydro-2H-pyran-4-yl)-2-azaspiro[3.3]heptane (15.1 g) and MeOH (200 mL) was added 10% palladium-carbon (2.19 g). After being stirred under normal pressure of hydrogen atmosphere at room temperature for 15 hr, the insoluble material was removed by filtration, and the filtrate was concentrated in vacuo. The residue was purified by silica gel column chromatography (ethyl acetate/hexane) to give the title compound (11.1 g).

$^1$H NMR (300 MHz, DMSO-d$_6$) δ1.02-1.19 (2H, m), 1.48-1.62 (2H, m), 2.04-2.18 (1H, m), 2.39-2.49 (4H, m), 3.06 (2H, s), 3.15 (2H, s), 3.19-3.30 (2H, m), 3.71-3.86 (2H, m), 4.22 (2H, s), 4.55-4.73 (1H, m), 7.25 (1H, s); MS m/z 331.2 [M+1]+.

E) (S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(trifluoromethyl)-1H-pyrazol-4-yl)pyrimidin-2-amine To a mixture of 1-[2-(tetrahydro-2H-pyran-4-yl)-2-azaspiro[3.3]heptan-6-yl]-3-(trifluoromethyl)-1H-pyrazol-4-amine (10.1 g), 2-chloro-5-(4-chloro-3-(((2S)-1-(1H-tetrazol-1-yl)propan-2-yl)oxy)phenyl)pyrimidine (11.0 g), Pd$_2$(dba)$_3$ (838 mg), BINAP (1.13 g) and DMA (200 mL) was added DBU (9.0 mL). After being under nitrogen atmosphere stirred at 100° C. for 2 hr, the mixture was poured into water and extracted with ethyl acetate. The organic layer was washed with saturated brine, dried over Na$_2$SO$_4$ and concentrated in vacuo. The residue was purified by silica gel column chromatography (ethyl acetate/hexane and MeOH/ethyl acetate) and crystallized from ethyl acetate/hexane to give the title compound (8.02 g). $^1$H NMR (300 MHz, DMSO-d$_6$) δ1.03-1.20 (2H, m), 1.33 (3H, d, J=6.1 Hz), 1.51-1.62 (2H, m), 2.07-2.19 (1H, m), 2.54-2.63 (4H, m), 3.10 (2H, s), 3.20 (2H, s), 3.21-3.30 (2H, m), 3.74-3.85 (2H, m), 4.74-4.96 (3H, m), 5.11-5.24 (1H, m), 7.25 (1H, d, J=8.3 Hz), 7.38 (1H, s), 7.46 (1H, d, J=8.2 Hz), 8.16 (1H, s), 8.73 (2H, s), 8.99 (1H, s), 9.37 (1H, s).

Example 843

5-(3-(((S)-1-(1H-tetrazol-1-yl)propan-2-yl)oxy)-4-chlorophenyl)-N-(3-isopropyl-1-(trans-4-morpholinocyclohexyl)-1H-pyrazol-4-yl)pyrimidin-2-amine

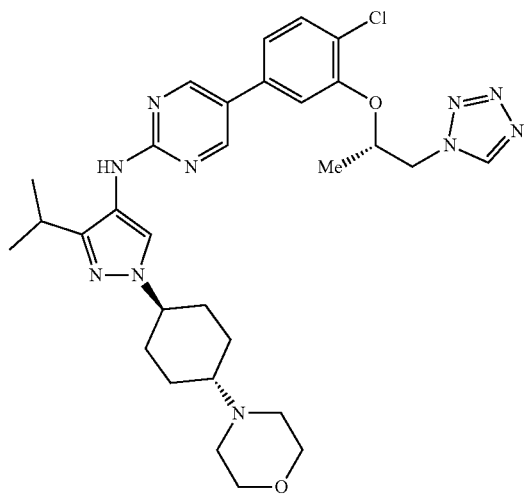 [SMILES: CC(C)c1nn([C@H]2CC[C@H](N3CCOCC3)CC2)cc1Nc1ncc(-c2ccc(Cl)c(O[C@@H](C)Cn3cnnn3)c2)cn1]

A) 1-{1,4-dioxaspiro[4.5]decan-8-yl}-4-nitro-3-isopropyl-1H-pyrazole

A mixture of 4-nitro-3-isopropyl-1H-pyrazole (3.86 g), 1,4-dioxaspiro[4.5]decan-8-yl methanesulfonate (7.60 g) and cesium carbonate (16.1 g) in DMF (100 mL) was stirred at 120° C. for 4 hr. The reaction mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane) to give the title compound (5.21 g). $^1$H NMR (300 MHz, CDCl$_3$) δ1.30 (6H, d, J=6.9 Hz), 1.75 (2H, dd, J=13.2, 4.1 Hz), 1.84-2.04 (4H, m), 2.15-2.25 (2H, m), 3.59 (1H, spt, J=6.7 Hz), 3.98 (4H, s), 4.14-4.23 (1H, m), 8.15 (1H, s); MS m/z 296.2 [M+1]+.

B) 1-{1,4-dioxaspiro[4.5]decan-8-yl}-3-isopropyl-1H-pyrazol-4-amine

A mixture of 1-{1,4-dioxaspiro[4.5]decan-8-yl}-4-nitro-3-isopropyl-1H-pyrazole (5.20 g) and 10% palladium-carbon (1.70 g) in MeOH (60 mL) and THF (60 mL) was stirred at room temperature for 21 hr under normal pressure of hydrogen atmosphere. The reaction mixture was filtered. The filtrate was concentrated under reduced pressure to give the title compound (4.13 g). This product was used in the next step without further purification.

MS m/z 266.2 [M+1]+.

C) 5-(4-chloro-3-{[(2S)-1-(1H-tetrazol-1-yl)propan-2-yl]oxy}phenyl)-N-(1-{1,4-dioxaspiro[4.5]decan-8-yl}-3-isopropyl-1H-pyrazol-4-yl)pyrimidin-2-amine A mixture of 2-chloro-5-(4-chloro-3-(((2S)-1-(1H-tetrazol-1-yl)propan-2-yl)oxy)phenyl)pyrimidine (5.68 g), 1-{1,4-dioxaspiro[4.5]decan-8-yl}-3-isopropyl-1H-pyrazol-4- amine (4.13 g), Pd$_2$(dba)$_3$ (886 mg), BINAP (965 mg) and DBU (3.53 g) in DMA (50 mL) was stirred at 100° C. for 3.5 hr. The reaction mixture was partitioned between ethyl acetate and water. The organic layer was separated, washed with saturated brine, dried over anhydrous sodium sulfate and concentrated under reduced pressure. The residue was purified by silica gel column chromatography (ethyl acetate/hexane and MeOH/ethyl acetate) and silica gel column chromatography (NH, ethyl acetate/hexane) to give the title compound (4.93 g).

$^1$H NMR (300 MHz, CDCl$_3$) δ1.32 (6H, d, J=7.0 Hz), 1.44 (3H, d, J=6.2 Hz), 1.71-1.81 (2H, m), 1.87-1.95 (2H, m), 1.99-2.04 (2H, m), 2.16-2.26 (2H, m), 2.95-3.00 (1H, m), 3.99 (4H, s), 4.17-4.28 (1H, m), 4.68-4.78 (1H, m), 4.82-4.92 (2H, m), 6.64 (1H, s), 6.89 (1H, s), 7.08 (1H, d, J=8.4 Hz), 7.45 (1H, d, J=8.3 Hz), 7.94 (1H, s), 8.51 (2H, s), 8.97 (1H, s); MS m/z 580.4 [M+1]$^+$.

D) 4-(4-{[5-(4-chloro-3-{[(2S)-1-(1H-tetrazol-1-yl)propan-2-yl]oxy}phenyl)pyrimidin-2-yl]amino}-3-isopropyl-1H-pyrazol-1-yl)cyclohexan-1-one 2 M Aqueous hydrogen chloride solution (25.5 mL) was added to a solution of 5-(4-chloro-3-{[(2S)-1-(1H-tetrazol-1-yl)propan-2-yl]oxy}phenyl)-N-(1-{1,4-dioxaspiro[4.5]decan-8-yl}-3-isopropyl-1H-pyrazol-4-yl)pyrimidin-2-amine (4.93 g) in MeOH (100 mL) at room temperature. The mixture was stirred at room temperature for 15.5 hr. The reaction mixture was concentrated under reduced pressure. The residue was partitioned between ethyl acetate and saturated aqueous sodium hydrogencarbonate solution. The organic layer was separated, washed with saturated brine, dried over anhydrous sodium sulfate and concentrated under reduced pressure. The residue was purified by silica gel column chromatography (ethyl acetate/hexane and MeOH/ethyl acetate) and by recrystallization from ethyl acetate/hexane to give the title compound (2.09 g).

$^1$H NMR (300 MHz, DMSO-d$_6$) δ1.17 (6H, d, J=6.9 Hz), 1.33 (3H, d, J=6.1 Hz), 2.08-2.23 (2H, m), 2.25-2.40 (4H, m), 2.54-2.68 (2H, m), 3.07 (1H, dt, J=13.9, 6.9 Hz), 4.54-4.67 (1H, m), 4.75-4.85 (1H, m), 4.86-4.95 (1H, m), 5.10-5.25 (1H, m), 7.25 (1H, d, J=8.6 Hz), 7.37 (1H, s), 7.45 (1H, d, J=8.3 Hz), 7.89 (1H, s), 8.71 (2H, s), 8.85 (1H, s), 9.37 (1H, s); MS m/z 536.4 [M+1]$^+$.

E) 5-(3-(((S)-1-(1H-tetrazol-1-yl)propan-2-yl)oxy)-4-chlorophenyl)-N-(3-isopropyl-1-(trans-4-morpholinocyclohexyl)-1H-pyrazol-4-yl)pyrimidin-2-amine A mixture of 4-(4-{[5-(4-chloro-3-{[(2S)-1-(1H-tetrazol-1-yl)propan-2-yl]oxy}phenyl)pyrimidin-2-yl]amino}-3-isopropyl-1H-pyrazol-1-yl)cyclohexan-1-one (200 mg), morpholine (96.7 mg) and 2-methylpyridine-borane (117 mg) in MeOH (10 mL) and AcOH (1.0 mL) was stirred at 60° C. for 1 hr. The reaction mixture was concentrated under reduced pressure. The residue was partitioned between ethyl acetate and saturated aqueous sodium hydrogencarbonate solution. The organic layer was separated, washed with saturated brine, dried over anhydrous sodium sulfate and concentrated under reduced pressure. The residue was purified by silica gel column chromatography (NH, ethyl acetate/hexane and MeOH/ethyl acetate) to give the more polar compound, the title compound (80.3 mg) and the less polar compound, the compound of Example 842 (134 mg, cis form), respectively.

$^1$H NMR (300 MHz, DMSO-d$_6$) δ1.15 (6H, d, J=6.9 Hz), 1.33 (3H, d, J=6.2 Hz), 1.35-1.47 (2H, m), 1.62-1.79 (2H, m), 1.88-1.97 (2H, m), 2.07 (2H, d, J=11.2 Hz), 2.26-2.33 (1H, m), 2.44-2.49 (4H, m), 2.99-3.10 (1H, m), 3.57 (4H, d, J=3.4 Hz), 3.96-4.06 (1H, m), 4.75-4.85 (1H, m), 4.86-4.96 (1H, m), 5.13-5.23 (1H, m), 7.25 (1H, d, J=8.3 Hz), 7.37 (1H, s), 7.45 (1H, d, J=8.3 Hz), 7.80 (1H, s), 8.71 (2H, s), 8.81 (1H, s), 9.37 (1H, s).

Example 844

5-(3-(((S)-1-(1H-tetrazol-1-yl)propan-2-yl)oxy)-4-chlorophenyl)-N-(1-(trans-4-((1R,5S)-3-oxa-8-azabicyclo[3.2.1]octan-8-yl)cyclohexyl)-3-(2,2-difluoroethoxy)-1H-pyrazol-4-yl)pyrimidin-2-amine

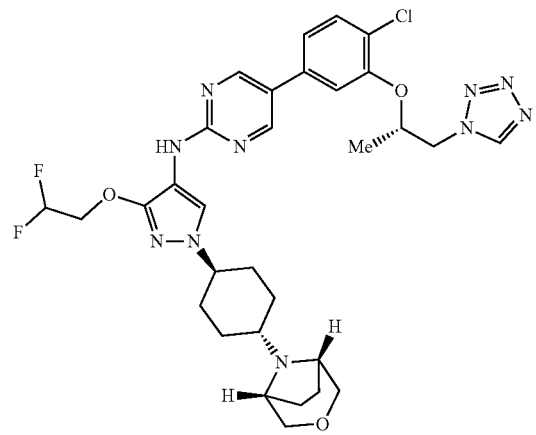 [SMILES: C[C@@H](Cn1cnnn1)Oc1cc(-c2cnc(Nc3cn([C@H]4CC[C@H](N5[C@@H]6CC[C@H]5COC6)CC4)nc3OCC(F)F)nc2)ccc1Cl]

To a solution of 4-(4-{[5-(4-chloro-3-{[(2S)-1-(1H-tetrazol-1-yl)propan-2-yl]oxy}phenyl)pyrimidin-2-yl]amino}-3-(2,2-difluoroethoxy)-1H-pyrazol-1-yl)cyclohexan-1-one (200 mg) and (1R,5S)-3-oxa-8-azabicyclo[3.2.1]octane hydrochloride (104 mg) in MeOH (10 mL)/AcOH (1.00 mL) was 2-methylpyridine-borane (74.5 mg) at room temperature. The mixture was stirred at room temperature under nitrogen atmosphere overnight. The mixture was neutralized with saturated aqueous sodium hydrogencarbonate solution at room temperature and extracted with ethyl acetate. The organic layer was separated, washed with water and saturated brine, dried over anhydrous magnesium sulfate and concentrated in vacuo. The residue was purified by silica gel column chromatography (MeOH/ethyl acetate). The residue was triturated with diisopropyl ether, filtered and dried in vacuo to give the title compound (15.0 mg).

$^1$H NMR (300 MHz, DMSO-d$_6$) δ1.13-1.26 (2H, m), 1.33 (3H, d, J=6.2 Hz), 1.64-1.83 (6H, m), 1.96-2.06 (4H, m), 2.09-2.19 (1H, m), 2.54 (2H, brs), 3.37-3.44 (2H, m), 3.49-3.56 (2H, m), 3.87-4.00 (1H, m), 4.29-4.44 (2H, m), 4.74-4.84 (1H, m), 4.86-4.96 (1H, m), 5.10-5.22 (1H, m), 6.10-6.57 (1H, m), 7.24 (1H, d, J=8.1 Hz), 7.36 (1H, s), 7.45 (1H, d, J=8.8 Hz), 7.77 (1H, s), 8.67 (1H, s), 8.70 (2H, s), 9.37 (1H, s).

Example 854

(S)-5-(3-((1-(1H-tetrazol-1-yl)propan-2-yl)oxy)-4-chlorophenyl)-N-(1-(2-(oxetan-3-yl)-2-azaspiro[3.3]heptan-6-yl)-3-(2,2,2-trifluoroethoxy)-1H-pyrazol-4-yl)pyrimidin-2-amine

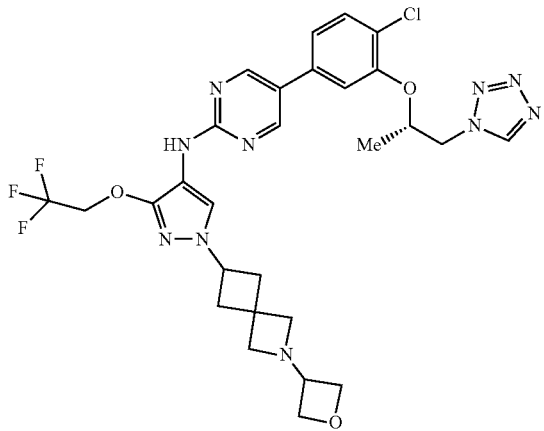 [SMILES: C[C@@H](Cn1cnnn1)Oc1cc(-c2cnc(Nc3cn(C4CC5(C4)CN(C4COC4)C5)nc3OCC(F)(F)F)nc2)ccc1Cl]

A) 6-[4-nitro-3-(2,2,2-trifluoroethoxy)-1H-pyrazol-1-yl]-2-(oxetan-3-yl)-2-azaspiro[3.3]heptane To a mixture of 6-[4-nitro-3-(2,2,2-trifluoroethoxy)-1H-pyrazol-1-yl]-2-azaspiro[3.3]heptane (379 mg), MeOH (10 mL) and AcOH (1 mL), was added oxetan-3-one (0.30 mL). After being stirred at room temperature for 1 hr, 2-methylpyridine-borane (584 mg) was added to the mixture. After being stirred at room temperature for 2 days, the mixture was neutralized with saturated aqueous sodium hydrogencarbonate solution and extracted with ethyl acetate. The organic layer was washed with saturated brine, dried over anhydrous sodium sulfate and concentrated in vacuo. The residue was purified by silica gel column chromatography (ethyl acetate/hexane) to give the title compound (130 mg).

$^1$H NMR (300 MHz, DMSO-d$_6$) δ2.58 (4H, d, J=7.9 Hz), 3.19 (2H, s), 3.26 (2H, s), 3.64 (1H, quin, J=5.8 Hz), 4.31 (2H, t, J=5.8 Hz), 4.52 (2H, t, J=6.5 Hz), 4.70 (1H, quin, J=7.9 Hz), 5.00 (2H, q, J=8.9 Hz), 8.85 (1H, s); MS m/z 363.2 [M+1]$^+$.

B) 1-[2-(oxetan-3-yl)-2-azaspiro[3.3]heptan-6-yl]-3-(2,2,2-trifluoroethoxy)-1H-pyrazol-4-amine To a mixture of 6-[4-nitro-3-(2,2,2-trifluoroethoxy)-1H-pyrazol-1-yl]-2-(oxetan-3-yl)-2-azaspiro[3.3]heptane (129 mg) and MeOH (3 mL) was added 10% palladium-carbon (19 mg). After being stirred under normal pressure of hydrogen atmosphere at room temperature for 2 hr, the insoluble material was removed by filtration, and the filtrate was concentrated in vacuo. The residue was subjected to the next step without further purification.

MS m/z 333.2 [M+1]$^+$.

[0468]

C) (S)-5-(3-((1-(1H-tetrazol-1-yl)propan-2-yl)oxy)-4-chlorophenyl)-N-(1-(2-(oxetan-3-yl)-2-azaspiro[3.3]heptan-6-yl)-3-(2,2,2-trifluoroethoxy)-1H-pyrazol-4-yl)pyrimidin-2-amine To a mixture of 1-[2-(oxetan-3-yl)-2-azaspiro[3.3]heptan-6-yl]-3-(2,2,2-trifluoroethoxy)-1H-pyrazol-4-amine (118 mg), 2-chloro-5-(4-chloro-3-(((2S)-1-(1H-tetrazol-1-yl)propan-2-yl)oxy)phenyl)pyrimidine (145 mg), Pd$_2$(dba)$_3$ (16 mg), BINAP (23 mg) and DMA (5.00 mL) was added DBU (0.11 mL). After being stirred under nitrogen atmosphere at 100° C. for 2 hr, the mixture was poured into water and extracted with ethyl acetate. The organic layer was washed with saturated brine, dried over anhydrous sodium sulfate and concentrated in vacuo. The residue was purified by silica gel column chromatography (ethyl acetate/hexane and MeOH/ethyl acetate) to give the title compound (14.0 mg).

$^1$H NMR (300 MHz, DMSO-d$_6$) δ1.33 (3H, d, J=6.1 Hz), 2.52-2.57 (4H, m), 3.19 (2H, s), 3.27 (2H, s), 3.65 (1H, quin, J=5.9 Hz), 4.32 (2H, t, J=5.8 Hz), 4.48-4.62 (3H, m), 4.72-4.85 (3H, m), 4.86-4.95 (1H, m), 5.12-5.22 (1H, m), 7.24 (1H, d, J=8.3 Hz), 7.36 (1H, s), 7.45 (1H, d, J=8.3 Hz), 7.82 (1H, s), 8.70 (2H, s), 8.75 (1H, s), 9.37 (1H, s).

Example 859

(S)-1-(6-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-azaspiro[3.3]heptan-2-yl)-2-methylpropan-2-ol

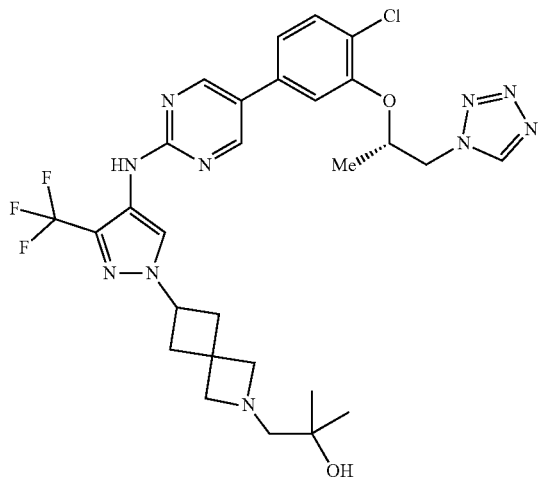 [SMILES: C[C@@H](Cn1cnnn1)Oc1cc(-c2cnc(Nc3cn(C4CC5(C4)CN(CC(C)(C)O)C5)nc3C(F)(F)F)nc2)ccc1Cl]

A) 2-methyl-1-{6-[4-nitro-3-(trifluoromethyl)-1H-pyrazol-1-yl]-2-azaspiro[3.3]heptan-2-yl}propan-2-ol To a mixture of 6-[4-nitro-3-(trifluoromethyl)-1H-pyrazol-1-yl]-2-azaspiro[3.3]heptane (1.02 g), 2,2-dimethyloxirane (1.00 mL) and THF (15 mL) was added N,N-diisopropylethylamine (1.9 mL). After being stirred under microwave irradiation at 100° C. for 4 hr, the mixture was concentrated in vacuo. The residue was purified by silica gel column chromatography (ethyl acetate/hexane) to give the title compound (638 mg).

$^1$H NMR (300 MHz, DMSO-d$_6$) δ1.02 (6H, s), 2.26 (2H, s), 2.57-2.66 (4H, m), 3.20 (2H, s), 3.29 (2H, s), 3.99 (1H, s), 4.80-4.98 (1H, m), 9.24 (1H, s); MS m/z 349.2 [M+1]$^+$.

B) 1-{6-[4-amino-3-(trifluoromethyl)-1H-pyrazol-1-yl]-2-azaspiro[3.3]heptan-2-yl}-2-methylpropan-2-ol To a mixture of 2-methyl-1-{6-[4-nitro-3-(trifluoromethyl)-1H-pyrazol-1-yl]-2-azaspiro[3.3]heptan-2-yl}propan-2-ol (638 mg) and MeOH (10 mL) was added 10% palladium-carbon (97 mg). After being stirred under normal pressure of hydrogen atmosphere at room temperature for 1 hr, the insoluble material was removed by filtration, and the filtrate was concentrated in vacuo. The residue was dissolved in ethyl acetate, and the solution was passed through NH silica gel pad and concentrated in vacuo. The residue was subjected to the next step without further purification.
MS m/z 319.2 [M+1]$^+$.

C) (S)-1-(6-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-azaspiro[3.3]heptan-2-yl)-2-methylpropan-2-ol To a mixture of 1-{6-[4-amino-3-(trifluoromethyl)-1H-pyrazol-1-yl]-2-azaspiro[3.3]heptan-2-yl}-2-methylpropan-2-ol (582 mg), 2-chloro-5-(4-chloro-3-(((2S)-1-(1H-tetrazol-1-yl)propan-2-yl)oxy)phenyl)pyrimidine (698 mg), Pd$_2$(dba)$_3$ (51 mg), BINAP (68 mg) and DMA (15 mL) was added DBU (0.55 mL). After being stirred under nitrogen atmosphere at 100° C. for 2 hr, the mixture was poured into water and extracted with ethyl acetate. The organic layer was washed with saturated brine, dried over anhydrous sodium sulfate and concentrated in vacuo. The residue was purified by silica gel column chromatography (ethyl acetate/hexane and MeOH/ethyl acetate) and crystallized from EtOH/hexane to give the title compound (300 mg).
$^1$H NMR (300 MHz, DMSO-d$_6$) δ1.02 (6H, s), 1.33 (3H, d, J=6.1 Hz), 2.27 (2H, s), 2.52-2.66 (6H, m), 3.22 (2H, s), 3.99 (1H, s), 4.74-4.85 (2H, m), 4.86-4.95 (1H, m), 5.12-5.25 (1H, m), 7.25 (1H, d, J=8.3 Hz), 7.38 (1H, s), 7.46 (1H, d, J=8.2 Hz), 8.15 (1H, s), 8.73 (2H, s), 8.98 (1H, s), 9.37 (1H, s).

Example 869

5-(3-(((S)-1-(1H-tetrazol-1-yl)propan-2-yl)oxy)-4-chlorophenyl)-N-(3-(((S)-2,2-difluorocyclopropyl)methoxy)-1-(trans-4-morpholinocyclohexyl)-1H-pyrazol-4-yl)pyrimidin-2-amine

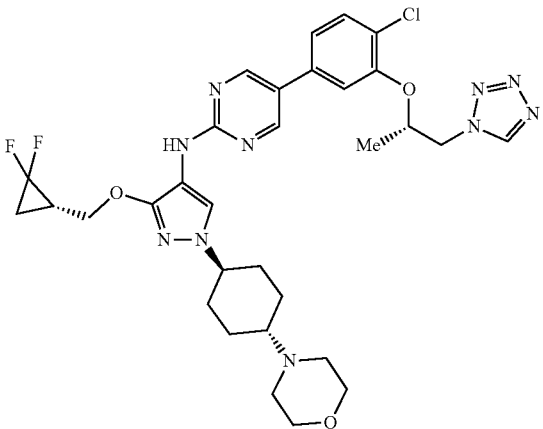 [SMILES: C[C@@H](Cn1cnnn1)Oc1cc(-c2cnc(Nc3cn([C@H]4CC[C@H](N5CCOCC5)CC4)nc3OC[C@@H]3CC3(F)F)nc2)ccc1Cl]

A) ethyl 3-{[(1S)-2,2-difluorocyclopropyl]methoxy}-1H-pyrazole-4-carboxylate

To a solution of ethyl 1-acetyl-3-hydroxy-1H-pyrazole-4-carboxylate (2.00 g) and [(1S)-2,2-difluorocyclopropyl]methyl 4-nitrobenzene-1-sulfonate (2.93 g) in DMF (30 mL) was added dipotassium carbonate (1.65 g) at room temperature. The mixture was stirred at 80° C. under nitrogen atmosphere overnight. The mixture was poured into water at room temperature and extracted with ethyl acetate. The organic layer was separated, washed with water and saturated brine, dried over anhydrous magnesium sulfate and concentrated in vacuo. The residue was purified by silica gel column chromatography (ethyl acetate/hexane) to give the title compound (1.70 g).
$^1$H NMR (300 MHz, DMSO-d$_6$) δ1.23 (3H, t, J=7.1 Hz), 1.43-1.56 (1H, m), 1.62-1.77 (1H, m), 2.15-2.31 (1H, m), 4.09-4.20 (3H, m), 4.28-4.36 (1H, m), 8.09 (1H, s), 12.60 (1H, brs); MS m/z 247.1 [M+1]$^+$.

B) ethyl 3-{[(1S)-2,2-difluorocyclopropyl]methoxy}-1-{1,4-dioxaspiro[4.5]decan-8-yl}-1H-pyrazole-4-carboxylate To a solution of ethyl 3-{[(1S)-2,2-difluorocyclopropyl]methoxy}-1H-pyrazole-4-carboxylate (1.70 g) and 1,4-dioxaspiro[4.5]decan-8-yl methanesulfonate (2.28 g) in DMF (30 mL) was added cesium carbonate (2.92 g) at room temperature. The mixture was stirred at 120° C. under nitrogen atmosphere overnight. The mixture was quenched with water at room temperature and extracted with ethyl acetate. The organic layer was separated, washed with water and saturated brine, dried over anhydrous magnesium sulfate and concentrated in vacuo. The residue was purified by silica gel column chromatography (NH, ethyl acetate/hexane) to give the title compound (2.55 g).
$^1$H NMR (300 MHz, DMSO-d$_6$) δ1.23 (2H, t, J=7.1 Hz), 1.45-1.81 (7H, m), 1.89-1.98 (4H, m), 2.13-2.32 (1H, m), 3.82-3.92 (4H, m), 4.05-4.23 (4H, m), 4.26-4.36 (1H, m), 8.10 (1H, s); MS m/z 387.3 [M+1]$^+$.

C) 3-{[(1S)-2,2-difluorocyclopropyl]methoxy}-1-{1,4-dioxaspiro[4.5]decan-8-yl}-1H-pyrazole-4-carboxylic acid To a solution of ethyl 3-{[(1S)-2,2-difluorocyclopropyl]methoxy}-1-{1,4-dioxaspiro[4.5]decan-8-yl}-1H-pyrazole-4-carboxylate (2.55 g) in EtOH (20 mL) was added 8 M aqueous sodium hydroxide solution (1.63 mL) at room temperature. The mixture was stirred at 50° C. under nitrogen atmosphere overnight. 6 M Aqueous hydrogen chloride solution was added to the solution to adjust the pH of the solution to 4-5 and the mixture was extracted with ethyl acetate. The organic layer was separated, washed with water and saturated brine, dried over anhydrous magnesium sulfate and concentrated in vacuo. The title compound was subjected to the next reaction without further purification.
$^1$H NMR (300 MHz, DMSO-d$_6$) δ1.45-1.81 (6H, m), 1.87-1.99 (4H, m), 2.21 (1H, brs), 3.88 (4H, s), 4.08-4.18 (2H, m), 4.25-4.34 (1H, m), 8.02 (1H, s), 11.99 (1H, brs); MS m/z 359.3 [M+1]$^+$.

D) benzyl N-(3-{[(1S)-2,2-difluorocyclopropyl]methoxy}-1-{1,4-dioxaspiro[4.5]decan-8-yl}-1H-pyrazol-4-yl)carbamate To a mixture of 3-{[(1S)-2,2-difluorocyclopropyl]methoxy}-1-{1,4-dioxaspiro[4.5]decan-8-yl}-1H-pyrazole- 4-carboxylic acid (2.4 g), triethylamine (1.07 g) and benzyl alcohol (1.09 g) in toluene (30 mL) was added diphenylphosphoryl azide (2.73 g). After being stirred at room temperature for 1 hr, the mixture was stirred at 100° C. for 2 hr, and the mixture was concentrated in vacuo. The residue was purified by silica gel column chromatography (ethyl acetate/hexane) to give the title compound (2.20 g).

$^1$H NMR (300 MHz, DMSO-d$_6$) δ1.40-1.55 (1H, m), 1.58-1.98 (9H, m), 2.08-2.26 (1H, m), 3.88 (4H, s), 3.99-4.09 (2H, m), 4.17-4.27 (1H, m), 5.07 (2H, s), 7.29-7.42 (5H, m), 7.59 (1H, s), 8.70 (1H, brs); MS m/z 464.3 [M+1]$^+$.

E) 3-{[(1S)-2,2-difluorocyclopropyl]methoxy}-1-{1,4-dioxaspiro[4.5]decan-8-yl}-1H-pyrazol-4-amine To a solution of benzyl N-(3-{[(1S)-2,2-difluorocyclopropyl]methoxy}-1-{1,4-dioxaspiro[4.5]decan-8-yl}-1H-pyrazol-4-yl)carbamate (2.00 g) in EtOH (30 mL) was added 8 M aqueous sodium hydroxide solution (1.07 mL) at room temperature. The mixture was stirred at 80° C. under nitrogen atmosphere for 24 hr. 6 M Aqueous hydrogen chloride solution was added to the solution to adjust the pH of the solution to 5-6 and the mixture was concentrated in vacuo. The residue was poured into water at room temperature and the mixture was extracted with ethyl acetate. The organic layer was separated, washed with water and saturated brine, dried over anhydrous magnesium sulfate and concentrated in vacuo. The residue was purified by silica gel column chromatography (ethyl acetate/hexane) to give the title compound (900 mg).

$^1$H NMR (300 MHz, DMSO-d$_6$) δ1.38-1.52 (1H, m), 1.57-1.77 (5H, m), 1.78-1.90 (4H, m), 2.09-2.29 (1H, m), 3.81-3.93 (6H, m), 3.95-4.09 (2H, m), 4.14-4.23 (1H, m), 6.96 (1H, s); MS m/z 330.2 [M+1]$^+$.

F) 5-(4-chloro-3-{[(2S)-1-(1H-tetrazol-1-yl)propan-2-yl]oxy}phenyl)-N-(3-{[(1S)-2,2-difluorocyclopropyl]methoxy}-1-{1,4-dioxaspiro[4.5]decan-8-yl}-1H-pyrazol-4-yl)pyrimidin-2-amine A mixture of 3-{[(1S)-2,2-difluorocyclopropyl]methoxy}-1-{1,4-dioxaspiro[4.5]decan-8-yl}-1H-pyrazol-4-amine (900 mg), 2-chloro-5-(4-chloro-3-(((2S)-1-(1H-tetrazol-1-yl)propan-2-yl)oxy)phenyl)pyrimidine (958 mg), BINAP (339 mg), DBU (249 mg) and Pd$_2$(dba)$_3$ (43.7 mg) in DMA (15 mL) was heated at 100° C. for 2 hr under microwave irradiation. The mixture was poured into water at room temperature and extracted with ethyl acetate. The organic layer was separated, washed with water and saturated brine, dried over anhydrous magnesium sulfate and concentrated in vacuo. The residue was purified by silica gel column chromatography (ethyl acetate/hexane) to give the title compound (440 mg).

$^1$H NMR (300 MHz, DMSO-d$_6$) δ1.33 (3H, d, J=6.0 Hz), 1.39-1.55 (1H, m), 1.59-1.82 (5H, m), 1.87-1.97 (4H, m), 2.13-2.24 (1H, m), 3.89 (4H, s), 4.06-4.14 (2H, m), 4.25 (1H, ddd, J=10.4, 6.6, 3.8 Hz), 4.75-4.85 (1H, m), 4.86-4.96 (1H, m), 5.12-5.22 (1H, m), 7.24 (1H, d, J=8.1 Hz), 7.37 (1H, s), 7.45 (1H, d, J=8.3 Hz), 7.77 (1H, s), 8.65 (1H, s), 8.71 (2H, s), 9.37 (1H, s); MS m/z 645.4 [M+1]$^+$.

G) 4-(4-{[5-(4-chloro-3-{[(2S)-1-(1H-tetrazol-1-yl)propan-2-yl]oxy}phenyl)pyrimidin-2-yl]amino}-3-{[(1S)-2,2-difluorocyclopropyl]methoxy}-1H-pyrazol-1-yl)cyclohexan-1-one To a solution of 5-(4-chloro-3-{[(2S)-1-(1H-tetrazol-1-yl)propan-2-yl]oxy}phenyl)-N-(3-{[(1S)-2,2-difluorocyclopropyl]methoxy}-1-{1,4-dioxaspiro[4.5]decan-8-yl}-1H-pyrazol-4-yl)pyrimidin-2-amine (430 mg) in MeOH (5.00 mL) was added 2 M aqueous hydrogen chloride solution (665 μL) at room temperature. The mixture was stirred at 50° C. under nitrogen atmosphere for 4 hr. The mixture was concentrated in vacuo, the residue was diluted with water/ethyl acetate, and saturated aqueous sodium hydrogencarbonate solution was added to the solution to adjust the pH of the solution to 8-9. The mixture was extracted with ethyl acetate. The organic layer was separated, washed with water and saturated brine, dried over anhydrous magnesium sulfate and concentrated in vacuo. The residue was purified by silica gel column chromatography (ethyl acetate/hexane) to give the title compound (222 mg).

$^1$H NMR (300 MHz, DMSO-d$_6$) δ1.33 (3H, d, J=6.1 Hz), 1.40-1.57 (1H, m), 1.60-1.76 (1H, m), 2.06-2.41 (7H, m), 2.53-2.67 (2H, m), 4.06-4.15 (1H, m), 4.21-4.31 (1H, m), 4.46-4.56 (1H, m), 4.75-4.85 (1H, m), 4.86-4.95 (1H, m), 5.11-5.23 (1H, m), 7.24 (1H, d, J=8.4 Hz), 7.36 (1H, s), 7.45 (1H, d, J=8.3 Hz), 7.84 (1H, s), 8.67 (1H, s), 8.71 (2H, s), 9.37 (1H, s); MS m/z 601.4 [M+1]$^+$;

H) 5-(3-(((S)-1-(1H-tetrazol-1-yl)propan-2-yl)oxy)-4-chlorophenyl)-N-(3-(((S)-2,2-difluorocyclopropyl)methoxy)-1-(trans-4-morpholinocyclohexyl)-1H-pyrazol-4-yl)pyrimidin-2-amine To a solution of 4-(4-{[5-(4-chloro-3-{[(2S)-1-(1H-tetrazol-1-yl)propan-2-yl]oxy}phenyl)pyrimidin-2-yl]amino}-3-{[(1S)-2,2-difluorocyclopropyl]methoxy}-1H-pyrazol-1-yl)cyclohexan-1-one (100 mg) and morpholine (43.5 mg) in MeOH (10 mL)/AcOH (2.00 mL) was added 2-methylpyridine-borane (53.4 mg) at room temperature. The mixture was stirred at 60° C. under nitrogen atmosphere for 4 hr. 8 M Aqueous sodium hydroxide solution was added to the solution to adjust the pH of the solution to 8-9 and then the mixture was concentrated in vacuo. The residue was diluted with water/ethyl acetate and the mixture was extracted with ethyl acetate. The organic layer was separated, washed with water and saturated brine, dried over anhydrous magnesium sulfate and concentrated in vacuo. The residue was purified by silica gel column chromatography (NH, MeOH/ethyl acetate) and column chromatography (MeOH/ethyl acetate) to give the title compound (30.0 mg) and the compound of Example 870 (44.0 mg, cis form), respectively.

$^1$H NMR (300 MHz, DMSO-d$_6$) δ0.86 (2H, t, J=6.2 Hz), 1.28-1.53 (7H, m), 1.59-1.80 (4H, m), 1.86-1.98 (2H, m), 2.01-2.11 (2H, m), 2.13-2.27 (2H, m), 3.53-3.63 (4H, m), 3.79-3.97 (1H, m), 4.03-4.13 (1H, m), 4.16-4.29 (1H, m), 4.74-4.84 (1H, m), 4.86-4.97 (1H, m), 5.08-5.26 (1H, m), 7.24 (1H, d, J=8.4 Hz), 7.36 (1H, s), 7.45 (1H, d, J=7.9 Hz), 7.75 (1H, s), 8.62 (1H, s), 8.70 (2H, s), 9.37 (1H, s).

Example 932

(S)-5-(3-((1-(1H-tetrazol-1-yl)propan-2-yl)oxy)-4-chlorophenyl)-N-(1-(2-(2,2-dimethyl-1,3-dioxan-5-yl)-2-azaspiro[3.3]heptan-6-yl)-3-(2,2,2-trifluoroethoxy)-1H-pyrazol-4-yl)pyrimidin-2-amine

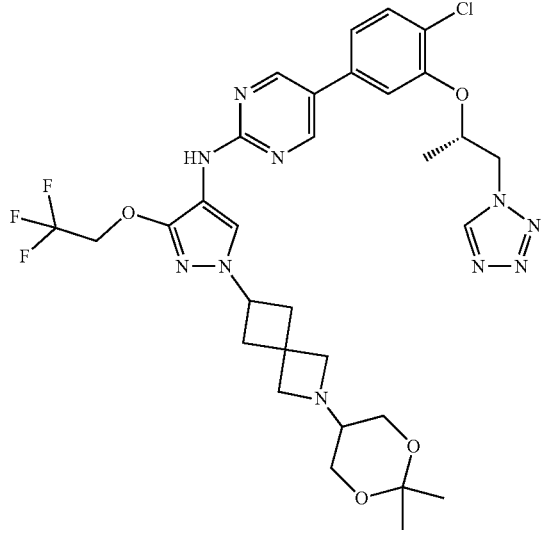 [SMILES: C[C@@H](Cn1cnnn1)Oc1cc(-c2cnc(Nc3cn(C4CC5(C4)CN(C4COC(C)(C)OC4)C5)nc3OCC(F)(F)F)nc2)ccc1Cl]

To a mixture of N-(1-{2-azaspiro[3.3]heptan-6-yl}-3-(2,2,2-trifluoroethoxy)-1H-pyrazol-4-yl)-5-(4-chloro-3-{[(2-S)-1-(1H-tetrazol-1-yl)propan-2-yl]oxy}phenyl)pyrimidin-2-amine (150 mg) and 2,2-dimethyl-1,3-dioxan-5-one (163 mg) in AcOH (0.2 mL) and MeOH (2.0 mL) was added 2-methylpyridine-borane (134 mg) at room temperature. The mixture was stirred at 60° C. under nitrogen atmosphere for 4 hr. The mixture was poured into water and extracted with ethyl acetate. The organic layer was separated, washed with saturated brine, dried over anhydrous magnesium sulfate and concentrated in vacuo. The residue was purified by column chromatography (NH, ethyl acetate/hexane) to give the title compound (54.0 mg).

$^1$H NMR (300 MHz, CDCl$_3$) δ1.37-1.46 (9H, m), 2.39-2.55 (1H, m), 2.63 (4H, d, J=7.89 Hz), 3.27-3.32 (2H, m), 3.27-3.32 (2H, m), 3.33-3.39 (2H, m), 3.53-3.65 (2H, m), 3.72-3.83 (2H, m), 4.36-4.52 (1H, m), 4.58-4.78 (3H, m), 4.80-4.93 (2H, m), 6.79-6.90 (2H, m), 7.02-7.11 (1H, m), 7.41-7.48 (1H, m), 7.88 (1H, s), 8.52 (2H, s), 8.96 (1H, s).

Example 935

(S)-5-(3-((1-(1H-tetrazol-1-yl)propan-2-yl)oxy)-4-chlorophenyl)-N-(3-isopropyl-1-(2-(oxetan-3-yl)-2-azaspiro[3.3]heptan-6-yl)-1H-pyrazol-4-yl)pyrimidin-2-amine

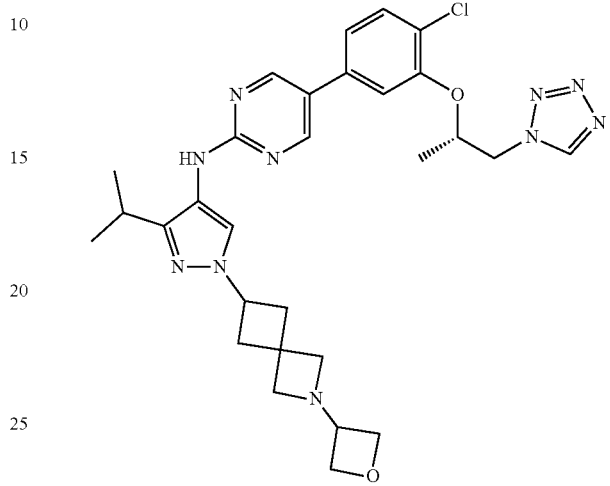

A) tert-butyl 6-[4-nitro-3-(propan-2-yl)-1H-pyrazol-1-yl]-2-azaspiro[3.3]heptane-2-carboxylate A mixture of 4-nitro-3-(propan-2-yl)-1H-pyrazole (4.88 g), tert-butyl 6-(methanesulfonyloxy)-2-azaspiro[3.3]heptane-2-carboxylate (9.11 g) and cesium carbonate (30.6 g) in DMA (100 mL) was stirred at 100° C. for 12 hr. The reaction mixture was partitioned between ethyl acetate and water. The organic layer was washed with saturated brine, dried over anhydrous sodium sulfate and concentrated under reduced pressure. The residue was purified by silica gel column chromatography (ethyl acetate/hexane) to give the title compound (7.89 g).

$^1$H NMR (300 MHz, CDCl$_3$) δ1.30 (6H, d, J=7.0 Hz), 1.44 (9H, s), 2.66-2.80 (4H, m), 3.59 (1H, dt, J=13.8, 6.9 Hz), 4.00 (2H, s), 4.02 (2H, s), 4.59 (1H, quintet, J=7.7 Hz), 8.10 (1H, s); MS m/z 351.3 [M+1]$^+$.

B) tert-butyl 6-[4-amino-3-(propan-2-yl)-1H-pyrazol-1-yl]-2-azaspiro[3.3]heptane-2-carboxylate A mixture of tert-butyl 6-[4-nitro-3-(propan-2-yl)-1H-pyrazol-1-yl]-2-azaspiro[3.3]heptane-2-carboxylate (7.88 g) and 10% palladium-carbon (2.45 g) in MeOH (110 mL) and THF (110 mL) was stirred at room temperature for 4 hr under normal pressure of hydrogen atmosphere. The catalyst was removed by filtration, and the filtrate was concentrated under reduced pressure to give the title compound. This product was subjected to the next reaction without further purification.

MS m/z 321.3 [M+1]$^+$.

C) tert-butyl (S)-6-(4-((5-(3-((1-(1H-tetrazol-1-yl)propan-2-yl)oxy)-4-chlorophenyl)pyrimidin-2-yl)amino)-3-isopropyl-1H-pyrazol-1-yl)-2-azaspiro[3.3]heptane-2-carboxylate A mixture of 2-chloro-5-(4-chloro-3-(((2S)-1-(1H-tetrazol-1-yl)propan-2-yl)oxy)phenyl)pyrimidine (8.63 g), tert-butyl 6-[4-amino-3-(propan-2-yl)-1H-pyrazol-1-yl]-2-azaspiro[3.3]heptane-2-carboxylate (7.17 g), Pd₂(dba)₃ (1.02 g), BINAP (1.39 g) and DBU (5.10 g) in DMA (110 mL) was stirred at 100° C. for 1 hr under argon atmosphere. The reaction mixture was partitioned between ethyl acetate and saturated aqueous sodium hydrogencarbonate solution. The organic layer was washed with saturated brine, dried over anhydrous sodium sulfate and concentrated under reduced pressure. The residue was purified by silica gel column chromatography (ethyl acetate/hexane then MeOH/ethyl acetate, and then NH, ethyl acetate/hexane then MeOH/ethyl acetate) to give the title compound (6.58 g).

¹H NMR (300 MHz, CDCl₃) δ1.32 (6H, d, J=6.9 Hz), 1.41-1.43 (2H, m), 1.45 (9H, s), 2.69 (2H, s), 2.72 (2H, s), 2.94-3.02 (2H, m), 3.98 (2H, s), 4.02 (2H, s), 4.53-4.64 (1H, m), 4.67-4.77 (1H, m), 4.81-4.91 (2H, m), 6.63 (1H, s), 6.86 (1H, s), 7.07 (1H, d, J=8.5 Hz), 7.44 (1H, d, J=7.7 Hz), 7.89 (1H, s), 8.52 (2H, s), 8.96 (1H, s); MS m/z 635.4 [M+1]⁺.

D) (S)-5-(3-((1-(1H-tetrazol-1-yl)propan-2-yl)oxy)-4-chlorophenyl)-N-(3-isopropyl-1-(2-azaspiro[3.3]heptan-6-yl)-1H-pyrazol-4-yl)pyrimidin-2-amine TFA (11.7 g) was added to a solution of tert-butyl (S)-6-(4-((5-(3-((1-(1H-tetrazol-1-yl)propan-2-yl)oxy)-4-chlorophenyl)pyrimidin-2-yl)amino)-3-isopropyl-1H-pyrazol-1-yl)-2-azaspiro[3.3]heptane-2-carboxylate (6.57 g) in toluene (100 mL) at 0° C. The mixture was stirred at room temperature for 13 hr. The reaction mixture was neutralized with saturated aqueous sodium hydrogencarbonate solution at 0° C. THF and 8 M aqueous sodium hydroxide solution were added thereto. The resulting mixture was extracted with ethyl acetate. The organic layer was washed with saturated brine, dried over anhydrous sodium sulfate and concentrated under reduced pressure. The residue was purified by silica gel column chromatography (NH, MeOH/ethyl acetate) to give the title compound (3.30 g).

¹H NMR (300 MHz, DMSO-d₆) δ1.15 (6H, d, J=6.8 Hz), 1.33 (3H, d, J=6.1 Hz), 2.39-2.48 (2H, m), 2.53-2.61 (2H, m), 3.00-3.10 (1H, m), 3.44 (2H, s), 3.54 (2H, s), 4.49-4.63 (1H, m), 4.75-4.86 (1H, m), 4.87-4.97 (1H, m), 5.14-5.24 (1H, m), 7.25 (1H, d, J=8.9 Hz), 7.37 (1H, s), 7.45 (1H, d, J=8.4 Hz), 7.83 (1H, s), 8.71 (2H, s), 8.84 (1H, s), 9.37 (1H, s), NH was not assigned; MS m/z 535.3 [M+1]⁺.

E) (S)-5-(3-((1-(1H-tetrazol-1-yl)propan-2-yl)oxy)-4-chlorophenyl)-N-(3-isopropyl-1-(2-(oxetan-3-yl)-2-azaspiro[3.3]heptan-6-yl)-1H-pyrazol-4-yl)pyrimidin-2-amine A mixture of (S)-5-(3-((1-(1H-tetrazol-1-yl)propan-2-yl)oxy)-4-chlorophenyl)-N-(3-isopropyl-1-(2-azaspiro[3.3]heptan-6-yl)-1H-pyrazol-4-yl)pyrimidin-2-amine (200 mg), oxetan-3-one (268 mg) and 2-methylpyridine-borane (117 mg) in MeOH (10 mL) and AcOH (1.0 mL) was stirred at 60° C. for 1 hr. The reaction mixture was concentrated under reduced pressure. The residue was partitioned between ethyl acetate and saturated aqueous sodium hydrogencarbonate solution. The organic layer was washed with saturated brine, dried over anhydrous sodium sulfate and concentrated under reduced pressure. The residue was purified by silica gel column chromatography (NH, ethyl acetate/hexane then MeOH/ethyl acetate) to give the title compound (57.4 mg).

¹H NMR (300 MHz, DMSO-d₆) δ1.16 (6H, d, J=6.6 Hz), 1.33 (3H, d, J=5.7 Hz), 2.52-2.61 (4H, m), 3.05 (1H, dt, J=13.3, 6.7 Hz), 3.20 (2H, s), 3.28 (2H, brs), 3.59-3.71 (1H, m), 4.32 (2H, t, J=5.2 Hz), 4.53 (2H, t, J=6.3 Hz), 4.60-4.70 (1H, m), 4.76-4.85 (1H, m), 4.87-4.97 (1H, m), 5.13-5.25 (1H, m), 7.25 (1H, d, J=8.3 Hz), 7.37 (1H, s), 7.45 (1H, d, J=8.3 Hz), 7.85 (1H, s), 8.71 (2H, s), 8.85 (1H, s), 9.37 (1H, s).

Example 936

(S)-5-(3-((1-(1H-tetrazol-1-yl)propan-2-yl)oxy)-4-chlorophenyl)-N-(3-isopropyl-1-(2-(tetrahydro-2H-pyran-4-yl)-2-azaspiro[3.3]heptan-6-yl)-1H-pyrazol-4-yl)pyrimidin-2-amine

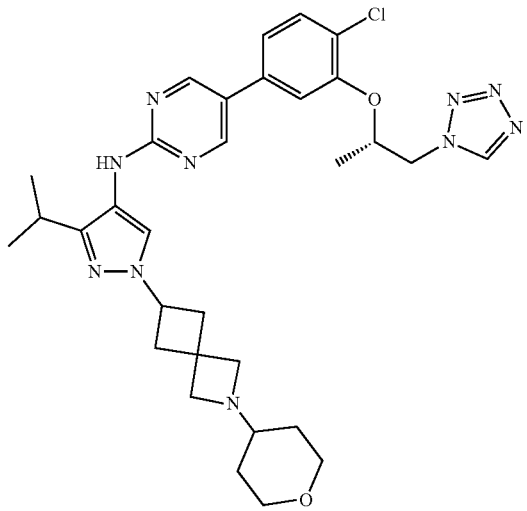 [SMILES: CC(C)c1nn(C2CC3(C2)CN(C2CCOCC2)C3)cc1Nc1ncc(-c2ccc(Cl)c(O[C@@H](C)Cn3cnnn3)c2)cn1]

A mixture of (S)-5-(3-((1-(1H-tetrazol-1-yl)propan-2-yl)oxy)-4-chlorophenyl)-N-(3-isopropyl-1-(2-azaspiro[3.3]heptan-6-yl)-1H-pyrazol-4-yl)pyrimidin-2-amine (200 mg), dihydro-2H-pyran-4(3H)-one (373 mg) and 2-methylpyridine-borane (117 mg) in MeOH (10 mL) and AcOH (1.0 mL) was stirred at 60° C. for 1 hr. The reaction mixture was concentrated under reduced pressure. The residue was partitioned between ethyl acetate and saturated aqueous sodium hydrogencarbonate solution. The organic layer was washed with saturated brine, dried over anhydrous sodium sulfate and concentrated under reduced pressure. The residue was purified by silica gel column chromatography (NH, ethyl acetate/hexane then MeOH/acetate) to give the title compound (161 mg). 15 ¹H NMR (300 MHz, DMSO-d₆) δ1.02-1.13 (2H, m), 1.16 (6H, d, J=7.0 Hz), 1.33 (3H, d, J=6.0 Hz), 1.56 (2H, d, J=12.9 Hz), 2.07-2.19 (1H, m), 2.99-3.07 (1H, m), 3.09 (2H, s), 3.18 (2H, s), 3.22-3.30 (2H, m), 3.75-3.84 (2H, m), 4.62 (1H, quin, J=7.9 Hz), 4.76-4.85 (1H, m), 4.87-4.96 (1H, m), 5.12-5.26 (1H, m), 7.25 (1H, d, J=8.6 Hz), 7.37 (1H, s), 7.45 (1H, d, J=8.5 Hz), 7.85 (1H, s), 8.71 (2H, s), 8.85 (1H, s), 9.37 (1H, s), 4H were not assigned.

Example 937

(S)-5-(3-((1-(1H-tetrazol-1-yl)propan-2-yl)oxy)-4-chlorophenyl)-N-(1-(2-(4-methyltetrahydro-2H-pyran-4-yl)-2-azaspiro[3.3]heptan-6-yl)-3-(2,2,2-trifluoroethoxy)-1H-pyrazol-4-yl)pyrimidin-2-amine

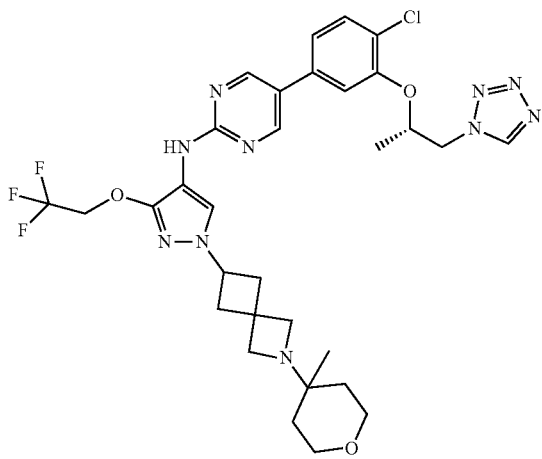 [SMILES: C[C@@H](Cn1cnnn1)Oc1cc(-c2cnc(Nc3cn(C4CC5(C4)CN(C4(C)CCOCC4)C5)nc3OCC(F)(F)F)nc2)ccc1Cl]

A) tert-butyl 6-[(tert-butyldiphenylsilyl)oxy]-2-azaspiro[3.3]heptane-2-carboxylate A mixture of tert-butyl 6-hydroxy-2-azaspiro[3.3]heptane-2-carboxylate (10.0 g), tert-butyl(chloro)diphenylsilane (16.7 g) and 1H-imidazole (6.37 g) in DMF (150 mL) was stirred at room temperature for 16 hr. The reaction mixture was partitioned between ethyl acetate, hexane and water. The organic layer was washed with saturated brine, dried over anhydrous sodium sulfate and concentrated under reduced pressure. The residue was purified by silica gel column chromatography (ethyl acetate/hexane) to give the title compound (21.1 g).

$^1$H NMR (300 MHz, CDCl$_3$) δ1.01 (9H, s), 1.40 (9H, s), 2.12-2.24 (2H, m), 2.26-2.40 (2H, m), 3.73 (2H, s), 3.84 (2H, s), 4.12 (1H, d, J=7.6 Hz), 7.35-7.41 (6H, m), 7.63 (4H, d, J=6.6 Hz); MS m/z 396.2 [M+1-(tBu)]$^+$.

B) 6-[(tert-butyldiphenylsilyl)oxy]-2-azaspiro[3.3]heptane

TFA (5.24 g) was added to a solution of tert-butyl 6-[(tert-butyldiphenylsilyl)oxy]-2-azaspiro[3.3]heptane-2-carboxylate (2.55 g) in toluene (20 mL) at 0° C. The mixture was stirred at room temperature for 2.5 hr. The reaction mixture was quenched with saturated aqueous sodium hydrogencarbonate solution at 0° C. The resulting mixture was partitioned between ethyl acetate and water. The organic layer was washed with saturated brine, dried over anhydrous sodium sulfate and concentrated under reduced pressure to give desired product. This product was purified by recrystallization from ethyl acetate/hexane to give the title compound (1.28 g).

$^1$H NMR (300 MHz, CDCl$_3$) δ1.00 (9H, s), 2.20-2.28 (2H, m), 2.43-2.52 (2H, m), 3.84 (2H, s), 3.95 (2H, s), 4.02-4.14 (1H, m), 7.34-7.47 (6H, m), 7.59 (4H, d, J=6.6 Hz), NH was not assigned; MS m/z 352.2 [M+1]$^+$.

C) 4-{6-[(tert-butyldiphenylsilyl)oxy]-2-azaspiro[3.3]heptan-2-yl}-tetrahydro-2H-pyran-4-carbonitrile Dihydro-2H-pyran-4(3H)-one (426 mg) was added to a solution of 6-[(tert-butyldiphenylsilyl)oxy]-2-azaspiro[3.3] heptane (1.50 g) in AcOH (5.0 mL) at 0° C. Trimethylsilanecarbonitrile (422 mg) was added thereto at 0° C. The mixture was stirred at room temperature for 19.5 hr. Dihydro-2H-pyran-4(3H)-one (852 mg) and trimethylsilanecarbonitrile (844 mg) were added thereto at room temperature. The mixture was stirred at room temperature for 7.5 hr. The reaction mixture was partitioned between diethyl ether and water. The organic layer was washed with saturated aqueous sodium hydrogencarbonate solution and saturated brine, dried over anhydrous sodium sulfate and concentrated under reduced pressure. The residue was purified by silica gel column chromatography (ethyl acetate/hexane) to give the title compound (1.38 g).

$^1$H NMR (300 MHz, CDCl$_3$) δ1.02 (9H, s), 1.46-1.54 (2H, m), 1.66-1.83 (2H, m), 2.12-2.25 (2H, m), 2.31-2.45 (2H, m), 3.17 (2H, s), 3.28 (2H, s), 3.58 (2H, t, J=11.0 Hz), 3.83-3.95 (2H, m), 4.13-4.20 (1H, m), 7.28-7.49 (6H, m), 7.63 (4H, d, J=6.5 Hz);

MS m/z 434.3 [M+1-(CN)]$^+$.

D) 6-[(tert-butyldiphenylsilyl)oxy]-2-(4-methyltetrahydro-2H-pyran-4-yl)-2-azaspiro[3.3]heptane A solution of 3 M methylmagnesium bromide in 2-methyltetrahydrofuran (2.96 mL) was added to a solution of 4-{6-[(tert-butyldiphenylsilyl)oxy]-2-azaspiro[3.3]heptan-2-yl}-tetrahydro-2H-pyran-4-carbonitrile (1.37 g) in THF (30 mL) at 0° C. The mixture was stirred at 0° C. for 5 min and at room temperature for 3 hr. 3 M methylmagnesium bromide in 2-methyltetrahydrofuran (1.0 mL) was added thereto at 0° C. The mixture was stirred at room temperature for 18.5 hr. The reaction mixture was quenched with saturated aqueous ammonium chloride solution at 0° C. The reaction mixture was partitioned between diethyl ether and water. The organic layer was washed with saturated brine, dried over anhydrous sodium sulfate and concentrated under reduced pressure. The residue was purified by silica gel column chromatography (NH, ethyl acetate/hexane) to give the title compound (926 mg).

$^1$H NMR (300 MHz, CDCl$_3$) δ0.90 (3H, s), 1.02 (9H, s), 1.16-1.25 (2H, m), 1.39 (1H, d, J=3.0 Hz), 2.09-2.20 (2H, m), 2.27-2.38 (2H, m), 3.01 (2H, s), 3.12 (2H, s), 3.42-3.53 (2H, m), 3.75-3.85 (2H, m), 4.05-4.19 (2H, m), 7.34-7.46 (6H, m), 7.64 (4H, d, J=6.4 Hz); MS m/z 450.3 [M+1]$^+$.

E) 2-(4-methyltetrahydro-2H-pyran-4-yl)-2-azaspiro[3.3]heptan-6-ol

A solution of tetrabutylammonium fluoride in THF (1 M, 6.1 mL) was added to a solution of 6-[(tert-butyldiphenylsilyl)oxy]-2-(4-methyltetrahydro-2H-pyran-4-yl)-2-azaspiro[3.3]heptane (923 mg) in THF (10 mL) at room temperature. The mixture was stirred at room temperature for 61.5 hr. The reaction mixture was partitioned between ethyl acetate and saturated brine. The organic layer was dried over anhydrous sodium sulfate and concentrated under reduced pressure. The residue was purified by silica gel column chromatography (NH, ethyl acetate/hexane) to give the title compound (308 mg).

$^1$H NMR (300 MHz, CDCl$_3$) δ0.95 (3H, s), 1.27 (2H, d, J=7.0 Hz), 1.40-1.52 (2H, m), 1.67-1.81 (1H, m), 1.94-2.04

(2H, m), 2.45-2.57 (2H, m), 3.16 (4H, d, J=4.5 Hz), 3.45-3.58 (2H, m), 3.76-3.89 (2H, m), 4.15-4.26 (1H, m); MS m/z 212.2 [M+1]+.

F) 2-(4-methyltetrahydro-2H-pyran-4-yl)-2-azaspiro [3.3]heptan-6-yl methanesulfonate Methanesulfonyl chloride (180 mg) was added to a solution of 2-(4-methyltetrahydro-2H-pyran-4-yl)-2-azaspiro [3.3]heptan-6-ol (305 mg) in THF (10 mL) at 0° C. The mixture was stirred at 0° C. for 30 min. The reaction mixture was filtered and washed with THF. The filtrate was concentrated under reduced pressure to give the title compound. This product was subjected to the next reaction without further purification.
MS m/z 290.2 [M+1]+.

G) 2-(4-methyltetrahydro-2H-pyran-4-yl)-6-[4-nitro-3-(2,2,2-trifluoroethoxy)-1H-pyrazol-1-yl]-2-azaspiro[3.3]heptane A mixture of 4-nitro-3-(2,2,2-trifluoroethoxy)-1H-pyrazole (303 mg), cesium carbonate (938 mg) and 2-(4-methyltetrahydro-2H-pyran-4-yl)-2-azaspiro[3.3]heptan-6-yl methanesulfonate (416 mg) in DMA (100 mL) was stirred at 100° C. for 12 hr. The reaction mixture was partitioned between ethyl acetate and water. The organic layer was washed with saturated brine, dried over anhydrous sodium sulfate and concentrated under reduced pressure. The residue was purified by silica gel column chromatography (NH, ethyl acetate/hexane then MeOH/ethyl acetate) to give the title compound (278 mg).
$^1$H NMR (300 MHz, CDCl$_3$) δ1.02 (3H, brs), 1.30-1.41 (2H, m), 1.43-1.52 (2H, m), 2.56-2.78 (4H, m), 3.18-3.49 (4H, m), 3.49-3.57 (2H, m), 3.81-3.91 (2H, m), 4.44-4.56 (1H, m), 4.73 (2H, q, J=7.8 Hz), 8.02 (1H, s); MS m/z 405.3 [M+1]+.

H) 1-[2-(4-methyltetrahydro-2H-pyran-4-yl)-2-azaspiro[3.3]heptan-6-yl]-3-(2,2,2-trifluoroethoxy)-1H-pyrazol-4-amine A mixture of 2-(4-methyltetrahydro-2H-pyran-4-yl)-6-[4-nitro-3-(2,2,2-trifluoroethoxy)-1H-pyrazol-1-yl]-2-azaspiro [3.3]heptane (275 mg) and 10% palladium-carbon (74.4 mg) in MeOH (6.5 mL) and THF (6.5 mL) was stirred at room temperature for 1.5 hr under normal pressure of hydrogen atmosphere. The catalyst was removed by filtration, and the filtrate was concentrated under reduced pressure to give the title compound. This product was subjected to the next reaction without further purification.
MS m/z 375.4 [M+1]+.

I) (S)-5-(3-((1-(1H-tetrazol-1-yl)propan-2-yl)oxy)-4-chlorophenyl)-N-(1-(2-(4-methyltetrahydro-2H-pyran-4-yl)-2-azaspiro[3.3]heptan-6-yl)-3-(2,2,2-trifluoroethoxy)-1H-pyrazol-4-yl)pyrimidin-2-amine A mixture of 2-chloro-5-(4-chloro-3-(((2S)-1-(1H-tetrazol-1-yl)propan-2-yl)oxy)phenyl)pyrimidine (262 mg), 1-[2-(4-methyltetrahydro-2H-pyran-4-yl)-2-azaspiro[3.3] heptan-6-yl]-3-(2,2,2-trifluoroethoxy)-1H-pyrazol-4-amine (254 mg), Pd$_2$(dba)$_3$ (31.1 mg), BINAP (42.3 mg) and DBU (155 mg) in DMA (110 mL) was stirred at 100° C. for 1 hr under argon atmosphere. The reaction mixture was partitioned between ethyl acetate and saturated aqueous sodium hydrogencarbonate solution. The organic layer was washed with saturated brine, dried over anhydrous sodium sulfate and concentrated under reduced pressure. The residue was purified by silica gel column chromatography (NH, ethyl acetate/hexane) and by preparative HPLC (water/CH$_3$CN containing 0.1% TFA) to give the title compound (167 mg).
$^1$H NMR (300 MHz, DMSO-d$_6$) δ0.81-0.88 (1H, m), 0.91 (3H, s), 1.10-1.26 (4H, m), 1.32 (6H, d, J=5.7 Hz), 3.12 (2H, s), 3.20 (2H, s), 3.39-3.47 (2H, m), 3.63-3.73 (2H, m), 4.57 (1H, t, J=7.7 Hz), 4.73-4.83 (3H, m), 4.87-4.96 (1H, m), 5.12-5.22 (1H, m), 7.24 (1H, d, J=8.4 Hz), 7.36 (1H, s), 7.45 (1H, d, J=8.2 Hz), 7.82 (1H, s), 8.70 (2H, s), 8.76 (1H, s), 9.37 (1H, s).

Example 942

5-(3-(((S)-1-(1H-tetrazol-1-yl)propan-2-yl)oxy)-4-chlorophenyl)-N-(1-(trans-3-((tetrahydro-2H-pyran-4-yl)amino)cyclobutyl)-3-(2,2,2-trifluoroethoxy)-1H-pyrazol-4-yl)pyrimidin-2-amine

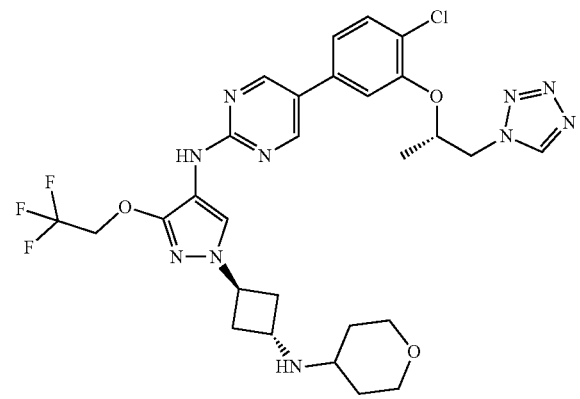 [SMILES: C[C@@H](Cn1cnnn1)Oc1cc(-c2cnc(Nc3cn([C@H]4C[C@H](NC5CCOCC5)C4)nc3OCC(F)(F)F)nc2)ccc1Cl]

A) tert-butyl N-[cis-3-(methanesulfonyloxy)cyclobutyl]carbamate

Methanesulfonyl chloride (2.84 g) was added to a solution of tert-butyl N-[cis-3-hydroxycyclobutyl]carbamate (3.89 g) and triethylamine (3.13 g) in THF (80 mL) at 0° C. The mixture was stirred at room temperature for 3 hr. The reaction mixture was partitioned between ethyl acetate and water. The organic layer was washed with saturated brine, dried over anhydrous sodium sulfate and concentrated under reduced pressure to give the title compound (5.48 g). This product was subjected to the next reaction without further purification.
$^1$H NMR (300 MHz, CDCl$_3$) δ1.44 (9H, s), 2.13-2.25 (2H, m), 2.85-2.96 (2H, m), 2.99 (3H, s), 3.69-3.94 (1H, m), 4.45-4.81 (2H, m); MS m/z 210.1 [M+1-(tBu)]+.

B) tert-butyl N-[trans-3-[4-nitro-3-(2,2,2-trifluoroethoxy)-1H-pyrazol-1-yl]cyclobutyl]carbamate A mixture of 4-nitro-3-(2,2,2-trifluoroethoxy)-1H-pyrazole (2.11 g), cesium carbonate (6.48 g) and tert-butyl N-[cis-3-(methanesulfonyloxy)cyclobutyl]carbamate (3.92 g) in DMA (100 mL) was stirred at 100° C. for 15.5 hr. The reaction mixture was partitioned between ethyl acetate and water. The organic layer was washed with saturated brine, dried over anhydrous sodium sulfate and concentrated under reduced pressure. The residue was purified by silica gel column chromatography (ethyl acetate/hexane) to give the title compound (2.08 g).

$^1$H NMR (300 MHz, CDCl$_3$) δ1.46 (9H, s), 2.47-2.64 (2H, m), 2.77-2.92 (2H, m), 4.28-4.48 (1H, m), 4.62-4.88 (4H, m), 8.05 (1H, s); MS m/z 325.2 [M+1-(tBu)]$^+$.

C) tert-butyl N-[trans-3-[4-amino-3-(2,2,2-trifluoroethoxy)-1H-pyrazol-1-yl]cyclobutyl]carbamate A mixture of tert-butyl N-[trans-3-[4-nitro-3-(2,2,2-trifluoroethoxy)-1H-pyrazol-1-yl]cyclobutyl]carbamate (2.07 g) and 10% palladium-carbon (59.6 mg) in MeOH (30 mL) and THF (30 mL) was stirred at room temperature for 8 hr under normal pressure of hydrogen atmosphere. The reaction mixture was filtered. The filtrate was concentrated under reduced pressure to give the title compound. This product was subjected to the next reaction without further purification.

MS m/z 351.2 [M+1]$^+$.

D) tert-butyl (trans-3-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclobutyl)carbamate A mixture of 2-chloro-5-(4-chloro-3-(((2S)-1-(1H-tetrazol-1-yl)propan-2-yl)oxy)phenyl)pyrimidine (2.10 g), tert-butyl N-[trans-3-[4-amino-3-(2,2,2-trifluoroethoxy)-1H-pyrazol-1-yl]cyclobutyl]carbamate (1.90 g), Pd$_2$(dba)$_3$ (249 mg), BINAP (338 mg) and DBU (1.24 g) in DMA (30 mL) was stirred at 100° C. for 1 hr under argon atmosphere. The reaction mixture was partitioned between ethyl acetate and saturated aqueous sodium hydrogencarbonate solution. The organic layer was washed with saturated brine, dried over anhydrous sodium sulfate and concentrated under reduced pressure. The residue was purified by silica gel column chromatography (ethyl acetate/hexane then MeOH/ethyl acetate) to give the title compound (2.20 g).

$^1$H NMR (300 MHz, CDCl$_3$) δ1.43 (3H, d, the other peak was hidden by 1.46), 1.46 (9H, s), 2.39-2.51 (2H, m), 2.80-2.91 (2H, m), 4.30-4.48 (1H, m), 4.60-4.79 (5H, m), 4.83-4.92 (2H, m), 6.83 (1H, s), 6.89 (1H, s), 7.08 (1H, d, J=8.3 Hz), 7.45 (1H, d, J=8.3 Hz), 7.94 (1H, s), 8.53 (2H, s), 8.97 (1H, s); MS m/z 665.3 [M+1]$^+$.

E) 5-(4-chloro-3-{[(2S)-1-(1H-tetrazol-1-yl)propan-2-yl]oxy}phenyl)-N-{1-[trans-3-aminocyclobutyl]-3-(2,2,2-trifluoroethoxy)-1H-pyrazol-4-yl}pyrimidin-2-amine TFA (7.52 g) was added to a solution of tert-butyl (trans-3-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclobutyl)carbamate (2.20 g) in toluene (10 mL) at room temperature. The mixture was stirred at room temperature for 2.5 hr. The reaction mixture was partitioned between ethyl acetate and saturated aqueous sodium hydrogencarbonate solution. The organic layer was washed with saturated brine, dried over anhydrous sodium sulfate and concentrated under reduced pressure. The residue was purified by silica gel column chromatography (NH, MeOH/ethyl acetate) to give the title compound (1.26 g).

$^1$H NMR (300 MHz, DMSO-d$_6$) δ1.26-1.36 (3H, m), 1.76-1.99 (2H, m), 2.06-2.16 (2H, m), 2.54-2.61 (1H, m), 3.54-3.65 (1H, m), 4.72-4.96 (5H, m), 5.12-5.26 (1H, m), 7.20-7.29 (1H, m), 7.37 (1H, s), 7.45 (1H, d, J=8.3 Hz), 7.84 (1H, s), 8.71 (1H, s), 8.75 (1H, brs), 9.37 (1H, s), NH$_2$ was not detected; MS m/z 565.3 [M+1]$^+$.

F) 5-(3-(((S)-1-(1H-tetrazol-1-yl)propan-2-yl)oxy)-4-chlorophenyl)-N-(1-(trans-3-((tetrahydro-2H-pyran-4-yl)amino)cyclobutyl)-3-(2,2,2-trifluoroethoxy)-1H-pyrazol-4-yl)pyrimidin-2-amine A mixture of 5-(4-chloro-3-{[(2S)-1-(1H-tetrazol-1-yl)propan-2-yl]oxy}phenyl)-N-{1-[trans-3-aminocyclobutyl]-3-(2,2,2-trifluoroethoxy)-1H-pyrazol-4-yl}pyrimidin-2-amine (280 mg), dihydro-2H-pyran-4(3H)-one (52.2 mg) and sodium triacetoxyborohydride (391 mg) in THF (10 mL) and AcOH (1.0 mL) was stirred at room temperature for 20 min. The reaction mixture was partitioned between ethyl acetate and saturated aqueous sodium hydrogencarbonate solution. The organic layer was washed with saturated brine, dried over anhydrous sodium sulfate and concentrated under reduced pressure. The residue was purified by silica gel column chromatography (NH, ethyl acetate/hexane and then MeOH/ethyl acetate) to give the title compound (183 mg).

$^1$H NMR (300 MHz, DMSO-d$_6$) δ1.17-1.29 (4H, m), 1.33 (3H, d, J=6.1 Hz), 1.68-1.75 (2H, m), 2.15-2.23 (2H, m), 2.54-2.66 (2H, m), 3.22-3.30 (2H, m), 3.50-3.58 (1H, m), 3.82 (2H, d, J=11.8 Hz), 4.72-4.84 (4H, m), 4.86-4.96 (1H, m), 5.11-5.21 (1H, m), 7.24 (1H, d, J=8.1 Hz), 7.36 (1H, s), 7.45 (1H, d, J=8.4 Hz), 7.85 (1H, s), 8.70 (2H, s), 8.75 (1H, s), 9.37 (1H, s); MS m/z 649.5 [M+1]$^+$.

Example 943

5-(3-(((S)-1-(1H-tetrazol-1-yl)propan-2-yl)oxy)-4-chlorophenyl)-N-(1-(trans-3-morpholinocyclobutyl)-3-(2,2,2-trifluoroethoxy)-1H-pyrazol-4-yl)pyrimidin-2-amine

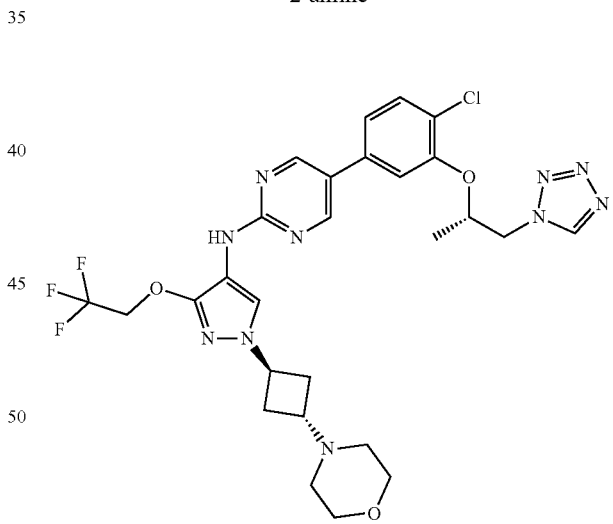

A mixture of 5-(4-chloro-3-{[(2S)-1-(1H-tetrazol-1-yl)propan-2-yl]oxy}phenyl)-N-{1-[trans-3-aminocyclobutyl]-3-(2,2,2-trifluoroethoxy)-1H-pyrazol-4-yl}pyrimidin-2-amine (280 mg), 1-bromo-2-(2-bromoethoxy)ethane (114 mg) and triethylamine (149 mg) in CH$_3$CN (10 mL) was stirred at 60° C. for 19.5 hr. The reaction mixture was partitioned between ethyl acetate and water. The organic layer was washed with saturated brine, dried over anhydrous sodium sulfate and concentrated under reduced pressure. The residue was purified by silica gel column chromatography (NH, ethyl acetate/hexane) to give the title compound (88.1 mg).

$^1$H NMR (300 MHz, DMSO-d$_6$) δ1.33 (3H, d, J=6.2 Hz), 2.29-2.36 (4H, m), 2.37-2.46 (4H, m), 2.86-2.96 (1H, m), 3.61 (4H, brs), 4.65-4.74 (1H, m), 4.76-4.96 (4H, m), 5.13-5.23 (1H, m), 7.24 (1H, d, J=7.9 Hz), 7.37 (1H, s), 7.45 (1H, d, J=8.3 Hz), 7.86 (1H, s), 8.70 (2H, s), 8.76 (1H, s), 9.37 (1H, s); MS m/z 635.5 [M+1]$^+$.

Example 944

5-(4-chloro-3-{[(2S)-1-(1H-tetrazol-1-yl)propan-2-yl]oxy}phenyl)-N-(1-{2-[(4-$^2$H)tetrahydro-2H-pyran-4-yl]-2-azaspiro[3.3]heptan-6-yl}-3-(2,2,2-trifluoroethoxy)-1H-pyrazol-4-yl)pyrimidin-2-amine

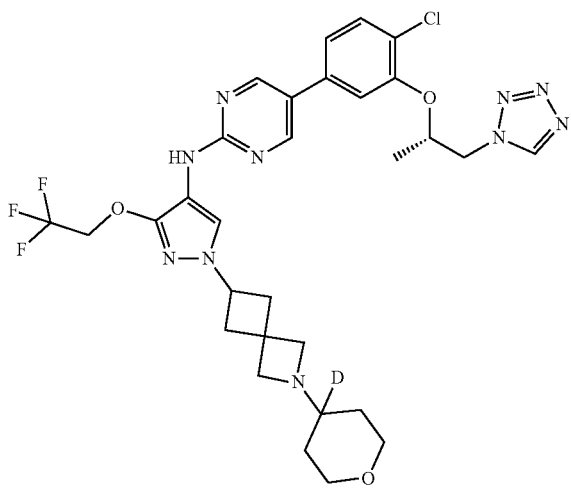 [SMILES: [2H]C1(N2CC3(CC(n4cc(Nc5ncc(-c6ccc(Cl)c(O[C@@H](C)Cn7cnnn7)c6)cn5)c(OCC(F)(F)F)n4)C3)C2)CCOCC1]

A) tert-butyl 6-[4-amino-3-(2,2,2-trifluoroethoxy)-1H-pyrazol-1-yl]-2-azaspiro[3.3]heptane-2-carboxylate A mixture of tert-butyl 6-[4-nitro-3-(2,2,2-trifluoroethoxy)-1H-pyrazol-1-yl]-2-azaspiro[3.3]heptane-2-carboxylate (21 g, 51.6 mmol) and 10% palladium-carbon (1.12 g, 5.16 mmol) in ethyl acetate (100 mL)/EtOH (100 mL) was stirred under normal pressure of hydrogen atmosphere at room temperature for 10 hr. The catalyst was removed by filtration, and then the filtrate was concentrated in vacuo. The residue was purified by column chromatography (NH, ethyl acetate/hexane) to give the title compound (15.6 g).

$^1$H NMR (300 MHz, DMSO-d$_6$) δ1.36 (9H, s), 2.39-2.49 (4H, m), 3.48 (2H, s), 3.82 (2H, brs), 3.90 (2H, brs), 4.38 (1H, quin, J=7.9 Hz), 4.71 (2H, q, J=9.1 Hz), 7.04 (1H, s); MS m/z 377.2 [M+1]$^+$.

B) tert-butyl 6-(4-{[5-(4-chloro-3-{[(2S)-1-(1H-tetrazol-1-yl)propan-2-yl]oxy}phenyl)pyrimidin-2-yl]amino}-3-(2,2,2-trifluoroethoxy)-1H-pyrazol-1-yl)-2-azaspiro[3.3]heptane-2-carboxylate To a mixture of tert-butyl 6-[4-amino-3-(2,2,2-trifluoroethoxy)-1H-pyrazol-1-yl]-2-azaspiro[3.3]heptane-2-carboxylate (5.2 g) and 2-chloro-5-(4-chloro-3-(((2S)-1-(1H-tetrazol-1-yl)propan-2-yl)oxy)phenyl)pyrimidine (4.84 g) in DMA (50 mL) were added BINAP (1.71 g), DBU (3.15 g) and Pd$_2$(dba)$_3$ (1.26 g) at room temperature. The mixture was stirred at 100° C. under nitrogen atmosphere for 10 hr.

The mixture was quenched with water at room temperature and extracted with ethyl acetate. The organic layer was separated, washed with water and saturated brine, dried over anhydrous magnesium sulfate and concentrated in vacuo. The residue was purified by column chromatography (NH, ethyl acetate/hexane) and column chromatography (ethyl acetate/hexane) to give the title compound (3.66 g).

$^1$H NMR (300 MHz, DMSO-d$_6$) δ1.33 (3H, d, J=5.9 Hz), 1.37 (9H, s), 2.53-2.67 (4H, m), 3.86 (2H, brs), 3.94 (2H, brs), 4.50-4.63 (1H, m), 4.73-4.85 (3H, m), 4.86-4.95 (1H, m), 5.13-5.22 (1H, m), 7.24 (1H, d, J=8.9 Hz), 7.36 (1H, s), 7.45 (1H, d, J=7.9 Hz), 7.82 (1H, s), 8.71 (2H, s), 8.78 (1H, s), 9.37 (1H, s); MS m/z 691.3 [M+1]$^+$.

C) N-(1-{2-azaspiro[3.3]heptan-6-yl}-3-(2,2,2-trifluoroethoxy)-1H-pyrazol-4-yl)-5-(4-chloro-3-{[(2S)-1-(1H-tetrazol-1-yl)propan-2-yl]oxy}phenyl)pyrimidin-2-amine To a mixture of tert-butyl 6-(4-{[5-(4-chloro-3-{[(2S)-1-(1H-tetrazol-1-yl)propan-2-yl]oxy}phenyl)pyrimidin-2-yl]amino}-3-(2,2,2-trifluoroethoxy)-1H-pyrazol-1-yl)-2-azaspiro[3.3]heptane-2-carboxylate (2.7 g) in toluene (50 mL) was added TFA (4.44 g) at room temperature. The mixture was stirred at room temperature under nitrogen atmosphere for 10 hr. The mixture was diluted with water/ethyl acetate, 8 M aqueous sodium hydroxide solution was added thereto to bring the pH of the solution to 11 or more, and the resulting mixture was extracted with ethyl acetate. The organic layer was separated, washed with water and saturated brine, dried over anhydrous magnesium sulfate and concentrated in vacuo. The title compound (2.4 g) was subjected to the next reaction without further purification.

$^1$H NMR (300 MHz, DMSO-d$_6$) δ1.33 (3H, d, J=5.8 Hz), 2.56-2.69 (4H, m), 3.75 (2H, s), 3.80 (2H, s), 4.51-4.63 (1H, m), 4.74-4.85 (3H, m), 4.87-4.96 (1H, m), 5.11-5.21 (1H, m), 7.20-7.27 (1H, m), 7.35 (1H, s), 7.46 (1H, d, J=8.5 Hz), 7.82 (1H, s), 8.70 (2H, s), 8.79 (1H, s), 9.37 (1H, s), NH (1H, offset); MS m/z 591.3 [M+1]$^+$.

D) 5-(4-chloro-3-{[(2S)-1-(1H-tetrazol-1-yl)propan-2-yl]oxy}phenyl)-N-(1-{2-[(4-$^2$H)tetrahydro-2H-pyran-4-yl]-2-azaspiro[3.3]heptan-6-yl}-3-(2,2,2-trifluoroethoxy)-1H-pyrazol-4-yl)pyrimidin-2-amine A solution of N-(1-{2-azaspiro[3.3]heptan-6-yl}-3-(2,2,2-trifluoroethoxy)-1H-pyrazol-4-yl)-5-(4-chloro-3-{[(2S)-1-(1H-tetrazol-1-yl)propan-2-yl]oxy}phenyl)pyrimidin-2-amine (150 mg, 0.25 mmol) and dihydro-2H-pyran-4(3H)-one (38 mg, 0.38 mmol, 1.5 eq.) in MeOH (2 mL) was stirred at 50° C. for 1 hr. To the solution was added NaBD$_4$ at 0° C. and the mixture was stirred for 1 hr. The reaction mixture was poured into ice-water and extracted with ethyl acetate. The extract was dried over anhydrous sodium sulfate and concentrated in vacuo. The residue was purified by column chromatography (NH, ethyl acetate/hexane) to give the title compound (48 mg).

$^1$H NMR (300 MHz, CDCl$_3$) δ1.19-1.53 (4H, m), 1.53-1.96 (4H, m), 2.63 (3H, d, J=7.9 Hz), 3.10-3.48 (6H, m), 3.79-4.13 (2H, m), 4.46 (1H, t, J=7.9 Hz), 4.57-4.77 (3H, m), 4.77-4.98 (2H, m), 6.86 (2H, d, J=6.8 Hz), 7.07 (1H, d, J=7.6 Hz), 7.44 (1H, d, J=8.3 Hz), 7.89 (1H, s), 8.52 (2H, s), 8.95 (1H, s).

Example 946

(S)-1-(6-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-azaspiro[3.3]heptan-2-yl)-2-methylpropan-2-ol

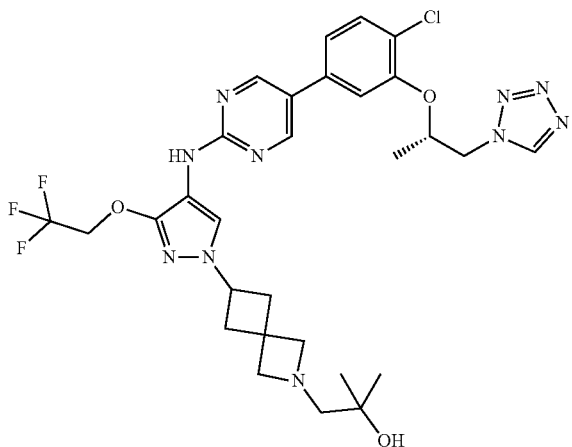 [SMILES: C[C@@H](Cn1cnnn1)Oc1cc(-c2cnc(Nc3cn(C4CC5(C4)CN(CC(C)(C)O)C5)nc3OCC(F)(F)F)nc2)ccc1Cl]

A mixture of N-(1-{2-azaspiro[3.3]heptan-6-yl}-3-(2,2,2-trifluoroethoxy)-1H-pyrazol-4-yl)-5-(4-chloro-3-{[(2S)-1-(1H-tetrazol-1-yl)propan-2-yl]oxy}phenyl)pyrimidin-2-amine (100 mg) and 2,2-dimethyloxirane (61.0 mg) in EtOH (4.0 mL) was heated at 100° C. for 2 hr under microwave irradiation. The mixture was concentrated in vacuo. The residue was purified by column chromatography (NH, MeOH/ethyl acetate) to give the title compound (60.0 mg).
$^1$H NMR (300 MHz, DMSO-d$_6$) δ1.02 (6H, s), 1.14-1.31 (4H, m), 1.32 (3H, d, J=5.9 Hz), 2.26 (2H, s), 3.20 (2H, s), 3.29 (2H, s), 4.00 (1H, s), 4.45-4.61 (1H, m), 4.70-4.85 (1H, m), 4.86-4.95 (1H, m), 5.10-5.24 (1H, m), 7.23 (1H, d, J=8.3 Hz), 7.36 (1H, s), 7.45 (1H, d, J=7.7 Hz), 7.81 (1H, s), 8.70 (2H, s), 8.76 (1H, s), 9.37 (1H, s).

Example 947

(S)-1-(6-(4-((5-(3-((1-(1H-tetrazol-1-yl)propan-2-yl)oxy)-4-chlorophenyl)pyrimidin-2-yl)amino)-3-isopropyl-1H-pyrazol-1-yl)-2-azaspiro[3.3]heptan-2-yl)-2-methylpropan-2-ol

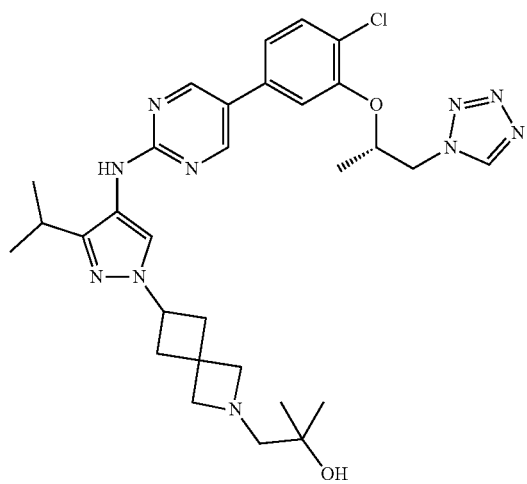 [SMILES: CC(C)c1nn(C2CC3(C2)CN(CC(C)(C)O)C3)cc1Nc1ncc(-c2ccc(Cl)c(O[C@@H](C)Cn3cnnn3)c2)cn1]

A mixture of (S)-5-(3-((1-(1H-tetrazol-1-yl)propan-2-yl)oxy)-4-chlorophenyl)-N-(3-isopropyl-1-(2-azaspiro[3.3]heptan-6-yl)-1H-pyrazol-4-yl)pyrimidin-2-amine (207 mg), 2,2-dimethyloxirane (0.17 mL) and EtOH (5.0 mL) was stirred under microwave irradiation at 100° C. for 2 hr. After being cooled, the mixture was concentrated in vacuo. The residue was purified by silica gel column chromatography (MeOH/ethyl acetate) and silica gel column chromatography (NH, ethyl acetate/hexane) to give the title compound (51.0 mg).
$^1$H NMR (300 MHz, DMSO-d$_6$) δ1.02 (6H, s), 1.15 (6H, d, J=6.9 Hz), 1.33 (3H, d, J=6.2 Hz), 2.27 (2H, s), 2.45-2.49 (2H, m), 2.52-2.57 (2H, m), 2.99-3.12 (1H, m), 3.21 (2H, s), 3.30 (2H, s), 4.00 (1H, s), 4.52-4.66 (1H, m), 4.75-4.85 (1H, m), 4.86-4.96 (1H, m), 5.12-5.25 (1H, m), 7.25 (1H, d, J=8.3 Hz), 7.37 (1H, s), 7.45 (1H, d, J=8.3 Hz), 7.84 (1H, s), 8.71 (2H, s), 8.84 (1H, s), 9.37 (1H, s); MS m/z 607.4 [M+1]$^+$.

Example 951

1-[6-(4-{[5-(4-chloro-3-{[(2S)-1-(1H-tetrazol-1-yl)propan-2-yl]oxy}phenyl)pyrimidin-2-yl]amino}-3-(2,2,2-trifluoroethoxy)-1H-pyrazol-1-yl)-2-azaspiro[3.3]heptan-2-yl]-2-methylpropan-2-yl acetate

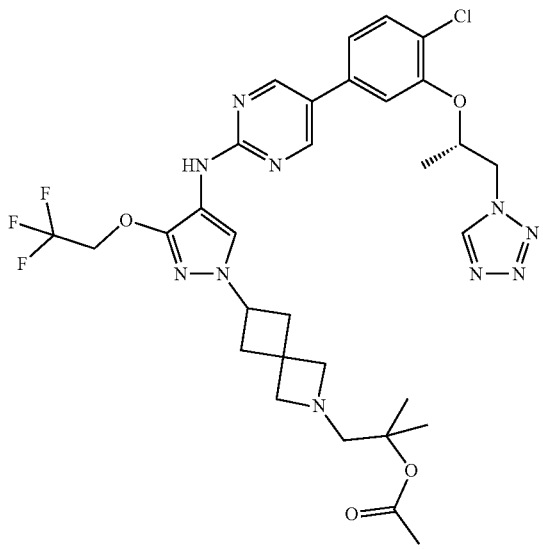 [SMILES: CC(=O)OC(C)(C)CN1CC2(CC(n3cc(Nc4ncc(-c5ccc(Cl)c(O[C@@H](C)Cn6cnnn6)c5)cn4)c(OCC(F)(F)F)n3)C2)C1]

A) 2-methyl-1-{6-[4-nitro-3-(2,2,2-trifluoroethoxy)-1H-pyrazol-1-yl]-2-azaspiro[3.3]heptan-2-yl}propan-2-ol A mixture of 6-[4-nitro-3-(2,2,2-trifluoroethoxy)-1H-pyrazol-1-yl]-2-azaspiro[3.3]heptane (1.58 g), 2,2-dimethyloxirane (1.11 g) and N,N-diisopropylethylamine (1.99 g) in THF (15 mL) was heated at 100° C. for 1 hr under microwave irradiation. Additional 2,2-dimethyloxirane (742 mg) was added thereto, and the mixture was heated at 100° C. for 4 hr under microwave irradiation. The mixture was poured into water and extracted with ethyl acetate. The organic layer was separated, washed with saturated brine, dried over anhydrous magnesium sulfate and concentrated in vacuo. The residue was purified by column chromatography (NH, ethyl acetate/hexane). The obtained solid was crystallized from ethyl acetate/hexane to give the title compound (508 mg).

¹H NMR (300 MHz, CDCl₃) δ1.11 (6H, s), 2.41 (2H, s), 2.65 (4H, t, J=8.53 Hz), 2.95-3.14 (1H, m), 3.41 (2H, s), 3.46 (2H, s), 4.48 (1H, t, J=7.89 Hz), 4.72 (2H, q, J=8.16 Hz), 8.01 (1H, s); 379.2 [M+1]⁺.

B) 2-methyl-1-{6-[4-nitro-3-(2,2,2-trifluoroethoxy)-1H-pyrazol-1-yl]-2-azaspiro[3.3]heptan-2-yl}propan-2-yl acetate To a mixture of 2-methyl-1-{6-[4-nitro-3-(2,2,2-trifluoroethoxy)-1H-pyrazol-1-yl]-2-azaspiro[3.3]heptan-2-yl}propan-2-ol (200 mg), DMAP (6.45 mg) and pyridine (83.0 mg) in ethyl acetate (1.0 mL) was added acetic anhydride (107 mg) at room temperature. The mixture was stirred at 50° C. under nitrogen atmosphere for 2 hr. The mixture was poured into water and extracted with ethyl acetate. The organic layer was separated, washed with water and saturated brine, dried over anhydrous magnesium sulfate and concentrated in vacuo. The residue was purified by column chromatography (ethyl acetate/hexane) to give the title compound (170 mg).

¹H NMR (300 MHz, CDCl₃) δ1.41 (6H, s), 1.97 (3H, s), 2.64 (6H, s), 3.32 (2H, s), 3.37 (2H, s), 4.37-4.55 (1H, m), 4.65-4.80 (2H, m), 7.99-8.03 (1H, m).

C) 1-{6-[4-amino-3-(2,2,2-trifluoroethoxy)-1H-pyrazol-1-yl]-2-azaspiro[3.3]heptan-2-yl}-2-methylpropan-2-yl acetate A mixture of 2-methyl-1-{6-[4-nitro-3-(2,2,2-trifluoroethoxy)-1H-pyrazol-1-yl]-2-azaspiro[3.3]heptan-2-yl}propan-2-yl acetate (170 mg) and 10% palladium-carbon (42.9 mg) in MeOH (15 mL) was stirred under normal pressure of hydrogen atmosphere at room temperature for 14 hr. The catalyst was removed by filtration, and then the filtrate was concentrated in vacuo to give the title compound (157 mg).

¹H NMR (300 MHz, CDCl₃) δ1.53 (6H, s), 2.02 (3H, s), 2.52-2.81 (4H, m), 3.00 (2H, brs), 3.70-3.94 (4H, m), 4.22-4.37 (1H, m), 4.49-4.64 (2H, m), 6.88 (1H, s), 2H of amine were omitted due to overlapping with solvent peaks; MS m/z 391.2 [M+1]⁺.

D) 1-[6-(4-{[5-(4-chloro-3-{[(2S)-1-(1H-tetrazol-1-yl)propan-2-yl]oxy}phenyl)pyrimidin-2-yl]amino}-3-(2,2,2-trifluoroethoxy)-1H-pyrazol-1-yl)-2-azaspiro[3.3]heptan-2-yl]-2-methylpropan-2-yl acetate To a mixture of 1-{6-[4-amino-3-(2,2,2-trifluoroethoxy)-1H-pyrazol-1-yl]-2-azaspiro[3.3]heptan-2-yl}-2-methylpropan-2-yl acetate (343 mg), 2-chloro-5-(4-chloro-3-(((2S)-1-(1H-tetrazol-1-yl)propan-2-yl)oxy)phenyl)pyrimidine (460 mg), BINAP (54.7 mg) and DBU (266 mg) in DMA (2.0 mL) was added Pd₂(dba)₃ (40.2 mg). The mixture was stirred at 100° C. under nitrogen atmosphere for 2 hr. The mixture was poured into water and extracted with ethyl acetate. The organic layer was separated, washed with saturated aqueous ammonium chloride solution and saturated brine, dried over anhydrous magnesium sulfate and concentrated in vacuo. The residue was purified by column chromatography (NH, ethyl acetate/hexane) and then by column chromatography (MeOH/ethyl acetate) to give the title compound (120 mg).

¹H NMR (300 MHz, CDCl₃) δ1.42 (9H, s), 1.98 (3H, s), 2.57-2.63 (4H, m), 2.64-2.67 (2H, m), 3.30-3.34 (2H, m), 3.36-3.40 (2H, m), 4.34-4.49 (1H, m), 4.56-4.77 (3H, m), 4.79-4.93 (2H, m), 6.78-6.92 (2H, m), 7.01-7.12 (1H, m), 7.40-7.49 (1H, m), 7.84-7.92 (1H, m), 8.52 (2H, s), 8.93-8.99 (1H, m).

Example 958

(S)-1-(4-((5-(3-((1-(1H-tetrazol-1-yl)propan-2-yl)oxy)-4-chlorophenyl)pyrimidin-2-yl)amino)-1-(2-(tetrahydro-2H-pyran-4-yl)-2-azaspiro[3.3]heptan-6-yl)-1H-pyrazol-3-yl)propan-1-one

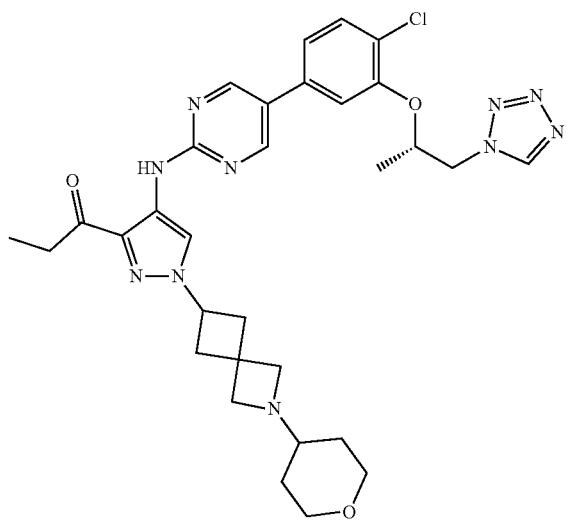 [SMILES: CCC(=O)c1nn(C2CC3(C2)CN(C2CCOCC2)C3)cc1Nc1ncc(-c2ccc(Cl)c(O[C@@H](C)Cn3cnnn3)c2)cn1]

A) N-methoxy-N-methyl-4-nitro-1H-pyrazole-3-carboxamide

To a mixture of 4-nitro-1H-pyrazole-3-carboxylic acid (1.02 g), N,O-dimethylhydroxylamine hydrochloride (689 mg), 1H-benzotriazol-1-yloxytripyrrolidinophosphonium hexafluorophosphate (3.39 g) and DMF (10 mL) was added N,N-diisopropylethylamine (2.80 mL). After being stirred at room temperature for 14 hr, the mixture was poured into aqueous saturated ammonium chloride and extracted with ethyl acetate. The organic layer was separated, washed with saturated brine, dried over anhydrous sodium sulfate and concentrated in vacuo. The residue was purified by column chromatography (ethyl acetate/hexane and NH, MeOH) to give the title compound (926 mg).

MS m/z 201.1 [M+1]⁺.

B) tert-butyl 6-{3-[methoxy(methyl)carbamoyl]-4-nitro-1H-pyrazol-1-yl}-2-azaspiro[3.3]heptane-2-carboxylate To a mixture of N-methoxy-N-methyl-4-nitro-1H-pyrazole-3-carboxamide (925 mg), tert-butyl 6-(methanesulfonyloxy)-2-azaspiro[3.3]heptane-2-carboxylate (1.37 g) and DMF (20 mL) was added cesium carbonate (1.80 g). After being stirred at 100° C. for 7 hr, the mixture was poured into aqueous saturated ammonium chloride solution and extracted with ethyl acetate. The organic layer was washed separated, washed with saturated brine, dried over anhydrous sodium sulfate and concentrated in vacuo. The residue was purified by column chromatography (NH, ethyl acetate/hexane) to give the title compound (756 mg) and 336 mg of the regioisomer.

$^1$H NMR (300 MHz, CDCl$_3$) δ1.44 (9H, s), 2.79 (4H, d, J=7.9 Hz), 3.42 (3H, s), 3.54 (3H, s), 3.96 (2H, s), 4.04 (2H, s), 4.60-4.74 (1H, m), 8.10 (1H, s); MS m/z 396.2 [M+1]$^+$.

C) N-methoxy-N-methyl-4-nitro-1-[2-(tetrahydro-2H-pyran-4-yl)-2-azaspiro[3.3]heptan-6-yl]-1H-pyrazole-3-carboxamide To a mixture of tert-butyl 6-{3-[methoxy(methyl)carbamoyl]-4-nitro-1H-pyrazol-1-yl}-2-azaspiro[3.3]heptane-2-carboxylate (721 mg) and toluene (10 mL) was added TFA (2.0 mL). After being stirred at room temperature for 2 hr, the mixture was concentrated in vacuo. The residue was dissolved in MeOH and the solution was treated with Amberlyst® A21. The insoluble material was removed by filtration, and the filtrate was concentrated in vacuo. To a mixture of the residue, dihydro-2H-pyran-4(3H)-one (0.35 mL), MeOH (10 mL) and AcOH (1.0 mL) was added 2-methylpyridine-borane (389 mg). After being stirred at room temperature for 3 days, the mixture was neutralized with aqueous saturated sodium hydrogencarbonate solution and extracted with ethyl acetate. The organic layer was separated, washed with saturated brine, dried over anhydrous sodium sulfate and concentrated in vacuo. The residue was purified by column chromatography (NH, ethyl acetate/hexane) to give the title compound (290 mg).
MS m/z 380.2 [M+1]$^+$;

D) tert-butyl N-{3-[methoxy(methyl)carbamoyl]-1-[2-(tetrahydro-2H-pyran-4-yl)-2-azaspiro[3.3]heptan-6-yl]-1H-pyrazol-4-yl}carbamate To a mixture of N-methoxy-N-methyl-4-nitro-1-[2-(tetrahydro-2H-pyran-4-yl)-2-azaspiro[3.3]heptan-6-yl]-1H-pyrazole-3-carboxamide (290 mg), di-tert-butyl dicarbonate (0.40 mL), triethylamine (0.25 mL) and MeOH (5.0 mL) was added 10% palladium-carbon (112 mg). After being stirred under hydrogen atmosphere at room temperature for 14 hr, the insoluble material was removed by filtration, and the filtrate was concentrated in vacuo. The residue was purified by column chromatography (NH, ethyl acetate/hexane) to give the title compound (184 mg).
$^1$H NMR (300 MHz, CDCl$_3$) δ1.25-1.40 (2H, m), 1.48 (9H, s), 1.59-1.68 (2H, m), 2.08-2.24 (1H, m), 2.58-2.76 (4H, m), 3.20 (2H, s), 3.30 (2H, s), 3.36 (2H, t, J=11.0 Hz), 3.48-3.61 (3H, m), 3.84 (3H, s), 3.92-4.02 (2H, m), 4.54-4.75 (1H, m), 7.96 (1H, s), 8.80 (1H, s); MS m/z 450.3 [M+1]$^+$.

E) tert-butyl N-{1-[2-(tetrahydro-2H-pyran-4-yl)-2-azaspiro[3.3]heptan-6-yl]-3-propanoyl-1H-pyrazol-4-yl}carbamate To a mixture of tert-butyl N-{3-[methoxy(methyl)carbamoyl]-1-[2-(tetrahydro-2H-pyran-4-yl)-2-azaspiro[3.3]heptan-6-yl]-1H-pyrazol-4-yl}carbamate (183 mg) and THF (5.0 mL) was added dropwise 1.0 M ethylmagnesium bromide/THF (1.0 mL) at 0° C. under nitrogen atmosphere. After being stirred under nitrogen atmosphere at 0° C. for 1 hr, the mixture was quenched with water and extracted with ethyl acetate. The organic layer was separated, washed with saturated brine, dried over anhydrous sodium sulfate and concentrated in vacuo. The residue was purified by column chromatography (NH, ethyl acetate/hexane) to give the title compound (133 mg).
$^1$H NMR (300 MHz, CDCl$_3$) δ1.19 (3H, t, J=7.3 Hz), 1.26-1.41 (2H, m), 1.49 (9H, s), 1.59-1.69 (2H, m), 2.09-2.24 (1H, m), 2.59-2.78 (4H, m), 3.00 (2H, q, J=7.2 Hz), 3.23 (2H, s), 3.30 (2H, s), 3.36 (2H, t, J=11.6 Hz), 3.89-4.05 (2H, m), 4.54-4.73 (1H, m), 7.93 (1H, s), 8.62 (1H, s); MS m/z 419.3 [M+1]$^+$.

F) 1-{4-amino-1-[2-(tetrahydro-2H-pyran-4-yl)-2-azaspiro[3.3]heptan-6-yl]-1H-pyrazol-3-yl}propan-1-one To a mixture of tert-butyl N-{1-[2-(tetrahydro-2H-pyran-4-yl)-2-azaspiro[3.3]heptan-6-yl]-3-propanoyl-1H-pyrazol-4-yl}carbamate (132 mg) and toluene (2.0 mL) was added TFA (0.50 mL). After being stirred at room temperature for 1 hr, the mixture was concentrated in vacuo. The residue was dissolved in MeOH and the solution was treated with Amberlyst® A21. The insoluble material was removed by filtration, and the filtrate was concentrated in vacuo. The residue was subjected to the next step without further purification.

G) (S)-1-(4-((5-(3-(((1-(1H-tetrazol-1-yl)propan-2-yl)oxy)-4-chlorophenyl)pyrimidin-2-yl)amino)-1-(2-(tetrahydro-2H-pyran-4-yl)-2-azaspiro[3.3]heptan-6-yl)-1H-pyrazol-3-yl)propan-1-one To a mixture of 1-{4-amino-1-[2-(tetrahydro-2H-pyran-4-yl)-2-azaspiro[3.3]heptan-6-yl]-1H-pyrazol-3-yl}propan-1-one (100 mg), 2-chloro-5-(4-chloro-3-(((2S)-1-(1H-tetrazol-1-yl)propan-2-yl)oxy)phenyl)pyrimidine (137 mg), Pd$_2$(dba)$_3$ (15 mg), BINAP (21 mg) and DMA (3.0 mL) was added DBU (0.10 mL). After being stirred under nitrogen atmosphere at 100° C. for 14 hr, the mixture was poured into water and extracted with ethyl acetate. The organic layer was separated, washed with saturated brine, dried over anhydrous sodium sulfate and concentrated in vacuo. The residue was purified by column chromatography (MeOH/ethyl acetate and NH, ethyl acetate/hexane) and crystallized from ethyl acetate-hexane to give the title compound (109 mg).
$^1$H NMR (300 MHz, DMSO-d$_6$) δ1.03-1.20 (5H, m), 1.34 (3H, d, J=5.6 Hz), 1.50-1.63 (2H, m), 2.06-2.21 (1H, m), 2.54-2.69 (4H, m), 2.96-3.07 (2H, m), 3.13 (2H, s), 3.18-3.31 (4H, m), 3.74-3.86 (2H, m), 4.75-4.86 (1H, m), 4.87-4.99 (2H, m), 5.14-5.28 (1H, m), 7.32 (1H, d, J=8.3 Hz), 7.43-7.53 (2H, m), 8.39 (1H, d, J=1.9 Hz), 8.91 (2H, d, J=1.7 Hz), 9.36 (2H, d, J=7.0 Hz); MS m/z 633.4 [M+1]$^+$.

Example 959

(S)-5-(3-((1-(1H-tetrazol-1-yl) propan-2-yl)oxy)-4-chlorophenyl)-N-(3-(perfluoroethyl)-1-(2-(tetrahydro-2H-pyran-4-yl)-2-azaspiro[3.3]heptan-6-yl)-1H-pyrazol-4-yl)pyrimidin-2-amine

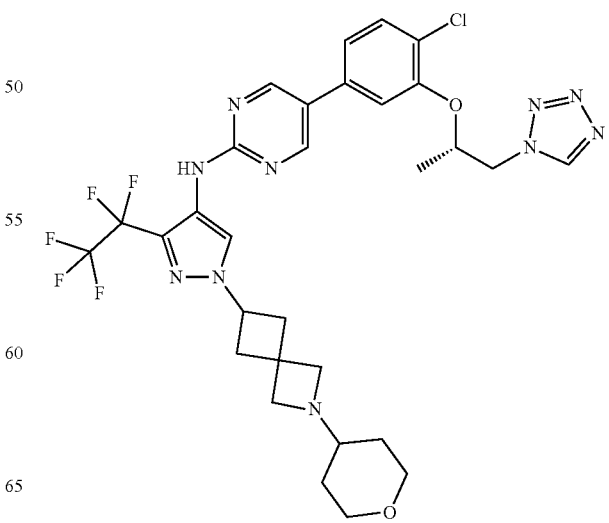

A) 4-nitro-3-(1,1,2,2,2-pentafluoroethyl)-1H-pyrazole

To a mixture of 3-(1,1,2,2,2-pentafluoroethyl)-1H-pyrazole (1.1 g) in sulfuric acid (1.72 g) was added dropwise nitric acid (1.05 g) at 0° C. The mixture was stirred at 60° C. for 14 hr. The mixture was quenched with iced water at 0° C. Then, 8 M aqueous sodium hydroxide solution was added thereto to bring the pH of the solution to 4-5 and the mixture was extracted with ethyl acetate. The organic layer was separated, washed with water and saturated brine, dried over anhydrous magnesium sulfate and concentrated in vacuo. The residue was purified by column chromatography (ethyl acetate/hexane) to give the title compound (600 mg).

$^1$H NMR (300 MHz, DMSO-$d_6$) δ9.20 (1H, s), 14.83 (1H, d, J=3.1 Hz).

B) tert-butyl 6-[4-nitro-3-(1,1,2,2,2-pentafluoroethyl)-1H-pyrazol-1-yl]-2-azaspiro[3.3]heptane-2-carboxylate To a mixture of 4-nitro-3-(1,1,2,2,2-pentafluoroethyl)-1H-pyrazole (900 mg) and tert-butyl 6-(methanesulfonyloxy)-2-azaspiro[3.3]heptane-2-carboxylate (1.24 g) in DMF (15 mL) was added cesium carbonate (1.77 g) at room temperature. The mixture was stirred at 100° C. under nitrogen atmosphere for 5 hr. The mixture was quenched with water at room temperature and extracted with ethyl acetate. The organic layer was separated, washed with water and saturated brine, dried over anhydrous magnesium sulfate and concentrated in vacuo. The residue was purified by column chromatography (ethyl acetate/hexane) to give the title compound (1.0 g).

$^1$H NMR (300 MHz, DMSO-$d_6$) δ1.36 (9H, brs), 2.31-2.42 (2H, m), 2.70-2.81 (2H, m), 3.82 (2H, brs), 3.94 (2H, brs), 4.91-4.99 (1H, m), 9.31 (1H, s); MS m/z 326.2 [M+H-Boc]$^+$.

C) tert-butyl 6-[4-amino-3-(1,1,2,2,2-pentafluoroethyl)-1H-pyrazol-1-yl]-2-azaspiro[3.3]heptane-2-carboxylate A mixture of tert-butyl 6-[4-nitro-3-(1,1,2,2,2-pentafluoroethyl)-1H-pyrazol-1-yl]-2-azaspiro[3.3]heptane-2-carboxylate (1.0 g) and 10% palladium-carbon (50.8 mg) in ethyl acetate (20 mL)/EtOH (20 mL) was stirred at room temperature under normal pressure of hydrogen atmosphere for 10 hr. The catalyst was removed by filtration, and then the filtrate was concentrated in vacuo to give the title compound (700 mg).

$^1$H NMR (300 MHz, DMSO-$d_6$) δ1.36 (9H, s), 2.31-2.43 (2H, m), 2.61 (2H, d, J=7.9 Hz), 3.85 (2H, brs), 3.92 (2H, brs), 4.25 (2H, s), 4.57-4.72 (1H, m), 7.29 (1H, s); MS m/z 397.2 [M+1]$^+$.

D) tert-butyl 6-(4-{[5-(4-chloro-3-{[(2S)-1-(1H-tetrazol-1-yl)propan-2-yl]oxy}phenyl)pyrimidin-2-yl]amino}-3-(1,1,2,2,2-pentafluoroethyl)-1H-pyrazol-1-yl)-2-azaspiro[3.3]heptane-2-carboxylate To a mixture of tert-butyl 6-[4-amino-3-(1,1,2,2,2-pentafluoroethyl)-1H-pyrazol-1-yl]-2-azaspiro[3.3]heptane-2-carboxylate (700 mg) and 2-chloro-5-(4-chloro-3-(((2S)-1-(1H-tetrazol-1-yl)propan-2-yl)oxy)phenyl)pyrimidine (618 mg) in DMA (10 mL) were added DBU (401 mg), Pd$_2$(dba)$_3$ (161 mg) and BINAP (219 mg) at room temperature. The mixture was stirred at 100° C. under nitrogen atmosphere for 2 hr. The mixture was quenched with water at room temperature and extracted with ethyl acetate. The organic layer was separated, washed with water and saturated brine, dried over anhydrous magnesium sulfate and concentrated in vacuo. The residue was purified by column chromatography (ethyl acetate/hexane) to give the title compound (130 mg).

MS m/z 712.3 [M+1]$^+$.

E) N-(1-{2-azaspiro[3.3]heptan-6-yl}-3-(1,1,2,2,2-pentafluoroethyl)-1H-pyrazol-4-yl)-5-(4-chloro-3-{[(2S)-1-(1H-tetrazol-1-yl)propan-2-yl]oxy}phenyl)pyrimidin-2-amine To a mixture of tert-butyl 6-(4-{[5-(4-chloro-3-{[(2S)-1-(1H-tetrazol-1-yl)propan-2-yl]oxy}phenyl)pyrimidin-2-yl]amino}-3-(1,1,2,2,2-pentafluoroethyl)-1H-pyrazol-1-yl)-2-azaspiro[3.3]heptane-2-carboxylate (130 mg) in toluene (10 mL) was added TFA (104 mg) at room temperature. The mixture was stirred at 50° C. under nitrogen atmosphere for 10 hr. The mixture was concentrated in vacuo. The residue and Amberlyst® A21 (200 mg) in MeOH (10 mL) was stirred at room temperature for 15 min. The insoluble material was removed by filtration, and the filtrate was concentrated in vacuo. This product was subjected to the next reaction without further purification.

MS m/z 611.2 [M+1]$^+$.

F) (S)-5-(3-((1-(1H-tetrazol-1-yl)propan-2-yl)oxy)-4-chlorophenyl)-N-(3-(perfluoroethyl)-1-(2-(tetrahydro-2H-pyran-4-yl)-2-azaspiro[3.3]heptan-6-yl)-1H-pyrazol-4-yl)pyrimidin-2-amine To a solution of N-(1-{2-azaspiro[3.3]heptan-6-yl}-3-(1,1,2,2,2-pentafluoroethyl)-1H-pyrazol-4-yl)-5-(4-chloro-3-{[(2S)-1-(1H-tetrazol-1-yl)propan-2-yl]oxy}phenyl)pyrimidin-2-amine (111 mg) and dihydro-2H-pyran-4(3H)-one (36.3 mg) in MeOH (5.0 mL)/AcOH (0.5 mL) was added 2-methylpyridine-borane (21.3 mg) at room temperature. The mixture was stirred at 60° C. under nitrogen atmosphere for 1 hr. The mixture was concentrated in vacuo. The residue was purified by column chromatography (NH, ethyl acetate/hexane) and then the desired product (61 mg) was purified by preparative HPLC (water/CH$_3$CN containing 0.1% TFA). The desired fraction was azeotroped with toluene. A mixture of the residue and Amberlyst® A21 (100 mg) in MeOH (5.0 mL) was stirred at room temperature for 30 min. The insoluble material was removed by filtration, and the filtrate was concentrated in vacuo. The residue was crystallized from ethyl acetate-IPE to give the title compound (35.0 mg).

$^1$H NMR (300 MHz, DMSO-$d_6$) δ1.21-1.29 (2H, m), 1.33 (3H, d, J=6.1 Hz), 1.75-1.91 (2H, m), 2.60-2.79 (4H, m), 3.19-3.30 (4H, m), 3.85-3.99 (2H, m), 4.03-4.39 (3H, m), 4.75-4.85 (1H, m), 4.87-4.94 (2H, m), 5.10-5.23 (1H, m), 7.19-7.28 (1H, m), 7.37 (1H, s), 7.46 (1H, d, J=8.3 Hz), 8.27 (1H, s), 8.73 (2H, s), 8.90 (1H, s), 9.37 (1H, s).

Example 960

(S)-5-(3-((1-(1H-tetrazol-1-yl)propan-2-yl)oxy)-4-chlorophenyl)-N-(3-isopropyl-1-(2-(4-methyltetrahydro-2H-pyran-4-yl)-2-azaspiro[3.3]heptan-6-yl)-1H-pyrazol-4-yl)pyrimidin-2-amine

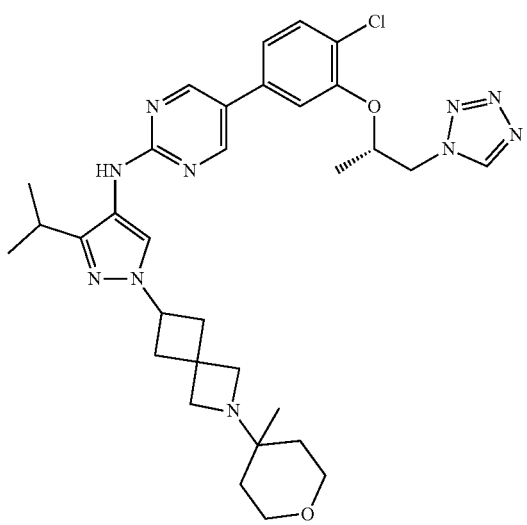 [SMILES: CC(C)c1nn(C2CC3(C2)CN(C2(C)CCOCC2)C3)cc1Nc1ncc(-c2ccc(Cl)c(O[C@@H](C)Cn3cnnn3)c2)cn1]

A) 2-(4-methyltetrahydro-2H-pyran-4-yl)-6-[4-nitro-3-(propan-2-yl)-1H-pyrazol-1-yl]-2-azaspiro[3.3]heptane A mixture of 4-nitro-3-(propan-2-yl)-1H-pyrazole (398 mg), cesium carbonate (1.67 g) and 2-(4-methyltetrahydro-2H-pyran-4-yl)-2-azaspiro[3.3]heptan-6-yl methanesulfonate (743 mg) in DMA (15 mL) was stirred at 100° C. for 18 hr. The reaction mixture was partitioned between ethyl acetate and water. The organic layer was washed with saturated brine, dried over anhydrous sodium sulfate and concentrated under reduced pressure. The residue was purified by column chromatography (ethyl acetate/hexane) to give the title compound (932 mg).

$^1$H NMR (300 MHz, CDCl$_3$) δ0.98 (3H, s), 1.30 (8H, d, J=6.9 Hz), 1.43-1.52 (2H, m), 2.56-2.64 (2H, m), 2.67-2.75 (2H, m), 3.24 (2H, s), 3.28 (2H, s), 3.49-3.64 (3H, m), 3.79-3.88 (2H, m), 4.60 (1H, quin, J=8.1 Hz), 8.12 (1H, s); MS m/z 349.2 [M+1]$^+$.

B) 1-[2-(4-methyltetrahydro-2H-pyran-4-yl)-2-azaspiro[3.3]heptan-6-yl]-3-(propan-2-yl)-1H-pyrazol-4-amine A mixture of 2-(4-methyltetrahydro-2H-pyran-4-yl)-6-[4-nitro-3-(propan-2-yl)-1H-pyrazol-1-yl]-2-azaspiro[3.3]heptane (895 mg) and 10% palladium-carbon (280 mg) in MeOH (20 mL) and THF (20 mL) was stirred at room temperature for 14 hr under normal pressure of hydrogen atmosphere. The reaction mixture was filtered. The filtrate was concentrated under reduced pressure to give the title compound. This product was used in the next step without further purification.

MS m/z 319.3 [M+1]$^+$.

C) (S)-5-(3-((1-(1H-tetrazol-1-yl)propan-2-yl)oxy)-4-chlorophenyl)-N-(3-isopropyl-1-(2-(4-methyltetrahydro-2H-pyran-4-yl)-2-azaspiro[3.3]heptan-6-yl)-1H-pyrazol-4-yl)pyrimidin-2-amine A mixture of 2-chloro-5-(4-chloro-3-(((2S)-1-(1H-tetrazol-1-yl)propan-2-yl)oxy)phenyl)pyrimidine (990 mg), 1-[2-(4-methyltetrahydro-2H-pyran-4-yl)-2-azaspiro[3.3]heptan-6-yl]-3-(propan-2-yl)-1H-pyrazol-4-amine (818 mg), Pd$_2$(dba)$_3$ (117 mg), BINAP (160 mg) and DBU (586 mg) in DMA (10 mL) was stirred at 100° C. for 1 hr under argon atmosphere. The reaction mixture was partitioned between ethyl acetate and water. The organic layer was washed with saturated brine, dried over anhydrous sodium sulfate and concentrated under reduced pressure. The residue was purified by column chromatography (ethyl acetate/hexane) to give the title compound (427 mg). This product was purified by prep-HPLC (water/CH$_3$CN containing 0.1% TFA). The desired fractions were concentrated under reduced pressure. The residue was partitioned between ethyl acetate and saturated aqueous sodium hydrogencarbonate solution. The organic layer was separated, washed with saturated brine, dried over anhydrous sodium sulfate and concentrated under reduced pressure to give the title compound (211 mg).

$^1$H NMR (300 MHz, DMSO-d$_6$) δ0.91 (3H, s), 1.16 (6H, d, J=6.8 Hz), 1.25 (2H, brs), 1.33 (5H, d, J=6.0 Hz), 2.57 (4H, brs) (almost hidden by DMSO), 3.00-3.10 (1H, m), 3.13 (1H, s), 3.21 (2H, s), 3.39-3.49 (2H, m), 3.64-3.72 (2H, m), 4.62 (1H, quin, J=8.1 Hz), 4.76-4.84 (1H, m), 4.87-4.96 (1H, m), 5.14-5.24 (1H, m), 7.25 (1H, d, J=8.6 Hz), 7.37 (1H, s), 7.45 (1H, d, J=8.3 Hz), 7.85 (1H, s), 8.71 (2H, s), 8.84 (1H, s), 9.37 (1H, s).

Example 965

(S)—N-(1-(2-(1,3-dioxan-5-yl)-2-azaspiro[3.3]heptan-6-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine

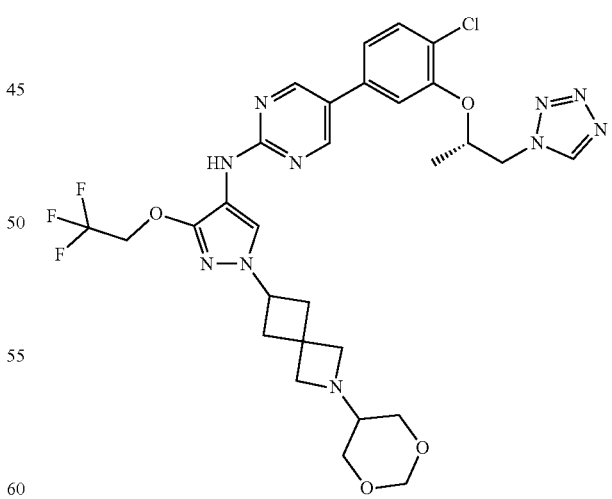

To a mixture of N-(1-{2-azaspiro[3.3]heptan-6-yl}-3-(2,2,2-trifluoroethoxy)-1H-pyrazol-4-yl)-5-(4-chloro-3-{[(2-S)-1-(1H-tetrazol-1-yl)propan-2-yl]oxy}phenyl)pyrimidin-2-amine (0.1 g) in DMF (5.0 mL) were added 1,3-dioxan-5-yl 4-methylbenzene-1-sulfonate (65.5 mg) and cesium carbonate (71.6 mg) at room temperature. The mixture was stirred at 60° C. under nitrogen atmosphere for 10 hr. The mixture was quenched with water at room temperature and extracted with ethyl acetate. The organic layer was separated, washed with water and saturated brine, dried over anhydrous magnesium sulfate and concentrated in vacuo. The residue was purified by column chromatography (MeOH/ethyl acetate). The residue was purified by preparative HPLC (water/CH$_3$CN containing 0.1% TFA). The desired fraction was concentrated in vacuo. A mixture of the residue and Amberlyst® A21 (100 mg) in MeOH (5.0 mL) was stirred for 10 min. The insoluble material was removed by filtration, and the filtrate was concentrated in vacuo. The residue was purified by column chromatography (NH, ethyl acetate/hexane) to give the title compound (15.0 mg).

$^1$H NMR (300 MHz, DMSO-d$_6$) δ1.33 (3H, d, J=5.9 Hz), 2.50 (4H, brs), 3.19 (2H, s), 3.27 (2H, s), 3.32-3.38 (2H, m), 3.40-3.48 (1H, m), 3.84-3.94 (2H, m), 4.48-4.62 (1H, m), 4.72-4.94 (6H, m), 5.10-5.22 (1H, m), 7.24 (1H, d, J=8.1 Hz), 7.36 (1H, s), 7.45 (1H, d, J=8.4 Hz), 7.81 (1H, s), 8.70 (2H, s), 8.76 (1H, s), 9.37 (1H, s).

Example 974

(S)-1-(6-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-azaspiro[3.3]heptan-2-yl)-2-methylpropan-2-yl acetate

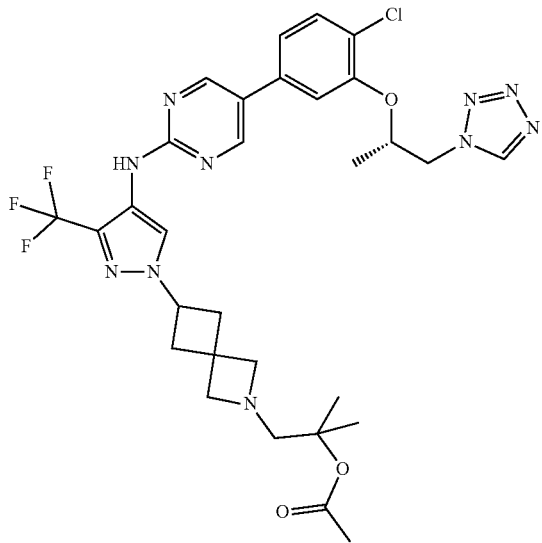 [SMILES: CC(=O)OC(C)(C)CN1CC2(CC(n3cc(Nc4ncc(-c5ccc(Cl)c(O[C@@H](C)Cn6cnnn6)c5)cn4)c(C(F)(F)F)n3)C2)C1]

A) 2-methyl-1-{6-[4-nitro-3-(trifluoromethyl)-1H-pyrazol-1-yl]-2-azaspiro[3.3]heptan-2-yl}propan-2-yl acetate To a mixture of 2-methyl-1-{6-[4-nitro-3-(trifluoromethyl)-1H-pyrazol-1-yl]-2-azaspiro[3.3]heptan-2-yl}propan-2-ol (0.514 g), DMAP (17.9 mg) and pyridine (232 mg) in ethyl acetate (1.0 mL) was added acetic anhydride (300 mg) at room temperature. The mixture was stirred at 50° C. under nitrogen atmosphere for 2 hr. The mixture was poured into water and extracted with ethyl acetate. The organic layer was separated, washed with water and saturated brine, dried over anhydrous magnesium sulfate and concentrated in vacuo. The residue was purified by column chromatography (NH, ethyl acetate/hexane) to give the title compound (510 mg).

$^1$H NMR (300 MHz, CDCl$_3$) δ1.42 (6H, s), 1.97 (3H, s), 2.64 (6H, s), 3.34 (2H, s), 3.39 (2H, s), 4.58-4.82 (1H, m), 8.19-8.30 (1H, m); 391.2 [M+1]$^+$.

B) 1-{6-[4-amino-3-(trifluoromethyl)-1H-pyrazol-1-yl]-2-azaspiro[3.3]heptan-2-yl}-2-methylpropan-2-yl acetate A mixture of 2-methyl-1-{6-[4-nitro-3-(trifluoromethyl)-1H-pyrazol-1-yl]-2-azaspiro[3.3]heptan-2-yl}propan-2-yl acetate (510 mg) and 10% palladium-carbon (138 mg) in MeOH (10 mL) was stirred at room temperature for 2 hr under normal pressure of hydrogen atmosphere. The catalyst was removed by filtration, and then the filtrate was concentrated in vacuo to give the title compound (410 mg). 361.2 [M+1]$^+$.

C) (S)-1-(6-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-azaspiro[3.3]heptan-2-yl)-2-methylpropan-2-yl acetate To a mixture of 1-{6-[4-amino-3-(trifluoromethyl)-1H-pyrazol-1-yl]-2-azaspiro[3.3]heptan-2-yl}-2-methylpropan-2-yl acetate (410 mg) and 2-chloro-5-(4-chloro-3-(((2S)-1-(1H-tetrazol-1-yl)propan-2-yl)oxy)phenyl)pyrimidine (593 mg) in DMA (2.0 mL) were added BINAP (70.3 mg), Pd$_2$(dba)$_3$ (51.7 mg) and DBU (344 mg) at room temperature. The mixture was stirred at 100° C. under argon atmosphere for 2 hr. The mixture was poured into water and extracted with ethyl acetate. The organic layer was separated, washed with saturated aqueous ammonium chloride solution and saturated brine, dried over anhydrous magnesium sulfate and concentrated in vacuo. The residue was purified by column chromatography (NH, ethyl acetate/hexane) to give the title compound (158 mg).

$^1$H NMR (300 MHz, CDCl$_3$) δ1.39-1.50 (9H, m), 1.98 (3H, s), 2.63-2.67 (2H, m), 2.70 (4H, d, J=8.07 Hz), 3.34 (2H, s), 3.40 (2H, s), 4.57-4.78 (2H, m), 4.80-4.95 (2H, m), 6.87 (1H, s), 7.08 (1H, d, J=8.16 Hz), 7.15 (1H, s), 7.46 (1H, d, J=8.16 Hz), 8.29 (1H, s), 8.56 (2H, s), 8.95 (1H, s).

Example 982

(S)—N-(1-(2-(1,4-dioxepan-6-yl)-2-azaspiro[3.3]heptan-6-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine

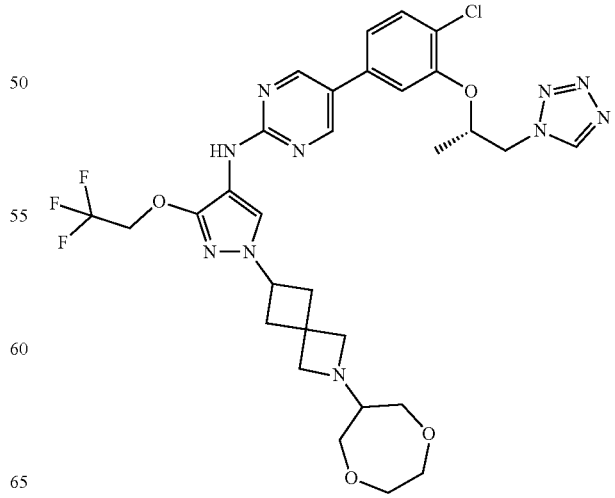

To a mixture of N-(1-{2-azaspiro[3.3]heptan-6-yl}-3-(2,2,2-trifluoroethoxy)-1H-pyrazol-4-yl)-5-(4-chloro-3-{[(2S)-1-(1H-tetrazol-1-yl)propan-2-yl]oxy}phenyl)pyrimidin-2-amine (100 mg) and 1,4-dioxepan-6-one (39.2 mg) in MeOH (5.0 mL)/AcOH (0.5 mL) was added 2-methylpyridine-borane (36.1 mg) at room temperature. The mixture was stirred at 50° C. under nitrogen atmosphere for 2 hr. The mixture was concentrated in vacuo. The residue was purified by column chromatography (MeOH/ethyl acetate) to give the title compound (40.0 mg).

$^1$H NMR (300 MHz, DMSO-$d_6$) δ1.32 (3H, d, J=6.1 Hz), 2.46-2.66 (5H, m), 3.09-3.15 (2H, m), 3.17-3.25 (2H, m), 3.38-3.50 (2H, m), 3.57-3.63 (4H, m), 3.64-3.72 (2H, m), 4.48 (1H, s), 4.72-4.97 (4H, m), 5.11-5.22 (1H, m), 7.23 (1H, d, J=8.2 Hz), 7.36 (1H, s), 7.45 (1H, d, J=7.8 Hz), 7.81 (1H, s), 8.70 (2H, s), 8.76 (1H, s), 9.37 (1H, s).

The compounds of the Examples 2 to 5, 7, 11 to 59, 61 to 69, 71 to 74, 76 to 150, 152 to 160, 162 to 167, 169 to 205, 207 to 318, 320 to 380, 382 to 385, 387 to 483, 485 to 663, 665 to 676, 678 to 681, 683 to 694, 696 to 771, 773 to 789, 791 to 794, 796 to 800, 803, 804, 807 to 816, 819, 822 to 830, 832 to 841, 845 to 853, 855 to 858, 860 to 868, 871 to 931, 933, 934, 938 to 941, 945, 948 to 950, 952 to 956, 975, 979 to 981, 983, 984, 998, 1000, 1001 and 1010 to 1014 in the following tables were produced according to the methods described in the above-mentioned Examples, or methods analogous thereto. The compounds of Examples are shown in the following Table 1 and Table 2. MS in the tables means actual measured value.

TABLE 1

| Ex. No. | IUPAC NAME | STRUCTURE | ADDITIVE | MS |
|---|---|---|---|---|
| 1 | 4-(2-((2-methoxy-4-(4-(morpholin-4-yl)piperidin-1-yl)phenyl)amino)pyrimidin-5-yl)-2-(((2S)-1-(1H-1,2,4-triazol-1-yl)propan-2-yl)oxy)benzonitrile | 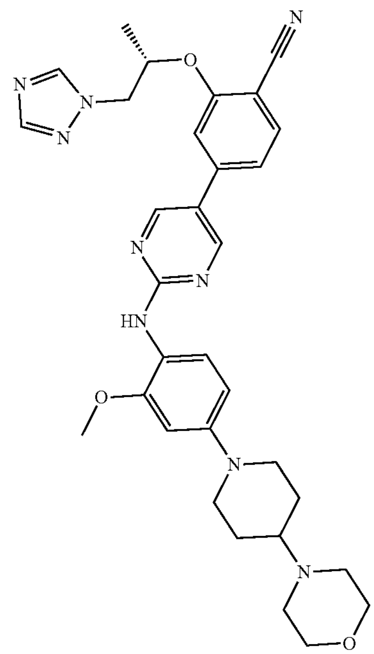 [SMILES: COc1cc(N2CCC(N3CCOCC3)CC2)ccc1Nc1ncc(-c2ccc(C#N)c(O[C@@H](C)Cn3cncn3)c2)cn1] | | 596.3 |
| 2 | 4-(2-((2-methoxyphenyl)amino)pyrimidin-5-yl)-2-(((2S)-1-(1H-1,2,4-triazol-1-yl)propan-2-yl)oxy)benzonitrile | 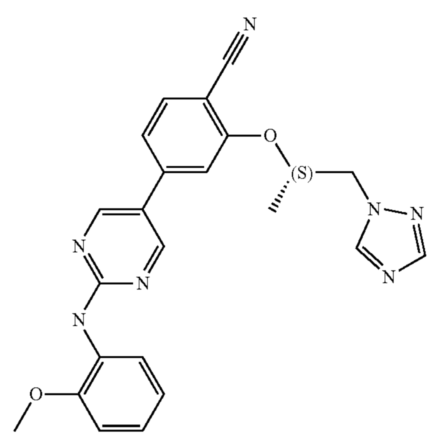 | | 428.1 |

TABLE 1-continued

| Ex. No. | IUPAC NAME | STRUCTURE | ADDITIVE | MS |
|---|---|---|---|---|
| 3 | 4-(2-((5-chloro-2-methoxyphenyl)amino)pyrimidin-5-yl)-2-(((2S)-1-(1H-1,2,4-triazol-1-yl)propan-2-yl)oxy)benzonitrile | 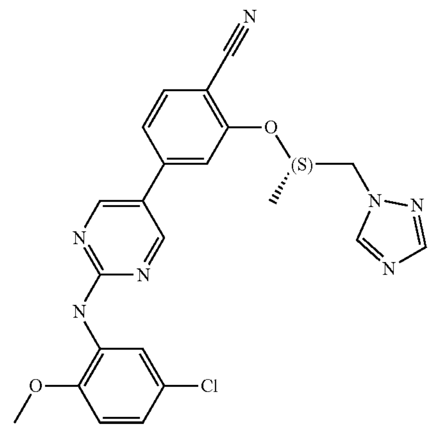 | | 462.2 |
| 4 | 4-(2-((3-chlorophenyl)amino)pyrimidin-5-yl)-2-(((2S)-1-(1H-1,2,4-triazol-1-yl)propan-2-yl)oxy)benzonitrile | 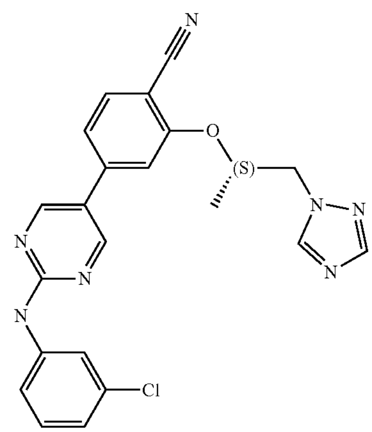 | | 430 |
| 5 | 4-(2-((2-methoxy-4-(4-(morpholin-4-yl)piperidin-1-yl)phenyl)amino)pyrimidin-5-yl)-2-(((2S)-1-(2H-tetrazol-2-yl)propan-2-yl)oxy)benzonitrile | 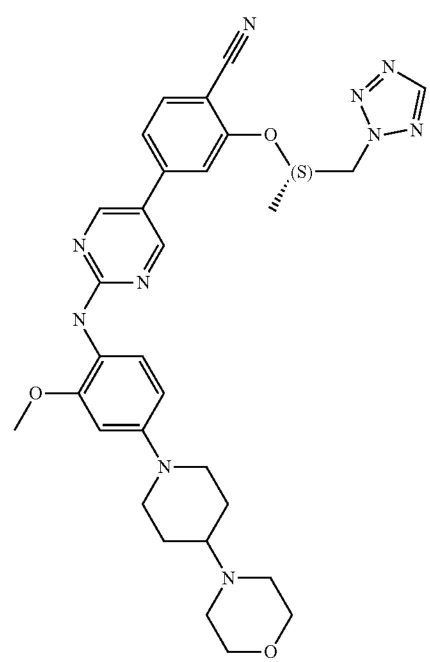 | | 597.4 |

| Ex. No. | IUPAC NAME | STRUCTURE | ADDITIVE | MS |
|---|---|---|---|---|
| 7 | 4-(2-((2-methoxy-4-(4-(morpholin-4-yl)piperidin-1-yl)phenyl)amino)pyrimidin-5-yl)-2-((4-(1H-1,2,4-triazol-1-yl)butan-2-yl)oxy)benzonitrile | 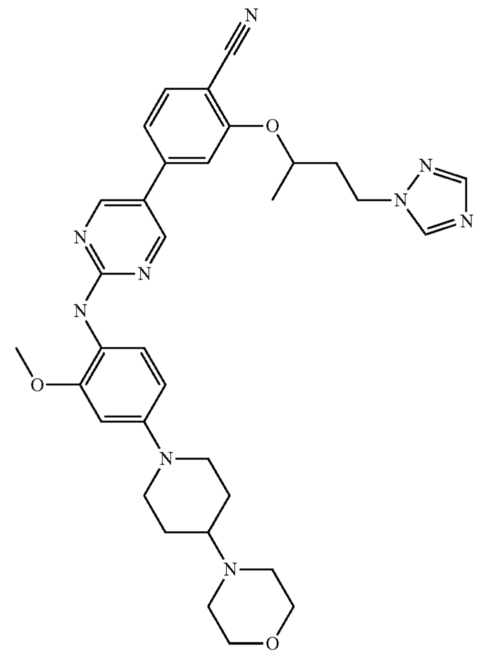 [SMILES: COc1cc(N2CCC(N3CCOCC3)CC2)ccc1Nc1ncc(-c2ccc(C#N)c(OC(C)CCn3cncn3)c2)cn1] | | 610.4 |
| 8 | 4-(2-((2-methoxy-4-(4-(morpholin-4-yl)piperidin-1-yl)phenyl)amino)pyrimidin-5-yl)-2-(((2S)-1-(1H-1,2,4-triazol-1-yl)propan-2-yl)oxy)benzonitrile hydrochloride | 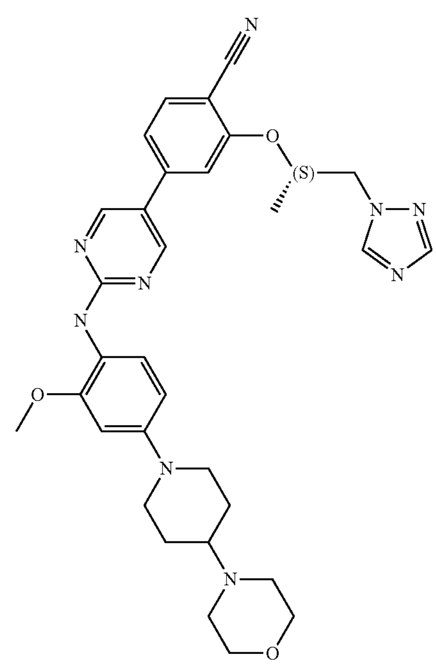 | HCl | 596.5 |

TABLE 1-continued

| Ex. No. | IUPAC NAME | STRUCTURE | ADDITIVE | MS |
|---|---|---|---|---|
| 9 | 4-(2-((2-methoxy-4-(4-(morpholin-4-yl)piperidin-1-yl)phenyl)amino)pyrimidin-5-yl)-2-(((2S)-1-(1H-tetrazol-1-yl)propan-2-yl)oxy)benzonitrile | 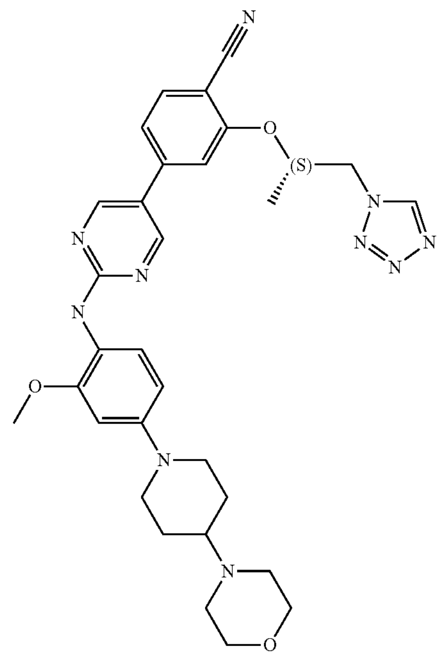 | | 597.3 |
| 10 | 4-(2-((2-methoxy-4-(4-(morpholin-4-yl)piperidin-1-yl)phenyl)amino)pyrimidin-5-yl)-2-(((2S)-1-(1H-tetrazol-1-yl)propan-2-yl)oxy)benzonitrile hydrochloride | 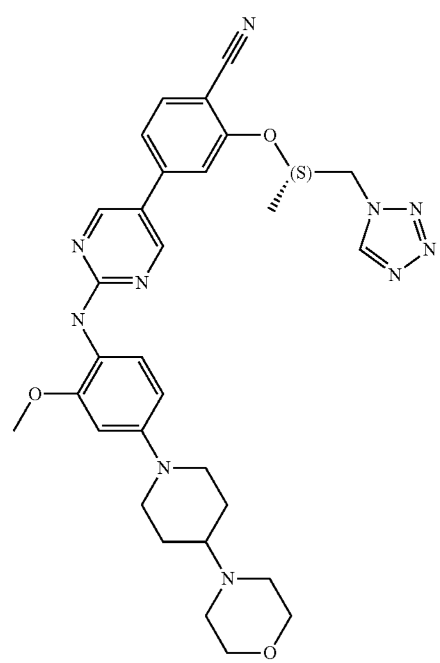 | HCl | 597.5 |

TABLE 1-continued
| Ex. No. | IUPAC NAME | STRUCTURE | ADDITIVE | MS |
|---|---|---|---|---|
| 11 | 4-(2-((3-chloro-2-methoxy-phenyl)amino)pyrimidin-5-yl)-2-(((2S)-1-(1H-tetrazol-1-yl)propan-2-yl)oxy)benzonitrile | 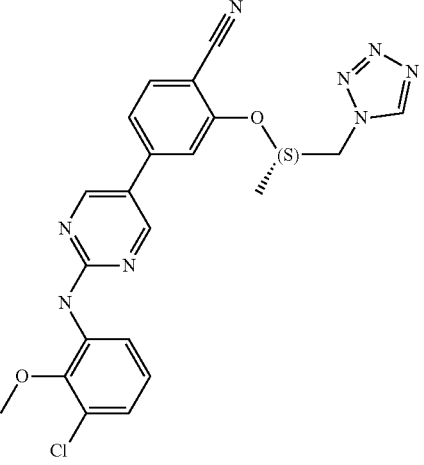 | | 461 |
| 12 | 4-(2-((2-ethyl-phenyl)amino)pyrimidin-5-yl)-2-(((2S)-1-(1H-tetrazol-1-yl)propan-2-yl)oxy)benzonitrile | 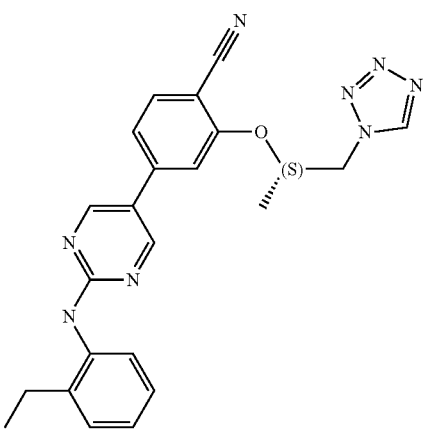 | | 425 |
| 13 | 4-(2-((2-ethoxy-phenyl)amino)pyrimidin-5-yl)-2-(((2S)-1-(1H-tetrazol-1-yl)propan-2-yl)oxy)benzonitrile | 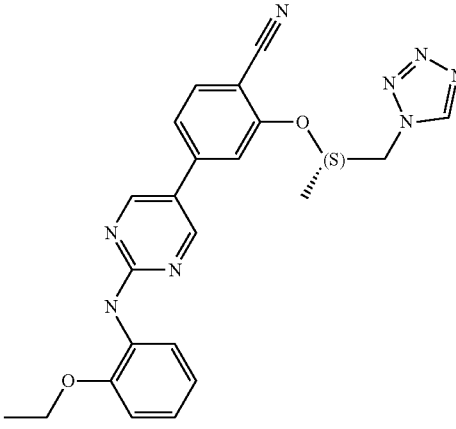 | | 441.1 |

TABLE 1-continued

| Ex. No. | IUPAC NAME | STRUCTURE | ADDITIVE | MS |
|---|---|---|---|---|
| 14 | 2-(((2S)-1-(1H-1,2,4-triazol-1-yl)propan-2-yl)oxy)-4-(2-((2-(trifluoromethyl)phenyl)amino)pyrimidin-5-yl)benzonitrile | 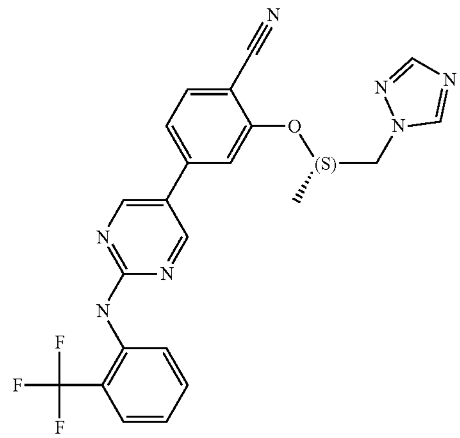 | | 463.9 |
| 15 | tert-butyl 4-(1-(4-((5-(4-cyano-3-(((2S)-1-(1H-tetrazol-1-yl)propan-2-yl)oxy)phenyl)pyrimidin-2-yl)amino)-3-methoxyphenyl)piperidin-4-yl)piperazine-1-carboxylate | 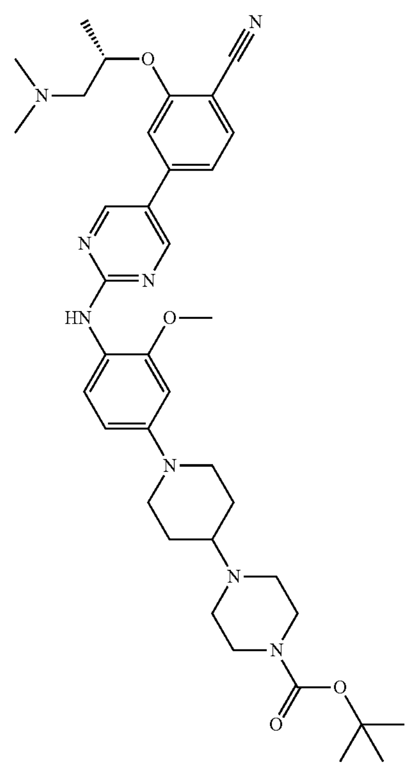 [SMILES: COc1cc(N2CCC(N3CCN(C(=O)OC(C)(C)C)CC3)CC2)ccc1Nc1ncc(-c2ccc(C#N)c(O[C@@H](C)CN(C)C)c2)cn1] | | 694.5 |

| Ex. No. | IUPAC NAME | STRUCTURE | ADDITIVE | MS |
|---|---|---|---|---|
| 16 | 4-(2-((2-methoxyphenyl)amino)pyrimidin-5-yl)-2-(((2S)-1-(1H-tetrazol-1-yl)propan-2-yl)oxy)benzonitrile | 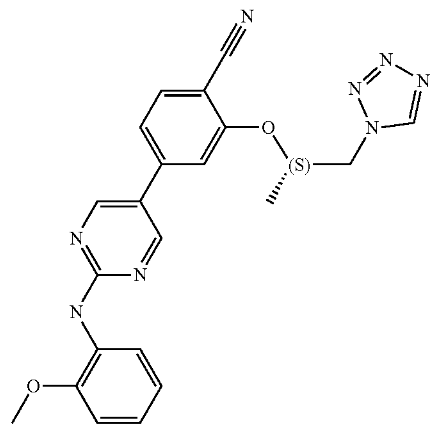 | | 429.3 |
| 17 | 4-(2-((2-methoxy-4-(4-(morpholin-4-yl)piperidin-1-yl)phenyl)amino)pyrimidin-5-yl)-2-(((2S)-1-(4H-1,2,4-triazol-4-yl)propan-2-yl)oxy)benzonitrile | 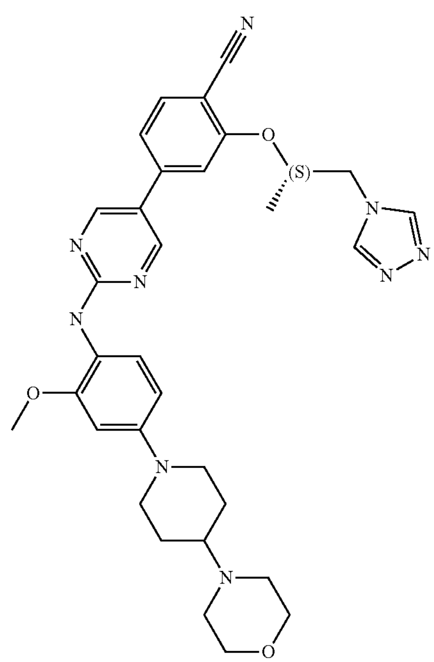 | | 596.4 |

TABLE 1-continued

| Ex. No. | IUPAC NAME | STRUCTURE | ADDITIVE | MS |
|---|---|---|---|---|
| 18 | 1-((2S)-2-(2-cyano-5-(2-((2-methoxy-4-(4-(morpholin-4-yl)piperidin-1-yl)phenyl)amino)pyrimidin-5-yl)phenoxy)propyl)-1H-1,2,4-triazole-3-carbonitrile | 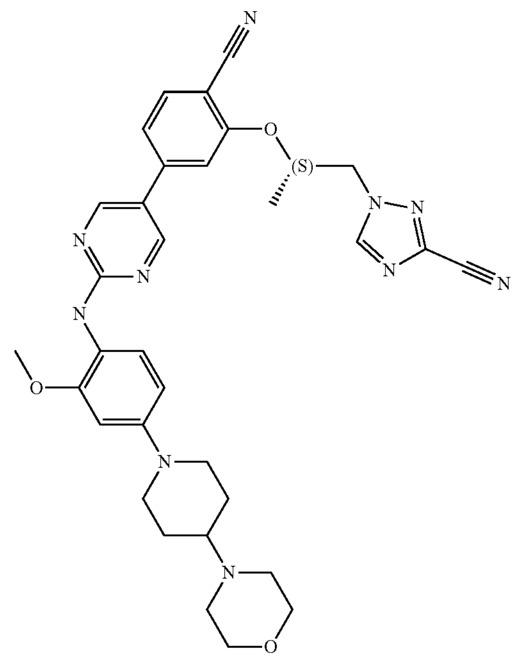 | | 621.5 |
| 19 | 2-(((2S)-1-aminopropan-2-yl)oxy)-4-(2-((2-methoxy-4-(4-(morpholin-4-yl)piperidin-1-yl)phenyl)amino)pyrimidin-5-yl)benzonitrile | 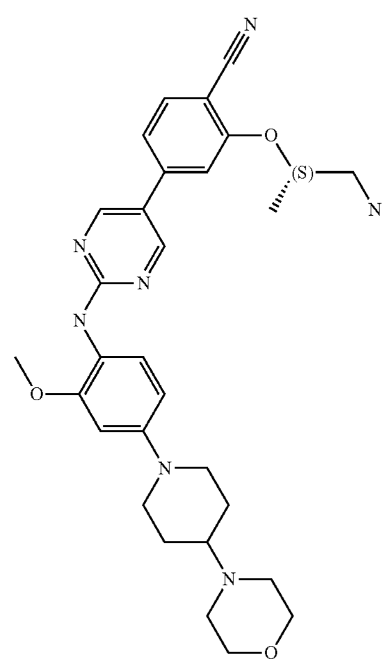 | | 544.4 |

TABLE 1-continued

| Ex. No. | IUPAC NAME | STRUCTURE | ADDITIVE | MS |
|---|---|---|---|---|
| 20 | N-((2S)-2-(2-cyano-5-(2-((2-methoxy-4-(4-(morpholin-4-yl)piperidin-1-yl)phenyl)amino)pyrimidin-5-yl)phenoxy)propyl)acetamide | 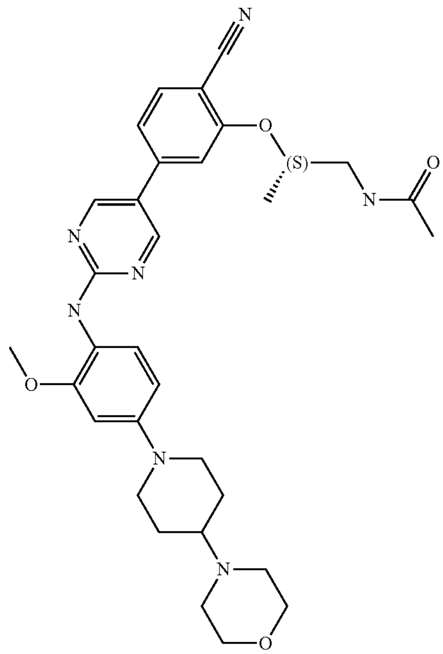 | | 586.4 |
| 21 | N-((2S)-2-(2-cyano-5-(2-((2-methoxy-4-(4-(morpholin-4-yl)piperidin-1-yl)phenyl)amino)pyrimidin-5-yl)phenoxy)propyl)-2-methoxyacetamide | 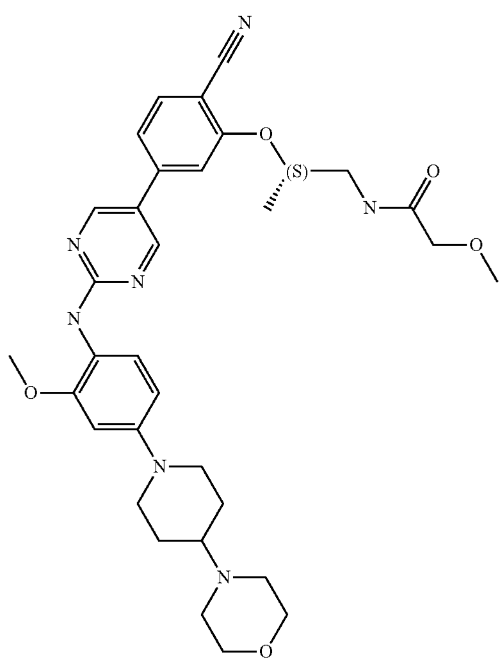 | | 616.4 |

TABLE 1-continued

| Ex. No. | IUPAC NAME | STRUCTURE | ADDITIVE | MS |
|---|---|---|---|---|
| 22 | N-(3-(2-cyano-5-(2-((2-methoxy-4-(4-(morpholin-4-yl)piperidin-1-yl)phenyl)amino)pyrimidin-5-yl)phenoxy)butyl)acetamide | 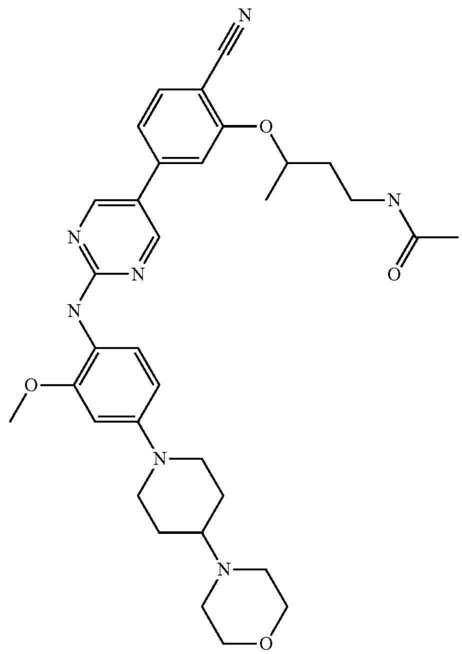 [SMILES: COc1cc(N2CCC(N3CCOCC3)CC2)ccc1Nc1ncc(-c2ccc(C#N)c(OC(C)CCNC(C)=O)c2)cn1] | | 600.4 |
| 23 | 2-(((2S)-1-hydroxypropan-2-yl)oxy)-4-(2-((2-methoxy-4-(4-(morpholin-4-yl)piperidin-1-yl)phenyl)amino)pyrimidin-5-yl)benzonitrile | 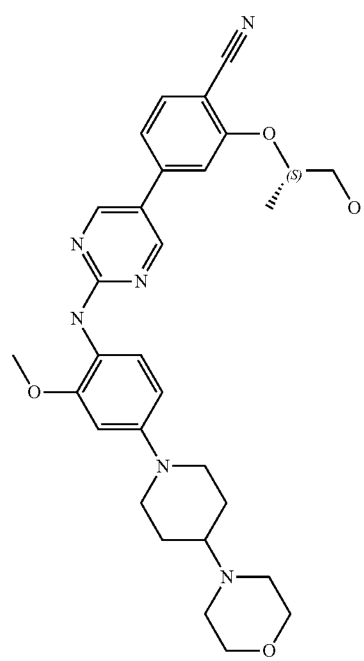 | | 545.4 |

TABLE 1-continued

| Ex. No. | IUPAC NAME | STRUCTURE | ADDITIVE | MS |
|---|---|---|---|---|
| 24 | 4-(2-((2-methoxy-4-(4-(morpholin-4-yl)piperidin-1-yl)phenyl)amino)pyrimidin-5-yl)-2-((1-(1-trityl-1H-pyrazol-4-yl)propan-2-yl)oxy)benzonitrile | 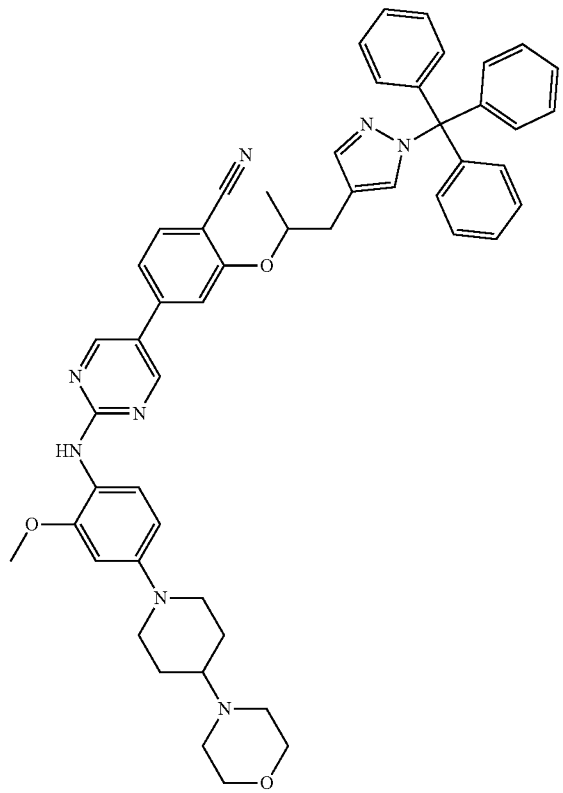 [SMILES: COc1cc(N2CCC(N3CCOCC3)CC2)ccc1Nc1ncc(-c2ccc(C#N)c(OC(C)Cc3cnn(C(c4ccccc4)(c4ccccc4)c4ccccc4)c3)c2)cn1] | | 837.5 |
| 25 | 4-(2-((2-methoxy-4-(4-(morpholin-4-yl)piperidin-1-yl)phenyl)amino)pyrimidin-5-yl)-2-(((2S)-1-(2-oxoimidazolidin-1-yl)propan-2-yl)oxy)benzonitrile | 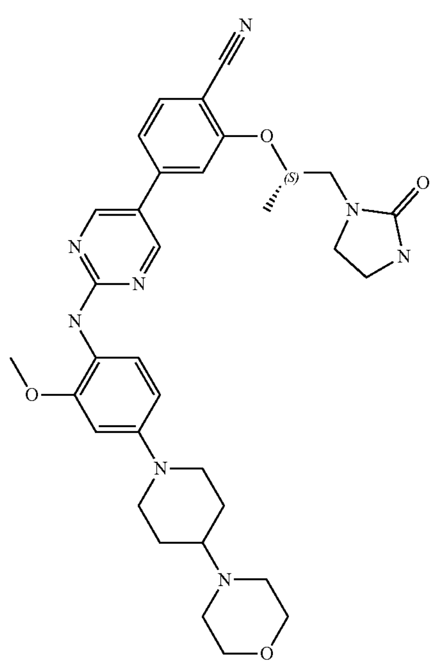 | | 613.4 |

TABLE 1-continued

| Ex. No. | IUPAC NAME | STRUCTURE | ADDITIVE | MS |
|---|---|---|---|---|
| 26 | 4-(2-((2-methoxy-4-(4-(morpholin-4-yl)piperidin-1-yl)phenyl)amino)pyrimidin-5-yl)-2-(((2S)-1-(3-methyl-2-oxoimidazolidin-1-yl)propan-2-yl)oxy)benzonitrile | 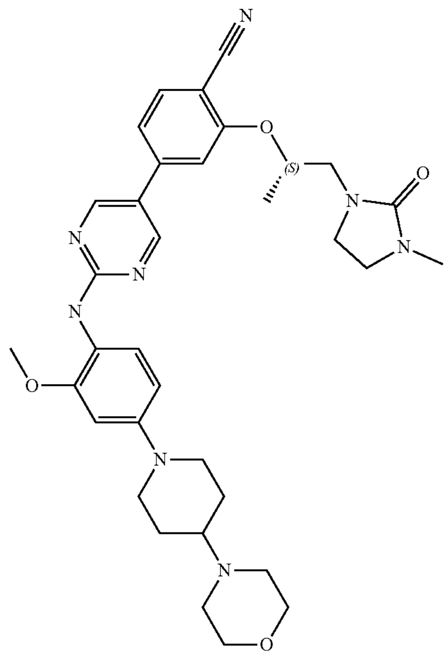 | | 627.4 |
| 27 | 4-(2-((2-methoxy-4-(4-(morpholin-4-yl)piperidin-1-yl)phenyl)amino)pyrimidin-5-yl)-2-((1-(4-methyl-4H-1,2,4-triazol-3-yl)propan-2-yl)oxy)benzonitrile | 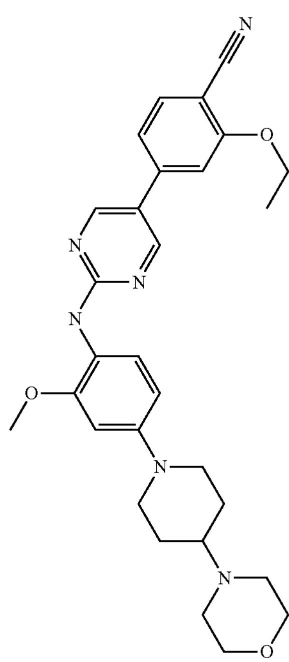 | | 610.4 |

| Ex. No. | IUPAC NAME | STRUCTURE | ADDITIVE | MS |
|---|---|---|---|---|
| 28 | 4-(2-((2-methoxy-4-(4-(morpholin-4-yl)piperidin-1-yl)phenyl)amino)pyrimidin-5-yl)-2-((1-(1-methyl-1H-1,2,4-triazol-5-yl)propan-2-yl)oxy)benzonitrile | 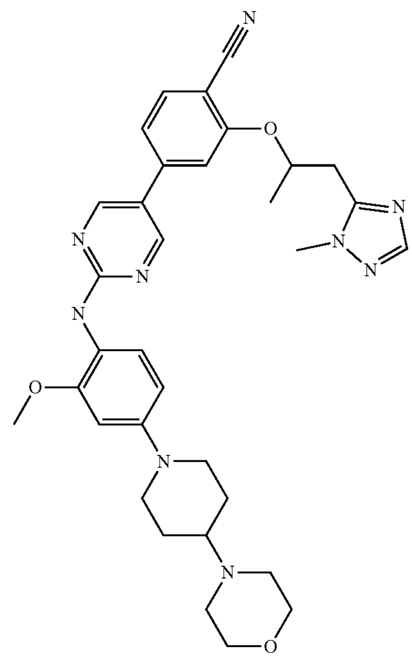 [SMILES: COc1cc(N2CCC(N3CCOCC3)CC2)ccc1Nc1ncc(-c2ccc(C#N)c(OC(C)Cc3ncnn3C)c2)cn1] | | 610.4 |
| 29 | 4-(2-((2-methoxy-4-(4-(morpholin-4-yl)piperidin-1-yl)phenyl)amino)pyrimidin-5-yl)-2-((1-(1H-pyrazol-4-yl)propan-2-yl)oxy)benzonitrile | 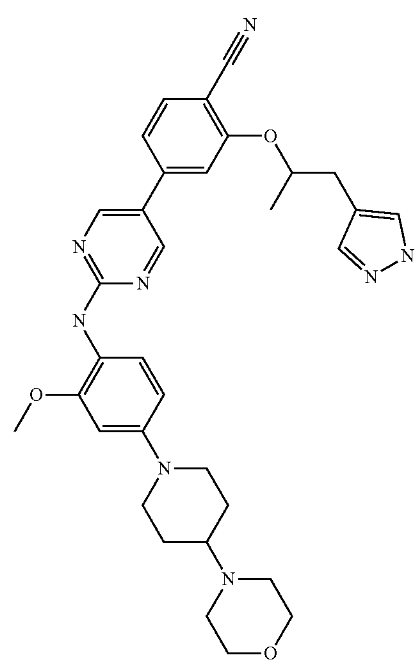 [SMILES: COc1cc(N2CCC(N3CCOCC3)CC2)ccc1Nc1ncc(-c2ccc(C#N)c(OC(C)Cc3cn[nH]c3)c2)cn1] | | 595.4 |

TABLE 1-continued

| Ex. No. | IUPAC NAME | STRUCTURE | ADDITIVE | MS |
|---|---|---|---|---|
| 30 | 4-(2-((2-methoxypyridin-3-yl)amino)pyrimidin-5-yl)-2-(((2S)-1-(1H-1,2,4-triazol-1-yl)propan-2-yl)oxy)benzonitrile | 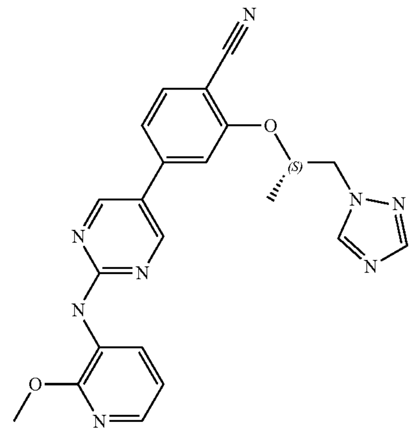 | | 427 |
| 31 | 4-(2-((3-methoxypyridin-4-yl)amino)pyrimidin-5-yl)-2-(((2S)-1-(1H-1,2,4-triazol-1-yl)propan-2-yl)oxy)benzonitrile | 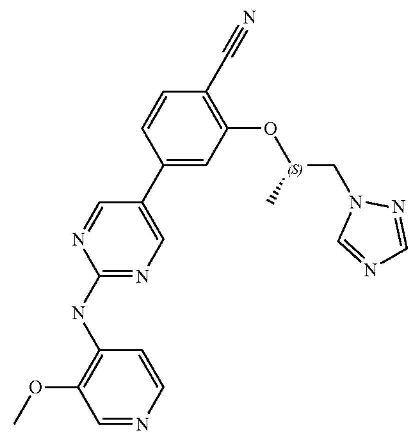 | | 429.3 |
| 32 | tert-butyl (4-((5-(4-cyano-3-(((2S)-1-(1H-1,2,4-triazol-1-yl)propan-2-yl)oxy)phenyl)pyrimidin-2-yl)amino)-3-methoxybenzyl)cyclopropyl carbamate | 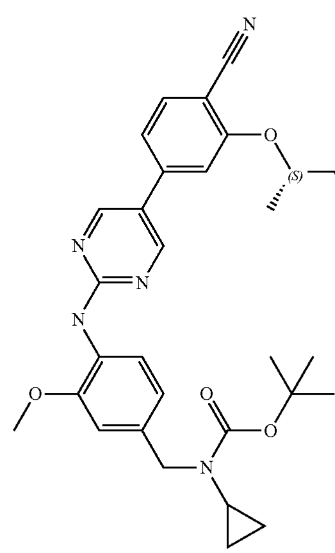 | | 597.4 |

TABLE 1-continued

| Ex. No. | IUPAC NAME | STRUCTURE | ADDITIVE | MS |
|---|---|---|---|---|
| 33 | 4-(2-((4-((cyclopropylamino)methyl)-2-methoxyphenyl)amino)pyrimidin-5-yl)-2-(((2S)-1-(1H-1,2,4-triazol-1-yl)propan-2-yl)oxy)benzonitrile dihydrochloride | 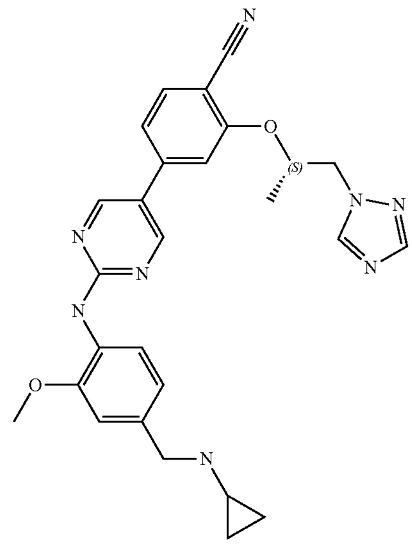 | 2HCl | 495.1 |
| 34 | 4-(2-((2-methoxy-4-(4-(piperazin-1-yl)piperidin-1-yl)phenyl)amino)pyrimidin-5-yl)-2-(((2S)-1-(1H-tetrazol-1-yl)propan-2-yl)oxy)benzonitrile | 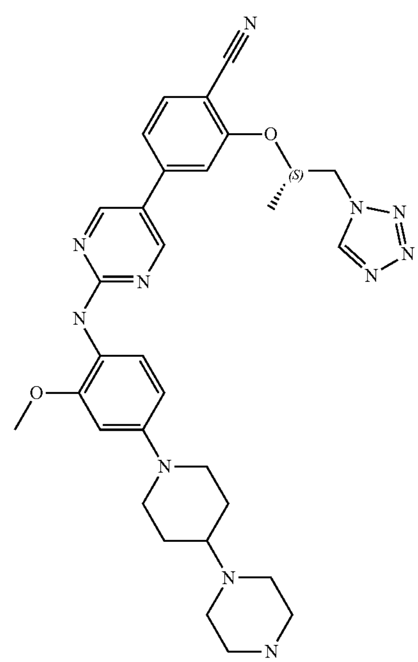 | | 596.4 |

TABLE 1-continued

| Ex. No. | IUPAC NAME | STRUCTURE | ADDITIVE | MS |
|---|---|---|---|---|
| 35 | 4-(2-((4-(4-(4-acetylpiperazin-1-yl)piperidin-1-yl)-2-methoxy-phenyl)amino)pyrimidin-5-yl)-2-(((2S)-1-(1H-tetrazol-1-yl)propan-2-yl)oxy)benzonitrile | 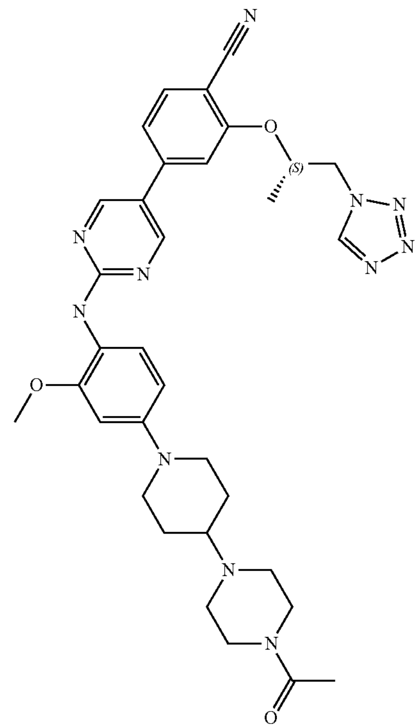 | | 638.5 |
| 36 | 4-(2-((2-methoxy-4-(4-(morpholin-4-yl)piperidin-1-yl)phenyl)amino)pyrimidin-5-yl)-2-((1-(1-methyl-1H-pyrazol-4-yl)propan-2-yl)oxy)benzonitrile | 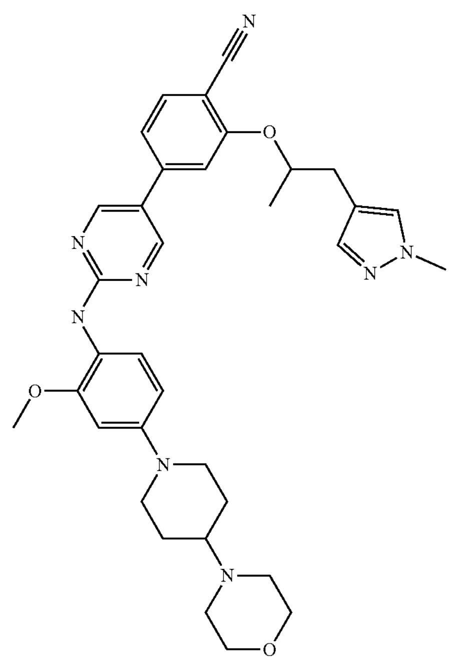 | | 609.4 |

TABLE 1-continued

| Ex. No. | IUPAC NAME | STRUCTURE | ADDITIVE | MS |
|---|---|---|---|---|
| 37 | 4-(2-((2-methoxy-4-(piperidin-1-yl)phenyl)amino)pyrimidin-5-yl)-2-(((2S)-1-(1H-tetrazol-1-yl)propan-2-yl)oxy)benzonitrile | 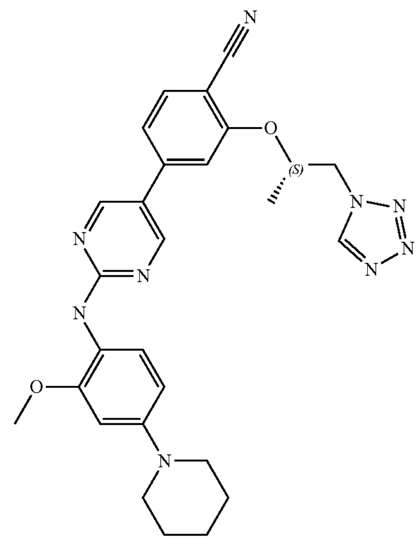 | | 512.4 |
| 38 | 4-(2-((2-cyano-phenyl)amino)pyrimidin-5-yl)-2-(((2S)-1-(1H-1,2,4-triazol-1-yl)propan-2-yl)oxy)benzonitrile | 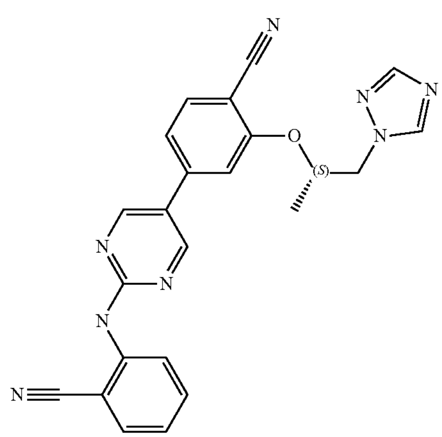 | | 421 |

TABLE 1-continued

| Ex. No. | IUPAC NAME | STRUCTURE | ADDITIVE | MS |
|---|---|---|---|---|
| 39 | 2-(((2S)-1-(1H-imidazol-1-yl)propan-2-yl)oxy)-4-(2-((2-methoxy-4-(4-(morpholin-4-yl)piperidin-1-yl)phenyl)amino)pyrimidin-5-yl)benzonitrile | 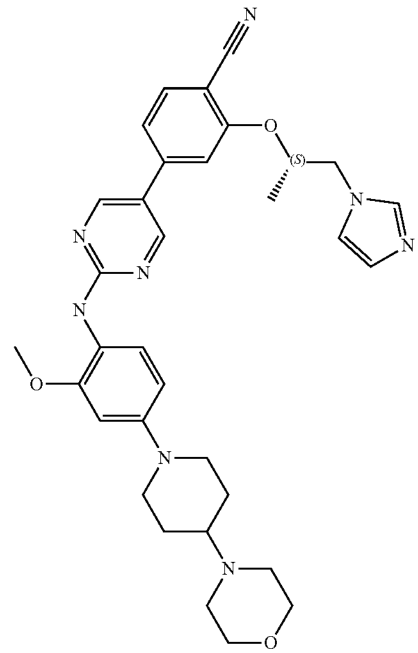 | | 595.4 |
| 40 | 4-(2-((2-methoxy-4-(4-(morpholin-4-yl)piperidin-1-yl)phenyl)amino)pyrimidin-5-yl)-2-(((2S)-1-(2H-1,2,3-triazol-2-yl)propan-2-yl)oxy)benzonitrile | 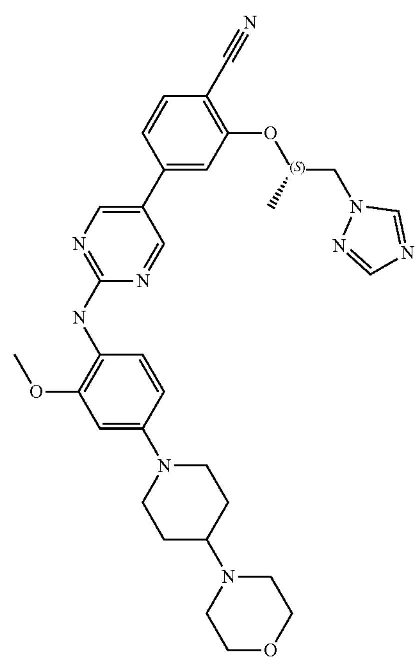 | | 596.4 |

TABLE 1-continued

| Ex. No. | IUPAC NAME | STRUCTURE | ADDITIVE | MS |
|---|---|---|---|---|
| 41 | 4-(2-((2-methoxy-4-(4-(morpholin-4-yl)piperidin-1-yl)phenyl)amino)pyrimidin-5-yl)-2-(((2S)-1-(1H-1,2,3-triazol-1-yl)propan-2-yl)oxy)benzonitrile | 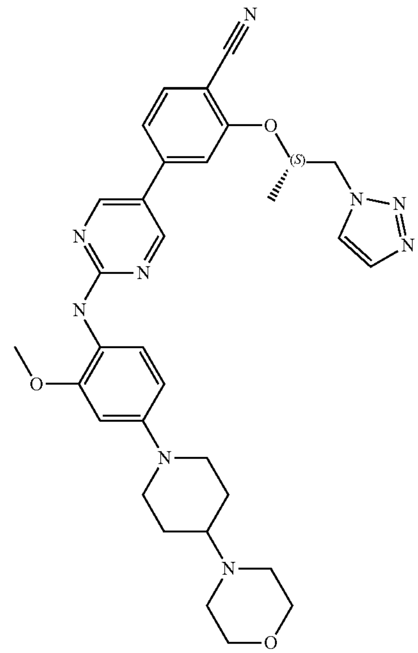 | | 596.5 |
| 42 | 4-(2-((2-methoxy-4-(4-(morpholin-4-yl)piperidin-1-yl)phenyl)amino)pyrimidin-5-yl)-2-(((2S)-1-(2-methyl-1H-imidazol-1-yl)propan-2-yl)oxy)benzonitrile | 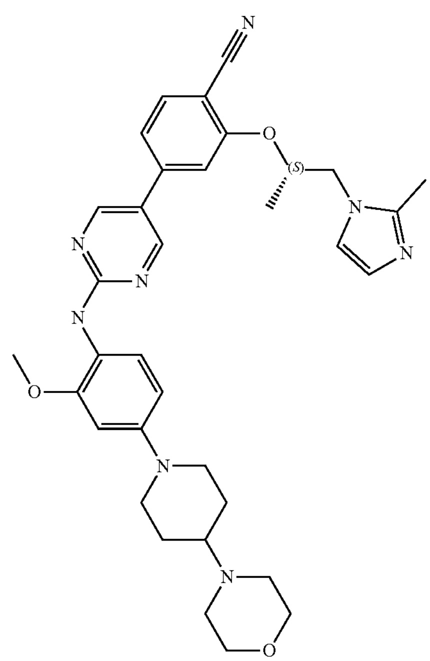 | | 609.4 |

TABLE 1-continued

| Ex. No. | IUPAC NAME | STRUCTURE | ADDITIVE | MS |
|---|---|---|---|---|
| 43 | 4-(2-((2-methoxy-4-(4-(morpholin-4-yl)piperidin-1-yl)phenyl)amino)pyrimidin-5-yl)-2-(((2S)-1-(4-methyl-1H-pyrazol-1-yl)propan-2-yl)oxy)benzonitrile | 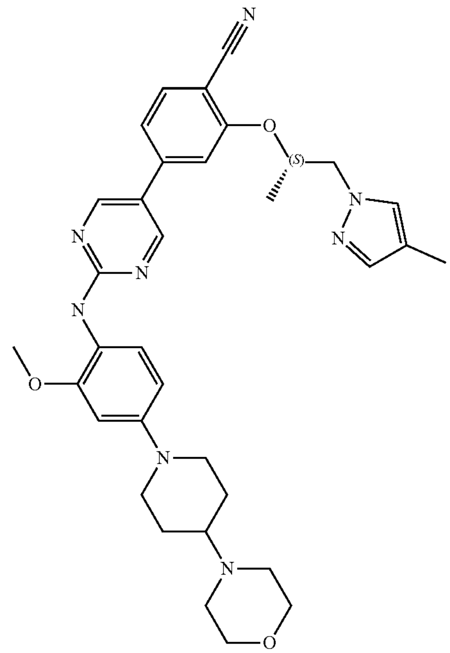 | | 609.4 |
| 44 | 4-(2-((2-methoxy-4-(4-(morpholin-4-yl)piperidin-1-yl)phenyl)amino)pyrimidin-5-yl)-2-(((2S)-1-(1H-pyrazol-1-yl)propan-2-yl)oxy)benzonitrile | 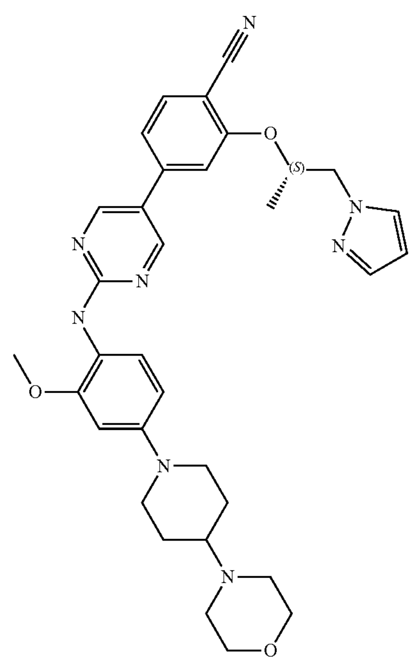 | | 595.4 |

| Ex. No. | IUPAC NAME | STRUCTURE | ADDITIVE | MS |
|---|---|---|---|---|
| 45 | 4-(2-((4-(1,4'-bipiperidine-1'-yl)-2-methoxyphenyl)amino)pyrimidin-5-yl)-2-(((2S)-1-(1H-tetrazol-1-yl)propan-2-yl)oxy)benzonitrile | 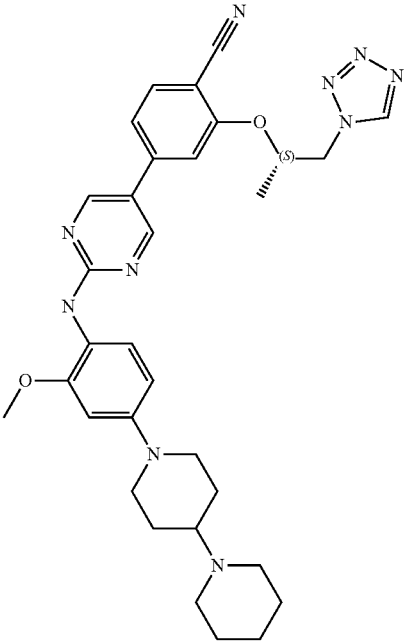 | | 595.4 |
| 46 | 4-(2-anilinopyrimidin-5-yl)-2-(((2S)-1-(1H-1,2,4-triazol-1-yl)propan-2-2-yl)oxy)benzonitrile | 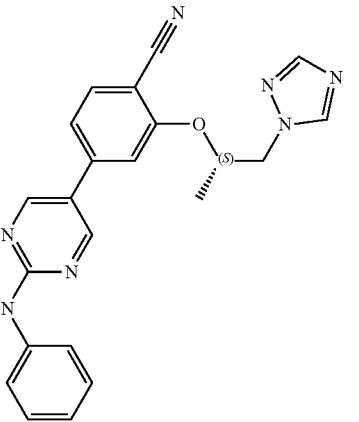 | | 396.1 |

TABLE 1-continued

| Ex. No. | IUPAC NAME | STRUCTURE | ADDITIVE | MS |
|---|---|---|---|---|
| 47 | 4-(2-((2-methoxy-4-(4-(morpholin-4-yl)piperidin-1-yl)phenyl)amino)pyrimidin-yl)-2-(((2S)-1-(3-oxomorpholin-4-yl)propan-2-yl)oxy)benzonitrile | 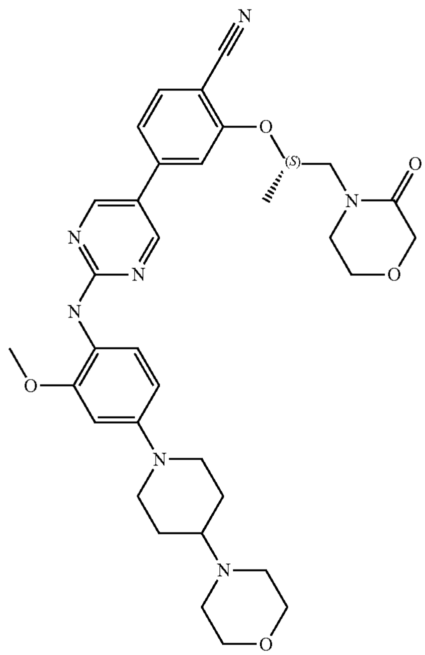 | | 628.4 |
| 48 | tert-butyl 4-(4-((5-(4-cyano-3-(((2S)-1-(1H-1,2,4-triazol-1-yl)propan-2-yl)oxy)phenyl)pyrimidin-2-yl)amino)-3-methoxy-phenyl)piperidine-1-carboxylate | 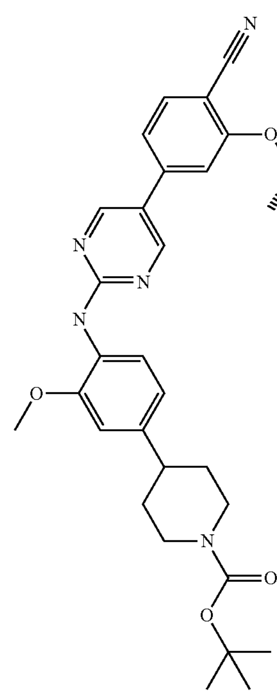 | | 611.4 |

TABLE 1-continued

| Ex. No. | IUPAC NAME | STRUCTURE | ADDITIVE | MS |
|---|---|---|---|---|
| 49 | 2-(((2S)-1-(1H-benzimidazol-1-yl)propan-2-yl)oxy)-4-(2-((2-methoxy-4-(4-(morpholin-4-yl)piperidin-1-yl)phenyl)amino)pyrimidin-5-yl)benzonitrile | 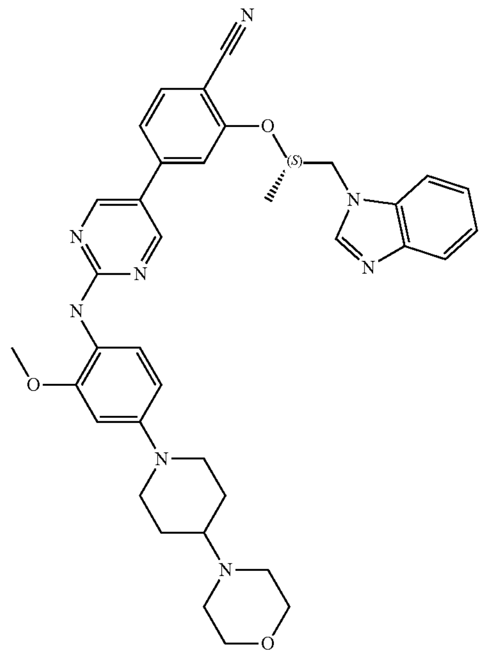 | | 645.5 |
| 50 | 4-(2-((2-methoxy-4-(piperidin-4-yl)phenyl)amino)pyrimidin-5-yl)-2-(((2S)-1-(1H-1,2,4-triazol-1-yl)propan-2-yl)oxy)benzonitrile | 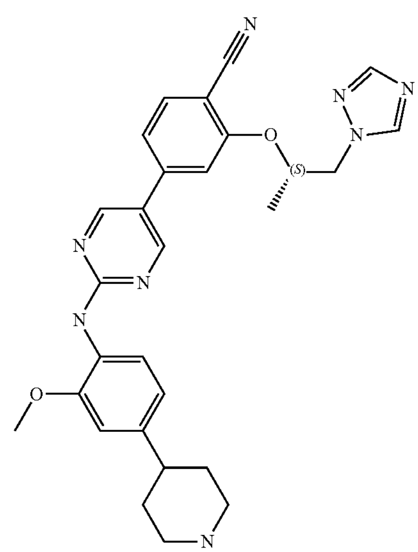 | | 511.4 |

| Ex. No. | IUPAC NAME | STRUCTURE | ADDITIVE | MS |
|---|---|---|---|---|
| 51 | tert-butyl (4-((5-(4-cyano-3-(((2S)-1-(1H-tetrazol-1-yl)propan-2-yl)oxy)phenyl)pyrimidin-2-yl)amino)-3-methoxybenzyl)cyclopropyl carbamate | 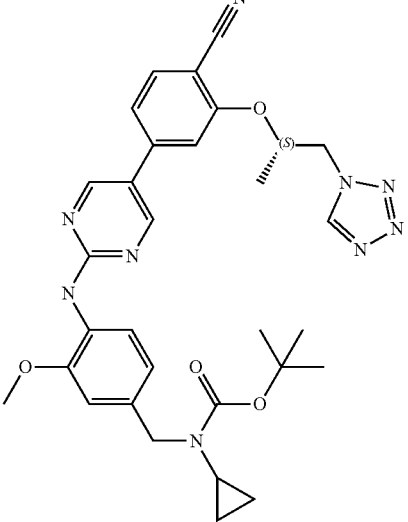 | | 598.4 |
| 52 | 4-(2-((4-((cyclopropylamino)methyl)-2-methoxyphenyl)amino)pyrimidin-5-yl)-2-(((2S)-1-(1H-tetrazol-1-yl)propan-2-yl)oxy)benzonitrile hydrochloride | 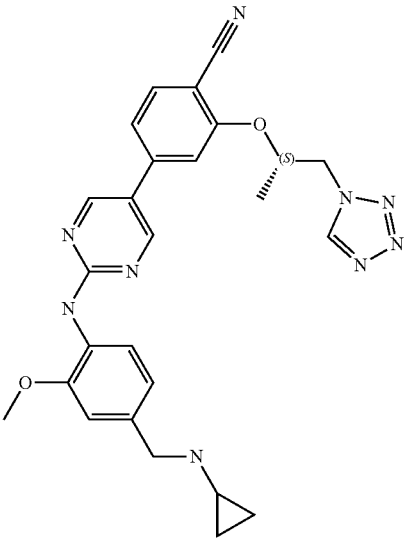 | HCl | 496 |

TABLE 1-continued

| Ex. No. | IUPAC NAME | STRUCTURE | ADDITIVE | MS |
|---|---|---|---|---|
| 53 | 4-(2-((3-((cyclo-propylamino)methyl)-2-methoxyphenyl)amino)pyrimidin-5-yl)-2-(((2S)-1-(1H-1,2,4-triazol-1-yl)propan-2-yl)oxy)benzonitrile hydrochloride | 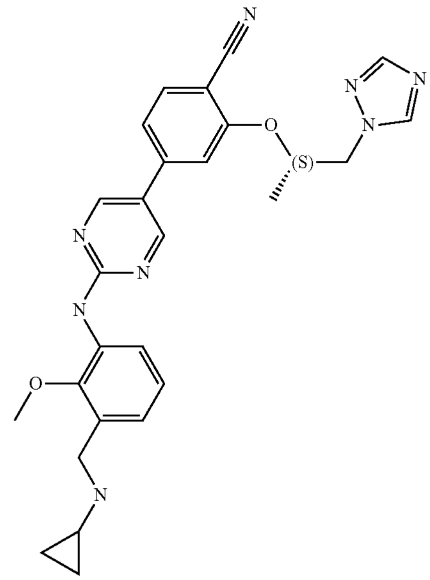 | HCl | 497.4 |
| 54 | 4-(2-((2-methoxy-4-(4-(morpholin-4-yl)piperidin-1-yl)phenyl)amino)pyrimidin-5-yl)-2-(((2S)-1-(5-oxo-1,5-dihydro-4H-1,2,4-triazol-4-yl)propan-2-yl)oxy)benzonitrile | 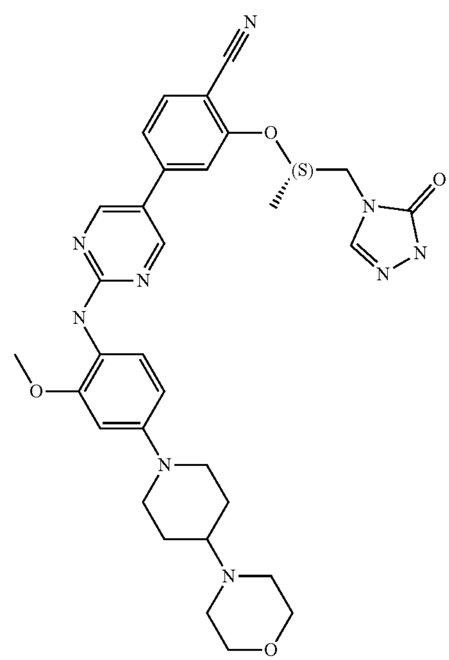 | | 612.4 |

| Ex. No. | IUPAC NAME | STRUCTURE | ADDITIVE | MS |
|---|---|---|---|---|
| 55 | 4-(2-((2-methoxy-4-(4-(morpholin-4-yl)piperidin-1-yl)phenyl)amino)pyrimidin-5-yl)-2-(((2S)-1-(1H-1,2,4-triazol-3-yloxy)propan-2-yl)oxy)benzonitrile | 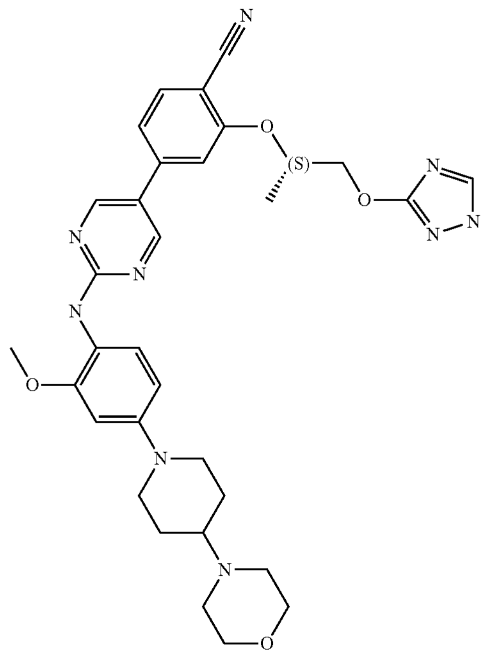 | | 612.4 |
| 56 | 4-(2-((4-methoxy-2-(4-(morpholin-4-yl)piperidin-1-yl)pyrimidin-5-yl)amino)pyrimidin-5-yl)-2-(((2S)-1-(1H-tetrazol-1-yl)propan-2-yl)oxy)benzonitrile | 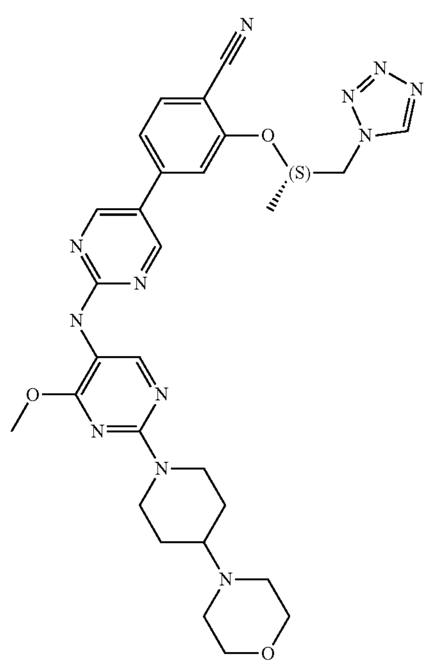 | | 599.4 |

TABLE 1-continued

| Ex. No. | IUPAC NAME | STRUCTURE | ADDITIVE | MS |
|---|---|---|---|---|
| 57 | 4-(2-((4-methoxy-6-(4-(morpholin-4-yl)piperidin-1-yl)pyridin-3-yl)amino)pyrimidin-5-yl)-2-(((2S)-1-(1H-tetrazol-1-yl)propan-2-yl)oxy)benzonitrile | 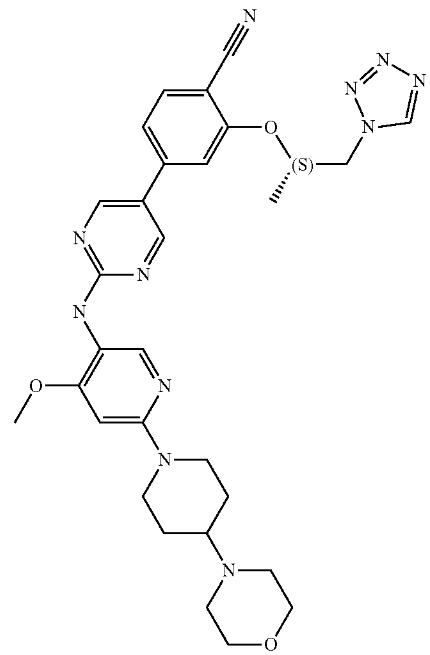 | | 598.4 |
| 58 | 5-(4-chloro-3-(((2S)-1-(1H-imidazol-1-yl)propan-2-yl)oxy)phenyl)-N-(2-methoxy-4-(4-(morpholin-4-yl)piperidin-1-yl)phenyl)pyrimidin-2-amine | 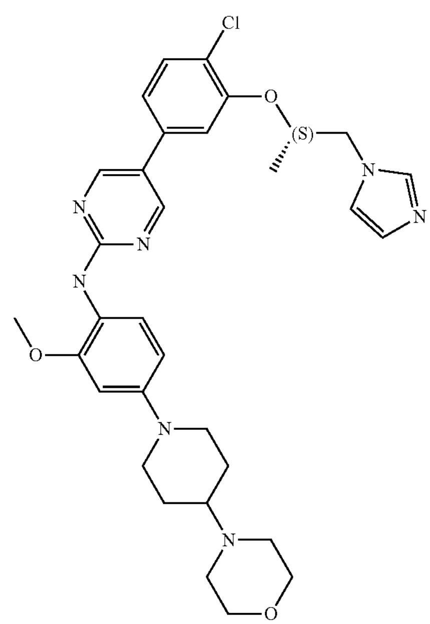 | | 604.5 |

TABLE 1-continued

| Ex. No. | IUPAC NAME | STRUCTURE | ADDITIVE | MS |
|---|---|---|---|---|
| 59 | 5-(4-chloro-3-(((2S)-1-(2H-tetrazol-2-yl)propan-2-yl)oxy)phenyl)-N-(2-methoxy-4-(4-(morpholin-4-yl)piperidin-1-yl)phenyl)pyrimidin-2-amine | 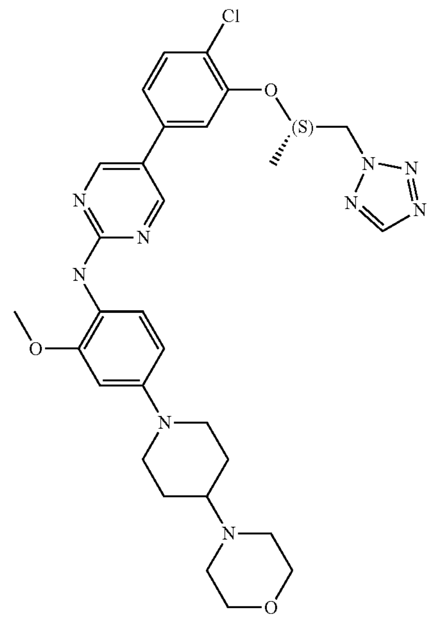 | | 606.4 |
| 60 | 5-(4-chloro-3-(((2S)-1-(1H-tetrazol-1-yl)propan-2-yl)oxy)phenyl)-N-(2-methoxy-4-(4-(morpholin-4-yl)piperidin-1-yl)phenyl)pyrimidin-2-amine | 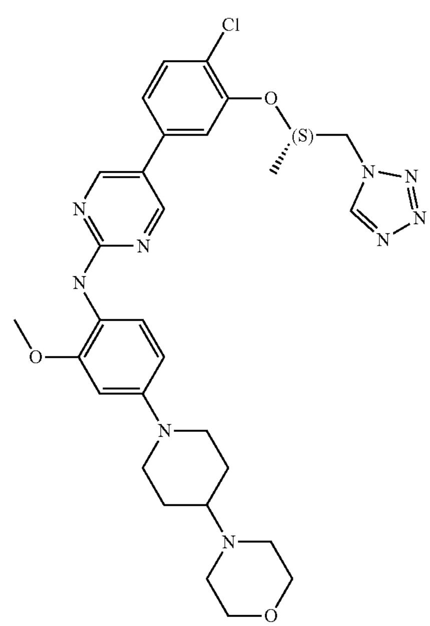 | | 606.3 |

TABLE 1-continued

| Ex. No. | IUPAC NAME | STRUCTURE | ADDITIVE | MS |
|---|---|---|---|---|
| 61 | methyl 4-((5-(4-cyano-3-(((2S)-1-(1H-1,2,4-triazol-1-yl)propan-2-yl)oxy)phenyl)pyrimidin-2-yl)amino)-3-methoxybenzoate | 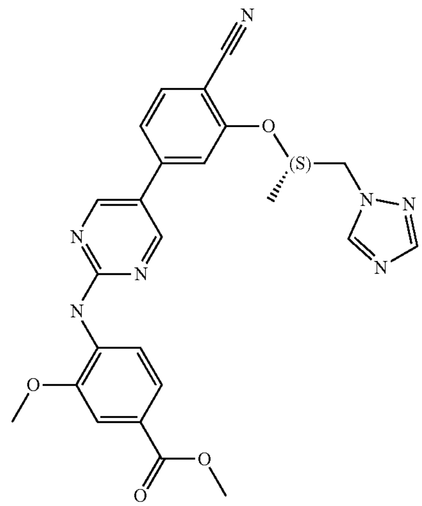 | | 486.3 |
| 62 | 4-((5-(4-cyano-3-(((2S)-1-(1H-1,2,4-triazol-1-yl)propan-2-yl)oxy)phenyl)pyrimidin-2-yl)amino)-3-methoxybenzoic acid | 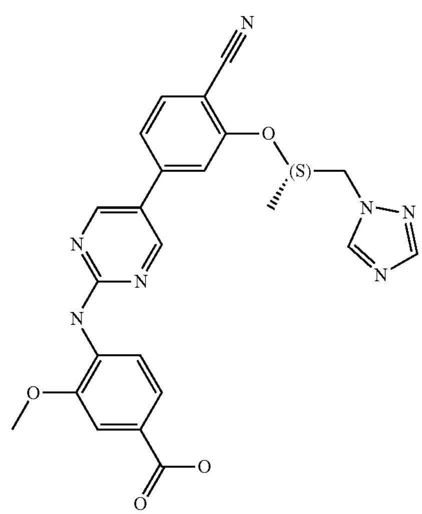 | | 469.9 |

TABLE 1-continued

| Ex. No. | IUPAC NAME | STRUCTURE | ADDITIVE | MS |
|---|---|---|---|---|
| 63 | 4-(2-((4-(1-acetylpiperidin-4-yl)-2-methoxy-phenyl)amino)pyrimidin-5-yl)-2-(((2S)-1-(1H-1,2,4-triazol-1-yl)propan-2-yl)oxy)benzonitrile | 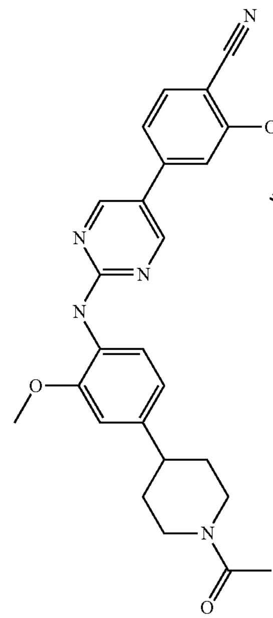 | | 553.4 |
| 64 | 4-(2-((2-methoxy-5-(morpholin-4-ylmethyl)phenyl)amino)pyrimidin-5-yl)-2-(((2S)-1-(1H-tetrazol-1-yl)propan-2-yl)oxy)benzonitrile | 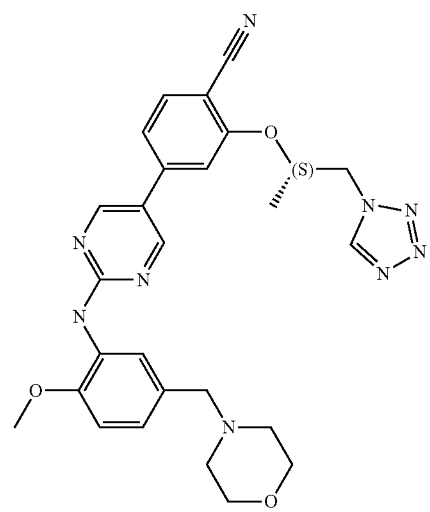 | | 528.4 |
| 65 | 4-(2-((2-isopropoxy-phenyl)amino)pyrimidin-5-yl)-2-(((2S)-1-(1H-tetrazol-1-yl)propan-2-yl)oxy)benzonitrile | 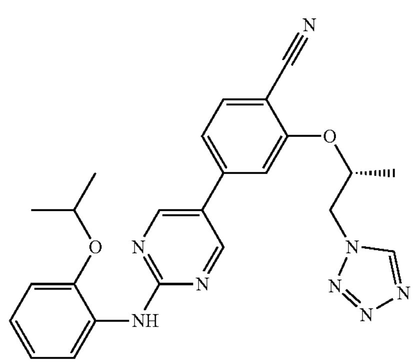 [SMILES: CC(C)Oc1ccccc1Nc1ncc(-c2ccc(C#N)c(O[C@H](C)Cn3cnnn3)c2)cn1] | | 455.1 |

TABLE 1-continued

| Ex. No. | IUPAC NAME | STRUCTURE | ADDITIVE | MS |
|---|---|---|---|---|
| 66 | 2-(((2S)-1-(1H-tetrazol-1-yl)propan-2-yl)oxy)-4-(2-((2-(trifluoromethoxy)phenyl)amino)pyrimidin-5-yl)benzonitrile | 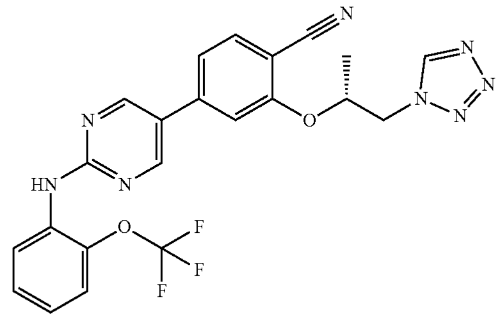 [SMILES: C[C@H](Cn1cnnn1)Oc1cc(-c2cnc(Nc3ccccc3OC(F)(F)F)nc2)ccc1C#N] | | 481 |
| 67 | 4-(2-((2-methoxy-4-(4-(morpholin-4-yl)piperidin-1-yl)phenyl)amino)pyrimidin-5-yl)-2-((1,1,1-trifluoro-3-(1H-imidazol-1-yl)propan-2-yl)oxy)benzonitrile | 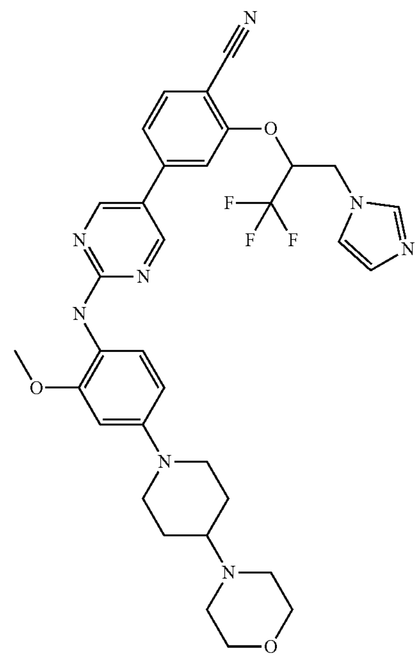 [SMILES: COc1cc(N2CCC(N3CCOCC3)CC2)ccc1Nc1ncc(-c2ccc(C#N)c(OC(Cn3ccnc3)C(F)(F)F)c2)cn1] | | 649.5 |
| 68 | 3-((5-(4-cyano-3-(((2S)-1-(1H-tetrazol-1-yl)propan-2-yl)oxy)phenyl)pyrimidin-2-yl)amino)-N-cyclopropyl-4-methoxybenzamide | 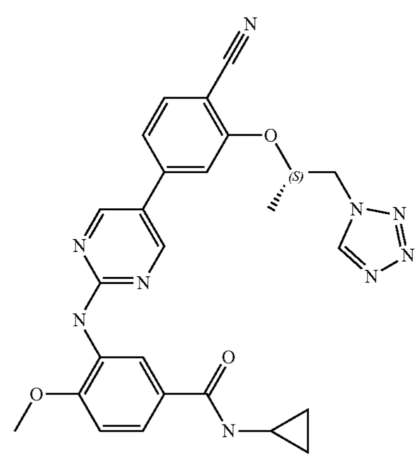 | | 512.4 |

| Ex. No. | IUPAC NAME | STRUCTURE | ADDITIVE | MS |
|---|---|---|---|---|
| 69 | 4-(2-((2-methoxy-5-(morpholin-4-ylcarbonyl)phenyl)amino)pyrimidin-5-yl)-2-(((2S)-1-(1H-tetrazol-1-yl)propan-2-yl)oxy)benzonitrile | 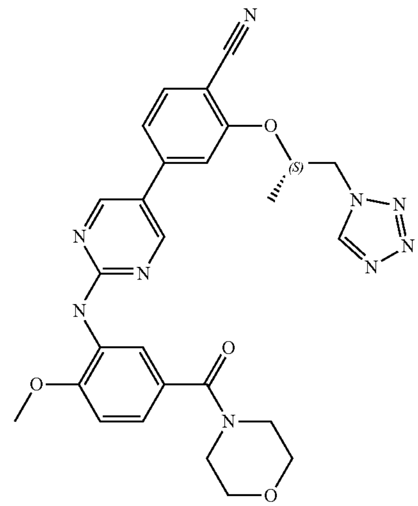 | | 542.4 |
| 71 | 4-((5-(4-cyano-3-(((2S)-1-(1H-1,2,4-triazol-1-yl)propan-2-yl)oxy)phenyl)pyrimidin-2-yl)amino)-N-cyclopropyl-3-methoxybenzamide | 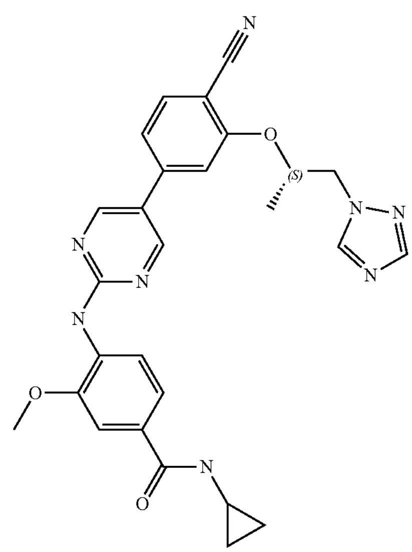 | | 511.4 |

TABLE 1-continued

| Ex. No. | IUPAC NAME | STRUCTURE | ADDITIVE | MS |
|---|---|---|---|---|
| 72 | 4-(2-((2-methoxy-4-(morpholin-4-ylcarbonyl)phenyl)amino)pyrimidin-5-yl)-2-(((2S)-1-(1H-1,2,4-triazol-1-yl)propan-2-yl)oxy)benzonitrile | 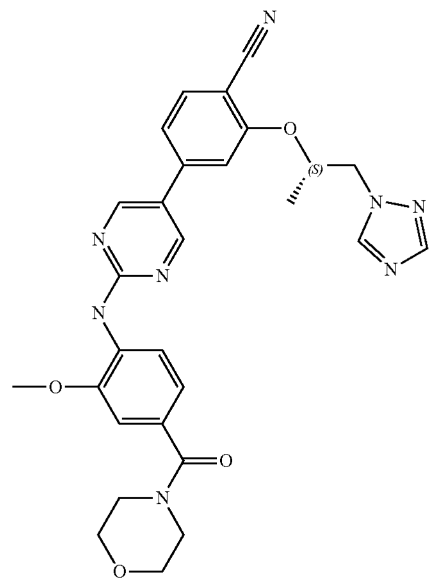 | | 541.4 |
| 73 | 4-(2-((2-methoxy-4-((4-methylpiperazin-1-yl)carbonyl)phenyl)amino)pyrimidin-5-yl)-2-(((2S)-1-(1H-1,2,4-triazol-1-yl)propan-2-yl)oxy)benzonitrile | 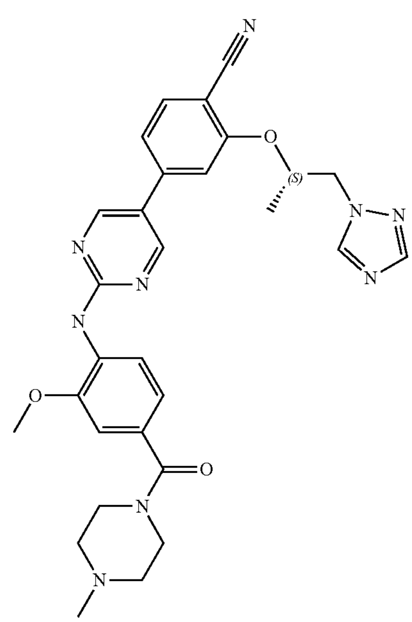 | | 554.4 |

TABLE 1-continued

| Ex. No. | IUPAC NAME | STRUCTURE | ADDITIVE | MS |
|---|---|---|---|---|
| 74 | 4-(2-((2-methoxy-4-(4-(morpholin-4-yl)piperidin-1-yl)phenyl)amino)pyrimidin-5-yl)-2-(3-methyl-2-(1H-1,2,4-triazol-1-yl)butoxy)benzonitrile | 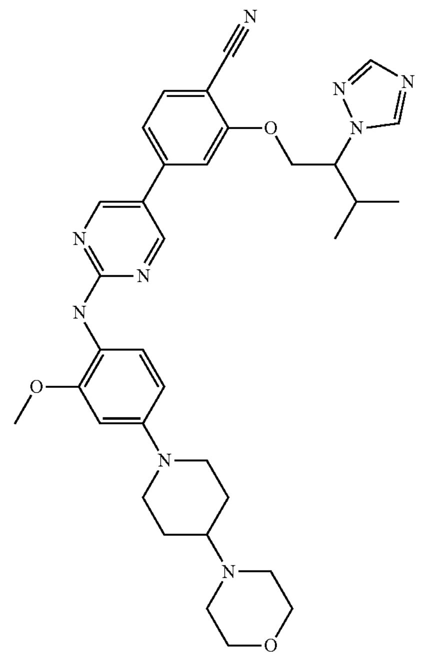 [SMILES: COc1cc(N2CCC(N3CCOCC3)CC2)ccc1Nc1ncc(-c2ccc(C#N)c(OCC(C(C)C)n3cncn3)c2)cn1] | | 624.5 |
| 75 | 4-(2-((2-methoxy-4-(1-(oxetan-3-yl)piperidin-4-yl)phenyl)amino)pyrimidin-5-yl)-2-(((2S)-1-(1H-tetrazol-1-yl)propan-2-yl)oxy)benzonitrile | 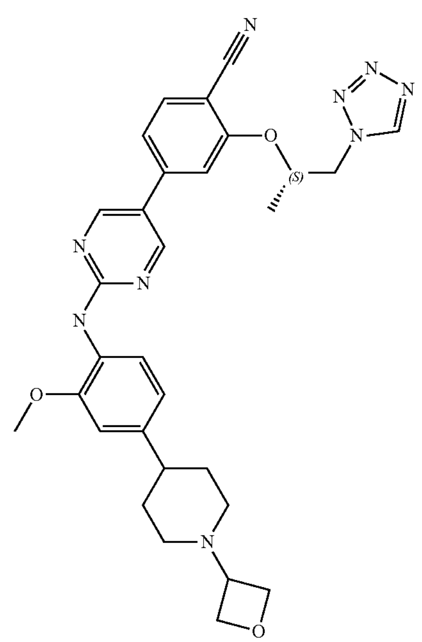 | | 566.2 |

TABLE 1-continued

| Ex. No. | IUPAC NAME | STRUCTURE | ADDITIVE | MS |
|---|---|---|---|---|
| 76 | 4-(2-((2-methoxy-4-(1-(oxetan-3-yl)piperidin-4-yl)phenyl)amino)pyrimidin-5-yl)-2-(((2S)-1-(1H-1,2,4-triazol-1-yl)propan-2-yl)oxy)benzonitrile | 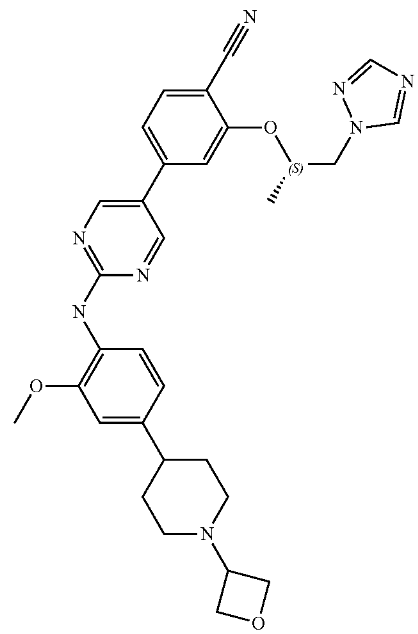 | | 567.4 |
| 77 | 4-(2-((2-methoxy-4-(4-(morpholin-4-yl)piperidin-1-yl)phenyl)amino)pyrimidin-5-yl)-2-(2-(1H-1,2,4-triazol-1-yl)propoxy)benzonitrile | 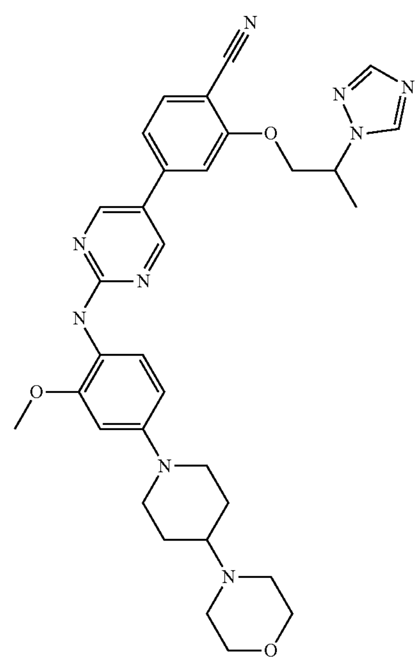 [SMILES: COc1cc(N2CCC(N3CCOCC3)CC2)ccc1Nc1ncc(-c2ccc(C#N)c(OCC(C)n3cncn3)c2)cn1] | | 596.5 |

TABLE 1-continued

| Ex. No. | IUPAC NAME | STRUCTURE | ADDITIVE | MS |
|---|---|---|---|---|
| 78 | 4-(2-((2-methoxy-4-(morpholin-4-ylmethyl)phenyl)amino)pyrimidin-5-yl)-2-(((2S)-1-(1H-tetrazol-1-yl)propan-2-yl)oxy)benzonitrile | 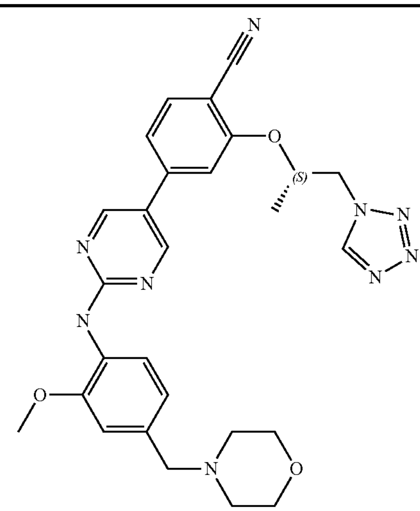 | | 526.2 |
| 79 | 4-(2-((2-methoxy-4-((4-methylpiperazin-1-yl)methyl)phenyl)amino)pyrimidin-5-yl)-2-(((2S)-1-(1H-tetrazol-1-yl)propan-2-yl)oxy)benzonitrile | 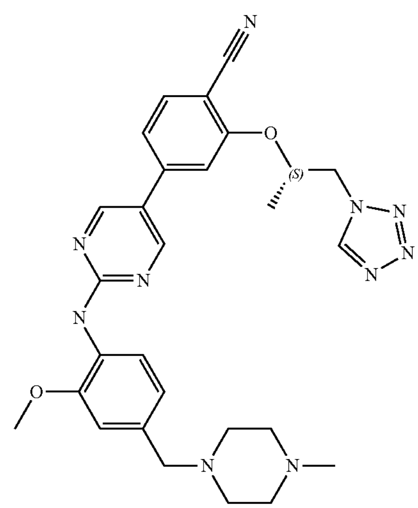 | | 541.5 |
| 80 | 4-(2-((4-(1-glycoloylpiperidin-4-yl)-2-methoxyphenyl)amino)pyrimidin-5-yl)-2-(((2S)-1-(1H-tetrazol-1-yl)propan-2-yl)oxy)benzonitrile | 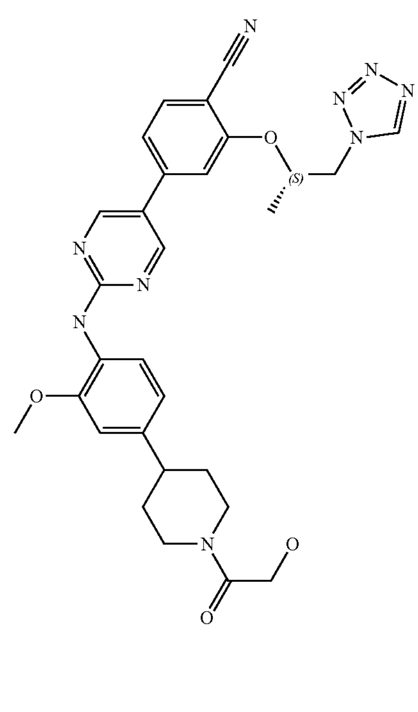 | | 568.2 |

TABLE 1-continued

| Ex. No. | IUPAC NAME | STRUCTURE | ADDITIVE | MS |
|---|---|---|---|---|
| 81 | 4-((5-(4-cyano-3-(((2S)-1-(1H-tetrazol-1-yl)propan-2-yl)oxy)phenyl)pyrimidin-2-yl)amino)-N-cyclopropyl-3-methoxybenzamide | 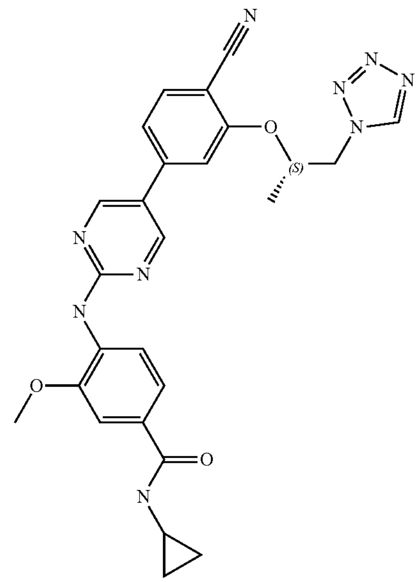 | | 510.1 |
| 82 | 4-(2-((2-methoxy-4-(morpholin-4-ylcarbonyl)phenyl)amino)pyrimidin-5-yl)-2-(((2S)-1-(1H-tetrazol-1-yl)propan-2-yl)oxy)benzonitrile | 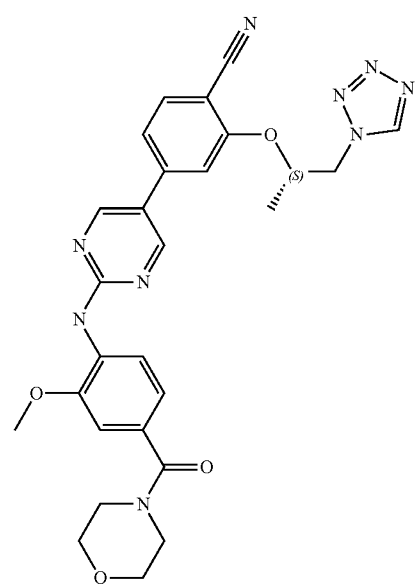 | | 540.1 |

TABLE 1-continued

| Ex. No. | IUPAC NAME | STRUCTURE | ADDITIVE | MS |
|---|---|---|---|---|
| 83 | 4-(2-((2-methoxy-4-((4-methylpiperazin-1-yl)carbonyl)phenyl)amino)pyrimidin-5-yl)-2-(((2S)-1-(1H-tetrazol-1-yl)propan-2-yl)oxy)benzonitrile | 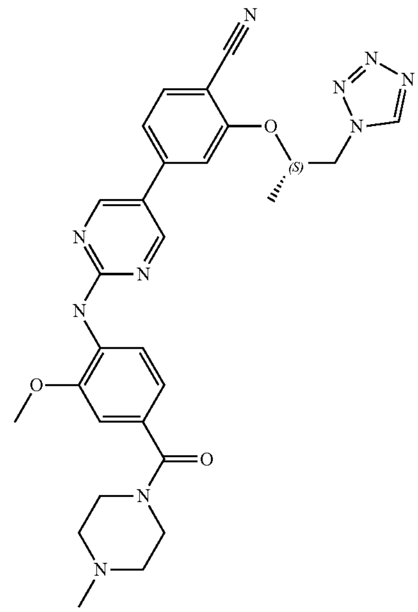 | | 555.4 |
| 84 | 4-(2-((4-((4,4-difluoropiperidin-1-yl)carbonyl)-2-methoxyphenyl)amino)pyrimidin-5-yl)-2-(((2S)-1-(1H-tetrazol-1-yl)propan-2-yl)oxy)benzonitrile | 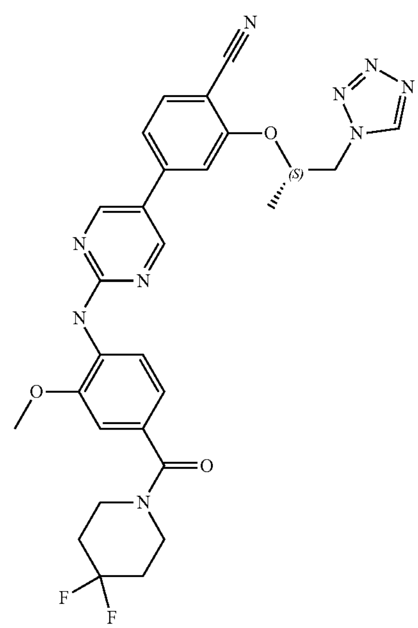 | | 574.1 |

TABLE 1-continued

| Ex. No. | IUPAC NAME | STRUCTURE | ADDITIVE | MS |
|---|---|---|---|---|
| 85 | 4-(2-((2-methoxy-4-(1-(2-methoxyethyl)piperidin-4-yl)phenyl)amino)pyrimidin-5-yl)-2-(((2S)-1-(1H-tetrazol-1-yl)propan-2-yl)oxy)benzonitrile | 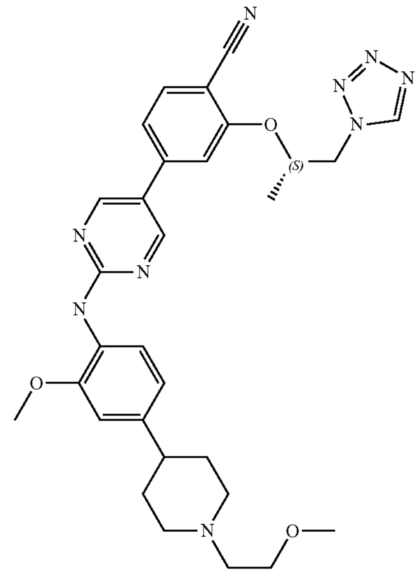 | | 570.4 |
| 86 | 4-(2-((4-((4-hydroxy-4-methylpiperidin-1-yl)carbonyl)-2-methoxyphenyl)amino)pyrimidin-5-yl)-2-(((2S)-1-(1H-tetrazol-1-yl)propan-2-yl)oxy)benzonitrile | 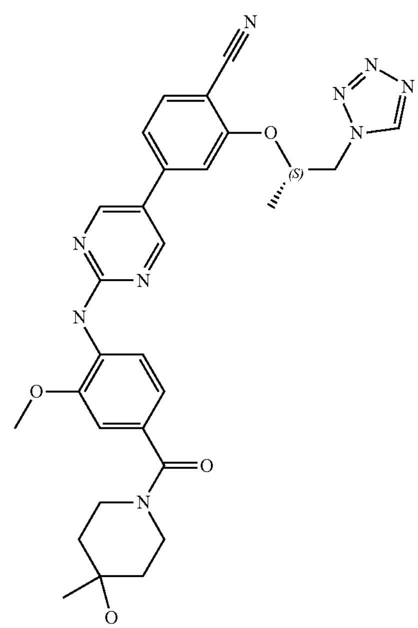 | | 570.4 |

| Ex. No. | IUPAC NAME | STRUCTURE | ADDITIVE | MS |
|---|---|---|---|---|
| 87 | 4-((5-(4-cyano-3-(((2S)-1-(1H-tetrazol-1-yl)propan-2-yl)oxy)phenyl)pyrimidin-2-yl)amino)-3-methoxy-N-(tetrahydro-2H-pyran-4-yl)benzamide | 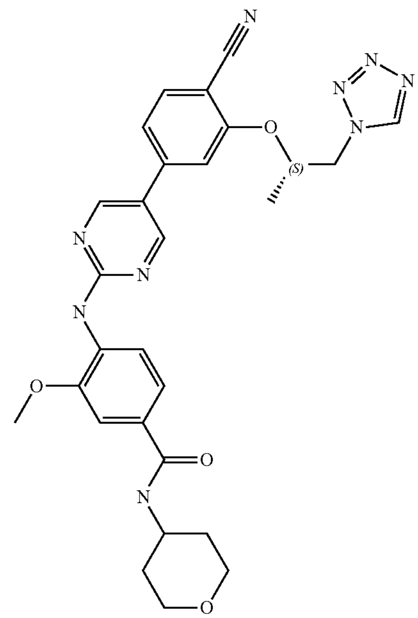 | | 556.4 |
| 88 | 4-((5-(4-cyano-3-(((2S)-1-(1H-1,2,4-triazol-1-yl)propan-2-yl)oxy)phenyl)pyrimidin-2-yl)amino)-3-methoxy-N-methylbenzamide | 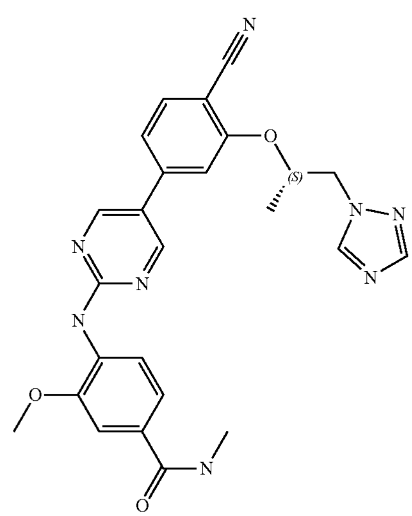 | | 485.3 |

TABLE 1-continued

| Ex. No. | IUPAC NAME | STRUCTURE | ADDITIVE | MS |
|---|---|---|---|---|
| 89 | 4-((5-(4-cyano-3-(((2S)-1-(1H-1,2,4-triazol-1-yl)propan-2-yl)oxy)phenyl)pyrimidin-2-yl)amino)-3-methoxy-N,N-dimethylbenzamide | 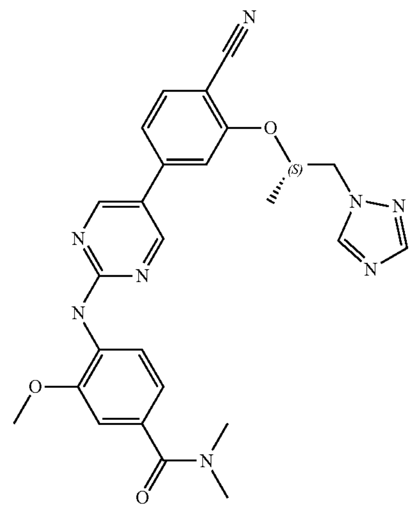 | | 499.3 |
| 90 | 4-(2-((4-(azetidin-1-ylcarbonyl)-2-methoxyphenyl)amino)pyrimidin-5-yl)-2-(((2S)-1-(1H-1,2,4-triazol-1-yl)propan-2-yl)oxy)benzonitrile | 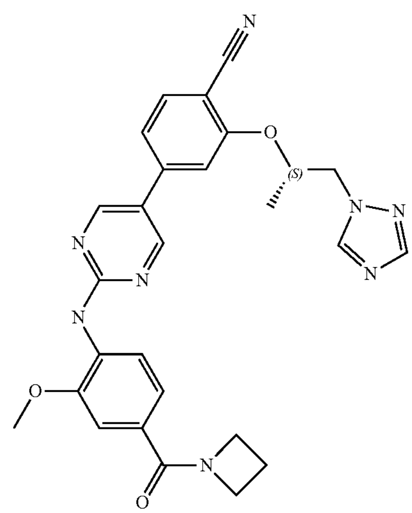 | | 511.3 |
| 91 | 4-((5-(4-cyano-3-(((2S)-1-(1H-1,2,4-triazol-1-yl)propan-2-yl)oxy)phenyl)pyrimidin-2-yl)amino)-N-(2-hydroxyethyl)-3-methoxybenzamide | 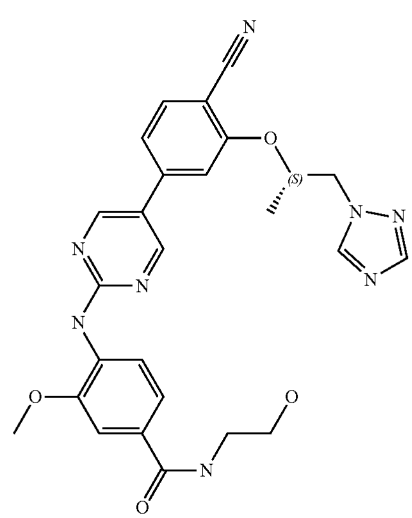 | | 515.3 |

TABLE 1-continued

| Ex. No. | IUPAC NAME | STRUCTURE | ADDITIVE | MS |
|---|---|---|---|---|
| 92 | 4-((5-(4-cyano-3-(((2S)-1-(1H-1,2,4-triazol-1-yl)propan-2-yl)oxy)phenyl)pyrimidin-2-yl)amino)-N-(cyclopropylmethyl)-3-methoxybenzamide | 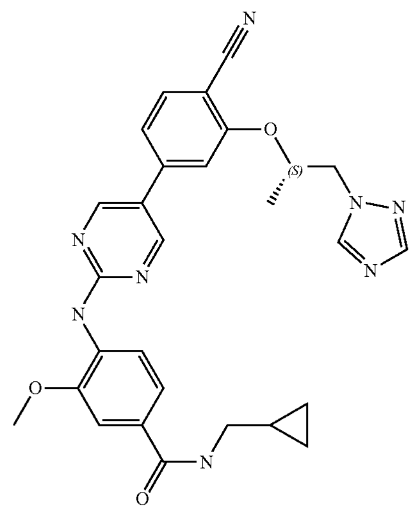 | | 525.3 |
| 93 | 4-(2-((2-methoxy-4-(pyrrolidin-1-ylcarbonyl)phenyl)amino)pyrimidin-5-yl)-2-(((2S)-1-(1H-1,2,4-triazol-1-yl)propan-2-yl)oxy)benzonitrile | 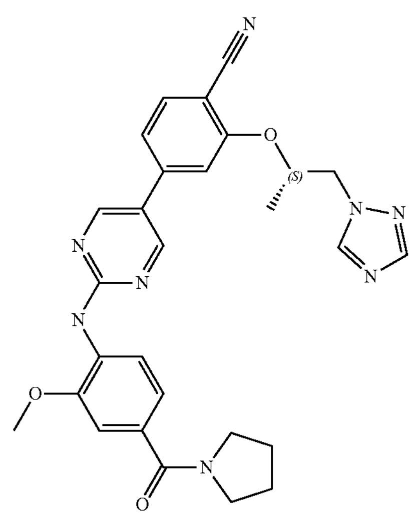 | | 525.4 |
| 94 | 4-((5-(4-cyano-3-(((2S)-1-(1H-1,2,4-triazol-1-yl)propan-2-yl)oxy)phenyl)pyrimidin-2-yl)amino)-N-cyclopropyl-3-methoxy-N-methylbenzamide | 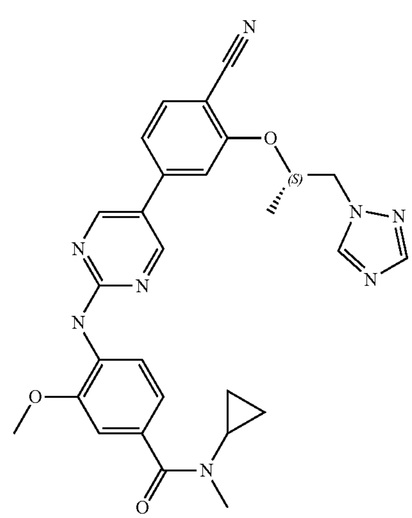 | | 525.4 |

TABLE 1-continued

| Ex. No. | IUPAC NAME | STRUCTURE | ADDITIVE | MS |
|---|---|---|---|---|
| 95 | 4-((5-(4-cyano-3-(((2S)-1-(1H-1,2,4-triazol-1-yl)propan-2-yl)oxy)phenyl)pyrimidin-2-yl)amino)-3-methoxy-N-(oxetan-3-yl)benzamide | 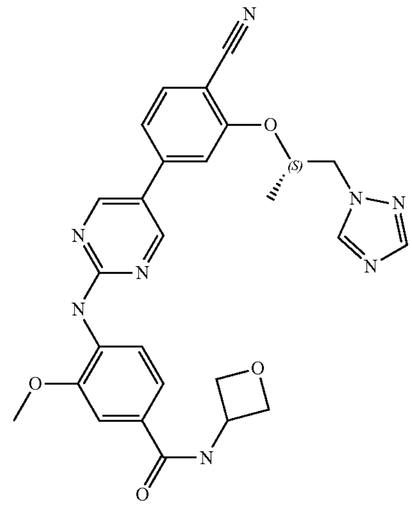 | | 527.3 |
| 96 | 4-((5-(4-cyano-3-(((2S)-1-(1H-1,2,4-triazol-1-yl)propan-2-yl)oxy)phenyl)pyrimidin-2-yl)amino)-N-((2S)-2-hydroxypropyl)-3-methoxybenzamide | 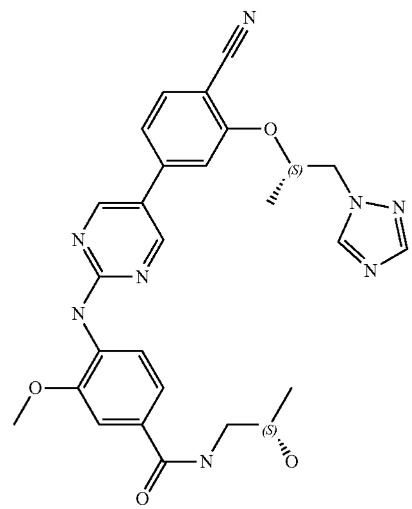 | | 529.3 |
| 97 | 4-((5-(4-cyano-3-(((2S)-1-(1H-1,2,4-triazol-1-yl)propan-2-yl)oxy)phenyl)pyrimidin-2-yl)amino)-N-((2R)-2-hydroxypropyl)-3-methoxybenzamide | 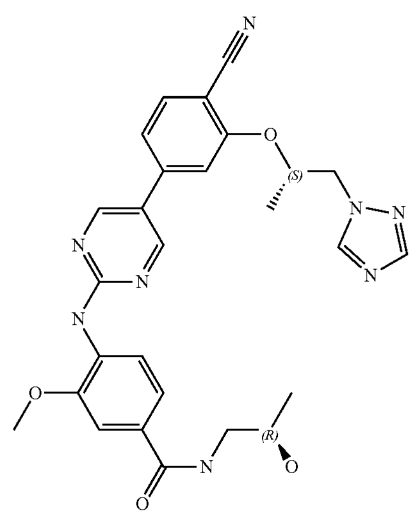 | | 529.3 |

TABLE 1-continued

| Ex. No. | IUPAC NAME | STRUCTURE | ADDITIVE | MS |
|---|---|---|---|---|
| 98 | 4-((5-(4-cyano-3-(((2S)-1-(1H-1,2,4-triazol-1-yl)propan-2-yl)oxy)phenyl)pyrimidin-2-yl)amino)-3-methoxy-N-(2-methoxyethyl)benzamide | 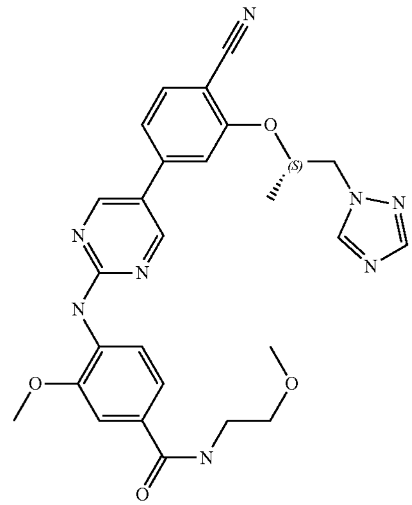 | | 529.3 |
| 99 | 4-((5-(4-cyano-3-(((2S)-1-(1H-1,2,4-triazol-1-yl)propan-2-yl)oxy)phenyl)pyrimidin-2-yl)amino)-N-(2,2-difluoroethyl)-3-methoxybenzamide | 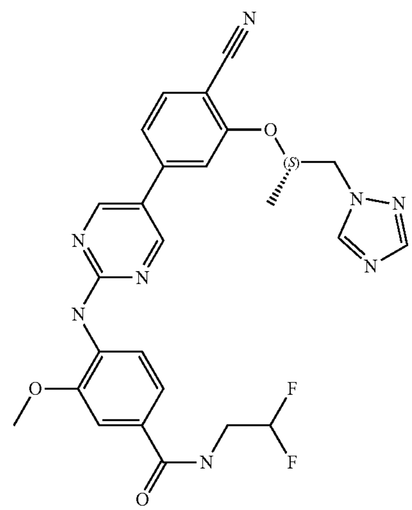 | | 535.3 |
| 100 | 4-(2-((2-methoxy-4-(piperidin-1-ylcarbonyl)phenyl)amino)pyrimidin-5-yl)-2-(((2S)-1-(1H-1,2,4-triazol-1-yl)propan-2-yl)oxy)benzonitrile | 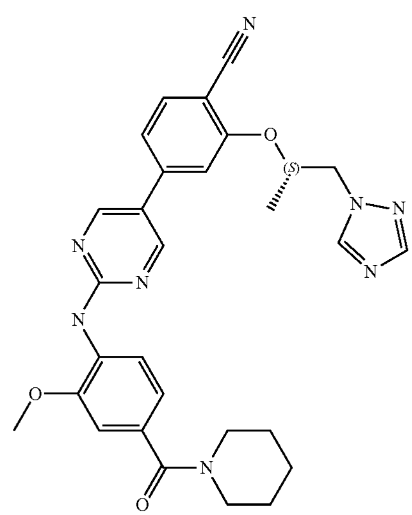 | | 539.4 |

TABLE 1-continued

| Ex. No. | IUPAC NAME | STRUCTURE | ADDITIVE | MS |
|---|---|---|---|---|
| 101 | 4-((5-(4-cyano-3-(((2S)-1-(1H-1,2,4-triazol-1-yl)propan-2-yl)oxy)phenyl)pyrimidin-2-yl)amino)-3-methoxy-N-(oxetan-3-ylmethyl)benzamide | 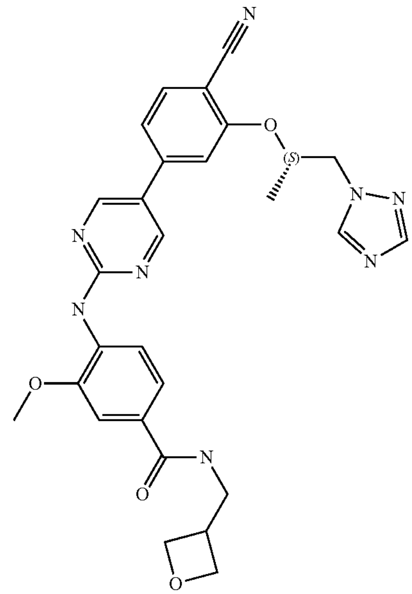 | | 541.4 |
| 102 | 4-((5-(4-cyano-3-(((2S)-1-(1H-1,2,4-triazol-1-yl)propan-2-yl)oxy)phenyl)pyrimidin-2-yl)amino)-N-(1,3-dihydroxypropan-2-yl)-3-methoxybenzamide | 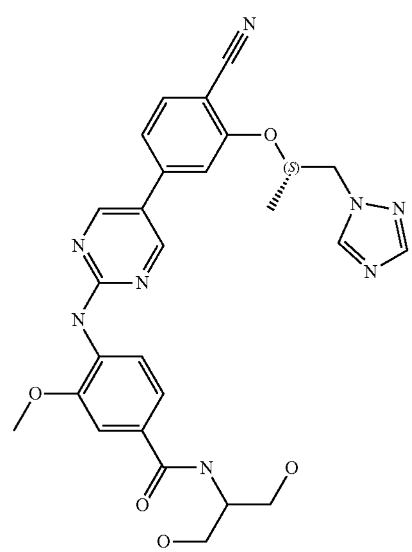 | | 545.3 |

TABLE 1-continued

| Ex. No. | IUPAC NAME | STRUCTURE | ADDITIVE | MS |
|---|---|---|---|---|
| 103 | 4-((5-(4-cyano-3-(((2S)-1-(1H-1,2,4-triazol-1-yl)propan-2-yl)oxy)phenyl)pyrimidin-2-yl)amino)-3-methoxy-N-(2,2,2-trifluoroethyl)benzamide | 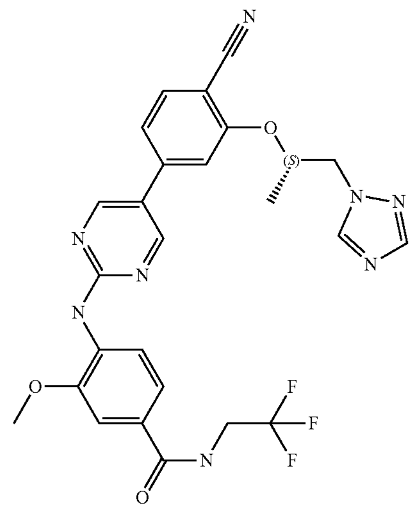 | | 553.3 |
| 104 | 4-(2-((2-methoxy-4-((1S,4S)-2-oxa-5-azabicyclo[2.2.1]hept-5-ylcarbonyl)phenyl)amino)pyrimidin-5-yl)-2-(((2S)-1-(1H-1,2,4-triazol-1-yl)propan-2-yl)oxy)benzonitrile | 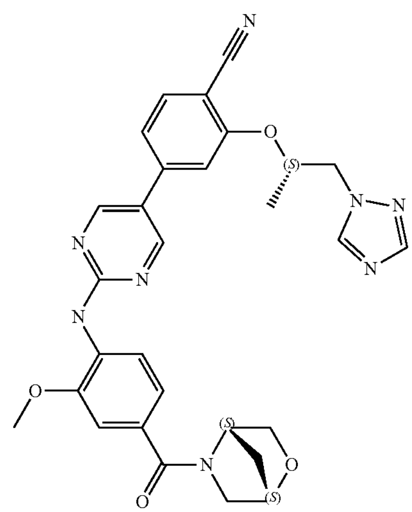 | | 553.3 |
| 105 | 4-(2-((4-(azepan-1-ylcarbonyl)-2-methoxy-phenyl)amino)pyrimidin-5-yl)-2-(((2S)-1-(1H-1,2,4-triazol-1-yl)propan-2-yl)oxy)benzonitrile | 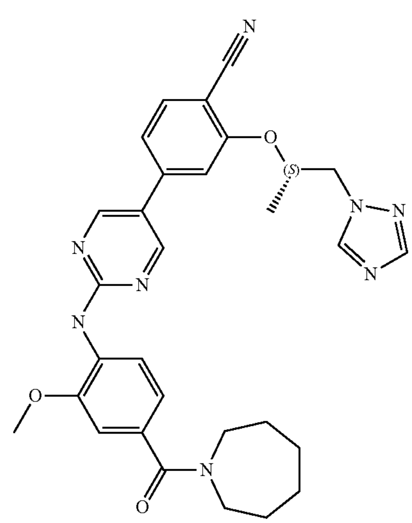 | | 553.4 |

| Ex. No. | IUPAC NAME | STRUCTURE | ADDITIVE | MS |
|---|---|---|---|---|
| 106 | 4-((5-(4-cyano-3-(((2S)-1-(1H-1,2,4-triazol-1-yl)propan-2-yl)oxy)phenyl)pyrimidin-2-yl)amino)-N-cyclohexyl-3-methoxybenzamide | 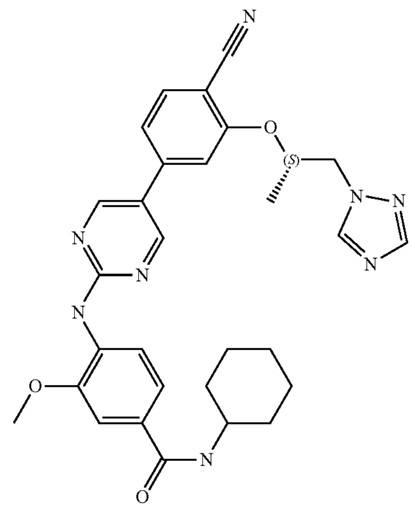 | | 553.4 |
| 107 | 4-((5-(4-cyano-3-(((2S)-1-(1H-1,2,4-triazol-1-yl)propan-2-yl)oxy)phenyl)pyrimidin-2-yl)amino)-N-(2-fluoroethyl)-3-methoxybenzamide | 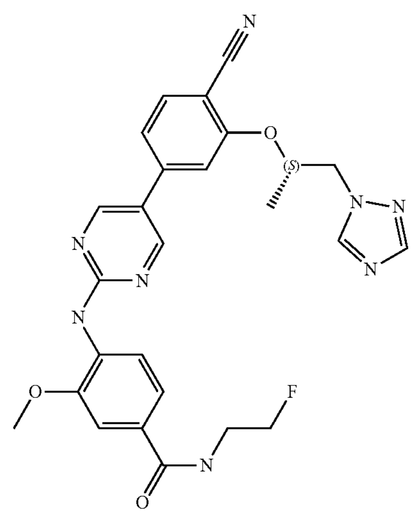 | | 517.2 |
| 108 | 4-((5-(4-cyano-3-(((2S)-1-(1H-1,2,4-triazol-1-yl)propan-2-yl)oxy)phenyl)pyrimidin-2-yl)amino)-3-methoxy-N-(tetrahydro-2H-pyran-4-yl)benzamide | 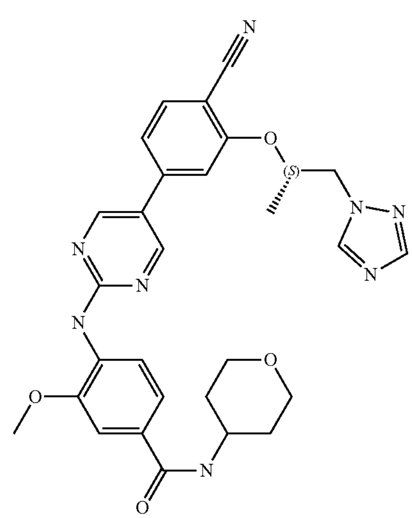 | | 555.3 |

TABLE 1-continued

| Ex. No. | IUPAC NAME | STRUCTURE | ADDITIVE | MS |
|---|---|---|---|---|
| 109 | 4-(2-((4-((4-hydroxypiperidin-1-yl)carbonyl)-2-methoxyphenyl)amino)pyrimidin-5-yl)-2-(((2S)-1-(1H-1,2,4-triazol-1-yl)propan-2-yl)oxy)benzonitrile | 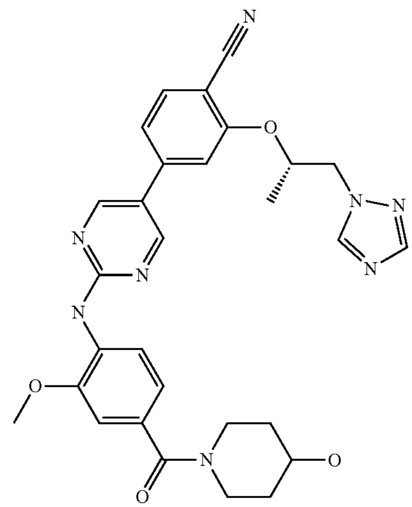 [SMILES: COc1cc(C(=O)N2CCC(O)CC2)ccc1Nc1ncc(-c2ccc(C#N)c(O[C@@H](C)Cn3cncn3)c2)cn1] | | 555.4 |
| 110 | 4-((5-(4-cyano-3-(((2S)-1-(1H-1,2,4-triazol-1-yl)propan-2-yl)oxy)phenyl)pyrimidin-2-yl)amino)-N-(2,2-difluoro-3-hydroxypropyl)-3-methoxybenzamide | 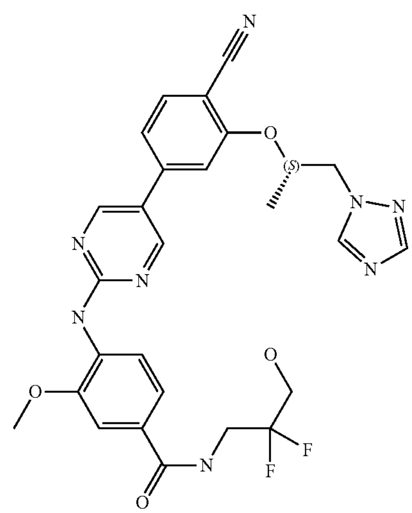 | | 565.3 |
| 111 | 4-((5-(4-cyano-3-(((2S)-1-(1H-1,2,4-triazol-1-yl)propan-2-yl)oxy)phenyl)pyrimidin-2-yl)amino)-3-methoxy-N-(3,3,3-trifluoropropyl)benzamide | 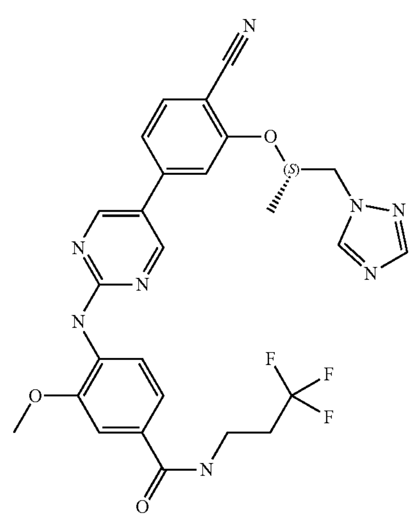 | | 567.3 |

TABLE 1-continued

| Ex. No. | IUPAC NAME | STRUCTURE | ADDITIVE | MS |
|---|---|---|---|---|
| 112 | 4-((5-(4-cyano-3-(((2S)-1-(1H-1,2,4-triazol-1-yl)propan-2-yl)oxy)phenyl)pyrimidin-2-yl)amino)-3-methoxy-N-methyl-N-(2,2,2-trifluoroethyl)benzamide | 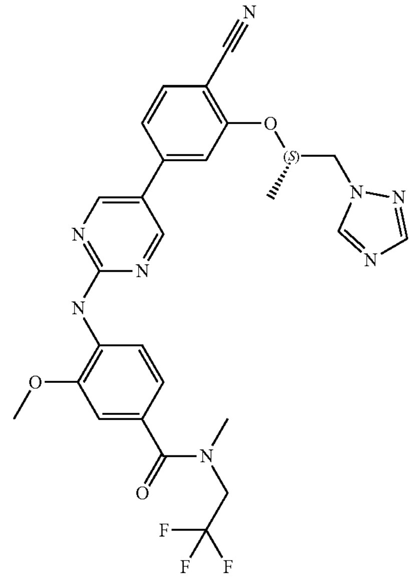 | | 567.3 |
| 113 | 4-(2-((2-methoxy-4-(7-oxa-4-azaspiro[2.5]oct-4-ylcarbonyl)phenyl)amino)pyrimidin-5-yl)-2-(((2S)-1-(1H-1,2,4-triazol-1-yl)propan-2-yl)oxy)benzonitrile | 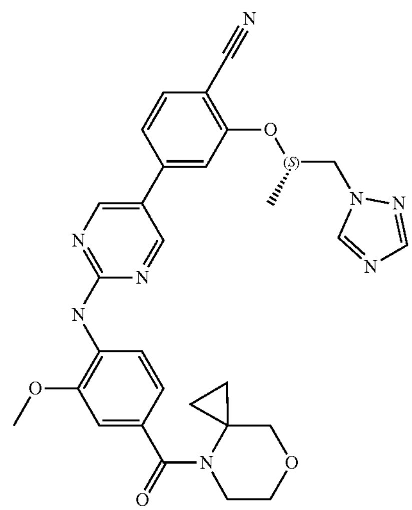 | | 567.3 |
| 114 | 4-(2-((2-methoxy-4-((1R,5S)-8-oxa-3-azabicyclo[3.2.1]oct-3-ylcarbonyl)phenyl)amino)pyrimidin-5-yl)-2-(((2S)-1-(1H-1,2,4-triazol-1-yl)propan-2-yl)oxy)benzonitrile | 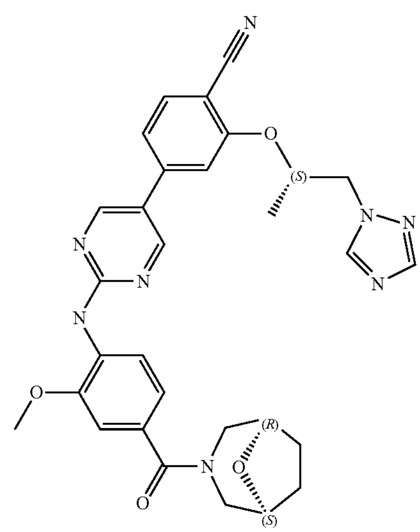 | | 567.3 |

TABLE 1-continued

| Ex. No. | IUPAC NAME | STRUCTURE | ADDITIVE | MS |
|---|---|---|---|---|
| 115 | 4-((5-(4-cyano-3-(((2S)-1-(1H-1,2,4-triazol-1-yl)propan-2-yl)oxy)phenyl)pyrimidin-2-yl)amino)-N-(cyclohexylmethyl)-3-methoxybenzamide | 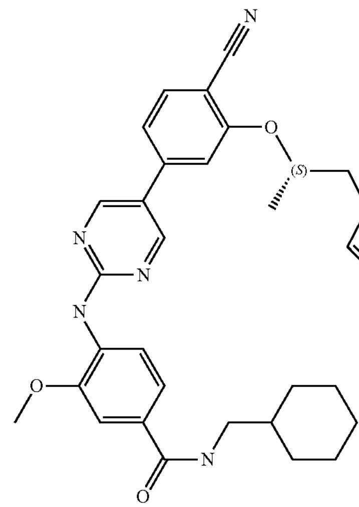 | | 567.4 |
| 116 | 4-(2-((2-methoxy-4-((4-methyl-1,4-diazepan-1-yl)carbonyl)phenyl)amino)pyrimidin-5-yl)-2-(((2S)-1-(1H-1,2,4-triazol-1-yl)propan-2-yl)oxy)benzonitrile | 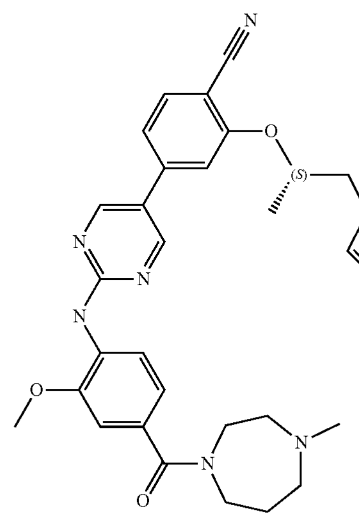 | | 568.4 |
| 117 | 4-((5-(4-cyano-3-(((2S)-1-(1H-1,2,4-triazol-1-yl)propan-2-yl)oxy)phenyl)pyrimidin-2-yl)amino)-3-methoxy-N-(1-methylpiperidin-4-yl)benzamide | 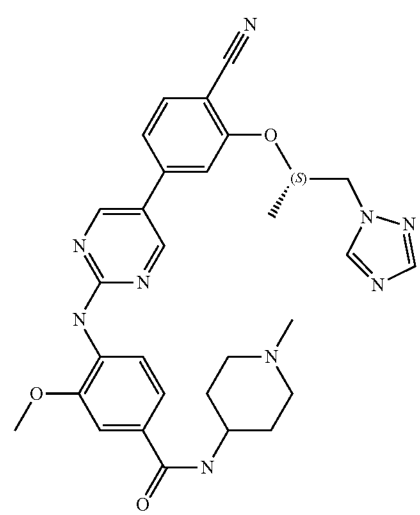 | | 568.4 |

TABLE 1-continued

| Ex. No. | IUPAC NAME | STRUCTURE | ADDITIVE | MS |
|---|---|---|---|---|
| 118 | 4-((5-(4-cyano-3-(((2S)-1-(1H-1,2,4-triazol-1-yl)propan-2-yl)oxy)phenyl)pyrimidin-2-yl)amino)-3-methoxy-N-(tetrahydro-2H-pyran-4-ylmethyl)benzamide | 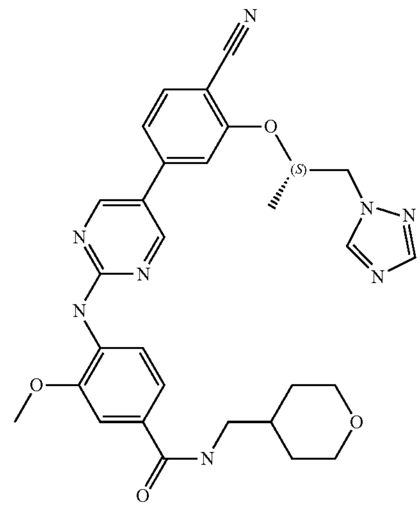 | | 569.4 |
| 119 | 4-(2-((2-methoxy-4-((4-methoxypiperidin-1-yl)carbonyl)phenyl)amino)pyrimidin-5-yl)-2-(((2S)-1-(1H-1,2,4-triazol-1-yl)propan-2-yl)oxy)benzonitrile | 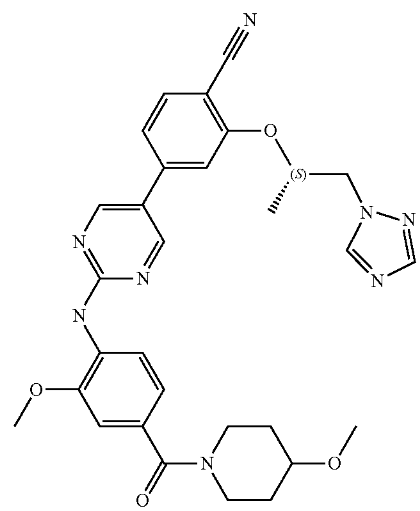 | | 569.4 |
| 120 | 4-(2-((2-methoxy-4-(2-oxa-7-azaspiro[3.5]non-7-ylcarbonyl)phenyl)amino)pyrimidin-5-yl)-2-(((2S)-1-(1H-1,2,4-triazol-1-yl)propan-2-yl)oxy)benzonitrile | 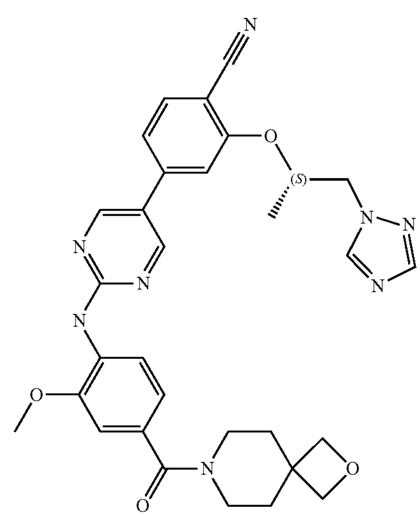 | | 581.4 |

TABLE 1-continued

| Ex. No. | IUPAC NAME | STRUCTURE | ADDITIVE | MS |
|---|---|---|---|---|
| 121 | 4-((5-(4-cyano-3-(((2S)-1-(1H-1,2,4-triazol-1-yl)propan-2-yl)oxy)phenyl)pyrimidin-2-yl)amino)-3-methoxy-N-((1-methylpiperidin-4-yl)methyl)benzamide | 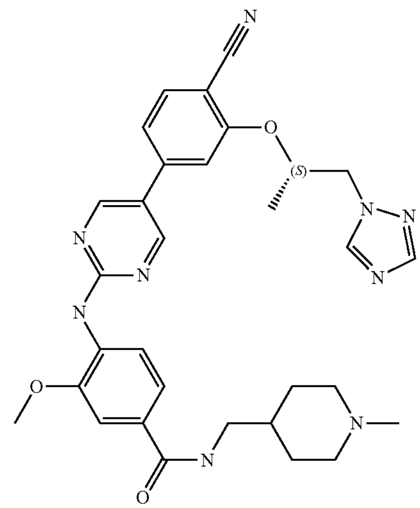 | | 582.4 |
| 122 | 4-((5-(4-cyano-3-(((2S)-1-(1H-1,2,4-triazol-1-yl)propan-2-yl)oxy)phenyl)pyrimidin-2-yl)amino)-N-(2,2-difluorocyclopropyl)-3-methoxybenzamide | 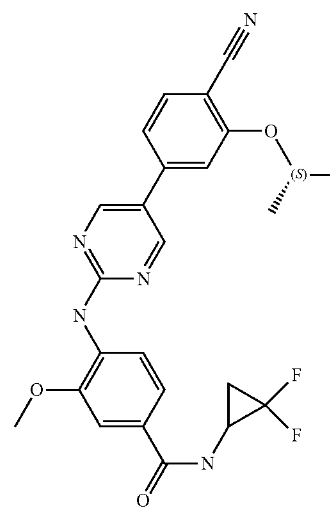 | | 547.3 |
| 123 | 4-(2-((4-((4-(2-hydroxyethyl)piperazin-1-yl)carbonyl)-2-methoxy-phenyl)amino)pyrimidin-5-yl)-2-(((2S)-1-(1H-1,2,4-triazol-1-yl)propan-2-yl)oxy)benzonitrile | 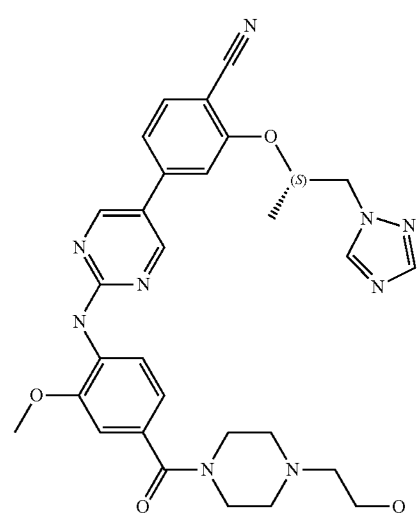 | | 584.4 |

TABLE 1-continued

| Ex. No. | IUPAC NAME | STRUCTURE | ADDITIVE | MS |
|---|---|---|---|---|
| 124 | 4-((5-(4-cyano-3-(((2S)-1-(1H-1,2,4-triazol-1-yl)propan-2-yl)oxy)phenyl)pyrimidin-2-yl)amino)-3-methoxy-N-(2-(morpholin-4-yl)ethyl)benzamide | 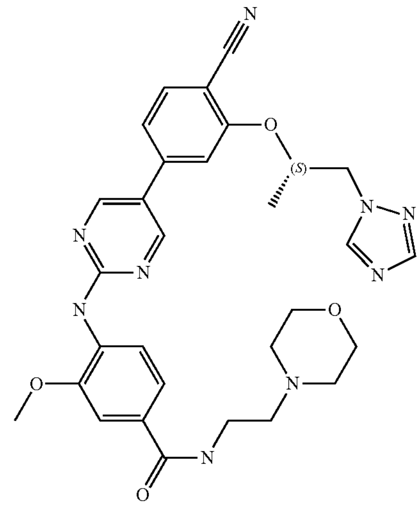 | | 584.4 |
| 125 | 4-(2-((4-((1,1-dioxidothiomorpholin-4-yl)carbonyl)-2-methoxyphenyl)amino)pyrimidin-5-yl)-2-(((2S)-1-(1H-1,2,4-triazol-1-yl)propan-2-yl)oxy)benzonitrile | 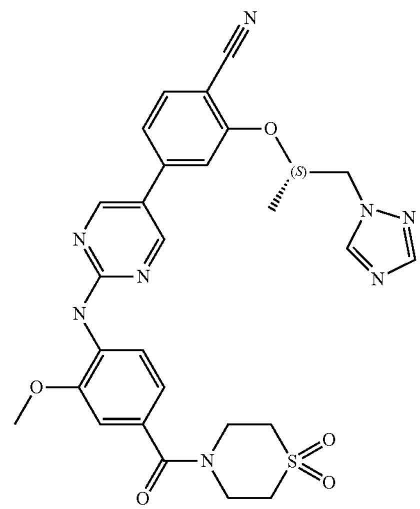 | | 589.4 |
| 126 | 4-(2-((2-methoxy-4-(((2R)-2-methylmorpholin-4-yl)carbonyl)phenyl)amino)pyrimidin-5-yl)-2-(((2S)-1-(1H-1,2,4-triazol-1-yl)propan-2-yl)oxy)benzonitrile | 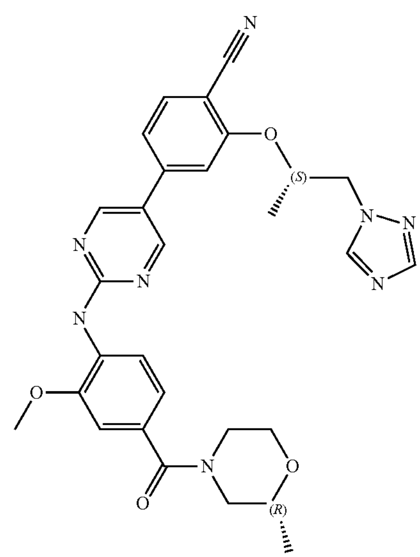 | | 555.4 |

TABLE 1-continued

| Ex. No. | IUPAC NAME | STRUCTURE | ADDITIVE | MS |
|---|---|---|---|---|
| 127 | 4-(2-((2-methoxy-4-(((2S)-2-methyl-morpholin-4-yl)carbonyl)phenyl)amino)pyrimidin-5-yl)-2-(((2S)-1-(1H-1,2,4-triazol-1-yl)propan-2-yl)oxy)benzonitrile | 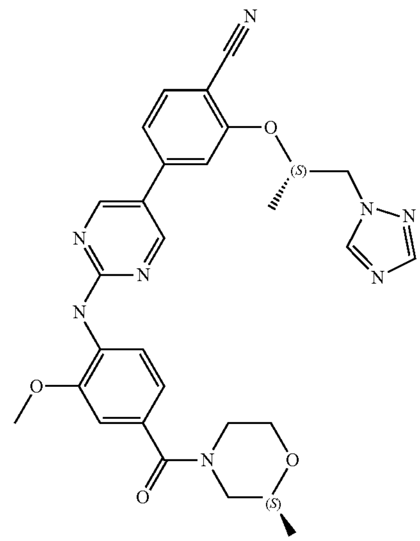 | | 555.4 |
| 128 | 4-(2-((2-methoxy-4-(((3R)-3-methyl-morpholin-4-yl)carbonyl)phenyl)amino)pyrimidin-5-yl)-2-(((2S)-1-(1H-1,2,4-triazol-1-yl)propan-2-yl)oxy)benzonitrile | 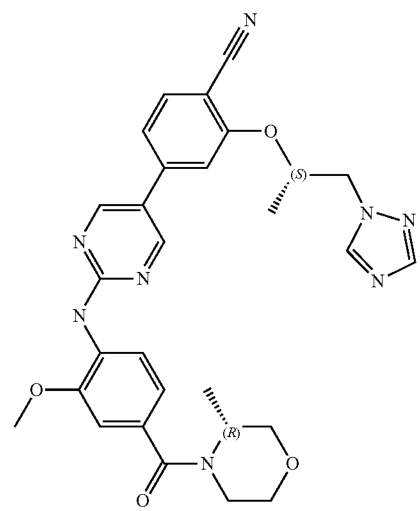 | | 555.4 |
| 129 | 4-(2-((2-methoxy-4-(1,4-oxazepan-4-ylcarbonyl)phenyl)amino)pyrimidin-5-yl)-2-(((2S)-1-(1H-1,2,4-triazol-1-yl)propan-2-yl)oxy)benzonitrile | 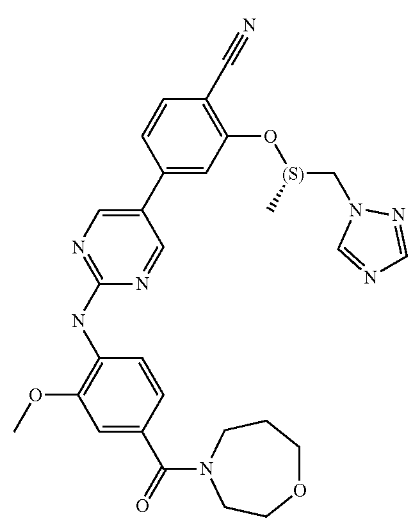 | | 555.4 |

TABLE 1-continued

| Ex. No. | IUPAC NAME | STRUCTURE | ADDITIVE | MS |
|---|---|---|---|---|
| 130 | 4-((5-(4-cyano-3-(((2S)-1-(1H-1,2,4-triazol-1-yl)propan-2-yl)oxy)phenyl)pyrimidin-2-yl)amino)-N-(3,3-difluorocyclobutyl)-3-methoxybenzamide | 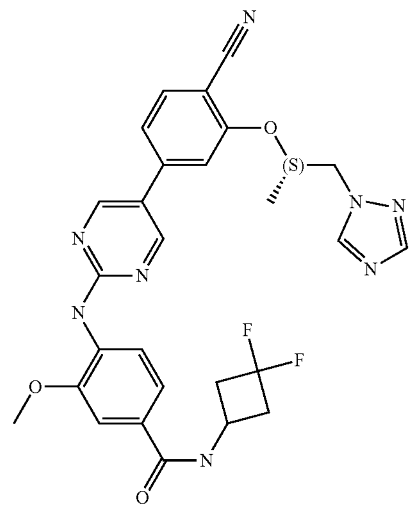 | | 561.3 |
| 131 | 4-(2-((4-((3-(difluoromethyl)azetidin-1-yl)carbonyl)-2-methoxy-phenyl)amino)pyrimidin-5-yl)-2-(((2S)-1-(1H-1,2,4-triazol-1-yl)propan-2-yl)oxy)benzonitrile | 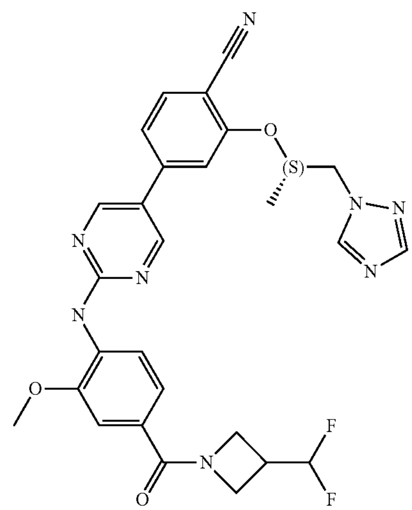 | | 561.4 |
| 132 | 4-((5-(4-cyano-3-(((2S)-1-(1H-1,2,4-triazol-1-yl)propan-2-yl)oxy)phenyl)pyrimidin-2-yl)amino)-3-methoxy-N-methyl-N-(2-(morpholin-4-yl)ethyl)benzamide | 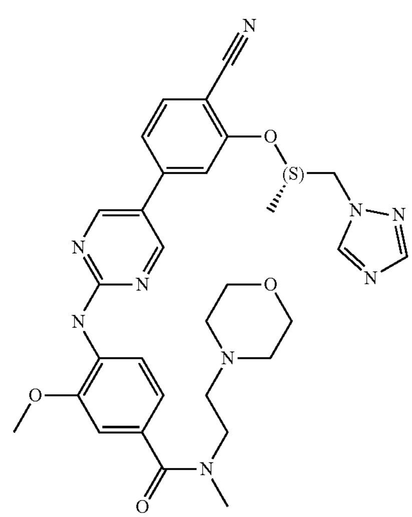 | | 598.4 |

TABLE 1-continued

| Ex. No. | IUPAC NAME | STRUCTURE | ADDITIVE | MS |
|---|---|---|---|---|
| 133 | 4-(2-((2-methoxy-4-(((1R,4R)-5-methyl-2,5-diazabicyclo[2.2.1]hept-2-yl)carbonyl)phenyl)amino)pyrimidin-5-yl)-2-(((2S)-1-(1H-1,2,4-triazol-1-yl)propan-2-yl)oxy)benzonitrile | 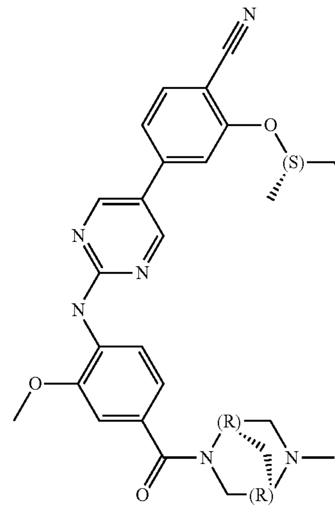 | | 566.4 |
| 134 | 4-(2-((2-methoxy-4-(4-oxa-7-azaspiro[2.5]oct-7-ylcarbonyl)phenyl)amino)pyrimidin-5-yl)-2-(((2S)-1-(1H-1,2,4-triazol-1-yl)propan-2-yl)oxy)benzonitrile | 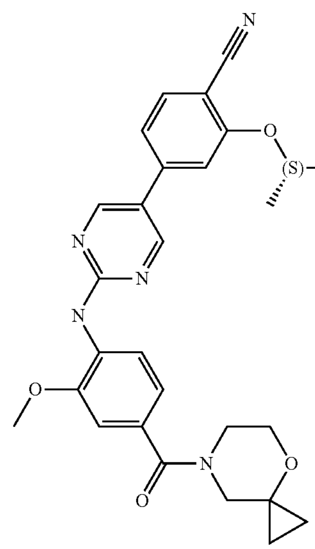 | | 567.3 |
| 135 | 4-(2-((4-((4-(cyclopropylcarbonyl)piperazin-1-yl)carbonyl)-2-methoxyphenyl)amino)pyrimidin-5-yl)-2-(((2S)-1-(1H-1,2,4-triazol-1-yl)propan-2-yl)oxy)benzonitrile | 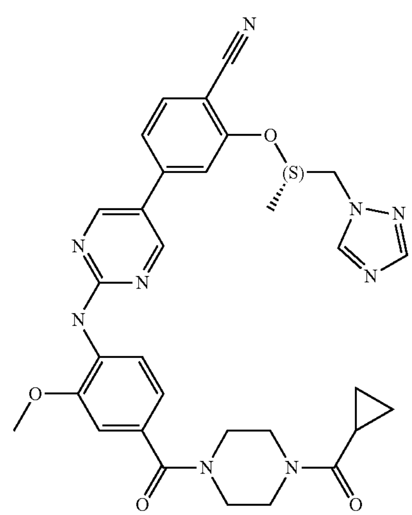 | | 608.3 |

TABLE 1-continued

| Ex. No. | IUPAC NAME | STRUCTURE | ADDITIVE | MS |
|---|---|---|---|---|
| 136 | N-((1-acetylpiperidin-4-yl)methyl)-4-((5-(4-cyano-3-(((2S)-1-(1H-1,2,4-triazol-1-yl)propan-2-yl)oxy)phenyl)pyrimidin-2-yl)amino)-3-methoxybenzamide | 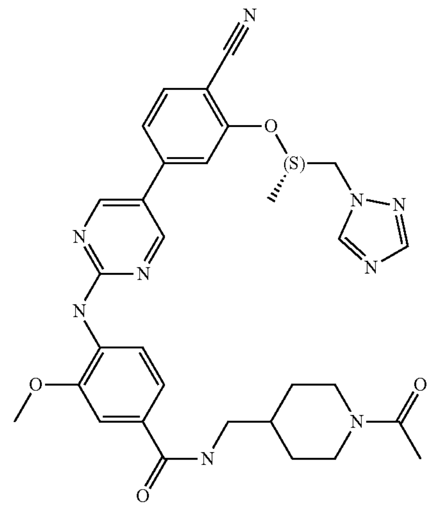 | | 610.4 |
| 137 | 4-(2-((4-((2,2-difluoromorpholin-4-yl)carbonyl)-2-methoxy-phenyl)amino)pyrimidin-5-yl)-2-(((2S)-1-(1H-1,2,4-triazol-1-yl)propan-2-yl)oxy)benzonitrile | 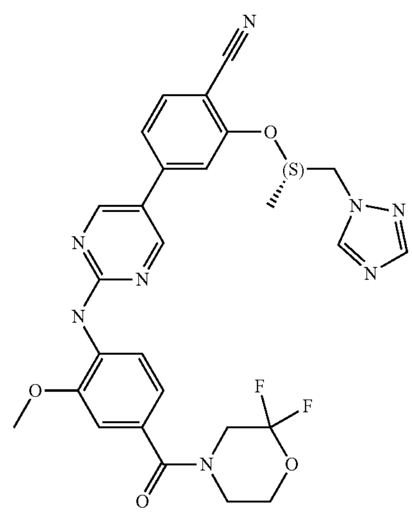 | | 577.3 |
| 138 | 4-((5-(4-cyano-3-(((2S)-1-(1H-1,2,4-triazol-1-yl)propan-2-yl)oxy)phenyl)pyrimidin-2-yl)amino)-3-methoxy-N-(2-(trifluoromethyl)cyclopropyl)benzamide | 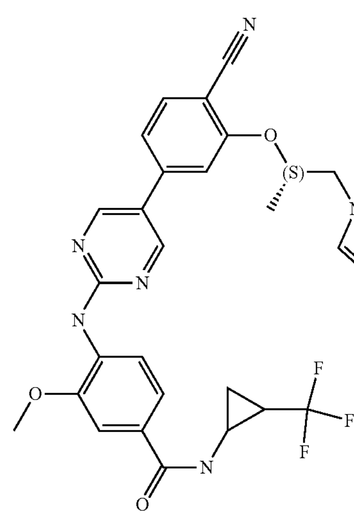 | | 579.3 |

TABLE 1-continued

| Ex. No. | IUPAC NAME | STRUCTURE | ADDITIVE | MS |
|---|---|---|---|---|
| 139 | 4-(2-((2-methoxy-4-((4-(methylsulfonyl)piperazin-1-yl)carbonyl)phenyl)amino)pyrimidin-5-yl)-2-(((2S)-1-(1H-1,2,4-triazol-1-yl)propan-2-yl)oxy)benzonitrile | 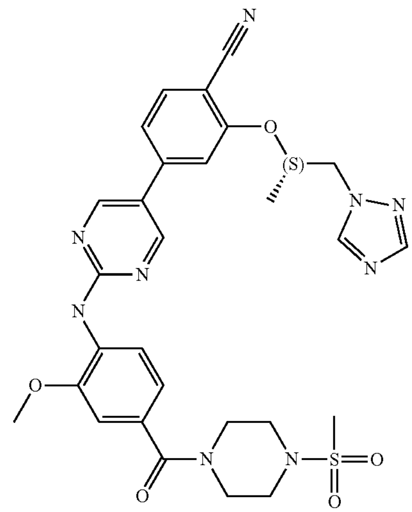 | | 618.4 |
| 140 | 4-((5-(4-cyano-3-(((2S)-1-(1H-1,2,4-triazol-1-yl)propan-2-yl)oxy)phenyl)pyrimidin-2-yl)amino)-3-methoxy-N-(2-(trifluoromethoxy)ethyl)benzamide | 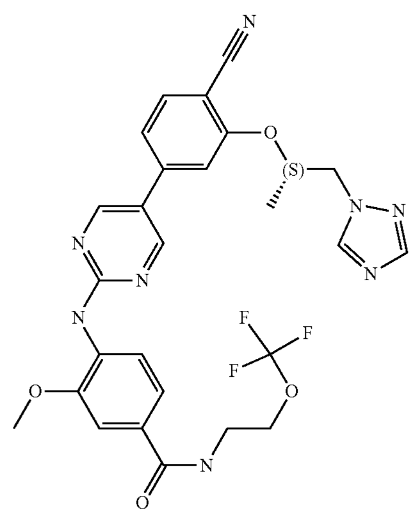 | | 583.3 |
| 141 | 4-((5-(4-cyano-3-(((2S)-1-(1H-1,2,4-triazol-1-yl)propan-2-yl)oxy)phenyl)pyrimidin-2-yl)amino)-N-(1,1,1,3,3,3-hexafluoropropan-2-yl)-3-methoxybenzamide | 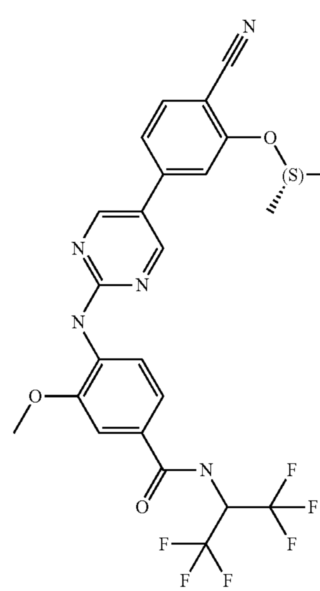 | | 621.4 |

TABLE 1-continued

| Ex. No. | IUPAC NAME | STRUCTURE | ADDITIVE | MS |
|---|---|---|---|---|
| 142 | 4-(2-((4-(1,4'-bipiperidine-1'-ylcarbonyl)-2-methoxyphenyl)amino)pyrimidin-5-yl)-2-(((2S)-1-(1H-1,2,4-triazol-1-yl)propan-2-yl)oxy)benzonitrile | 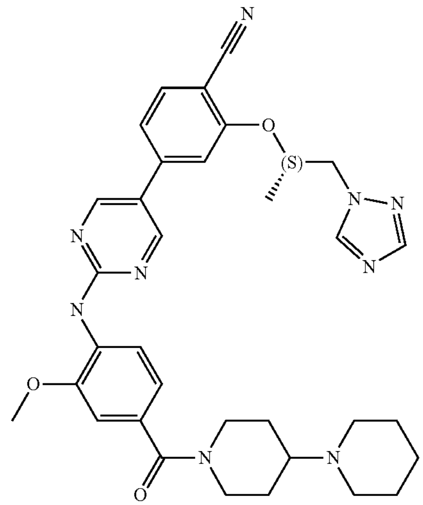 | | 622.4 |
| 143 | 4-((5-(4-cyano-3-(((2S)-1-(1H-1,2,4-triazol-1-yl)propan-2-yl)oxy)phenyl)pyrimidin-2-yl)amino)-3-methoxy-N,N-bis(2,2,2-trifluoroethyl)benzamide | 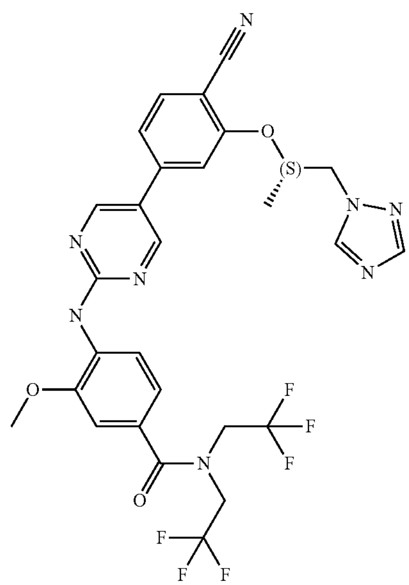 | | 635.4 |
| 144 | 4-((5-(4-cyano-3-(((2S)-1-(1H-1,2,4-triazol-1-yl)propan-2-yl)oxy)phenyl)pyrimidin-2-yl)amino)-3-methoxy-N-(1-(2,2,2-trifluoroethyl)piperidin-4-yl)benzamide | 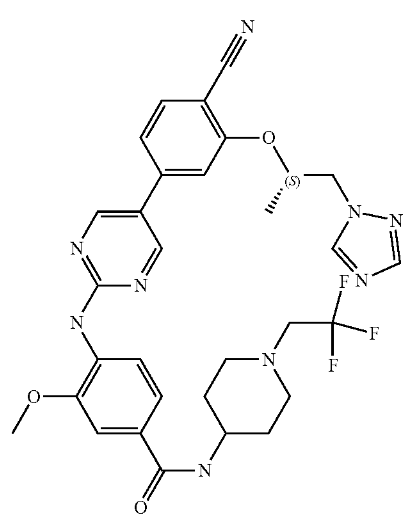 | | 636.5 |

TABLE 1-continued

| Ex. No. | IUPAC NAME | STRUCTURE | ADDITIVE | MS |
|---|---|---|---|---|
| 145 | 4-(2-((2-methoxy-4-((4-(1-methylpiperidin-4-yl)piperazin-1-yl)carbonyl)phenyl)amino)pyrimidin-5-yl)-2-(((2S)-1-(1H-1,2,4-triazol-1-yl)propan-2-yl)oxy)benzonitrile | 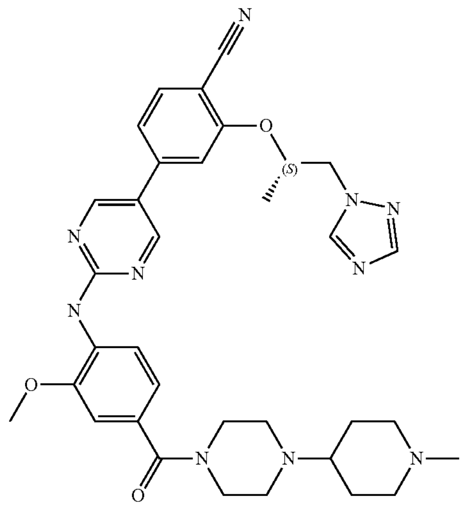 | | 637.5 |
| 146 | 4-(2-((2-methoxy-4-((4-(4-methylpiperazin-1-yl)piperidin-1-yl)carbonyl)phenyl)amino)pyrimidin-5-yl)-2-(((2S)-1-(1H-1,2,4-triazol-1-yl)propan-2-yl)oxy)benzonitrile | 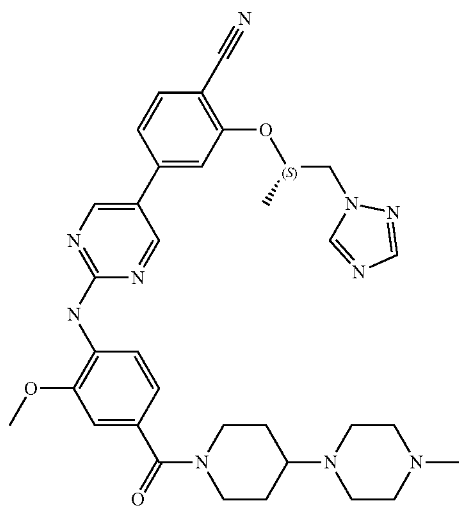 | | 637.5 |
| 147 | 4-(2-((2-methoxy-4-((6-methyl-2,6-diazaspiro[3.3]hept-2-yl)carbonyl)phenyl)amino)pyrimidin-5-yl)-2-(((2S)-1-(1H-1,2,4-triazol-1-yl)propan-2-yl)oxy)benzonitrile | 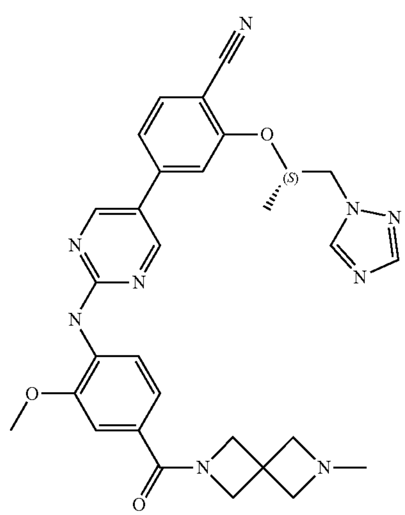 | | 566.4 |

TABLE 1-continued

| Ex. No. | IUPAC NAME | STRUCTURE | ADDITIVE | MS |
|---|---|---|---|---|
| 148 | 4-(2-((2-methoxy-4-(2-oxa-6-azaspiro[3.3]hept-6-ylcarbonyl)phenyl)amino)pyrimidin-5-yl)-2-(((2S)-1-(1H-1,2,4-triazol-1-yl)propan-2-yl)oxy)benzonitrile | 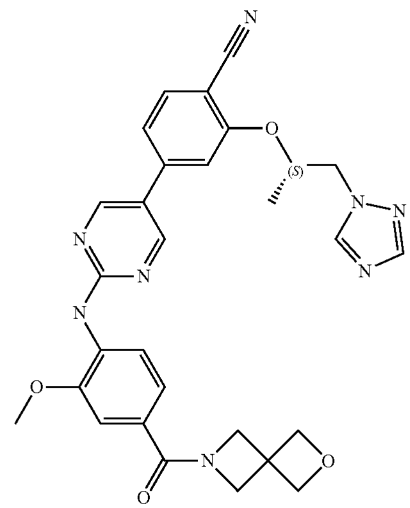 | | 553.3 |
| 149 | 4-(2-((4-((4-cyclopropylpiperazin-1-yl)carbonyl)-2-methoxyphenyl)amino)pyrimidin-5-yl)-2-(((2S)-1-(1H-1,2,4-triazol-1-yl)propan-2-yl)oxy)benzonitrile | 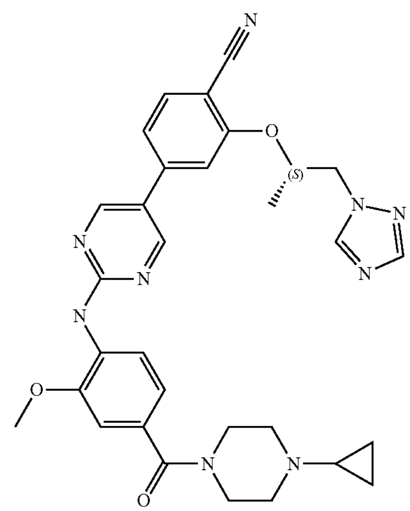 | | 580.4 |
| 150 | 4-(2-((2-methoxy-4-((8-methyl-3,8-diazabicyclo[3.2.1]oct-3-yl)carbonyl)phenyl)amino)pyrimidin-5-yl)-2-(((2S)-1-(1H-1,2,4-triazol-1-yl)propan-2-yl)oxy)benzonitrile | 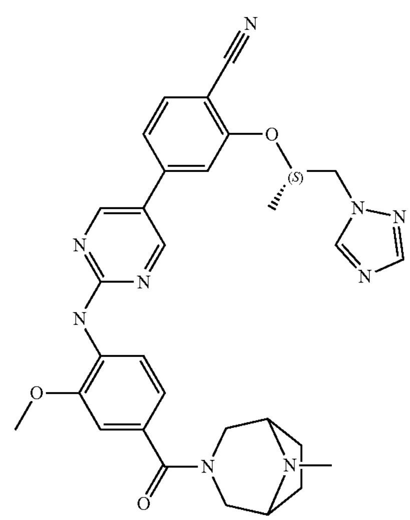 | | 580.4 |

TABLE 1-continued

| Ex. No. | IUPAC NAME | STRUCTURE | ADDITIVE | MS |
|---|---|---|---|---|
| 152 | 4-(2-((2-methoxy-4-((4-methoxypiperidin-1-yl)carbonyl)phenyl)amino)pyrimidin-5-yl)-2-(((2S)-1-(1H-tetrazol-1-yl)propan-2-yl)oxy)benzonitrile | 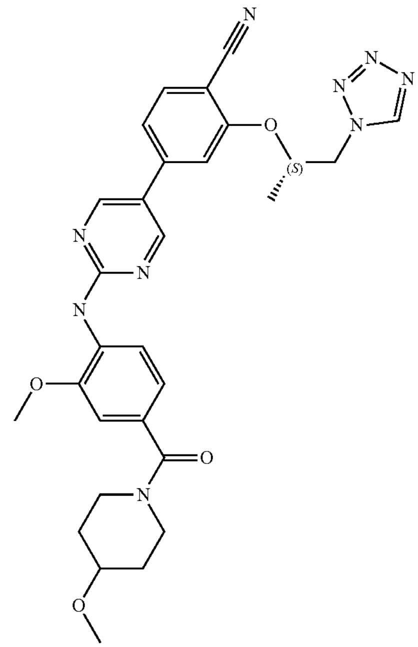 | | 570.4 |
| 153 | 4-((5-(4-cyano-3-(((2S)-1-(1H-tetrazol-1-yl)propan-2-yl)oxy)phenyl)pyrimidin-2-yl)amino)-N,N-diethyl-3-methoxybenzamide | 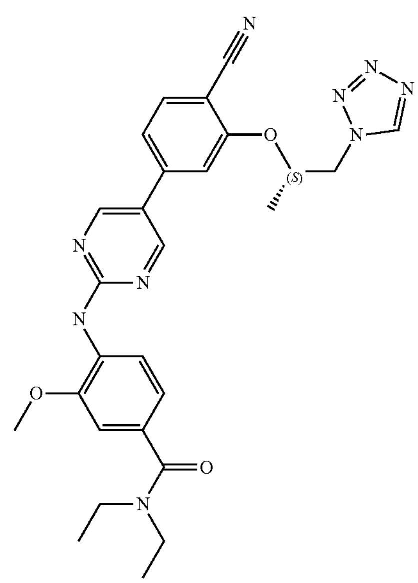 | | 526.1 |

TABLE 1-continued

| Ex. No. | IUPAC NAME | STRUCTURE | ADDITIVE | MS |
|---|---|---|---|---|
| 154 | 4-(2-((2-methoxy-4-((4-(morpholin-4-yl)piperidin-1-yl)carbonyl)phenyl)amino)pyrimidin-5-yl)-2-(((2S)-1-(1H-tetrazol-1-yl)propan-2-yl)oxy)benzonitrile | 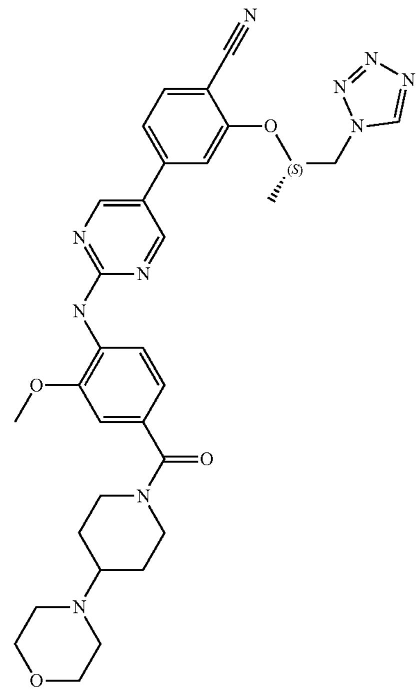 | | 625.4 |
| 155 | N-(2-methoxy-4-(4-(morpholin-4-yl)piperidin-1-yl)phenyl)-5-(3-(((2S)-1-(1H-tetrazol-1-yl)propan-2-yl)oxy)-4-(trifluoromethyl)phenyl)pyrimidin-2-amine | 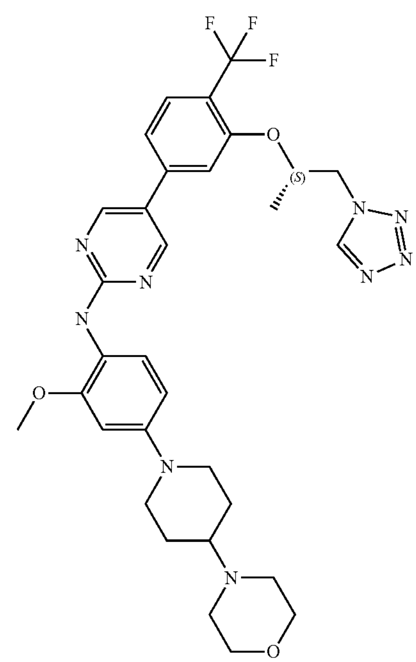 | | 640.4 |

| Ex. No. | IUPAC NAME | STRUCTURE | ADDITIVE | MS |
|---|---|---|---|---|
| 156 | (3-methoxy-4-((5-(3-(((2S)-1-(1H-tetrazol-1-yl)propan-2-yl)oxy)-4-(trifluoromethyl)phenyl)pyrimidin-2-yl)amino)phenyl)(morpholin-4-yl)methanone | 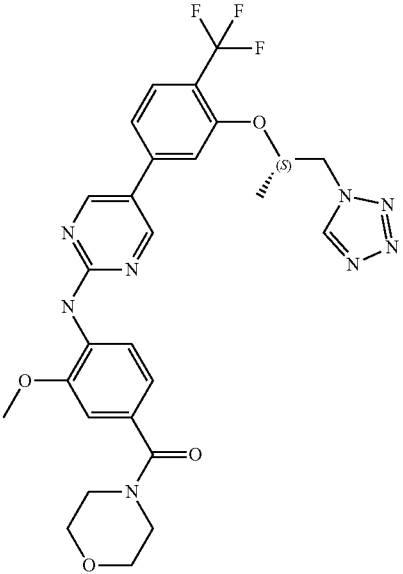 | | 583.1 |
| 157 | N-(2-methoxy-4-(4-(morpholin-4-yl)piperidin-1-yl)phenyl)-5-(4-methyl-3-(((2S)-1-(1H-tetrazol-1-yl)propan-2-yl)oxy)phenyl)pyrimidin-2-amine | 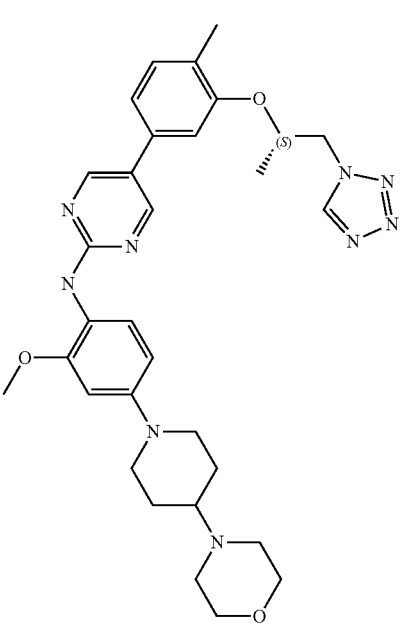 | | 586.4 |

TABLE 1-continued

| Ex. No. | IUPAC NAME | STRUCTURE | ADDITIVE | MS |
|---|---|---|---|---|
| 158 | (3-methoxy-4-((5-(4-methyl-3-(((2S)-1-(1H-tetrazol-1-yl)propan-2-yl)oxy)phenyl)pyrimidin-2-yl)amino)phenyl)(morpholin-4-yl)methanone | 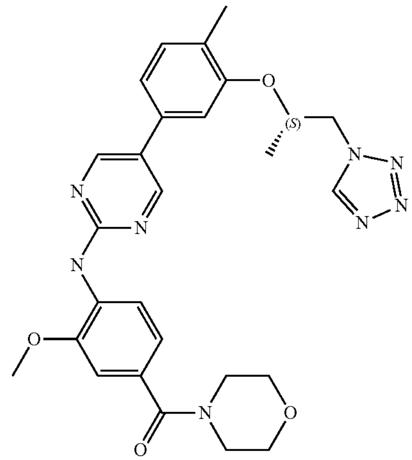 | | 529.1 |
| 159 | 4-(2-((2-methoxy-4-(1-(2,2,2-trifluoroethyl)piperidin-4-yl)phenyl)amino)pyrimidin-5-yl)-2-(((2S)-1-(1H-tetrazol-1-yl)propan-2-yl)oxy)benzonitrile | 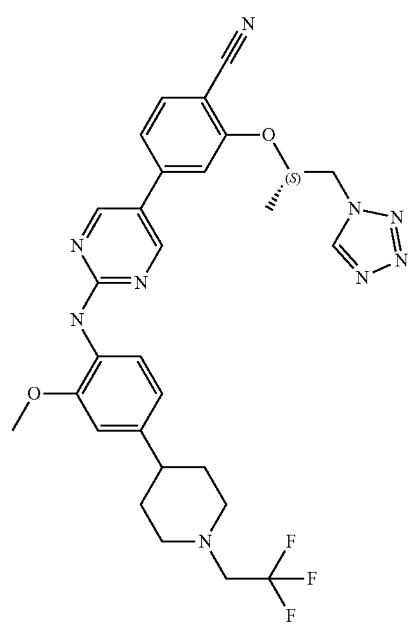 | | 594.3 |

TABLE 1-continued

| Ex. No. | IUPAC NAME | STRUCTURE | ADDITIVE | MS |
|---|---|---|---|---|
| 160 | 4-(2-((4-(1-(2-hydroxyethyl)piperidin-4-yl)-2-methoxyphenyl)amino)pyrimidin-5-yl)-2-(((2S)-1-(1H-tetrazol-1-yl)propan-2-yl)oxy)benzonitrile | 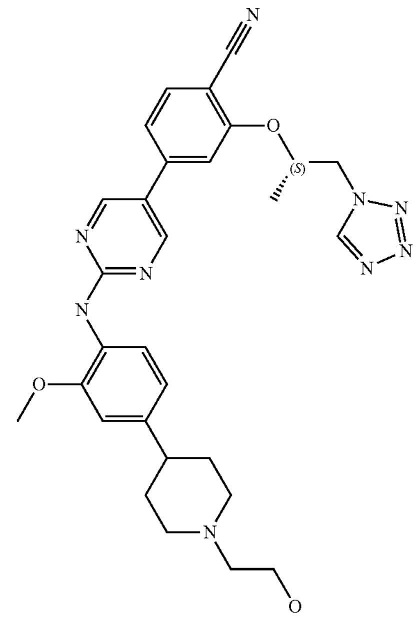 | | 556.4 |
| 162 | 4-(2-((4-((3-(hydroxymethyl)azetidin-1-yl)carbonyl)-2-methoxyphenyl)amino)pyrimidin-5-yl)-2-(((2S)-1-(1H-tetrazol-1-yl)propan-2-yl)oxy)benzonitrile | 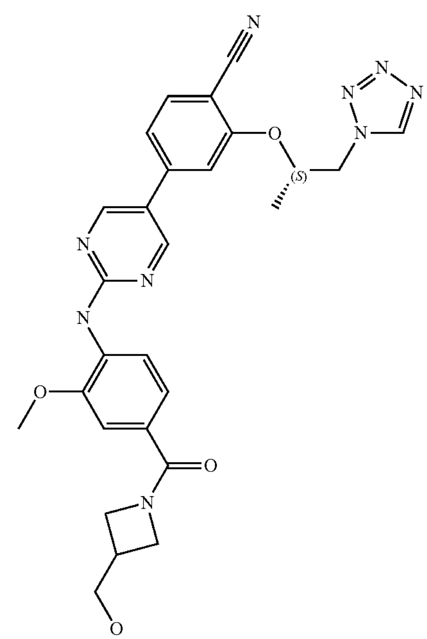 | | 540.2 |

TABLE 1-continued

| Ex. No. | IUPAC NAME | STRUCTURE | ADDITIVE | MS |
|---|---|---|---|---|
| 163 | 4-(2-((2-methoxy-6-(4-(morpholin-4-yl)piperidin-1-yl)pyridin-3-yl)amino)pyrimidin-5-yl)-2-(((2S)-1-(1H-1,2,4-triazol-1-yl)propan-2-yl)oxy)benzonitrile | 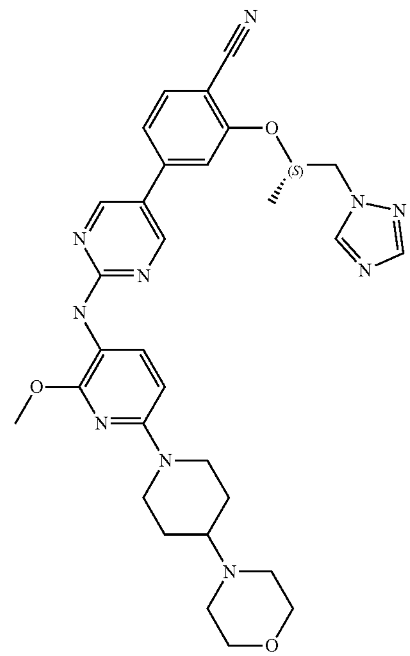 | | 597.4 |
| 164 | 4-(2-((4-(4-(morpholin-4-yl)piperidin-1-yl)phenyl)amino)pyrimidin-5-yl)-2-(((2S)-1-(1H-tetrazol-1-yl)propan-2-yl)oxy)benzonitrile | 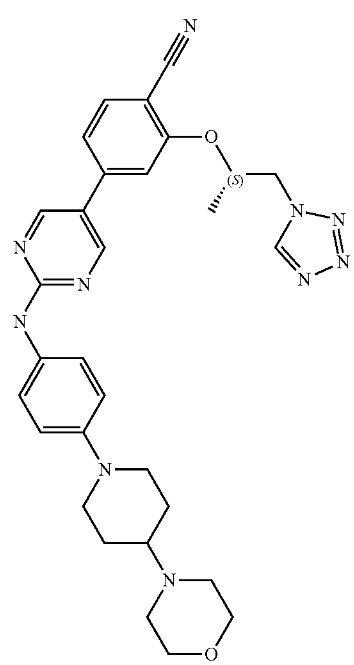 | | 567.4 |

TABLE 1-continued

| Ex. No. | IUPAC NAME | STRUCTURE | ADDITIVE | MS |
|---|---|---|---|---|
| 165 | 4-(2-((2-methoxy-6-(4-(morpholin-4-yl)piperidin-1-yl)pyridin-3-yl)amino)pyrimidin-5-yl)-2-(((2S)-1-(1H-tetrazol-1-yl)propan-2-yl)oxy)benzonitrile | 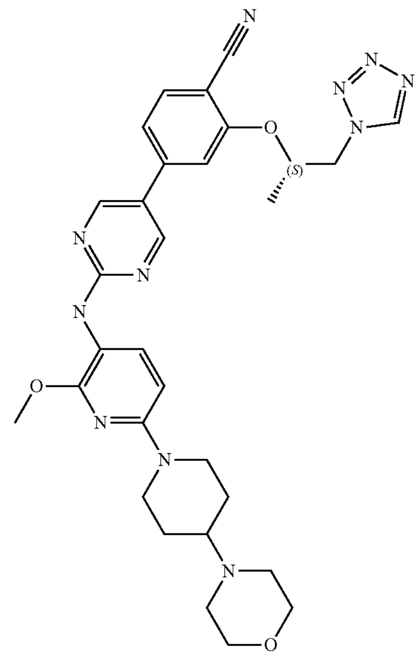 | | 598.4 |
| 166 | 4-(2-((2-methoxy-4-(4-(morpholin-4-yl)piperidin-1-yl)phenyl)amino)pyrimidin-5-yl)-2-(((2S)-1-(5-methyl-1H-tetrazol-1-yl)propan-2-yl)oxy)benzonitrile | 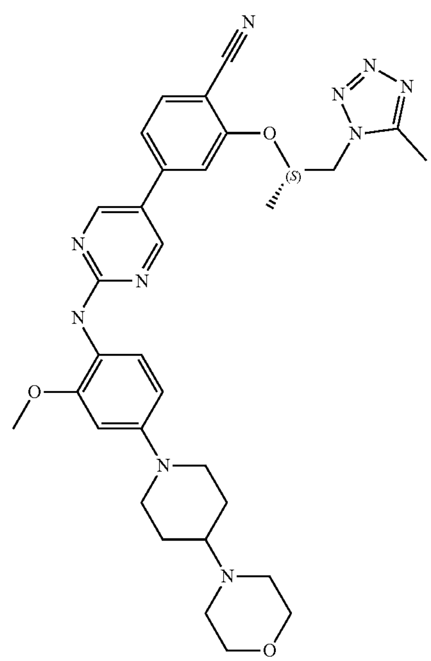 | | 611.4 |

TABLE 1-continued

| Ex. No. | IUPAC NAME | STRUCTURE | ADDITIVE | MS |
|---|---|---|---|---|
| 167 | 4-(2-((2-methoxy-4-(4-(morpholin-4-yl)piperidin-1-yl)phenyl)amino)pyrimidin-5-yl)-2-(((2S)-1-(5-methyl-2H-tetrazol-2-yl)propan-2-yl)oxy)benzonitrile | 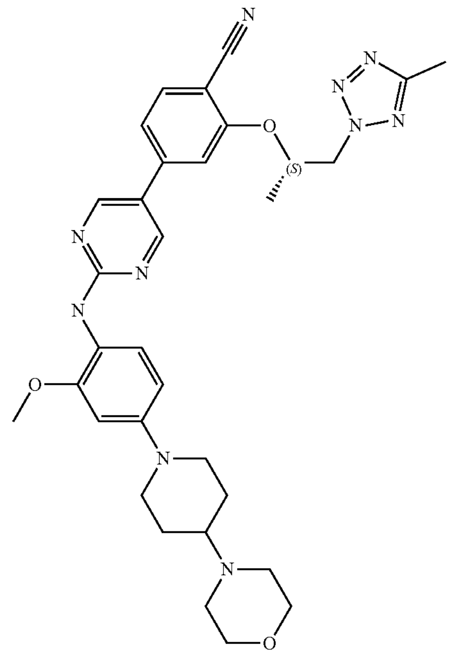 | | 611.4 |
| 169 | 4-(2-((5-fluoro-2-methoxy-4-(4-(morpholin-4-yl)piperidin-1-yl)phenyl)amino)pyrimidin-5-yl)-2-(((2S)-1-(1H-tetrazol-1-yl)propan-2-yl)oxy)benzonitrile | 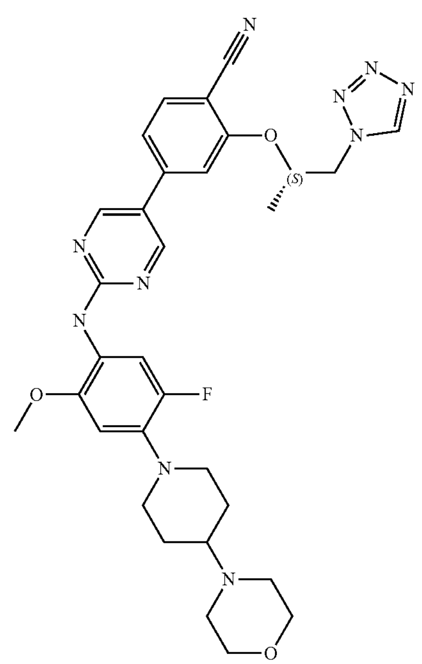 | | 615.4 |

TABLE 1-continued

| Ex. No. | IUPAC NAME | STRUCTURE | ADDITIVE | MS |
|---|---|---|---|---|
| 170 | 4-(2-((4-(4-(morpholin-4-yl)piperidin-1-yl)-2-(2,2,2-trifluoroethoxy)phenyl)amino)pyrimidin-5-yl)-2-(((2S)-1-(1H-tetrazol-1-yl)propan-2-yl)oxy)benzonitrile | 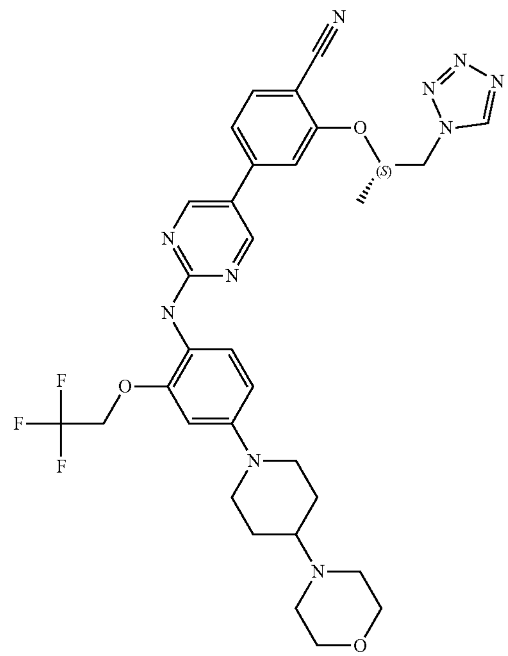 | | 665.4 |
| 171 | 4-((5-(4-cyano-3-(((2S)-1-(1H-tetrazol-1-yl)propan-2-yl)oxy)phenyl)pyrimidin-2-yl)amino)-3-methoxy-N-(2-(trifluoromethoxy)ethyl)benzamide | 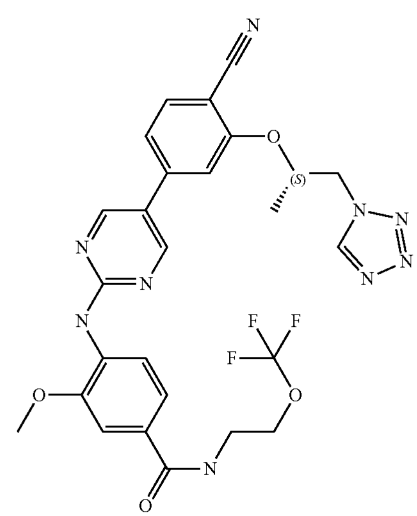 | | 584.3 |

TABLE 1-continued

| Ex. No. | IUPAC NAME | STRUCTURE | ADDITIVE | MS |
|---|---|---|---|---|
| 172 | 4-(2-((2-methoxy-4-((6-methyl-2,6-diazaspiro[3.3]hept-2-yl)carbonyl)phenyl)amino)pyrimidin-5-yl)-2-(((2S)-1-(1H-tetrazol-1-yl)propan-2-yl)oxy)benzonitrile | 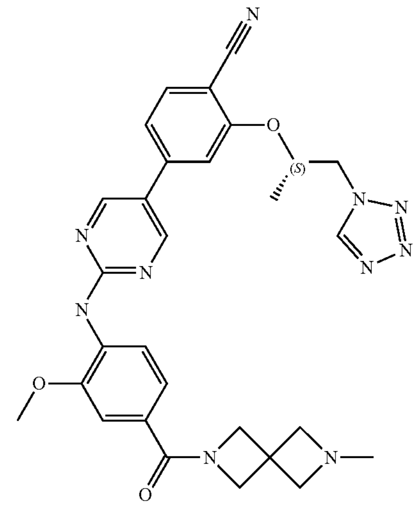 | | 565.1 |
| 173 | 4-(2-((4-((3-hydroxyazetidin-1-yl)carbonyl)-2-methoxyphenyl)amino)pyrimidin-5-yl)-2-(((2S)-1-(1H-tetrazol-1-yl)propan-2-yl)oxy)benzonitrile | 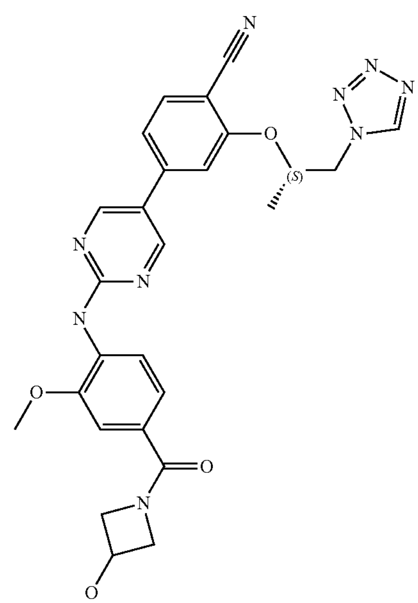 | | 526.1 |

TABLE 1-continued

| Ex. No. | IUPAC NAME | STRUCTURE | ADDITIVE | MS |
|---|---|---|---|---|
| 174 | 4-(2-((2-methoxy-4-((3-methoxyazetidin-1-yl)carbonyl)phenyl)amino)pyrimidin-5-yl)-2-(((2S)-1-(1H-tetrazol-1-yl)propan-2-yl)oxy)benzonitrile | 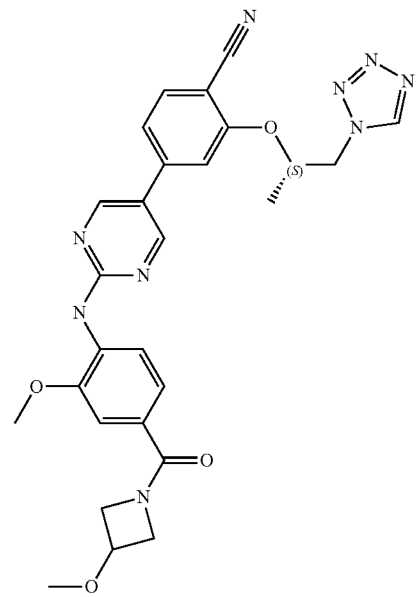 | | 540.1 |
| 175 | (4-(2-((2-methoxy-4-(4-(morpholin-4-yl)piperidin-1-yl)phenyl)amino)pyrimidin-5-yl)-2-(((2S)-1-(1H-tetrazol-1-yl)propan-2-yl)oxy)phenyl)(pyrrolidin-1-yl)methanone | 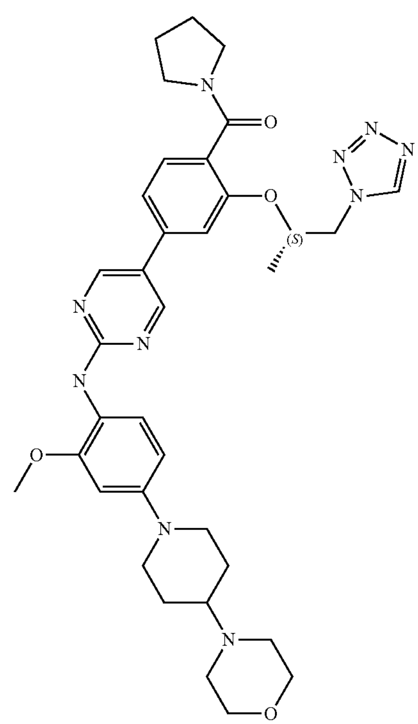 | | 669.6 |

TABLE 1-continued

| Ex. No. | IUPAC NAME | STRUCTURE | ADDITIVE | MS |
|---|---|---|---|---|
| 176 | tert-butyl 6-(4-((5-(4-cyano-3-(((2S)-1-(1H-tetrazol-1-yl)propan-2-yl)oxy)phenyl)pyrimidin-2-yl)amino)-3-methoxybenzoyl)-2,6-diazaspiro[3.3]heptane-2-carboxylate | 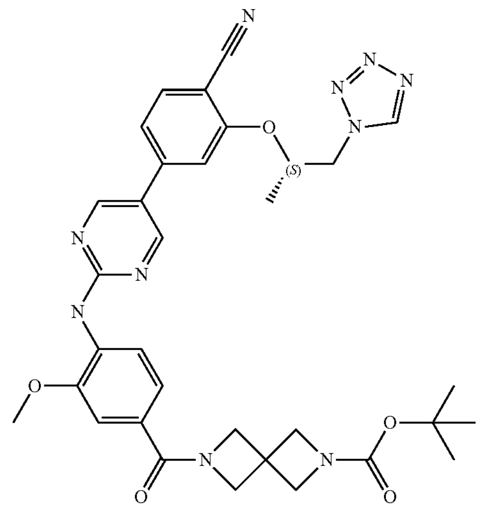 | | 653.5 |
| 177 | 4-(2-((2-methoxy-4-((6-(methoxyacetyl)-2,6-diazaspiro[3.3]hept-2-yl)carbonyl)phenyl)amino)pyrimidin-5-yl)-2-(((2S)-1-(1H-tetrazol-1-yl)propan-2-yl)oxy)benzonitrile | 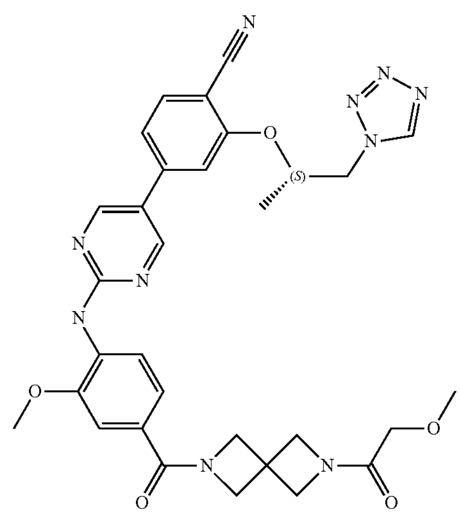 | | 625.4 |
| 178 | 4-(2-((4-((6-glycoloyl-2,6-diazaspiro[3.3]hept-2-yl)carbonyl)-2-methoxyphenyl)amino)pyrimidin-5-yl)-2-(((2S)-1-(1H-tetrazol-1-yl)propan-2-yl)oxy)benzonitrile | 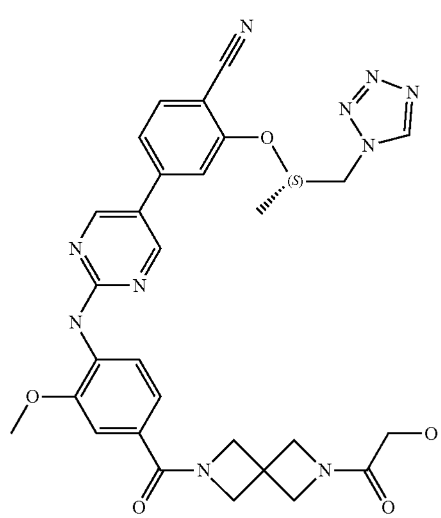 | | 611.3 |

| Ex. No. | IUPAC NAME | STRUCTURE | ADDITIVE | MS |
|---|---|---|---|---|
| 179 | 4-(2-((2-methoxy-4-((6-(oxetan-3-yl)-2,6-diazaspiro[3.3]hept-2-yl)carbonyl)phenyl)amino)pyrimidin-5-yl)-2-(((2S)-1-(1H-tetrazol-1-yl)propan-2-yl)oxy)benzonitrile | 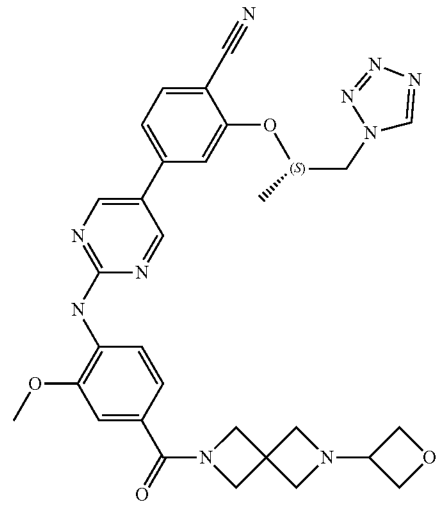 | | 609.4 |
| 180 | 4-(2-((4-(2,6-diazaspiro[3.3]hept-2-ylcarbonyl)-2-methoxyphenyl)amino)pyrimidin-5-yl)-2-(((2S)-1-(1H-tetrazol-1-yl)propan-2-yl)oxy)benzonitrile | 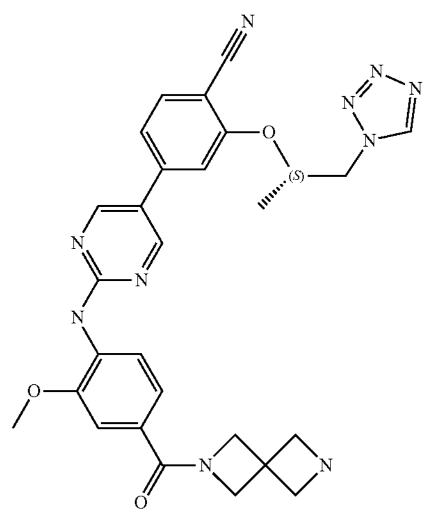 | | 553.3 |

TABLE 1-continued

| Ex. No. | IUPAC NAME | STRUCTURE | ADDITIVE | MS |
|---|---|---|---|---|
| 181 | 5-(4-fluoro-3-(((2S)-1-(1H-tetrazol-1-yl)propan-2-yl)oxy)phenyl)-N-(2-methoxy-4-(4-(morpholin-4-yl)piperidin-1-yl)phenyl)pyrimidin-2-amine | 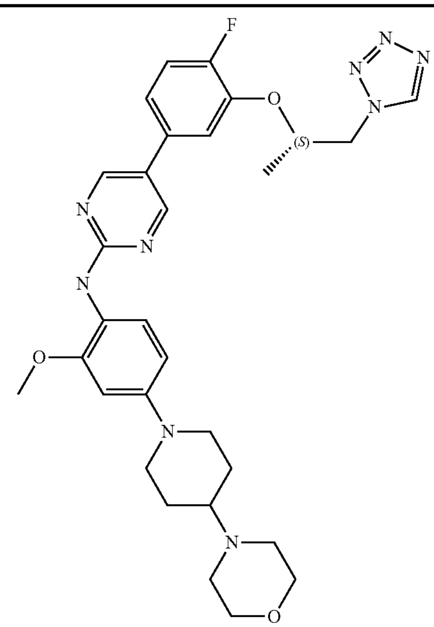 | | 590.4 |
| 182 | (4-((5-(4-fluoro-3-(((2S)-1-(1H-tetrazol-1-yl)propan-2-yl)oxy)phenyl)pyrimidin-2-yl)amino)-3-methoxyphenyl)(morpholin-4-yl)methanone | 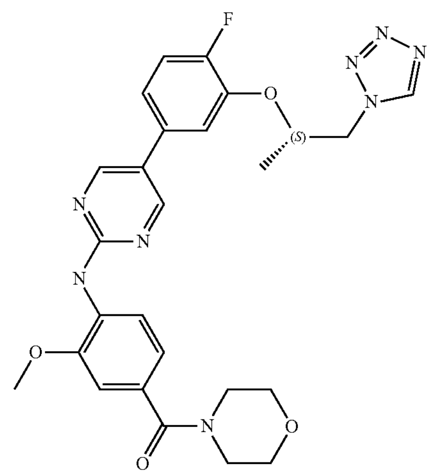 | | 535.3 |
| 183 | 4-(2-((2-methoxy-4-(2-oxa-6-azaspiro[3.3]hept-6-ylcarbonyl)phenyl)amino)pyrimidin-5-yl)-2-(((2S)-1-(1H-tetrazol-1-yl)propan-2-yl)oxy)benzonitrile | 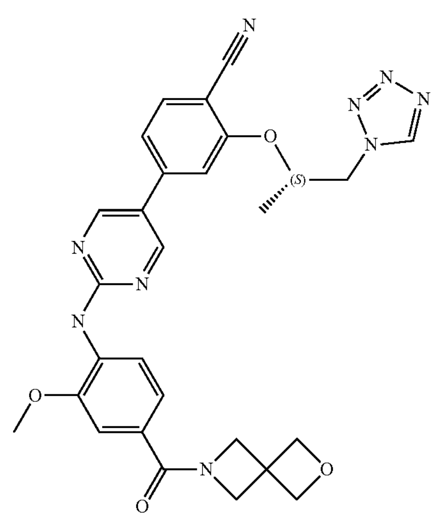 | | 552.2 |

TABLE 1-continued

| Ex. No. | IUPAC NAME | STRUCTURE | ADDITIVE | MS |
|---|---|---|---|---|
| 184 | 4-(2-((4-((3-hydroxypiperidin-1-yl)carbonyl)-2-methoxyphenyl)amino)pyrimidin-5-yl)-2-(((2S)-1-(1H-tetrazol-1-yl)propan-2-yl)oxy)benzonitrile | 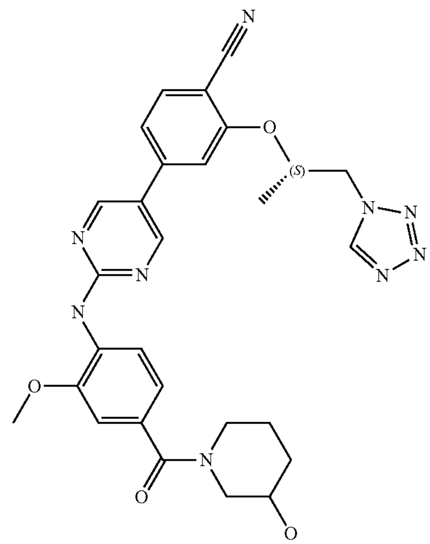 | | 556.4 |
| 185 | 1-(4-((5-(4-cyano-3-(((2S)-1-(1H-tetrazol-1-yl)propan-2-yl)oxy)phenyl)pyrimidin-2-yl)amino)-3-methoxybenzoyl)azetidine-3-carbonitrile | 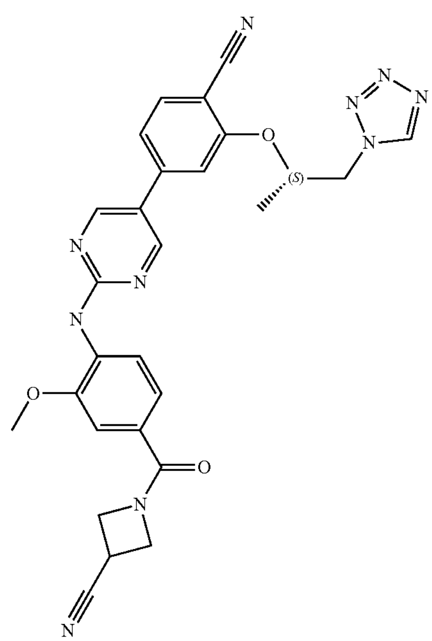 | | 537.3 |

| Ex. No. | IUPAC NAME | STRUCTURE | ADDITIVE | MS |
|---|---|---|---|---|
| 186 | 4-(2-((4-(2,7-diazaspiro[3.5]non-7-ylcarbonyl)-2-methoxyphenyl)amino)pyrimidin-5-yl)-2-(((2S)-1-(1H-tetrazol-1-yl)propan-2-yl)oxy)benzonitrile | 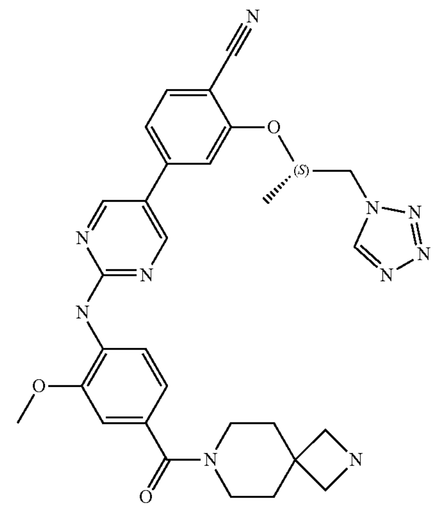 | | 581.4 |
| 187 | 4-(2-((4-((3-(difluoromethyl)azetidin-1-yl)carbonyl)-2-methoxyphenyl)amino)pyrimidin-5-yl)-2-(((2S)-1-(1H-tetrazol-1-yl)propan-2-yl)oxy)benzonitrile | 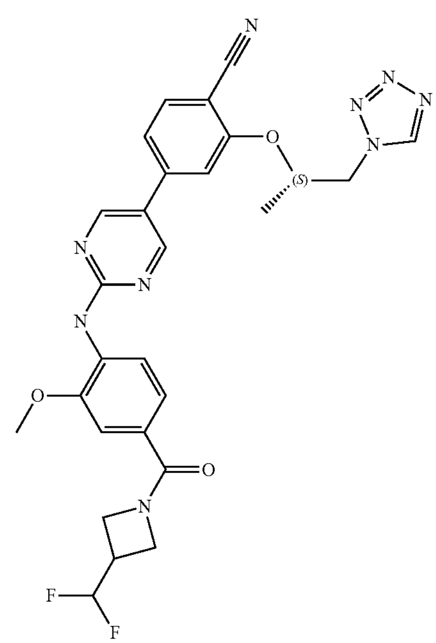 | | 560.1 |

| Ex. No. | IUPAC NAME | STRUCTURE | ADDITIVE | MS |
|---|---|---|---|---|
| 188 | tert-butyl 7-(4-((5-(4-cyano-3-(((2S)-1-(1H-tetrazol-1-yl)propan-2-yl)oxy)phenyl)pyrimidin-2-yl)amino)-3-methoxybenzoyl)-2,7-diazaspiro[3.5]nonane-2-carboxylate | 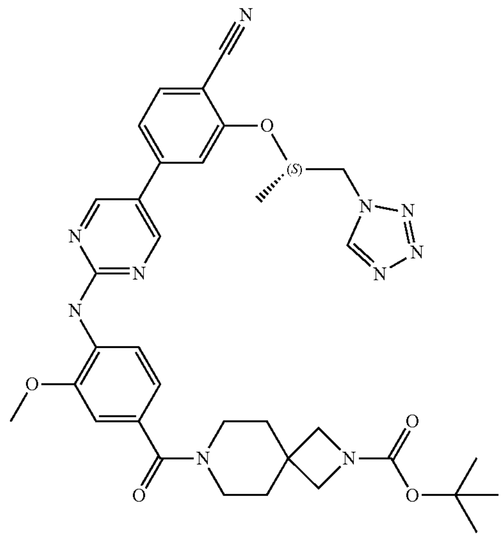 | | 679.3 |
| 189 | 4-(2-((4-((3-(difluoromethoxy)azetidin-1-yl)carbonyl)-2-methoxyphenyl)amino)pyrimidin-5-yl)-2-(((2S)-1-(1H-tetrazol-1-yl)propan-2-yl)oxy)benzonitrile | 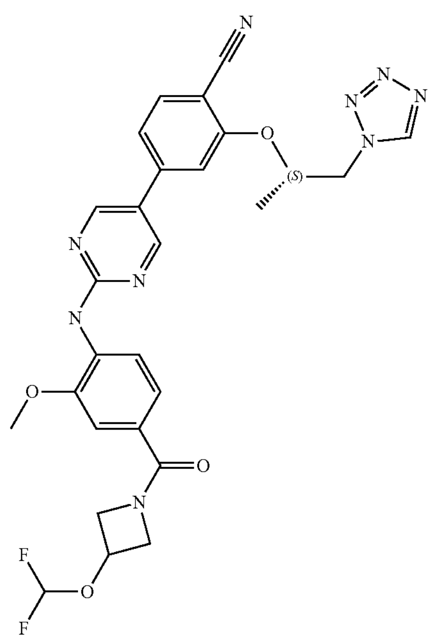 | | 576.1 |

TABLE 1-continued

| Ex. No. | IUPAC NAME | STRUCTURE | ADDITIVE | MS |
|---|---|---|---|---|
| 190 | 4-(2-((2-methoxy-4-(4-(morpholin-4-yl)piperidin-1-yl)phenyl)amino)pyrimidin-5-yl)-N,N-dimethyl-2-(((2S)-1-(1H-tetrazol-1-yl)propan-2-yl)oxy)benzamide | 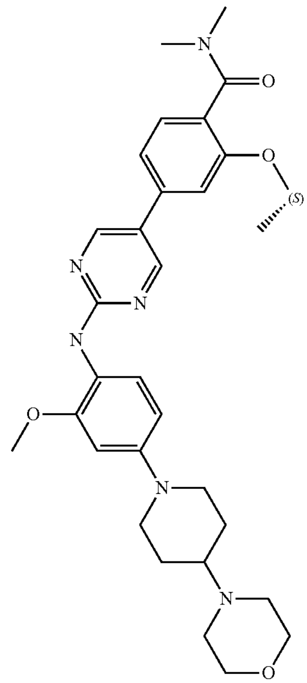 | | 643.4 |
| 191 | 4-(2-((2-methoxy-4-((6-(2-methoxyethyl)-2,6-diazaspiro[3.3]hept-2-yl)carbonyl)phenyl)amino)pyrimidin-5-yl)-2-(((2S)-1-(1H-tetrazol-1-yl)propan-2-yl)oxy)benzonitrile | 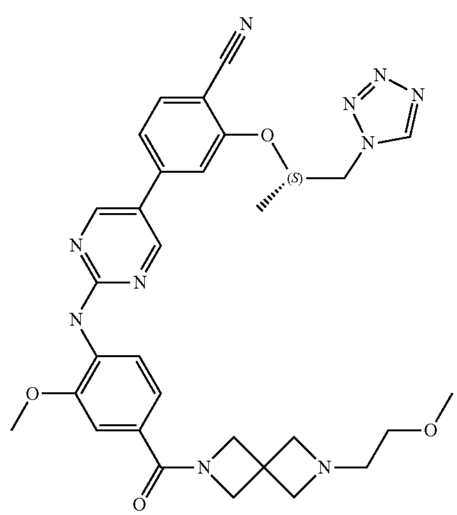 | | 611.3 |

TABLE 1-continued

| Ex. No. | IUPAC NAME | STRUCTURE | ADDITIVE | MS |
|---|---|---|---|---|
| 192 | 4-(2-((2-methoxy-4-(4-(oxetan-3-yl)piperazin-1-yl)phenyl)amino)pyrimidin-5-yl)-2-(((2S)-1-(1H-tetrazol-1-yl)propan-2-yl)oxy)benzonitrile | 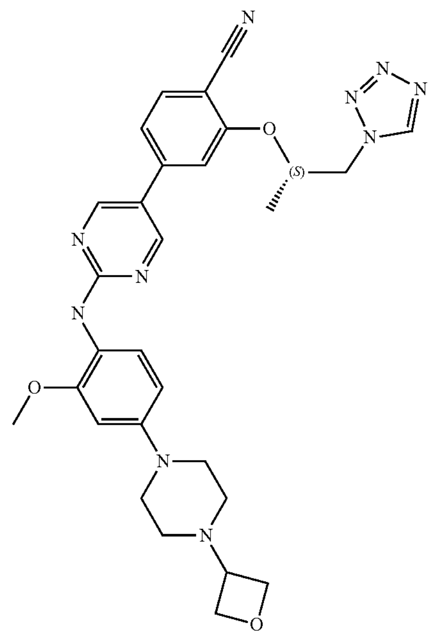 | | 569.4 |
| 193 | (4-((5-(4-chloro-3-(((2S)-1-(1H-tetrazol-1-yl)propan-2-yl)oxy)phenyl)pyrimidin-2-yl)amino)-3-methoxyphenyl)(morpholin-4-yl)methanone | 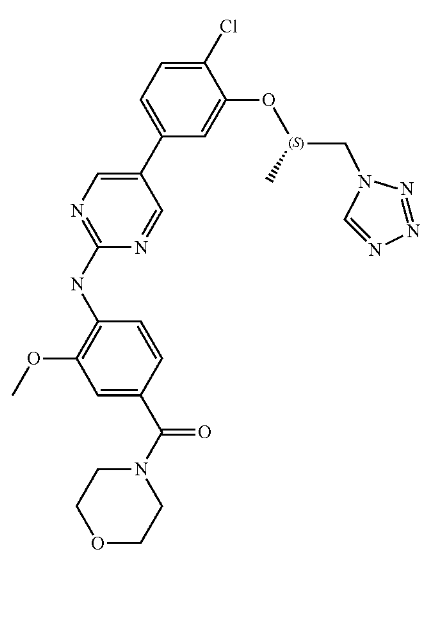 | | 551.3 |

| Ex. No. | IUPAC NAME | STRUCTURE | ADDITIVE | MS |
|---|---|---|---|---|
| 194 | 4-(2-((4-(2-(hydroxymethyl)pyrrolidin-1-yl)-2-methoxyphenyl)amino)pyrimidin-5-yl)-2-(((2S)-1-(1H-tetrazol-1-yl)propan-2-yl)oxy)benzonitrile | 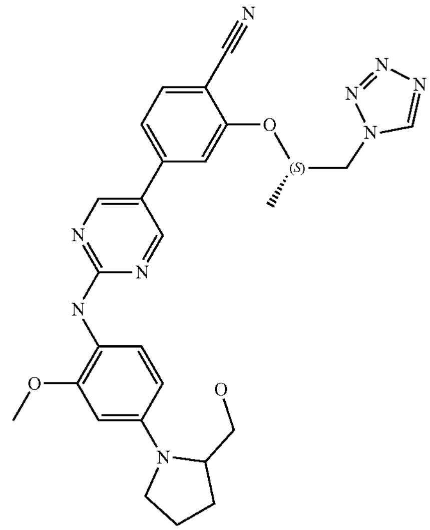 | | 526.1 |
| 195 | 1-(4-(4-((5-(4-chloro-3-(((2S)-1-(1H-tetrazol-1-yl)propan-2-yl)oxy)phenyl)pyrimidin-2-yl)amino)-3-methoxyphenyl)piperazin-1-yl)-2,2,2-trifluoroethanone | 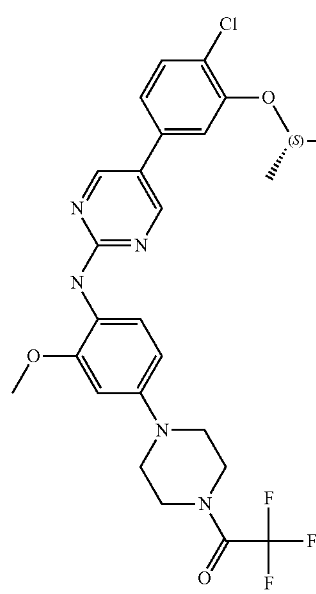 | | 618.4 |

| Ex. No. | IUPAC NAME | STRUCTURE | ADDITIVE | MS |
|---|---|---|---|---|
| 196 | 5-(4-chloro-3-(((2S)-1-(1H-tetrazol-1-yl)propan-2-yl)oxy)phenyl)-N-(2-methoxy-4-(piperazin-1-yl)phenyl)pyrimidin-2-amine | 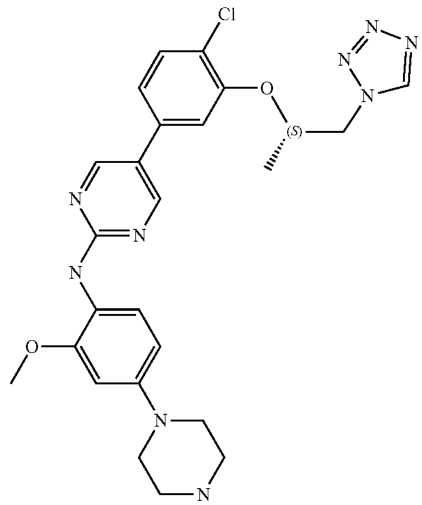 | | 522.3 |
| 197 | 5-(4-chloro-3-(((2S)-1-(1H-tetrazol-1-yl)propan-2-yl)oxy)phenyl)-N-(2-methoxy-4-(4-(oxetan-3-yl)piperazin-1-yl)phenyl)pyrimidin-2-amine | 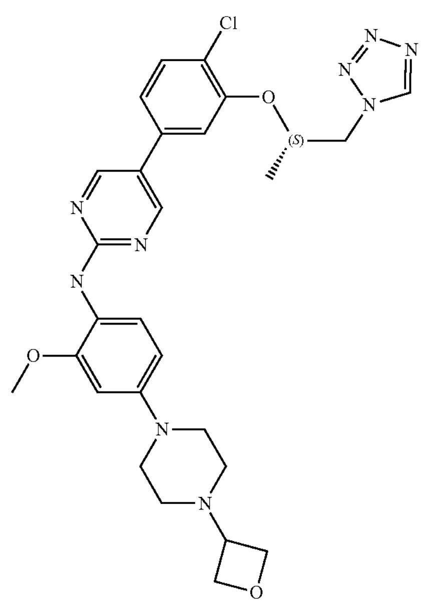 | | 578.3 |

| Ex. No. | IUPAC NAME | STRUCTURE | ADDITIVE | MS |
|---|---|---|---|---|
| 198 | 4-(2-((2-methoxy-4-(4-(oxetan-3-yl)-1,4-diazepan-1-yl)phenyl)amino)pyrimidin-5-yl)-2-(((2S)-1-(1H-tetrazol-1-yl)propan-2-yl)oxy)benzonitrile | 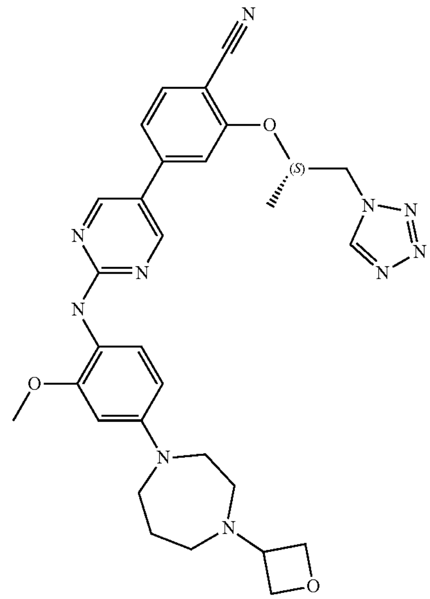 | | 581.2 |
| 199 | 5-(4-chloro-3-(((2S)-1-(1H-tetrazol-1-yl)propan-2-yl)oxy)phenyl)-N-(2-methoxy-4-(4-methylpiperazin-1-yl)phenyl)pyrimidin-2-amine | 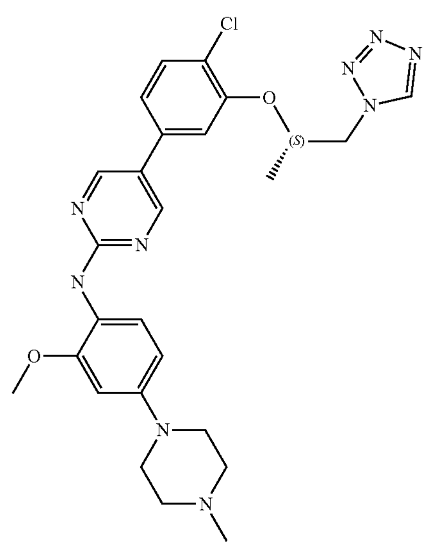 | | 536.3 |

TABLE 1-continued

| Ex. No. | IUPAC NAME | STRUCTURE | ADDITIVE | MS |
|---|---|---|---|---|
| 200 | (4-(4-((5-(4-chloro-3-(((2S)-1-(1H-tetrazol-1-yl)propan-2-yl)oxy)phenyl)pyrimidin-2-yl)amino)-3-methoxyphenyl)piperazin-1-yl)acetonitrile | 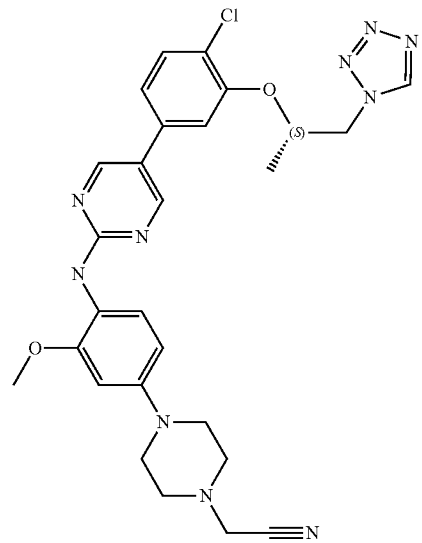 | | 561.3 |
| 201 | 4-(2-((2-methoxy-4-(2-(morpholin-4-ylmethyl)pyrrolidin-1-yl)phenyl)amino)pyrimidin-5-yl)-2-(((2S)-1-(1H-tetrazol-1-yl)propan-2-yl)oxy)benzonitrile | 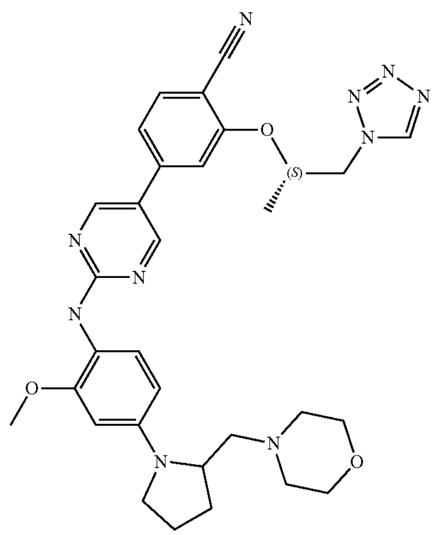 | | 597.4 |
| 202 | 4-(2-((2-methoxy-5-(4-(morpholin-4-yl)piperidin-1-yl)phenyl)amino)pyrimidin-5-yl)-2-(((2S)-1-(1H-tetrazol-1-yl)propan-2-yl)oxy)benzonitrile | 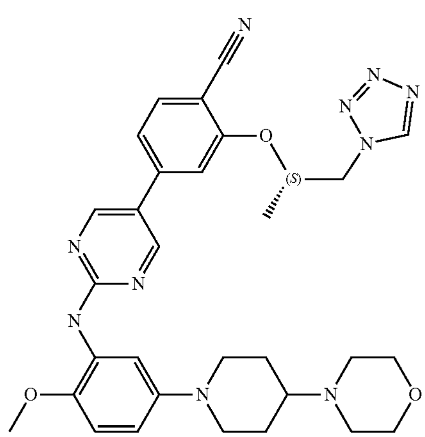 | | 597.4 |

TABLE 1-continued

| Ex. No. | IUPAC NAME | STRUCTURE | ADDITIVE | MS |
|---|---|---|---|---|
| 203 | 1-(4-(4-((5-(4-chloro-3-(((2S)-1-(1H-tetrazol-1-yl)propan-2-yl)oxy)phenyl)pyrimidin-2-yl)amino)-3-methoxyphenyl)piperidin-1-yl)-2,2,2-trifluoroethanone | 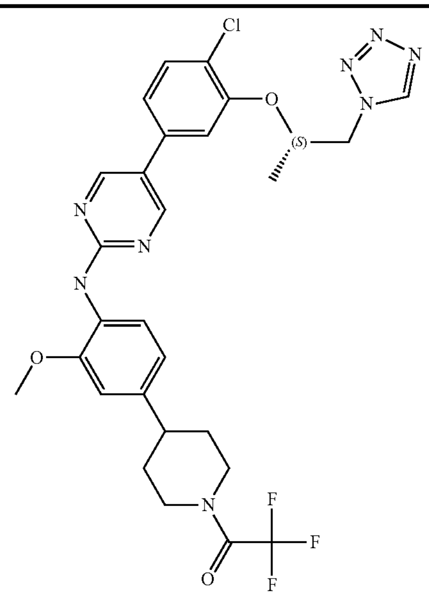 | | 615.2 |
| 204 | 5-(4-chloro-3-(((2S)-1-(1H-tetrazol-1-yl)propan-2-yl)oxy)phenyl)-N-(2-methoxy-4-(piperidin-4-yl)phenyl)pyrimidin-2-amine | 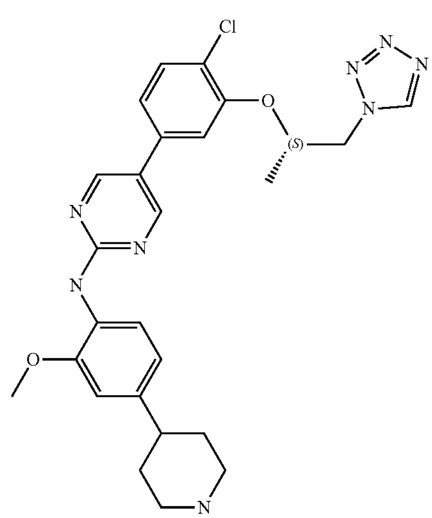 | | 521.3 |

TABLE 1-continued

| Ex. No. | IUPAC NAME | STRUCTURE | ADDITIVE | MS |
|---|---|---|---|---|
| 205 | 5-(4-chloro-3-(((2S)-1-(1H-tetrazol-1-yl)propan-2-yl)oxy)phenyl)-N-(5-fluoro-2-methoxy-4-(4-(morpholin-4-yl)piperidin-1-yl)phenyl)pyrimidin-2-amine | 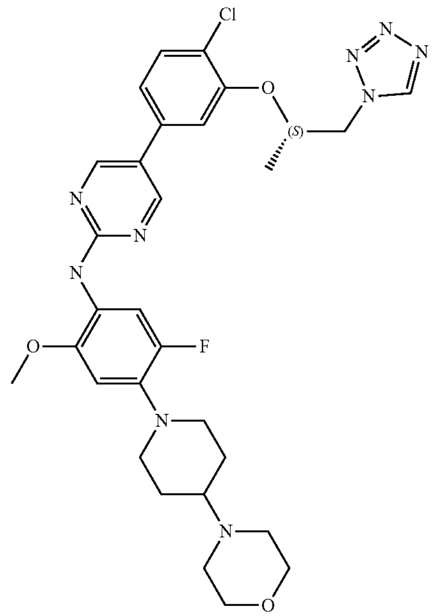 | | 624.4 |
| 206 | 5-(4-chloro-3-(((2S)-1-(1H-tetrazol-1-yl)propan-2-yl)oxy)phenyl)-N-(2-methoxy-4-(1-(oxetan-3-yl)piperidin-4-yl)phenyl)pyrimidin-2-amine | 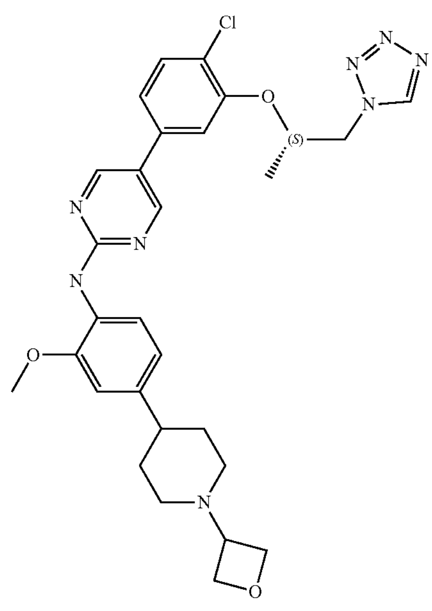 | | 577.3 |

TABLE 1-continued

| Ex. No. | IUPAC NAME | STRUCTURE | ADDITIVE | MS |
|---|---|---|---|---|
| 207 | 4-(2-((2-methoxy-4-(1-(trifluoroacetyl)piperidin-4-yl)phenyl)amino)pyrimidin-5-yl)-2-(((2S)-1-(1H-tetrazol-1-yl)propan-2-yl)oxy)benzonitrile | 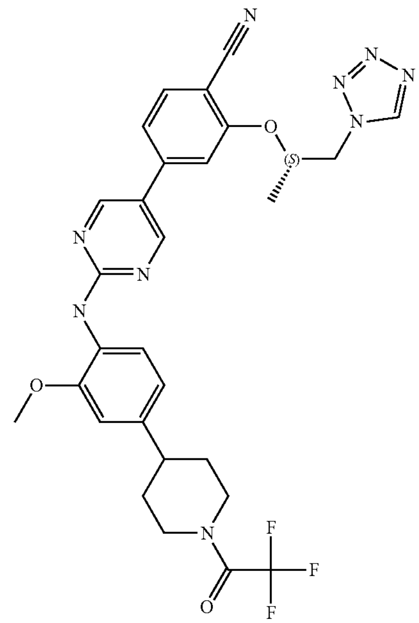 | | 606.2 |
| 208 | 4-(2-((2-methoxy-4-(piperidin-4-yl)phenyl)amino)pyrimidin-5-yl)-2-(((2S)-1-(1H-tetrazol-1-yl)propan-2-yl)oxy)benzonitrile | 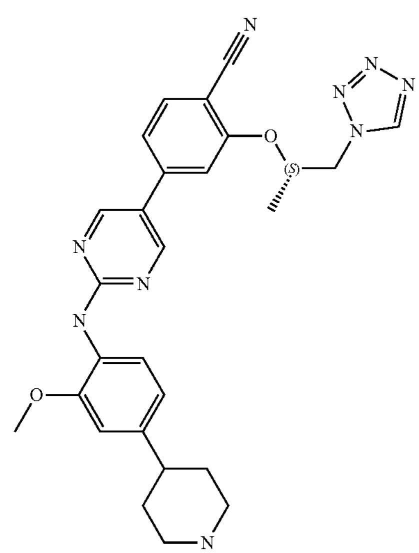 | | 512.4 |

TABLE 1-continued

| Ex. No. | IUPAC NAME | STRUCTURE | ADDITIVE | MS |
|---|---|---|---|---|
| 209 | 5-(4-chloro-3-(((2S)-1-(1H-tetrazol-1-yl)propan-2-yl)oxy)phenyl)-N-(5-fluoro-2-methoxy-4-(piperazin-1-yl)phenyl)pyrimidin-2-amine | 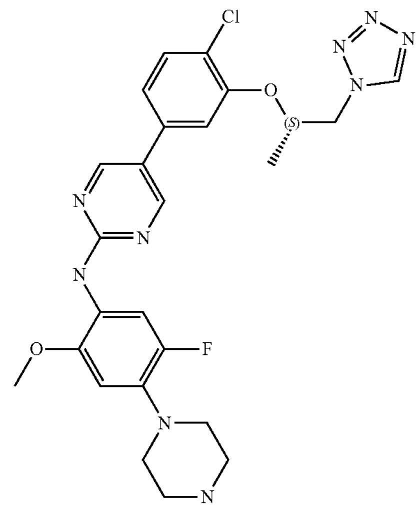 | | 540.3 |
| 210 | 5-(4-chloro-3-(((2S)-1-(1H-tetrazol-1-yl)propan-2-yl)oxy)phenyl)-N-(2-methoxy-4-(4-(3-oxa-8-azabicyclo[3.2.1]oct-8-yl)piperidin-1-yl)phenyl)pyrimidin-2-amine | 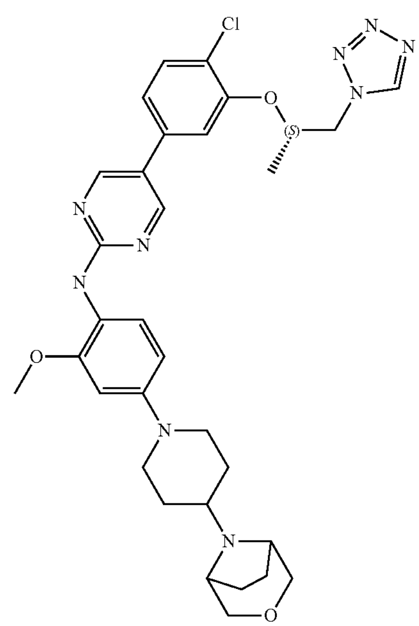 | | 633.2 |

TABLE 1-continued

| Ex. No. | IUPAC NAME | STRUCTURE | ADDITIVE | MS |
|---|---|---|---|---|
| 211 | 5-(4-chloro-3-(((2S)-1-(1H-tetrazol-1-yl)propan-2-yl)oxy)phenyl)-N-(5-fluoro-2-methoxy-4-(4-(oxetan-3-yl)piperazin-1-yl)phenyl)pyrimidin-2-amine | 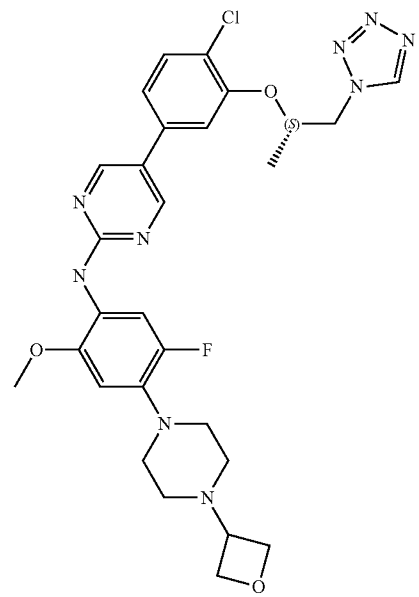 | | 596.2 |
| 212 | 5-(4-chloro-3-(((2S)-1-(1H-tetrazol-1-yl)propan-2-yl)oxy)phenyl)-N-(2-methoxy-6-(4-(morpholin-4-yl)piperidin-1-yl)pyridin-3-yl)pyrimidin-2-amine | 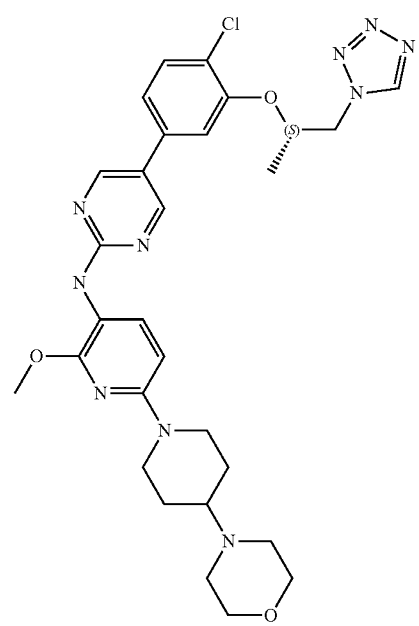 | | 607.3 |

TABLE 1-continued

| Ex. No. | IUPAC NAME | STRUCTURE | ADDITIVE | MS |
|---|---|---|---|---|
| 213 | 5-(4-chloro-3-(((2S)-1-(1H-tetrazol-1-yl)propan-2-yl)oxy)phenyl)-N-(2-methoxy-4-(4-((1R,5S)-8-oxa-3-azabicyclo[3.2.1]oct-3-yl)piperidin-1-yl)phenyl)pyrimidin-2-amine | 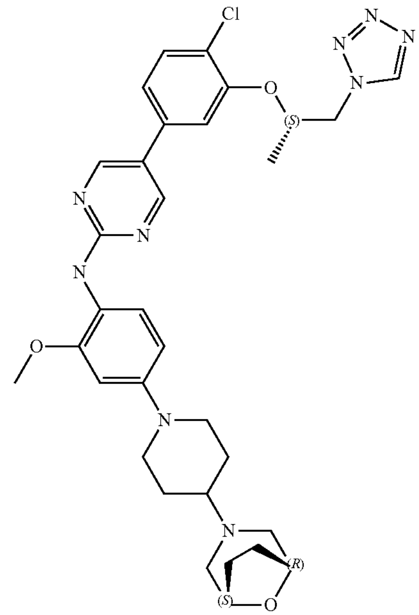 | | 632.3 |
| 214 | 5-(4-chloro-3-(((2S)-1-(1H-tetrazol-1-yl)propan-2-yl)oxy)phenyl)-N-(2-methoxy-5-(4-(morpholin-4-yl)piperidin-1-yl)phenyl)pyrimidin-2-amine | 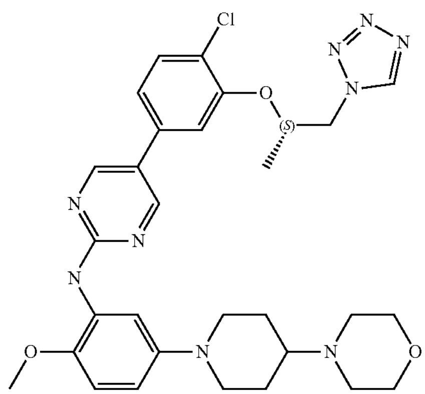 | | 606.3 |
| 215 | 1-(4-(4-((5-(4-chloro-3-(((2S)-1-(1H-tetrazol-1-yl)propan-2-yl)oxy)phenyl)pyrimidin-2-yl)amino)-3-methoxyphenyl)-1,4-diazepan-1-yl)-2,2,2-trifluoroethanone | 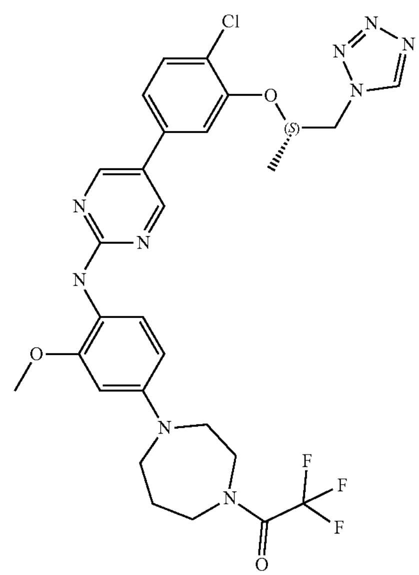 | | 632.3 |

TABLE 1-continued

| Ex. No. | IUPAC NAME | STRUCTURE | ADDITIVE | MS |
|---|---|---|---|---|
| 216 | 5-(4-chloro-3-(((2S)-1-(1H-tetrazol-1-yl)propan-2-yl)oxy)phenyl)-N-(4-(1,4-diazepan-1-yl)-2-methoxyphenyl)pyrimidin-2-amine | 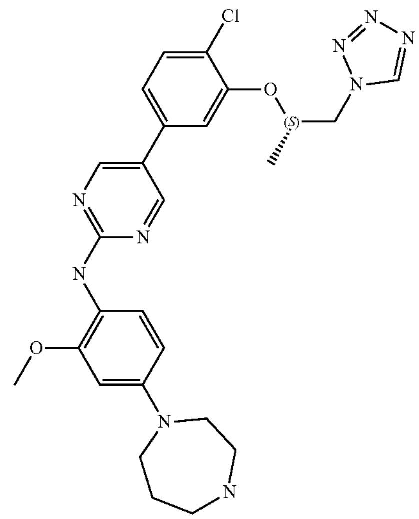 | | 536.3 |
| 217 | 5-(4-chloro-3-(((2S)-1-(1H-tetrazol-1-yl)propan-2-yl)oxy)phenyl)-N-(2-methoxy-4-(4-(oxetan-3-yl)-1,4-diazepan-1-yl)phenyl)pyrimidin-2-amine | 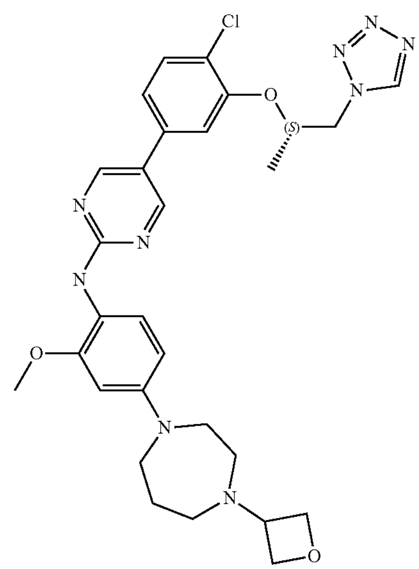 | | 592.3 |
| 218 | 2-(4-(4-((5-(4-chloro-3-(((2S)-1-(1H-tetrazol-1-yl)propan-2-yl)oxy)phenyl)pyrimidin-2-yl)amino)-3-methoxyphenyl)-1,4-diazepan-1-yl)ethanol | 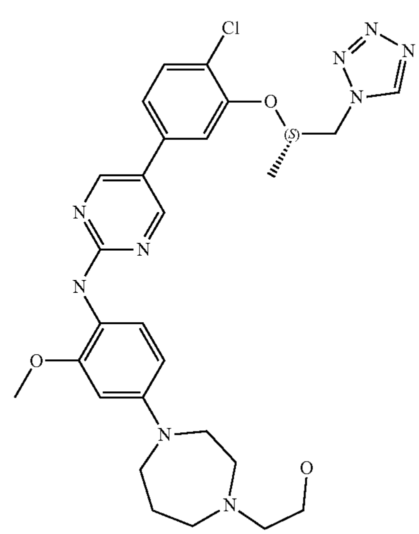 | | 580.3 |

| Ex. No. | IUPAC NAME | STRUCTURE | ADDITIVE | MS |
|---|---|---|---|---|
| 219 | 5-(4-chloro-3-(((2S)-1-(1H-tetrazol-1-yl)propan-2-yl)oxy)phenyl)-N-(4-(4-(3,3-difluoroazetidin-1-yl)piperidin-1-yl)-2-methoxyphenyl)pyrimidin-2-amine | 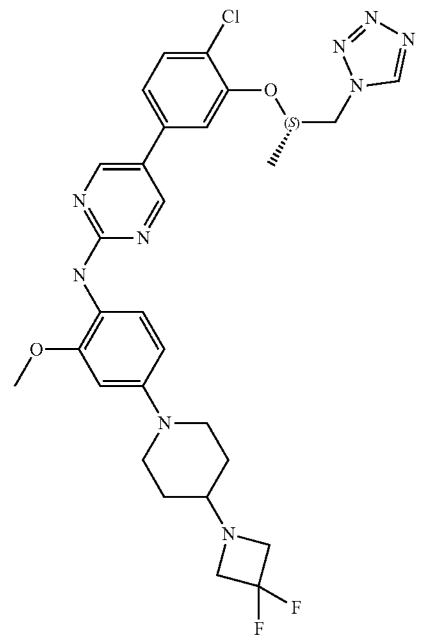 | | 612.2 |
| 220 | (4-((5-(4-chloro-3-(((2S)-1-(1H-tetrazol-1-yl)propan-2-yl)oxy)phenyl)pyrimidin-2-yl)amino)-3-(trifluoromethoxy)phenyl)(6-methyl-2,6-diazaspiro[3.3]hept-2-yl)methanone | 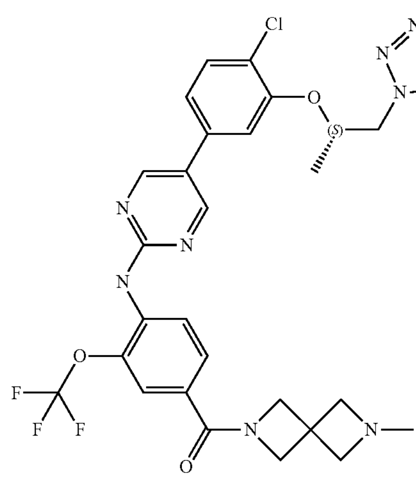 | | 630.3 |

TABLE 1-continued

| Ex. No. | IUPAC NAME | STRUCTURE | ADDITIVE | MS |
|---|---|---|---|---|
| 221 | 5-(4-chloro-3-(((2S)-1-(1H-tetrazol-1-yl)propan-2-yl)oxy)phenyl)-N-(2-methoxy-4-(4-(morpholin-4-yl)piperidin-1-yl)phenyl)pyrimidin-2-amine hydrochloride | 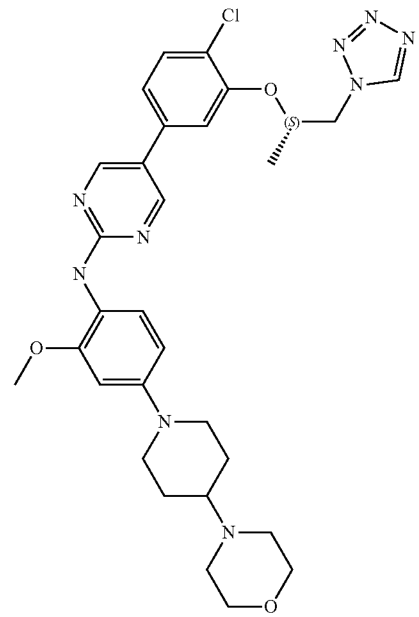 | HCl | 606.3 |
| 222 | 5-(4-chloro-3-(((2S)-1-(1H-tetrazol-1-yl)propan-2-yl)oxy)phenyl)-N-(2-methoxy-4-(4-(morpholin-4-yl)piperidin-1-yl)phenyl)pyrimidin-2-amine dihydrochloride | 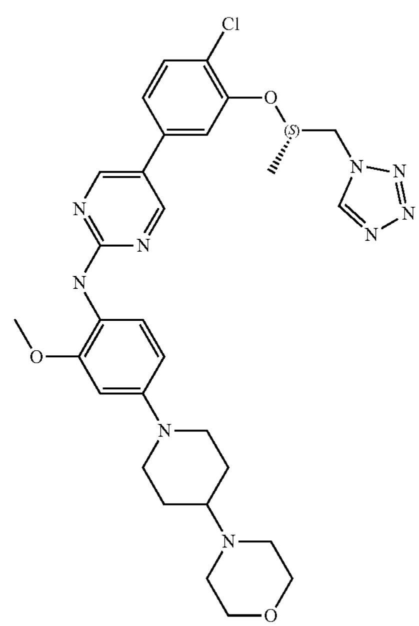 | 2HCl | 606.3 |

| Ex. No. | IUPAC NAME | STRUCTURE | ADDITIVE | MS |
|---|---|---|---|---|
| 223 | 4-(2-((2-methoxy-4-(1-(oxetan-3-yl)piperidin-4-yl)phenyl)amino)pyrimidin-5-yl)-2-(((2S)-1-(1H-tetrazol-1-yl)propan-2-yl)oxy)benzonitrile fumarate | 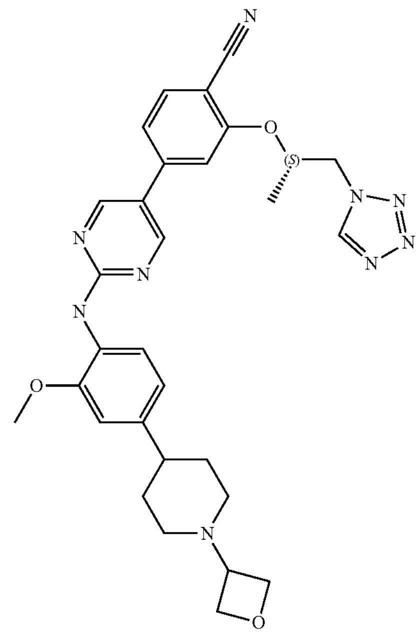 | fumaric acid | 568.3 |
| 224 | 5-(4-chloro-3-(((2S)-1-(1H-tetrazol-1-yl)propan-2-yl)oxy)phenyl)-N-(2-methoxy-4-(1-(2-(methylsulfonyl)ethyl)piperidin-4-yl)phenyl)pyrimidin-2-amine | 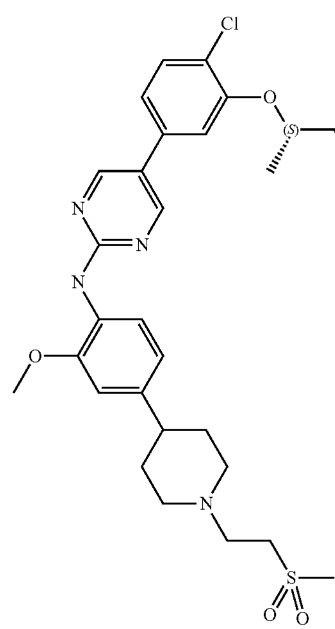 | | 627.2 |

TABLE 1-continued
| Ex. No. | IUPAC NAME | STRUCTURE | ADDITIVE | MS |
|---|---|---|---|---|
| 225 | 4-(2-((2-methoxy-5-(1-(trifluoroacetyl)piperidin-4-yl)phenyl)amino)pyrimidin-5-yl)-2-(((2S)-1-(1H-tetrazol-1-yl)propan-2-yl)oxy)benzonitrile | 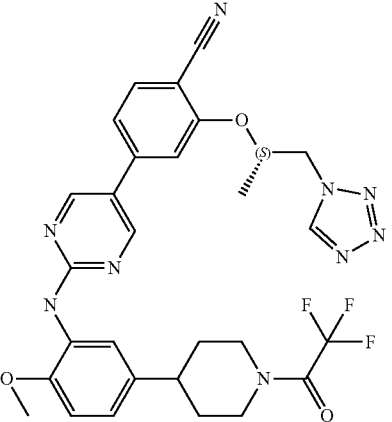 | | 608.2 |
| 226 | 4-(2-((2-methoxy-4-(4-(morpholin-4-yl)piperidin-1-yl)phenyl)amino)pyrimidin-5-yl)-2-(((2S)-1-(oxetan-3-yloxy)propan-2-yl)oxy)benzonitrile | 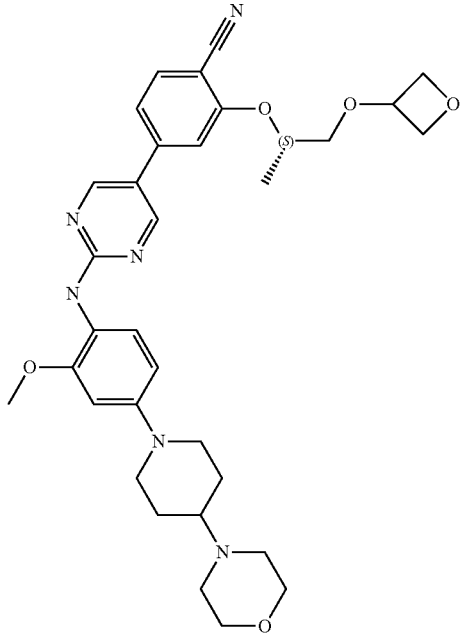 | | 601.3 |
| 227 | 4-(2-((2-methoxy-5-(piperidin-4-yl)phenyl)amino)pyrimidin-5-yl)-2-(((2S)-1-(1H-tetrazol-1-yl)propan-2-yl)oxy)benzonitrile | 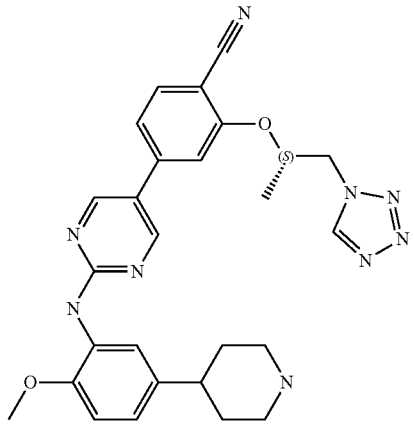 | | 512.3 |

TABLE 1-continued

| Ex. No. | IUPAC NAME | STRUCTURE | ADDITIVE | MS |
|---|---|---|---|---|
| 228 | 1-(4-(4-((5-(4-chloro-3-(((2S)-1-(1H-tetrazol-1-yl)propan-2-yl)oxy)phenyl)pyrimidin-2-yl)amino)-3-methoxyphenyl)-1,4-diazepan-1-yl)propan-2-ol | 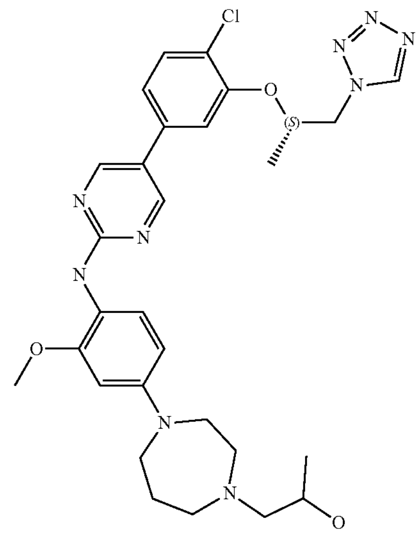 | | 594.3 |
| 229 | 1-(4-(4-((5-(4-chloro-3-(((2S)-1-(1H-tetrazol-1-yl)propan-2-yl)oxy)phenyl)pyrimidin-2-yl)amino)-3-methoxyphenyl)-1,4-diazepan-1-yl)-2-methylpropan-2-ol | 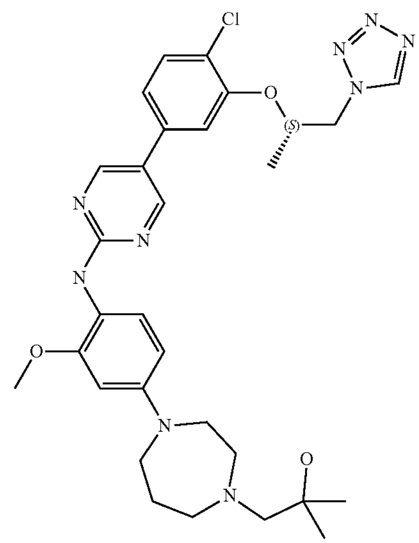 | | 608.3 |
| 230 | 4-(2-((2-methoxy-5-(1-(oxetan-3-yl)piperidin-4-yl)phenyl)amino)pyrimidin-5-yl)-2-(((2S)-1-(1H-tetrazol-1-yl)propan-2-yl)oxy)benzonitrile | 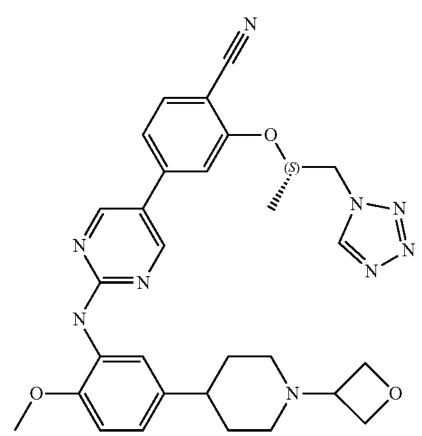 | | 566.3 |

| Ex. No. | IUPAC NAME | STRUCTURE | ADDITIVE | MS |
|---|---|---|---|---|
| 231 | 5-(4-chloro-3-(((2S)-1-(1H-tetrazol-1-yl)propan-2-yl)oxy)phenyl)-N-(2-methoxy-4-(4-(2,2,3,3-tetrafluoropropyl)-1,4-diazepan-1-yl)phenyl)pyrimidin-2-amine | 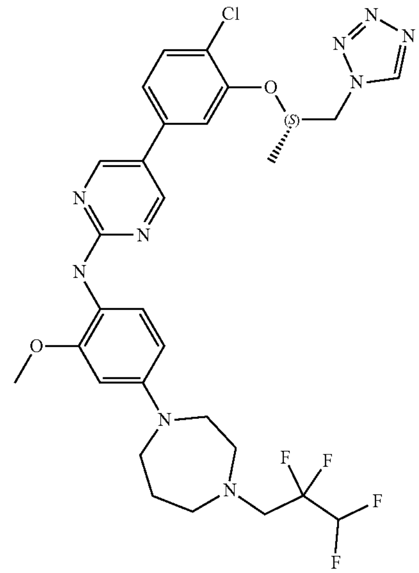 | | 650.3 |
| 232 | 1-(4-(4-((5-(4-chloro-3-(((2S)-1-(1H-tetrazol-1-yl)propan-2-yl)oxy)phenyl)pyrimidin-2-yl)amino)-3-methoxyphenyl)piperidin-1-yl)propan-2-ol | 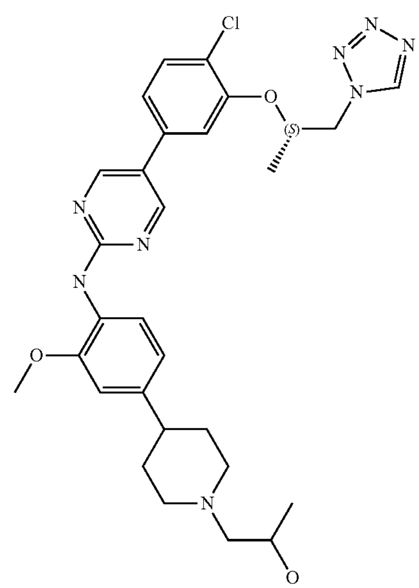 | | 579.3 |

TABLE 1-continued

| Ex. No. | IUPAC NAME | STRUCTURE | ADDITIVE | MS |
|---|---|---|---|---|
| 233 | 4-(2-((1-(1-(oxetan-3-yl)piperidin-4-yl)-1H-pyrazol-4-yl)amino)pyrimidin-5-yl)-2-(((2S)-1-(1H-1,2,4-triazol-1-yl)propan-2-yl)oxy)benzonitrile | 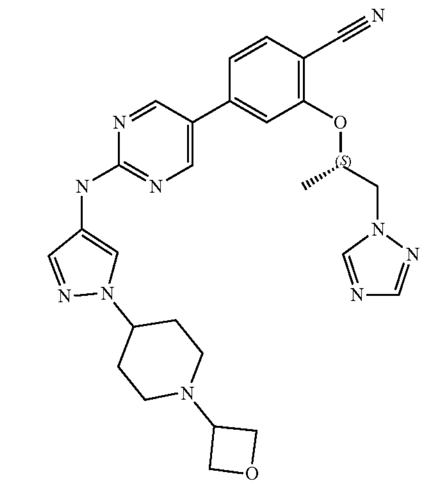 | | 527.3 |
| 234 | 4-(2-((2-methoxy-4-(3-(3-oxa-8-azabicyclo[3.2.1]oct-8-yl)azetidin-1-yl)phenyl)amino)pyrimidin-5-yl)-2-(((2S)-1-(1H-tetrazol-1-yl)propan-2-yl)oxy)benzonitrile | 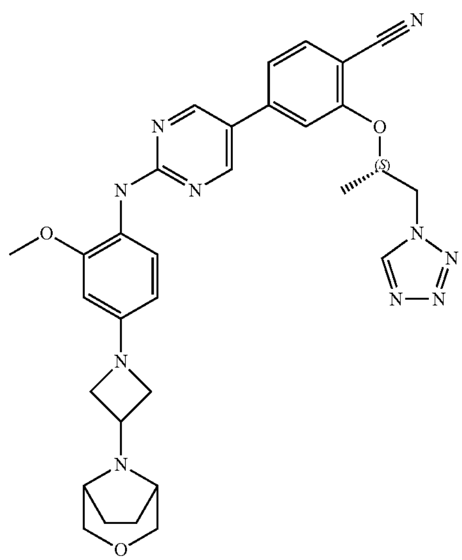 | | 595.3 |
| 235 | 5-(4-chloro-3-(((2S)-1-(1H-tetrazol-1-yl)propan-2-yl)oxy)phenyl)-N-(2-methoxy-4-(3-(3-oxa-8-azabicyclo[3.2.1]oct-8-yl)azetidin-1-yl)phenyl)pyrimidin-2-amine | 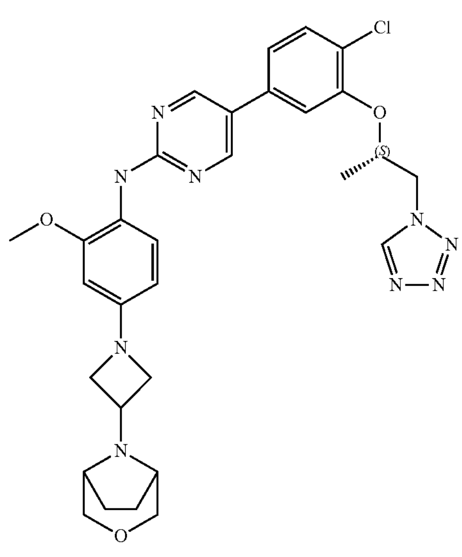 | | 604.3 |

TABLE 1-continued

| Ex. No. | IUPAC NAME | STRUCTURE | ADDITIVE | MS |
|---|---|---|---|---|
| 236 | tert-butyl 4-(5-((5-(4-cyano-3-(((2S)-1-(1H-tetrazol-1-yl)propan-2-yl)oxy)phenyl)pyrimidin-2-yl)amino)-2-fluoro-4-methoxyphenyl)piperidine-1-carboxylate | 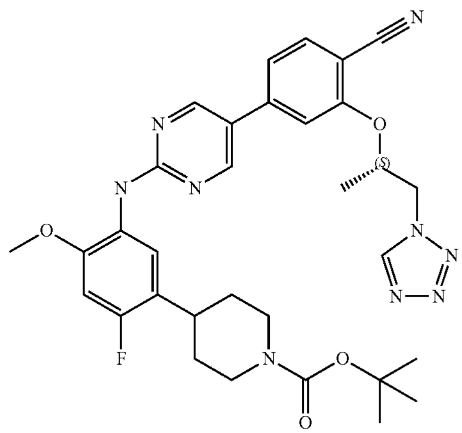 | | 628.4 |
| 237 | 4-(2-((4-fluoro-2-methoxy-5-(piperidin-4-yl)phenyl)amino)pyrimidin-5-yl)-2-(((2S)-1-(1H-tetrazol-1-yl)propan-2-yl)oxy)benzonitrile hydrochloride | 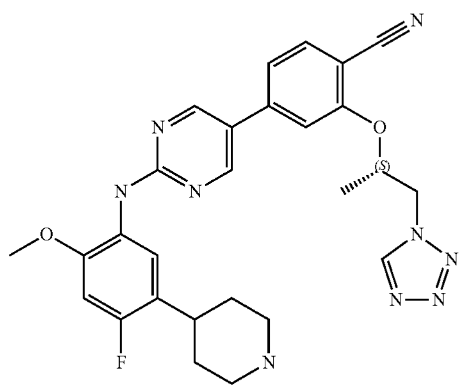 | HCl | 530.2 |
| 238 | 4-(2-((4-fluoro-2-methoxy-5-(1-(oxetan-3-yl)piperidin-4-yl)phenyl)amino)pyrimidin-5-yl)-2-(((2S)-1-(1H-tetrazol-1-yl)propan-2-yl)oxy)benzonitrile | 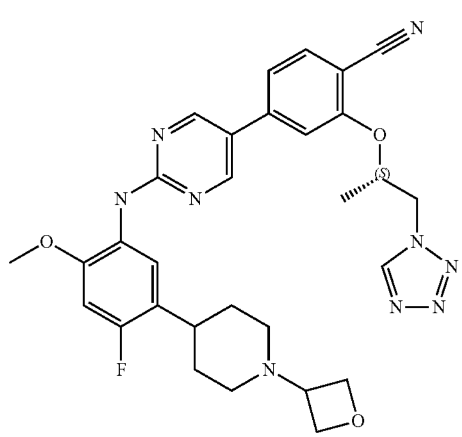 | | 584.3 |

TABLE 1-continued

| Ex. No. | IUPAC NAME | STRUCTURE | ADDITIVE | MS |
|---|---|---|---|---|
| 239 | tert-butyl 4-(4-((5-(4-chloro-3-(((2S)-1-(1H-tetrazol-1-yl)propan-2-yl)oxy)phenyl)pyrimidin-2-yl)amino)-3-methoxyphenyl)-3-oxopiperazine-1-carboxylate | 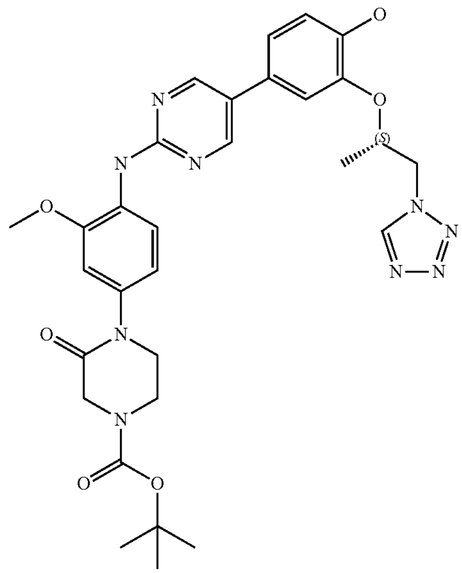 | | 636.3 |
| 240 | 1-(4-((5-(4-chloro-3-(((2S)-1-(1H-tetrazol-1-yl)propan-2-yl)oxy)phenyl)pyrimidin-2-yl)amino)-3-methoxyphenyl)piperazin-2-one | 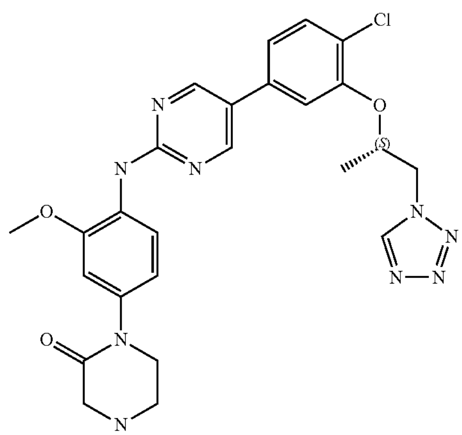 | | 536.2 |
| 241 | 1-(4-((5-(4-chloro-3-(((2S)-1-(1H-tetrazol-1-yl)propan-2-yl)oxy)phenyl)pyrimidin-2-yl)amino)-3-methoxyphenyl)-4-(oxetan-3-yl)piperazin-2-one | 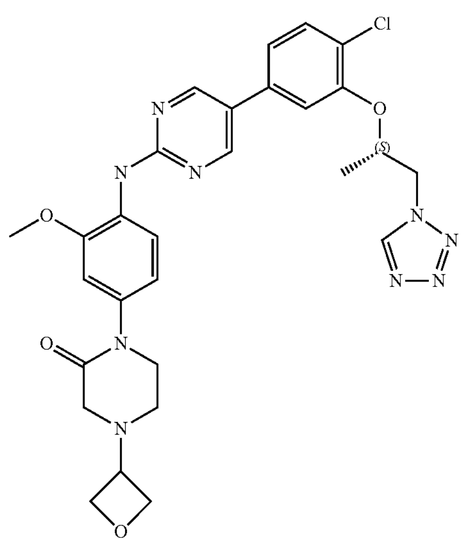 | | 592.2 |

TABLE 1-continued

| Ex. No. | IUPAC NAME | STRUCTURE | ADDITIVE | MS |
|---|---|---|---|---|
| 242 | butyl 3-((5-(4-cyano-3-(((2S)-1-(1H-tetrazol-1-yl)propan-2-yl)oxy)phenyl)pyrimidin-2-yl)amino)-4-methoxybenzoate | 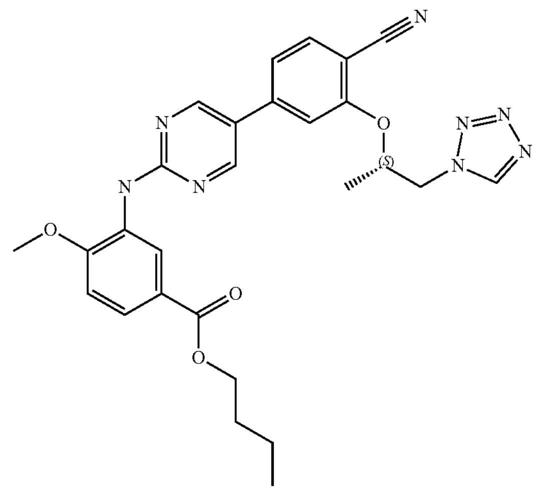 | | 529.2 |
| 243 | 4-(2-((5-chloro-2-methoxyphenyl)amino)pyrimidin-5-yl)-2-(((2S)-1-(1H-tetrazol-1-yl)propan-2-yl)oxy)benzonitrile | 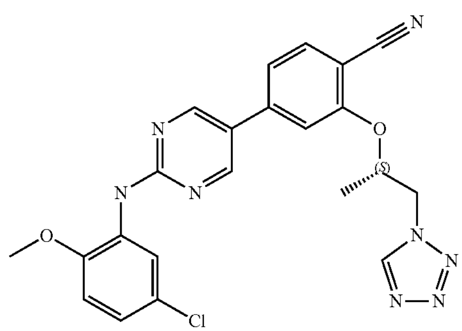 | | 463.1 |
| 244 | 3-((5-(4-cyano-3-(((2S)-1-(1H-tetrazol-1-yl)propan-2-yl)oxy)phenyl)pyrimidin-2-yl)amino)-4-methoxybenzoic acid | 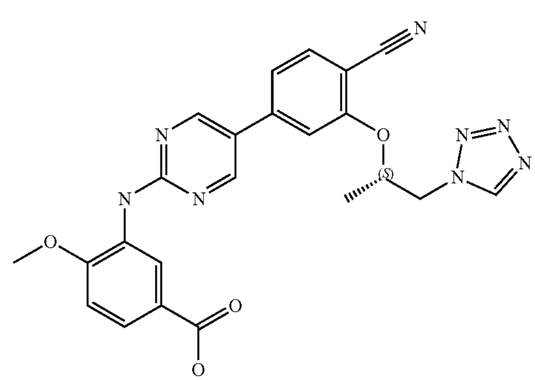 | | 471 |

TABLE 1-continued

| Ex. No. | IUPAC NAME | STRUCTURE | ADDITIVE | MS |
|---|---|---|---|---|
| 245 | 3-((5-(4-cyano-3-(((2S)-1-(1H-tetrazol-1-yl)propan-2-yl)oxy)phenyl)pyrimidin-2-yl)amino)-N-(2-hydroxyethyl)-4-methoxybenzamide | 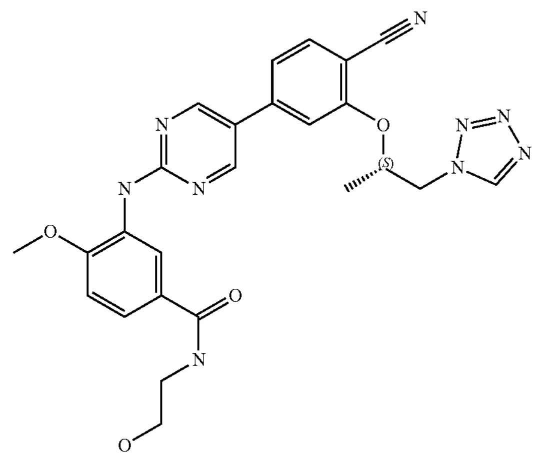 | | 516.2 |
| 246 | 3-((5-(4-cyano-3-(((2S)-1-(1H-tetrazol-1-yl)propan-2-yl)oxy)phenyl)pyrimidin-2-yl)amino)-4-methoxy-N-(2-methoxy-ethyl)benzamide | 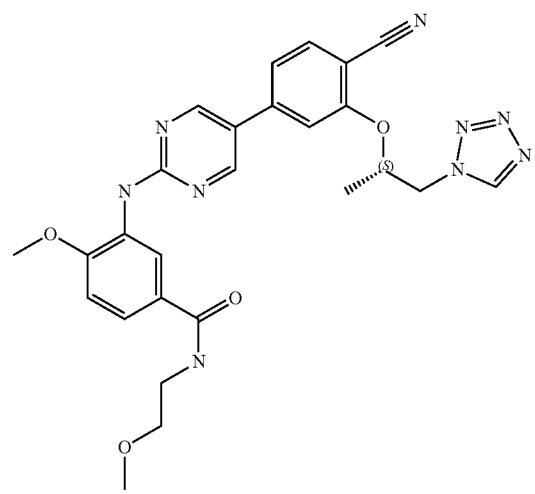 | | 530.2 |
| 247 | 4-(2-((5-((4-hydroxypiperidin-1-yl)carbonyl)-2-methoxy-phenyl)amino)pyrimidin-5-yl)-2-(((2S)-1-(1H-tetrazol-1-yl)propan-2-yl)oxy)benzonitrile | 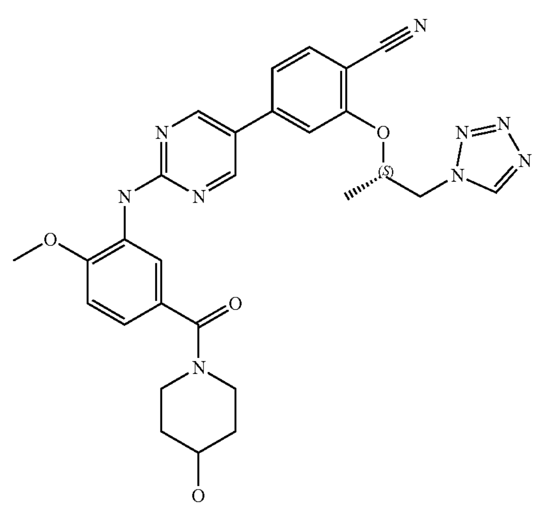 | | 556.2 |

TABLE 1-continued

| Ex. No. | IUPAC NAME | STRUCTURE | ADDITIVE | MS |
|---|---|---|---|---|
| 248 | 3-((5-(4-cyano-3-(((2S)-1-(1H-tetrazol-1-yl)propan-2-yl)oxy)phenyl)pyrimidin-2-yl)amino)-4-methoxy-N-(1-methylpiperidin-4-yl)benzamide | 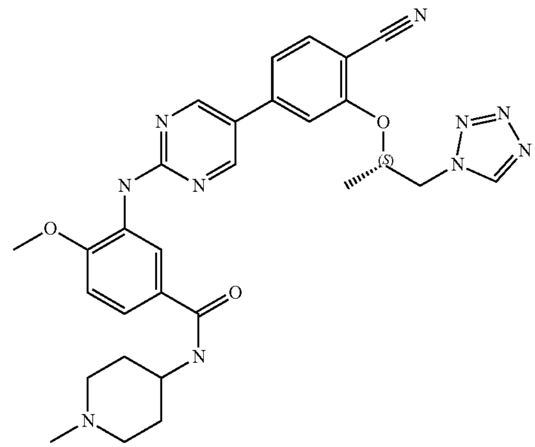 | | 569.2 |
| 249 | 3-((5-(4-cyano-3-(((2S)-1-(1H-tetrazol-1-yl)propan-2-yl)oxy)phenyl)pyrimidin-2-yl)amino)-4-methoxy-N-(2-(morpholin-4-yl)ethyl)benzamide | 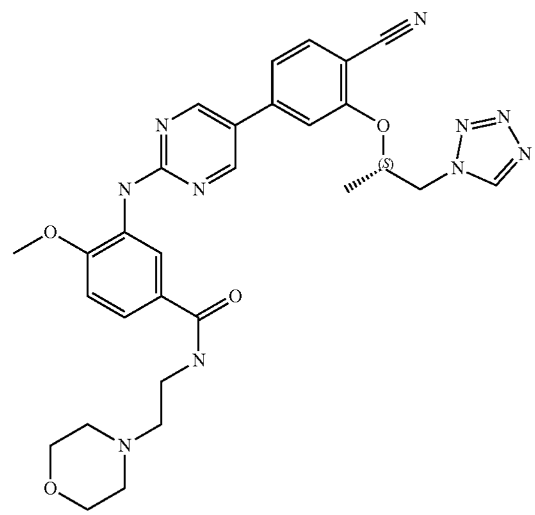 | | 585.2 |
| 250 | 3-((5-(4-cyano-3-(((2S)-1-(1H-tetrazol-1-yl)propan-2-yl)oxy)phenyl)pyrimidin-2-yl)amino)-4-methoxy-N-methyl-N-(2-(morpholin-4-yl)ethyl)benzamide | 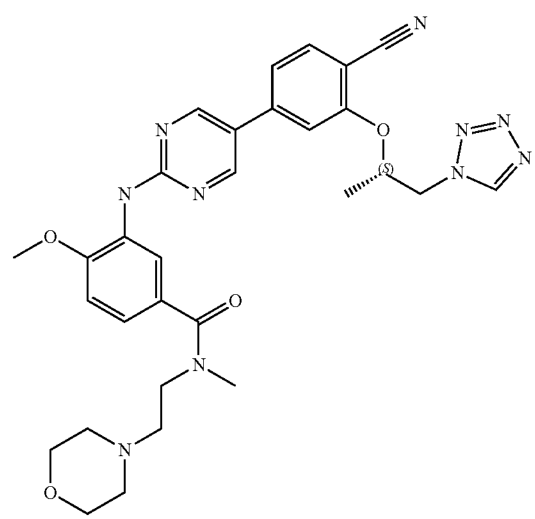 | | 599.3 |

| Ex. No. | IUPAC NAME | STRUCTURE | ADDITIVE | MS |
|---|---|---|---|---|
| 251 | 4-(2-((5-(1,4'-bipiperidine-1'-ylcarbonyl)-2-methoxyphenyl)amino)pyrimidin-5-yl)-2-(((2S)-1-(1H-tetrazol-1-yl)propan-2-yl)oxy)benzonitrile | 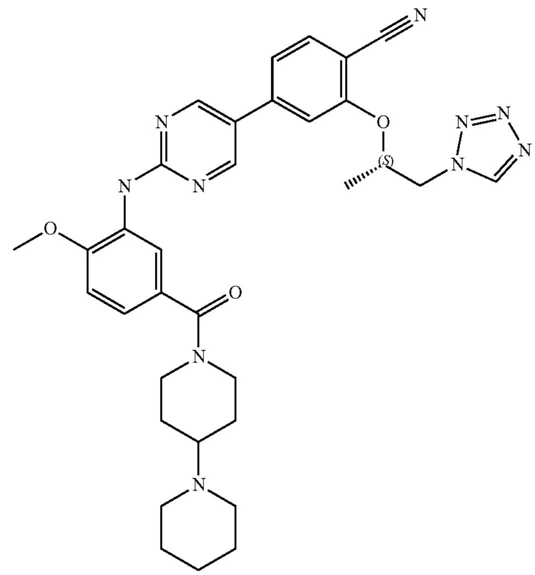 | | 623.3 |
| 252 | 4-(2-((2-methoxy-5-((4-(1-methylpiperidin-4-yl)piperazin-1-yl)carbonyl)phenyl)amino)pyrimidin-5-yl)-2-(((2S)-1-(1H-tetrazol-1-yl)propan-2-yl)oxy)benzonitrile | 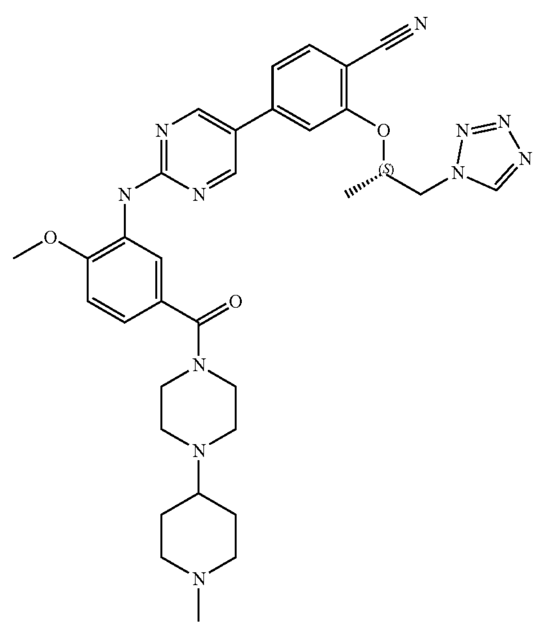 | | 638.4 |

TABLE 1-continued

| Ex. No. | IUPAC NAME | STRUCTURE | ADDITIVE | MS |
|---|---|---|---|---|
| 253 | 4-(2-((2-methoxy-5-((4-(4-methylpiperazin-1-yl)piperidin-1-yl)carbonyl)phenyl)amino)pyrimidin-5-yl)-2-(((2S)-1-(1H-tetrazol-1-yl)propan-2-yl)oxy)benzonitrile | 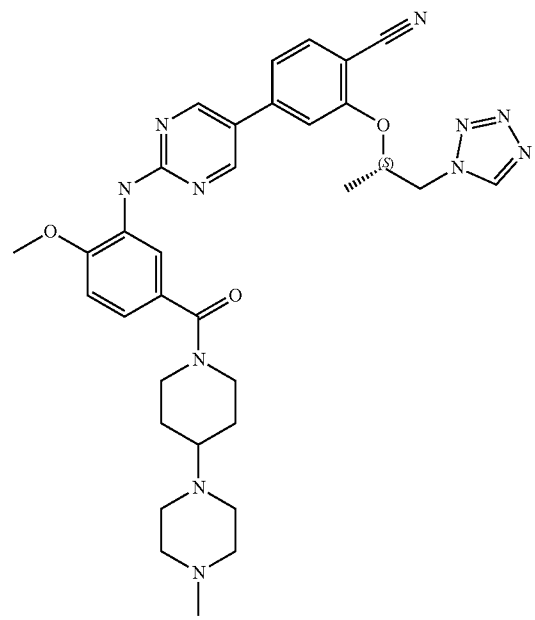 | | 638.4 |
| 254 | 4-(2-((2-methoxy-5-((6-methyl-2,6-diazaspiro[3.3]hept-2-yl)carbonyl)phenyl)amino)pyrimidin-5-yl)-2-(((2S)-1-(1H-tetrazol-1-yl)propan-2-yl)oxy)benzonitrile | 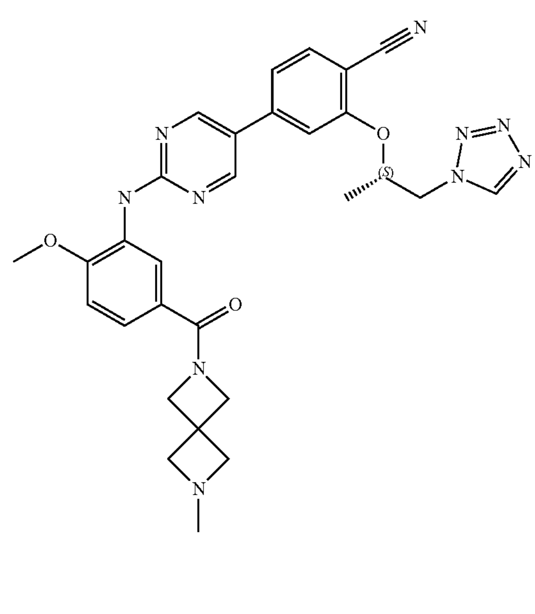 | | 567.2 |

TABLE 1-continued

| Ex. No. | IUPAC NAME | STRUCTURE | ADDITIVE | MS |
|---|---|---|---|---|
| 255 | 4-(2-((2-methoxy-5-((4-(morpholin-4-yl)piperidin-1-yl)carbonyl)phenyl)amino)pyrimidin-5-yl)-2-(((2S)-1-(1H-tetrazol-1-yl)propan-2-yl)oxy)benzonitrile | 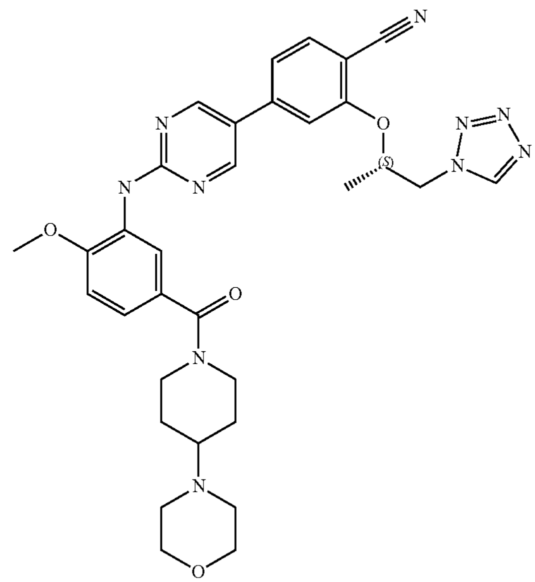 | | 625.3 |
| 256 | 3-((5-(4-cyano-3-(((2S)-1-(1H-tetrazol-1-yl)propan-2-yl)oxy)phenyl)pyrimidin-2-yl)amino)-4-methoxy-N-(1-methylpiperidin-3-yl)benzamide | 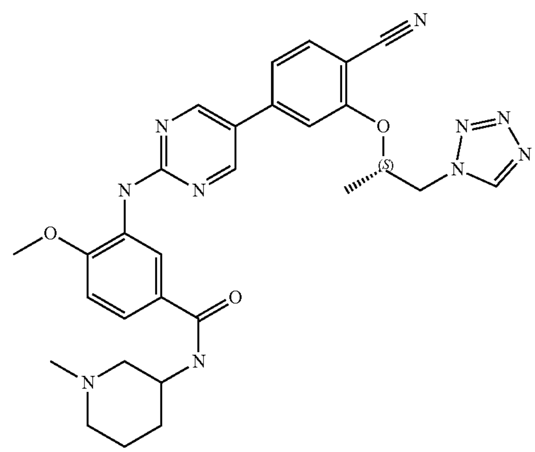 | | 569.2 |
| 257 | 3-((5-(4-cyano-3-(((2S)-1-(1H-tetrazol-1-yl)propan-2-yl)oxy)phenyl)pyrimidin-2-yl)amino)-4-methoxy-N-methyl-N-(1-methylpiperidin-4-yl)benzamide | 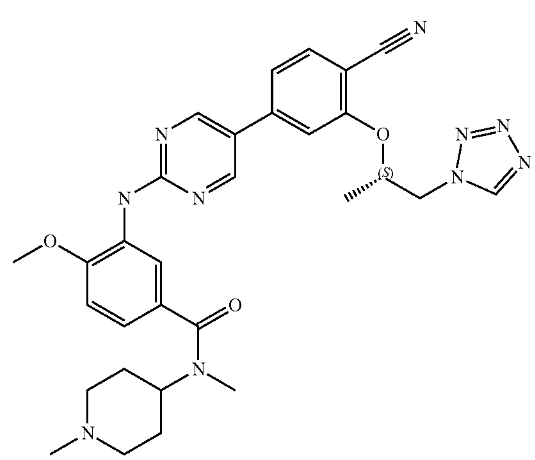 | | 583.2 |

TABLE 1-continued

| Ex. No. | IUPAC NAME | STRUCTURE | ADDITIVE | MS |
|---|---|---|---|---|
| 258 | 4-(2-((2-methoxy-5-((4-methylpiperazin-1-yl)carbonyl)phenyl)amino)pyrimidin-5-yl)-2-(((2S)-1-(1H-tetrazol-1-yl)propan-2-yl)oxy)benzonitrile | 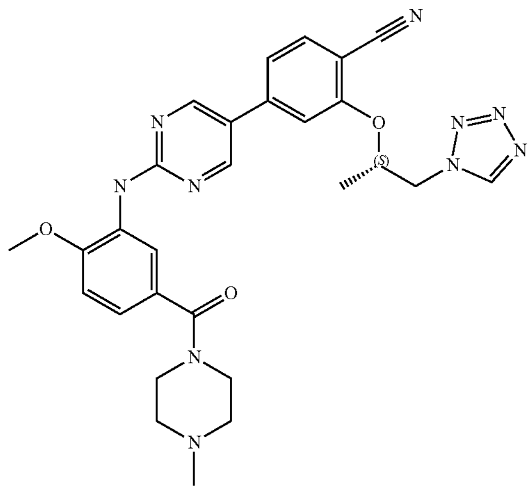 | | 555.3 |
| 259 | 3-((5-(4-cyano-3-(((2S)-1-(1H-tetrazol-1-yl)propan-2-yl)oxy)phenyl)pyrimidin-2-yl)amino)-N-(3-hydroxypropyl)-4-methoxy-N-methylbenzamide | 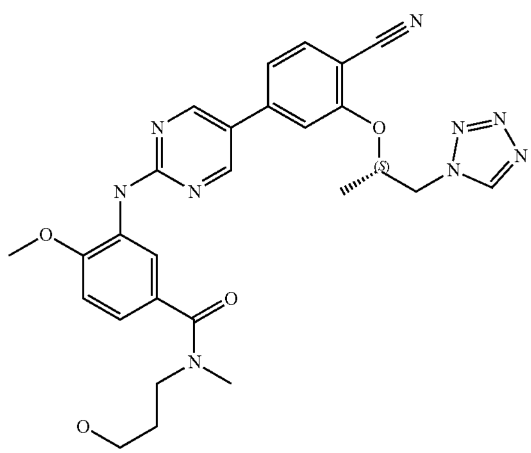 | | 544.2 |
| 260 | 3-((5-(4-cyano-3-(((2S)-1-(1H-tetrazol-1-yl)propan-2-yl)oxy)phenyl)pyrimidin-2-yl)amino)-4-methoxy-N-(3-methoxypropyl)-N-methylbenzamide | 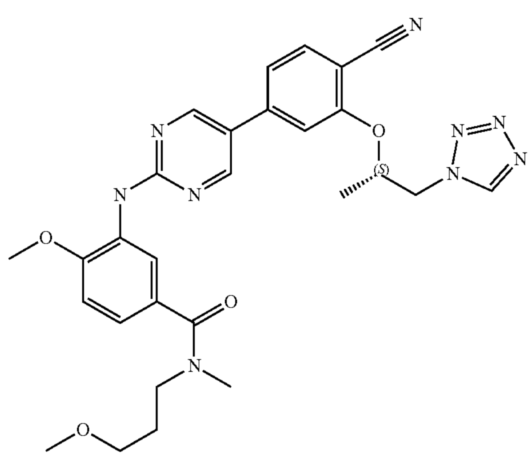 | | 558.3 |

TABLE 1-continued

| Ex. No. | IUPAC NAME | STRUCTURE | ADDITIVE | MS |
|---|---|---|---|---|
| 261 | 4-(2-((5-((2-((dimethyl-amino)methyl)piperidin-1-yl)carbonyl)-2-methoxy-phenyl)amino)pyrimidin-5-yl)-2-(((2S)-1-(1H-tetrazol-1-yl)propan-2-yl)oxy)benzonitrile | 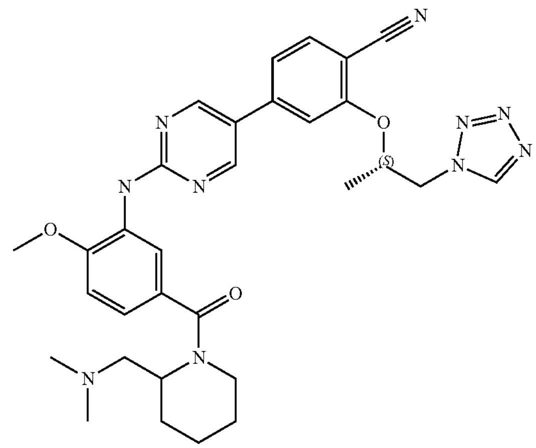 | | 597.3 |
| 262 | 3-((5-(4-cyano-3-(((2S)-1-(1H-tetrazol-1-yl)propan-2-yl)oxy)phenyl)pyrimidin-2-yl)amino)-N-(2-(dimethylamino)ethyl)-4-methoxy-N-methylbenzamide | 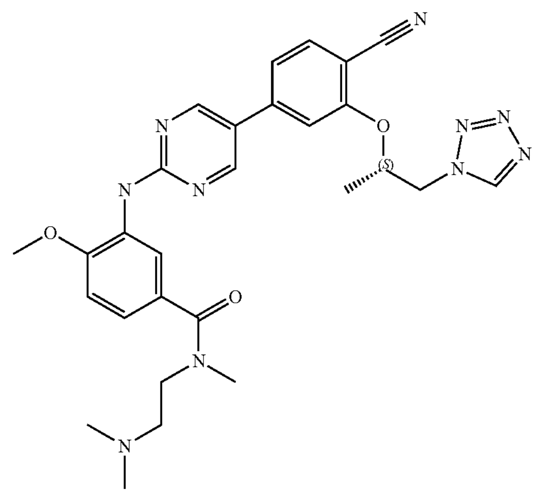 | | 557.3 |
| 263 | 3-((5-(4-cyano-3-(((2S)-1-(1H-tetrazol-1-yl)propan-2-yl)oxy)phenyl)pyrimidin-2-yl)amino)-N-(2-(dimethylamino)ethyl)-4-methoxybenzamide | 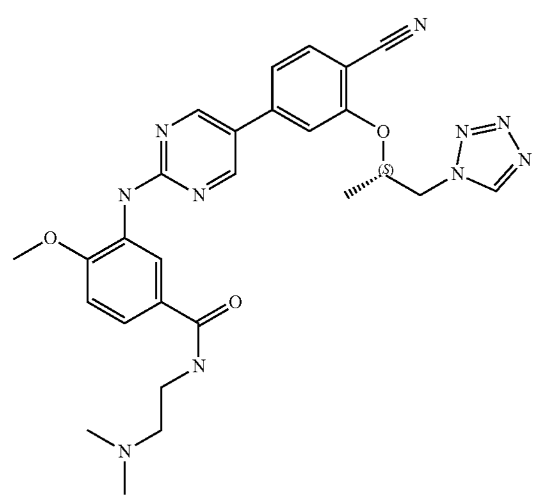 | | 543.3 |

TABLE 1-continued

| Ex. No. | IUPAC NAME | STRUCTURE | ADDITIVE | MS |
|---|---|---|---|---|
| 264 | 3-((5-(4-cyano-3-(((2S)-1-(1H-tetrazol-1-yl)propan-2-yl)oxy)phenyl)pyrimidin-2-yl)amino)-N-(3-(dimethylamino)propyl)-4-methoxy-N-methylbenzamide | 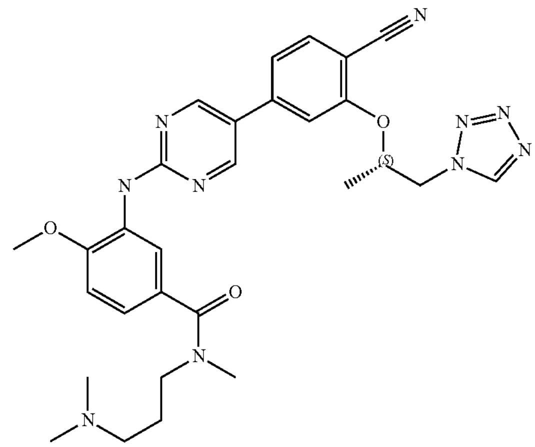 | | 571.3 |
| 265 | 3-((5-(4-cyano-3-(((2S)-1-(1H-tetrazol-1-yl)propan-2-yl)oxy)phenyl)pyrimidin-2-yl)amino)-N-(3-(dimethylamino)propyl)-4-methoxybenzamide | 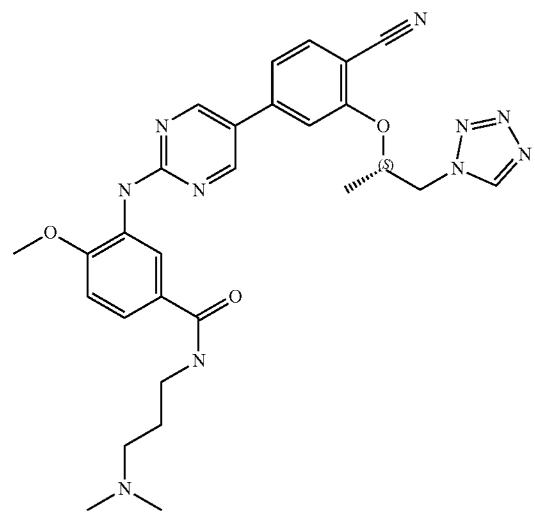 | | 557.3 |
| 266 | 3-((5-(4-cyano-3-(((2S)-1-(1H-tetrazol-1-yl)propan-2-yl)oxy)phenyl)pyrimidin-2-yl)amino)-4-methoxy-N-(oxetan-3-yl)benzamide | 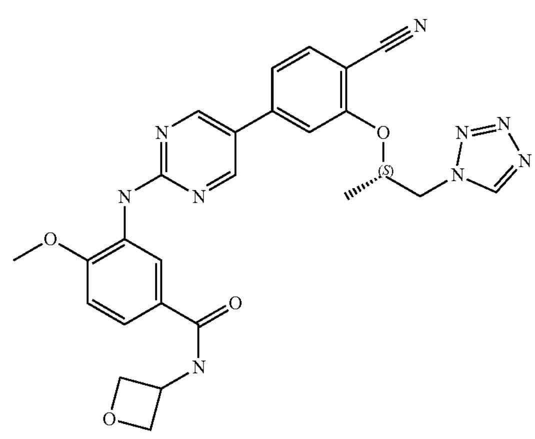 | | 528.2 |

TABLE 1-continued

| Ex. No. | IUPAC NAME | STRUCTURE | ADDITIVE | MS |
|---|---|---|---|---|
| 267 | 4-(2-((2-methoxy-5-(piperidin-1-ylcarbonyl)phenyl)amino)pyrimidin-5-yl)-2-(((2S)-1-(1H-tetrazol-1-yl)propan-2-yl)oxy)benzonitrile | 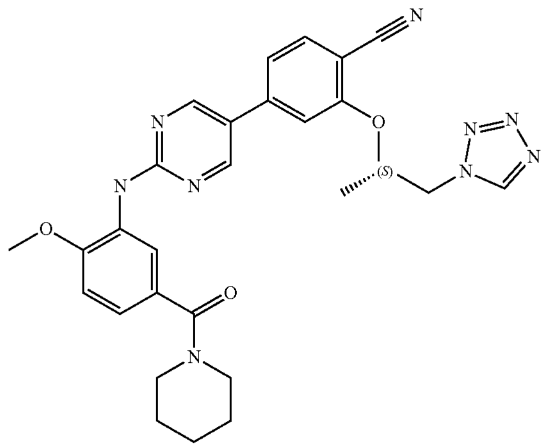 | | 540.3 |
| 268 | 3-((5-(4-cyano-3-(((2S)-1-(1H-tetrazol-1-yl)propan-2-yl)oxy)phenyl)pyrimidin-2-yl)amino)-4-methoxy-N-(oxetan-3-ylmethyl)benzamide | 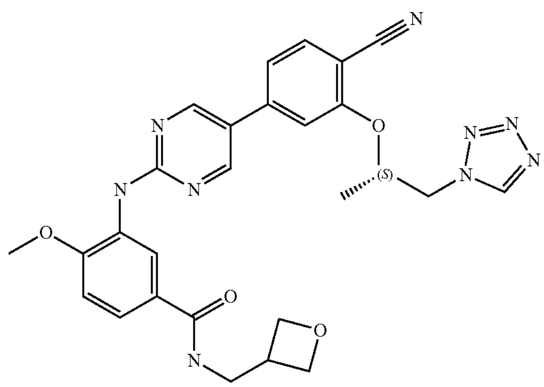 | | 542.2 |
| 269 | 3-((5-(4-cyano-3-(((2S)-1-(1H-tetrazol-1-yl)propan-2-yl)oxy)phenyl)pyrimidin-2-yl)amino)-4-methoxy-N-(tetrahydro-2H-pyran-4-yl)benzamide | 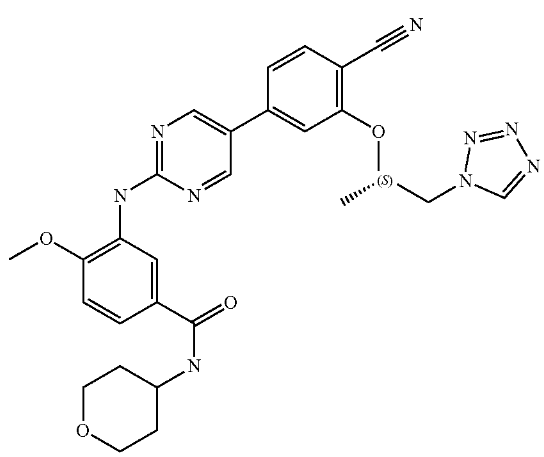 | | 556.2 |

TABLE 1-continued

| Ex. No. | IUPAC NAME | STRUCTURE | ADDITIVE | MS |
|---|---|---|---|---|
| 270 | 4-(2-((2-methoxy-5-((4-methyl-1,4-diazepan-1-yl)carbonyl)phenyl)amino)pyrimidin-5-yl)-2-(((2S)-1-(1H-tetrazol-1-yl)propan-2-yl)oxy)benzonitrile | 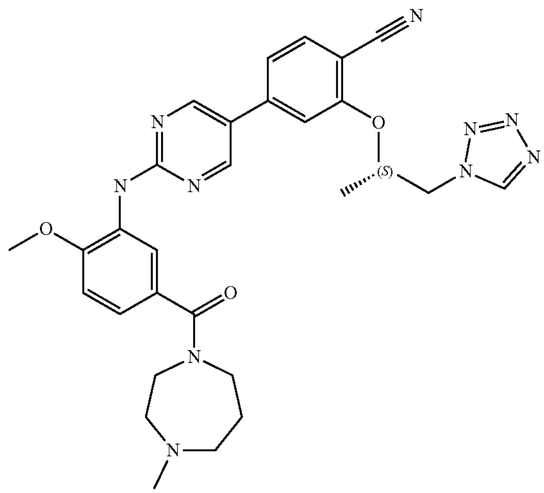 | | 569.3 |
| 271 | 3-((5-(4-cyano-3-(((2S)-1-(1H-tetrazol-1-yl)propan-2-yl)oxy)phenyl)pyrimidin-2-yl)amino)-4-methoxy-N-(tetrahydro-2H-pyran-4-ylmethyl)benzamide | 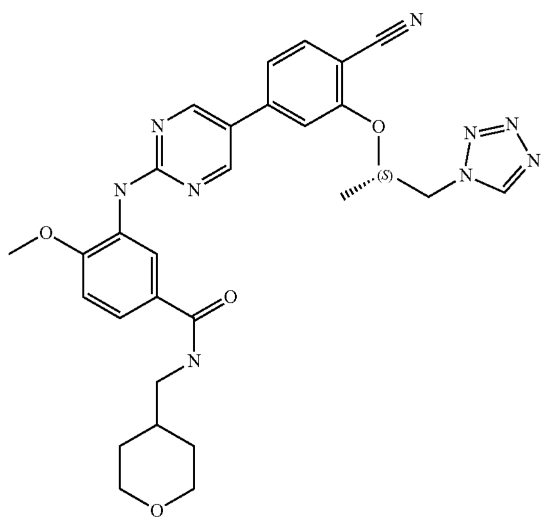 | | 570.2 |
| 272 | 4-(2-((2-methoxy-5-((4-methoxypiperidin-1-yl)carbonyl)phenyl)amino)pyrimidin-5-yl)-2-(((2S)-1-(1H-tetrazol-1-yl)propan-2-yl)oxy)benzonitrile | 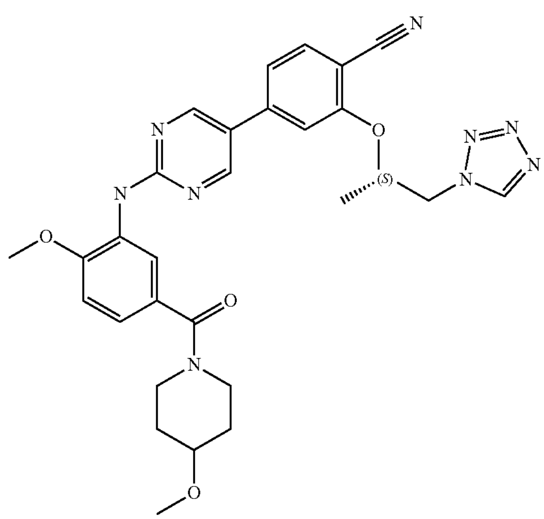 | | 570.2 |

TABLE 1-continued

| Ex. No. | IUPAC NAME | STRUCTURE | ADDITIVE | MS |
|---|---|---|---|---|
| 273 | 3-((5-(4-cyano-3-(((2S)-1-(1H-tetrazol-1-yl)propan-2-yl)oxy)phenyl)pyrimidin-2-yl)amino)-4-methoxy-N-((1-methylpiperidin-4-yl)methyl)benzamide | 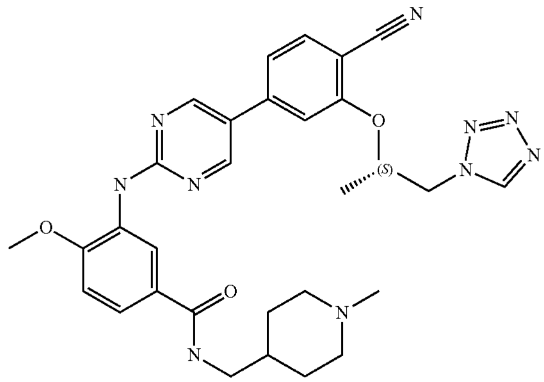 | | 583.3 |
| 274 | 4-(2-((2-methoxy-5-(1,4-oxazepan-4-ylcarbonyl)phenyl)amino)pyrimidin-5-yl)-2-(((2S)-1-(1H-tetrazol-1-yl)propan-2-yl)oxy)benzonitrile | 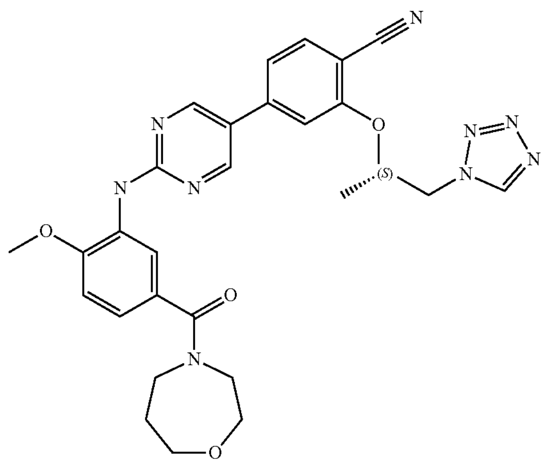 | | 556.2 |
| 275 | N-((1-acetylpiperidin-4-yl)methyl)-3-((5-(4-cyano-3-(((2S)-1-(1H-tetrazol-1-yl)propan-2-yl)oxy)phenyl)pyrimidin-2-yl)amino)-4-methoxybenzamide | 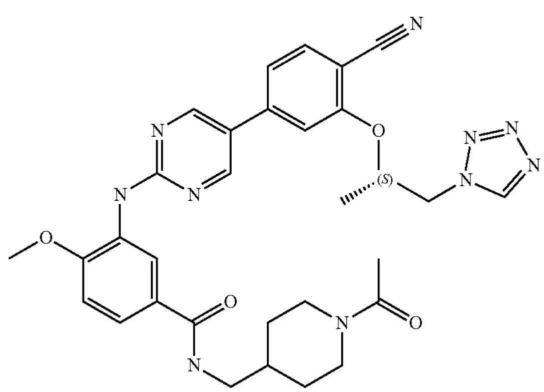 | | 611.2 |

TABLE 1-continued

| Ex. No. | IUPAC NAME | STRUCTURE | ADDITIVE | MS |
|---|---|---|---|---|
| 276 | methyl 4-((3-((5-(4-cyano-3-(((2S)-1-(1H-tetrazol-1-yl)propan-2-yl)oxy)phenyl)pyrimidin-2-yl)amino)-4-methoxybenzoyl)amino)cyclohexanecarboxylate | 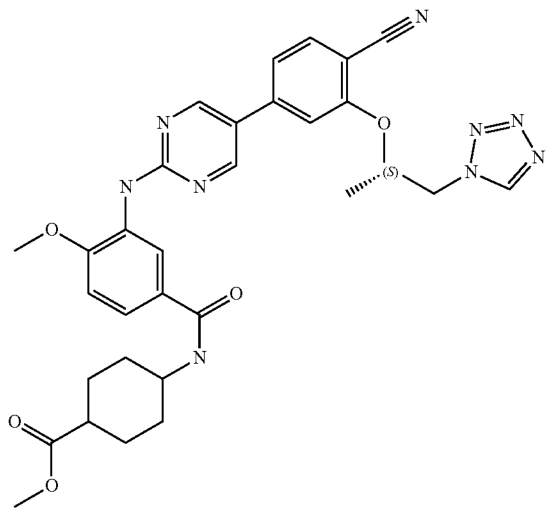 | | 612.2 |
| 277 | 4-((3-((5-(4-cyano-3-(((2S)-1-(1H-tetrazol-1-yl)propan-2-yl)oxy)phenyl)pyrimidin-2-yl)amino)-4-methoxybenzoyl)amino)cyclohexanecarboxylic acid | 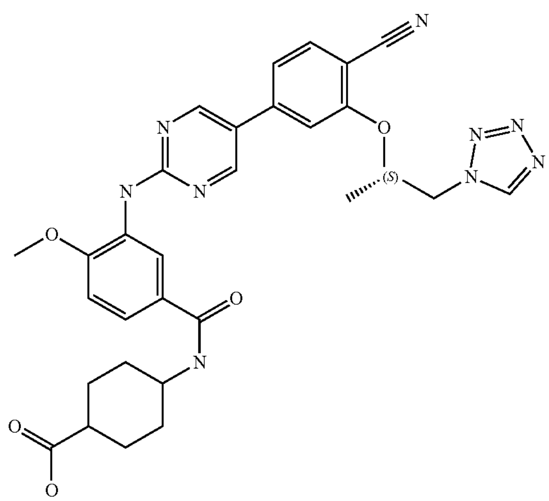 | | 596.1 |
| 278 | 4-(2-((2-methoxy-5-(4-(morpholin-4-yl)cyclohexyl)phenyl)amino)pyrimidin-5-yl)-2-(((2S)-1-(1H-tetrazol-1-yl)propan-2-yl)oxy)benzonitrile | 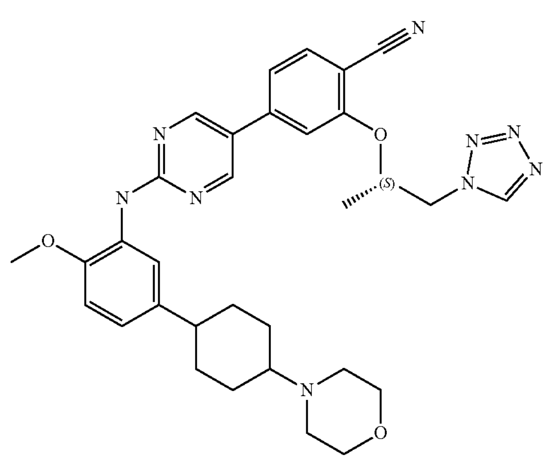 | | 596.3 |

| Ex. No. | IUPAC NAME | STRUCTURE | ADDITIVE | MS |
|---|---|---|---|---|
| 279 | 4-(2-((2-methoxy-4-(trans-4-(morpholin-4-yl)cyclohexyl)phenyl)amino)pyrimidin-5-yl)-2-(((2S)-1-(1H-tetrazol-1-yl)propan-2-yl)oxy)benzonitrile | 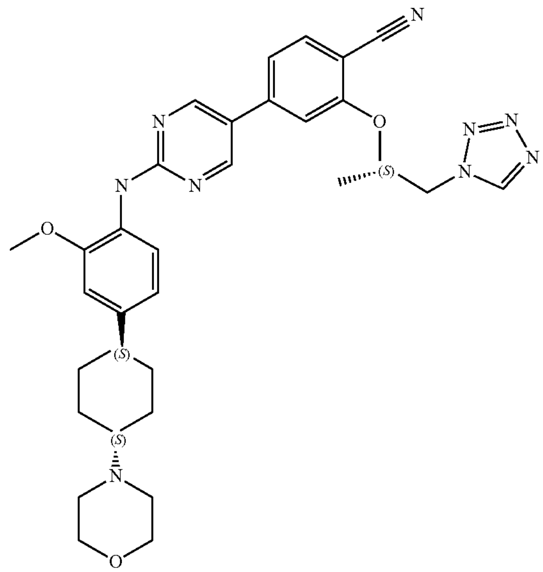 | | 596.2 |
| 280 | 4-(2-((2-methoxy-4-(cis-4-(morpholin-4-yl)cyclohexyl)phenyl)amino)pyrimidin-5-yl)-2-(((2S)-1-(1H-tetrazol-1-yl)propan-2-yl)oxy)benzonitrile | 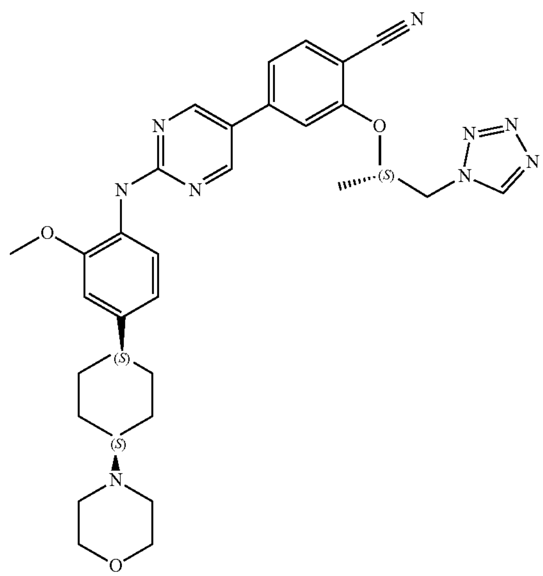 | | 596.3 |
| 281 | 4-(2-((2-methoxy-5-(1,2,3,6-tetrahydropyridin-4-yl)phenyl)amino)pyrimidin-5-yl)-2-(((2S)-1-(1H-tetrazol-1-yl)propan-2-yl)oxy)benzonitrile | 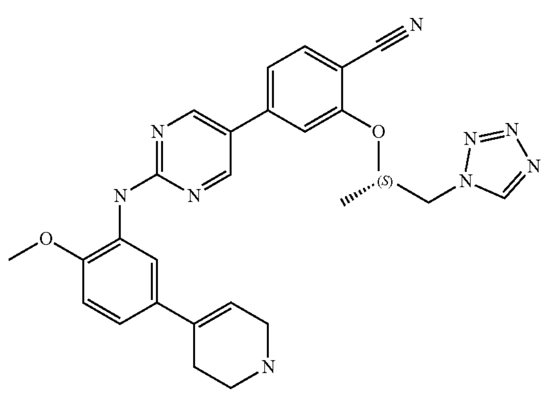 | | 510.2 |

TABLE 1-continued

| Ex. No. | IUPAC NAME | STRUCTURE | ADDITIVE | MS |
|---|---|---|---|---|
| 282 | 4-(2-((2-methoxy-5-(1-(oxetan-3-yl)-1,2,3,6-tetrahydropyridin-4-yl)phenyl)amino)pyrimidin-5-yl)-2-(((2S)-1-(1H-tetrazol-1-yl)propan-2-yl)oxy)benzonitrile | 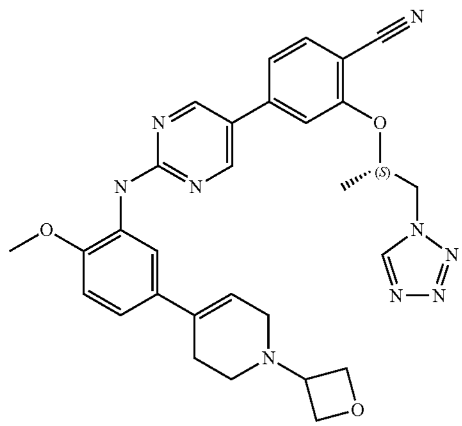 | | 566.2 |
| 283 | 4-(2-((3-(4-(morpholin-4-yl)piperidin-1-yl)phenyl)amino)pyrimidin-5-yl)-2-(((2S)-1-(1H-tetrazol-1-yl)propan-2-yl)oxy)benzonitrile | 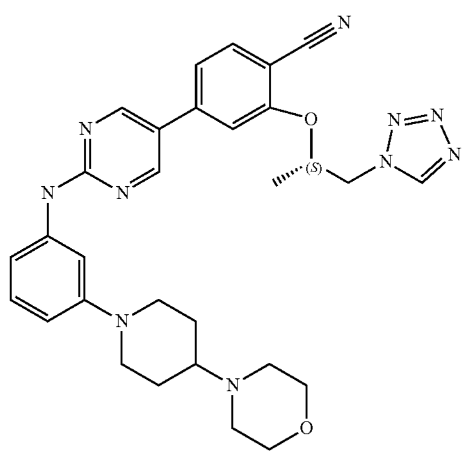 | | 567.2 |

TABLE 1-continued

| Ex. No. | IUPAC NAME | STRUCTURE | ADDITIVE | MS |
|---|---|---|---|---|
| 284 | 3-((5-(4-chloro-3-(((2S)-1-(1H-tetrazol-1-yl)propan-2-yl)oxy)phenyl)pyrimidin-2-yl)amino)-4-methoxy-N-(1-methylpiperidin-4-yl)benzenesulfonamide | 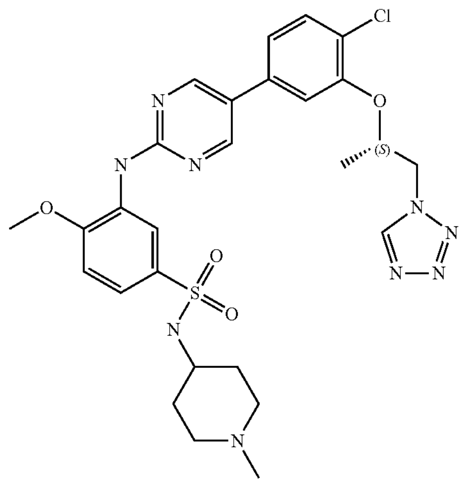 | | 613.9 |
| 285 | 4-(2-((4-methoxy-1-oxo-2-(tetrahydro-2H-pyran-4-yl)-2,3-dihydro-1H-isoindol-5-yl)amino)pyrimidin-5-yl)-2-(((2S)-1-(1H-tetrazol-1-yl)propan-2-yl)oxy)benzonitrile | 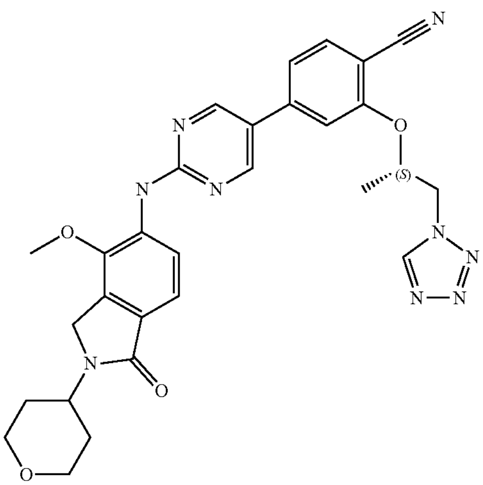 | | 568.1 |
| 286 | 4-(2-((2-chloro-4-(4-(morpholin-4-yl)piperidin-1-yl)phenyl)amino)pyrimidin-5-yl)-2-(((2S)-1-(1H-tetrazol-1-yl)propan-2-yl)oxy)benzonitrile | 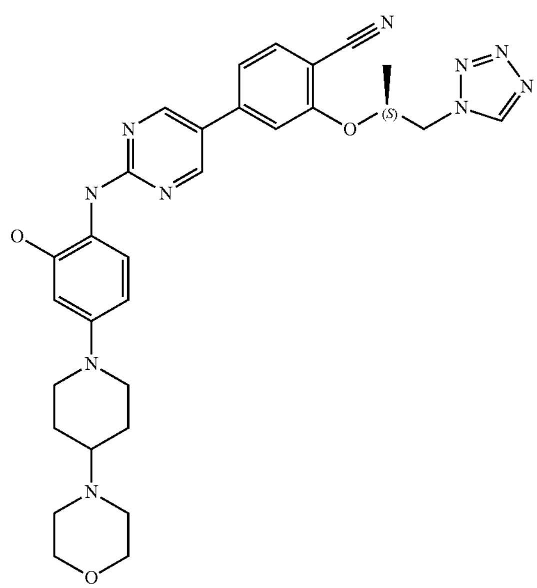 | | 601.2 |

TABLE 1-continued

| Ex. No. | IUPAC NAME | STRUCTURE | ADDITIVE | MS |
|---|---|---|---|---|
| 287 | 4-(2-((5-(1,4-diazabicyclo[3.2.1]oct-4-ylcarbonyl)-2-methoxy-phenyl)amino)pyrimidin-5-yl)-2-(((2S)-1-(1H-tetrazol-1-yl)propan-2-yl)oxy)benzonitrile | 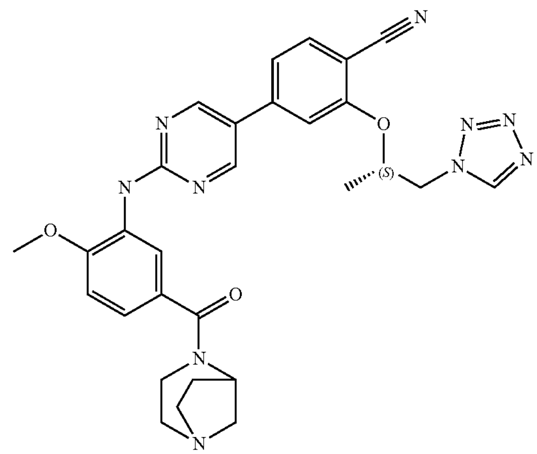 | | 567.2 |
| 288 | 4-(2-((5-(1,4'-bipiperidine-1'-ylsulfonyl)-2-methoxyphenyl)amino)pyrimidin-5-yl)-2-(((2S)-1-(1H-tetrazol-1-yl)propan-2-yl)oxy)benzonitrile | 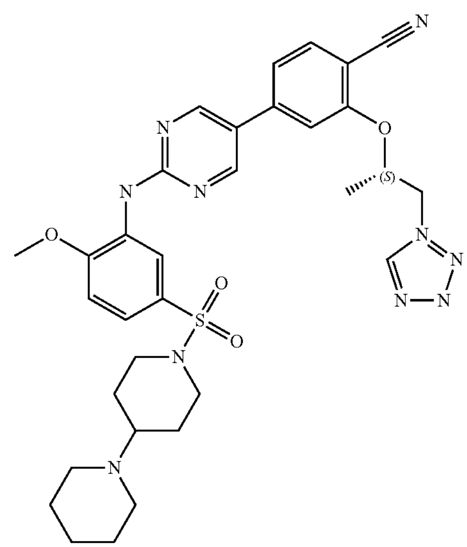 | | 659.2 |
| 289 | tert-butyl 6-((5-(4-chloro-3-(((2S)-1-(1H-tetrazol-1-yl)propan-2-yl)oxy)phenyl)pyrimidin-2-yl)amino)indoline-1-carboxylate | 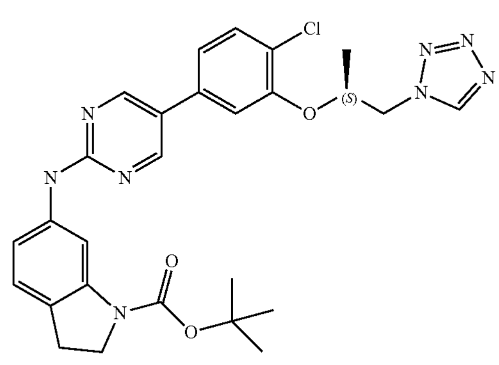 | | 549.2 |

TABLE 1-continued

| Ex. No. | IUPAC NAME | STRUCTURE | ADDITIVE | MS |
|---|---|---|---|---|
| 290 | 4-(2-((2-chloro-5-(4-(morpholin-4-yl)piperidin-1-yl)phenyl)amino)pyrimidin-5-yl)-2-(((2S)-1-(1H-tetrazol-1-yl)propan-2-yl)oxy)benzonitrile | 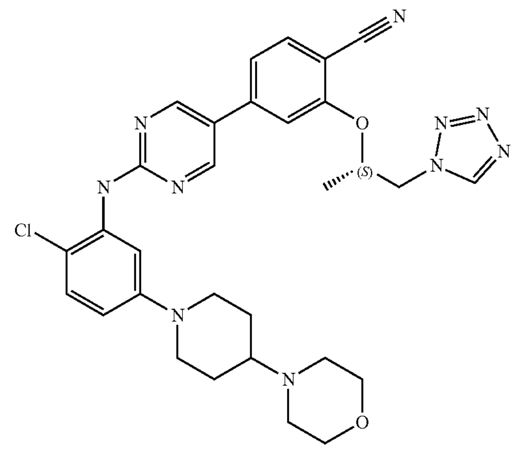 | | 601.2 |
| 291 | 4-(2-((2-(($^2$H$_3$)methyloxy)-5-(4-(morpholin-4-yl)piperidin-1-yl)phenyl)amino)pyrimidin-5-yl)-2-(((2S)-1-(1H-tetrazol-1-yl)propan-2-yl)oxy)benzonitrile | 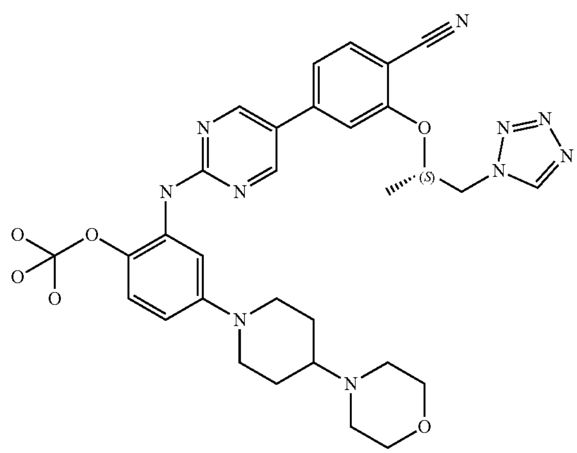 | | 600.3 |
| 292 | 5-(4-chloro-3-(((2S)-1-(1H-tetrazol-1-yl)propan-2-yl)oxy)phenyl)-N-(2-methoxyphenyl)pyrimidin-2-amine | 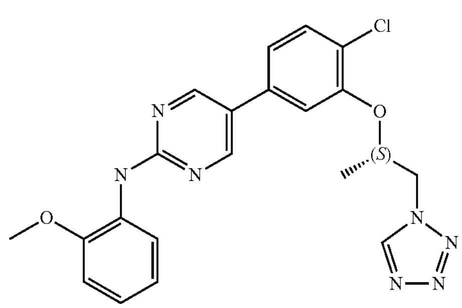 | | 438.1 |
| 293 | N-(5-(4-chloro-3-(((2S)-1-(1H-tetrazol-1-yl)propan-2-yl)oxy)phenyl)pyrimidin-2-yl)indolin-6-amine hydrochloride | 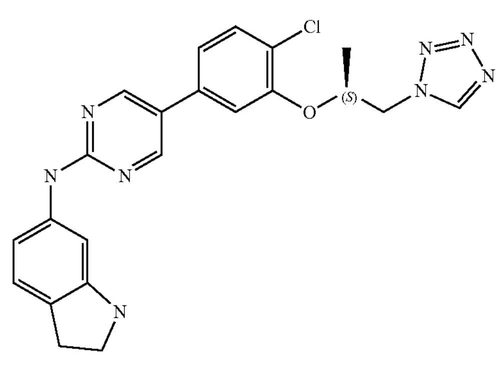 | HCl | 449.1 |

TABLE 1-continued

| Ex. No. | IUPAC NAME | STRUCTURE | ADDITIVE | MS |
|---|---|---|---|---|
| 294 | N-(5-(4-chloro-3-(((2S)-1-(1H-tetrazol-1-yl)propan-2-yl)oxy)phenyl)pyrimidin-2-yl)-1-(1-methylpiperidin-4-yl)indolin-6-amine | 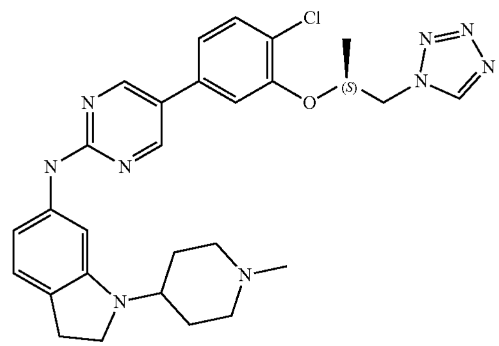 | | 546.2 |
| 295 | N-(5-(4-chloro-3-(((2S)-1-(1H-tetrazol-1-yl)propan-2-yl)oxy)phenyl)pyrimidin-2-yl)-1-((1-methylpiperidin-4-yl)methyl)indolin-6-amine | 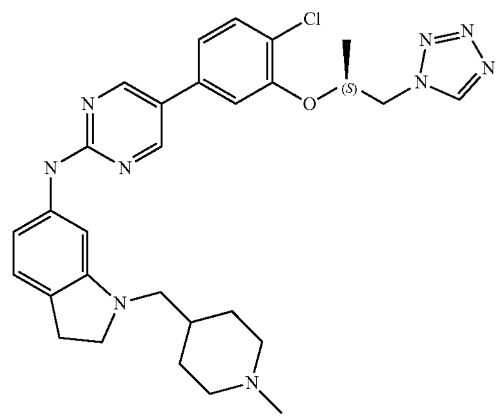 | | 560.2 |
| 296 | 4-(2-((5-(1,4'-bipiperidine-1'-ylsulfonyl)-2,3-dihydro-1-benzofuran-7-yl)amino)pyrimidin-5-yl)-2-(((2S)-1-(1H-tetrazol-1-yl)propan-2-yl)oxy)benzonitrile | 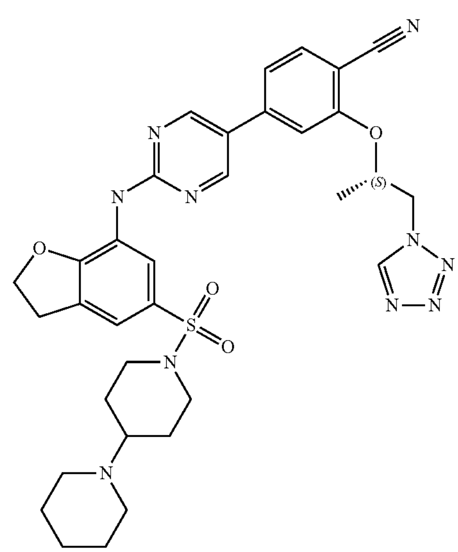 | | 671.3 |

TABLE 1-continued

| Ex. No. | IUPAC NAME | STRUCTURE | ADDITIVE | MS |
|---|---|---|---|---|
| 297 | 2-((5-(4-chloro-3-(((2S)-1-(1H-tetrazol-1-yl)propan-2-yl)oxy)phenyl)pyrimidin-2-yl)amino)-4-(4-(morpholin-4-yl)piperidin-1-yl)benzamide | 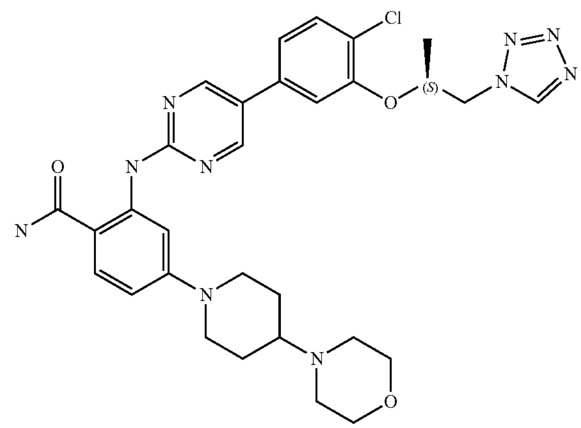 | | 619.2 |
| 298 | 5-((5-(4-chloro-3-(((2S)-1-(1H-tetrazol-1-yl)propan-2-yl)oxy)phenyl)pyrimidin-2-yl)amino)-4-methoxy-2-(tetrahydro-2H-pyran-4-yl)isoindolin-1-one | 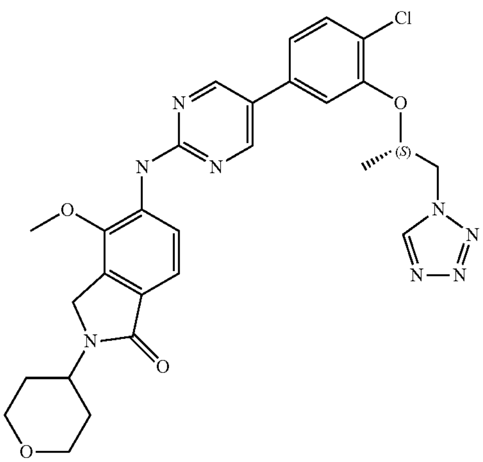 | | 577.1 |
| 299 | 5-(4-chloro-3-(((2S)-1-(1H-tetrazol-1-yl)propan-2-yl)oxy)phenyl)-N-phenylpyrimidin-2-amine | 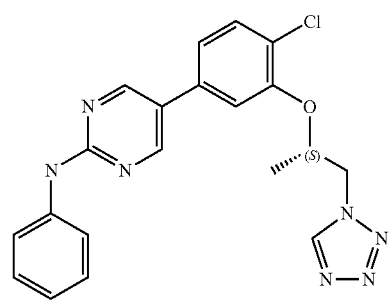 | | 408 |
| 300 | 5-(4-chloro-3-(((2S)-1-(1H-tetrazol-1-yl)propan-2-yl)oxy)phenyl)-N-(pyridin-4-yl)pyrimidin-2-amine | 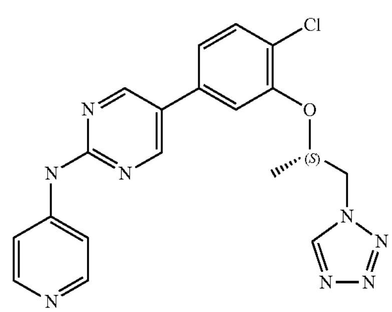 | | 409 |

TABLE 1-continued

| Ex. No. | IUPAC NAME | STRUCTURE | ADDITIVE | MS |
|---|---|---|---|---|
| 301 | 5-(4-chloro-3-(((2S)-1-(1H-tetrazol-1-yl)propan-2-yl)oxy)phenyl)-N-(pyridin-3-yl)pyrimidin-2-amine | 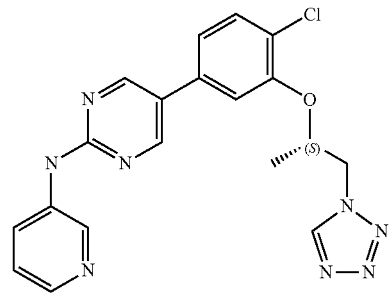 | | 407 |
| 302 | N-(5-(4-chloro-3-(((2S)-1-(1H-tetrazol-1-yl)propan-2-yl)oxy)phenyl)pyrimidin-2-yl)pyridazin-4-amine | 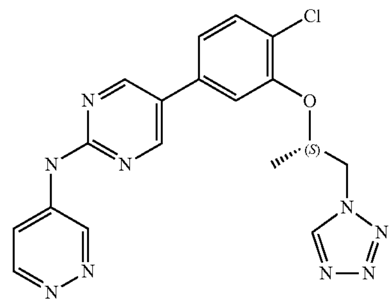 | | 410.1 |
| 303 | 5-(4-chloro-3-(((2S)-1-(1H-tetrazol-1-yl)propan-2-yl)oxy)phenyl)-N-(pyrimidin-5-yl)pyrimidin-2-amine | 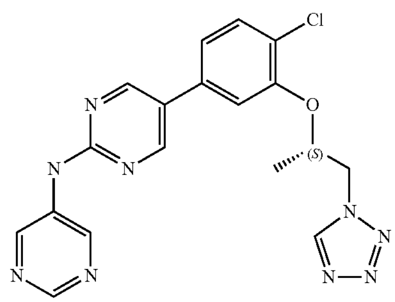 | | 408.1 |
| 304 | 5-(4-chloro-3-(((2S)-1-(1H-tetrazol-1-yl)propan-2-yl)oxy)phenyl)-N-(2-methylphenyl)pyrimidin-2-amine | 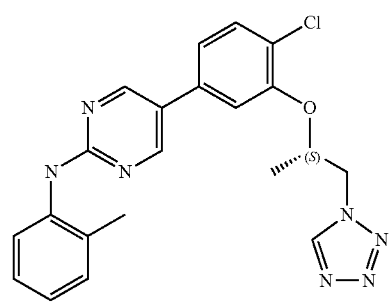 | | 420.1 |
| 305 | 5-(4-chloro-3-(((2S)-1-(1H-tetrazol-1-yl)propan-2-yl)oxy)phenyl)-N-(2-ethylphenyl)pyrimidin-2-amine | 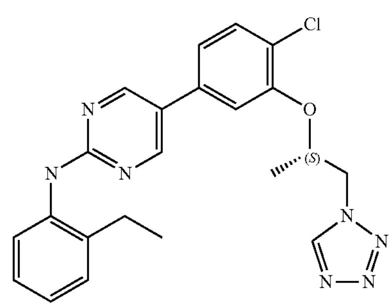 | | 434.1 |

TABLE 1-continued

| Ex. No. | IUPAC NAME | STRUCTURE | ADDITIVE | MS |
|---|---|---|---|---|
| 306 | (2-((5-(4-chloro-3-(((2S)-1-(1H-tetrazol-1-yl)propan-2-yl)oxy)phenyl)pyrimidin-2-yl)amino)phenyl)methanol | 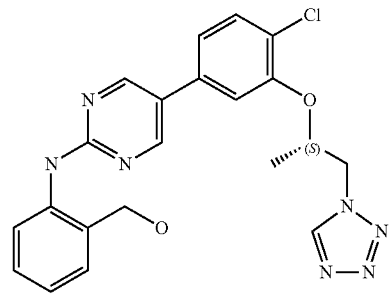 | | 438 |
| 307 | 5-(4-chloro-3-(((2S)-1-(1H-tetrazol-1-yl)propan-2-yl)oxy)phenyl)-N-(3-methoxyphenyl)pyrimidin-2-amine | 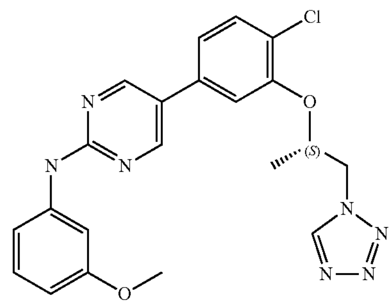 | | 436.1 |
| 308 | 5-(4-chloro-3-(((2S)-1-(1H-tetrazol-1-yl)propan-2-yl)oxy)phenyl)-N-(3-methoxypyridin-4-yl)pyrimidin-2-amine | 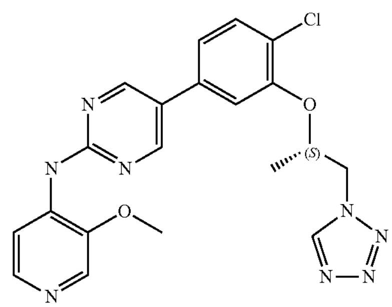 | | 439.1 |
| 309 | 5-(4-chloro-3-(((2S)-1-(1H-tetrazol-1-yl)propan-2-yl)oxy)phenyl)-N-(2-methoxypyridin-3-yl)pyrimidin-2-amine | 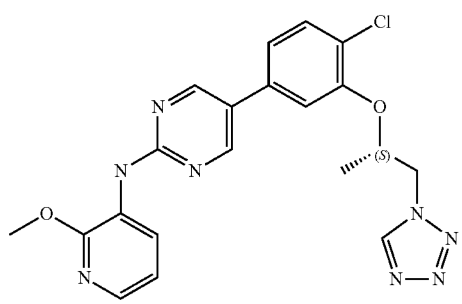 | | 437.1 |
| 310 | 5-(4-chloro-3-(((2S)-1-(1H-tetrazol-1-yl)propan-2-yl)oxy)phenyl)-N-(2,3-dihydro-1H-inden-4-yl)pyrimidin-2-amine | 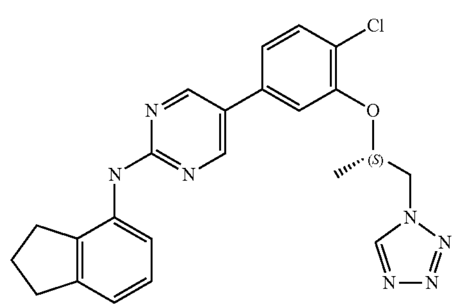 | | 448.1 |

TABLE 1-continued

| Ex. No. | IUPAC NAME | STRUCTURE | ADDITIVE | MS |
|---|---|---|---|---|
| 311 | 5-(4-chloro-3-(((2S)-1-(1H-tetrazol-1-yl)propan-2-yl)oxy)phenyl)-N-(2-cyclopropylphenyl)pyrimidin-2-amine | 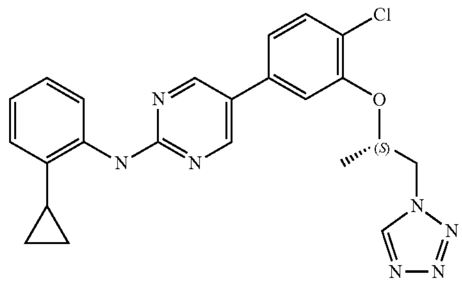 | | 448.1 |
| 312 | 5-(4-chloro-3-(((2S)-1-(1H-tetrazol-1-yl)propan-2-yl)oxy)phenyl)-N-(2,3-dihydro-1-benzofuran-7-yl)pyrimidin-2-amine | 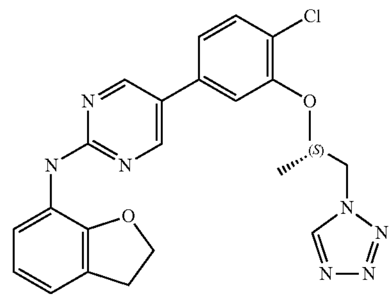 | | 450 |
| 313 | 5-(4-chloro-3-(((2S)-1-(1H-tetrazol-1-yl)propan-2-yl)oxy)phenyl)-N-(2-propylphenyl)pyrimidin-2-amine | 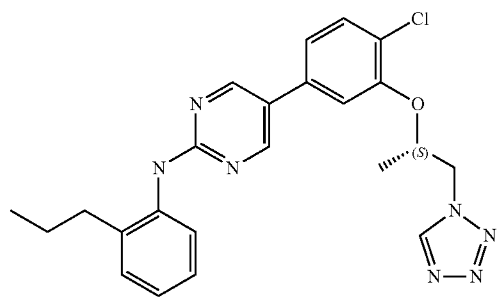 | | 450.1 |
| 314 | 5-(4-chloro-3-(((2S)-1-(1H-tetrazol-1-yl)propan-2-yl)oxy)phenyl)-N-(2-isopropylphenyl)pyrimidin-2-amine | 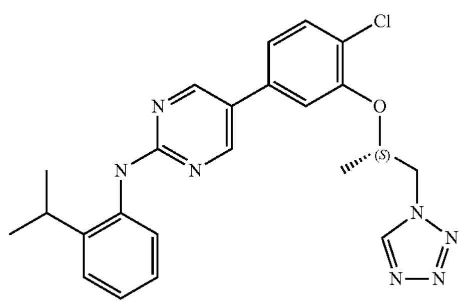 | | 448.1 |
| 315 | 5-(4-chloro-3-(((2S)-1-(1H-tetrazol-1-yl)propan-2-yl)oxy)phenyl)-N-(2-methoxy-5-methylphenyl)pyrimidin-2-amine | 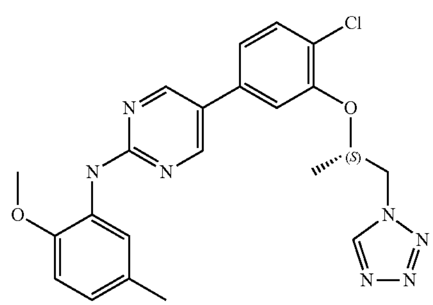 | | 452.1 |

TABLE 1-continued

| Ex. No. | IUPAC NAME | STRUCTURE | ADDITIVE | MS |
|---|---|---|---|---|
| 316 | 5-(4-chloro-3-(((2S)-1-(1H-tetrazol-1-yl)propan-2-yl)oxy)phenyl)-N-(2-methoxy-4-methylphenyl)pyrimidin-2-amine | 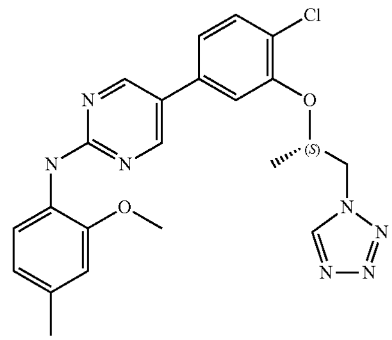 | | 452.1 |
| 317 | 5-(4-chloro-3-(((2S)-1-(1H-tetrazol-1-yl)propan-2-yl)oxy)phenyl)-N-(2-ethoxyphenyl)pyrimidin-2-amine | 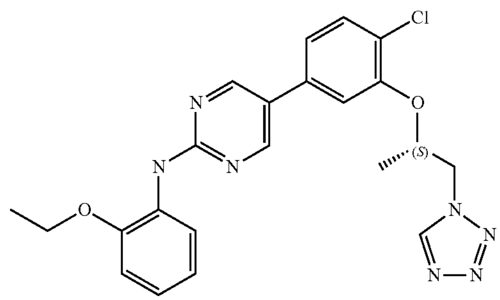 | | 452.1 |
| 318 | 5-(4-chloro-3-(((2S)-1-(1H-tetrazol-1-yl)propan-2-yl)oxy)phenyl)-N-(2-methoxy-3-methylphenyl)pyrimidin-2-amine | 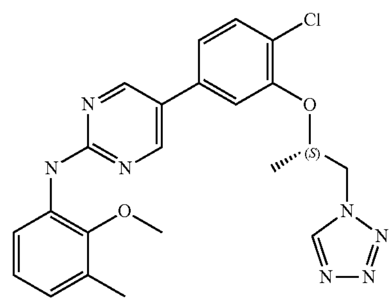 | | 452.1 |
| 320 | 5-(4-chloro-3-(((2S)-1-(1H-tetrazol-1-yl)propan-2-yl)oxy)phenyl)-N-(2-(methylsulfanyl)phenyl)pyrimidin-2-amine | 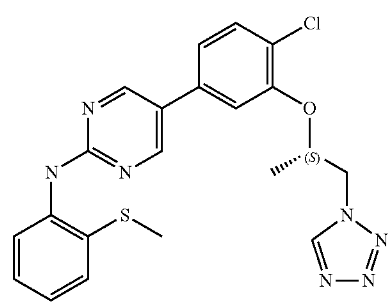 | | 454 |
| 321 | 5-(4-chloro-3-(((2S)-1-(1H-tetrazol-1-yl)propan-2-yl)oxy)phenyl)-N-(5-fluoro-2-methoxyphenyl)pyrimidin-2-amine | 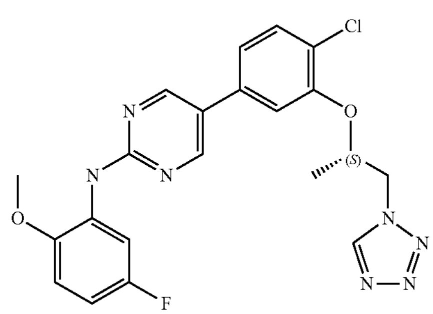 | | 454.1 |

TABLE 1-continued

| Ex. No. | IUPAC NAME | STRUCTURE | ADDITIVE | MS |
|---|---|---|---|---|
| 322 | 5-(4-chloro-3-(((2S)-1-(1H-tetrazol-1-yl)propan-2-yl)oxy)phenyl)-N-(3-fluoro-2-methoxyphenyl)pyrimidin-2-amine | 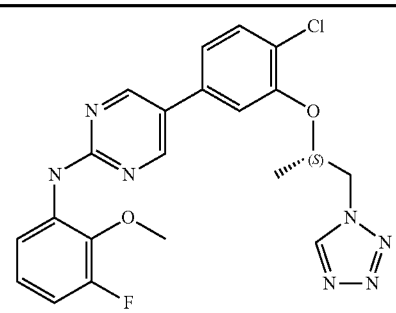 | | 456 |
| 323 | 5-(4-chloro-3-(((2S)-1-(1H-tetrazol-1-yl)propan-2-yl)oxy)phenyl)-N-(2-(difluoromethyl)phenyl)pyrimidin-2-amine | 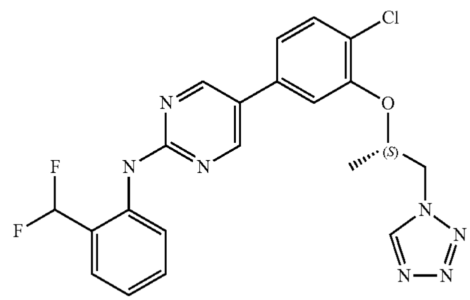 | | 458.1 |
| 324 | N-(2-tert-butylphenyl)-5-(4-chloro-3-(((2S)-1-(1H-tetrazol-1-yl)propan-2-yl)oxy)phenyl)pyrimidin-2-amine | 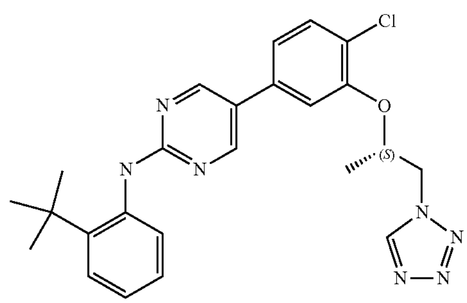 | | 464.1 |
| 325 | 5-(4-chloro-3-(((2S)-1-(1H-tetrazol-1-yl)propan-2-yl)oxy)phenyl)-N-(2,4-dimethoxyphenyl)pyrimidin-2-amine | 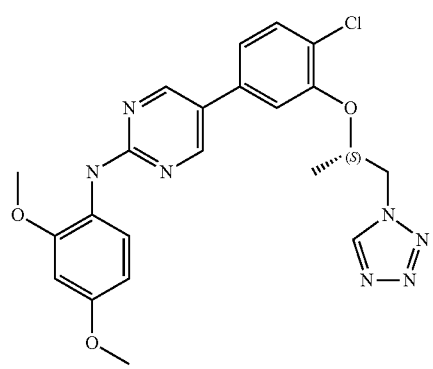 | | 468.1 |
| 326 | 5-(4-chloro-3-(((2S)-1-(1H-tetrazol-1-yl)propan-2-yl)oxy)phenyl)-N-(2,3-dimethoxyphenyl)pyrimidin-2-amine | 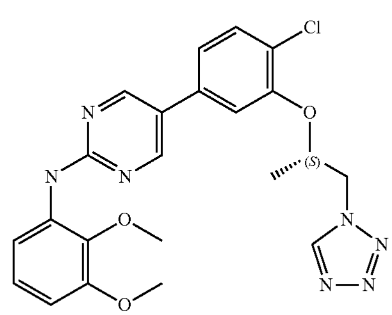 | | 468.1 |

TABLE 1-continued

| Ex. No. | IUPAC NAME | STRUCTURE | ADDITIVE | MS |
|---|---|---|---|---|
| 327 | 5-(4-chloro-3-(((2S)-1-(1H-tetrazol-1-yl)propan-2-yl)oxy)phenyl)-N-(2,5-dimethoxyphenyl)pyrimidin-2-amine | 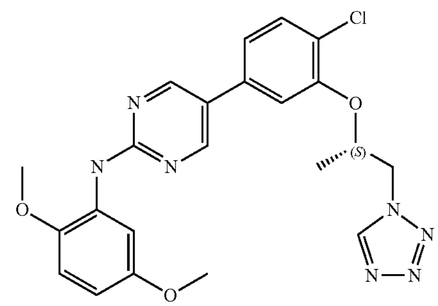 | | 468.1 |
| 328 | 5-(4-chloro-3-(((2S)-1-(1H-tetrazol-1-yl)propan-2-yl)oxy)phenyl)-N-(2-(difluoromethoxy)phenyl)pyrimidin-2-amine | 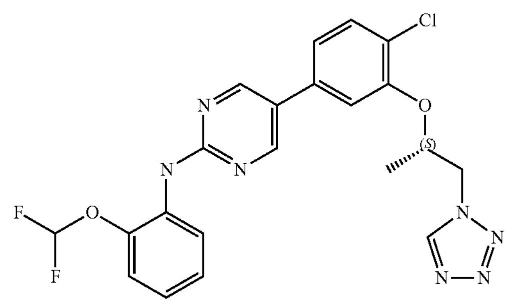 | | 474 |
| 329 | N-(5-(4-chloro-3-(((2S)-1-(1H-tetrazol-1-yl)propan-2-yl)oxy)phenyl)pyrimidin-2-yl)-2-methyl-1,2,3,4-tetrahydroisoquinolin-7-amine | 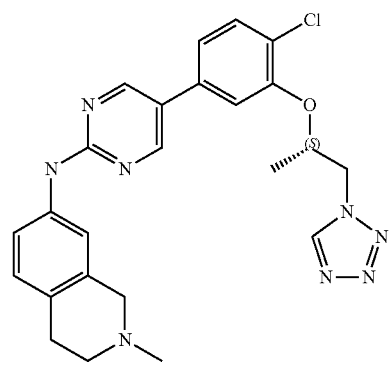 | | 477.2 |
| 330 | 6-((5-(4-chloro-3-(((2S)-1-(1H-tetrazol-1-yl)propan-2-yl)oxy)phenyl)pyrimidin-2-yl)amino)-2H-1,4-benzoxazin-3(4H)-one | 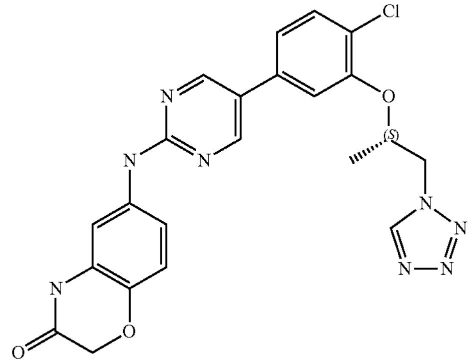 | | 477.1 |

TABLE 1-continued

| Ex. No. | IUPAC NAME | STRUCTURE | ADDITIVE | MS |
|---|---|---|---|---|
| 331 | 5-(4-chloro-3-(((2S)-1-(1H-tetrazol-1-yl)propan-2-yl)oxy)phenyl)-N-(4-(1-methyl-1H-pyrazol-4-yl)phenyl)pyrimidin-2-amine | 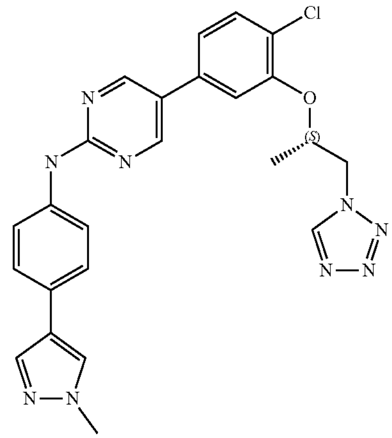 | | 486.1 |
| 332 | 5-(4-chloro-3-(((2S)-1-(1H-tetrazol-1-yl)propan-2-yl)oxy)phenyl)-N-(4-(3-methyl-1H-pyrazol-1-yl)phenyl)pyrimidin-2-amine | 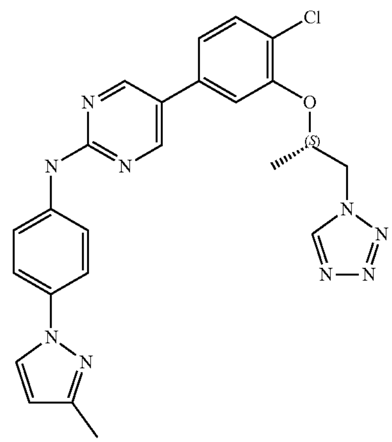 | | 488.1 |
| 333 | 5-(4-chloro-3-(((2S)-1-(1H-tetrazol-1-yl)propan-2-yl)oxy)phenyl)-N-(4-(1H-pyrazol-1-ylmethyl)phenyl)pyrimidin-2-amine | 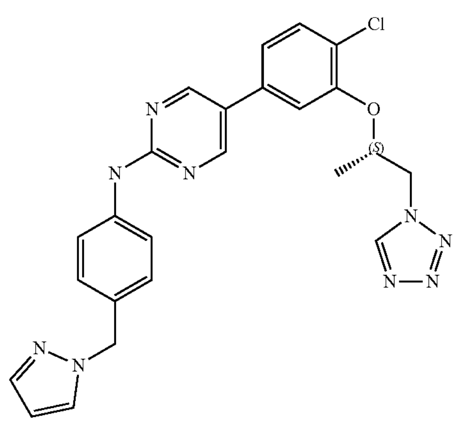 | | 486.2 |

TABLE 1-continued

| Ex. No. | IUPAC NAME | STRUCTURE | ADDITIVE | MS |
|---|---|---|---|---|
| 334 | 8-((5-(4-chloro-3-(((2S)-1-(1H-tetrazol-1-yl)propan-2-yl)oxy)phenyl)pyrimidin-2-yl)amino)-1,3,4,5-tetrahydro-2H-1-benzazepin-2-one | 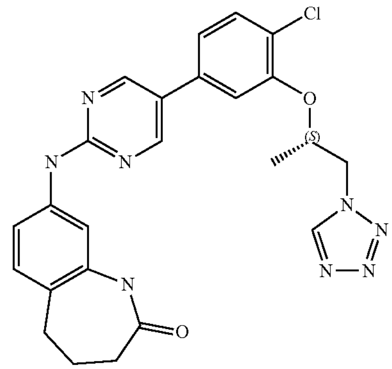 | | 489.1 |
| 335 | 5-(4-chloro-3-(((2S)-1-(1H-tetrazol-1-yl)propan-2-yl)oxy)phenyl)-N-(2-methoxy-5-(methylsulfonyl)phenyl)pyrimidin-2-amine | 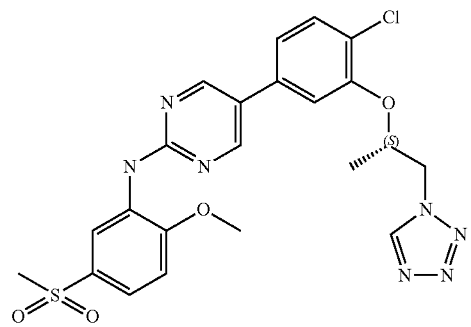 | | 514 |
| 336 | tert-butyl 7-((5-(4-chloro-3-(((2S)-1-(1H-tetrazol-1-yl)propan-2-yl)oxy)phenyl)pyrimidin-2-yl)amino)-3,4-dihydroisoquinoline-2(1H)-carboxylate | 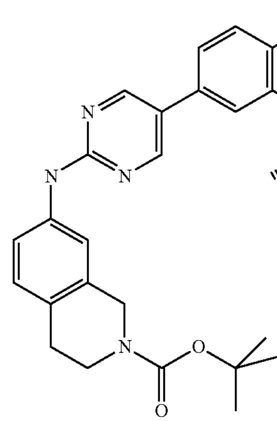 | | 563.1 |

TABLE 1-continued

| Ex. No. | IUPAC NAME | STRUCTURE | ADDITIVE | MS |
|---|---|---|---|---|
| 337 | tert-butyl 6-((5-(4-chloro-3-(((2S)-1-(1H-tetrazol-1-yl)propan-2-yl)oxy)phenyl)pyrimidin-2-yl)amino)-3,4-dihydroisoquinoline-2(1H)-carboxylate | 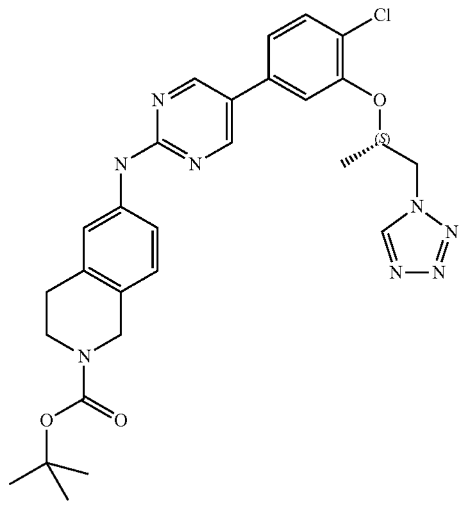 | | 563.1 |
| 338 | N-(5-(4-chloro-3-(((2S)-1-(1H-tetrazol-1-yl)propan-2-yl)oxy)phenyl)pyrimidin-2-yl)-1,2,3,4-tetrahydroisoquinolin-7-amine trifluoroacetate | 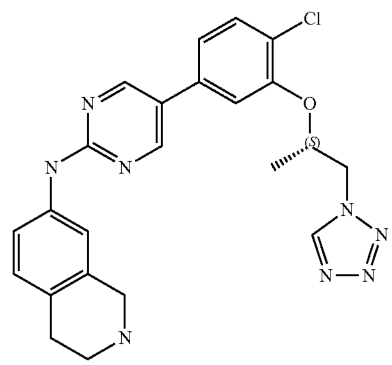 | CF$_3$COOH | 463.1 |
| 339 | N-(5-(4-chloro-3-(((2S)-1-(1H-tetrazol-1-yl)propan-2-yl)oxy)phenyl)pyrimidin-2-yl)-1,2,3,4-tetrahydroisoquinolin-6-amine trifluoroacetate | 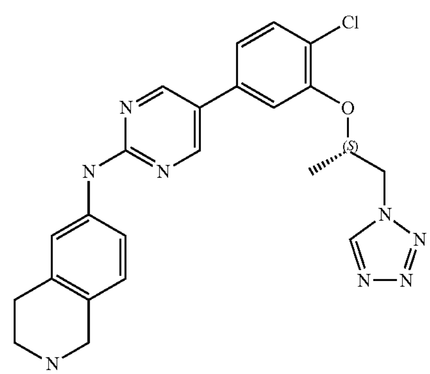 | CF$_3$COOH | 463.1 |
| 340 | 5-(4-chloro-3-(((2S)-1-(1H-tetrazol-1-yl)propan-2-yl)oxy)phenyl)-N-(pyridin-2-yl)pyrimidin-2-amine | 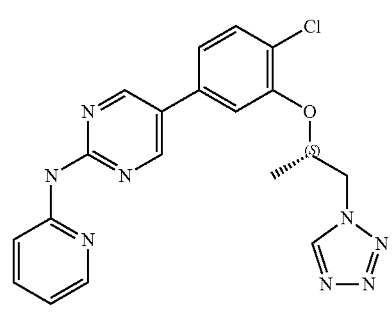 | | 409 |

TABLE 1-continued

| Ex. No. | IUPAC NAME | STRUCTURE | ADDITIVE | MS |
|---|---|---|---|---|
| 341 | 5-(4-chloro-3-(((2S)-1-(1H-tetrazol-1-yl)propan-2-yl)oxy)phenyl)-N-(pyrimidin-4-yl)pyrimidin-2-amine | 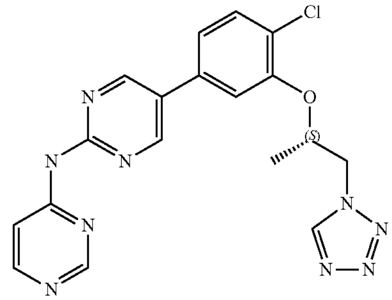 | | 410.1 |
| 342 | 5-(4-chloro-3-(((2S)-1-(1H-tetrazol-1-yl)propan-2-yl)oxy)phenyl)-N-(pyrazin-2-yl)pyrimidin-2-amine | 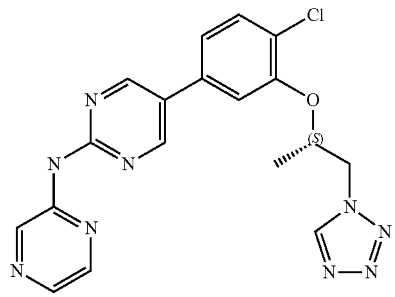 | | 410.1 |
| 343 | N-(5-(4-chloro-3-(((2S)-1-(1H-tetrazol-1-yl)propan-2-yl)oxy)phenyl)pyrimidin-2-yl)pyridazin-3-amine | 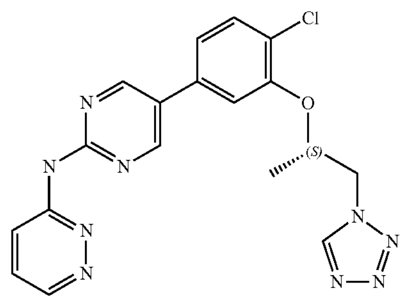 | | 410.1 |
| 344 | 5-(4-chloro-3-(((2S)-1-(1H-tetrazol-1-yl)propan-2-yl)oxy)phenyl)-N-(2-fluorophenyl)pyrimidin-2-amine | 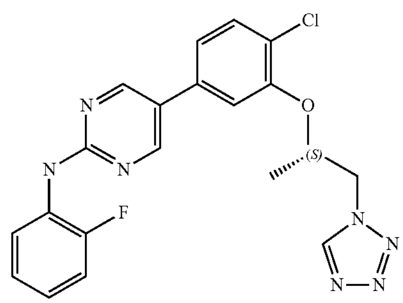 | | 424 |
| 345 | N-(2-chlorophenyl)-5-(4-chloro-3-(((2S)-1-(1H-tetrazol-1-yl)propan-2-yl)oxy)phenyl)pyrimidin-2-amine | 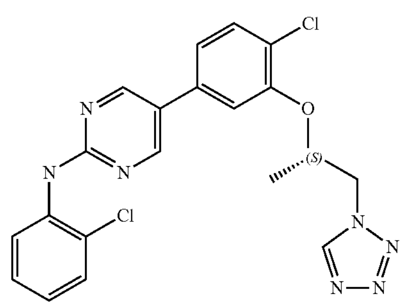 | | 442 |

TABLE 1-continued

| Ex. No. | IUPAC NAME | STRUCTURE | ADDITIVE | MS |
|---|---|---|---|---|
| 346 | 5-(4-chloro-3-(((2S)-1-(1H-tetrazol-1-yl)propan-2-yl)oxy)phenyl)-N-(2-(trifluoromethyl)phenyl)pyrimidin-2-amine | 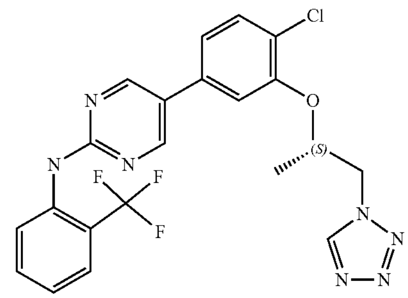 | | 474 |
| 347 | 5-(4-chloro-3-(((2S)-1-(1H-tetrazol-1-yl)propan-2-yl)oxy)phenyl)-N-(2-(trifluoromethoxy)phenyl)pyrimidin-2-amine | 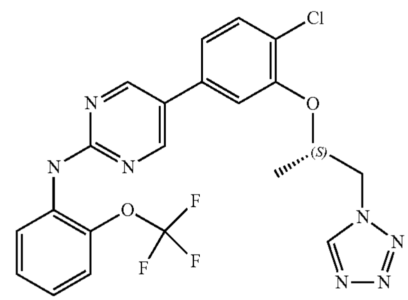 | | 490.1 |
| 348 | N-(5-(4-chloro-3-(((2S)-1-(1H-tetrazol-1-yl)propan-2-yl)oxy)phenyl)pyrimidin-2-yl)-1,3-benzothiazol-2-amine | 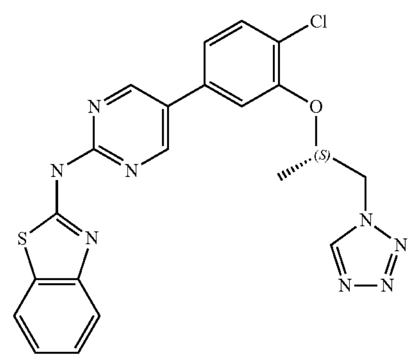 | | 465 |
| 349 | N-(5-(4-chloro-3-(((2S)-1-(1H-tetrazol-1-yl)propan-2-yl)oxy)phenyl)pyrimidin-2-yl)-1H-benzimidazol-2-amine | 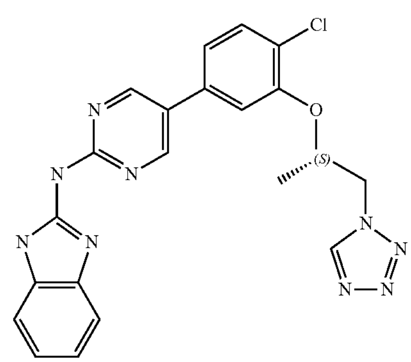 | | 448.1 |

TABLE 1-continued

| Ex. No. | IUPAC NAME | STRUCTURE | ADDITIVE | MS |
|---|---|---|---|---|
| 350 | N-(5-(4-chloro-3-(((2S)-1-(1H-tetrazol-1-yl)propan-2-yl)oxy)phenyl)pyrimidin-2-yl)-1-methyl-1H-benzimidazol-2-amine | 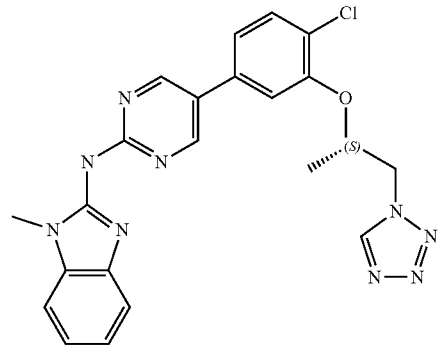 | | 462.1 |
| 351 | 4-(2-((2-methoxy-4-(4-(tetrahydro-2H-pyran-4-yl)piperazin-1-yl)phenyl)amino)pyrimidin-5-yl)-2-(((2S)-1-(1H-tetrazol-1-yl)propan-2-yl)oxy)benzonitrile | 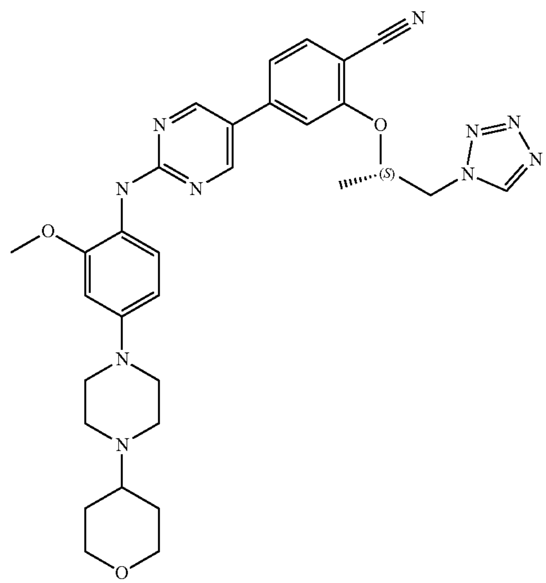 | | 597.3 |
| 352 | 5-(4-chloro-3-(((2S)-1-(1H-tetrazol-1-yl)propan-2-yl)oxy)phenyl)-N-(2-methoxy-4-(4-(tetrahydro-2H-pyran-4-yl)piperazin-1-yl)phenyl)pyrimidin-2-amine | 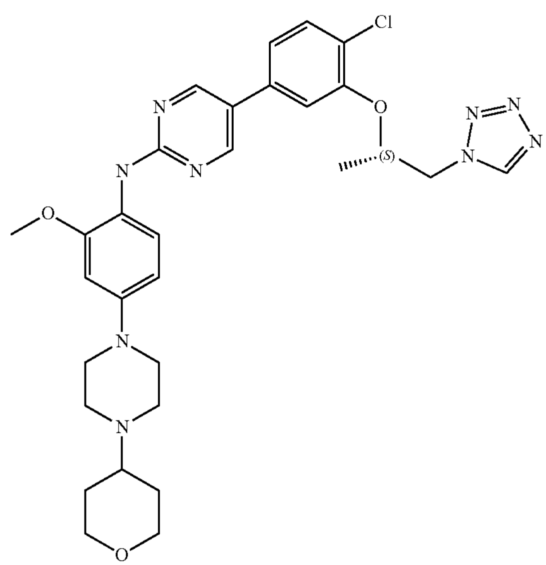 | | 606.2 |

| Ex. No. | IUPAC NAME | STRUCTURE | ADDITIVE | MS |
|---|---|---|---|---|
| 353 | 4-(2-((2-(difluoromethyl)-4-(4-(morpholin-4-yl)piperidin-1-yl)phenyl)amino)pyrimidin-5-yl)-2-(((2S)-1-(1H-tetrazol-1-yl)propan-2-yl)oxy)benzonitrile | 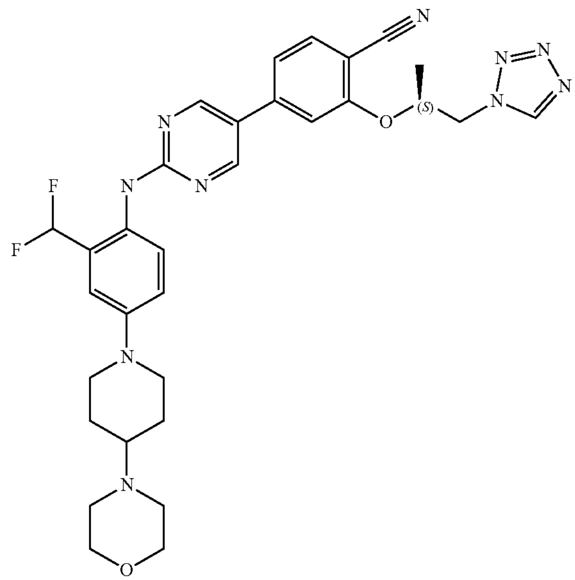 | | 617.2 |
| 354 | 5-(4-chloro-3-((1-(1H-tetrazol-1-yl)propan-2-yl)oxy)phenyl)-N-(2-methoxy-4-(4-(morpholin-4-yl)piperidin-1-yl)phenyl)pyrimidin-2-amine | 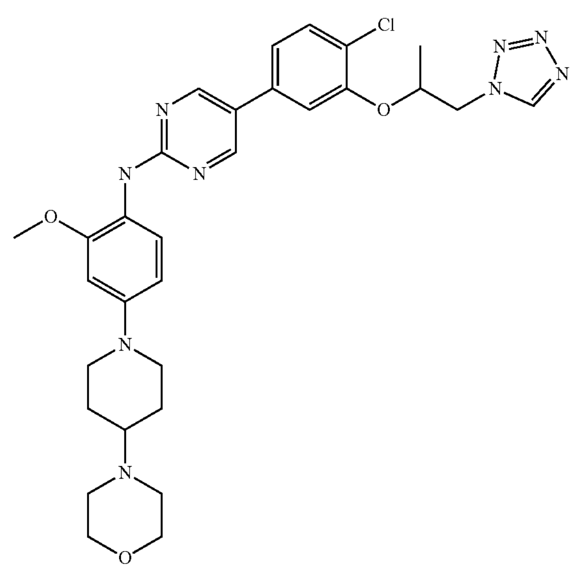 [SMILES: COc1cc(N2CCC(N3CCOCC3)CC2)ccc1Nc1ncc(-c2ccc(Cl)c(OC(C)Cn3cnnn3)c2)cn1] | | 606.2 |

TABLE 1-continued

| Ex. No. | IUPAC NAME | STRUCTURE | ADDITIVE | MS |
|---|---|---|---|---|
| 355 | 5-(4-chloro-3-(1-cyclopropyl-2-(1H-tetrazol-1-yl)ethoxy)phenyl)-N-(2-methoxy-4-(4-(morpholin-4-yl)piperidin-1-yl)phenyl)pyrimidin-2-amine | 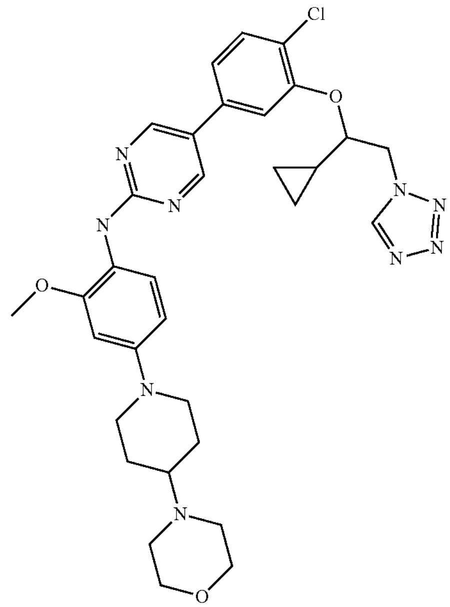 [SMILES: COc1cc(N2CCC(N3CCOCC3)CC2)ccc1Nc1ncc(-c2ccc(Cl)c(OC(Cn3cnnn3)C3CC3)c2)cn1] | | 632.2 |
| 356 | 5-(4-chloro-2-fluoro-3-(((2S)-1-(1H-tetrazol-1-yl)propan-2-yl)oxy)phenyl)-N-(2-methoxy-4-(4-(morpholin-4-yl)piperidin-1-yl)phenyl)pyrimidin-2-amine | 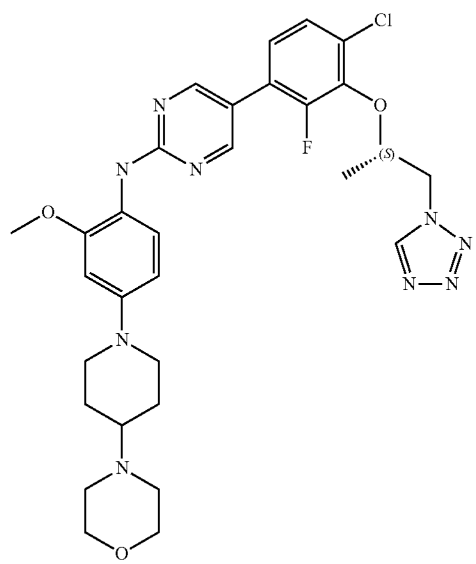 | | 624.2 |
| 357 | 4-(2-((1,3-dimethyl-1H-pyrazol-4-yl)amino)pyrimidin-5-yl)-2-(((2S)-1-(1H-1,2,4-triazol-1-yl)propan-2-yl)oxy)benzonitrile | 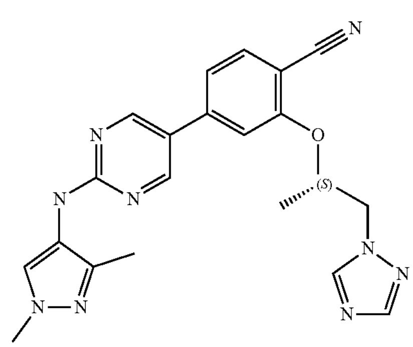 | | 414 |

TABLE 1-continued

| Ex. No. | IUPAC NAME | STRUCTURE | ADDITIVE | MS |
|---|---|---|---|---|
| 358 | 4-(2-((1-isopropyl-3-methyl-1H-pyrazol-4-yl)amino)pyrimidin-5-yl)-2-(((2S)-1-(1H-1,2,4-triazol-1-yl)propan-2-yl)oxy)benzonitrile | 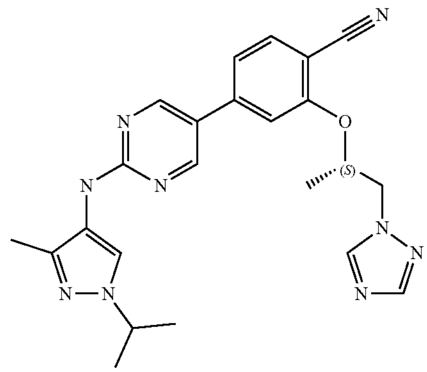 | | 442.1 |
| 359 | 4-(2-((1-(2-hydroxy-2-methylpropyl)-5-methyl-1H-pyrazol-4-yl)amino)pyrimidin-5-yl)-2-(((2S)-1-(1H-1,2,4-triazol-1-yl)propan-2-yl)oxy)benzonitrile | 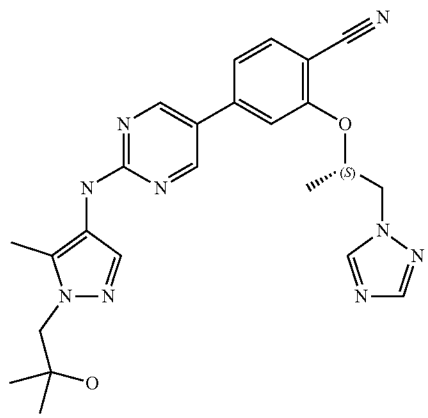 | | 472.1 |
| 360 | 4-(2-((1-(2-hydroxy-2-methylpropyl)-3-methyl-1H-pyrazol-4-yl)amino)pyrimidin-5-yl)-2-(((2S)-1-(1H-1,2,4-triazol-1-yl)propan-2-yl)oxy)benzonitrile | 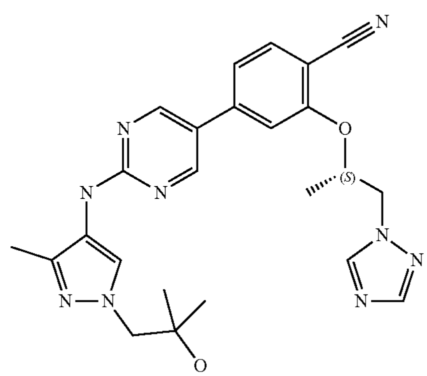 | | 472.2 |
| 361 | 4-(2-((1-cyclopropyl-1H-pyrazol-4-yl)amino)pyrimidin-5-yl)-2-(((2S)-1-(1H-1,2,4-triazol-1-yl)propan-2-yl)oxy)benzonitrile | 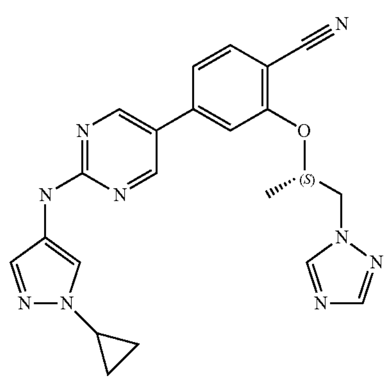 | | 426.1 |

TABLE 1-continued

| Ex. No. | IUPAC NAME | STRUCTURE | ADDITIVE | MS |
|---|---|---|---|---|
| 362 | 2-(((2S)-1-(1H-1,2,4-triazol-1-yl)propan-2-yl)oxy)-4-(2-((1-(2,2,2-trifluoroethyl)-1H-pyrazol-4-yl)amino)pyrimidin-5-yl)benzonitrile | 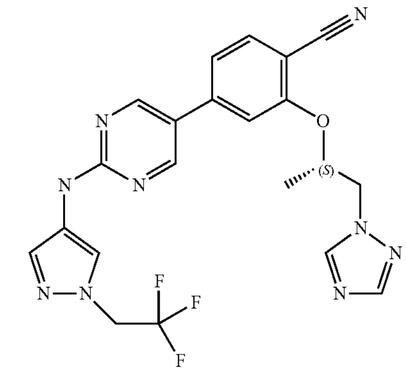 | | 468.1 |
| 363 | 4-(2-((1,3-dimethyl-1H-pyrazol-4-yl)amino)pyrimidin-5-yl)-2-(((2S)-1-(1H-1,2,4-triazol-1-yl)propan-2-yl)oxy)benzamide | 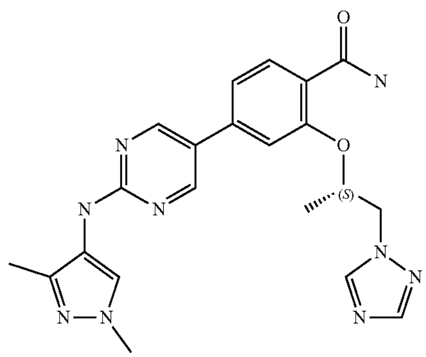 | | 432.1 |
| 364 | 4-(2-((1-(2,2-dimethylpropyl)-1H-pyrazol-4-yl)amino)pyrimidin-5-yl)-2-(((2S)-1-(1H-1,2,4-triazol-1-yl)propan-2-yl)oxy)benzonitrile | 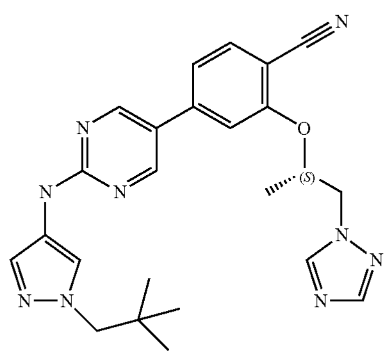 | | 456.1 |
| 365 | 4-(2-((1-(2-cyano-2-methylpropyl)-1H-pyrazol-4-yl)amino)pyrimidin-5-yl)-2-(((2S)-1-(1H-1,2,4-triazol-1-yl)propan-2-yl)oxy)benzonitrile | 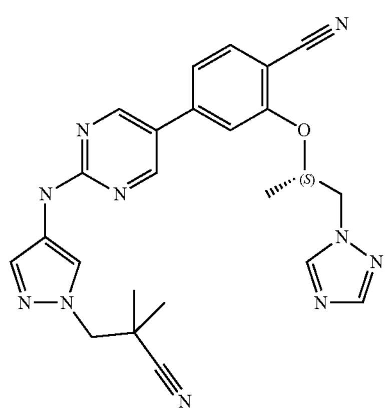 | | 467.1 |

TABLE 1-continued

| Ex. No. | IUPAC NAME | STRUCTURE | ADDITIVE | MS |
|---|---|---|---|---|
| 366 | 4-(2-((1-isopropyl-1H-pyrazol-4-yl)amino)pyrimidin-5-yl)-2-(((2S)-1-(1H-1,2,4-triazol-1-yl)butan-2-yl)oxy)benzonitrile | 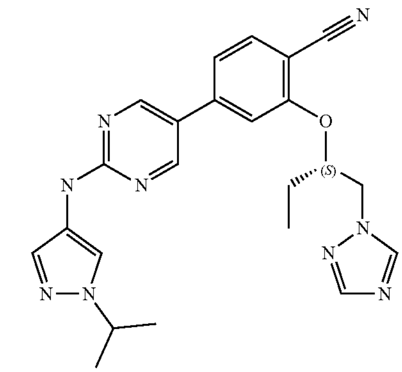 | | 444.3 |
| 367 | 4-(2-((1,3-dimethyl-1H-pyrazol-4-yl)amino)pyrimidin-5-yl)-2-(((2S)-1-(1H-1,2,4-triazol-1-yl)butan-2-yl)oxy)benzonitrile | 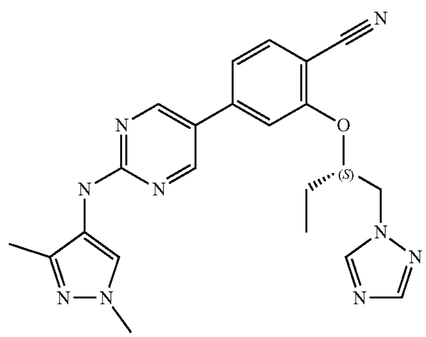 | | 428.1 |
| 368 | 4-(5-((1,3-dimethyl-1H-pyrazol-4-yl)amino)pyrazin-2-yl)-2-(((2S)-1-(1H-1,2,4-triazol-1-yl)propan-2-yl)oxy)benzonitrile | 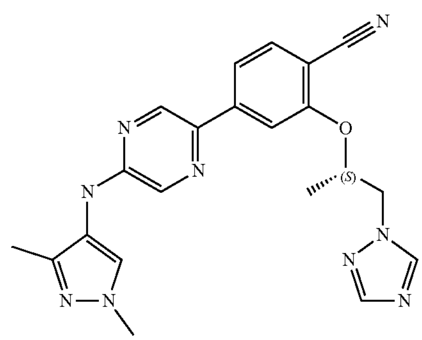 | | 414 |
| 369 | 4-(6-((1,3-dimethyl-1H-pyrazol-4-yl)amino)pyridin-3-yl)-2-(((2S)-1-(1H-1,2,4-triazol-1-yl)propan-2-yl)oxy)benzonitrile | 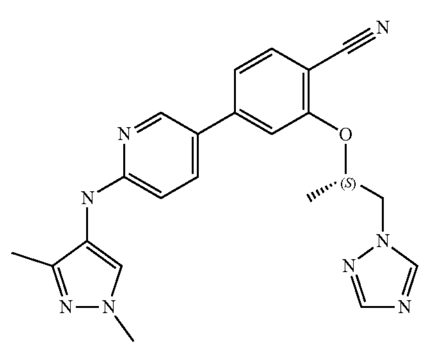 | | 413.1 |

TABLE 1-continued

| Ex. No. | IUPAC NAME | STRUCTURE | ADDITIVE | MS |
|---|---|---|---|---|
| 370 | 4-(2-((1,3-dimethyl-1H-pyrazol-4-yl)amino)pyrimidin-5-yl)-2-(((2S)-1-(2H-tetrazol-2-yl)propan-2-yl)oxy)benzonitrile | 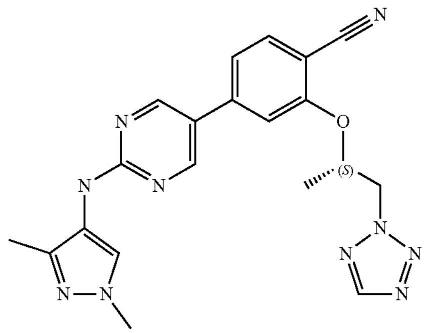 | | 415.1 |
| 371 | 4-(2-((1-isopropyl-1H-pyrazol-4-yl)amino)pyrimidin-5-yl)-2-(((2S)-1-(2H-tetrazol-2-yl)propan-2-yl)oxy)benzonitrile | 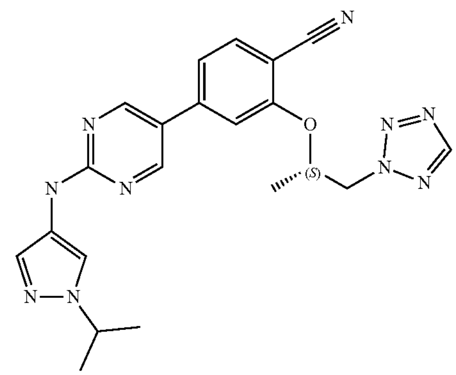 | | 429.1 |
| 372 | 4-(2-((1,3-dimethyl-1H-pyrazol-4-yl)amino)pyrimidin-5-yl)-2-(((2S)-1-(1H-tetrazol-1-yl)propan-2-yl)oxy)benzonitrile | 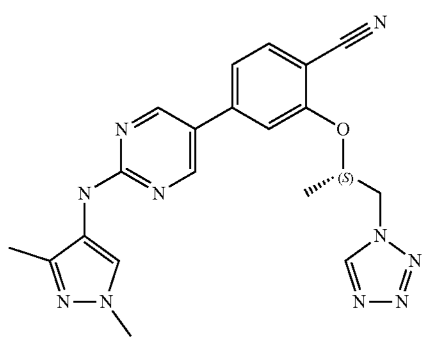 | | 415.1 |
| 373 | 4-(2-((1-tert-butyl-1H-pyrazol-4-yl)amino)pyrimidin-5-yl)-2-(((2S)-1-(1H-1,2,4-triazol-1-yl)propan-2-yl)oxy)benzonitrile | 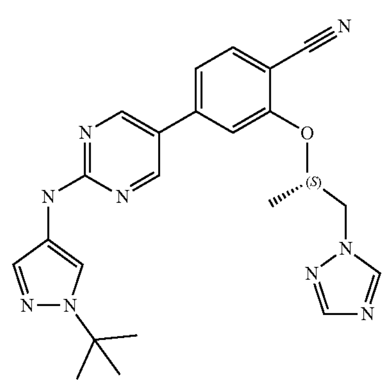 | | 444.3 |

TABLE 1-continued

| Ex. No. | IUPAC NAME | STRUCTURE | ADDITIVE | MS |
|---|---|---|---|---|
| 374 | 4-(2-((1-isopropyl-1H-pyrazol-4-yl)amino)pyrimidin-5-yl)-2-(((2S)-1-(1H-tetrazol-1-yl)propan-2-yl)oxy)benzonitrile | 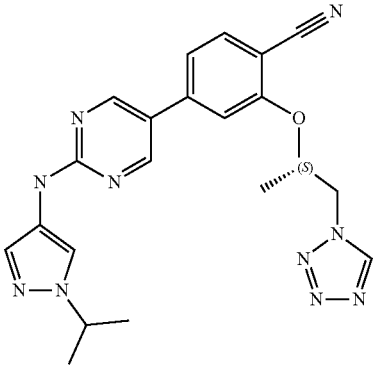 | | 429.1 |
| 375 | 4-(2-((3-methoxy-1-methyl-1H-pyrazol-4-yl)amino)pyrimidin-5-yl)-2-(((2S)-1-(1H-1,2,4-triazol-1-yl)propan-2-yl)oxy)benzonitrile | 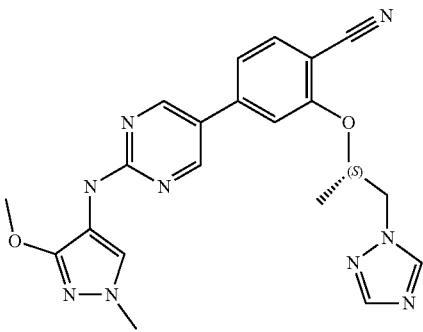 | | 430.1 |
| 376 | 4-(2-((1-methyl-3-(trifluoromethyl)-1H-pyrazol-4-yl)amino)pyrimidin-5-yl)-2-(((2S)-1-(1H-1,2,4-triazol-1-yl)propan-2-yl)oxy)benzonitrile | 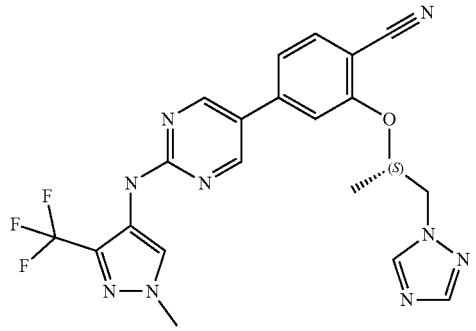 | | 470.3 |
| 377 | 2-(((2S)-1-(1H-1,2,4-triazol-1-yl)propan-2-yl)oxy)-4-(2-((1,3,5-trimethyl-1H-pyrazol-4-yl)amino)pyrimidin-5-yl)benzonitrile | 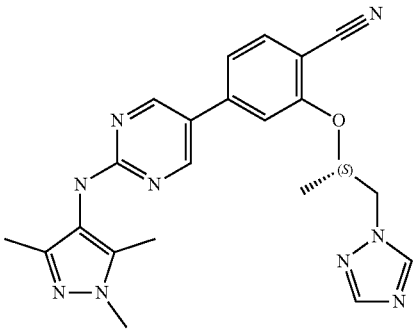 | | 428.1 |

TABLE 1-continued

| Ex. No. | IUPAC NAME | STRUCTURE | ADDITIVE | MS |
|---|---|---|---|---|
| 378 | 4-(2-((3,5-dimethyl-1,2-oxazol-4-yl)amino)pyrimidin-5-yl)-2-(((2S)-1-(1H-1,2,4-triazol-1-yl)propan-2-yl)oxy)benzonitrile | 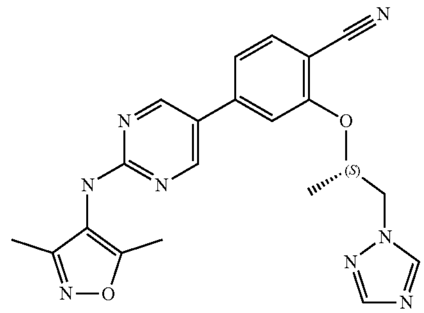 | | 415.1 |
| 379 | 4-(2-(1H-pyrazol-4-ylamino)pyrimidin-5-yl)-2-(((2S)-1-(1H-1,2,4-triazol-1-yl)propan-2-yl)oxy)benzonitrile | 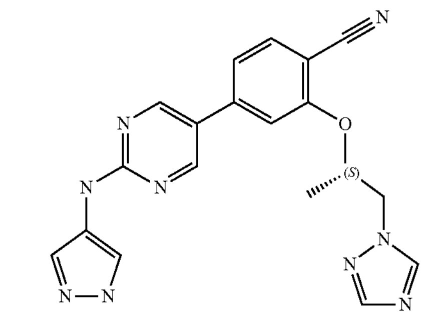 | | 386 |
| 380 | 4-(2-((1-methyl-3-(trifluoromethyl)-1H-pyrazol-4-yl)amino)pyrimidin-5-yl)-2-(((2S)-1-(1H-tetrazol-1-yl)propan-2-yl)oxy)benzonitrile | 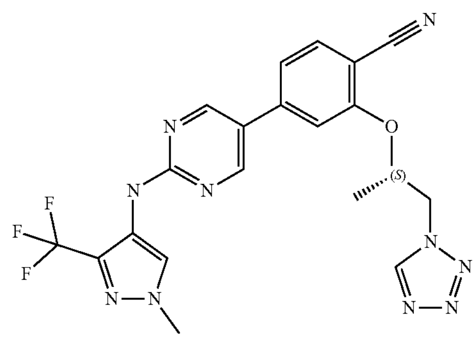 | | 469 |
| 382 | 5-(4-chloro-3-((1-(1H-tetrazol-1-yl)propan-2-yl)oxy)phenyl)-N-(2-methoxy-4-(1-(oxetan-3-yl)piperidin-4-yl)phenyl)pyrimidin-2-amine | 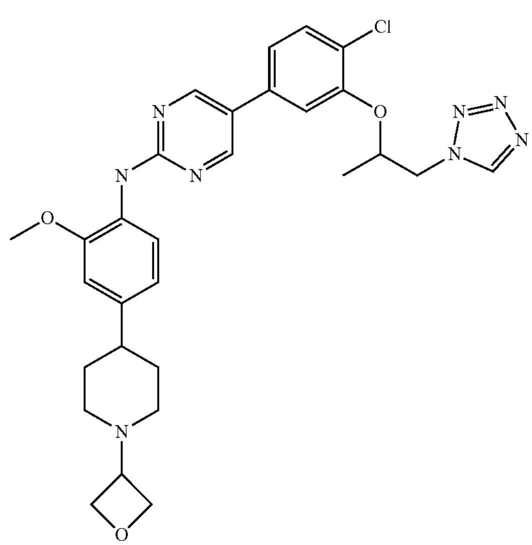 [SMILES: COc1cc(C2CCN(C3COC3)CC2)ccc1Nc1ncc(-c2ccc(Cl)c(OC(C)Cn3cnnn3)c2)cn1] | | 577.2 |

TABLE 1-continued

| Ex. No. | IUPAC NAME | STRUCTURE | ADDITIVE | MS |
|---|---|---|---|---|
| 383 | 4-(2-((1-((2S)-1-hydroxypropan-2-yl)-3-(trifluoromethyl)-1H-pyrazol-4-yl)amino)pyrimidin-5-yl)-2-(((2S)-1-(1H-tetrazol-1-yl)propan-2-yl)oxy)benzonitrile | 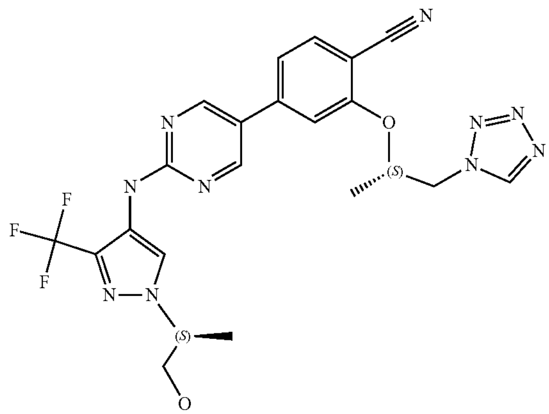 | | 513.2 |
| 384 | (2S)-2-(4-((5-(4-chloro-3-(((2S)-1-(1H-tetrazol-1-yl)propan-2-yl)oxy)phenyl)pyrimidin-2-yl)amino)-3-(trifluoromethyl)-1H-pyrazol-1-yl)propan-1-ol | 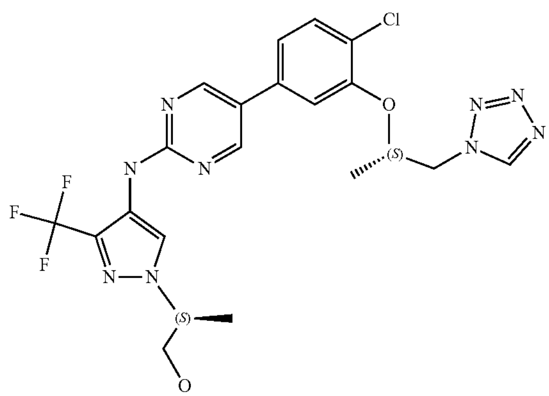 | | 524.2 |
| 385 | 5-(5-chloro-6-(((2S)-1-methoxypropan-2-yl)oxy)pyridin-2-yl)-N-(1-methyl-1H-pyrazol-4-yl)pyrimidin-2-amine | 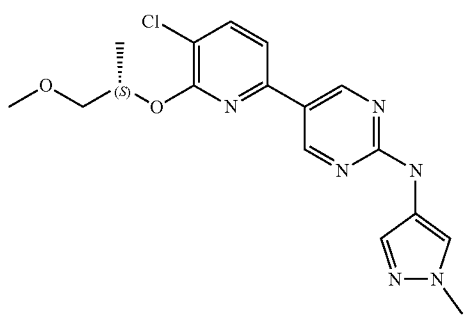 | | 375 |
| 387 | 4-(2-((1-(1-hydroxypropan-2-yl)-1H-pyrazol-4-yl)amino)pyrimidin-5-yl)-2-(((2S)-1-(2H-1,2,3-triazol-2-yl)propan-2-yl)oxy)benzonitrile | 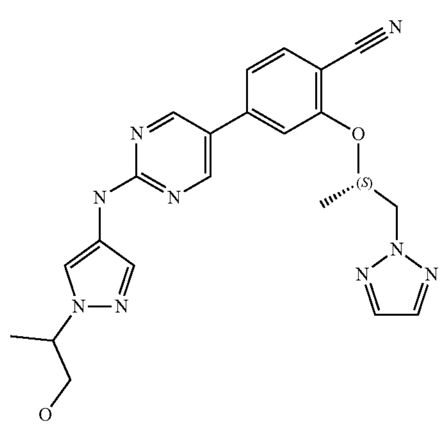 | | 446 |

TABLE 1-continued

| Ex. No. | IUPAC NAME | STRUCTURE | ADDITIVE | MS |
|---|---|---|---|---|
| 388 | 2-(((2S)-1-(difluoromethoxy)propan-2-yl)oxy)-4-(2-((1-((2S)-2-hydroxypropyl)-1H-pyrazol-4-yl)amino)pyrimidin-5-yl)benzonitrile | 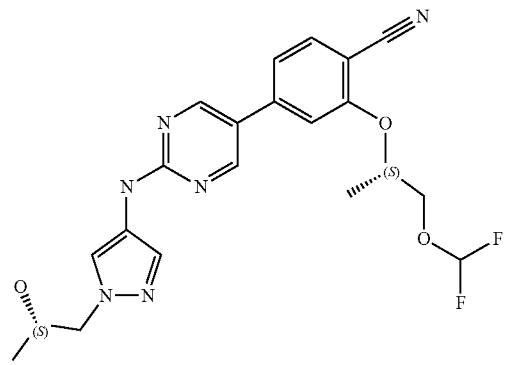 | | 443.1 |
| 389 | N-(2-(2-cyano-5-(2-((1-(2-cyanoethyl)-1H-pyrazol-4-yl)amino)pyrimidin-5-yl)phenoxy)propyl)-N-methylmethanesulfonamide | 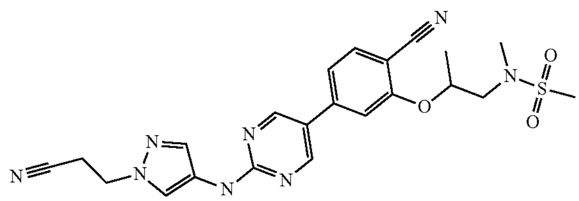 [SMILES: CC(CN(C)S(C)(=O)=O)Oc1cc(-c2cnc(Nc3cnn(CCC#N)c3)nc2)ccc1C#N] | | 481 |
| 390 | 5-fluoro-2-(((2S)-1-methoxypropan-2-yl)oxy)-4-(2-(1H-pyrazol-4-ylamino)pyrimidin-5-yl)benzonitrile | 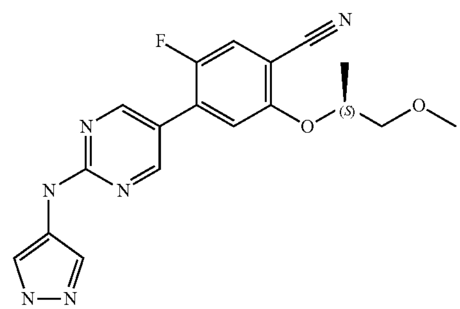 | | 369 |
| 391 | 3-chloro-2-(((2S)-1-methoxypropan-2-yl)oxy)-4-(2-(1H-pyrazol-4-ylamino)pyrimidin-5-yl)benzonitrile | 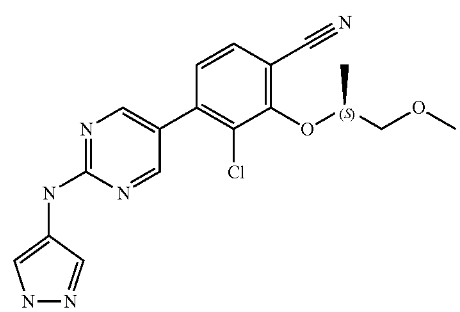 | | 385 |
| 392 | 2-(((2S)-1-methoxypropan-2-yl)oxy)-6-(2-((1-(oxetan-3-yl)-1H-pyrazol-4-yl)amino)pyrimidin-5-yl)nicotinonitrile | 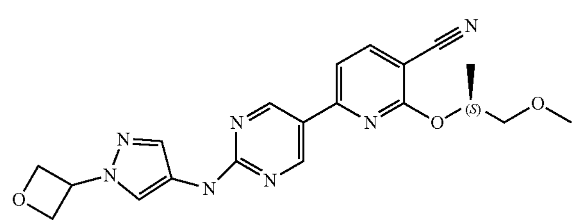 | | 408 |

TABLE 1-continued

| Ex. No. | IUPAC NAME | STRUCTURE | ADDITIVE | MS |
|---|---|---|---|---|
| 393 | 2-(((2S)-1-(4-fluoro-1H-pyrazol-1-yl)propan-2-yl)oxy)-4-(2-((1-methyl-1H-pyrazol-4-yl)amino)pyrimidin-5-yl)benzonitrile | 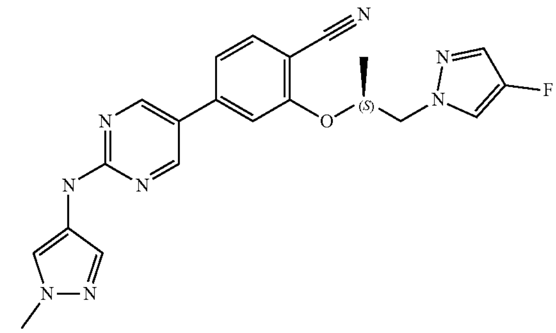 | | 419 |
| 394 | 6-(2-((1-methyl-1H-pyrazol-4-yl)amino)pyrimidin-5-yl)-2-((4,4,4-trifluorobutan-2-yl)oxy)nicotinonitrile | 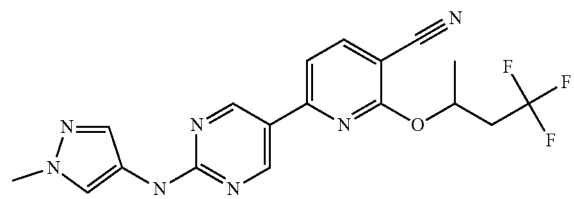 [SMILES: CC(CC(F)(F)F)Oc1nc(-c2cnc(Nc3cnn(C)c3)nc2)ccc1C#N] | | 404 |
| 395 | 2-(((2S)-1-(4-fluoro-1H-pyrazol-1-yl)propan-2-yl)oxy)-4-(2-((1-isopropyl-1H-pyrazol-4-yl)amino)pyrimidin-5-yl)benzonitrile | 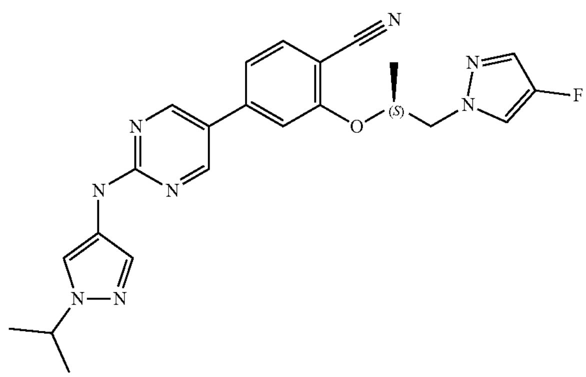 | | 447 |
| 396 | 2-(((2S)-1-methoxypropan-2-yl)oxy)-4-(2-(1,3-thiazol-5-ylamino)pyrimidin-5-yl)benzonitrile | 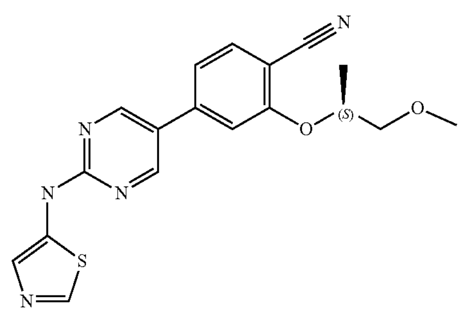 | | 368 |
| 397 | 4-(((2S)-1-methoxypropan-2-yl)oxy)-6-(2-((1-methyl-1H-pyrazol-4-yl)amino)pyrimidin-5-yl)nicotinonitrile | 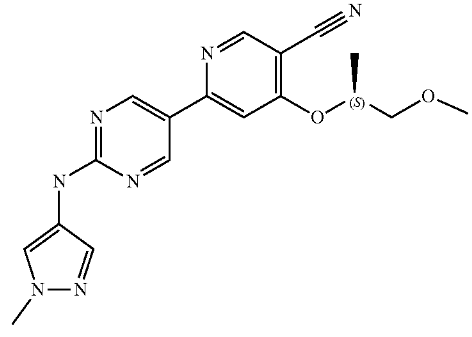 | | 366 |

TABLE 1-continued

| Ex. No. | IUPAC NAME | STRUCTURE | ADDITIVE | MS |
|---|---|---|---|---|
| 398 | 6-(2-((1-isopropyl-1H-pyrazol-4-yl)amino)pyrimidin-5-yl)-2-((1-(pyridin-2-yl)propan-2-yl)oxy)nicotinonitrile | 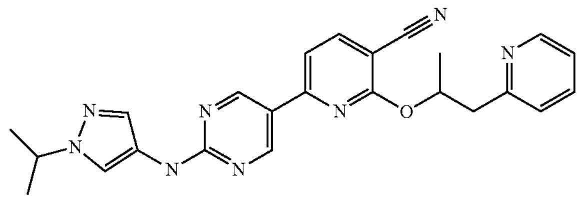 [SMILES: CC(Cc1ccccn1)Oc1nc(-c2cnc(Nc3cnn(C(C)C)c3)nc2)ccc1C#N] | | 441 |
| 399 | 6-(2-((1-isopropyl-1H-pyrazol-4-yl)amino)pyrimidin-5-yl)-2-(2-(pyridin-2-yl)ethoxy)nicotinonitrile | 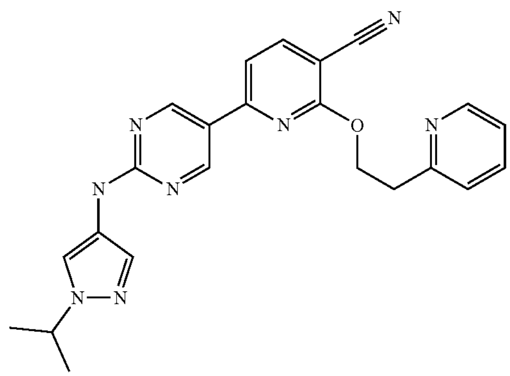 [SMILES: CC(C)n1cc(Nc2ncc(-c3ccc(C#N)c(OCCc4ccccn4)n3)cn2)cn1] | | 427 |
| 400 | 6-(2-((1-isopropyl-1H-pyrazol-4-yl)amino)pyrimidin-5-yl)-2-(2-(pyridin-3-yl)ethoxy)nicotinonitrile | 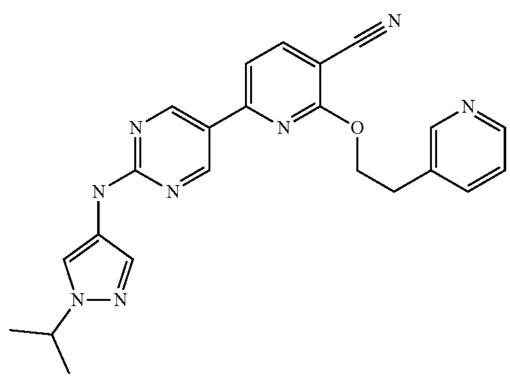 [SMILES: CC(C)n1cc(Nc2ncc(-c3ccc(C#N)c(OCCc4cccnc4)n3)cn2)cn1] | | 427 |
| 401 | 2-(((2S)-1-(4-fluoro-1H-imidazol-1-yl)propan-2-yl)oxy)-4-(2-((1-methyl-1H-pyrazol-4-yl)amino)pyrimidin-5-yl)benzonitrile | 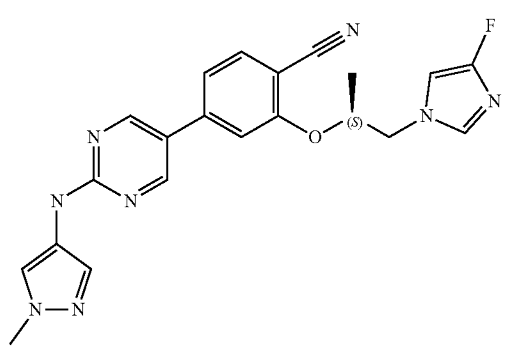 | | 419 |

TABLE 1-continued

| Ex. No. | IUPAC NAME | STRUCTURE | ADDITIVE | MS |
|---|---|---|---|---|
| 402 | 2-(((2R)-1-hydroxy-3-(1H-pyrazol-1-yl)propan-2-yl)oxy)-4-(2-((1-methyl-1H-pyrazol-4-yl)amino)pyrimidin-5-yl)benzonitrile | 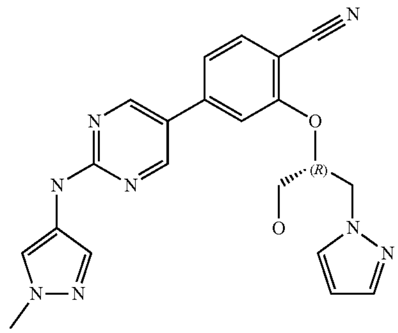 | | 417.1 |
| 403 | N[3]-(3-cyano-6-(2-((1-isopropyl-1H-pyrazol-4-yl)amino)pyrimidin-5-yl)pyridin-2-yl)-N-methyl-beta-alanine amide | 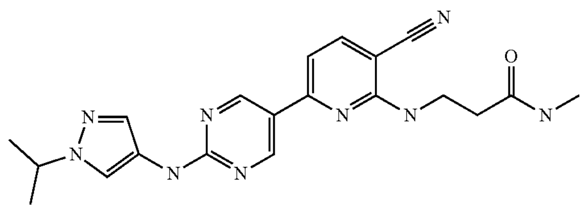 [SMILES: CNC(=O)CCNc1nc(-c2cnc(Nc3cnn(C(C)C)c3)nc2)ccc1C#N] | | 406 |
| 404 | (2S)-2-((3-cyano-6-(2-((1-methyl-1H-pyrazol-4-yl)amino)pyrimidin-5-yl)pyridin-2-yl)oxy)-N-(2,2-difluoroethyl)propanamide | 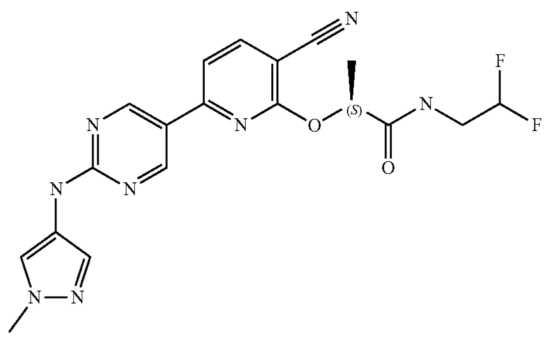 | | 429 |
| 405 | 2-((((3S)-1-methyl-2-oxopiperidin-3-yl)methyl)amino)-6-(2-((1-methyl-1H-pyrazol-4-yl)amino)pyrimidin-5-yl)nicotinonitrile | 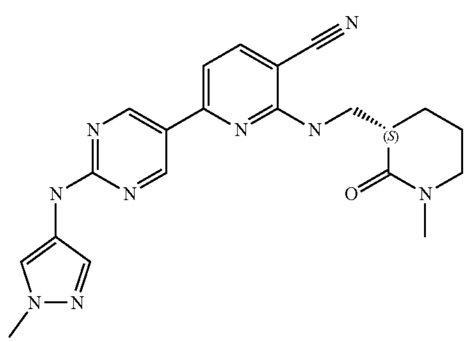 | | 418 |
| 406 | 2-(((2S)-4-hydroxy-4-methylpentan-2-yl)oxy)-4-(2-((3-methyl-1,2-thiazol-5-yl)amino)pyrimidin-5-yl)benzonitrile | 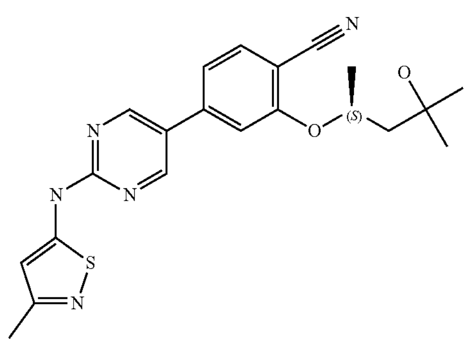 | | 410 |

TABLE 1-continued

| Ex. No. | IUPAC NAME | STRUCTURE | ADDITIVE | MS |
|---|---|---|---|---|
| 407 | 2-(((2S)-1-(difluoromethoxy)propan-2-yl)oxy)-4-(2-(1H-pyrazol-3-ylamino)pyrimidin-5-yl)benzonitrile | 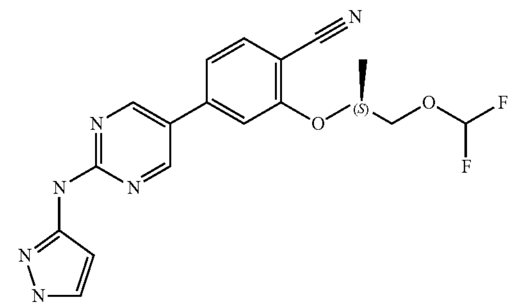 | | 387 |
| 408 | 4-(2-((6-aminopyridin-3-yl)amino)pyrimidin-5-yl)-2-(((2S)-1-(1H-1,2,4-triazol-1-yl)propan-2-yl)oxy)benzonitrile | 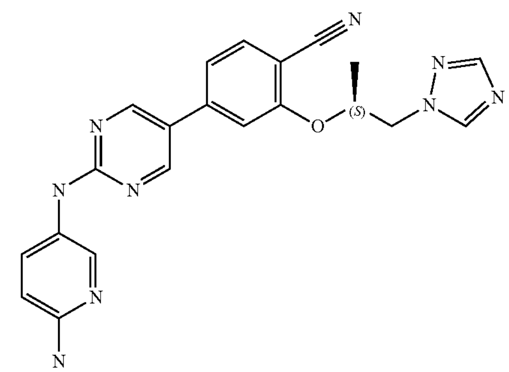 | | 414 |
| 409 | 2-(((2S)-1-(5-methyl-1H-imidazol-1-yl)propan-2-yl)oxy)-4-(2-((1-methyl-1H-pyrazol-4-yl)amino)pyrimidin-5-yl)benzonitrile | 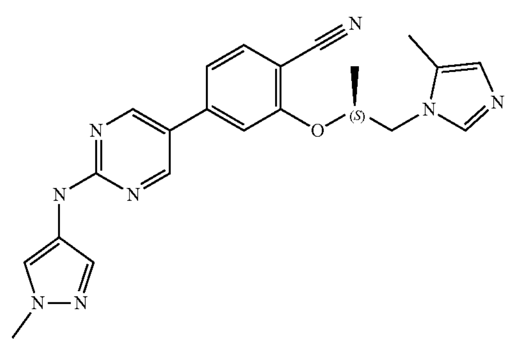 | | 415 |
| 410 | 4-(2-((1-methyl-1H-pyrazol-4-yl)amino)pyrimidin-5-yl)-2-(((2S)-1-(1H-tetrazol-1-yl)propan-2-yl)oxy)benzonitrile | 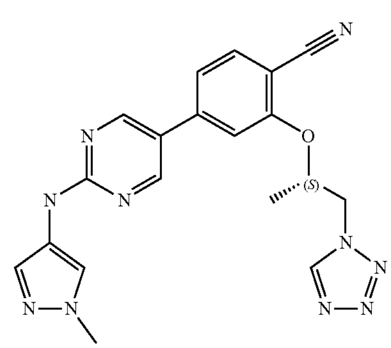 | | 403.2 |

TABLE 1-continued

| Ex. No. | IUPAC NAME | STRUCTURE | ADDITIVE | MS |
|---|---|---|---|---|
| 411 | 4-(2-((1-methyl-1H-pyrazol-4-yl)amino)pyrimidin-5-yl)-2-(((2S)-1-(2H-tetrazol-2-yl)propan-2-yl)oxy)benzonitrile | 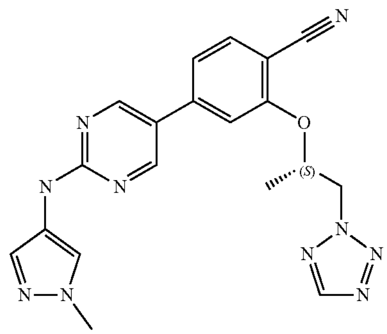 | | 402 |
| 412 | 4-(2-((1-methyl-1H-pyrazol-4-yl)amino)pyrimidin-5-yl)-2-(((2S)-1-(1H-pyrazol-5-yl)propan-2-yl)oxy)benzonitrile | 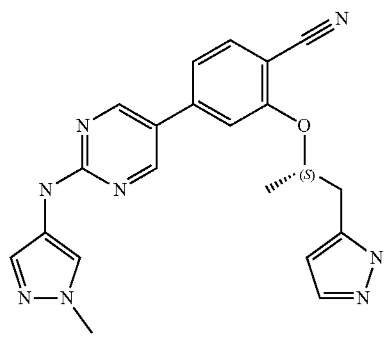 | | 401.1 |
| 413 | 2-(((2S)-1-(difluoromethoxy)propan-2-yl)oxy)-4-(2-((2-methyl-1H-imidazol-5-yl)amino)pyrimidin-5-yl)benzonitrile | 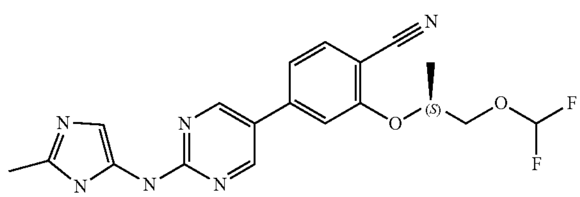 | | 401 |
| 414 | N-(2-((3-cyano-6-(2-((1-methyl-1H-pyrazol-4-yl)amino)pyrimidin-5-yl)pyridin-2-yl)amino)propyl)acetamide | 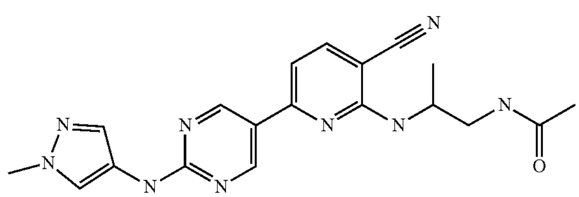 [SMILES: CC(=O)NCC(C)Nc1nc(-c2cnc(Nc3cnn(C)c3)nc2)ccc1C#N] | | 392 |
| 415 | 4-(2-((1-((2S)-2-hydroxypropyl)-1H-pyrazol-4-yl)amino)pyrimidin-5-yl)-(((2S)-1-(1H-1,2,4-triazol-1-yl)propan-2-yl)oxy)benzonitrile | 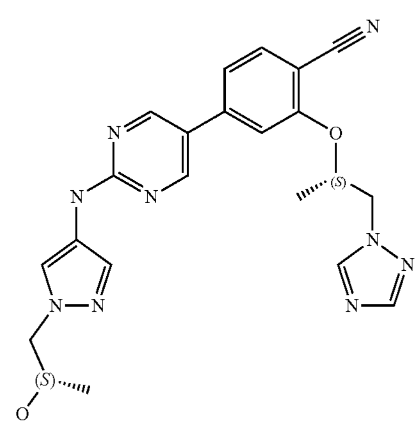 | | 443.9 |

TABLE 1-continued

| Ex. No. | IUPAC NAME | STRUCTURE | ADDITIVE | MS |
|---|---|---|---|---|
| 416 | 4-(2-((1-((2R)-2-hydroxypropyl)-1H-pyrazol-4-yl)amino)pyrimidin-5-yl)-2-(((2S)-1-(1H-1,2,4-triazol-1-yl)propan-2-yl)oxy)benzonitrile | 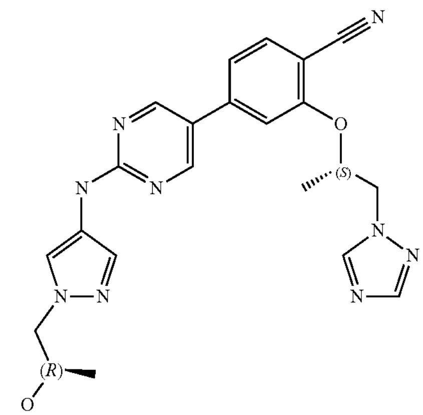 | | 443.9 |
| 417 | 4-(2-((1-(2-hydroxypropyl)-1H-pyrazol-4-yl)amino)pyrimidin-5-yl)-2-(((2S)-1-methoxypropan-2-yl)oxy)benzonitrile | 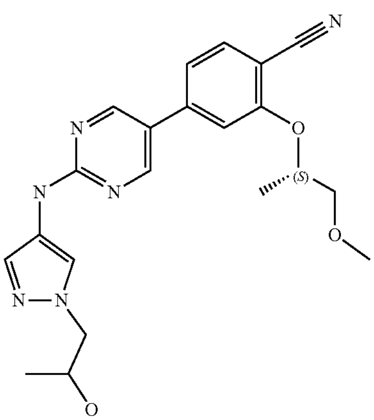 | | 409 |
| 418 | 2-(((2S)-1-(difluoromethoxy)propan-2-yl)oxy)-4-(2-((1-((2R)-2-hydroxypropyl)-1H-pyrazol-4-yl)amino)pyrimidin-5-yl)benzonitrile | 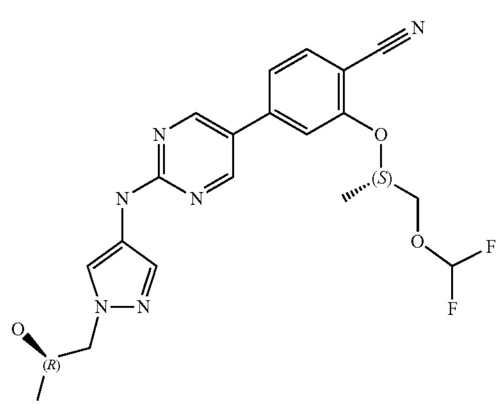 | | 445 |

TABLE 1-continued

| Ex. No. | IUPAC NAME | STRUCTURE | ADDITIVE | MS |
|---|---|---|---|---|
| 419 | 4-(2-((1-(1-hydroxypropan-2-yl)-1H-pyrazol-4-yl)amino)pyrimidin-5-yl)-2-(((2S)-1-(1H-1,2,3-triazol-1-yl)propan-2-yl)oxy)benzonitrile | 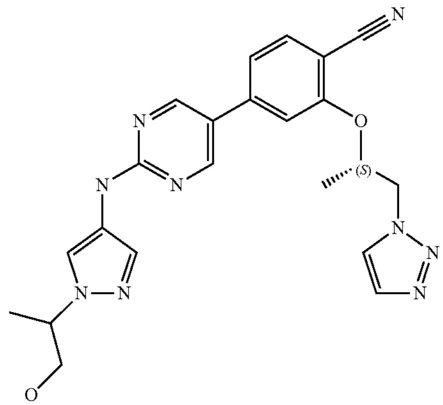 | | 446 |
| 420 | 4-(2-((1-(2-hydroxy-2-methylpropyl)-1H-pyrazol-4-yl)amino)pyrimidin-5-yl)-2-(((2S)-1-(1H-1,2,3-triazol-1-yl)propan-2-yl)oxy)benzonitrile | 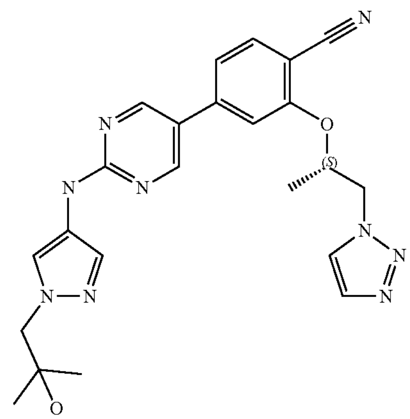 | | 460 |
| 421 | 4-(2-((1-(1-hydroxypropan-2-yl)-1H-pyrazol-4-yl)amino)pyrimidin-5-yl)-2-(((2S)-1-(1H-pyrazol-5-yl)propan-2-yl)oxy)benzonitrile | 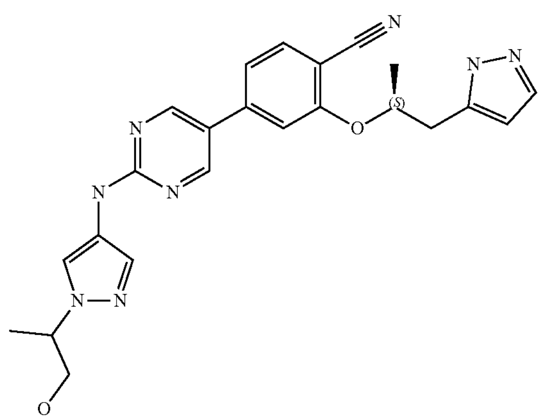 | | 445 |
| 422 | 4-(2-((1-methyl-1H-pyrazol-4-yl)amino)pyrimidin-5-yl)-2-(((2S)-1-(2H-1,2,3-triazol-4-yl)propan-2-yl)oxy)benzonitrile | 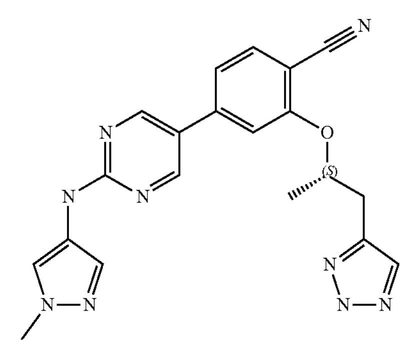 | | 402 |

TABLE 1-continued

| Ex. No. | IUPAC NAME | STRUCTURE | ADDITIVE | MS |
|---|---|---|---|---|
| 423 | 2-((1-(3-methyl-1,2,4-oxadiazol-5-yl)propan-2-yl)oxy)-4-(2-((1-methyl-1H-pyrazol-4-yl)amino)pyrimidin-5-yl)benzonitrile | 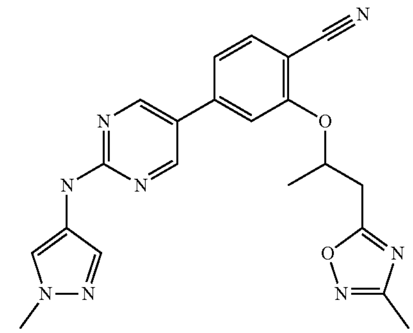 | | 417 |
| 424 | 4-(2-((3-(hydroxymethyl)-1,2-thiazol-5-yl)amino)pyrimidin-5-yl)-2-(((2S)-1-(1H-1,2,4-triazol-1-yl)propan-2-yl)oxy)benzonitrile | 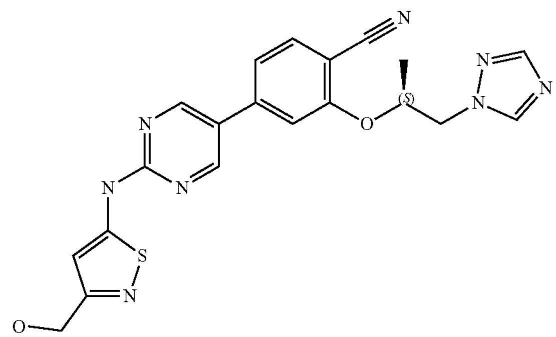 | | 435 |
| 425 | 4-(2-((1-methyl-1H-pyrazol-4-yl)amino)pyrimidin-5-yl)-2-((1-(1,3,4-oxadiazol-2-yl)propan-2-yl)oxy)benzonitrile | 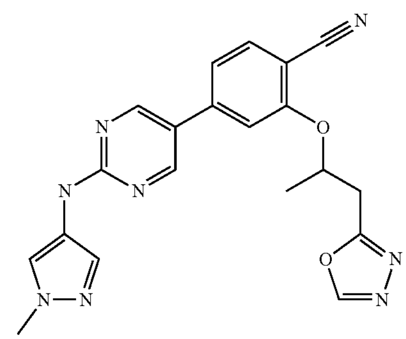 | | 403 |
| 426 | 5-(4-chloro-3-(((2S)-1-(1H-1,2,4-triazol-1-yl)propan-2-yl)oxy)phenyl)-N-(1-methyl-1H-pyrazol-4-yl)pyrimidin-2-amine | 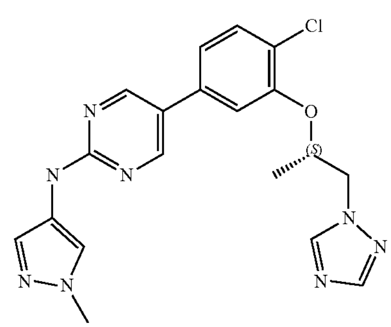 | | 411 |

TABLE 1-continued

| Ex. No. | IUPAC NAME | STRUCTURE | ADDITIVE | MS |
|---|---|---|---|---|
| 427 | 2-(((2S)-1-(difluoromethoxy)propan-2-yl)oxy)-4-(2-((1-((1-hydroxycyclopropyl)methyl)-1H-pyrazol-4-yl)amino)pyrimidin-5-yl)benzonitrile | 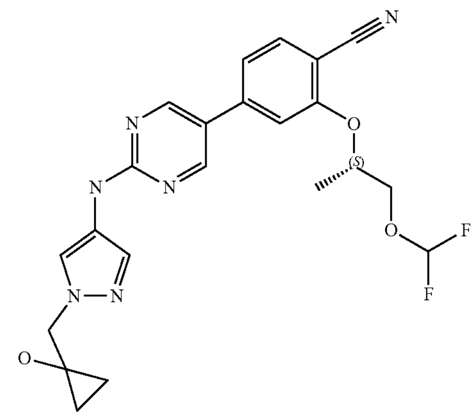 | | 457 |
| 428 | 4-(2-((1-methyl-1H-pyrazol-4-yl)amino)pyrimidin-5-yl)-2-(((2R)-1-(1H-1,2,4-triazol-1-yl)propan-2-yl)oxy)benzonitrile | 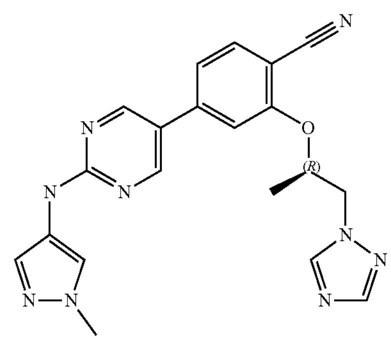 | | 402 |
| 429 | 4-(2-((1-methyl-1H-pyrazol-4-yl)amino)pyrimidin-5-yl)-2-((1-(4H-1,2,4-triazol-3-yl)propan-2-yl)oxy)benzonitrile | 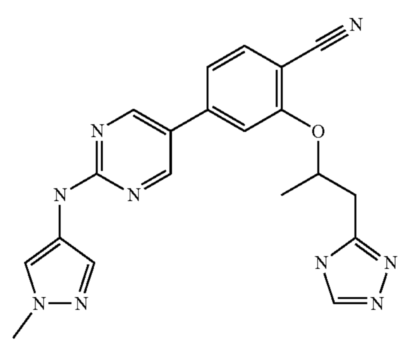 [SMILES: CC(Cc1nnc[nH]1)Oc1cc(-c2cnc(Nc3cnn(C)c3)nc2)ccc1C#N] | | 402 |
| 430 | 2-(4-((5-(4-chloro-3-(((2S)-1-(1H-1,2,4-triazol-1-yl)propan-2-yl)oxy)phenyl)pyrimidin-2-yl)amino)-1H-pyrazol-1-yl)ethanol | 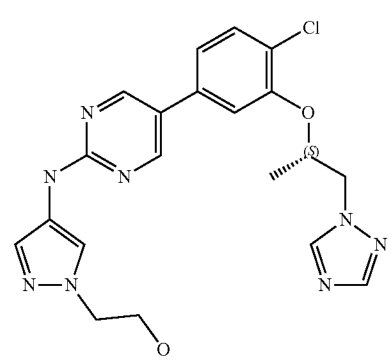 | | 441 |

TABLE 1-continued

| Ex. No. | IUPAC NAME | STRUCTURE | ADDITIVE | MS |
|---|---|---|---|---|
| 431 | 6-(2-((1-((1-amino-cyclopropyl)methyl)-1H-pyrazol-4-yl)amino)pyrimidin-5-yl)-2-(((2S)-1-methoxypropan-2-yl)oxy)nicotinonitrile | 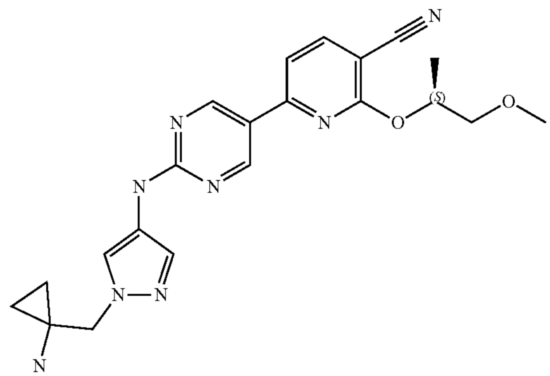 | | 421 |
| 432 | 4-(2-((1-((1-aminocyclopropyl)methyl)-1H-pyrazol-4-yl)amino)pyrimidin-5-yl)-2-(((2S)-1-(difluoromethoxy)propan-2-yl)oxy)benzonitrile | 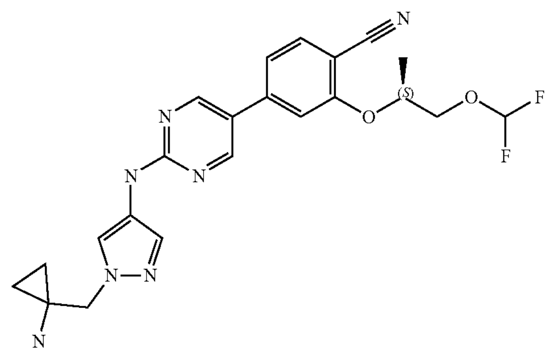 | | 456 |
| 433 | 2-((4-cyanobutan-2-yl)amino)-6-(2-((1-methyl-1H-pyrazol-4-yl)amino)pyrimidin-5-yl)nicotinonitrile | 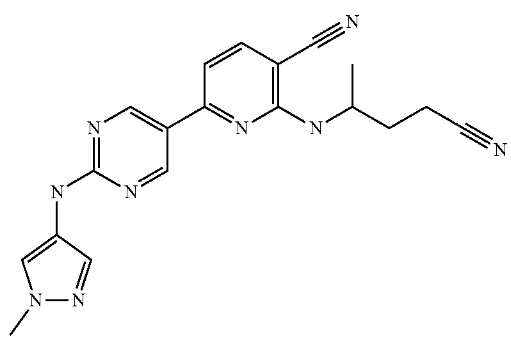 [SMILES: CC(CCC#N)Nc1nc(-c2cnc(Nc3cnn(C)c3)nc2)ccc1C#N] | | 374 |
| 434 | 5-(4-chloro-3-((1-(1H-1,2,4-triazol-1-yl)propan-2-yl)amino)phenyl)-N-(1-methyl-1H-pyrazol-4-yl)pyrimidin-2-amine | 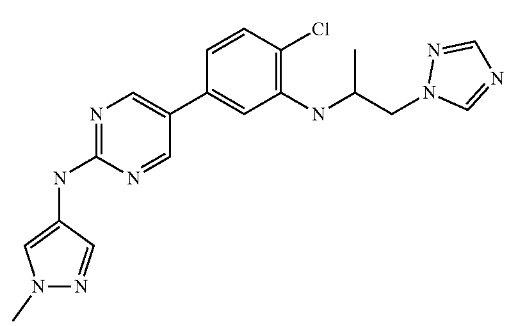 [SMILES: CC(Cn1cncn1)Nc1cc(-c2cnc(Nc3cnn(C)c3)nc2)ccc1Cl] | | 410 |

TABLE 2

| Ex. No. | IUPAC NAME | ADDITIVE | MS | ACTIVITY |
|---|---|---|---|---|
| 435 | (S)-(6-((5-(3-((1-(1H-tetrazol-1-yl)propan-2-yl)oxy)-4-chlorophenyl)pyrimidin-2-yl)amino)indolin-1-yl) (1-methylpiperidin-4-yl)methanone | | 574.2 | A |
| 436 | (S)-1-(6-((5-(3-((1-(1H-tetrazol-1-yl)propan-2-yl)oxy)-4-chlorophenyl)pyrimidin-2-yl)amino)indolin-1-yl)-4-(dimethylamino)butan-1-one | | 562.2 | A |
| 437 | (S)-1-(6-((5-(3-((1-(1H-tetrazol-1-yl)propan-2-yl)oxy)-4-chlorophenyl)pyrimidin-2-yl)amino)indolin-1-yl)-3-(dimethylamino)propan-1-one | | 548.2 | A |
| 438 | (S)-6-((5-(3-((1-(1H-tetrazol-1-yl)propan-2-yl)oxy)-4-chlorophenyl)pyrimidin-2-yl)amino)-5-methoxy-2-(tetrahydro-2H-pyran-4-yl)isoindolin-1-one | | 577.2 | B |
| 439 | (S)-(5-((5-(3-((1-(1H-tetrazol-1-yl)propan-2-yl)oxy)-4-chlorophenyl)pyrimidin-2-yl)amino)-4-methoxy-2-methylphenyl)(morpholino)methanone | | 565.1 | A |
| 440 | (S)-2-((1-(1H-tetrazol-1-yl)propan-2-yl)oxy)-4-(2-((2-methoxy-4-methyl-5-(morpholine-4-carbonyl)phenyl)amino)pyrimidin-5-yl)benzonitrile | | 556.2 | A |
| 441 | (S)-6-((5-(3-((1-(1H-tetrazol-1-yl)propan-2-yl)oxy)-4-chlorophenyl)pyrimidin-2-yl)amino)-2-cyclobutyl-5-methoxyisoindolin-1-one | | 547.1 | B |
| 442 | (S)-2-((1-(1H-tetrazol-1-yl)propan-2-yl)oxy)-4-(2-((2-cyclobutyl-6-methoxy-3-oxoisoindolin-5-yl)amino)pyrimidin-5-yl)benzonitrile | | 538.2 | B |
| 443 | (S)-2-((1-(1H-1,2,4-triazol-1-yl)propan-2-yl)oxy)-4-(2-((2-cyclobutyl-6-methoxy-3-oxoisoindolin-5-yl)amino)pyrimidin-5-yl)benzonitrile | | 537.2 | B |
| 444 | (S)-2-((5-(3-((1-(1H-tetrazol-1-yl)propan-2-yl)oxy)-4-chlorophenyl)pyrimidin-2-yl)amino)-5-(4-morpholinopiperidin-1-yl)benzamide | | 619.2 | C |
| 445 | (S)-6-((5-(3-((1-(1H-tetrazol-1-yl)propan-2-yl)oxy)-4-chlorophenyl)pyrimidin-2-yl)amino)-5-methoxy-2-(oxetan-3-ylmethyl)isoindolin-1-one | | 563.1 | B |
| 446 | (S)-2-((1-(1H-tetrazol-1-yl)propan-2-yl)oxy)-4-(2-((6-methoxy-2-(oxetan-3-ylmethyl)-3-oxoisoindolin-5-yl)amino)pyrimidin-5-yl)benzonitrile | | 554.2 | B |
| 447 | (S)-N-(5-(3-((1-(1H-tetrazol-1-yl)propan-2-yl)oxy)-4-chlorophenyl)pyrimidin-2-yl)-8-methoxy-3-(oxetan-3-yl)-2,3,4,5-tetrahydro-1H-benzo[d]azepin-7-amine | | 563.2 | A |
| 448 | (S)-5-(3-((1-(1H-tetrazol-1-yl)propan-2-yl)oxy)-4-chlorophenyl)-N-(2-methoxy-5-(morpholinomethyl)phenyl)pyrimidin-2-amine | | 537.2 | B |
| 449 | (S)-4-(3-((5-(3-((1-(1H-tetrazol-1-yl)propan-2-yl)oxy)-4-chlorophenyl)pyrimidin-2-yl)amino)-4-methoxybenzyl)thiomorpholine 1,1-dioxide | | 585.1 | B |
| 450 | tert-butyl (S)-5-((5-(3-((1-(1H-tetrazol-1-yl)propan-2-yl)oxy)-4-chlorophenyl)pyrimidin-2-yl)amino)indoline-1-carboxylate | | 549.1 | C |
| 451 | (S)-N-(5-(3-((1-(1H-tetrazol-1-yl)propan-2-yl)oxy)-4-chlorophenyl)pyrimidin-2-yl)indolin-5-amine | HCl | 449.1 | B |
| 452 | (S)-(5-((5-(3-((1-(1H-tetrazol-1-yl)propan-2-yl)oxy)-4-chlorophenyl)pyrimidin-2-yl)amino)indolin-1-yl) (1-methylpiperidin-4-yl)methanone | 2HCl | 574.2 | A |
| 453 | (S)-5-(3-((1-(1H-tetrazol-1-yl)propan-2-yl)oxy)-4-chlorophenyl)-N-(2-methyl-4-(4-morpholinopiperidin-1-yl)phenyl)pyrimidin-2-amine | 2HCl | 590.3 | A |
| 454 | (S)-N-(5-(3-((1-(1H-tetrazol-1-yl)propan-2-yl)oxy)-4-chlorophenyl)pyrimidin-2-yl)-8-methoxy-4-(oxetan-3-yl)-2,3,4,5-tetrahydrobenzo[f][1,4]oxazepin-7-amine | HCl | 565.2 | C |
| 455 | 5-(3-(((S)-1-(1H-tetrazol-1-yl)propan-2-yl)oxy)-4-chlorophenyl)-N-(2-methoxy-5-(3-morpholinopiperidin-1-yl)phenyl)pyrimidin-2-amine | 2HCl | 606.2 | B |
| 456 | (S)-5-(3-((1-(1H-tetrazol-1-yl)propan-2-yl)oxy)-4-chlorophenyl)-N-(5-methoxy-2-(4-morpholinopiperidin-1-yl)pyridin-4-yl)pyrimidin-2-amine | 2HCl | 607.3 | A |
| 457 | 5-(3-(((S)-1-(1H-tetrazol-1-yl)propan-2-yl)oxy)-4-chlorophenyl)-N-(5-methoxy-2-(3-morpholinopiperidin-1-yl)pyridin-4-yl)pyrimidin-2-amine | HCl | 607.2 | B |
| 458 | (S)-2-((1-(1H-tetrazol-1-yl)propan-2-yl)oxy)-4-(2-((7-methoxy-2-(2,2,2-trifluoroacetyl)-1,2,3,4-tetrahydroisoquinolin-6-yl)amino)pyrimidin-5-yl)benzonitrile | HCl | 580.2 | B |
| 459 | (S)-1-(6-((5-(3-((1-(1H-tetrazol-1-yl)propan-2-yl)oxy)-4-chlorophenyl)pyrimidin-2-yl)amino)-7-methoxy-3,4-dihydroisoquinolin-2(1H)-yl)-2-(dimethylamino)ethan-1-one | HCl | 578.2 | A |
| 460 | (S)-1-(7-((5-(3-((1-(1H-tetrazol-1-yl)propan-2-yl)oxy)-4-chlorophenyl)pyrimidin-2-yl)amino)-6-methoxy-3,4-dihydroisoquinolin-2(1H)-yl)-2,2,2-trifluoroethan-1-one | HCl | 589.1 | C |
| 461 | (S)-N-(5-(3-((1-(1H-tetrazol-1-yl)propan-2-yl)oxy)-4-chlorophenyl)pyrimidin-2-yl)-6-methoxy-1,2,3,4-tetrahydroisoquinolin-7-amine | 2HCl | 493.2 | A |
| 462 | (S)-5-(3-((1-(1H-tetrazol-1-yl)propan-2-yl)oxy)-4-chlorophenyl)-N-(2-methyl-5-(4-morpholinopiperidin-1-yl)pyridin-3-yl)pyrimidin-2-amine | HCl | 591.2 | A |
| 463 | (S)-N-(5-(3-((1-(1H-tetrazol-1-yl)propan-2-yl)oxy)-4-chlorophenyl)pyrimidin-2-yl)-6-methoxy-2-(oxetan-3-yl)-1,2,3,4-tetrahydroisoquinolin-7-amine | HCl | 549.2 | A |

TABLE 2-continued

| Ex. No. | IUPAC NAME | ADDITIVE | MS | ACTIVITY |
|---|---|---|---|---|
| 464 | (S)-1-(7-((5-(3-((1-(1H-tetrazol-1-yl)propan-2-yl)oxy)-4-chlorophenyl)pyrimidin-2-yl)amino)-6-methoxy-3,4-dihydroisoquinolin-2(1H)-yl)-2-(dimethylamino)ethan-1-one | HCl | 578.1 | A |
| 465 | (S)-N-(5-(3-((1-(1H-tetrazol-1-yl)propan-2-yl)oxy)-4-chlorophenyl)pyrimidin-2-yl)-7-methoxy-1,2,3,4-tetrahydroisoquinolin-6-amine | HCl | 493.1 | A |
| 466 | (S)-1-(6-((5-(3-((1-(1H-tetrazol-1-yl)propan-2-yl)oxy)-4-chlorophenyl)pyrimidin-2-yl)amino)-5-methoxyindolin-1-yl)ethan-1-one | HCl | 521.2 | B |
| 467 | (S)-N-(5-(3-((1-(1H-tetrazol-1-yl)propan-2-yl)oxy)-4-chlorophenyl)pyrimidin-2-yl)-7-methoxy-2-(oxetan-3-yl)-2,3,4,5-tetrahydro-1H-benzo[c]azepin-8-amine | HCl | 563.2 | B |
| 468 | (S)-N-(5-(3-((1-(1H-tetrazol-1-yl)propan-2-yl)oxy)-4-chlorophenyl)pyrimidin-2-yl)-7-methoxy-2-(oxetan-3-yl)-1,2,3,4-tetrahydroisoquinolin-6-amine | HCl | 549.2 | A |
| 469 | (S)-1-(6-((5-(3-((1-(1H-tetrazol-1-yl)propan-2-yl)oxy)-4-chlorophenyl)pyrimidin-2-yl)amino)-7-methoxy-3,4-dihydroisoquinolin-2(1H)-yl)-2-methoxyethan-1-one | HCl | 565.2 | B |
| 470 | (S)-1-(6-((5-(3-((1-(1H-tetrazol-1-yl)propan-2-yl)oxy)-4-chlorophenyl)pyrimidin-2-yl)amino)-7-methoxy-3,4-dihydroisoquinolin-2(1H)-yl)-2-morpholinoethan-1-one | | 620.2 | A |
| 471 | (S)-6-((5-(3-((1-(1H-tetrazol-1-yl)propan-2-yl)oxy)-4-chlorophenyl)pyrimidin-2-yl)amino)-7-methoxy-3,4-dihydroisoquinoline-2(1H)-carbaldehyde | | 521.2 | B |
| 472 | 2-(((S)-1-(1H-tetrazol-1-yl)propan-2-yl)oxy)-4-(2-((2-methoxy-4-(piperidin-3-yl)phenyl)amino)pyrimidin-5-yl)benzonitrile | 2HCl | 512.2 | A |
| 473 | 5-(3-(((S)-1-(1H-tetrazol-1-yl)propan-2-yl)oxy)-4-chlorophenyl)-N-(2-methoxy-4-(piperidin-3-yl)phenyl)pyrimidin-2-amine | 2HCl | 521.2 | A |
| 474 | (S)-N-(5-(3-((1-(1H-tetrazol-1-yl)propan-2-yl)oxy)-4-chlorophenyl)pyrimidin-2-yl)-7-methoxy-2-(tetrahydro-2H-pyran-4-yl)-1,2,3,4-tetrahydroisoquinolin-6-amine | | 577.2 | A |
| 475 | (S)-N-(5-(3-((1-(1H-tetrazol-1-yl)propan-2-yl)oxy)-4-chlorophenyl)pyrimidin-2-yl)-7-methoxy-2-(oxetan-3-ylmethyl)-1,2,3,4-tetrahydroisoquinolin-6-amine | | 563.1 | A |
| 476 | (S)-N-(5-(3-((1-(1H-tetrazol-1-yl)propan-2-yl)oxy)-4-chlorophenyl)pyrimidin-2-yl)-2-(2,2-difluoroethyl)-7-methoxy-1,2,3,4-tetrahydroisoquinolin-6-amine | | 557.1 | B |
| 477 | (S)-N-(5-(3-((1-(1H-tetrazol-1-yl)propan-2-yl)oxy)-4-chlorophenyl)pyrimidin-2-yl)-5-methoxyindolin-6-amine | | 479.2 | B |
| 478 | (S)-5-(3-((1-(1H-tetrazol-1-yl)propan-2-yl)oxy)-4-chlorophenyl)-N-(5-methyl-2-(4-morpholinopiperidin-1-yl)pyridin-4-yl)pyrimidin-2-amine | | 591.2 | B |
| 479 | (S)-1-(6-((5-(3-((1-(1H-tetrazol-1-yl)propan-2-yl)oxy)-4-chlorophenyl)pyrimidin-2-yl)amino)-7-methoxy-3,4-dihydroisoquinolin-2(1H)-yl)propan-2-one | | 549.1 | A |
| 480 | (S)-2-(6-((5-(3-((1-(1H-tetrazol-1-yl)propan-2-yl)oxy)-4-chlorophenyl)pyrimidin-2-yl)amino)-7-methoxy-3,4-dihydroisoquinolin-2(1H)-yl)ethan-1-ol | | 537.2 | A |
| 481 | (S)-1-(4-((5-(3-((1-(1H-tetrazol-1-yl)propan-2-yl)oxy)-4-chlorophenyl)pyrimidin-2-yl)amino)-5-methoxypyridin-2-yl)-4-methylpiperidin-4-ol | | 552.2 | B |
| 482 | tert-butyl (S)-4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)piperidine-1-carboxylate | | 647.3 | B |
| 483 | (S)-5-(3-((1-(1H-tetrazol-1-yl)propan-2-yl)oxy)-4-chlorophenyl)-N-(1-(piperidin-4-yl)-3-(trifluoromethyl)-1H-pyrazol-4-yl)pyrimidin-2-amine | HCl | 549.1 | A |
| 484 | (S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(trifluoromethyl)-1H-pyrazol-4-yl)pyrimidin-2-amine | | 633.3 | A |
| 485 | (S)-5-(3-((1-(1H-tetrazol-1-yl)propan-2-yl)oxy)-4-chlorophenyl)-N-(1-(1-(2,2-difluoroethyl)piperidin-4-yl)-3-(trifluoromethyl)-1H-pyrazol-4-yl)pyrimidin-2-amine | | 613.1 | B |
| 486 | (S)-5-(3-((1-(1H-tetrazol-1-yl)propan-2-yl)oxy)-4-chlorophenyl)-N-(1-(1-(2,2,2-trifluoroethyl)piperidin-4-yl)-3-(trifluoromethyl)-1H-pyrazol-4-yl)pyrimidin-2-amine | | 631.3 | B |
| 487 | (S)-5-(3-((1-(1H-tetrazol-1-yl)propan-2-yl)oxy)-4-chlorophenyl)-N-(1-(1-methylpiperidin-4-yl)-3-(trifluoromethyl)-1H-pyrazol-4-yl)pyrimidin-2-amine | | 563.1 | A |
| 488 | (S)-1-(4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)piperidin-1-yl)ethan-1-one | | 591.1 | A |
| 489 | (S)-5-(3-((1-(1H-tetrazol-1-yl)propan-2-yl)oxy)-4-chlorophenyl)-N-(1-(1-(oxetan-3-ylmethyl)piperidin-4-yl)-3-(trifluoromethyl)-1H-pyrazol-4-yl)pyrimidin-2-amine | | 619.2 | A |
| 490 | (S)-N-(5-(3-((1-(1H-tetrazol-1-yl)propan-2-yl)oxy)-4-chlorophenyl)pyrimidin-2-yl)-7-methoxy-2-(2,2,2-trifluoroethyl)-1,2,3,4-tetrahydroisoquinolin-6-amine | | 575.1 | B |
| 491 | (S)-5-(3-((1-(1H-tetrazol-1-yl)propan-2-yl)oxy)-4-chlorophenyl)-N-(2-methyl-5-(4-morpholinopiperidin-1-yl)phenyl)pyrimidin-2-amine | | 590.2 | A |

TABLE 2-continued

| Ex. No. | IUPAC NAME | ADDITIVE | MS | ACTIVITY |
|---|---|---|---|---|
| 492 | (S)-N-(5-(3-((1-(1H-tetrazol-1-yl)propan-2-yl)oxy)-4-chlorophenyl)pyrimidin-2-yl)-7-methoxy-2-(2-methoxyethyl)-1,2,3,4-tetrahydroisoquinolin-6-amine | | 551.2 | A |
| 493 | 2-(((S)-1-(1H-tetrazol-1-yl)propan-2-yl)oxy)-4-(2-((2-methoxy-4-(1-(oxetan-3-yl)piperidin-3-yl)phenyl)amino)pyrimidin-5-yl)benzonitrile | | 568.3 | A |
| 494 | 5-(3-(((S)-1-(1H-tetrazol-1-yl)propan-2-yl)oxy)-4-chlorophenyl)-N-(2-methoxy-4-(1-(oxetan-3-yl)piperidin-3-yl)phenyl)pyrimidin-2-amine | | 577.2 | A |
| 495 | (S)-2-((1-(difluoromethoxy)propan-2-yl)oxy)-4-(2-((2-methoxy-5-(4-morpholinopiperidin-1-yl)phenyl)amino)pyrimidin-5-yl)benzonitrile | | 595.3 | B |
| 496 | (S)-N-(5-(3-((1-(1H-tetrazol-1-yl)propan-2-yl)oxy)-4-chlorophenyl)pyrimidin-2-yl)-5-methoxy-1H-indol-6-amine | | 477.2 | B |
| 497 | (S)-1-(6-((5-(3-((1-(1H-tetrazol-1-yl)propan-2-yl)oxy)-4-chlorophenyl)pyrimidin-2-yl)amino)-5-methoxyindolin-1-yl)-2-(dimethylamino)ethan-1-one | | 564.2 | A |
| 498 | (S)-1-(6-((5-(3-((1-(1H-tetrazol-1-yl)propan-2-yl)oxy)-4-chlorophenyl)pyrimidin-2-yl)amino)-5-methoxyindolin-1-yl)-2-morpholinoethan-1-one | | 606.2 | C |
| 499 | (S)-N-(5-(3-((1-(1H-tetrazol-1-yl)propan-2-yl)oxy)-4-chlorophenyl)pyrimidin-2-yl)-6-methoxy-2-(oxetan-3-ylmethyl)-1,2,3,4-tetrahydroisoquinolin-7-amine | | 563.2 | A |
| 500 | (S)-1-(7-((5-(3-((1-(1H-tetrazol-1-yl)propan-2-yl)oxy)-4-chlorophenyl)pyrimidin-2-yl)amino)-6-methoxy-3,4-dihydroisoquinolin-2(1H)-yl)-2-methoxyethan-1-one | | 565.2 | B |
| 501 | (S)-1-(7-((5-(3-((1-(1H-tetrazol-1-yl)propan-2-yl)oxy)-4-chlorophenyl)pyrimidin-2-yl)amino)-6-methoxy-3,4-dihydroisoquinolin-2(1H)-yl)-2-morpholinoethan-1-one | | 620.2 | B |
| 502 | (S)-N-(5-(3-((1-(1H-tetrazol-1-yl)propan-2-yl)oxy)-4-chlorophenyl)pyrimidin-2-yl)-6-methoxy-2-(tetrahydro-2H-pyran-4-yl)-1,2,3,4-tetrahydroisoquinolin-7-amine | | 577.1 | A |
| 503 | (S)-N-(5-(3-((1-(1H-tetrazol-1-yl)propan-2-yl)oxy)-4-chlorophenyl)pyrimidin-2-yl)-5-methoxy-1-(oxetan-3-ylmethyl)indolin-6-amine | | 549.2 | B |
| 504 | (S)-N-(5-(3-((1-(1H-tetrazol-1-yl)propan-2-yl)oxy)-4-chlorophenyl)pyrimidin-2-yl)-6-methoxy-2-(2-methylpyrimidin-4-yl)-1,2,3,4-tetrahydroisoquinolin-7-amine | | 585.2 | B |
| 505 | (S)-N-(5-(3-((1-(1H-tetrazol-1-yl)propan-2-yl)oxy)-4-chlorophenyl)pyrimidin-2-yl)-7-methoxy-2-(2-methylpyrimidin-4-yl)-1,2,3,4-tetrahydroisoquinolin-6-amine | | 585.1 | B |
| 506 | (S)-2-(6-((5-(3-((1-(1H-tetrazol-1-yl)propan-2-yl)oxy)-4-chlorophenyl)pyrimidin-2-yl)amino)-7-methoxy-3,4-dihydroisoquinolin-2(1H)-yl)acetic acid | | 551.1 | A |
| 507 | (S)-N-(5-(3-((1-(1H-tetrazol-1-yl)propan-2-yl)oxy)-4-chlorophenyl)pyrimidin-2-yl)-8-chloro-2,3,4,5-tetrahydro-1H-benzo[d]azepin-7-amine | | 511.1 | A |
| 508 | (S)-5-(3-((1-(1H-tetrazol-1-yl)propan-2-yl)oxy)-4-chlorophenyl)-N-(2-(4,4-difluorocyclohexyl)-5-methoxypyridin-4-yl)pyrimidin-2-amine | | 557.1 | C |
| 509 | (S)-2-((1-(1H-tetrazol-1-yl)propan-2-yl)oxy)-4-(2-((5-methyl-2-(4-morpholinopiperidin-1-yl)pyridin-4-yl)amino)pyrimidin-5-yl)benzonitrile | | 582.3 | B |
| 510 | (S)-1-(7-((5-(3-((1-(1H-tetrazol-1-yl)propan-2-yl)oxy)-4-chlorophenyl)pyrimidin-2-yl)amino)-6-methoxy-3,4-dihydroisoquinolin-2(1H)-yl)propan-2-one | | 549.1 | A |
| 511 | (S)-2-(7-((5-(3-((1-(1H-tetrazol-1-yl)propan-2-yl)oxy)-4-chlorophenyl)pyrimidin-2-yl)amino)-6-methoxy-3,4-dihydroisoquinolin-2(1H)-yl)ethan-1-ol | | 537.1 | A |
| 512 | (S)-6-((5-(3-((1-(1H-tetrazol-1-yl)propan-2-yl)oxy)-4-chlorophenyl)pyrimidin-2-yl)amino)-2-(2-(dimethylamino)ethyl)-5-methoxyisoindolin-1-one | | 564.2 | B |
| 513 | (S)-N-(5-(3-((1-(1H-tetrazol-1-yl)propan-2-yl)oxy)-4-chlorophenyl)pyrimidin-2-yl)-8-chloro-3-(oxetan-3-yl)-2,3,4,5-tetrahydro-1H-benzo[d]azepin-7-amine | | 567.1 | A |
| 514 | (S)-1-(6-((5-(3-((1-(1H-tetrazol-1-yl)propan-2-yl)oxy)-4-chlorophenyl)pyrimidin-2-yl)amino)-7-methoxy-3,4-dihydroisoquinolin-2(1H)-yl)-2-(ethyl(methyl)amino)ethan-1-one | | 592.2 | A |
| 515 | (S)-N-(5-(3-((1-(1H-tetrazol-1-yl)propan-2-yl)oxy)-4-chlorophenyl)pyrimidin-2-yl)-6-ethyl-2-(oxetan-3-yl)-1,2,3,4-tetrahydroisoquinolin-7-amine | | 547.2 | B |
| 516 | (S)-2-((1-(1H-tetrazol-1-yl)propan-2-yl)oxy)-4-(2-((6-ethyl-2-(oxetan-3-yl)-1,2,3,4-tetrahydroisoquinolin-7-yl)amino)pyrimidin-5-yl)benzonitrile | | 538.2 | B |
| 517 | (S)-5-(3-((1-(1H-tetrazol-1-yl)propan-2-yl)oxy)-4-chlorophenyl)-N-(5-methoxy-2-(tetrahydro-2H-pyran-4-yl)pyridin-4-yl)pyrimidin-2-amine | | 523.1 | B |
| 518 | (S)-N-(5-(3-((1-(1H-tetrazol-1-yl)propan-2-yl)oxy)-4-chlorophenyl)pyrimidin-2-yl)-6-methoxy-2-(2-methoxyethyl)-1,2,3,4-tetrahydroisoquinolin-7-amine | | 551.2 | A |
| 519 | (S)-2-(7-((5-(3-((1-(1H-tetrazol-1-yl)propan-2-yl)oxy)-4-chlorophenyl)pyrimidin-2-yl)amino)-6-methoxy-3,4-dihydroisoquinolin-2(1H)-yl)-2-oxoethyl acetate | | 593.1 | B |

TABLE 2-continued

| Ex. No. | IUPAC NAME | ADDITIVE | MS | ACTIVITY |
|---|---|---|---|---|
| 520 | (S)-1-(7-((5-(3-((1-(1H-tetrazol-1-yl)propan-2-yl)oxy)-4-chlorophenyl)pyrimidin-2-yl)amino)-6-methoxy-3,4-dihydroisoquinolin-2(1H)-yl)-2-methyl-1-oxopropan-2-yl acetate | | 621.2 | C |
| 521 | (S)-1-(7-((5-(3-((1-(1H-tetrazol-1-yl)propan-2-yl)oxy)-4-chlorophenyl)pyrimidin-2-yl)amino)-6-methoxy-3,4-dihydroisoquinolin-2(1H)-yl)-2-hydroxy-2-methylpropan-1-one | | 579.1 | B |
| 522 | (S)-1-(7-((5-(3-((1-(1H-tetrazol-1-yl)propan-2-yl)oxy)-4-chlorophenyl)pyrimidin-2-yl)amino)-6-methoxy-3,4-dihydroisoquinolin-2(1H)-yl)-2-hydroxyethan-1-one | | 551.1 | B |
| 523 | (S)-1-(5-((5-(3-((1-(1H-tetrazol-1-yl)propan-2-yl)oxy)-4-chlorophenyl)pyrimidin-2-yl)amino)-6-methylpyridin-3-yl)azetidin-3-ol | | 494.1 | B |
| 524 | (S)-2-((1-(1H-tetrazol-1-yl)propan-2-yl)oxy)-4-(2-(6-cyclopropyl-2-(oxetan-3-yl)-1,2,3,4-tetrahydroisoquinolin-7-yl)amino)pyrimidin-5-yl)benzonitrile | | 550.2 | B |
| 525 | (S)-2-((1-(1H-tetrazol-1-yl)propan-2-yl)oxy)-4-(2-((8-chloro-3-(2,2,2-trifluoroacetyl)-2,3,4,5-tetrahydro-1H-benzo[d]azepin-7-yl)amino)pyrimidin-5-yl)benzonitrile | | 597.9 | B |
| 526 | methyl (S)-3-((5-(3-((1-(1H-tetrazol-1-yl)propan-2-yl)oxy)-4-chlorophenyl)pyrimidin-2-yl)amino)-4-methoxybenzoate | | 495.9 | B |
| 527 | (S)-2-((1-(1H-tetrazol-1-yl)propan-2-yl)oxy)-4-(2-((8-chloro-2,3,4,5-tetrahydro-1H-benzo[d]azepin-7-yl)amino)pyrimidin-5-yl)benzonitrile | | 502.0 | A |
| 528 | (S)-2-((1-(1H-tetrazol-1-yl)propan-2-yl)oxy)-4-(2-((2-methoxy-5-methyl-4-(1-(oxetan-3-yl)piperidin-4-yl)phenyl)amino)pyrimidin-5-yl)benzonitrile | | 582.0 | A |
| 529 | (S)-5-(3-((1-(1H-tetrazol-1-yl)propan-2-yl)oxy)-4-chlorophenyl)-N-(2-methoxy-5-methyl-4-(1-(oxetan-3-yl)piperidin-4-yl)phenyl)pyrimidin-2-amine | | 591.1 | A |
| 530 | (S)-2-((1-(1H-tetrazol-1-yl)propan-2-yl)oxy)-4-(2-((2-methoxy-5-methyl-4-(1-(oxetan-3-yl)-1,2,3,6-tetrahydropyridin-4-yl)phenyl)amino)pyrimidin-5-yl)benzonitrile | | 580.1 | A |
| 531 | (S)-5-(3-((1-(1H-tetrazol-1-yl)propan-2-yl)oxy)-4-chlorophenyl)-N-(2-methoxy-5-methyl-4-(1-(oxetan-3-yl)-1,2,3,6-tetrahydropyridin-4-yl)phenyl)pyrimidin-2-amine | | 589.0 | B |
| 532 | (S)-5-(3-((1-(1H-tetrazol-1-yl)propan-2-yl)oxy)-4-chlorophenyl)-N-(5-(piperidin-4-yl)-6-(trifluoromethoxy)phenyl)pyrimidin-2-amine | 2HCl | 574.9 | A |
| 533 | (S)-5-(3-((1-(1H-tetrazol-1-yl)propan-2-yl)oxy)-4-chlorophenyl)-N-(2-methoxy-5-(piperazin-1-yl)phenyl)pyrimidin-2-amine | 2HCl | 522.0 | A |
| 534 | (S)-5-(4-((1-(1H-tetrazol-1-yl)propan-2-yl)oxy)-5-chloropyridin-2-yl)-N-(2-methoxy-4-(4-morpholinopiperidin-1-yl)phenyl)pyrimidin-2-amine | | 607.1 | C |
| 535 | (S)-2-(4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)piperidin-1-yl)ethan-1-ol | | 592.9 | A |
| 536 | (S)-2-(4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)piperidin-1-yl)acetonitrile | | 587.9 | B |
| 537 | (S)-5-(3-((1-(1H-tetrazol-1-yl)propan-2-yl)oxy)-4-chlorophenyl)-N-(2-(4-morpholinopiperidin-1-yl)-5-(trifluoromethoxy)pyridin-4-yl)pyrimidin-2-amine | | 661.0 | A |
| 538 | (S)-2-((1-(1H-tetrazol-1-yl)propan-2-yl)oxy)-4-(2-((8-chloro-3-(tetrahydro-2H-pyran-4-yl)-2,3,4,5-tetrahydro-1H-benzo[d]azepin-7-yl)amino)pyrimidin-5-yl)benzonitrile | | 586.0 | A |
| 539 | (S)-2-((1-(1H-tetrazol-1-yl)propan-2-yl)oxy)-4-(2-((8-chloro-3-(oxetan-3-yl)-2,3,4,5-tetrahydro-1H-benzo[d]azepin-7-yl)amino)pyrimidin-5-yl)benzonitrile | | 558.0 | A |
| 540 | (S)-3-((5-(3-((1-(1H-tetrazol-1-yl)propan-2-yl)oxy)-4-chlorophenyl)pyrimidin-2-yl)amino)-4-methoxybenzoic acid | | 481.9 | C |
| 541 | (S)-5-(3-((1-(1H-tetrazol-1-yl)propan-2-yl)oxy)-4-chlorophenyl)-N-(2-(4-(tetrahydro-2H-pyran-4-yl)piperazin-1-yl)-5-(trifluoromethoxy)pyridin-4-yl)pyrimidin-2-amine | | 661.0 | A |
| 542 | (S)-2-((1-(1H-tetrazol-1-yl)propan-2-yl)oxy)-4-(2-((2-(4-(tetrahydro-2H-pyran-4-yl)piperazin-1-yl)-5-(trifluoromethoxy)pyridin-4-yl)amino)pyrimidin-5-yl)benzonitrile | | 652.0 | A |
| 543 | (S)-2-((1-(1H-tetrazol-1-yl)propan-2-yl)oxy)-4-(2-((2-(4-morpholinopiperidin-1-yl)-5-(trifluoromethoxy)pyridin-4-yl)amino)pyrimidin-5-yl)benzonitrile | | 652.0 | A |
| 544 | (S)-(3-((5-(3-((1-(1H-tetrazol-1-yl)propan-2-yl)oxy)-4-chlorophenyl)pyrimidin-2-yl)amino)-4-methoxyphenyl) (4-methyl-1,4-diazepan-1-yl)methanone | | 578.0 | A |
| 545 | (S)-5-(3-((1-(1H-tetrazol-1-yl)propan-2-yl)oxy)-4-chlorophenyl)-N-(3-cyclopropyl-1-(1-(tetrahydro-2H-pyran-4-yl)piperidin-4-yl)-1H-pyrazol-4-yl)pyrimidin-2-amine | | 605.0 | A |
| 546 | (S)-2-((1-(1H-tetrazol-1-yl)propan-2-yl)oxy)-4-(2-((3-cyclopropyl-1-(1-(tetrahydro-2H-pyran-4-yl)piperidin-4-yl)-1H-pyrazol-4-yl)amino)pyrimidin-5-yl)benzonitrile | | 596.1 | A |

TABLE 2-continued

| Ex. No. | IUPAC NAME | ADDITIVE | MS | ACTIVITY |
|---|---|---|---|---|
| 547 | (S)-5-(3-((1-(1H-tetrazol-1-yl)propan-2-yl)oxy)-4-chlorophenyl)-N-(1-(1-(3,3-dimethylbutyl)piperidin-4-yl)-3-(trifluoromethyl)-1H-pyrazol-4-yl)pyrimidin-2-amine | | 633.0 | A |
| 548 | (S)-5-(3-((1-(1H-tetrazol-1-yl)propan-2-yl)oxy)-4-chlorophenyl)-N-(1-(1-benzylpiperidin-4-yl)-3-(trifluoromethyl)-1H-pyrazol-4-yl)pyrimidin-2-amine | | 639.0 | A |
| 549 | (S)-5-(3-((1-(1H-tetrazol-1-yl)propan-2-yl)oxy)-4-chlorophenyl)-N-(1-(1-(cyclopropylmethyl)piperidin-4-yl)-3-(trifluoromethyl)-1H-pyrazol-4-yl)pyrimidin-2-amine | | 603.0 | A |
| 550 | (S)-5-(3-((1-(1H-tetrazol-1-yl)propan-2-yl)oxy)-4-chlorophenyl)-N-(1-(1-(pyridin-4-ylmethyl)piperidin-4-yl)-3-(trifluoromethyl)-1H-pyrazol-4-yl)pyrimidin-2-amine | | 639.9 | B |
| 551 | (S)-5-(3-((1-(1H-tetrazol-1-yl)propan-2-yl)oxy)-4-chlorophenyl)-N-(1-(1-(thiazol-2-ylmethyl)piperidin-4-yl)-3-(trifluoromethyl)-1H-pyrazol-4-yl)pyrimidin-2-amine | | 645.9 | B |
| 552 | 5-(3-(((S)-1-(1H-tetrazol-1-yl)propan-2-yl)oxy)-4-chlorophenyl)-N-(1-(1-(tetrahydrofuran-3-yl)piperidin-4-yl)-3-(trifluoromethyl)-1H-pyrazol-4-yl)pyrimidin-2-amine | | 619.0 | A |
| 553 | 5-(3-(((S)-1-(1H-tetrazol-1-yl)propan-2-yl)oxy)-4-chlorophenyl)-N-(1-(1-(1-methoxypropan-2-yl)piperidin-4-yl)-3-(trifluoromethyl)-1H-pyrazol-4-yl)pyrimidin-2-amine | | 621.0 | A |
| 554 | 5-(3-(((S)-1-(1H-tetrazol-1-yl)propan-2-yl)oxy)-4-chlorophenyl)-N-(1-(1-(2-methoxycyclohexyl)piperidin-4-yl)-3-(trifluoromethyl)-1H-pyrazol-4-yl)pyrimidin-2-amine | | 661.0 | A |
| 555 | (S)-5-(3-((1-(1H-tetrazol-1-yl)propan-2-yl)oxy)-4-chlorophenyl)-N-(1-(1-(4,4-difluorocyclohexyl)piperidin-4-yl)-3-(trifluoromethyl)-1H-pyrazol-4-yl)pyrimidin-2-amine | | 666.9 | A |
| 556 | (S)-5-(3-((1-(1H-tetrazol-1-yl)propan-2-yl)oxy)-4-chlorophenyl)-N-(1-(1-(cis or trans-4-methoxycyclohexyl)piperidin-4-yl)-3-(trifluoromethyl)-1H-pyrazol-4-yl)pyrimidin-2-amine, more polar | | 661.0 | A |
| 557 | 5-(3-(((S)-1-(1H-tetrazol-1-yl)propan-2-yl)oxy)-4-chlorophenyl)-N-(1-(1-(2,2-dimethyltetrahydro-2H-pyran-4-yl)piperidin-4-yl)-3-(trifluoromethyl)-1H-pyrazol-4-yl)pyrimidin-2-amine | | 661.0 | A |
| 558 | (S)-5-(3-((1-(1H-tetrazol-1-yl)propan-2-yl)oxy)-4-chlorophenyl)-N-(1-(1'-cyclopropyl-[1,4'-bipiperidin]-4-yl)-3-(trifluoromethyl)-1H-pyrazol-4-yl)pyrimidin-2-amine | | 672.0 | A |
| 559 | (S)-5-(3-((1-(1H-tetrazol-1-yl)propan-2-yl)oxy)-4-chlorophenyl)-N-(1-(1'-methyl-[1,4'-bipiperidin]-4-yl)-3-(trifluoromethyl)-1H-pyrazol-4-yl)pyrimidin-2-amine | | 646.0 | A |
| 560 | (S)-5-(3-((1-(1H-tetrazol-1-yl)propan-2-yl)oxy)-4-chlorophenyl)-N-(1-(1-(thiophen-3-ylmethyl)piperidin-4-yl)-3-(trifluoromethyl)-1H-pyrazol-4-yl)pyrimidin-2-amine | | 644.9 | A |
| 561 | (S)-N-(1-(1-(((1H-pyrazol-3-yl)methyl)piperidin-4-yl)-3-(trifluoromethyl)-1H-pyrazol-4-yl)-5-(3-((1-(1H-tetrazol-1-yl)propan-2-yl)oxy)-4-chlorophenyl)pyrimidin-2-amine | | 628.9 | A |
| 562 | (S)-5-(3-((1-(1H-tetrazol-1-yl)propan-2-yl)oxy)-4-chlorophenyl)-N-(1-(1-(oxetan-3-yl)piperidin-4-yl)-3-(trifluoromethyl)-1H-pyrazol-4-yl)pyrimidin-2-amine | | 604.9 | B |
| 563 | (S)-5-(3-((1-(1H-tetrazol-1-yl)propan-2-yl)oxy)-4-chlorophenyl)-N-(1-(1-(pyridin-3-ylmethyl)piperidin-4-yl)-3-(trifluoromethyl)-1H-pyrazol-4-yl)pyrimidin-2-amine | | 640.0 | B |
| 564 | (S)-5-(3-((1-(1H-tetrazol-1-yl)propan-2-yl)oxy)-4-chlorophenyl)-N-(1-(1-(pyridin-2-ylmethyl)piperidin-4-yl)-3-(trifluoromethyl)-1H-pyrazol-4-yl)pyrimidin-2-amine | | 640.0 | A |
| 565 | (S)-4-(4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)piperidin-1-yl)tetrahydro-2H-thiopyran 1,1-dioxide | | 680.9 | A |
| 566 | (S)-5-(3-((1-(1H-tetrazol-1-yl)propan-2-yl)oxy)-4-chlorophenyl)-N-(1-(1-(((1-methyl-1H-pyrrol-2-yl)methyl)piperidin-4-yl)-3-(trifluoromethyl)-1H-pyrazol-4-yl)pyrimidin-2-amine | | 640.0 | A |
| 567 | (S)-5-(3-((1-(1H-tetrazol-1-yl)propan-2-yl)oxy)-4-chlorophenyl)-N-(1-(1-(((1-methyl-1H-pyrazol-4-yl)methyl)piperidin-4-yl)-3-(trifluoromethyl)-1H-pyrazol-4-yl)pyrimidin-2-amine | | 643.0 | A |
| 568 | (S)-5-(3-((1-(1H-tetrazol-1-yl)propan-2-yl)oxy)-4-chlorophenyl)-N-(1-(1-(cis or trans-4-methoxycyclohexyl)piperidin-4-yl)-3-(trifluoromethyl)-1H-pyrazol-4-yl)pyrimidin-2-amine, less polar | | 661.0 | A |
| 569 | (S)-(3-((5-(3-((1-(1H-tetrazol-1-yl)propan-2-yl)oxy)-4-chlorophenyl)pyrimidin-2-yl)amino)-4-methoxyphenyl) (4-methylpiperazin-1-yl)methanone | | 563.9 | A |
| 570 | (3-((5-(3-(((S)-1-(1H-tetrazol-1-yl)propan-2-yl)oxy)-4-chlorophenyl)pyrimidin-2-yl)amino)-4-methoxyphenyl) (cis-3,5-dimethylpiperazin-1-yl)methanone | | 577.9 | A |
| 571 | tert-butyl 3-((4-((5-(3-(((S)-1-(1H-tetrazol-1-yl)propan-2-yl)oxy)-4-chlorophenyl)pyrimidin-2-yl) amino)-3- (trifluoromethyl)-1H-pyrazol-1-yl) methyl) pyrrolidine-1-carboxylate | | 647.0 | C |

TABLE 2-continued

| Ex. No. | IUPAC NAME | ADDITIVE | MS | ACTIVITY |
|---|---|---|---|---|
| 572 | 5-(3-(((S)-1-(1H-tetrazol-1-yl)propan-2-yl)oxy)-4-chlorophenyl)-N-(1-(pyrrolidin-3-ylmethyl)-3-(trifluoromethyl)-1H-pyrazol-4-yl)pyrimidin-2-amine | HCl | 548.9 | A |
| 573 | (S)-(3-((5-(3-((1-(1H-tetrazol-1-yl)propan-2-yl)oxy)-4-chlorophenyl)pyrimidin-2-yl)amino)-4-methoxyphenyl) (4-(oxetan-3-yl)-1,4-diazepan-1-yl)methanone | | 619.9 | A |
| 574 | 5-(3-(((S)-1-(1H-tetrazol-1-yl)propan-2-yl)oxy)-4-chlorophenyl)-N-(1-((oxetan-3-yl)pyrrolidin-3-yl)methyl)-3-(trifluoromethyl)-1H-pyrazol-4-yl)pyrimidin-2-amine | HCl | 604.9 | A |
| 575 | (S)-5-(3-((1-(1H-tetrazol-1-yl)propan-2-yl)oxy)-4-chlorophenyl)-N-(2,4-difluoro-5-(piperidin-4-yl)phenyl)pyrimidin-2-amine | HCl | 526.9 | A |
| 576 | (S)-5-(3-((1-(1H-tetrazol-1-yl)propan-2-yl)oxy)-4-chlorophenyl)-N-(2-methoxy-5-(4-(oxetan-3-yl)piperazin-1-yl)phenyl)pyrimidin-2-amine | | 577.9 | B |
| 577 | (S)-5-(3-((1-(1H-tetrazol-1-yl)propan-2-yl)oxy)-4-chlorophenyl)-N-(5-(1-(oxetan-3-yl)piperidin-4-yl)-2-(trifluoromethoxy)phenyl)pyrimidin-2-amine | | 631.0 | B |
| 578 | (S)-5-(3-((1-(1H-tetrazol-1-yl)propan-2-yl)oxy)-4-chlorophenyl)-N-(2,4-difluoro-5-(1-(oxetan-3-yl)piperidin-4-yl)phenyl)pyrimidin-2-amine | | 582.9 | B |
| 579 | (S)-2-(4-(3-((5-(3-((1-(1H-tetrazol-1-yl)propan-2-yl)oxy)-4-chlorophenyl)pyrimidin-2-yl)amino)-4-methoxyphenyl)piperazin-1-yl)acetamide | | 578.9 | A |
| 580 | (S)-5-(3-((1-(1H-tetrazol-1-yl)propan-2-yl)oxy)-4-chlorophenyl)-N-(2-fluoro-5-(4-morpholinopiperidin-1-yl)phenyl)pyrimidin-2-amine | | 593.9 | A |
| 581 | (S)-5-(3-((1-(1H-tetrazol-1-yl)propan-2-yl)oxy)-4-chlorophenyl)-N-(5-(4-morpholinopiperidin-1-yl)-2-(2,2,2-trifluoroethoxy)pyridin-3-yl)pyrimidin-2-amine | | 675.0 | A |
| 582 | (S)-5-(3-((1-(1H-tetrazol-1-yl)propan-2-yl)oxy)-4-chlorophenyl)-N-(2-methoxy-5-(4-(tetrahydro-2H-pyran-4-yl)piperazin-1-yl)phenyl)pyrimidin-2-amine | | 606.0 | A |
| 583 | (S)-1-(4-(3-((5-(3-((1-(1H-tetrazol-1-yl)propan-2-yl)oxy)-4-chlorophenyl)pyrimidin-2-yl)amino)-4-methoxyphenyl)piperazin-1-yl)-2-(dimethylamino)ethan-1-one | | 607.0 | A |
| 584 | (S)-5-(3-((1-(1H-tetrazol-1-yl)propan-2-yl)oxy)-4-chlorophenyl)-N-(2-methoxy-5-(4-methylpiperazin-1-yl)phenyl)pyrimidin-2-amine | | 536.2 | A |
| 585 | (S)-2-((1-(1H-tetrazol-1-yl)propan-2-yl)oxy)-4-(2-((6-methoxy-1-(2,2,2-trifluoroacetyl)-1,2,3,4-tetrahydroquinolin-7-yl)amino)pyrimidin-5-yl)benzonitrile | | 580.2 | B |
| 586 | (S)-1-(7-((5-(3-((1-(1H-tetrazol-1-yl)propan-2-yl)oxy)-4-chlorophenyl)pyrimidin-2-yl)amino)-6-methoxy-3,4-dihydroquinolin-1(2H)-yl)-2,2,2-trifluoroethan-1-one | | 589.2 | C |
| 587 | (S)-5-(3-((1-(1H-tetrazol-1-yl)propan-2-yl)oxy)-4-chlorophenyl)-N-(3-ethoxy-1-(1-(tetrahydro-2H-pyran-4-yl)piperidin-4-yl)-1H-pyrazol-4-yl)pyrimidin-2-amine | | 609.3 | A |
| 588 | (S)-(3-((5-(3-((1-(1H-tetrazol-1-yl)propan-2-yl)oxy)-4-chlorophenyl)pyrimidin-2-yl)amino)-4-methoxyphenyl) (4-(2-hydroxyethyl)-1,4-diazepan-1-yl)methanone | | 607.9 | A |
| 589 | (S)-(3-((5-(3-((1-(1H-tetrazol-1-yl)propan-2-yl)oxy)-4-chlorophenyl)pyrimidin-2-yl)amino)-4-methoxyphenyl) (4-(oxetan-3-yl)piperazin-1-yl)methanone | | 605.9 | B |
| 590 | (S)-2-((1-(1H-tetrazol-1-yl)propan-2-yl)oxy)-4-(2-((6-methoxy-1,2,3,4-tetrahydroquinolin-7-yl)amino)pyrimidin-5-yl)benzonitrile | | 484.0 | A |
| 591 | (S)-N-(5-(3-((1-(1H-tetrazol-1-yl)propan-2-yl)oxy)-4-chlorophenyl)pyrimidin-2-yl)-6-methoxy-1,2,3,4-tetrahydroquinolin-7-amine | | 492.9 | A |
| 592 | (S)-4-((5-(3-((1-(1H-tetrazol-1-yl)propan-2-yl)oxy)-4-chlorophenyl)pyrimidin-2-yl)amino)-1-(1-(tetrahydro-2H-pyran-4-yl)piperidin-4-yl)-1H-pyrazole-3-carbonitrile | | 590.0 | A |
| 593 | (S)-(3-((5-(3-((1-(1H-tetrazol-1-yl)propan-2-yl)oxy)-4-chlorophenyl)pyrimidin-2-yl)amino)-4-methoxyphenyl) (1,4-diazepan-1-yl)methanone | | 563.9 | A |
| 594 | (4-(4-((5-(3-(((S)-1-(1H-tetrazol-1-yl)propan-2-yl)oxy)-4-chlorophenyl)pyrimidin-2-yl)amino)-3-methoxyphenyl)morpholin-2-yl)methanol | | 552.9 | B |
| 595 | (S)-5-(3-((1-(1H-tetrazol-1-yl)propan-2-yl)oxy)-4-chlorophenyl)-N-(2-methoxy-5-(3-morpholinoazetidin-1-yl)phenyl)pyrimidin-2-amine | | 578.2 | B |
| 596 | tert-butyl (S)-3-((4-((5-(3-((1-(1H-tetrazol-1-yl)propan-2-yl)oxy)-4-chlorophenyl)pyrimidin-2-yl) amino)-3- (trifluoromethyl) -1H-pyrazol-1-yl) methyl)azetidine-1-carboxylate | | 635.3 | C |
| 597 | (S)-5-(3-((1-(1H-tetrazol-1-yl)propan-2-yl)oxy)-4-chlorophenyl)-N-(1-(azetidin-3-ylmethyl)-3-(trifluoromethyl)-1H-pyrazol-4-yl)pyrimidin-2-amine | | 535.1 | A |
| 598 | (S)-5-(3-((1-(1H-tetrazol-1-yl)propan-2-yl)oxy)-4-chlorophenyl)-N-(1-((1-(oxetan-3-yl)azetidin-3-yl)methyl)-3-(trifluoromethyl)-1H-pyrazol-4-yl)pyrimidin-2-amine | | 591.2 | A |
| 599 | tert-butyl 3-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)piperidine-1-carboxylate | | 649.2 | C |

TABLE 2-continued

| Ex. No. | IUPAC NAME | ADDITIVE | MS | ACTIVITY |
|---|---|---|---|---|
| 600 | 5-(3-(((S)-1-(1H-tetrazol-1-yl)propan-2-yl)oxy)-4-chlorophenyl)-N-(1-(piperidin-3-yl)-3-(trifluoromethyl)-1H-pyrazol-4-yl)pyrimidin-2-amine | | 549.2 | A |
| 601 | 5-(3-(((S)-1-(1H-tetrazol-1-yl)propan-2-yl)oxy)-4-chlorophenyl)-N-(1-(1-(oxetan-3-yl)piperidin-3-yl)-3-(trifluoromethyl)-1H-pyrazol-4-yl)pyrimidin-2-amine | | 605.2 | B |
| 602 | 5-(3-(((S)-1-(1H-tetrazol-1-yl)propan-2-yl)oxy)-4-chlorophenyl)-N-(1-(pyrrolidin-2-ylmethyl)-3-(trifluoromethyl)-1H-pyrazol-4-yl)pyrimidin-2-amine | | 549.1 | A |
| 603 | ethyl (S)-4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)cyclohexane-1-carboxylate | | 619.9 | B |
| 604 | (S)-4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)cyclohexane-1-carboxylic acid | | 591.9 | B |
| 605 | (S)-5-(3-((1-(1H-tetrazol-1-yl)propan-2-yl)oxy)-4-chlorophenyl)-N-(2-methyl-5-(3-morpholinoazetidin-1-yl)pyridin-3-yl)pyrimidin-2-amine | | 562.9 | B |
| 606 | (S)-2-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-N,N-diethylacetamide | | 578.8 | B |
| 607 | (S)-2-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-1-morpholinoethan-1-one | | 592.9 | A |
| 608 | 5-(3-(((S)-1-(1H-tetrazol-1-yl)propan-2-yl)oxy)-4-chlorophenyl)-N-(1-(sec-butyl)-3-(trifluoromethyl)-1H-pyrazol-4-yl)pyrimidin-2-amine | | 521.9 | B |
| 609 | 5-(3-(((S)-1-(1H-tetrazol-1-yl)propan-2-yl)oxy)-4-chlorophenyl)-N-(1-((1-(oxetan-3-yl)pyrrolidin-2-yl)methyl)-3-(trifluoromethyl)-1H-pyrazol-4-yl)pyrimidin-2-amine | | 604.9 | B |
| 610 | (S)-5-(3-((1-(1H-tetrazol-1-yl)propan-2-yl)oxy)-4-chlorophenyl)-N-(2-methyl-5-(3-(morpholinomethyl)azetidin-1-yl)pyridin-3-yl)pyrimidin-2-amine | | 576.9 | A |
| 611 | 5-(3-(((S)-1-(1H-tetrazol-1-yl)propan-2-yl)oxy)-4-chlorophenyl)-N-(1-((1-((tetrahydro-2H-pyran-4-yl)pyrrolidin-2-yl)methyl)-3-(trifluoromethyl)-1H-pyrazol-4-yl)pyrimidin-2-amine | | 633.0 | A |
| 612 | 5-(3-(((S)-1-(1H-tetrazol-1-yl)propan-2-yl)oxy)-4-chlorophenyl)-N-(5-(cis-3,5-dimethylpiperazin-1-yl)-2-methoxyphenyl)pyrimidin-2-amine | | 549.9 | A |
| 613 | tert-butyl (S)-4-(5-((5-(3-((1-(1H-tetrazol-1-yl)propan-2-yl)oxy)-4-chlorophenyl)pyrimidin-2-yl)amino)-6-methoxypyridin-2-yl)piperazine-1-carboxylate | | 623.0 | C |
| 614 | (S)-5-(3-((1-(1H-tetrazol-1-yl)propan-2-yl)oxy)-4-chlorophenyl)-N-(2-methoxy-6-(piperazin-1-yl)pyridin-3-yl)pyrimidin-2-amine | | 522.9 | A |
| 615 | 5-(3-(((S)-1-(1H-tetrazol-1-yl)propan-2-yl)oxy)-4-chlorophenyl)-N-(4-(2-((dimethylamino)methyl)morpholino)-2-methoxyphenyl)pyrimidin-2-amine | | 579.9 | A |
| 616 | (S)-5-(3-((1-(1H-tetrazol-1-yl)propan-2-yl)oxy)-4-chlorophenyl)-N-(2-methoxy-6-(4-(tetrahydro-2H-pyran-4-yl)piperazin-1-yl)pyridin-3-yl)pyrimidin-2-amine | | 607.0 | A |
| 617 | (S)-2-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-N-phenylacetamide | | 598.9 | B |
| 618 | 5-(3-(((S)-1-(1H-tetrazol-1-yl)propan-2-yl)oxy)-4-chlorophenyl)-N-(1-(pyrrolidin-3-yl)-3-(trifluoromethyl)-1H-pyrazol-4-yl)pyrimidin-2-amine | | 534.9 | A |
| 619 | 5-(3-(((S)-1-(1H-tetrazol-1-yl)propan-2-yl)oxy)-4-chlorophenyl)-N-(1-(1-(oxetan-3-yl)pyrrolidin-3-yl)-3-(trifluoromethyl)-1H-pyrazol-4-yl)pyrimidin-2-amine | | 590.9 | B |
| 620 | (S)-2-(2-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)ethoxy)ethan-1-ol | | 553.8 | B |
| 621 | (S)-5-(3-((1-(1H-tetrazol-1-yl)propan-2-yl)oxy)-4-chlorophenyl)-N-(3-methoxy-5-(piperazin-1-yl)pyridin-2-yl)pyrimidin-2-amine | | 522.9 | B |
| 622 | (S)-5-(3-((1-(1H-tetrazol-1-yl)propan-2-yl)oxy)-4-chlorophenyl)-N-(4-methoxy-6-(piperazin-1-yl)pyridin-3-yl)pyrimidin-2-amine | | 522.9 | A |
| 623 | (S)-5-(3-((1-(1H-tetrazol-1-yl)propan-2-yl)oxy)-4-chlorophenyl)-N-(3-isopropyl-1-(1-(tetrahydro-2H-pyran-4-yl)piperidin-4-yl)-1H-pyrazol-4-yl)pyrimidin-2-amine | | 607.0 | A |
| 624 | (S)-5-(3-((1-(1H-tetrazol-1-yl)propan-2-yl)oxy)-4-chlorophenyl)-N-(1-ethyl-3-morpholino-1H-pyrazol-4-yl)pyrimidin-2-amine | | 510.9 | C |
| 625 | cis-(S)-4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)cyclohexane-1-carboxylic acid | | 591.8 | C |
| 626 | trans-(S)-4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)cyclohexane-1-carboxylic acid | | 591.9 | B |
| 627 | (S)-5-(3-((1-(1H-tetrazol-1-yl)propan-2-yl)oxy)-4-chlorophenyl)-N-(2-(3-morpholinoazetidin-1-yl)-5-(trifluoromethoxy)pyridin-4-yl)pyrimidin-2-amine | | 632.9 | B |

TABLE 2-continued

| Ex. No. | IUPAC NAME | ADDITIVE | MS | ACTIVITY |
|---|---|---|---|---|
| 628 | (S)-5-(3-((1-(1H-tetrazol-1-yl)propan-2-yl)oxy)-4-chlorophenyl)-N-(3-(trifluoromethyl)-1H-pyrazol-4-yl)pyrimidin-2-amine | | 465.8 | B |
| 629 | 3-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)azepan-2-one | | 576.8 | A |
| 630 | (S)-N-(2-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)ethyl)benzamide | | 612.9 | C |
| 631 | (S)-5-(3-((1-(1H-tetrazol-1-yl)propan-2-yl)oxy)-4-chlorophenyl)-N-(1-(2-(pyrrolidin-1-yl)ethyl)-3-(trifluoromethyl)-1H-pyrazol-4-yl)pyrimidin-2-amine | | 562.9 | A |
| 632 | (S)-5-(3-((1-(1H-tetrazol-1-yl)propan-2-yl)oxy)-4-chlorophenyl)-N-(3-ethyl-1-(1-(tetrahydro-2H-pyran-4-yl)piperidin-4-yl)-1H-pyrazol-4-yl)pyrimidin-2-amine | | 592.9 | A |
| 633 | (S)-5-(3-((1-(1H-tetrazol-1-yl)propan-2-yl)oxy)-4-chlorophenyl)-N-(1-(2-morpholinoethyl)-3-(trifluoromethyl)-1H-pyrazol-4-yl)pyrimidin-2-amine | | 578.9 | B |
| 634 | 5-(3-(((S)-1-(1H-tetrazol-1-yl)propan-2-yl)oxy)-4-chlorophenyl)-N-(4-((1S,4S)-2,5-diazabicyclo[2.2.1]heptan-2-yl)-2-methoxyphenyl)pyrimidin-2-amine | | 533.9 | B |
| 635 | 5-(3-(((S)-1-(1H-tetrazol-1-yl)propan-2-yl)oxy)-4-chlorophenyl)-N-(1-((1-methylpiperidin-3-yl)methyl)-3-(trifluoromethyl)-1H-pyrazol-4-yl)pyrimidin-2-amine | | 576.9 | B |
| 636 | (S)-5-(3-((1-(1H-tetrazol-1-yl)propan-2-yl)oxy)-4-chlorophenyl)-N-(6-(4-(4,4-difluorocyclohexyl)piperazin-1-yl)-2-methoxypyridin-3-yl)pyrimidin-2-amine | | 641.0 | B |
| 637 | (S)-5-(3-((1-(1H-tetrazol-1-yl)propan-2-yl)oxy)-4-chlorophenyl)-N-(2-methoxy-6-(4-(2,2,2-trifluoroethyl)piperazin-1-yl)pyridin-3-yl)pyrimidin-2-amine | | 604.9 | C |
| 638 | (S)-1-(4-(5-(5-(3-((1-(1H-tetrazol-1-yl)propan-2-yl)oxy)-4-chlorophenyl)pyrimidin-2-yl)amino)-6-methoxypyridin-2-yl)piperazin-1-yl)-2,2,2-trifluoroethan-1-one | | 618.9 | C |
| 639 | (S)-5-(3-((1-(1H-tetrazol-1-yl)propan-2-yl)oxy)-4-chlorophenyl)-N-(2-methoxy-6-(4-(oxetan-3-ylmethyl)piperazin-1-yl)pyridin-3-yl)pyrimidin-2-amine | | 593.0 | B |
| 640 | 5-(3-(((S)-1-(1H-tetrazol-1-yl)propan-2-yl)oxy)-4-chlorophenyl)-N-(2-methoxy-6-(4-(tetrahydrofuran-3-yl)piperazin-1-yl)pyridin-3-yl)pyrimidin-2-amine | | 592.9 | B |
| 641 | 5-(3-(((S)-1-(1H-tetrazol-1-yl)propan-2-yl)oxy)-4-chlorophenyl)-N-(1-((4-benzylmorpholin-2-yl)methyl)-3-(trifluoromethyl)-1H-pyrazol-4-yl)pyrimidin-2-amine | | 655.0 | C |
| 642 | (S)-5-(3-((1-(1H-tetrazol-1-yl)propan-2-yl)oxy)-4-chlorophenyl)-N-(3-cyclopropyl-1-ethyl-1H-pyrazol-4-yl)pyrimidin-2-amine | | 466.0 | B |
| 643 | (S)-5-(3-((1-(1H-tetrazol-1-yl)propan-2-yl)oxy)-4-chlorophenyl)-N-(1-ethyl-3-phenyl-1H-pyrazol-4-yl)pyrimidin-2-amine | | 501.9 | B |
| 644 | 5-(3-(((S)-1-(1H-tetrazol-1-yl)propan-2-yl)oxy)-4-chlorophenyl)-N-(1-(tetrahydrofuran-3-yl)-3-(trifluoromethyl)-1H-pyrazol-4-yl)pyrimidin-2-amine | | 535.9 | B |
| 645 | (S)-5-(3-((1-(1H-tetrazol-1-yl)propan-2-yl)oxy)-4-chlorophenyl)-N-(1-(tetrahydro-2H-pyran-4-yl)-3-(trifluoromethyl)-1H-pyrazol-4-yl)pyrimidin-2-amine | | 549.8 | B |
| 646 | tert-butyl (S)-4-(4-((5-(3-((1-(1H-tetrazol-1-yl)propan-2-yl)oxy)-4-chlorophenyl)pyrimidin-2-yl)amino)-3-methoxy-1H-pyrazol-1-yl)piperidine-1-carboxylate | | 611.0 | B |
| 647 | (S)-5-(3-((1-(1H-tetrazol-1-yl)propan-2-yl)oxy)-4-chlorophenyl)-N-(3-methoxy-5-(4-(tetrahydro-2H-pyran-4-yl)piperazin-1-yl)pyridin-2-yl)pyrimidin-2-amine | | 607.0 | B |
| 648 | (S)-5-(3-((1-(1H-tetrazol-1-yl)propan-2-yl)oxy)-4-chlorophenyl)-N-(3-methoxy-5-(4-(oxetan-3-ylmethyl)piperazin-1-yl)pyridin-2-yl)pyrimidin-2-amine | | 592.9 | B |
| 649 | 5-(3-(((S)-1-(1H-tetrazol-1-yl)propan-2-yl)oxy)-4-chlorophenyl)-N-(2-methoxy-4-((S)-2-methylpiperazin-1-yl)phenyl)pyrimidin-2-amine | | 535.9 | A |
| 650 | (S)-5-(3-((1-(1H-tetrazol-1-yl)propan-2-yl)oxy)-4-chlorophenyl)-N-(4-methoxy-6-(4-(tetrahydro-2H-pyran-4-yl)piperazin-1-yl)pyridin-3-yl)pyrimidin-2-amine | | 607.0 | A |
| 651 | 5-(3-(((S)-1-(1H-tetrazol-1-yl)propan-2-yl)oxy)-4-chlorophenyl)-N-(4-methoxy-6-(4-(tetrahydrofuran-3-yl)piperazin-1-yl)pyridin-3-yl)pyrimidin-2-amine | | 593.0 | B |
| 652 | (S)-5-(3-((1-(1H-tetrazol-1-yl)propan-2-yl)oxy)-4-chlorophenyl)-N-(4-methoxy-6-(4-(oxetan-3-ylmethyl)piperazin-1-yl)pyridin-3-yl)pyrimidin-2-amine | | 592.9 | B |
| 653 | 5-(3-(((S)-1-(1H-tetrazol-1-yl)propan-2-yl)oxy)-4-chlorophenyl)-N-(2-methoxy-4-((1S,4S)-5-(tetrahydro-2H-pyran-4-yl)-2,5-diazabicyclo[2.2.1]heptan-2-yl)phenyl)pyrimidin-2-amine | | 618.0 | B |
| 654 | 5-(3-(((S)-1-(1H-tetrazol-1-yl)propan-2-yl)oxy)-4-chlorophenyl)-N-(2-methoxy-4-((S)-2-methyl-4-(tetrahydro-2H-pyran-4-yl)piperazin-1-yl)phenyl)pyrimidin-2-amine | | 620.0 | A |
| 655 | (S)-5-(3-((1-(1H-tetrazol-1-yl)propan-2-yl)oxy)-4-chlorophenyl)-N-(1-(2-methoxyethyl)-3-methyl-1H-pyrazol-5-yl)pyrimidin-2-amine | | 469.9 | C |

TABLE 2-continued

| Ex. No. | IUPAC NAME | ADDITIVE | MS | ACTIVITY |
|---|---|---|---|---|
| 656 | (S)-5-(3-((1-(1H-tetrazol-1-yl)propan-2-yl)oxy)-4-chlorophenyl)-N-(2-methoxy-5-(3-(morpholinomethyl)azetidin-1-yl)phenyl)pyrimidin-2-amine | | 591.9 | A |
| 657 | (S)-5-(3-((1-(1H-tetrazol-1-yl)propan-2-yl)oxy)-4-chlorophenyl)-N-(3-methoxy-1-(piperidin-4-yl)-1H-pyrazol-4-yl)pyrimidin-2-amine | | 510.9 | A |
| 658 | (S)-N-(1-((1H-benzo[d]imidazol-2-yl)methyl)-3-(trifluoromethyl)-1H-pyrazol-4-yl)-5-(3-((1-(1H-tetrazol-1-yl)propan-2-yl)oxy)-4-chlorophenyl)pyrimidin-2-amine | | 595.9 | B |
| 659 | (S)-5-(3-((1-(1H-tetrazol-1-yl)propan-2-yl)oxy)-4-chlorophenyl)-N-(3-methyl-1-(2,2,2-trifluoroethyl)-1H-pyrazol-5-yl)pyrimidin-2-amine | | 493.9 | B |
| 660 | (S)-5-(3-((1-(1H-tetrazol-1-yl)propan-2-yl)oxy)-4-chlorophenyl)-N-(3-methyl-1-(pyridin-2-yl)-1H-pyrazol-5-yl)pyrimidin-2-amine | | 489.1 | C |
| 661 | (S)-5-(3-((1-(1H-tetrazol-1-yl)propan-2-yl)oxy)-4-chlorophenyl)-N-(3-methoxy-1-(oxetan-3-yl)piperidin-4-yl)-1H-pyrazol-4-yl)pyrimidin-2-amine | | 567.2 | A |
| 662 | (S)-5-(3-((1-(1H-tetrazol-1-yl)propan-2-yl)oxy)-4-chlorophenyl)-N-(3-methoxy-1-(1-(tetrahydro-2H-pyran-4-yl)piperidin-4-yl)-1H-pyrazol-4-yl)pyrimidin-2-amine | | 595.3 | A |
| 663 | (S)-5-(3-((1-(1H-tetrazol-1-yl)propan-2-yl)oxy)-4-chlorophenyl)-N-(1-(tetrahydro-2H-thiopyran-4-yl)-3-(trifluoromethyl)-1H-pyrazol-4-yl)pyrimidin-2-amine | | 564.2 | B |
| 664 | (S)-5-(3-((1-(1H-tetrazol-1-yl)propan-2-yl)oxy)-4-chlorophenyl)-N-(3-(difluoromethoxy)-1-(1-(tetrahydro-2H-pyran-4-yl)piperidin-4-yl)-1H-pyrazol-4-yl)pyrimidin-2-amine | | 629.2 | A |
| 665 | tert-butyl (S)-4-(5-((5-(3-((1-(1H-tetrazol-1-yl)propan-2-yl)oxy)-4-chlorophenyl)pyrimidin-2-yl)amino)-6-methoxypyridin-2-yl)-1,4-diazepane-1-carboxylate | | 637.3 | C |
| 666 | (S)-N-(6-(1,4-diazepan-1-yl)-2-methoxypyridin-3-yl)-5-(3-((1-(1H-tetrazol-1-yl)propan-2-yl)oxy)-4-chlorophenyl)pyrimidin-2-amine | | 537.1 | A |
| 667 | (S)-5-(3-((1-(1H-tetrazol-1-yl)propan-2-yl)oxy)-4-chlorophenyl)-N-(2-methoxy-6-(4-(tetrahydro-2H-pyran-4-yl)-1,4-diazepan-1-yl)pyridin-3-yl)pyrimidin-2-amine | | 621.3 | A |
| 668 | (S)-5-(3-((1-(1H-tetrazol-1-yl)propan-2-yl)oxy)-4-chlorophenyl)-N-(3-(azetidin-1-yl)-1-ethyl-1H-pyrazol-4-yl)pyrimidin-2-amine | | 481.2 | C |
| 669 | (S)-5-(3-((1-(1H-tetrazol-1-yl)propan-2-yl)oxy)-4-chlorophenyl)-N-(1-ethyl-3-(pyrrolidin-1-yl)-1H-pyrazol-4-yl)pyrimidin-2-amine | | 495.2 | B |
| 670 | (S)-4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)cyclohexan-1-ol | | 564.2 | B |
| 671 | (S)-5-(3-((1-(1H-tetrazol-1-yl)propan-2-yl)oxy)-4-chlorophenyl)-N-(6-(4-cyclopropylpiperazin-1-yl)-2-methoxypyridin-3-yl)pyrimidin-2-amine | | 563.2 | A |
| 672 | 5-(3-(((S)-1-(1H-tetrazol-1-yl)propan-2-yl)oxy)-4-chlorophenyl)-N-(4-(hexahydropyrrolo[1,2-a]pyrazin-2(1H)-yl)-2-methoxyphenyl)pyrimidin-2-amine | | 560.2 | A |
| 673 | 5-(3-(((S)-1-(1H-tetrazol-1-yl)propan-2-yl)oxy)-4-chlorophenyl)-N-(4-(hexahydropyrazino[2,1-c][1,4]oxazin-8(1H)-yl)-2-methoxyphenyl)pyrimidin-2-amine | | 578.2 | A |
| 674 | (S)-5-(3-((1-(1H-tetrazol-1-yl)propan-2-yl)oxy)-4-chlorophenyl)-N-(1-ethyl-3-(trifluoromethyl)-1H-pyrazol-4-yl)pyrimidin-2-amine | | 494.1 | B |
| 675 | tert-butyl (S)-4-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)piperidine-1-carboxylate | | 679.3 | B |
| 676 | (S)-5-(3-((1-(1H-tetrazol-1-yl)propan-2-yl)oxy)-4-chlorophenyl)-N-(1-(piperidin-4-yl)-3-(2,2,2-trifluoroethoxy)-1H-pyrazol-4-yl)pyrimidin-2-amine | HCl | 577.2 | A |
| 677 | (S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(2,2,2-trifluoroethoxy)-1H-pyrazol-4-yl)pyrimidin-2-amine | | 662.9 | A |
| 678 | 5-(3-(((S)-1-(1H-tetrazol-1-yl)propan-2-yl)oxy)-4-chlorophenyl)-N-(1-(tetrahydro-2H-pyran-2-yl)-3-(2,2,2-trifluoroethoxy)-1H-pyrazol-4-yl)pyrimidin-2-amine | | 580.3 | A |
| 679 | (S)-1-(3-((5-(3-((1-(1H-tetrazol-1-yl)propan-2-yl)oxy)-4-chlorophenyl)pyrimidin-2-yl)amino)-4-methoxyphenyl)-N-methylazetidine-3-carboxamide | | 550.3 | A |
| 680 | (S)-4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)cyclohexan-1-one | | 562.2 | B |
| 681 | (S)-(3-((5-(3-((1-(1H-tetrazol-1-yl)propan-2-yl)oxy)-4-chlorophenyl)pyrimidin-2-yl)amino)-4-methoxyphenyl) (4-(cyclopropylmethyl)piperazin-1-yl)methanone | | 604.0 | A |
| 682 | (S)-5-(3-((1-(1H-tetrazol-1-yl)propan-2-yl)oxy)-4-chlorophenyl)-N-(3-isopropyl-1-(1-(tetrahydro-2H-pyran-4-yl)piperidin-4-yl)-1H-pyrazol-4-yl)pyrimidin-2-amine | | 607.0 | A |

TABLE 2-continued

| Ex. No. | IUPAC NAME | ADDITIVE | MS | ACTIVITY |
|---|---|---|---|---|
| 683 | (S)-5-(3-((1-(1H-tetrazol-1-yl)propan-2-yl)oxy)-4-chlorophenyl)-N-(2-(3-morpholinoazetidin-1-yl)-5-(trifluoromethoxy)pyridin-4-yl)pyrimidin-2-amine | | 632.9 | B |
| 684 | (S)-5-(3-((1-(1H-tetrazol-1-yl)propan-2-yl)oxy)-4-chlorophenyl)-N-(2,4-difluoro-5-(1-(oxetan-3-yl)piperidin-4-yl)phenyl)pyrimidin-2-amine | | 582.9 | B |
| 685 | (S)-5-(3-((1-(1H-tetrazol-1-yl)propan-2-yl)oxy)-4-chlorophenyl)-N-(3-ethyl-1-(1-(tetrahydro-2H-pyran-4-yl)piperidin-4-yl)-1H-pyrazol-4-yl)pyrimidin-2-amine | | 592.9 | A |
| 686 | (S)-2-(4-(3-((5-(3-((1-(1H-tetrazol-1-yl)propan-2-yl)oxy)-4-chlorophenyl)pyrimidin-2-yl)amino)-4-methoxyphenyl)piperazin-1-yl)acetamide | | 578.9 | A |
| 687 | (S)-5-(3-((1-(1H-tetrazol-1-yl)propan-2-yl)oxy)-4-chlorophenyl)-N-(3-methoxy-5-(4-(tetrahydro-2H-pyran-4-yl)piperazin-1-yl)pyridin-2-yl)pyrimidin-2-amine | | 607.0 | B |
| 688 | 5-(3-(((S)-1-(1H-tetrazol-1-yl)propan-2-yl)oxy)-4-chlorophenyl)-N-(4-(2-((dimethylamino)methyl)morpholino)-2-methoxyphenyl)pyrimidin-2-amine | | 579.9 | A |
| 689 | (S)-5-(3-((1-(1H-tetrazol-1-yl)propan-2-yl)oxy)-4-chlorophenyl)-N-(2-methoxy-5-(3-(morpholinomethyl)azetidin-1-yl)phenyl)pyrimidin-2-amine | | 591.9 | A |
| 690 | (S)-5-(3-((1-(1H-tetrazol-1-yl)propan-2-yl)oxy)-4-chlorophenyl)-N-(3-methoxy-1-(1-(tetrahydro-2H-pyran-4-yl)piperidin-4-yl)-1H-pyrazol-4-yl)pyrimidin-2-amine | | 595.3 | A |
| 691 | (S)-5-(3-((1-(1H-tetrazol-1-yl)propan-2-yl)oxy)-4-chlorophenyl)-N-(4-methoxy-6-(4-(tetrahydro-2H-pyran-4-yl)piperazin-1-yl)pyridin-3-yl)pyrimidin-2-amine | | 607.0 | A |
| 692 | 5-(3-(((S)-1-(1H-tetrazol-1-yl)propan-2-yl)oxy)-4-chlorophenyl)-N-(2-methoxy-4-((1S,4S)-5-(tetrahydro-2H-pyran-4-yl)-2,5-diazabicyclo[2.2.1]heptan-2-yl)phenyl)pyrimidin-2-amine | | 618.0 | B |
| 693 | (S)-5-(3-((1-(1H-tetrazol-1-yl)propan-2-yl)oxy)-4-chlorophenyl)-N-(2-methoxy-4-(4-(tetrahydro-2H-pyran-4-yl)-1,4-diazepan-1-yl)phenyl)pyrimidin-2-amine | | 621.3 | A |
| 694 | 5-(3-(((S)-1-(1H-tetrazol-1-yl)propan-2-yl)oxy)-4-chlorophenyl)-N-(2-methoxy-4-((S)-2-methyl-4-(tetrahydro-2H-pyran-4-yl)piperazin-1-yl)phenyl)pyrimidin-2-amine | | 620.0 | A |
| 695 | 5-(3-(((S)-1-(1H-tetrazol-1-yl)propan-2-yl)oxy)-4-chlorophenyl)-N-(1-(trans-4-morpholinocyclohexyl)-3-(trifluoromethyl)-1H-pyrazol-4-yl)pyrimidin-2-amine | | 633.2 | A |
| 696 | tert-butyl (S)-3-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)azetidine-1-carboxylate | | 621.3 | B |
| 697 | (S)-5-(3-((1-(1H-tetrazol-1-yl)propan-2-yl)oxy)-4-chlorophenyl)-N-(1-(azetidin-3-yl)-3-(trifluoromethyl)-1H-pyrazol-4-yl)pyrimidin-2-amine | | 521.1 | A |
| 698 | (S)-5-(3-((1-(1H-tetrazol-1-yl)propan-2-yl)oxy)-4-chlorophenyl)-N-(1-(1-(tetrahydro-2H-pyran-4-yl)azetidin-3-yl)-3-(trifluoromethyl)-1H-pyrazol-4-yl)pyrimidin-2-amine | | 605.3 | A |
| 699 | (S)-5-(3-((1-(1H-tetrazol-1-yl)propan-2-yl)oxy)-4-chlorophenyl)-N-(1-(1-(oxetan-3-yl)azetidin-3-yl)-3-(trifluoromethyl)-1H-pyrazol-4-yl)pyrimidin-2-amine | | 577.3 | B |
| 700 | (S)-5-(3-((1-(1H-tetrazol-1-yl)propan-2-yl)oxy)-4-chlorophenyl)-N-(1-ethyl-3-(2,2,2-trifluoroethoxy)-1H-pyrazol-4-yl)pyrimidin-2-amine | | 522.1 | A |
| 701 | tert-butyl (1R,3s,5S)-3-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)-8-azabicyclo[3.2.1]octane-8-carboxylate | | 675.3 | C |
| 702 | 5-(3-(((S)-1-(1H-tetrazol-1-yl)propan-2-yl)oxy)-4-chlorophenyl)-N-(1-((1R,3s,5S)-8-azabicyclo[3.2.1]octan-3-yl)-3-(trifluoromethyl)-1H-pyrazol-4-yl)pyrimidin-2-amine | | 575.2 | A |
| 703 | 5-(3-(((S)-1-(1H-tetrazol-1-yl)propan-2-yl)oxy)-4-chlorophenyl)-N-(1-((1R,3s,5S)-8-(tetrahydro-2H-pyran-4-yl)-8-azabicyclo[3.2.1]octan-3-yl)-3-(trifluoromethyl)-1H-pyrazol-4-yl)pyrimidin-2-amine | | 659.2 | A |
| 704 | trans-2-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)cyclohexan-1-ol | | 564.2 | A |
| 705 | (S)-5-(3-((1-(1H-tetrazol-1-yl)propan-2-yl)oxy)-4-chlorophenyl)-N-(2-(4-(tetrahydro-2H-pyran-4-yl)piperazin-1-yl)-5-(trifluoromethoxy)pyridin-4-yl)pyrimidin-2-amine | | 661.2 | A |
| 706 | (S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(trifluoromethyl)-1H-pyrazol-4-yl)pyrimidin-2-amine | | 633.1 | A |
| 707 | (S)-5-(3-((1-(1H-tetrazol-1-yl)propan-2-yl)oxy)-4-chlorophenyl)-N-(1-(pyridin-2-ylmethyl)-3-(trifluoromethyl)-1H-pyrazol-4-yl)pyrimidin-2-amine | | 557.2 | B |
| 708 | (S)-5-(3-((1-(1H-tetrazol-1-yl)propan-2-yl)oxy)-4-chlorophenyl)-N-(1-(pyridin-3-ylmethyl)-3-(trifluoromethyl)-1H-pyrazol-4-yl)pyrimidin-2-amine | | 557.1 | B |

TABLE 2-continued

| Ex. No. | IUPAC NAME | ADDITIVE | MS | ACTIVITY |
|---|---|---|---|---|
| 709 | (S)-5-(3-((1-(1H-tetrazol-1-yl)propan-2-yl)oxy)-4-chlorophenyl)-N-(1-(pyridin-4-ylmethyl)-3-(trifluoromethyl)-1H-pyrazol-4-yl)pyrimidin-2-amine | | 557.1 | B |
| 710 | 5-(3-(((S)-1-(1H-tetrazol-1-yl)propan-2-yl)oxy)-4-chlorophenyl)-N-(1-((tetrahydrofuran-2-yl)methyl)-3-(trifluoromethyl)-1H-pyrazol-4-yl)pyrimidin-2-amine | | 550.0 | B |
| 711 | (S)-5-(3-((1-(1H-tetrazol-1-yl)propan-2-yl)oxy)-4-chlorophenyl)-N-(1-methyl-5-(trifluoromethyl)-1H-pyrazol-3-yl)pyrimidin-2-amine | | 479.9 | C |
| 712 | 5-(3-(((S)-1-(1H-tetrazol-1-yl)propan-2-yl)oxy)-4-chlorophenyl)-N-(1-((tetrahydro-2H-pyran-2-yl)methyl)-3-(trifluoromethyl)-1H-pyrazol-4-yl)pyrimidin-2-amine | | 564.3 | B |
| 713 | 2-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)propanamide | | 537.1 | A |
| 714 | (S)-5-(3-((1-(1H-tetrazol-1-yl)propan-2-yl)oxy)-4-chlorophenyl)-N-(1-benzyl-1H-pyrazol-3-yl)pyrimidin-2-amine | | 487.9 | B |
| 715 | (S)-5-(3-((1-(1H-tetrazol-1-yl)propan-2-yl)oxy)-4-chlorophenyl)-N-(1-(tert-butyl)-1H-pyrazol-3-yl)pyrimidin-2-amine | | 454.0 | C |
| 716 | 2-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)propanenitrile | | 519.0 | B |
| 717 | 5-(3-(((S)-1-(1H-tetrazol-1-yl)propan-2-yl)oxy)-4-chlorophenyl)-N-(1-((1S,4R)-bicyclo[2.2.1]heptan-2-yl)-3-(trifluoromethyl)-1H-pyrazol-4-yl)pyrimidin-2-amine | | 559.8 | C |
| 718 | (S)-3-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)propan-1-ol | | 524.1 | B |
| 719 | (S)-5-(3-((1-(1H-tetrazol-1-yl)propan-2-yl)oxy)-4-chlorophenyl)-N-(1-methyl-3-phenyl-1H-pyrazol-5-yl)pyrimidin-2-amine | | 487.9 | B |
| 720 | (S)-5-(3-((1-(1H-tetrazol-1-yl)propan-2-yl)oxy)-4-chlorophenyl)-N-(1-methyl-3-(trifluoromethyl)-1H-pyrazol-5-yl)pyrimidin-2-amine | | 479.9 | B |
| 721 | (1S,2R)-2-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)-2,3-dihydro-1H-inden-1-ol | | 598.1 | B |
| 722 | (S)-5-((4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)methyl)-2,4-dihydro-3H-1,2,4-triazol-3-one | | 563.1 | C |
| 723 | (S)-5-(3-((1-(1H-tetrazol-1-yl)propan-2-yl)oxy)-4-chlorophenyl)-N-(1-isopropyl-1H-pyrazol-3-yl)pyrimidin-2-amine | | 440.0 | B |
| 724 | (S)-5-(3-((1-(1H-tetrazol-1-yl)propan-2-yl)oxy)-4-chlorophenyl)-N-(1-(2,3-dihydro-1H-inden-2-yl)-3-(trifluoromethyl)-1H-pyrazol-4-yl)pyrimidin-2-amine | | 581.9 | C |
| 725 | (S)-5-(3-((1-(1H-tetrazol-1-yl)propan-2-yl)oxy)-4-chlorophenyl)-N-(1-(cyclopropylmethyl)-1H-pyrazol-4-yl)pyrimidin-2-amine | | 452.0 | B |
| 726 | (S)-5-(3-((1-(1H-tetrazol-1-yl)propan-2-yl)oxy)-4-chlorophenyl)-N-(1-(prop-2-yn-1-yl)-3-(trifluoromethyl)-1H-pyrazol-4-yl)pyrimidin-2-amine | | 504.1 | B |
| 727 | (S)-5-(3-((1-(1H-tetrazol-1-yl)propan-2-yl)oxy)-4-chlorophenyl)-N-(1-(2-(trifluoromethoxy)ethyl)-3-(trifluoromethyl)-1H-pyrazol-4-yl)pyrimidin-2-amine | | 578.3 | B |
| 728 | 3-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)-1,1,1-trifluoropropan-2-ol | | 578.1 | B |
| 729 | (S)-5-(3-((1-(1H-tetrazol-1-yl)propan-2-yl)oxy)-4-chlorophenyl)-N-(1-methyl-3-(thiophen-2-yl)-1H-pyrazol-5-yl)pyrimidin-2-amine | | 493.9 | B |
| 730 | (R)-3-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)-2-methylpropan-1-ol | | 538.0 | B |
| 731 | (S)-5-(3-((1-(1H-tetrazol-1-yl)propan-2-yl)oxy)-4-chlorophenyl)-N-(1,5-dimethyl-1H-pyrazol-4-yl)pyrimidin-2-amine | | 426.0 | B |
| 732 | (S)-3-((4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)methyl)oxetan-3-yl)methanol | | 566.1 | B |
| 733 | 2-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)cyclohexan-1-ol | | 563.9 | A |
| 734 | (S)-5-(3-((1-(1H-tetrazol-1-yl)propan-2-yl)oxy)-4-chlorophenyl)-N-(1-((3,5-dimethylisoxazol-4-yl)methyl)-3-(trifluoromethyl)-1H-pyrazol-4-yl)pyrimidin-2-amine | | 575.1 | B |
| 735 | (S)-5-(3-((1-(1H-tetrazol-1-yl)propan-2-yl)oxy)-4-chlorophenyl)-N-(1-methyl-1H-pyrazol-5-yl)pyrimidin-2-amine | | 412.0 | B |
| 736 | 3-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)propane-1,2-diol | | 540.1 | A |
| 737 | (S)-5-(3-((1-(1H-tetrazol-1-yl)propan-2-yl)oxy)-4-chlorophenyl)-N-(1-(2-methoxyethyl)-3-(trifluoromethyl)-1H-pyrazol-4-yl)pyrimidin-2-amine | | 524.1 | B |
| 738 | 5-((4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)methyl)oxazolidin-2-one | | 565.1 | A |

TABLE 2-continued

| Ex. No. | IUPAC NAME | ADDITIVE | MS | ACTIVITY |
|---|---|---|---|---|
| 739 | (S)-5-(3-((1-(1H-tetrazol-1-yl)propan-2-yl)oxy)-4-chlorophenyl)-N-(1-cyclopentyl-3-(trifluoromethyl)-1H-pyrazol-4-yl)pyrimidin-2-amine | | 534.3 | B |
| 740 | (S)-5-(3-((1-(1H-tetrazol-1-yl)propan-2-yl)oxy)-4-chlorophenyl)-N-(3-(tert-butyl)-1-methyl-1H-pyrazol-5-yl)pyrimidin-2-amine | | 468.0 | C |
| 741 | (S)-2-((4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)methyl)quinazolin-4(3H)-one | | 624.2 | B |
| 742 | (S)-5-(3-((1-(1H-tetrazol-1-yl)propan-2-yl)oxy)-4-chlorophenyl)-N-(1-isopropyl-3-methyl-1H-pyrazol-5-yl)pyrimidin-2-amine | | 454.0 | B |
| 743 | (S)-5-(3-((1-(1H-tetrazol-1-yl)propan-2-yl)oxy)-4-chlorophenyl)-N-(1-(2,2-difluoroethyl)-3-(trifluoromethyl)-1H-pyrazol-4-yl)pyrimidin-2-amine | | 528.1 | B |
| 744 | (S)-2-((4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)methyl)-1,1,1,3,3,3-hexafluoropropan-2-ol | | 646.1 | C |
| 745 | (S)-N-(5-(3-((1-(1H-tetrazol-1-yl)propan-2-yl)oxy)-4-chlorophenyl)pyrimidin-2-yl)-1-methyl-1H-benzo[d]imidazol-2-amine | | 461.9 | C |
| 746 | (S)-3-(5-((5-(3-((1-(1H-tetrazol-1-yl)propan-2-yl)oxy)-4-chlorophenyl)pyrimidin-2-yl)amino)-3-methyl-1H-pyrazol-1-yl)propanenitrile | | 464.9 | C |
| 747 | (S)-N-(5-(3-((1-(1H-tetrazol-1-yl)propan-2-yl)oxy)-4-chlorophenyl)pyrimidin-2-yl)-3,5-dimethylisoxazol-4-amine | | 427.0 | B |
| 748 | (S)-N-(5-(3-((1-(1H-tetrazol-1-yl)propan-2-yl)oxy)-4-chlorophenyl)pyrimidin-2-yl)-4-(4-chlorophenyl)-1,2,3-thiadiazol-5-amine | | 525.8 | C |
| 749 | (S)-5-(3-((1-(1H-tetrazol-1-yl)propan-2-yl)oxy)-4-chlorophenyl)-N-(4-chloro-1H-pyrazol-3-yl)pyrimidin-2-amine | | 431.9 | B |
| 750 | (S)-(2-((5-(3-((1-(1H-tetrazol-1-yl)propan-2-yl)oxy)-4-chlorophenyl)pyrimidin-2-yl)amino)-1-methyl-1H-imidazol-5-yl)methanol | | 441.9 | C |
| 751 | (S)-5-(3-((1-(1H-tetrazol-1-yl)propan-2-yl)oxy)-4-chlorophenyl)-N-(1,3-dimethyl-1H-pyrazol-5-yl)pyrimidin-2-amine | | 426.0 | B |
| 752 | (S)-2-(5-(3-((1-(1H-tetrazol-1-yl)propan-2-yl)oxy)-4-chlorophenyl)pyrimidin-2-yl)amino)-4,5,6,7-tetrahydrobenzo[b]thiophene-3-carbonitrile | | 493.2 | B |
| 753 | (S)-2-((5-(3-((1-(1H-tetrazol-1-yl)propan-2-yl)oxy)-4-chlorophenyl)pyrimidin-2-yl)amino)-5,6-dihydro-4H-cyclopenta[b]thiophene-3-carbonitrile | | 479.2 | C |
| 754 | (S)-5-(3-((1-(1H-tetrazol-1-yl)propan-2-yl)oxy)-4-chlorophenyl)-N-(1-phenyl-1H-pyrazol-5-yl)pyrimidin-2-amine | | 473.9 | B |
| 755 | (S)-5-(3-((1-(1H-tetrazol-1-yl)propan-2-yl)oxy)-4-chlorophenyl)-N-(1-methyl-1H-pyrazol-3-yl)pyrimidin-2-amine | | 412.0 | B |
| 756 | (S)-5-(3-((1-(1H-tetrazol-1-yl)propan-2-yl)oxy)-4-chlorophenyl)-N-(3-(2,2,2-trifluoroethoxy)-1-(2,2,2-trifluoroethyl)-1H-pyrazol-4-yl)pyrimidin-2-amine | | 576.0 | B |
| 757 | 5-(3-(((S)-1-(1H-tetrazol-1-yl)propan-2-yl)oxy)-4-chlorophenyl)-N-(1-((1R,3s,5S)-8-cyclopropyl-8-azabicyclo[3.2.1]octan-3-yl)-3-(trifluoromethyl)-1H-pyrazol-4-yl)pyrimidin-2-amine | | 615.4 | A |
| 758 | 5-(3-(((S)-1-(1H-tetrazol-1-yl)propan-2-yl)oxy)-4-chlorophenyl)-N-(1-((1R,3s,5S)-8-methyl-8-azabicyclo[3.2.1]octan-3-yl)-3-(trifluoromethyl)-1H-pyrazol-4-yl)pyrimidin-2-amine | | 589.2 | A |
| 759 | (S)-5-(3-((1-(1H-tetrazol-1-yl)propan-2-yl)oxy)-4-chlorophenyl)-N-(1-methyl-3-(2,2,2-trifluoroethoxy)-1H-pyrazol-4-yl)pyrimidin-2-amine | | 509.9 | A |
| 760 | (S)-5-(3-((1-(1H-tetrazol-1-yl)propan-2-yl)oxy)-4-chlorophenyl)-N-(1-(2,2-difluoroethyl)-3-(2,2,2-trifluoroethoxy)-1H-pyrazol-4-yl)pyrimidin-2-amine | | 559.8 | A |
| 761 | (S)-2-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)-1-morpholinopropan-1-one | | 606.9 | B |
| 762 | (S)-2-((1-(1H-tetrazol-1-yl)propan-2-yl)oxy)-4-(2-((2-fluoro-5-(3-(morpholinomethyl)azetidin-1-yl)phenyl)amino)pyrimidin-5-yl)benzonitrile | | 570.9 | A |
| 763 | 2-(((S)-1-(1H-tetrazol-1-yl)propan-2-yl)oxy)-4-(2-((1-(tetrahydro-2H-pyran-2-yl)-3-(2,2,2-trifluoroethoxy)-1H-pyrazol-4-yl)amino)pyrimidin-5-yl)benzonitrile | | 570.9 | A |
| 764 | (S)-2-((1-(1H-tetrazol-1-yl)propan-2-yl)oxy)-4-(2-((1-ethyl-3-(2,2,2-trifluoroethoxy)-1H-pyrazol-4-yl)amino)pyrimidin-5-yl)benzonitrile | | 514.9 | A |
| 765 | (S)-2-((1-(1H-tetrazol-1-yl)propan-2-yl)oxy)-4-(2-((1-methyl-3-(2,2,2-trifluoroethoxy)-1H-pyrazol-4-yl)amino)pyrimidin-5-yl)benzonitrile | | 500.9 | A |
| 766 | tert-butyl (S)-4-(4-((5-(3-((1-(1H-tetrazol-1-yl)propan-2-yl)oxy)-4-chlorophenyl)pyrimidin-2-yl)amino)-3-(difluoromethyl)-1H-pyrazol-1-yl)piperidine-1-carboxylate | | 631.3 | B |
| 767 | (S)-2-((1-(1H-tetrazol-1-yl)propan-2-yl)oxy)-4-(2-((1-(2,2-difluoroethyl)-3-(2,2,2-trifluoroethoxy)-1H-pyrazol-4-yl)amino)pyrimidin-5-yl)benzonitrile | | 550.8 | A |
| 768 | (S)-5-(3-((1-(1H-tetrazol-1-yl)propan-2-yl)oxy)-4-chlorophenyl)-N-(5-(4-(tetrahydro-2H-pyran-4-yl)piperazin-1-yl)-2-(trifluoromethoxy)phenyl)pyrimidin-2-amine | | 660.0 | A |

TABLE 2-continued

| Ex. No. | IUPAC NAME | ADDITIVE | MS | ACTIVITY |
|---|---|---|---|---|
| 769 | (S)-5-(3-((1-(1H-tetrazol-1-yl)propan-2-yl)oxy)-4-chlorophenyl)-N-(3-(difluoromethyl)-1-(1-(tetrahydro-2H-pyran-4-yl)piperidin-4-yl)-1H-pyrazol-4-yl)pyrimidin-2-amine | | 615.2 | A |
| 770 | (S)-5-(3-((1-(1H-tetrazol-1-yl)propan-2-yl)oxy)-4-chlorophenyl)-N-(2-methoxy-5-(4-(tetrahydro-2H-pyran-4-yl)piperazin-1-yl)pyridin-3-yl)pyrimidin-2-amine | | 607.6 | A |
| 771 | (S)-5-(3-((1-(1H-tetrazol-1-yl)propan-2-yl)oxy)-4-chlorophenyl)-N-(3-(difluoromethyl)-1-(piperidin-4-yl)-1H-pyrazol-4-yl)pyrimidin-2-amine | | 531.1 | A |
| 772 | 5-(3-(((S)-1-(1H-tetrazol-1-yl)propan-2-yl)oxy)-4-chlorophenyl)-N-(1-(trans-4-morpholinocyclohexyl)-3-(2,2,2-trifluoroethoxy)-1H-pyrazol-4-yl)pyrimidin-2-amine | | 663.3 | A |
| 773 | 2-(((S)-1-(1H-tetrazol-1-yl)propan-2-yl)oxy)-4-(2-((1-(cis-4-(azetidin-1-yl)cyclohexyl)-3-(trifluoromethyl)-1H-pyrazol-4-yl)amino)pyrimidin-5-yl)benzonitrile | | 594.3 | A |
| 774 | (S)-5-(3-((1-(1H-tetrazol-1-yl)propan-2-yl)oxy)-4-chlorophenyl)-N-(1-cyclopropyl-3-(2,2,2-trifluoroethoxy)-1H-pyrazol-4-yl)pyrimidin-2-amine | | 535.9 | A |
| 775 | (S)-2-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)propan-1-ol | | 553.8 | A |
| 776 | 5-(3-(((S)-1-(1H-tetrazol-1-yl)propan-2-yl)oxy)-4-chlorophenyl)-N-(1-(1-methoxypropan-2-yl)-3-(2,2,2-trifluoroethoxy)-1H-pyrazol-4-yl)pyrimidin-2-amine | | 567.8 | A |
| 777 | 3-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)azepan-2-one | | 606.9 | A |
| 778 | 5-(3-(((S)-1-(1H-tetrazol-1-yl)propan-2-yl)oxy)-4-chlorophenyl)-N-(1-(cis-4-(azetidin-1-yl)cyclohexyl)-3-(trifluoromethyl)-1H-pyrazol-4-yl)pyrimidin-2-amine | | 603.0 | A |
| 779 | 5-(3-(((S)-1-(1H-tetrazol-1-yl)propan-2-yl)oxy)-4-chlorophenyl)-N-(1-(trans-4-(azetidin-1-yl)cyclohexyl)-3-(trifluoromethyl)-1H-pyrazol-4-yl)pyrimidin-2-amine | | 603.0 | A |
| 780 | 5-(3-(((S)-1-(1H-tetrazol-1-yl)propan-2-yl)oxy)-4-chlorophenyl)-N-(1-(cis-4-morpholinocyclohexyl)-3-(2,2,2-trifluoroethoxy)-1H-pyrazol-4-yl)pyrimidin-2-amine | | 662.9 | A |
| 781 | 5-(3-(((S)-1-(1H-tetrazol-1-yl)propan-2-yl)oxy)-4-chlorophenyl)-N-(1-(cis-4-morpholinocyclohexyl)-3-(trifluoromethyl)-1H-pyrazol-4-yl)pyrimidin-2-amine | | 633.0 | A |
| 782 | (S)-2-((1-(1H-pyrazol-1-yl)propan-2-yl)oxy)-4-(2-((1-(1-(tetrahydro-2H-pyran-4-yl)piperidin-4-yl)-3-(2,2,2-trifluoroethoxy)-1H-pyrazol-4-yl)amino)pyrimidin-5-yl)benzonitrile | 2HCl | 652.1 | A |
| 783 | (S)-4-(4-((5-(3-(((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)butan-1-ol | | 567.9 | A |
| 784 | (R)-3-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-methylpropan-1-ol | | 567.9 | A |
| 785 | 2-(((S)-1-(1H-pyrazol-1-yl)propan-2-yl)oxy)-4-(2-((1-(cis-4-morpholinocyclohexyl)-3-(trifluoromethyl)-1H-pyrazol-4-yl)amino)pyrimidin-5-yl)benzonitrile | HCl | 622.0 | B |
| 786 | 2-(((S)-1-(1H-pyrazol-1-yl)propan-2-yl)oxy)-4-(2-((1-(trans-4-morpholinocyclohexyl)-3-(trifluoromethyl)-1H-pyrazol-4-yl)amino)pyrimidin-5-yl)benzonitrile | HCl | 622.0 | B |
| 787 | (R)-2-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)propan-1-ol | | 553.9 | A |
| 788 | (S)-5-(3-((1-(1H-tetrazol-1-yl)propan-2-yl)oxy)-4-methylphenyl)-N-(1-(1-(tetrahydro-2H-pyran-4-yl)piperidin-4-yl)-3-(2,2,2-trifluoroethoxy)-1H-pyrazol-4-yl)pyrimidin-2-amine | | 643.1 | A |
| 789 | (S)-5-(3-((1-(1H-tetrazol-1-yl)propan-2-yl)oxy)-4-fluorophenyl)-N-(1-(1-(tetrahydro-2H-pyran-4-yl)piperidin-4-yl)-3-(2,2,2-trifluoroethoxy)-1H-pyrazol-4-yl)pyrimidin-2-amine | | 647.0 | A |
| 790 | (S)-2-((1-(1H-tetrazol-1-yl)propan-2-yl)oxy)-4-(2-((1-(1-(tetrahydro-2H-pyran-4-yl)piperidin-4-yl)-3-(2,2,2-trifluoroethoxy)-1H-pyrazol-4-yl)amino)pyrimidin-5-yl)benzonitrile | | 654.0 | A |
| 791 | (S)-5-(3-((1-(1H-tetrazol-1-yl)propan-2-yl)oxy)-4-chlorophenyl)-N-(3-(2,2-difluoroethoxy)-1-(piperidin-4-yl)-1H-pyrazol-4-yl)pyrimidin-2-amine | | 560.9 | A |
| 792 | (S)-5-(3-((1-(1H-tetrazol-1-yl)propan-2-yl)oxy)-4-chlorophenyl)-N-(3-(2,2-difluoroethoxy)-1-(1-(tetrahydro-2H-pyran-4-yl)piperidin-4-yl)-1H-pyrazol-4-yl)pyrimidin-2-amine | | 645.0 | A |
| 793 | (S)-5-(3-((1-(1H-tetrazol-1-yl)propan-2-yl)oxy)-4-chlorophenyl)-N-(3-(2,2-difluoroethoxy)-1-(1-methylpiperidin-4-yl)-1H-pyrazol-4-yl)pyrimidin-2-amine | | 574.9 | A |
| 794 | (S)-5-(3-((1-(1H-tetrazol-1-yl)propan-2-yl)oxy)-4-chlorophenyl)-N-(1-(1-cyclopropylpiperidin-4-yl)-3-(2,2,2-trifluoroethoxy)-1H-pyrazol-4-yl)pyrimidin-2-amine | | 618.9 | A |

TABLE 2-continued

| Ex. No. | IUPAC NAME | ADDITIVE | MS | ACTIVITY |
|---|---|---|---|---|
| 795 | (S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(2,2,2-trifluoroethoxy)-1H-pyrazol-4-yl)pyrimidin-2-amine | | 675.0 | A |
| 796 | 5-(3-(((S)-1-(1H-tetrazol-1-yl)propan-2-yl)oxy)-4-chlorophenyl)-N-(1-((R)-1-methoxypropan-2-yl)-3-(2,2,2-trifluoroethoxy)-1H-pyrazol-4-yl)pyrimidin-2-amine | | 567.8 | A |
| 797 | 2-(((S)-1-(1H-pyrazol-1-yl)propan-2-yl)oxy)-4-(2-((1-(cis-4-morpholinocyclohexyl)-3-(2,2,2-trifluoroethoxy)-1H-pyrazol-4-yl)amino)pyrimidin-5-yl)benzonitrile | | 652.0 | B |
| 798 | 2-(((S)-1-(1H-pyrazol-1-yl)propan-2-yl)oxy)-4-(2-((1-(trans-4-morpholinocyclohexyl)-3-(2,2,2-trifluoroethoxy)-1H-pyrazol-4-yl)amino)pyrimidin-5-yl)benzonitrile | | 652.0 | A |
| 799 | 1-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)propan-2-ol | | 553.8 | A |
| 800 | (S)-4-(4-((5-(3-((1-(1H-tetrazol-1-yl)propan-2-yl)oxy)-4-chlorophenyl)pyrimidin-2-yl)amino)-3-(2,2-difluoroethoxy)-1H-pyrazol-1-yl)cyclohexan-1-one | | 573.9 | A |
| 801 | 1-(cis-4-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclohexyl)-3-methylazetidin-3-ol | | 663.3 | A |
| 802 | 1-(trans-4-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclohexyl)-3-methylazetidin-3-ol | | 663.3 | A |
| 803 | 1-(cis-4-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)cyclohexyl)-3-methylazetidin-3-ol | | 633.3 | A |
| 804 | 1-(trans-4-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)cyclohexyl)-3-methylazetidin-3-ol | | 633.3 | A |
| 805 | 5-(3-(((S)-1-(1H-tetrazol-1-yl)propan-2-yl)oxy)-4-chlorophenyl)-N-(3-(2,2-difluoroethoxy)-1-(cis-4-morpholinocyclohexyl)-1H-pyrazol-4-yl)pyrimidin-2-amine | | 645.3 | A |
| 806 | 5-(3-(((S)-1-(1H-tetrazol-1-yl)propan-2-yl)oxy)-4-chlorophenyl)-N-(3-(2,2-difluoroethoxy)-1-(trans-4-morpholinocyclohexyl)-1H-pyrazol-4-yl)pyrimidin-2-amine | | 645.3 | A |
| 807 | 5-(3-(((S)-1-(1H-tetrazol-1-yl)propan-2-yl)oxy)-4-fluorophenyl)-N-(1-(cis-4-morpholinocyclohexyl)-3-(trifluoromethyl)-1H-pyrazol-4-yl)pyrimidin-2-amine | | 617.0 | B |
| 808 | 5-(3-(((S)-1-(1H-tetrazol-1-yl)propan-2-yl)oxy)-4-fluorophenyl)-N-(1-(trans-4-morpholinocyclohexyl)-3-(trifluoromethyl)-1H-pyrazol-4-yl)pyrimidin-2-amine | | 617.0 | A |
| 809 | 5-(3-(((S)-1-(1H-tetrazol-1-yl)propan-2-yl)oxy)-4-methylphenyl)-N-(1-(cis-4-morpholinocyclohexyl)-3-(trifluoromethyl)-1H-pyrazol-4-yl)pyrimidin-2-amine | | 613.4 | B |
| 810 | 5-(3-(((S)-1-(1H-tetrazol-1-yl)propan-2-yl)oxy)-4-methylphenyl)-N-(1-(trans-4-morpholinocyclohexyl)-3-(trifluoromethyl)-1H-pyrazol-4-yl)pyrimidin-2-amine | | 613.4 | A |
| 811 | 5-(3-(((S)-1-(1H-tetrazol-1-yl)propan-2-yl)oxy)-4-methylphenyl)-N-(1-(trans-4-morpholinocyclohexyl)-3-(2,2,2-trifluoroethoxy)-1H-pyrazol-4-yl)pyrimidin-2-amine | HCl | 643.0 | A |
| 812 | 5-(3-(((S)-1-(1H-tetrazol-1-yl)propan-2-yl)oxy)-4-methylphenyl)-N-(1-(cis-4-morpholinocyclohexyl)-3-(2,2,2-trifluoroethoxy)-1H-pyrazol-4-yl)pyrimidin-2-amine | | 643.4 | A |
| 813 | 5-(3-(((S)-1-(1H-tetrazol-1-yl)propan-2-yl)oxy)-4-fluorophenyl)-N-(1-(trans-4-morpholinocyclohexyl)-3-(2,2,2-trifluoroethoxy)-1H-pyrazol-4-yl)pyrimidin-2-amine | HCl | 647.4 | A |
| 814 | 5-(3-(((S)-1-(1H-tetrazol-1-yl)propan-2-yl)oxy)-4-fluorophenyl)-N-(1-(cis-4-morpholinocyclohexyl)-3-(2,2,2-trifluoroethoxy)-1H-pyrazol-4-yl)pyrimidin-2-amine | | 647.3 | B |
| 815 | (S)-5-(3-((1-(1H-tetrazol-1-yl)propan-2-yl)oxy)-4-chlorophenyl)-N-(1-(2-isopropyl-2-azaspiro[3.3]heptan-6-yl)-3-(2,2,2-trifluoroethoxy)-1H-pyrazol-4-yl)pyrimidin-2-amine | | 633.4 | A |
| 816 | (S)-1-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-methylpropan-2-ol | | 568.2 | A |
| 817 | 2-(((S)-1-(1H-tetrazol-1-yl)propan-2-yl)oxy)-4-(2-((1-(trans-4-morpholinocyclohexyl)-3-(2,2,2-trifluoroethoxy)-1H-pyrazol-4-yl)amino)pyrimidin-5-yl)benzonitrile | HCl | 654.0 | A |
| 818 | 2-(((S)-1-(1H-tetrazol-1-yl)propan-2-yl)oxy)-4-(2-((1-(cis-4-morpholinocyclohexyl)-3-(2,2,2-trifluoroethoxy)-1H-pyrazol-4-yl)amino)pyrimidin-5-yl)benzonitrile | HCl | 654.0 | A |
| 819 | (S)-2-((1-(4-fluoro-1H-pyrazol-1-yl)propan-2-yl)oxy)-4-(2-((1-(1-(tetrahydro-2H-pyran-4-yl)piperidin-4-yl)-3-(2,2,2-trifluoroethoxy)-1H-pyrazol-4-yl)amino)pyrimidin-5-yl)benzonitrile | | 670.0 | B |

TABLE 2-continued

| Ex. No. | IUPAC NAME | ADDITIVE | MS | ACTIVITY |
|---|---|---|---|---|
| 820 | 5-(3-(((S)-1-(1H-tetrazol-1-yl)propan-2-yl)oxy)-4-chlorophenyl)-N-(1-(cis-4-morpholinocyclohexyl)-3-(oxetan-3-yloxy)-1H-pyrazol-4-yl)pyrimidin-2-amine | | 637.0 | A |
| 821 | 5-(3-(((S)-1-(1H-tetrazol-1-yl)propan-2-yl)oxy)-4-chlorophenyl)-N-(1-(trans-4-morpholinocyclohexyl)-3-(oxetan-3-yloxy)-1H-pyrazol-4-yl)pyrimidin-2-amine | | 637.0 | A |
| 822 | 5-(3-(((S)-1-(1H-tetrazol-1-yl)propan-2-yl)oxy)-4-chlorophenyl)-N-(1-(trans-4-(2-oxa-6-azaspiro[3.3]heptan-6-yl)cyclohexyl)-3-(trifluoromethyl)-1H-pyrazol-4-yl)pyrimidin-2-amine | | 645.0 | A |
| 823 | 5-(3-(((S)-1-(1H-tetrazol-1-yl)propan-2-yl)oxy)-4-chlorophenyl)-N-(1-(cis-4-(2-oxa-6-azaspiro[3.3]heptan-6-yl)cyclohexyl)-3-(trifluoromethyl)-1H-pyrazol-4-yl)pyrimidin-2-amine | | 645.0 | A |
| 824 | (S)-5-(3-((1-(1H-tetrazol-1-yl)propan-2-yl)oxy)-4-chlorophenyl)-N-(3-(2-fluoroethoxy)-1-(piperidin-4-yl)-1H-pyrazol-4-yl)pyrimidin-2-amine | | 542.9 | A |
| 825 | (S)-5-(3-((1-(1H-tetrazol-1-yl)propan-2-yl)oxy)-4-chlorophenyl)-N-(3-(2-fluoroethoxy)-1-(1-(tetrahydro-2H-pyran-4-yl)piperidin-4-yl)-1H-pyrazol-4-yl)pyrimidin-2-amine | | 627.0 | A |
| 826 | (S)-5-(3-((1-(1H-tetrazol-1-yl)propan-2-yl)oxy)-4-chlorophenyl)-N-(1-(1-cyclobutylpiperidin-4-yl)-3-(2-fluoroethoxy)-1H-pyrazol-4-yl)pyrimidin-2-amine | | 597.0 | A |
| 827 | 5-(3-(((S)-1-(1H-tetrazol-1-yl)propan-2-yl)oxy)-4-chlorophenyl)-N-(1-(trans-4-(2-oxa-6-azaspiro[3.3]heptan-6-yl)cyclohexyl)-3-(2,2-difluoroethoxy)-1H-pyrazol-4-yl)pyrimidin-2-amine | | 657.0 | A |
| 828 | 5-(3-(((S)-1-(1H-tetrazol-1-yl)propan-2-yl)oxy)-4-chlorophenyl)-N-(1-(cis-4-(2-oxa-6-azaspiro[3.3]heptan-6-yl)cyclohexyl)-3-(2,2-difluoroethoxy)-1H-pyrazol-4-yl)pyrimidin-2-amine | | 656.9 | A |
| 829 | 2-(((S)-1-(4-fluoro-1H-pyrazol-1-yl)propan-2-yl)oxy)-4-(2-((1-(cis-4-morpholinocyclohexyl)-3-(2,2,2-trifluoroethoxy)-1H-pyrazol-4-yl)amino)pyrimidin-5-yl)benzonitrile | | 670.0 | B |
| 830 | 2-(((S)-1-(4-fluoro-1H-pyrazol-1-yl)propan-2-yl)oxy)-4-(2-((1-(trans-4-morpholinocyclohexyl)-3-(2,2,2-trifluoroethoxy)-1H-pyrazol-4-yl)amino)pyrimidin-5-yl)benzonitrile | | 670.0 | A |
| 831 | (S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(trifluoromethyl)-1H-pyrazol-4-yl)pyrimidin-2-amine | | 645.0 | A |
| 832 | (S)-5-(3-((1-(1H-tetrazol-1-yl)propan-2-yl)oxy)-4-chlorophenyl)-N-(1-(2-(oxetan-3-yl)-2-azaspiro[3.3]heptan-6-yl)-3-(trifluoromethyl)-1H-pyrazol-4-yl)pyrimidin-2-amine | | 617.0 | A |
| 833 | (S)-1-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)propan-2-ol | | 553.8 | A |
| 834 | 5-(3-(((S)-1-(1H-tetrazol-1-yl)propan-2-yl)oxy)-4-fluorophenyl)-N-(3-(2,2-difluoroethoxy)-1-(cis-4-morpholinocyclohexyl)-1H-pyrazol-4-yl)pyrimidin-2-amine | | 629.0 | B |
| 835 | 5-(3-(((S)-1-(1H-tetrazol-1-yl)propan-2-yl)oxy)-4-fluorophenyl)-N-(3-(2,2-difluoroethoxy)-1-(trans-4-morpholinocyclohexyl)-1H-pyrazol-4-yl)pyrimidin-2-amine | | 629.0 | A |
| 841 | (S)-4-(4-((5-(3-((1-(1H-tetrazol-1-yl)propan-2-yl)oxy)-4-chlorophenyl)pyrimidin-2-yl)amino)-3-isopropyl-1H-pyrazol-1-yl)cyclohexan-1-one | | 536.1 | A |
| 842 | 5-(3-(((S)-1-(1H-tetrazol-1-yl)propan-2-yl)oxy)-4-chlorophenyl)-N-(3-isopropyl-1-(cis-4-morpholinocyclohexyl)-1H-pyrazol-4-yl)pyrimidin-2-amine | | 607.3 | A |
| 843 | 5-(3-(((S)-1-(1H-tetrazol-1-yl)propan-2-yl)oxy)-4-chlorophenyl)-N-(3-isopropyl-1-(trans-4-morpholinocyclohexyl)-1H-pyrazol-4-yl)pyrimidin-2-amine | | 607.3 | A |
| 844 | 5-(3-(((S)-1-(1H-tetrazol-1-yl)propan-2-yl)oxy)-4-chlorophenyl)-N-(1-(trans-4-((1R,5S)-3-oxa-8-azabicyclo[3.2.1]octan-8-yl)cyclohexyl)-3-(2,2-difluoroethoxy)-1H-pyrazol-4-yl)pyrimidin-2-amine | | 671.3 | A |
| 845 | tert-butyl (S)-(2-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)ethyl)carbamate | | 606.9 | B |
| 846 | (S)-N-(2-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)ethyl)acetamide | | 550.8 | B |
| 847 | (S)-1-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-methylpropan-2-ol | | 538.2 | A |
| 848 | (S)-5-(3-((1-(1H-tetrazol-1-yl)propan-2-yl)oxy)-4-chlorophenyl)-N-(1-((methylsulfonyl)methyl)-3-(trifluoromethyl)-1H-pyrazol-4-yl)pyrimidin-2-amine | | 556.1 | A |
| 849 | (S)-5-(3-((1-(1H-tetrazol-1-yl)propan-2-yl)oxy)-4-chlorophenyl)-N-(3-(2,2-difluoroethoxy)-1-(cis-3-morpholinocyclobutyl)-1H-pyrazol-4-yl)pyrimidin-2-amine | | 617.4 | A |

TABLE 2-continued

| Ex. No. | IUPAC NAME | ADDITIVE | MS | ACTIVITY |
|---|---|---|---|---|
| 850 | (S)-5-(3-((1-(1H-tetrazol-1-yl)propan-2-yl)oxy)-4-chlorophenyl)-N-(3-(2,2-difluoroethoxy)-1-(cis-3-((tetrahydro-2H-pyran-4-yl)amino)cyclobutyl)-1H-pyrazol-4-yl)pyrimidin-2-amine | | 631.3 | A |
| 851 | (S)-2-(4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)cyclohexyl)acetic acid | | 604.2 | C |
| 852 | (S)-2-(4-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)cyclohexyl)acetamide | | 605.3 | C |
| 853 | (S)-1-((4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)cyclobutan-1-ol | | 578.1 | A |
| 854 | (S)-5-(3-((1-(1H-tetrazol-1-yl)propan-2-yl)oxy)-4-chlorophenyl)-N-(1-(2-(oxetan-3-yl)-2-azaspiro[3.3]heptan-6-yl)-3-(2,2,2-trifluoroethoxy)-1H-pyrazol-4-yl)pyrimidin-2-amine | | 647.3 | A |
| 855 | (S)-1-((4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)methyl)cyclobutan-1-ol | | 550.2 | A |
| 856 | 1-(cis-4-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)cyclohexyl)-3-(trifluoromethyl)azetidin-3-ol | | 687.3 | B |
| 857 | 1-(trans-4-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)cyclohexyl)-3-(trifluoromethyl)azetidin-3-ol | | 687.3 | A |
| 858 | (S)-1-((4-((5-(3-((1-(1H-tetrazol-1-yl)propan-2-yl)oxy)-4-fluorophenyl)pyrimidin-2-yl)amino)-3-(trifluoromethyl)-1H-pyrazol-1-yl)methyl)cyclobutan-1-ol | | 534.2 | B |
| 859 | (S)-1-(6-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-azaspiro[3.3]heptan-2-yl)-2-methylpropan-2-ol | | 633.0 | A |
| 860 | tert-butyl (S)-(1-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-methylpropan-2-yl)carbamate | | 635.0 | C |
| 861 | (S)-5-(3-((1-(1H-tetrazol-1-yl)propan-2-yl)oxy)-4-chlorophenyl)-N-(1-(2-amino-2-methylpropyl)-3-(trifluoromethyl)-1H-pyrazol-4-yl)pyrimidin-2-amine | | 536.9 | A |
| 862 | (S)-N-(1-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-methylpropan-2-yl)acetamide | | 578.9 | B |
| 863 | 5-(3-(((S)-1-(1H-tetrazol-1-yl)propan-2-yl)oxy)-4-chlorophenyl)-N-(1-(trans-4-(3-fluoroazetidin-1-yl)cyclohexyl)-3-(oxetan-3-yloxy)-1H-pyrazol-4-yl)pyrimidin-2-amine | | 625.3 | A |
| 864 | 5-(3-(((S)-1-(1H-tetrazol-1-yl)propan-2-yl)oxy)-4-chlorophenyl)-N-(1-(trans-4-(3,3-difluoropyrrolidin-1-yl)cyclohexyl)-3-(oxetan-3-yloxy)-1H-pyrazol-4-yl)pyrimidin-2-amine | | 657.4 | A |
| 865 | (S)-(4-((5-(3-((1-(1H-tetrazol-1-yl)propan-2-yl)oxy)-4-chlorophenyl)pyrimidin-2-yl)amino)-1-ethyl-1H-pyrazol-5-yl)(morpholino)methanone | | 537.1 | C |
| 866 | (S)-(4-((5-(3-((1-(1H-tetrazol-1-yl)propan-2-yl)oxy)-4-chlorophenyl)pyrimidin-2-yl)amino)-1-ethyl-1H-pyrazol-3-yl)(morpholino)methanone | | 537.1 | B |
| 867 | (S)-5-(3-((1-(1H-tetrazol-1-yl)propan-2-yl)oxy)-4-chlorophenyl)-N-(1-(6-methoxypyridin-3-yl)-3-(trifluoromethyl)-1H-pyrazol-4-yl)pyrimidin-2-amine | | 571.1 | C |
| 868 | (S)-5-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)pyridin-2(1H)-one | | 559.1 | B |
| 869 | 5-(3-(((S)-1-(1H-tetrazol-1-yl)propan-2-yl)oxy)-4-chlorophenyl)-N-(3-(((S)-2,2-difluorocyclopropyl)methoxy)-1-(trans-4-morpholinocyclohexyl)-1H-pyrazol-4-yl)pyrimidin-2-amine | | 671.4 | A |
| 870 | 5-(3-(((S)-1-(1H-tetrazol-1-yl)propan-2-yl)oxy)-4-chlorophenyl)-N-(3-(((S)-2,2-difluorocyclopropyl)methoxy)-1-(cis-4-morpholinocyclohexyl)-1H-pyrazol-4-yl)pyrimidin-2-amine | | 671.4 | A |
| 871 | ((S)-1-(trans-4-(4-((5-(3-(((S)-1-(1H-tetrazol-1-yl)propan-2-yl)oxy)-4-chlorophenyl)pyrimidin-2-yl)amino)-3-(((S)-2,2-difluorocyclopropyl)methoxy)-1H-pyrazol-1-yl)cyclohexyl)pyrrolidin-2-yl)methanol | | 685.3 | A |
| 872 | ethyl (S)-4-((5-(3-((1-(1H-tetrazol-1-yl)propan-2-yl)oxy)-4-chlorophenyl)pyrimidin-2-yl)amino)-1-ethyl-1H-pyrazole-5-carboxylate | | 498.2 | A |
| 873 | ethyl (S)-4-((5-(3-((1-(1H-tetrazol-1-yl)propan-2-yl)oxy)-4-chlorophenyl)pyrimidin-2-yl)amino)-1-ethyl-1H-pyrazole-3-carboxylate | | 498.1 | A |
| 874 | tert-butyl (S)-4-((4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)methyl)-4-hydroxypiperidine-1-carboxylate | | 679.3 | B |
| 875 | (S)-4-((5-(3-((1-(1H-tetrazol-1-yl)propan-2-yl)oxy)-4-chlorophenyl)pyrimidin-2-yl)amino)-1-ethyl-1H-pyrazole-5-carboxylic acid | | 468.2 | B |
| 876 | (S)-4-((5-(3-((1-(1H-tetrazol-1-yl)propan-2-yl)oxy)-4-chlorophenyl)pyrimidin-2-yl)amino)-1-ethyl-1H-pyrazole-3-carboxylic acid | | 470.1 | B |

TABLE 2-continued

| Ex. No. | IUPAC NAME | ADDITIVE | MS | ACTIVITY |
|---|---|---|---|---|
| 877 | (S)-5-(3-((1-(1H-tetrazol-1-yl)propan-2-yl)oxy)-4-chlorophenyl)-N-(1-(2-aminoethyl)-3-(trifluoromethyl)-1H-pyrazol-4-yl)pyrimidin-2-amine | HCl | 509.1 | A |
| 878 | (S)-5-(3-((1-(1H-tetrazol-1-yl)propan-2-yl)oxy)-4-chlorophenyl)-N-(1-(6-methoxypyridin-2-yl)-3-(2,2,2-trifluoroethoxy)-1H-pyrazol-4-yl)pyrimidin-2-amine | | 603.3 | C |
| 879 | (S)-6-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)pyridin-2(1H)-one | | 589.2 | B |
| 880 | (S)-(4-((5-(3-((1-(1H-tetrazol-1-yl)propan-2-yl)oxy)-4-chlorophenyl)pyrimidin-2-yl)amino)-1-ethyl-1H-pyrazol-5-yl)(4-morpholinopiperidin-1-yl)methanone | | 622.3 | C |
| 881 | (S)-2-((1-(difluoromethoxy)propan-2-yl)oxy)-4-(2-((1-(2-(tetrahydro-2H-pyran-4-yl)-2-azaspiro[3.3]heptan-6-yl)-3-(2,2,2-trifluoroethoxy)-1H-pyrazol-4-yl)amino)pyrimidin-5-yl)benzonitrile | | 664.3 | A |
| 882 | (S)-4-((4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)methyl)piperidin-4-ol | HCl | 579.2 | A |
| 883 | (S)-2-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-methylpropan-1-ol | | 568.2 | A |
| 884 | (S)-N-(2-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)ethyl)methanesulfonamide | | 587.1 | B |
| 885 | ethyl (S)-2-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-methylpropanoate | | 610.2 | A |
| 886 | (S)-4-((4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)tetrahydro-2H-pyran-4-ol | | 610.3 | A |
| 887 | (S)-1-(2-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)ethyl)urea | | 552.1 | B |
| 888 | (S)-4-((4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)methyl)-4-hydroxypiperidine-1-carboxamide | | 622.3 | A |
| 889 | (S)-2-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-methylpropanoic acid | | 582.2 | B |
| 890 | (S)-N-(5-(3-((1-(1H-tetrazol-1-yl)propan-2-yl)oxy)-4-chlorophenyl)pyrimidin-2-yl)-3-(trifluoromethyl)-1'H-[1,4'-bipyrazol]-4-amine | | 532.1 | B |
| 891 | (S)-4-((4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)methyl)-1-methylpiperidin-4-ol | | 593.2 | A |
| 892 | trans-4-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)piperidin-3-ol | | 565.2 | A |
| 893 | 5-(3-(((R)-1-(1H-tetrazol-1-yl)propan-2-yl)oxy)-4-chlorophenyl)-N-(1-(trans-4-morpholinocyclohexyl)-3-(trifluoromethyl)-1H-pyrazol-4-yl)pyrimidin-2-amine | | 633.3 | B |
| 894 | (S)-2-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-methylpropanamide | | 581.2 | A |
| 895 | (S)-2-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-methyl-1-morpholinopropan-1-one | | 651.3 | B |
| 896 | 5-(3-(((R)-1-(1H-tetrazol-1-yl)propan-2-yl)oxy)-4-chlorophenyl)-N-(1-(cis-4-morpholinocyclohexyl)-3-(trifluoromethyl)-1H-pyrazol-4-yl)pyrimidin-2-amine | | 633.3 | C |
| 897 | trans-4-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)-1-(tetrahydro-2H-pyran-4-yl)piperidin-3-ol | | 649.3 | A |
| 898 | trans-4-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)-1-cyclobutylpiperidin-3-ol | | 619.3 | A |
| 899 | (S)-8-((4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)-1,4-dioxaspiro[4.5]decan-8-ol | | 666.2 | A |
| 900 | 4-(2-((1-(trans-4-morpholinocyclohexyl)-3-(trifluoromethyl)-1H-pyrazol-4-yl)amino)pyrimidin-5-yl)-2-(((S)-1-(2-oxopyrrolidin-1-yl)propan-2-yl)oxy)benzonitrile | | 639.4 | B |
| 901 | (S)-5-(3-((1-(1H-tetrazol-1-yl)propan-2-yl)oxy)-4-chlorophenyl)-N-(1-(6-methoxypyridin-3-yl)-3-(2,2,2-trifluoroethoxy)-1H-pyrazol-4-yl)pyrimidin-2-amine | | 603.2 | B |
| 902 | (S)-5-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)pyridin-2(1H)-one | | 589.1 | A |
| 903 | (S)-4-((4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)-4-hydroxycyclohexan-1-one | | 622.2 | A |

TABLE 2-continued

| Ex. No. | IUPAC NAME | ADDITIVE | MS | ACTIVITY |
|---|---|---|---|---|
| 904 | trans-3-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)-1-cyclobutylpiperidin-4-ol | | 619.3 | A |
| 905 | (S)-4-((4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)methyl)-1-(tetrahydro-2H-pyran-4-yl)piperidin-4-ol | | 663.3 | A |
| 906 | trans-1-((4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)cyclohexane-1,4-diol | | 624.3 | A |
| 907 | cis-1-((4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)cyclohexane-1,4-diol | | 624.3 | A |
| 908 | (S)-4-((4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)-1-cyclobutylpiperidin-4-ol | | 663.4 | A |
| 909 | (S)-4-((4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)-1-(tetrahydro-2H-pyran-4-yl)piperidin-4-ol | | 693.3 | A |
| 910 | (S)-4-((4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)-1-methylpiperidin-4-ol | | 623.3 | A |
| 911 | trans-1-((4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)-4-morpholinocyclohexan-1-ol | | 693.4 | A |
| 912 | cis-1-((4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)-4-morpholinocyclohexan-1-ol | | 693.4 | A |
| 913 | 1-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-3-morpholinopropan-2-ol | | 639.3 | A |
| 914 | (S)-(1-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclobutyl)methanol | | 580.1 | A |
| 915 | ethyl (S)-1-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclobutane-1-carboxylate | | 622.2 | A |
| 916 | (S)-1-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclobutane-1-carboxylic acid | | 594.3 | B |
| 917 | (S)-1-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclobutane-1-carboxamide | | 591.3 | A |
| 918 | trans-4-(4-((5-(3-(((S)-1-(1H-tetrazol-1-yl)propan-2-yl)oxy)-4-chlorophenyl)pyrimidin-2-yl)amino)-3-(trifluoromethyl)-1H-pyrazol-1-yl)-1-(morpholinomethyl)cyclohexan-1-ol | | 663.3 | A |
| 919 | tert-butyl (S)-6-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-azaspiro[3.3]heptane-2-carboxylate | | 661.5 | C |
| 920 | (S)-5-(3-((1-(1H-tetrazol-1-yl)propan-2-yl)oxy)-4-chlorophenyl)-N-(1-(2-azaspiro[3.3]heptan-6-yl)-3-(trifluoromethyl)-1H-pyrazol-4-yl)pyrimidin-2-amine | | 561.3 | A |
| 921 | (S)-5-(3-((1-(1H-tetrazol-1-yl)propan-2-yl)oxy)-4-chlorophenyl)-N-(1-(2-cyclobutyl-2-azaspiro[3.3]heptan-6-yl)-3-(trifluoromethyl)-1H-pyrazol-4-yl)pyrimidin-2-amine | | 615.2 | A |
| 922 | (S)-5-(3-((1-(1H-tetrazol-1-yl)propan-2-yl)oxy)-4-chlorophenyl)-N-(1-(2-(2,2-dimethyl-1,3-dioxan-5-yl)-2-azaspiro[3.3]heptan-6-yl)-3-(trifluoromethyl)-1H-pyrazol-4-yl)pyrimidin-2-amine | | 675.3 | A |
| 923 | trans-1-((4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)-4-methylcyclohexane-1,4-diol | | 636.3 | A |
| 924 | cis-1-((4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)-4-methylcyclohexane-1,4-diol | | 638.4 | A |
| 925 | (S)-5-(3-((1-(1H-tetrazol-1-yl)propan-2-yl)oxy)-4-chlorophenyl)-N-(1-(2-azaspiro[3.3]heptan-6-yl)-3-(2,2,2-trifluoroethoxy)-1H-pyrazol-4-yl)pyrimidin-2-amine | | 591.2 | A |
| 926 | (S)-5-(3-((1-(1H-tetrazol-1-yl)propan-2-yl)oxy)-4-chlorophenyl)-N-(1-((6-methoxypyridin-3-yl)methyl)-3-(2,2,2-trifluoroethoxy)-1H-pyrazol-4-yl)pyrimidin-2-amine | | 615.2 | A |
| 927 | (S)-5-((4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)pyridin-2(1H)-one | | 601.2 | A |
| 928 | (S)-5-(3-((1-(1H-tetrazol-1-yl)propan-2-yl)oxy)-4-chlorophenyl)-N-(1-((6-methoxypyridin-2-yl)methyl)-3-(2,2,2-trifluoroethoxy)-1H-pyrazol-4-yl)pyrimidin-2-amine | | 615.2 | B |

TABLE 2-continued

| Ex. No. | IUPAC NAME | ADDITIVE | MS | ACTIVITY |
|---|---|---|---|---|
| 929 | (S)-6-((4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)methyl)pyridin-2(1H)-one | | 601.1 | A |
| 930 | 5-(3-(((S)-1-(1H-tetrazol-1-yl)propan-2-yl)oxy)-4-chlorophenyl)-N-(1-(2-(tetrahydrofuran-3-yl)-2-azaspiro[3.3]heptan-6-yl)-3-(trifluoromethyl)-1H-pyrazol-4-yl)pyrimidin-2-amine | | 631.4 | A |
| 931 | tert-butyl (S)-6-(4-((5-(3-((1-(1H-tetrazol-1-yl)propan-2-yl)oxy)-4-chlorophenyl)pyrimidin-2-yl)amino)-3-isopropyl-1H-pyrazol-1-yl)-2-azaspiro[3.3]heptane-2-carboxylate | | 635.4 | B |
| 932 | (S)-5-(3-((1-(1H-tetrazol-1-yl)propan-2-yl)oxy)-4-chlorophenyl)-N-(1-(2-(2,2-dimethyl-1,3-dioxan-5-yl)-2-azaspiro[3.3]heptan-6-yl)-3-(2,2,2-trifluoroethoxy)-1H-pyrazol-4-yl)pyrimidin-2-amine | | 705.3 | A |
| 933 | (S)-5-(3-((1-(1H-tetrazol-1-yl)propan-2-yl)oxy)-4-chlorophenyl)-N-(1-(2-cyclobutyl-2-azaspiro[3.3]heptan-6-yl)-3-(2,2,2-trifluoroethoxy)-1H-pyrazol-4-yl)pyrimidin-2-amine | | 645.3 | A |
| 934 | (S)-5-(3-((1-(1H-tetrazol-1-yl)propan-2-yl)oxy)-4-chlorophenyl)-N-(3-isopropyl-1-(2-azaspiro[3.3]heptan-6-yl)-1H-pyrazol-4-yl)pyrimidin-2-amine | | 535.3 | A |
| 935 | (S)-5-(3-((1-(1H-tetrazol-1-yl)propan-2-yl)oxy)-4-chlorophenyl)-N-(3-isopropyl-1-(2-(oxetan-3-yl)-2-azaspiro[3.3]heptan-6-yl)-1H-pyrazol-4-yl)pyrimidin-2-amine | | 591.6 | A |
| 936 | (S)-5-(3-((1-(1H-tetrazol-1-yl)propan-2-yl)oxy)-4-chlorophenyl)-N-(3-isopropyl-1-(2-(tetrahydro-2H-pyran-4-yl)-2-azaspiro[3.3]heptan-6-yl)-1H-pyrazol-4-yl)pyrimidin-2-amine | | 619.4 | A |
| 937 | (S)-5-(3-((1-(1H-tetrazol-1-yl)propan-2-yl)oxy)-4-chlorophenyl)-N-(1-(2-(4-methyltetrahydro-2H-pyran-4-yl)-2-azaspiro[3.3]heptan-6-yl)-3-(2,2,2-trifluoroethoxy)-1H-pyrazol-4-yl)pyrimidin-2-amine | | 689.3 | A |
| 938 | (S)-2-((1-(1H-tetrazol-1-yl)propan-2-yl)oxy)-4-((1-(2-(tetrahydro-2H-pyran-4-yl)-2-azaspiro[3.3]heptan-6-yl)-3-(2,2,2-trifluoroethoxy)-1H-pyrazol-4-yl)amino)pyrimidin-5-yl)benzonitrile | | 666.3 | A |
| 939 | (S)-5-(3-((1-(1H-tetrazol-1-yl)propan-2-yl)oxy)-4-(difluoromethyl)phenyl)-N-(1-(2-(tetrahydro-2H-pyran-4-yl)-2-azaspiro[3.3]heptan-6-yl)-3-(2,2,2-trifluoroethoxy)-1H-pyrazol-4-yl)pyrimidin-2-amine | | 691.3 | A |
| 940 | tert-butyl (trans-3-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclobutyl)carbamate | | 665.0 | B |
| 941 | 5-(3-(((S)-1-(1H-tetrazol-1-yl)propan-2-yl)oxy)-4-chlorophenyl)-N-(1-(trans-3-aminocyclobutyl)-3-(2,2,2-trifluoroethoxy)-1H-pyrazol-4-yl)pyrimidin-2-amine | | 565.2 | A |
| 942 | 5-(3-(((S)-1-(1H-tetrazol-1-yl)propan-2-yl)oxy)-4-chlorophenyl)-N-(1-(trans-3-((tetrahydro-2H-pyran-4-yl)amino)cyclobutyl)-3-(2,2,2-trifluoroethoxy)-1H-pyrazol-4-yl)pyrimidin-2-amine | | 649.3 | A |
| 943 | 5-(3-(((S)-1-(1H-tetrazol-1-yl)propan-2-yl)oxy)-4-chlorophenyl)-N-(1-(trans-3-morpholinocyclobutyl)-3-(2,2,2-trifluoroethoxy)-1H-pyrazol-4-yl)pyrimidin-2-amine | | 635.3 | A |
| 944 | 5-(4-chloro-3-{[(2S)-1-(1H-tetrazol-1-yl)propan-2-yl]oxy}phenyl)-N-(1-{2-[(4-$^2$H)tetrahydro-2H-pyran-4-yl]-2-azaspiro[3.3]heptan-6-yl})-3-(2,2,2-trifluoroethoxy)-1H-pyrazol-4-yl)pyrimidin-2-amine | | 676.3 | A |
| 945 | (S)-5-(3-((1-(1H-tetrazol-1-yl)propan-2-yl)oxy)-4-chlorophenyl)-N-(1-(2-cyclobutyl-2-azaspiro[3.3]heptan-6-yl)-3-(oxetan-3-yloxy)-1H-pyrazol-4-yl)pyrimidin-2-amine | | 619.3 | A |
| 946 | (S)-1-(6-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-azaspiro[3.3]heptan-2-yl)-2-methylpropan-2-ol | | 663.2 | A |
| 947 | (S)-1-(6-(4-((5-(3-((1-(1H-tetrazol-1-yl)propan-2-yl)oxy)-4-chlorophenyl)pyrimidin-2-yl)amino)-3-isopropyl-1H-pyrazol-1-yl)-2-azaspiro[3.3]heptan-2-yl)-2-methylpropan-2-ol | | 607.3 | A |
| 948 | tert-butyl (S)-6-(4-((5-(3-((1-(1H-tetrazol-1-yl)propan-2-yl)oxy)-4-(difluoromethyl)phenyl)pyrimidin-2-yl)amino)-3-(2,2,2-trifluoroethoxy)-1H-pyrazol-1-yl)-2-azaspiro[3.3]heptane-2-carboxylate | | 707.3 | C |
| 949 | (S)-5-(3-((1-(1H-tetrazol-1-yl)propan-2-yl)oxy)-4-(difluoromethyl)phenyl)-N-(1-(2-azaspiro[3.3]heptan-6-yl)-3-(2,2,2-trifluoroethoxy)-1H-pyrazol-4-yl)pyrimidin-2-amine | | 607.3 | A |
| 950 | (S)-5-(3-((1-(1H-tetrazol-1-yl)propan-2-yl)oxy)-4-(difluoromethyl)phenyl)-N-(1-(2-(oxetan-3-yl)-2-azaspiro[3.3]heptan-6-yl)-3-(2,2,2-trifluoroethoxy)-1H-pyrazol-4-yl)pyrimidin-2-amine | | 663.4 | A |
| 951 | 1-[6-(4-{[5-(4-chloro-3-{[(2S)-1-(1H-tetrazol-1-yl)propan-2-yl]oxy}phenyl)pyrimidin-2-yl]amino}-3-(2,2,2-trifluoroethoxy)-1H-pyrazol-1-yl)-2-azaspiro[3.3]heptan-2-yl]-2-methylpropan-2-yl acetate | | 705.3 | A |

TABLE 2-continued

| Ex. No. | IUPAC NAME | ADDITIVE | MS | ACTIVITY |
|---|---|---|---|---|
| 952 | (S)-5-(3-((1-(1H-tetrazol-1-yl)propan-2-yl)oxy)-4-chlorophenyl)-N-(1-(2-(pyrimidin-2-yl)-2-azaspiro[3.3]heptan-6-yl)-3-(2,2,2-trifluoroethoxy)-1H-pyrazol-4-yl)pyrimidin-2-amine | | 669.3 | A |
| 953 | (S)-5-(3-((1-(1H-tetrazol-1-yl)propan-2-yl)oxy)-4-chlorophenyl)-N-(1-(2-(4-ethyltetrahydro-2H-pyran-4-yl)-2-azaspiro[3.3]heptan-6-yl)-3-isopropyl-1H-pyrazol-4-yl)pyrimidin-2-amine | | 647.3 | A |
| 954 | 5-(3-(((S)-1-(1H-tetrazol-1-yl)propan-2-yl)oxy)-4-chlorophenyl)-N-(1-(2-(3-methyltetrahydrofuran-3-yl)-2-azaspiro[3.3]heptan-6-yl)-3-(2,2,2-trifluoroethoxy)-1H-pyrazol-4-yl)pyrimidin-2-amine | | 675.3 | A |
| 955 | (S)-5-(3-((1-(1H-tetrazol-1-yl)propan-2-yl)oxy)-4-chlorophenyl)-N-(1-(2-(4-ethyltetrahydro-2H-pyran-4-yl)-2-azaspiro[3.3]heptan-6-yl)-3-(2,2,2-trifluoroethoxy)-1H-pyrazol-4-yl)pyrimidin-2-amine | | 703.2 | A |
| 956 | 5-(3-(((S)-1-(1H-tetrazol-1-yl)propan-2-yl)oxy)-4-chlorophenyl)-N-(3-isopropyl-1-(2-(3-methyltetrahydrofuran-3-yl)-2-azaspiro[3.3]heptan-6-yl)-1H-pyrazol-4-yl)pyrimidin-2-amine | | 617.4 | A |
| 958 | (S)-1-(4-((5-(3-((1-(1H-tetrazol-1-yl)propan-2-yl)oxy)-4-chlorophenyl)pyrimidin-2-yl)amino)-1-(2-(tetrahydro-2H-pyran-4-yl)-2-azaspiro[3.3]heptan-6-yl)-1H-pyrazol-3-yl)propan-1-one | | 633.0 | A |
| 959 | (S)-5-(3-((1-(1H-tetrazol-1-yl)propan-2-yl)oxy)-4-chlorophenyl)-N-(3-(perfluoroethyl)-1-(2-(tetrahydro-2H-pyran-4-yl)-2-azaspiro[3.3]heptan-6-yl)-1H-pyrazol-4-yl)pyrimidin-2-amine | | 695.0 | A |
| 960 | (S)-5-(3-((1-(1H-tetrazol-1-yl)propan-2-yl)oxy)-4-chlorophenyl)-N-(3-isopropyl-1-(2-(4-methyltetrahydro-2H-pyran-4-yl)-2-azaspiro[3.3]heptan-6-yl)-1H-pyrazol-4-yl)pyrimidin-2-amine | | 633.3 | A |
| 965 | (S)-N-(1-(2-(1,3-dioxan-5-yl)-2-azaspiro[3.3]heptan-6-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine | | 677.0 | A |
| 974 | (S)-1-(6-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-azaspiro[3.3]heptan-2-yl)-2-methylpropan-2-yl acetate | | 675.2 | A |
| 975 | (S)-1-(6-(4-((5-(3-((1-(1H-tetrazol-1-yl)propan-2-yl)oxy)-4-chlorophenyl)pyrimidin-2-yl)amino)-3-isopropyl-1H-pyrazol-1-yl)-2-azaspiro[3.3]heptan-2-yl)-2-methylpropan-2-yl acetate | | 649.0 | A |
| 979 | (S)-5-(3-((1-(1H-tetrazol-1-yl)propan-2-yl)oxy)-4-chlorophenyl)-N-(1-(2-(2-methoxyethyl)-2-azaspiro[3.3]heptan-6-yl)-3-(2,2,2-trifluoroethoxy)-1H-pyrazol-4-yl)pyrimidin-2-amine | | 648.9 | A |
| 980 | 5-(3-(((S)-1-(1H-tetrazol-1-yl)propan-2-yl)oxy)-4-chlorophenyl)-N-(3-isopropyl-1-(2-((1r,4r)-4-methoxycyclohexyl)-2-azaspiro[3.3]heptan-6-yl)-1H-pyrazol-4-yl)pyrimidin-2-amine | | 647.1 | A |
| 981 | 5-(3-(((S)-1-(1H-tetrazol-1-yl)propan-2-yl)oxy)-4-chlorophenyl)-N-(1-(2-(oxepan-4-yl)-2-azaspiro[3.3]heptan-6-yl)-3-(2,2,2-trifluoroethoxy)-1H-pyrazol-4-yl)pyrimidin-2-amine | | 689.0 | A |
| 982 | (S)-N-(1-(2-(1,4-dioxepan-6-yl)-2-azaspiro[3.3]heptan-6-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine | | 690.9 | A |
| 983 | (S)-N-(1-(2-(1,4-dioxepan-6-yl)-2-azaspiro[3.3]heptan-6-yl)-3-isopropyl-1H-pyrazol-4-yl)-5-(3-((1-(1H-tetrazol-1-yl)propan-2-yl)oxy)-4-chlorophenyl)pyrimidin-2-amine | | 635.0 | A |
| 984 | (S)-5-(3-((1-(1H-tetrazol-1-yl)propan-2-yl)oxy)-4-chlorophenyl)-N-(1-(2-(pyrimidin-2-ylmethyl)-2-azaspiro[3.3]heptan-6-yl)-3-(2,2,2-trifluoroethoxy)-1H-pyrazol-4-yl)pyrimidin-2-amine | | 683.3 | A |
| 998 | (S)-5-(3-((1-(1H-tetrazol-1-yl)propan-2-yl)oxy)-4-chlorophenyl)-N-(3-(2,2,2-trifluoroethoxy)-1-(2-(3,3,3-trifluoropropyl)-2-azaspiro[3.3]heptan-6-yl)-1H-pyrazol-4-yl)pyrimidin-2-amine | | 687.3 | A |
| 1000 | (S)-5-(3-((1-(1H-tetrazol-1-yl)propan-2-yl)oxy)-4-chlorophenyl)-N-(1-(2-(2-methylpyrimidin-4-yl)-2-azaspiro[3.3]heptan-6-yl)-3-(2,2,2-trifluoroethoxy)-1H-pyrazol-4-yl)pyrimidin-2-amine | | 683.3 | A |
| 1001 | (S)-5-(3-((1-(1H-tetrazol-1-yl)propan-2-yl)oxy)-4-chlorophenyl)-N-(1-(2-(pyridin-2-yl)-2-azaspiro[3.3]heptan-6-yl)-3-(2,2,2-trifluoroethoxy)-1H-pyrazol-4-yl)pyrimidin-2-amine | | 668.3 | A |
| 1010 | (S)-4-(6-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-azaspiro[3.3]heptan-2-yl)tetrahydro-2H-pyran-4-carbonitrile | | 700.3 | A |
| 1011 | 5-(3-(((S)-1-(1H-tetrazol-1-yl)propan-2-yl)oxy)-4-chlorophenyl)-N-(3-isopropyl-1-(2-(cis-4-methoxycyclohexyl)-2-azaspiro[3.3]heptan-6-yl)-1H-pyrazol-4-yl)pyrimidin-2-amine | | 647.1 | A |
| 1012 | (S)-5-(3-((1-(1H-tetrazol-1-yl)propan-2-yl)oxy)-4-chlorophenyl)-N-(3-isopropyl-1-(2-(2-methoxyethyl)-2-azaspiro[3.3]heptan-6-yl)-1H-pyrazol-4-yl)pyrimidin-2-amine | | 593.3 | A |
| 1013 | (S)-N-(1-(2-(1,3-dioxan-5-yl)-2-azaspiro[3.3]heptan-6-yl)-3-isopropyl-1H-pyrazol-4-yl)-5-(3-((1-(1H-tetrazol-1-yl)propan-2-yl)oxy)-4-chlorophenyl)pyrimidin-2-amine | | 621.4 | A |

TABLE 2-continued

| Ex. No. | IUPAC NAME | ADDITIVE | MS | ACTIVITY |
|---|---|---|---|---|
| 1014 | 5-(3-(((S)-1-(1H-tetrazol-1-yl)propan-2-yl)oxy)-4-chlorophenyl)-N-(3-isopropyl-1-(2-(trans-4-methoxycyclohexyl)-2-azaspiro[3.3]heptan-6-yl)-1H-pyrazol-4-yl)pyrimidin-2-amine | | 647.3 | A |

Experimental Example 1

Evaluation of In Vitro CaMKII Inhibitory Activity (Enzyme Assay)

(i) Objective

In vitro CaMKIIδ inhibitory activity was evaluated by an enzyme assay.

(ii) Methods

Human CaMKII Enzyme Inhibition Assay

Kinase assay for CaMKIIs was performed using the radiometric assay. Human full-length CaMKIIδ (Cat #02-111) was obtained from Carna Biosciences (Kobe, Japan).

Enzyme reactions were performed in 25 mM HEPES, pH 7.5, with 5 mM magnesium chloride, 1 mM calcium chloride, 10 μg/mL Calmodulin, 2 mM DTT, 0.01% Tween20 and 500 nM ATP (0.2 μCi/well of [γ-33P] ATP) containing 0.5 nM CaMKIIδ and 0.1 μM autophosphorylation peptide (KKALRRQETVDAL) (Toray Research Center).

After incubating the enzyme, peptide, and compounds for 5 min, kinase reactions were initiated by adding ATP, followed by incubation for 60 min at room temperature in a total volume of 50 μL. The reactions were terminated by the addition of 10% trichloroacetic acid (final concentration). The [γ-33P]-phosphorylated proteins were filtered in a Harvest Plate (Merck Millipore) with a Cell Harvester (PerkinElmer) and then free [γ-33P] ATP was washed out with 3% phosphoric acid. The plates were dried, followed by the addition of 40 μl of MicroScint0 (PerkinElmer). The radioactivity was counted by a TopCount scintillation counter (PerkinElmer). The signals of the reaction without enzyme were defined as 100% inhibitory activity and those of the reaction without inhibitors as 0% inhibitory activity. In vitro CaMKIIδ inhibitory activity was evaluated by % inhibitory activity of 3 μM compound concentration.

(iii) Results

The results of the in vitro CaMKIIδ inhibitory activity assays are shown in Table 3.

TABLE 3

Results of in vitro CaMKIIδ inhibitory activity assays

| Example No. | CaMKIIδ inhibitory activity (%) at 3 μM |
|---|---|
| 1 | 99% |
| 2 | 96% |
| 5 | 98% |
| 8 | 98% |
| 9 | 99% |
| 10 | 98% |
| 16 | 99% |
| 17 | 98% |
| 33 | 98% |
| 34 | 99% |
| 39 | 98% |
| 45 | 99% |
| 50 | 99% |
| 52 | 100% |
| 56 | 98% |
| 57 | 99% |
| 58 | 99% |
| 60 | 99% |
| 72 | 97% |
| 73 | 97% |
| 75 | 98% |
| 82 | 98% |
| 85 | 98% |
| 87 | 98% |
| 147 | 95% |
| 152 | 98% |
| 160 | 99% |
| 172 | 100% |
| 192 | 99% |
| 197 | 97% |
| 202 | 99% |
| 205 | 99% |
| 206 | 99% |
| 210 | 100% |
| 211 | 98% |
| 212 | 99% |
| 213 | 100% |
| 214 | 100% |
| 357 | 96% |
| 358 | 93% |
| 361 | 98% |
| 362 | 97% |
| 365 | 98% |
| 371 | 94% |
| 372 | 98% |
| 373 | 98% |
| 374 | 97% |
| 375 | 97% |
| 376 | 97% |
| 379 | 98% |
| 380 | 99% |
| 402 | 82% |
| 410 | 99% |
| 411 | 93% |
| 412 | 96% |
| 416 | 98% |

Experimental Example 2

Evaluation of In Vitro CaMKII Inhibitory Activity (Binding Assay)

(i) Objective

In vitro CaMKIIδ inhibitory activity was evaluated by a binding assay.

(ii) Materials

Full-length, glutathione-S-transferase (GST)-tagged, human CaMKIIδ was purchased from Carna Biosciences (product #02-111, Kobe, Japan). Full-length bovine calmodulin was purchased from Wako Pure Chemical Industries (Osaka, Japan). Terbium-labeled anti-GST antibody (Tb-anti-GST Ab) was purchased from Life Technologies (Carlsbad, Calif., USA). Boron-dipyrromethene (BODIPY)-labeled probe ligand was synthesized as described below.

5,5-difluoro-7,9-dimethyl-3-(3-oxo-3-((3-((4-(3-(piperazin-1-yl)phenyl)pyrimidin-2-yl)amino)phenyl)amino)propyl)-5H-dipyrrolo[1,2-c:2',1'-f][1,3,2]diazaborinin-4-ium-5-uide

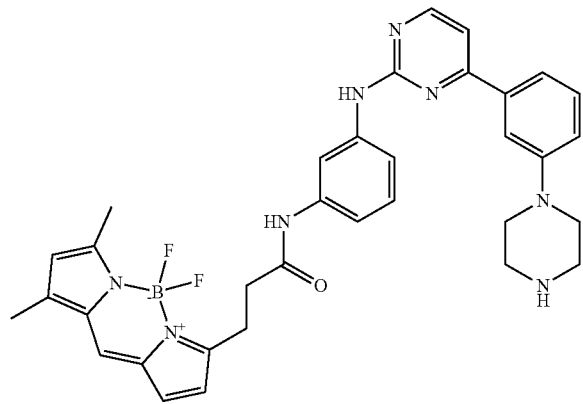

A) tert-butyl 4-(3-(2-chloropyrimidin-4-yl)phenyl)piperazine-1-carboxylate

The mixture of 2,4-dichloropyrimidine (500 mg, 3.36 mmol), tert-butyl 4-(3-(4,4,5,5-tetramethyl-1,3,2-dioxaborolan-2-yl)phenyl)piperazine-1-carboxylate (1.24 g), tetrakis(triphenylphosphine)palladium(0) (739 mg), sodium carbonate (508 mg), THF (20 mL) and water (2.00 mL) was stirred at 60° C. under nitrogen atmosphere for 24 hr. The mixture was quenched with water at room temperature and extracted with ethyl acetate. The organic layer was separated, washed with water and saturated brine, dried over anhydrous magnesium sulfate and concentrated in vacuo. The residue was purified by column chromatography (ethyl acetate/hexane) to give the title compound.
MS m/z 375.1 [M+1]$^+$.

B) tert-butyl 4-(3-(2-((3-nitrophenyl)amino)pyrimidin-4-yl)phenyl)piperazine-1-carboxylate The mixture of tert-butyl 4-(3-(2-chloropyrimidin-4-yl)phenyl)piperazine-1-carboxylate (704 mg), 3-nitroaniline (285 mg), palladium acetate (63.2 mg), BINAP (234 mg), cesium carbonate (857 mg) and toluene (10 mL) was stirred at 90° C. under nitrogen atmosphere overnight. The mixture was quenched with 1 M aqueous hydrogen chloride solution at room temperature and extracted with ethyl acetate. The organic layer was separated, washed with water and saturated brine, dried over anhydrous magnesium sulfate and concentrated in vacuo. The residue was purified by column chromatography (NH, ethyl acetate/hexane) to give the title compound (588 mg).
MS m/z 477.2 [M+1]$^+$.

C) tert-butyl 4-(3-(2-((3-aminophenyl)amino)pyrimidin-4-yl)phenyl)piperazine-1-carboxylate A mixture of tert-butyl 4-(3-(2-((3-nitrophenyl)amino)pyrimidin-4-yl)phenyl)piperazine-1-carboxylate (588 mg) and 10% palladium-carbon (131 mg) in MeOH (15 mL) was stirred under normal pressure of hydrogen atmosphere at room temperature for 3 hr. The catalyst was removed by filtration and the filtrate was concentrated in vacuo to give the title compound (167 mg).
MS m/z 447.3 [M+1]$^+$.

D) 3-(3-((3-((4-(3-(4-(tert-butoxycarbonyl)piperazin-1-yl)phenyl)pyrimidin-2-yl)amino)phenyl)amino)-3-oxopropyl)-5,5-difluoro-7,9-dimethyl-5H-dipyrrolo[1,2-c:2',1'-f][1,3,2]diazaborinin-4-ium-5-uide 1-Propanephosphonic acid cyclic anhydride (0.440 mL) was added to a solution of tert-butyl 4-(3-(2-((3-aminophenyl)amino)pyrimidin-4-yl)phenyl)piperazine-1-carboxylate (167 mg), 3-(2-carboxyethyl)-5,5-difluoro-7,9-dimethyl-5H-dipyrrolo[1,2-c:2',1'-f][1,3,2]diazaborinin-4-ium-5-uide (109 mg), N,N-diisopropylethylamine (0.196 mL) and N,N-dimethylaminopyridine (45.7 mg) in ethyl acetate (4 mL) at room temperature. The mixture was stirred at 80° C. under a dry atmosphere (calcium chloride tube) for 5 hr. The mixture was quenched with saturated aqueous sodium hydrogencarbonate solution at room temperature and extracted with ethyl acetate. The organic layer was separated, washed with water and saturated brine, dried over anhydrous magnesium sulfate and concentrated in vacuo. The residue was purified by column chromatography (ethyl acetate/hexane) to give the title compound (110 mg).
MS m/z 721.1 [M+1]$^+$.

E) 5,5-difluoro-7,9-dimethyl-3-(3-oxo-3-((3-((4-(3-(piperazin-1-yl)phenyl)pyrimidin-2-yl)amino)phenyl)amino)propyl)-5H-dipyrrolo[1,2-c:2',1'-f][1,3,2]diazaborinin-4-ium-5-uide 4 M hydrogen chloride-cyclopentyl methyl ether (0.382 mL) was added to a solution of 3-(3-((3-((4-(3-(4-(tert-butoxycarbonyl)piperazin-1-yl)phenyl)pyrimidin-2-yl)amino)phenyl)amino)-3-oxopropyl)-5,5-difluoro-7,9-dimethyl-5H-dipyrrolo[1,2-c:2',1'-f][1,3,2]diazaborinin-4-ium-5-uide (110 mg) in ethyl acetate (2.00 mL) at room temperature. The mixture was stirred at room temperature under a dry atmosphere (calcium chloride tube) for 5 hr. After evaporation of the solvent, the residue was purified by preparative HPLC (water/CH$_3$CN containing 0.1% TFA). The desired fraction was neutralized with saturated aqueous sodium hydrogencarbonate solution and extracted with ethyl acetate. The organic layer was separated, dried over anhydrous magnesium sulfate and concentrated in vacuo to give the title compound (15.0 mg).
$^1$H NMR (300 MHz, DMSO-d$_6$) δ1.23 (3H, s), 2.27 (3H, s), 2.72-2.80 (3H, m), 2.82-2.94 (4H, m), 3.09-3.23 (6H, m), 6.31 (1H, s), 6.41 (1H, d, J=3.9 Hz), 7.10 (2H, d, J=3.9 Hz), 7.21 (2H, d, J=7.7 Hz), 7.32-7.43 (2H, m), 7.49-7.56 (1H, m), 7.60 (1H, d, J=8.3 Hz), 7.71 (2H, s), 8.05 (1H, s), 8.51 (1H, d, J=5.0 Hz), 9.61 (1H, s), 9.99 (1H, s); MS m/z 621.2 [M+1]$^+$.

(iii) Methods
Time-Resolved Fluorescence Resonance Energy Transfer (TR-FRET) Assay All assays were conducted using 384-well, white, flat-bottomed plates (product #784075, Greiner Bio-One, Frickenhausen, Germany) in kinase assay buffer, which consists of 50 mM HEPES pH 7.6, 10 mM MgCl$_2$, 1 mM EGTA, 0.01% Brig-35, 0.1 mM DTT). The fluorescent probe ligand was added at a final concentration of 300 nM to solutions containing 0.21 nM Tb-anti-GST Ab, 1 mM CaCl$_2$, 10 µg/mL calmodulin, and 0.5 nM GST-tagged CaMKIIδ. After shaded incubation of the protein-probe mixture on ice for 30 min, the premix was dispensed in the assay plate including test inhibitors with 4 fold dilution series of eight concentrations. After 1 hr incubation at room temperature, TR-FRET signals were measured in duplicate using an EnVision microplate reader (Perkin Elmer, Waltham, Mass., USA). The solution in each well was excited with a laser (A=340 nm) reflected by a dichroic mirror (D400/D505 (Perkin Elmer) through an excitation filter (UV (TRF) 340, (Perkin Elmer)), and fluorescence from Tb and BODIPY were detected through two emission filters (CFP 495 (Perkin Elmer) for Tb, Emission 520 (Perkin Elmer) for BODIPY).

The percentage of inhibition of test compounds was calculated according to equation (1)

$$\text{Inhibition (\%)} = 100 \times (\mu_H - T)/(\mu_H - \mu_L) \quad (1)$$

Where T is the value of the wells containing test compounds and $\mu_H$ and $\mu_L$ are the mean values of the 0% and 100% inhibition control wells, respectively. The values of the 0 and 100% controls were the signals obtained in the absence and presence of 3 μM its parent compound, respectively. The half maximal inhibitory concentration ($IC_{50}$) of test compounds was calculated by fitting the data with the logistic equation using XLfit (IDBS, Guildford, UK). The $IC_{50}$ was classified according to the following activity ranks.
A: less than 10 nM
B: 10 nM or more and less than 100 nM
C: 100 nM or more
The results are shown in Table 2.

Experimental Example 3

Evaluation of In Vivo Cardiac CaMKII Inhibition
(i) Objective
To evaluate potency of test compounds to inhibit cardiac CaMKII kinase in vivo, phosphorylation levels of CaMKII-specific sites of phospholamban (Thr17, PLN) were measured in the heart of rats administered with test compounds at various doses.
(ii) Materials and Methods
Test compounds were suspended in 0.5% [w/v] methylcellulose/water solution and administered (10 or 30 mg/kg) to male CD (SD) IGS rat (6-8 weeks old, n=4) by the p.o. route (5 mL/kg). At 2-4 hours after the administration, rats were sacrificed and the hearts were harvested. After washing the isolated hearts with ice-cold saline, connective tissues were removed on ice, and the isolated left ventricle were frozen into liquid nitrogen gas and stored at −80° C.
The left ventricle samples were homogenized in RIPA-buffer containing phosphatase inhibitors and protease inhibitors. Samples were analyzed by Western blotting using anti-P-PLN (Thr17, Santa Cruz Biotechnology, sc-17024-R) antibody. The band intensities were quantified using an imaging system and were normalized relative to the vehicle-treated group.
(iii) Results
The results of the in vivo cardiac CaMKII inhibition are shown in Table 4.

TABLE 4

Results of P-PLN reduction rate of each test compound in comparison with vehicle-treated group

| Test compound (Example No.) | Dose | Time after administration | Reduction rate of P-PLN |
|---|---|---|---|
| 484 | 30 mg/kg | 2 hr | >50% |
| 677 | 30 mg/kg | 2 hr | >50% |

TABLE 4-continued

Results of P-PLN reduction rate of each test compound in comparison with vehicle-treated group

| Test compound (Example No.) | Dose | Time after administration | Reduction rate of P-PLN |
|---|---|---|---|
| 695 | 30 mg/kg | 2 hr | >50% |
| 772 | 30 mg/kg | 2 hr | >50% |
| 795 | 30 mg/kg | 2 hr | >50% |
| 806 | 30 mg/kg | 2 hr | >50% |
| 831 | 30 mg/kg | 4 hr | >50% |
| 843 | 10 mg/kg | 4 hr | >50% |
| 946 | 30 mg/kg | 4 hr | >50% |
| 951 | 30 mg/kg | 4 hr | >50% |

Formulation Examples

Medicaments containing the compound of the present invention as an active ingredient can be produced, for example, by the following formulations.

1. Capsule

| (1) | compound obtained in Example 1 | 10 mg |
|---|---|---|
| (2) | lactose | 90 mg |
| (3) | microcrystalline cellulose | 70 mg |
| (4) | magnesium stearate | 10 mg |
| | 1 capsule | 180 mg |

The total amount of the above-mentioned (1), (2) and (3) and 5 mg of (4) are blended and granulated, and 5 mg of the remaining (4) is added. The whole mixture is sealed in a gelatin capsule.

2. Tablet

| (1) | compound obtained in Example 1 | 10 mg |
|---|---|---|
| (2) | lactose | 35 mg |
| (3) | cornstarch | 150 mg |
| (4) | microcrystalline cellulose | 30 mg |
| (5) | magnesium stearate | 5 mg |
| | 1 tablet | 230 mg |

The total amount of the above-mentioned (1), (2) and (3), 20 mg of (4) and 2.5 mg of (5) are blended and granulated, and 10 mg of the remaining (4) and 2.5 mg of the remaining (5) are added and the mixture is compression formed to give a tablet.

According to the present invention, a compound having a superior CaMKII inhibitory action, which is expected to be useful as an agent for the prophylaxis or treatment of cardiac diseases (particularly catecholaminergic polymorphic ventricular tachycardia, postoperative atrial fibrillation, heart failure, fatal arrhythmia) and the like can be provided.

The invention claimed is:

1. A method for the prophylaxis or treatment of a cardiac disease in a mammal, which comprises administering to the mammal in need thereof a therapeutically effective amount of a compound represented by the formula (I):

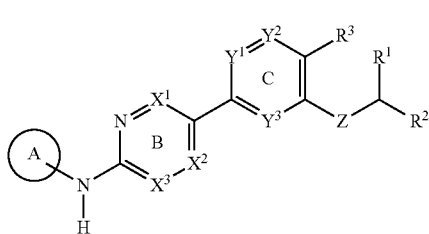

wherein:
Ring A is selected from the group consisting of
(1) a benzene ring substituted by 0 to 3 substituents independently selected from
   (a) a $C_{1-6}$ alkoxy group or a halogenated $C_{1-6}$ alkoxy group,
   (b) a $C_{1-6}$ alkyl group substituted by 0 to 3 substituents independently selected from
      (i) a halogen atom,
      (ii) a hydroxy group,
      (iii) an amino group optionally substituted by 1 or 2 substituents independently selected from
         (I) a $C_{3-10}$ cycloalkyl group, and
         (II) a $C_{1-6}$ alkoxy-carbonyl group,
      (iv) a 5- to 14-membered aromatic heterocyclic group, and
      (v) a 3- to 14-membered non-aromatic heterocyclic group substituted by 0 to 3 $C_{1-6}$ alkyl groups,
   (c) a $C_{3-10}$ cycloalkyl group substituted by 0 to 3 substituents independently selected from
      (i) a 3- to 14-membered non-aromatic heterocyclic group,
   (d) a halogen atom,
   (e) a cyano group,
   (f) a carboxy group,
   (g) a $C_{1-6}$ alkoxy-carbonyl group,
   (h) a $C_{1-6}$ alkylsulfanyl group,
   (i) a $C_{1-6}$ alkylsulfonyl group,
   (j) a carbamoyl group optionally substituted by 1 or 2 substituents independently selected from
      (i) a $C_{1-6}$ alkyl group substituted by 0 to 3 substituents independently selected from
         (I) a hydroxy group,
         (II) a halogen atom,
         (III) a $C_{1-6}$ alkoxy group or a halogenated $C_{1-6}$ alkoxy group,
         (IV) a mono- or di-$C_{1-6}$ alkylamino group,
         (V) a $C_{3-10}$ cycloalkyl group, and
         (VI) a 3- to 14-membered non-aromatic heterocyclic group substituted by 0 to 3 substituents independently selected from a $C_{1-6}$ alkyl group and a $C_{1-6}$ alkyl-carbonyl group,
      (ii) a $C_{3-10}$ cycloalkyl group substituted by 0 to 3 substituents independently selected from
         (I) a halogen atom,
         (II) an $C_{1-6}$ alkyl group or a halogenated $C_{1-6}$ alkyl group,
         (III) a carboxy group, and
         (IV) a $C_{1-6}$ alkoxy-carbonyl group, and
      (iii) a 3- to 14-membered non-aromatic heterocyclic group substituted by 0 to 3 substituents independently selected from $C_{1-6}$ alkyl groups and halogenated $C_{1-6}$ alkyl groups,
   (k) a sulfamoyl group optionally substituted by 1 or 2 substituents, a mono substituted amino group or a di substituted amino group wherein each substituent is independently selected from
      (i) a 3- to 14-membered non-aromatic heterocyclic group substituted by 0 to 3 $C_{1-6}$ alkyl groups,
   (l) a 5- to 14-membered aromatic heterocyclic group substituted by 0 to 3 $C_{1-6}$ alkyl groups,
   (m) a 3- to 14-membered non-aromatic heterocyclic group substituted by 0 to 3 substituents independently selected from
      (i) a $C_{1-6}$ alkyl group substituted by 0 to 3 substituents independently selected from
         (I) a halogen atom,
         (II) a hydroxy group,
         (III) a cyano group,
         (IV) a carbamoyl group,
         (V) a $C_{1-6}$ alkoxy group,
         (VI) a $C_{1-6}$ alkylsulfonyl group,
         (VII) a mono- or di-$C_{1-6}$ alkylamino group, and
         (VIII) a 3- to 14-membered non-aromatic heterocyclic group,
      (ii) a $C_{1-6}$ alkyl-carbonyl group substituted by 0 to 3 substituents independently selected from
         (I) a halogen atom,
         (II) a hydroxy group, and
         (III) a mono- or di-$C_{1-6}$ alkylamino group,
      (iii) a $C_{1-6}$ alkoxy-carbonyl group,
      (iv) a 3- to 14-membered non-aromatic heterocyclic group substituted by 0 to 3 substituents independently selected from
         (I) a halogen atom,
         (II) a $C_{1-6}$ alkyl-carbonyl group, and
         (III) a $C_{1-6}$ alkoxy-carbonyl group,
      (v) an oxo group, and
      (vi) a mono- or di-$C_{1-6}$ alkyl-carbamoyl group,
   (n) a 3- to 14-membered non-aromatic heterocyclylcarbonyl group substituted by 0 to 3 substituents independently selected from
      (i) a halogen atom,
      (ii) a hydroxy group,
      (iii) a cyano group,
      (iv) a $C_{1-6}$ alkyl group substituted by 0 to 3 substituents independently selected from
         (I) a hydroxy group,
         (II) a halogen atom,
         (III) a $C_{1-6}$ alkoxy group,
         (IV) a mono- or di-$C_{1-6}$ alkylamino group, and
         (V) a $C_{3-10}$ cycloalkyl group,
      (v) a $C_{1-6}$ alkoxy group or a halogenated Ci-6 alkoxy group,
      (vi) a $C_{1-6}$ alkyl-carbonyl group substituted by 0 to 3 substituents independently selected from
         (I) a hydroxy group, and
         (II) a $C_{1-6}$ alkoxy group,
      (vii) a $C_{1-6}$ alkoxy-carbonyl group,
      (viii) a $C_{3-10}$ cycloalkyl group,
      (ix) a $C_{3-10}$ cycloalkyl-carbonyl group,
      (x) a $C_{1-6}$ alkylsulfonyl group, and
      (xi) a 3- to 14-membered non-aromatic heterocyclic group substituted by 0 to 3 Ci-6 alkyl groups, and
   (o) a 3- to 14-membered non-aromatic heterocyclylsulfonyl group substituted by 0 to 3 of 3- to 14-membered non-aromatic heterocyclic groups;
or wherein two substituents on the benzene ring are bonded to each other to form a 5- or 6-membered monocyclic aromatic heterocycle, a 3- to 8-membered monocyclic non-aromatic heterocycle or a $C_{5-6}$ cycloalkene ring, each of which is substituted by 0 to 3 substituents independently selected from
(i) an oxo group,
(ii) a $C_{1-6}$ alkyl group substituted by 0 to 3 substituents independently selected from
 (I) a halogen atom,
 (II) a hydroxy group,
 (III) a carboxy group,
 (IV) a $C_{1-6}$ alkoxy group,
 (V) a $C_{1-6}$ alkyl-carbonyl group,
 (VI) a mono- or di-$C_{1-6}$ alkylamino group, and
 (VII) a 3- to 14-membered non-aromatic heterocyclic group substituted by 0 to 3 $C_{1-6}$ alkyl groups,
(iii) a C3-10 cycloalkyl group,
(iv) a formyl group,
(v) a $C_{1-6}$ alkyl-carbonyl group substituted by 0 to 3 substituents independently selected from
 (I) a halogen atom,
 (II) a hydroxy group,
 (III) a $C_{1-6}$ alkoxy group,
 (IV) a $C_{1-6}$ alkyl-carbonyloxy group,
 (V) a mono- or di-$C_{1-6}$ alkylamino group, and
 (VI) a 3- to 14-membered non-aromatic heterocyclic group,
(vi) a $C_{1-6}$ alkoxy-carbonyl group,
(vii) a 5- to 14-membered aromatic heterocyclic group substituted by 0 to 3 $C_{1-6}$ alkyl groups,
(viii) a 3- to 14-membered non-aromatic heterocyclic group substituted by 0 to 3 $C_{1-6}$ alkyl groups, and
(ix) a 3- to 14-membered non-aromatic heterocyclycarbonyl group substituted by 0 to 3 $C_{1-6}$ alkyl groups,
(2) a pyridine ring substituted by 0 to 3 substituents independently selected from
(a) a $C_{1-6}$ alkyl group,
(b) a $C_{1-6}$ alkoxy group or halogenated $C_{1-6}$ alkoxy group,
(c) a $C_{3-10}$ cycloalkyl group substituted by 0 to 3 halogen atoms,
(d) an amino group, and
(e) a 3- to 14-membered non-aromatic heterocyclic group substituted by 0 to 3 substituents independently selected from
 (i) a hydroxy group,
 (ii) a $C_{1-6}$ alkyl group substituted by 0 to 3 substituents independently selected from
  (I) a halogen atom, and
  (II) a 3- to 14-membered non-aromatic heterocyclic group,
 (iii) a $C_{1-6}$ alkyl-carbonyl group or a halogenated $C_{1-6}$ alkyl-carbonyl group,
 (iv) a $C_{1-6}$ alkoxy-carbonyl group,
 (v) a $C_{3-10}$ cycloalkyl group substituted by 0 to 3 halogen atoms, and
 (vi) a 3- to 14-membered non-aromatic heterocyclic group,
(3) a pyrimidine ring substituted by 0 to 3 substituents independently selected from
(a) a $C_{1-6}$ alkoxy group, and
(b) a 3- to 14-membered non-aromatic heterocyclic group substituted by 0 to 3 of 3- to 14-membered non-aromatic heterocyclic groups,
(4) a pyridazine ring,
(5) a pyrazine ring,
(6) a pyrazole ring substituted by 0 to 3 substituents independently selected from
(a) a halogen atom,
(b) a cyano group,
(c) a carboxy group,
(d) a $C_{1-6}$ alkyl group substituted by 0 to 5 substituents independently selected from
 (i) a $C_{3-10}$ cycloalkyl group substituted by 0 to 3 substituents independently selected from
  (I) an amino group,
  (II) a hydroxy group,
  (III) an oxo group,
  (IV) a $C_{1-6}$ alkyl group, and
  (V) a 3- to 14-membered non-aromatic heterocyclic group,
 (ii) a hydroxy group,
 (iii) a cyano group,
 (iv) a halogen atom,
 (v) a carboxy group,
 (vi) a $C_{1-6}$ alkoxy group substituted by 0 to 3 substituents independently selected from
  (I) a halogen atom, and
  (II) a hydroxy group,
 (vii) a $C_{1-6}$ alkoxy-carbonyl group,
 (viii) a $C_{1-6}$ alkylsulfonyl group,
 (ix) an amino group optionally substituted by 1 or 2 substituents is independently selected from
  (I) a $C_{1-6}$ alkyl-carbonyl group,
  (II) a $C_{1-6}$ alkoxy-carbonyl group,
  (III) a $C_{1-6}$ alkylsulfonyl group,
  (IV) a $C_{6-14}$ aryl-carbonyl group, and
  (V) a carbamoyl group,
 (x) a carbamoyl group optionally substituted by 1 or 2 substituents independently selected from
  (I) a $C_{1-6}$ alkyl group, and
  (II) a $C_{6-14}$ aryl group,
 (xi) a 5- to 14-membered aromatic heterocyclic group substituted by 0 to 3 substituents independently selected from
  (I) a $C_{1-6}$ alkyl group, and
  (II) a $C_{1-6}$ alkoxy group,
 (xii) a 3- to 14-membered non-aromatic heterocyclic group substituted by 0 to 3 substituents independently selected from
  (I) an oxo group,
  (II) a hydroxy group,
  (III) a carbamoyl group,
  (IV) a $C_{1-6}$ alkyl group substituted by 0 to 3 hydroxy groups,
  (V) a $C_{1-6}$ alkoxy-carbonyl group,
  (VI) a $C_{3-10}$ cycloalkyl group,
  (VII) a $C_{7-16}$ aralkyl group, and
  (VIII) a 3- to 14-membered non-aromatic heterocyclic group, and
 (xiii) a 3- to 14-membered non-aromatic heterocyclylcarbonyl group,
(e) a $C_{2-6}$ alkynyl group,
(f) a $C_{1-6}$ alkoxy group substituted by 0 to 5 substituents independently selected from
 (i) a halogen atom, and
 (ii) a $C_{3-10}$ cycloalkyl group substituted by 0 to 3 halogen atoms,
(g) a $C_{3-10}$ cycloalkyl group or a $C_{3-10}$ cycloalkyl group fused with a benzene ring wherein the fused ring may form a bridged or a spiro group, wherein the $C_{3-10}$ cycloalkyl group is substituted by 0 to 3 substituents independently selected from
 (i) an oxo group,
 (ii) a hydroxy group,
 (iii) a carbamoyl group,
 (iv) a carboxy group, (v) a $C_{1-6}$ alkyl group substituted by 0 to 3 substituents independently selected from
  (I) a hydroxy group,
  (II) a carboxy group,
  (III) a carbamoyl group, and
  (IV) a 3- to 14-membered non-aromatic heterocyclic group,
(vi) a $C_{1-6}$ alkoxy-carbonyl group,
(vii) a 3- to 14-membered non-aromatic heterocyclic group substituted by 0 to 3 substituents independently selected from
  (I) a halogen atom,
  (II) a hydroxy group, and
  (III) a $C_{1-6}$ alkyl group substituted by 0 to 3 substituents independently selected from a halogen atom and a hydroxy group, and
(viii) an amino group optionally substituted by 1 or 2 substituents independently selected from
  (I) a $C_{1-6}$ alkoxy-carbonyl group, and
  (II) a 3- to 14-membered non-aromatic heterocyclic group,
(h) a $C_{1-6}$ alkyl-carbonyl group or a halogenated $C_{1-6}$ alkyl-carbonyl group,
(i) a $C_{1-6}$ alkoxy-carbonyl group,
(j) a $C_{6-14}$ aryl group,
(k) a $C_{7-16}$ aralkyl group,
(l) a 5- to 14-membered aromatic heterocyclic group substituted by 0 to 3 $C_{1-6}$ alkoxy groups,
(m) a 3- to 14-membered non-aromatic heterocyclic group substituted by 0 to 3 substituents independently selected from
  (i) an oxo group,
  (ii) a hydroxy group,
  (iii) a $C_{1-6}$ alkyl group substituted by 0 to 3 substituents independently selected from
    (I) a halogen atom,
    (II) a hydroxy group,
    (III) a cyano group,
    (IV) a $C_{1-6}$ alkoxy group substituted by 0 to 3 substituents independently selected from
      (A) a halogen atom,
      (B) a $C_{1-6}$ alkyl-carbonyloxy group, and
      (C) a $C_{1-6}$ alkoxy-carbonyloxy group,
    (V) a $C_{1-6}$ alkyl-carbonyloxy group,
    (VI) a $C_{3-10}$ cycloalkyl group,
    (VII) a 5- to 14-membered aromatic heterocyclic group substituted by 0 to 3 $C_{1-6}$ alkyl groups, and
    (VIII) a 3- to 14-membered non-aromatic heterocyclic group,
  (iv) a $C_{3-10}$ cycloalkyl group substituted by 0 to 3 substituents independently selected from
    (I) a halogen atom,
    (II) a hydroxy group,
    (III) a $C_{1-6}$ alkyl group substituted by 0 to 3 $C_{1-6}$ alkoxy groups, and
    (IV) a $C_{1-6}$ alkoxy group,
  (v) a $C_{6-14}$ aryl group substituted by 0 to 3 halogen atoms,
  (vi) a $C_{7-16}$ aralkyl group,
  (vii) a $C_{1-6}$ alkyl-carbonyl group,
  (viii) a $C_{1-6}$ alkoxy-carbonyl group,
  (ix) a 5- to 14-membered aromatic heterocyclic group substituted by 0 to 3 $C_{1-6}$ alkyl groups, and
  (x) a 3- to 14-membered non-aromatic heterocyclic group substituted by 0 to 3 substituents independently selected from
    (I) a halogen atom,
    (II) a $C_{1-6}$ alkyl group substituted by 0 to 3 substituents independently selected from a halogen atom and a $C_{1-6}$ alkoxy group,
    (III) a $C_{3-10}$ cycloalkyl group,
    (VI) a cyano group, and
    (V) a deuterium atom,
  (n) a 3- to 14-membered non-aromatic heterocyclyloxy group, and
  (o) a 3- to 14-membered non-aromatic heterocyclylcarbonyl group substituted by 0 to 3 of 3- to 14-membered non-aromatic heterocyclic groups,
(7) a thiazole ring or a thiazole ring wherein two substituents on the thiazole ring are bonded to each other to form a benzene ring,
(8) an isothiazole ring substituted by 0 to 3 substituents independently selected from
  (a) a $C_{1-6}$ alkyl group substituted by 0 to 3 hydroxy groups,
(9) an imidazole ring substituted by 0 to 3 substituents independently selected from
  (a) a $C_{1-6}$ alkyl group substituted by 0 to 3 hydroxy groups
or an imidazole ring wherein two substituents on the imidazole ring are bonded to each other to form a benzene ring,
(10) an isoxazole ring substituted by 0 to 3 $C_{1-6}$ alkyl groups,
(11) a thiadiazole ring substituted by 0 to 3 substituents independently selected from
  (a) a $C_{6-14}$ aryl group substituted by 0 to 3 halogen atoms, and
(12) a thiophene ring substituted by 0 to 3 cyano groups or a thiophene ring wherein two substituents on the thiophene ring are bonded to each other to form a $C_{5-6}$ cycloalkene ring;

Ring B is

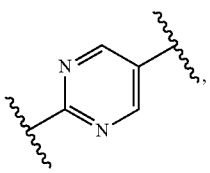

(1)

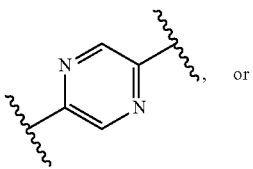

(2) or

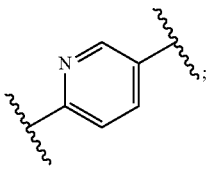

(3)

Ring C is

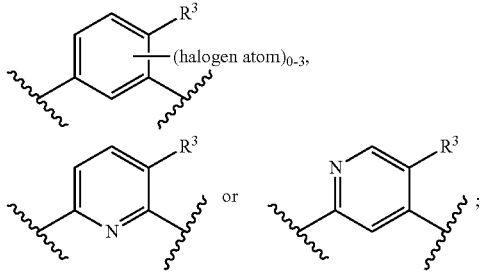

Z is CH$_2$—, —O—, —N(R$^Z$)—, —S—, —S(O)— or —S(O$_2$)—;
R$^z$ is a hydrogen atom;
R$^1$ is
(1) a hydrogen atom,
(2) a C$_{1-6}$ alkyl group substituted by 0 to 3 substituents independently selected from
  (a) a halogen atom, and
  (b) a hydroxy group, or
(3) a C$_{3-10}$ cycloalkyl group;
R$^2$ is
(1) a C$_{1-6}$ alkyl group substituted by 0 to 3 substituents independently selected from
  (a) a 5- to 14-membered aromatic heterocyclic group substituted by 0 to 3 substituents independently selected from
    (i) a cyano group,
    (ii) a halogen atom,
    (iii) a C$_{1-6}$ alkyl group, and
    (iv) a C$_{7-16}$ aralkyl group,
  (b) a 3- to 14-membered non-aromatic heterocyclic group substituted by 0 to 3 substituents independently selected from
    (i) an oxo group, and
    (ii) a C$_{1-6}$ alkyl group,
  (c) a halogen atom,
  (d) a hydroxy group,
  (e) a cyano group,
  (f) a C$_{1-6}$ alkoxy group or a halogenated C$_{1-6}$ alkoxy group,
  (g) a 5- to 14-membered aromatic heterocyclyloxy group,
  (h) a 3- to 14-membered non-aromatic heterocyclyloxy group,
  (i) an amino group optionally substituted by 1 or 2 substituents independently selected from
    (i) a C$_{1-6}$ alkyl group,
    (ii) a C$_{1-6}$ alkyl-carbonyl group substituted by 0 to 3 C$_{1-6}$ alkoxy groups, and
    (iii) a C$_{1-6}$ alkylsulfonyl group, and
  (j) a mono-C$_{1-6}$ alkyl-carbamoyl group or di-C$_{1-6}$ alkyl-carbamoyl group,
(2) a 3- to 14-membered non-aromatic heterocyclic group substituted by 0 to 3 substituents independently selected from
  (a) an oxo group, and
  (b) a C$_{1-6}$ alkyl group, or
(3) a mono-C$_{1-6}$ alkyl-carbamoyl group or di-C$_{1-6}$ alkyl-carbamoyl group substituted by 0 to 3 halogen atoms; and R$^3$ is
(1) a cyano group,
(2) a halogen atom,
(3) a C$_{1-6}$ alkyl group or a halogenated C$_{1-6}$ alkyl group,
(4) a carbamoyl group,
(5) a mono-C$_{1-6}$ alkyl-carbamoyl group or di-C$_{1-6}$ alkyl-carbamoyl group, or
(6) a 3- to 14-membered non-aromatic heterocyclylcarbonyl group,
or a pharmaceutically acceptable salt thereof;
wherein the cardiac disease is selected from the group consisting of catecholaminergic polymorphic ventricular tachycardia, postoperative atrial fibrillation, heart failure, and fatal arrhythmia.

2. The method according to claim 1, wherein the cardiac disease is heart failure.

3. The method according to claim 1, wherein the compound is selected from the group consisting of:
5-(3-(((S)-1-(1H-tetrazol-1-yl)propan-2-yl)oxy)-4-chlorophenyl)-N-(1-(trans-4-morpholinocyclohexyl)-3-(trifluoromethyl)-1H-pyrazol-4-yl)pyrimidin-2-amine;
5-(3-(((S)-1-(1H-tetrazol-1-yl)propan-2-yl)oxy)-4-chlorophenyl)-N-(1-(trans-4-morpholinocyclohexyl)-3-(2,2,2-trifluoroethoxy)-1H-pyrazol-4-yl)pyrimidin-2-amine;
5-(3-(((S)-1-(1H-tetrazol-1-yl)propan-2-yl)oxy)-4-chlorophenyl)-N-(3-(2,2-difluoroethoxy)-1-(trans-4-morpholinocyclohexyl)-1H-pyrazol-4-yl)pyrimidin-2-amine;
5-(3-(((S)-1-(1H-tetrazol-1-yl)propan-2-yl)oxy)-4-chlorophenyl)-N-(3-isopropyl-1-(trans-4-morpholinocyclohexyl)-1H-pyrazol-4-yl)pyrimidin-2-amine;
5-(3-(((S)-1-(1H-tetrazol-1-yl)propan-2-yl)oxy)-4-chlorophenyl)-N-(1-(trans-4-morpholinocyclohexyl)-3-(oxetan-3-yloxy)-1H-pyrazol-4-yl)pyrimidin-2-amine;
5-(3-(((S)-1-(1H-tetrazol-1-yl)propan-2-yl)oxy)-4-chlorophenyl)-N-(3-(((S)-2,2-difluorocyclopropyl)methoxy)-1-(trans-4-morpholinocyclohexyl)-1H-pyrazol-4-yl)pyrimidin-2-amine;
2-(((S)-1-(1H-tetrazol-1-yl)propan-2-yl)oxy)-4-(2-((1-(trans-4-morpholinocyclohexyl)-3-(2,2,2-trifluoroethoxy)-1H-pyrazol-4-yl)amino)pyrimidin-5-yl)benzonitrile;
5-(3-(((S)-1-(1H-tetrazol-1-yl)propan-2-yl)oxy)-4-chlorophenyl)-N-(1-(trans-4-((1R,5S)-3-oxa-8-azabicyclo[3.2.1]octan-8-yl)cyclohexyl)-3-(2,2-difluoroethoxy)-1H-pyrazol-4-yl)pyrimidin-2-amine;
1-(trans-4-(4-((5-(3-(((S)-1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)cyclohexyl)-3-methylazetidin 3-ol;
(S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(trifluoromethyl)-1H-pyrazol-4-yl)pyrimidin-2-amine;
(S)-5-(3-((1-(1H-tetrazol-1-yl)propan-2-yl)oxy)-4-chlorophenyl)-N-(1-(2-(tetrahydro-2H-pyran-4-yl)-2-azaspiro[3.3]heptan-6-yl)-3-(2,2,2-trifluoroethoxy)-1H-pyrazol-4-yl)pyrimidin-2-amine;
(S)-5-(3-((1-(1H-tetrazol-1-yl)propan-2-yl)oxy)-4-chlorophenyl)-N-(1-(2-(oxetan-3-yl)-2-azaspiro[3.3]heptan-6-yl)-3-(2,2,2-trifluoroethoxy)-1H-pyrazol-4-yl)pyrimidin-2-amine;
(S)-1-(6-(4-((5-(3-((1-(1H-tetrazol-1-yl)propan-2-yl)oxy)-4-chlorophenyl)pyrimidin-2-yl)amino)-3-(trifluoromethyl)-1H-pyrazol-1-yl)-2-azaspiro[3.3]heptan-2-yl)-2-methylpropan-2-ol;

(S)-5-(3-((1-(1H-tetrazol-1-yl)propan-2-yl)oxy)-4-chlorophenyl)-N-(1-(2-(2,2-dimethyl-1,3-dioxan-5-yl)-2-azaspiro[3.3]heptan-6-yl)-3-(2,2,2-trifluoroethoxy)-1H-pyrazol-4-yl)pyrimidin-2-amine;

(S)-5-(3-((1-(1H-tetrazol-1-yl)propan-2-yl)oxy)-4-chlorophenyl)-N-(3-isopropyl-1-(2-(oxetan-3-yl)-2-azaspiro[3.3]heptan-6-yl)-1H-pyrazol-4-yl)pyrimidin-2-amine;

(S)-5-(3-((1-(1H-tetrazol-1-yl)propan-2-yl)oxy)-4-chlorophenyl)-N-(3-isopropyl-1-(2-(tetrahydro-2H-pyran-4-yl)-2-azaspiro[3.3]heptan-6-yl)-1H-pyrazol-4-yl)pyrimidin-2-amine;

(S)-5-(3-((1-(1H-tetrazol-1-yl)propan-2-yl)oxy)-4-chlorophenyl)-N-(1-(2-(4-methyltetrahydro-2H-pyran-4-yl)-2-azaspiro[3.3]heptan-6-yl)-3-(2,2,2-trifluoroethoxy)-1H-pyrazol-4-yl)pyrimidin-2-amine;

5-(4-chloro-3-{[(2S)-1-(1H-tetrazol-1-yl)propan-2-yl]oxy}phenyl)-N-(1-{2-[(4-$^2$H)tetrahydro-2H-pyran-4-yl]-2-azaspiro[3.3]heptan-6-yl}-3-(2,2,2-trifluoroethoxy)-1H-pyrazol-4-yl)pyrimidin-2-amine;

(S)-1-(6-(4-((5-(3-((1-(1H-tetrazol-1-yl)propan-2-yl)oxy)-4-chlorophenyl)pyrimidin-2-yl)amino)-3-(2,2,2-trifluoroethoxy)-1H-pyrazol-1-yl)-2-azaspiro[3.3]heptan-2-yl)-2-methyl propan-2-ol;

(S)-1-(6-(4-((5-(3-((1-(1H-tetrazol-1-yl)propan-2-yl)oxy)-4-chlorophenyl)pyrimidin-2-yl)amino)-3-isopropyl-1H-pyrazol-1-yl)-2-azaspiro[3.3]heptan-2-yl)-2-methylpropan 2-ol;

(S)-1-(4-((5-(3-((1-(1H-tetrazol-1-yl)propan-2-yl)oxy)-4-chlorophenyl)pyrimidin-2-yl)amino)-1-(2-(tetrahydro-2H-pyran-4-yl)-2-azaspiro[3.3]heptan-6-yl)-1H-pyrazol-3-yl)propan-1-one;

(S)-5-(3-((1-(1H-tetrazol-1-yl)propan-2-yl)oxy)-4-chlorophenyl)-N-(3-(perfluoroethyl)-1-(2-(tetrahydro-2H-pyran-4-yl)-2-azaspiro[3.3]heptan-6-yl)-1H-pyrazol-4-yl)pyrimidin-2-amine;

(S)-5-(3-((1-(1H-tetrazol-1-yl)propan-2-yl)oxy)-4-chlorophenyl)-N-(3-isopropyl-1-(2-(4-methyltetrahydro-2H-pyran-4-yl)-2-azaspiro[3.3]heptan-6-yl)-1H-pyrazol-4-yl)pyrimidin-2-amine;

(S)—N-(1-(2-(1,3-dioxan-5-yl)-2-azaspiro[3.3]heptan-6-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine;

(S)—N-(1-(2-(1,4-dioxepan-6-yl)-2-azaspiro[3.3]heptan-6-yl)-3-(2,2,2-trifluoroethoxy)-1H-pyrazol-4-yl)-5-(3-((1-(1H-tetrazol-1-yl)propan-2-yl)oxy)-4-chlorophenyl)pyrimidin-2-amine;

(S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(trifluoromethyl)-1H-pyrazol-4-yl)pyrimidin-2-amine;

(S)-5-(3-((1-(1H-tetrazol-1-yl)propan-2-yl)oxy)-4-chlorophenyl)-N-(1-(1-(tetrahydro-2H-pyran-4-yl)piperidin-4-yl)-3-(2,2,2-trifluoroethoxy)-1H-pyrazol-4-yl)pyrimidin-2-amine;

(S)-5-(3-((1-(1H-tetrazol-1-yl)propan-2-yl)oxy)-4-chlorophenyl)-N-(3-(difluoromethoxy)-1-(1-(tetrahydro-2H-pyran-4-yl)piperidin-4-yl)-1H-pyrazol-4-yl)pyrimidin-2-amine;

(S)-5-(3-((1-(1H-tetrazol-1-yl)propan-2-yl)oxy)-4-chlorophenyl)-N-(3-isopropyl-1-(1-(tetrahydro-2H-pyran-4-yl)piperidin-4-yl)-1H-pyrazol-4-yl)pyrimidin-2-amine; and (S)-2-((1-(1H-tetrazol-1-yl)propan-2-yl)oxy)-4-(2-((1-(1-(tetrahydro-2H-pyran-4-yl)piperidin-4-yl)-3-(2,2,2-trifluoroethoxy)-1H-pyrazol-4-yl)amino)pyrimidin-5-yl)benzonitrile, or a pharmaceutically acceptable salt thereof.

4. The method according to claim 1, wherein the method further comprises administering administration to the mammal in need thereof a therapeutically effective amount of a concomitant drug.

5. The method according to claim 4, wherein the concomitant drug is selected from the group consisting of an alglucosidase inhibitor, an angiotensin converting enzyme inhibitor, an angiotensin II receptor antagonist, an angiotensin II receptor antagonist/neutral endopeptidase inhibitor combination agent, an antiarrhythmic drug, an anticoagulant, an antiobesity drug, a β-receptor antagonist, a biguanide, a calcium antagonist, a calcium channel blocker, a diuretic, a digitalis preparation, glucagon, a glucosidase inhibitor, insulin, an insulin sensitizer, a phosphodiesterase inhibitor, a potassium channel blocker, a sodium-glucose transport protein 2 inhibitor, a sulfonylurea, and a therapeutic drug for diabetic complications.

6. The method according to claim 1, wherein the method further comprises administering to the mammal in need thereof a therapeutically effective amount of a biological product.

7. The method according to claim 6, wherein the biological product is an antibody.

8. The method according to claim 1, wherein the method further comprises administering to the mammal in need thereof a therapeutically effective amount of a gene therapy.

\* \* \* \* \*